(12) United States Patent
Gabant

(10) Patent No.: US 12,297,422 B2
(45) Date of Patent: May 13, 2025

(54) CONTROLLED GROWTH OF MICROORGANISMS

(71) Applicant: Syngulon SA, Seraing (BE)

(72) Inventor: Philippe Gabant, Ottignies Louvain-la-Neuve (BE)

(73) Assignee: Syngulon SA, Seraing (BE)

( * ) Notice: Subject to any disclaimer, the term of this patent is extended or adjusted under 35 U.S.C. 154(b) by 93 days.

(21) Appl. No.: 17/822,663

(22) Filed: Aug. 26, 2022

(65) Prior Publication Data

US 2023/0193191 A1 Jun. 22, 2023

Related U.S. Application Data

(60) Continuation of application No. 16/227,371, filed on Dec. 20, 2018, now Pat. No. 11,427,800, which is a continuation of application No. 15/087,706, filed on Mar. 31, 2016, now Pat. No. 10,188,114, which is a division of application No. 14/459,810, filed on Aug. 14, 2014, now Pat. No. 9,333,227.

(60) Provisional application No. 61/867,510, filed on Aug. 19, 2013.

(51) Int. Cl.
| | | |
|---|---|---|
| C12N 1/12 | (2006.01) |
| A01N 63/50 | (2020.01) |
| A61K 35/74 | (2015.01) |
| A61K 36/02 | (2006.01) |
| A61K 36/06 | (2006.01) |
| C07K 14/195 | (2006.01) |
| C12N 1/16 | (2006.01) |
| C12N 1/20 | (2006.01) |
| C12N 1/38 | (2006.01) |

(52) U.S. Cl.
CPC .............. *C12N 1/12* (2013.01); *A01N 63/50* (2020.01); *A61K 35/74* (2013.01); *A61K 36/02* (2013.01); *A61K 36/06* (2013.01); *C07K 14/195* (2013.01); *C12N 1/16* (2013.01); *C12N 1/20* (2013.01); *C12N 1/38* (2013.01)

(58) Field of Classification Search
None
See application file for complete search history.

(56) References Cited

U.S. PATENT DOCUMENTS

| | | |
|---|---|---|
| 5,300,431 A | 4/1994 | Pierce et al. |
| 5,549,895 A | 8/1996 | Lyon et al. |
| 5,631,153 A | 5/1997 | Capecchi |
| 5,670,370 A | 9/1997 | Molin et al. |
| 5,855,732 A | 1/1999 | Yoshida |
| 5,888,732 A | 3/1999 | Hartley et al. |
| 5,910,438 A | 6/1999 | Bernard et al. |
| 5,922,583 A | 7/1999 | Morsey |
| 6,143,557 A | 11/2000 | Hartley et al. |
| 6,171,861 B1 | 1/2001 | Hartley et al. |
| 6,180,407 B1 | 1/2001 | Bernard et al. |
| 6,270,969 B1 | 8/2001 | Hartley et al. |
| 6,271,359 B1 | 8/2001 | Norris et al. |
| 6,528,285 B1 | 3/2003 | Biet et al. |
| 7,176,029 B2 | 2/2007 | Bernard et al. |
| 7,183,097 B1 | 2/2007 | Gerdes et al. |
| 7,595,185 B2 | 9/2009 | Gerdes et al. |
| 7,595,186 B2 | 9/2009 | Gerdes et al. |
| 8,318,497 B2 | 11/2012 | Szpirer et al. |
| 8,470,580 B2 | 6/2013 | Gabant et al. |
| 8,476,048 B2 | 7/2013 | Caimi et al. |
| 8,697,426 B2 | 4/2014 | Leana et al. |
| 8,877,504 B2 | 11/2014 | Gabant et al. |
| 9,333,227 B2 * | 5/2016 | Gabant .................. A61K 35/74 |
| 10,188,114 B2 * | 1/2019 | Gabant .................. A61K 36/02 |
| 11,427,800 B2 * | 8/2022 | Gabant .................. A61K 35/74 |
| 11,492,651 B2 | 11/2022 | Gabant |
| 11,932,672 B2 | 3/2024 | Gabant et al. |
| 2004/0115811 A1 | 6/2004 | Gabant |
| 2005/0130308 A1 | 6/2005 | Bernard |
| 2005/0260585 A1 | 11/2005 | Szpirer |
| 2010/0330041 A1 | 12/2010 | Bayrock |
| 2013/0115658 A1 | 5/2013 | Szpirer et al. |
| 2013/0280810 A1 | 10/2013 | Gabant et al. |
| 2014/0148379 A1 | 5/2014 | Liu et al. |
| 2014/0178956 A1 | 6/2014 | Leana et al. |
| 2015/0050253 A1 | 2/2015 | Gabant |

(Continued)

FOREIGN PATENT DOCUMENTS

| | | |
|---|---|---|
| DE | 10038573 | 2/2002 |
| EP | 1 111 061 | 6/2001 |

(Continued)

OTHER PUBLICATIONS (1992) Journal of Cellular Biochemistry, Keystone Symposia on Molecular & Cellular Biology, 104.
Abremski, et al. (1984) Bacteriophage P1 Site-specific Recombination. J. Bio. I. Chem. 259(3):1509-1514.
Acuna, et al., FEBS Open Bio, 2: 12-19, 2012.
Adetunji and Olaoye, Malaysian Journal of Microbiology 9: 130-13, 2013.

(Continued)

*Primary Examiner* — Blaine Lankford
(74) *Attorney, Agent, or Firm* — KNOBBE, MARTENS, OLSON & BEAR, LLP

(57) ABSTRACT

It can be useful to regulate the growth of microbial cells. Some embodiments herein provide genetically engineered microbial cells that can produce bacteriocins to control the growth of microbial cells. In some embodiments, microbial cells are contained within a desired environment. In some embodiments, contaminating microbial cells are neutralized. In some embodiments, a first microbial cell type regulates the growth of a second microbial cell type so as to maintain a desired ratio of the two cell types.

31 Claims, 8 Drawing Sheets

Specification includes a Sequence Listing.

(56) References Cited

U.S. PATENT DOCUMENTS

| | | |
|---|---|---|
| 2021/0070812 A1 | 3/2021 | Gabant et al. |
| 2021/0238645 A1 | 8/2021 | Gabant |
| 2022/0017573 A1 | 1/2022 | Mignolet et al. |
| 2023/0193191 A1 | 6/2023 | Gabant |

FOREIGN PATENT DOCUMENTS

| | | |
|---|---|---|
| EP | 2 543 255 | 1/2013 |
| JP | H05-56790 | 3/1993 |
| JP | 2014-502501 | 2/2014 |
| WO | WO 94/03616 | 2/1994 |
| WO | WO 97/13401 | 4/1997 |
| WO | WO 97/14805 | 4/1997 |
| WO | WO 99/02555 | 1/1999 |
| WO | WO 99/21977 | 5/1999 |
| WO | WO 99/58652 | 11/1999 |
| WO | WO 01/31039 | 5/2001 |
| WO | WO 01/42509 | 6/2001 |
| WO | WO 01/46444 | 6/2001 |
| WO | WO 02/12474 | 2/2002 |
| WO | WO 02/66657 | 8/2002 |
| WO | WO 2004/022745 | 3/2004 |
| WO | WO 2009/011940 | 1/2009 |
| WO | WO 2010/060057 | 5/2010 |
| WO | WO 2019/046577 | 3/2019 |
| WO | WO 2019/121983 | 6/2019 |
| WO | WO 2019/236761 | 12/2019 |
| WO | WO 2022/104320 | 11/2021 |
| WO | WO 2022/104321 | 11/2021 |

OTHER PUBLICATIONS

Aizenman, et al. (1996) An *Escherichia coli* chromosomal "addiction module" regulated by 3', 5'-bispyroohosohate: A modayk for programmed bacterial cell death. Proc. Nail. Acad. Sci. 93:6059-6063.

Allison et al., "Functional Analysis of the Gene Encoding Immunity to Lactacin F, lafl, and Its Use as a *Lactobacillus*-Specific, Food-Grade Genetic Marker", Applied and Environmental Microbiology, vol. 62, No. 12, pp. 4450-4460, Dec. 1996.

Altschul, S.F., et al., "Basic local alignment search tool", J. Mol. Biol. 215:403-410, 1990.

Backman, et al., (1983), "Tetracycline Resistance Determined by pBR322 is Mediated by one Polypeptide." Gene 26. pp. 197-203.

Bacteriocin, Wikipedia, http://en.wikipedia.org/wiki-Bacteriocin, Printed on Oct. 3, 2014.

Bahassi, et al. (1995) F plasmid CcdB killer protein: ccd8 gene mutants coding for non-cytotoxic proteins which retain their regulatory functions. Molecular Microbiology 15(6):1031-1037.

Basanta et al., "Development of Bacteriocinogenic Strains of Saccharomyces cerevisiae Heterologously Expressing and Secreting the Leaderless Enterocin L50 Peptides L50A and L50B from Enterococcus faecium L50", Applied and Environmental Microbiology, vol. 75, No. 8, pp. 2382-2392, Apr. 2009.

Baum, "Tn5401, a New Class II Transposable Element from Bacillus thuringiensis," Journal of Bacteriology, vol. 176. No. 10, May 1994, pp. 2835-2845.

Baunonis, et al. (1993) Genomic Targeting with Purified Cre Recombinase. Nucleic Acids Research 21 (9):2025-2029.

Bech et al., "Sequence of the reLB transcription unit from *Escherichia coli* and Identification of the reLB gene," The EMBO Journal, vol. 4, No. 4 00.1059-1066 1985.

Bernard (1996) Positive Selection of Recombinant DNA by CcdB. BioTechniques 21(2)320-323.

Bernard et al., 1992 "Cell killing, by the F plasmid CcdB protein involves poisoning of DNA-topoisomerase II complexes," J. Mol. Biol. 226:735-745.

Bernard, et al. (1991) The 41 carboxy-terminal residues of the miniF plasmid CcdA protein are sufficient to antagonize the killer activity of the CcdB protein. Mol. Gen Genet 226:297-304.

Bernard, P., et al. (1994) Positive-Selection Vectors Using the F Plasmid cedB Killer Gene. Gene 148, pp. 71-74.

Bex, et al. (1983) Mini-F encoded proteins: identification of a new 10.5 kilodalton species. The EMBO Journal,2(11):1853-1861.

Biswas, et al. (1993) High-Efficiency Gene Inactivation and Replacement System for Gram-Positive Bacteria. J. Bacteriology 175(11):3628-3635.

Bochner, et al. (1980) Positive Selection for loss of Tetracycline Resistance. J. Bacteriology 143(2):923-933.

Bondaryk et al., "Natural Antimicrobial Peptides as Inspiration for Design of a New Generation Antifungal Compounds", J. Fungi, vol. 3, No. 46, pp. 1-36, 2017.

Borrero et al., "Cloning, Production, and Functional Expressing of the Bacteriocin Enterocin A, Produced by Enterococcus faecium T136, by the Yeasts *Pichia pastoris, Kluyveromyces lactis, Hansenula polymorpha,* and *Arxula adeninivorans*", Applied and Environmental Microbiology, vol. 78, No. 16, oaaes 5956-5961, Aug. 2012.

Borrero, J. et al., Protein Expression Vector And Secretion Signal Peptide Optin1 ization To Drive The Production, Secretion, And Functional Expression Of The Bacteriocin Enterocin A In Lactic Acid Bacteria, Journal of Biotechnology, vol. 156, pp. 76-86, 2011.

Boyd (1993) Turbo Cloning: A Fast, Efficient Method for Cloning PCR Products and Other Blunt-Ended DNA Fragments into Plasmids. Nucleic Acids Research 21(4):817-821.

Bravo, et al. (1988) Killing of Escherichia coli cells modulated by components of the stability system ParD of plasmid R1. Mol. Gen. Genet. 215:146-151.

Bubeck, et al. (1993) Rapid Cloning by Homologous Recombination in vivo. Nucleic Acids Research 21(15):3601-3602.

Bult, "Complete Genome Sequence of the Methanogenic Archaeon, Methanococcus Jannaschii," Science, vol. 273 Aug. 23, 1996.00. 1058-1073.

Burns, et al. (1984) Positive Selection Vectors: A Small Plasmid Vector Useful for the Direct Selection of Sau2A-aenerated overlapping DNA Fragments. Gene 27:323-325.

Campelo et al., "A bacteriocin gene cluster able to enhance plasmid maintenance in *Lactococcus lactis*", Microbial Cell Factories 2014, 13:77. Accessible on the world wide web at www.microbialcellfactories.com/content/13/1/77. 9 pages.

Cole et al., "Deciphering the Biology of *Mycobacterium tuberculosis* from the Complete Genome Sequence," Nature vol. 393, Jun. 11, 1998 Do.537-544.

Communication pursuant to Article 94(3) EPC in European Application No. 14 758 511.1 dated Feb. 5, 2020.

Communication pursuant to Rule 45 EPC dated Aug. 9, 2021 in European Application No. 21178464.0.

Communication under Rule 164(2)(a) EPC dated Oct. 17, 2018 in European Application No. 14758511.1.

Cotter, P. D. et al., "Bacteriocins—a viable alternative to antibiotics", Nature Reviews Microbiology 11:95-105, 2013.

Couturier, et al. (1998) Bacterial death by DNA gyrase poisoning. Trends in Microbiology 6(7):269-275.

Craine, (1982) Novel Selection for Tetracycline-or Chloramphenicol-Sensitive *Escherichia coli.* J. Bacteriology 151(1):487-490.

Cui et al., "Class IIa Bacteriocins: Diversity and New Developments", Int. J. Mol. Sci., vol. 13, pp. 16668-16707, 2012.

D'Souza, S.F., "Microbial biosensors", Biosensors & Bioelectronics, vol. 16, 2001, pp. 337-353.

Daw et al., "Bacteriocins: Nature, Function and Structure", Micron, vol. 27, No. 6, pp. 467-479, 1996.

Ebert et al. "A Moloney MLV-Rat Somatotropin Fusion Gene Produces Biologically Active Somatotropin in a transgenic pig." Molecular Endocrinology. 2:277-283, 1988.

European Search Report Dated Mar. 8, 2022, in European Patent Application No. 21178464.0 in 12 pages.

File History of U.S. Appl. No. 09/700,130, filed Dec. 18, 2001.
File History of U.S. Appl. No. 10/468,536, filed Jan. 23, 2004.
File History of U.S. Appl. No. 10/526,525, filed Aug. 26, 2005.
File History of U.S. Appl. No. 11/558,856, filed Nov. 10, 2006.
File History of U.S. Appl. No. 11/837,456, filed Aug. 10, 2007.
File History of U.S. Appl. No. 13/660,907, filed Oct. 25, 2012.
File History of U.S. Appl. No. 13/919,952, filed Jun. 17, 2013.
File History of U.S. Appl. No. 14/459,810, filed Aug. 14, 2014.

(56) References Cited

OTHER PUBLICATIONS

File History of U.S. Appl. No. 15/087,706, filed Mar. 31, 2016.
File History of U.S. Appl. No. 16/227,371, filed Dec. 20, 2018.
Fleischmann et al., "Whole-Genome Random Sequencing and Assembly of Haemophilus Influenza Rd," Science, Vol.269. 00.496-512 Jul. 28, 1995.
Gabant et al., 1997 "Bifunctional lacZ a-ccdB genes for selective cloning of PCR products," Biotechniques 23:938-941.
Gabant et al., 1998 "Direct selection cloning vectors adapted to the genetic analysis of gram-negative bacteria and their plasmids," Gene 207:87-92.
Gabant et al., 2000 "New positive selection system based on the parD (kislkid) system of the R1 plasmid," Biotechniques 28:784-788.
Gabant et al., 2001 "Use of poison/antidote systems for selective cloning," in Plasmid Biology 2000: International, Symposium on Molecular Bioloy of Bacterial Plasmids, Meeting Abstracts, 00.135-170, Plasmid 45:160-161.
Gajic et al., "Novel Mechanism of Bacteriocin Secretion and Immunity Carried Out by Lactococcal Multidrug Resistance Proteins*", The Journal of Biological Chemistry, Sep. 5, 2003, vol. 278, No. 36, pp. 34291-34298.
Gerard et al., "Bactericidal Activity of Colicin V Is Mediated by an Inner Membrane Protein, SdaC, of *Escherichia coli*", Journal Of Bacteriology, vol. 187, No. 6, pp. 1945-1950, Mar. 2005.
Gerdes (2000) Toxin-Antitoxin modules may regulate synthesis of macromolecules during nutritional stress. Journal of Bacteriology 182:561-572.
Gerdes, et al. "RNA antitoxins." (2007) Current Opinion in Microbiology, vol. 10, p. 117-124.
Gibson et al., "Creation of a Bacterial Cell Controlled by a Chemically Synthesized Genome", Science, vol. 329, pp. 52-56, 2010.
Goni-Moreno, et al., "Multicellular Computing Using Conjugation for Wiring", PLoS ONE 8(6): e65986, 2013.
Gossen, J. A., et al. (1992) Application of Galactose-Sensitive *E. coli* Strains as Selective Hosts for LacZ Plasmids. Nucleic Acids Res. 20.0.3254.
Gotfredsen, et al., "The *Escherichia coli* relBE genes belong to a new toxin-antitoxin gene family" Molecular Microbiology (1998) 29(4): 1065-1076.
Green and Sambrook, "Molecular Cloning: a Laboratory Manual", Cold Spring Harbor Laboratory Press; $4^{th}$ edition, 2012.
Gronenborn (1978) Methylation of single-stranded DNA in vitro introduces new restriction endonuclease cleavage sites. Nature, 272:375-377.
Gronlund et al., "Toxin-Antitoxin Systems Homologous with relBE of *Escherichia coli* Plasmid P307 are Ubiquitous in Prokaryotes," Journal of Molecular Biology, Vol.285, No. 4, Jan. 29.1999, pp. 1401-1415.
Guilfoyle, R.A., and I.M. Smith (1994) "A Direct Selection Strategy for Stotgun Cloning and Sequencing in the Bacteriophage M13." Nucleic Acids Res.22, pp. 100-107.
Guzman et al. 1995 "Tight regulation, modulation, and high-level expression by vectors containing the arabinose PBAO promoter," J. Bacteriol. 177:4121-4130.
Hammer et al. "Genetic Engineering of Mammalian Embryos." J. Anim. Sci. 63:269-278, 1986.
Hartley et al., DNA cloning using in vitro site-specific recombination: Genome Res. 10:1788-1795, 2000.
Hasan et al., Gene, vol. 56, pp. 145, 1987.
Hebsgaard, S.M., et al. (1996) "Splice Site Prediction in *Arabidopsis thaliana* Pre-mRNA by Combining Local and Global Sequence information." Nucleic Acids Research, 24(17) 3439-3452.
Henrich et al. 1986 "Use of the lysis gene of bacteriophage X174 for the construction of a positive selection vector," Gene 42:345-349.
Herrero, M., et al., (1990) "Transposon Vectors Containing Non-Antibiotic Resistance Selection markers for Cloning and Stable Chromosomal Insertion of Foreign Genes in Gram-Negative Bacteria." J. Bact. 172,11, pp. 6557-6567.

Holt, et al. (1993) A Novel Phage A Replacement Cre-lox Vector that has Automatic Subcloning Capabilities, Gene 133:95-97.
Inglis, et al., "The Role of Bacteriocins as Selfish Genetic Elements". Biology Letters, Issue 9, vol. Jun. 3, 2013. Published Apr. 24, 2013, DOI: 10.1098/rsbl.2012.1173. 6 pages.
International Preliminary Examination Report from PCT/BE02/00021, dated Feb. 19, 2003.
International Preliminary Examination Report from PCT/BE03/00045, dated Feb. 24, 2004.
International Search Report and Written Opinion dated Feb. 5, 2015 in PCT Application No. PCT/EP2014/067418.
International Search Report from PCT/BE02/00021, dated Jul. 12, 2002.
International Search Report from PCT/BE02/00151, dated May 22, 2001.
Ioannou, et al. (1994) A new bacteriophage P1-derived vector for the propagation of large human DNA fragments, Nature Genetics 6:84-89.
Jaramillo, A., "Synthetic Biology—Engineered stable ecosystems", Nature Microbiology, vol. 2, No. 17119, pp. 1-2, Jul. 25, 2017.
Jensen et al., 1995 "Comparison of ccd of F, parDE of RP4, and parD of R1 using a novel conditional replication control system of plasmid R1," Molecular Microbiology 17:211-220.
Jensen et al., 1995 Programmed cell death in bacteria: protect plasmid stabilization systems, Molecular Microbiology 17:205-210.
Kaneko et al., "Sequence Analysis of the Genome of the Unicellular *Cyanobacterium synechocystis* sp. Strain PCC6803. II. Sequence Determination of the Entire Genome and Assignment of Potential Protein-Coding Regions" DNA Research, vol. 3, 00.109-136.1996.
Karoui, et al. (1983) Ham22, a mini-F mutation which is lethal to host cell and promotes recA-dependent induction of lambdoid prophage. The EMBO Journal. 2(11): 1863-1868.
Kristoffersen et al. "Bacterial Toxin-Antitoxin Gene Systems as Containment Control in Yeast Cells" Applied and Environmental Microbiology, vol. 66 No. 12, Dec. 2000, p. 5524-5526.
Kuhn et al. 1986 "Positive-selection vectors utilizing lethality of the EcoRI endonuclease," Gene 44:253-263.
Landy, Arthur, 1989 Dynamic, structural, and regulatory aspects of A site-specific recombination: Annu. Rev. Biochem 58:913-949.
Lehnherr, et al. (1993) Plasmid Addiction Genes of Bacteriophage P1: doc, which cause cell death on curing of prophage, and phd, which prevents host death when prophage is retained. J. Mol. Biol. 233:414-428.
Liu (1989) DNA Topoisomerase poisons as antitumor drugs. Annu. Rev. Biochem. 58:351-375.
Lum et al., "Activity of Novel Synthetic Peptides against Candida albicans", Scientific Reports, vol. 5, No. 9657, pp. 1-12, 2015.
Maki, et al (1992) Modulation of DNA Supercoiling Activity of *Escherichia coli* DNA Gyrase by F Plasmid Proteins, The Journal of Biological Chemistry vol. 267(17):12244-12251.
Maloy, et al. (1981) Selection for Loss of Tetracycline Resistance by *Escherichia coli*, Journal of Bacteriology, 145(2):1110-1112.
Manning, P.A., "Nucleotide Sequence encoding the Mannose-fucose-resistant Hemagglutinin of Vibrio Cholerae 01 and Construction of a Mutant," EMBL Sequence Database, Aug. 7, 1993. pp. 1-7.
Maxwell, et al. (1986) Mechanistic aspects of DNA Topoisomerases. Advan. Protein Chem. 38:69-107.
McAuliffe et al., "Identification and overexpression of Itnl, a novel gene which confers immunity to the two-component lantibiotic lacticin 3147", Microbiology, 2000, vol. 146, pp. 129-138.
McBride, et al., "Contamination management in Low Cost Open Algae Ponds for Biofuels Production", Industrial Biotechnology, vol. 10, pp. 221-227, 2014.
Messing, et al. (1977) Filamentous coliphage M13 as a cloning vehicle: Insertion of a HindII Fragment of the lac regulatory region in M13 replicative form in vitro. Proc Nail. Acad. Sci. 74(9):3642-3646.
Miki, et al. (1984) Control of Cell Division by Sex Factor F in *Escherichia coli*. J. Mol. Bioi. 174:627-646.
Miki, et al. (1984) Control of Cell Division by Sex Factor F in *Escherichia coli*. J. Mol. Biol. 174:605-625.
Moreadith et al. "Gene Targeting in Embryonic Stem Cells: The new Physiology and metabolism." J. Mol. Med. 75:208-216 1997.

(56) References Cited

OTHER PUBLICATIONS

Mori, Hirotada, et al., "Prophage A Induction Caused by Mini-F Plasmid Genes." (1984) Mol Gen Genet 196:185-193.

Mullins et al. "Perspective Series: Molecular Medicine in Genetically Engineered Animals." J. Clin. Invest. 98 (Suppl.): 837-S40, 1996.

Murphy, et al. (1991), pAZd39: A New Type of cDNA Expression Vector for Low Background, High Efficiency Directional Cloning. Nucleic Acids Research 19(12):3403-3408.

Muyrers et al. 2001 "Techniques: recombinogenic engineering—new options for cloning and manipulating DNA," Trends in Biochem. Sci. 26:325-331.

Nilsson, et al. (1983) An Improved Positive Selection Plasmid Vector Constructed by Oligonucleotide Mediated Mutagenesis. Nucleic Acids Research 11 (22):8019-8029.

Nomura M., "Colicins and Related Bacteriocins", Annual Review of Microbiology, vol. 21, pp. 257-284, Oct. 1967.

Norrander, et al. (1983) Construction of improved M13 vectors using oligodeoxynucleotide-directed mutagenesis. Gene 26:101-106.

Notice of Allowability from U.S. Appl. No. 08/379,614 Dated Mar. 3, 1998.

Notice of Allowance dated Feb. 11, 2016 in U.S. Appl. No. 14/459,810.

Notice of Allowance dated Sep. 12, 2018 in U.S. Appl. No. 15/087,706.

Office Action dated Apr. 20, 2009 in U.S. Appl. No. 10/526,525.

Office Action dated Apr. 20, 2021 in Brazilian Application No. BR 11 2016 003533 0 with English Translation.

Office Action dated Apr. 28, 2017 in U.S. Appl. No. 15/087,706.

Office Action dated Apr. 5, 2018 in U.S. Appl. No. 15/087,706.

Office Action dated Aug. 15, 2019 in Brazilian Application No. BR 11 2016 003533 0 with English Translation.

Office Action dated Aug. 28, 2015 in U.S. Appl. No. 14/459,810.

Office Action dated Feb. 10, 2012 in U.S. Appl. No. 10/526,525.

Office Action dated Jan. 29, 2009 in U.S. Appl. No. 10/468,536.

Office Action dated Jan. 5, 2006 in U.S. Appl. No. 09/700,130.

Office Action dated Jul. 27, 2012 in U.S. Appl. No. 10/468,536.

Office Action dated Jun. 14, 2005 in U.S. Appl. No. 09/700,130.

Office Action dated Jun. 14, 2010 in U.S. Appl. No. 10/526,525.

Office Action dated Jun. 19, 2007 in U.S. Appl. No. 10/468,536.

Office Action dated Mar. 12, 2021 in Indian Patent Application No. 201617008769 with English translation.

Office Action dated Mar. 2, 2011 in U.S. Appl. No. 10/526,525.

Office Action dated Mar. 25, 2008 in U.S. Appl. No. 10/468,536.

Office Action dated May 5, 2014 in U.S. Appl. No. 13/919,952.

Office Action dated Nov. 16, 2009 in U.S. Appl. No. 10/468,536.

Office Action dated Nov. 30, 2017 in Chinese Application No. 201480057387.2 with English translation.

Office Action dated Nov. 5, 2018 in Chinese Patent Application No. 201480057387.2; 4 pages.

Office Action dated Oct. 25, 2013 in U.S. Appl. No. 13/919,952.

Office Action dated Sep. 10, 2020 in European Application No. 14758511.1.

Office Action dated Sep. 14, 2017 in U.S. Appl. No. 15/087,706.

Office Action dated Sep. 29, 2006 in U.S. Appl. No. 10/468,536.

Office Action dated Sep. 9, 2011 in U.S. Appl. No. 10/526,525.

Office Action from U.S. Appl. No. 08/379,614, Dated Aug. 27, 1996.

Office Action from U.S. Appl. No. 08/379,614, Dated Aug. 4, 1997.

Office Action from U.S. Appl. No. 09/225,152 dated Sep. 13, 1999.

Office Action from U.S. Appl. No. 09/634 039, Dated Dec. 20, 2001.

Office Action from U.S. Appl. No. 09/634,039 Dated Jun. 29, 2005.

Office Action from U.S. Appl. No. 09/634,039, Dated Dec. 16, 2004.

Office Action from U.S. Appl. No. 09/634,039, Dated Jan. 15, 2003.

Office Action from U.S. Appl. No. 09/634,039, Dated Sep. 24, 2003.

Office Action with English Translation Dated Apr. 21, 2022 in Chinese Patent Application No. 201910882176. 7 in 8 pages.

Ogura, et al. (1983) Mini-F plasmid genes that couple host cell division to plasmid proliferation. Proc. Natl. Acad. Sci. USA 80:4784-4788.

Opinion of the Scientific Panel on Food Additives, Flavourings, Processing Aids and Materials in Contact with Food on a Request from the Commission Related to the use of Nisin (E 234) as a food additive. Question No. EFSA-Q-2005-031. Adopted on Jan. 26, 2006. The EFSA Journal (2006) 314, pp. 1-16.

Pag et al., "Molecular Analysis of Expression of the Lantibiotic Pep5 Immunity Phenotype", Applied and Environmental Microbiology, Feb. 1999, vol. 65, No. 2, pp. 591-598.

Partial International Search Report dated Jan. 13, 2015 in Application No. PCT/EP2014/067418.

Peakman, et al. (1992) Highly Efficient Generation of Recombinant Baculoviruses by Enzymatically Mediated Site-Specific in vitro Recombination. Nucleic Acids Research 20(3):495-500.

Pecota, et al. "Combining the hok/sok, parDE, and pnd Postsegregational Killer Loci to Enhance Plasmid Stability." (1997) Applied and Environmental Microbiology, vol. 63, p. 1917-1924.

PGT-N28 Vector DNA (catalog #N3728) New England Biolabs Online Catalog, Jun. 2, 99, p. 1, www.neb.comlneb/products/nucleicJ307-28.html the whole document.

Pierce et al. 1992 "A positive selection vector for cloning high molecular weight DNA by the bacteriophage P1 system: improved cloning efficacy," PNAS USA 89:2056-2060.

PKO Scrambler Series Gene Targeting Vectors for Knockout Mice. Stratagene Online Catalog, Jan. 1998, pp. 1-3; www.stratagene.com/cellbio/toxicology/pko.htm, the whole document.

Pomares et al., "Potential Applicability of Chymotrypsin-Susceptible Microcin J25 Derivatives to Food Preservation", Applied and Environmental Microbiology, vol. 75, No. 17, pp. 5734-5738, Sep. 2009.

Pre-Interview Communication dated Jan. 28, 2015 in U.S. Appl. No. 14/459,810.

Reeves et al., "Engineering Escherichia coli into a Protein Delivery System for Mammalian Cells", ACS Synth. Biol., vol. 4, pp. 644-654, 2015.

Riley et al., "Bacteriocins: Evolution, Ecology, and Application", Annu. Rev. Microbiol., 2002, vol. 56, pp. 117-137.

Roberts, et al. (1992) Definition of a Minimal Plasmid Stabilization System from the Broad-Host-Range Plasmid RK2. Journal of Bacteriology Dec. 1992:8119-8132.

Roberts, et al. (1994) The parDE operon of the broad-host-range plasmid RK2 specifies growth inhibition associated with plasmid loss. J. Mol. Biol. 18; 237 (1): 35-51.

Roca, et al. (1992) A Hit-and-Run System for Targeted Genetic Manipulations in Yeast. Nucleic Acid Research 20(17):4671-4672.

Ruiz-Echevarria et al. (1991) Structural and functional comparison between the stability systems ParD of plasmid R1 and Ccd of plasmid. F. Mol. Gen. Genet 225:355-362.

Ruiz-Echevarria et al. 1995 A mutation that decreases the efficiency of plasmid R1 replication leads to the activation of parD, a killer stability system of the plasmid: FEMS Microb. Letters 130: 129-136.

Ruiz-Echevarria, et al. (1991) The kis and kid genes of the parD maintenance system of plasmid R1 form an operon that is autoregulated at the level of transcription by the co-ordinated action of the Kis and Kid proteins. Molecular Microbiology 5(11):2685-2693.

Sadler, et al. (1980) Plasmids containing many tandem copies of a synthetic lactose operator. Gene 8:279-300.

Salmon et al., "The Antidote and Autoregulatory Functions of the F Plasmid CcdA Protein: a Genetic and biochemical Survey" Molecular and General Genetics vol. 244, pp. 530-538. 1994.

Sambrook, et al. (1989) Molecular Cloning: A Laboratory Manual. Cold Spring Harbor Laboratory Press, Cold Spring Harbor, NY, pp. xi-xxxviii.

Sambrook, et al. (1989) Molecular Cloning: A Laboratory Manual. Cold Spring Harbor Laboratory Press, Cold Spring Harbor, NY, pp. 4.12 A.9-A.13.

Sanchez, J. et al., Cloning and Heterologous Production of Hiracin JM79, a Sec-Dependent Bacteriocin Produced by Enterococcus

(56) References Cited

OTHER PUBLICATIONS

Hirae DCI-15, in Lactic Acid Bacteria and Pichia Pastoris, Applied And Environmental Microbiology, vol. 74, No. 8, pp. 2471-2479, 2008.
Saul, et al., "Nucleotide Sequence and Replication Characteristics of RepFIB, a Basic Replicon of IncF Plasmids," Journal of Bacteriology. vol. 171 No.5 00.2697-2707, May 1989.
Schlieper et al. 1998 "A positive selection vector for cloning of long polymerase chain reaction fragments based on a lethal mutant of the crp gene of *Escherichia coli,*" Anal. Biochem. 257:203-209.
Schoeman et al., "The Development of Bactericidal Yeast Strains by Expressing the Pediococcus acidilactici Pediocin Gene (ped A) in *Saccharomyces cerevisiae*", Yeast, vol. 15, pp. 647-656, 1999.
Seamark R.F. "Progress and Emerging Problems in Livestock Transgenesis: a Summary perspective." Repod. Fert. Dev. 6:653-657, 1994.
Shalani and Srivastava (2008) The Internet Journal of Microbiology. vol. 5 No. 2. DOI: 10.5580127dd—accessible on the worldwide web at archive.ispub.comljournallthe-internet-journal-of-microbiology/volume-5-number-2/screening-for-antifungal-activity-of-pseudomonas-fluorescens-against-phytopathogenic-fungi.html#sthash.dOYs03UO.1DKuT1US.dpuf.
Shekh and ROY, BMC Microbiology 12: 132, 2012.
Shenin et al., "Characteristics of Alirin B1, the major component of a fungicidal substance produced by Bacillus subtilis 10-VIZR". Antibiot Khimioter 1995 Vol. 50: pp. 3-7.
Sierra et al. 1998 "Functional interactions between chpB and parD, two homologous conditional killer systems found in the *Escherichia coli* chromosome and in plasmid R1," Fems Microb. Letters 168:51-58.
Simons, R. W., et al. (1987) "Improved Single and Multicopy Lac-Based Cloning Vectors for Protein and Operon Fusions." Gene 53 Do.85-96.
Smith, et al. (1985) Modification and Selection of Human Interleukin 2 Produced in Insect Cells by Baculovirus Expression Vector. Nalt Acad. Sci. 82:8404-8408.
Smith, et al. (1997) The poison-antidote stability system of the broad-host-range Thiobacilus ferroxidans plasmid pTF-FC2. Molecular Microbioloav 26(5):961-970.
Thisted, et al., "Mechanism of Post-segregational Killing by the hok/sok System of Plasmid R1; Sok Antisense RNA Regulates hok Gene Expression Indirectly Through the Overlapping mok Gene." (1992) J. Mol. Biol., vol. 223, p. 41-54.
Tomb et al, "The Complete Genome Sequence of the Gastric Pathogen Helicobacter Pylori," Nature. vol. 388 Aug. 7, 1997 pp. 539-547.
Trudel et al., (1996), pGATA: a positive selection vector based on the toxicity of the transcription factor GATA-1 to bacteria: BioTechniques 20:684-693.
Tsuchimoto et al. (1988) Two Genes, pelK and peml, responsible for stable maintenance of resistance plasmid R100. J. of Bateriol., 170(4):1461-1466.
Tsuchimoto et al.,"The Stable Maintenance System pem of Plasmid R100: Degradation of PemI Protein May Allow PemK Protein To Inhibit Cell Growth." Journal of Bacteriology, vol. 174, No. 13, pp. 4205-4211 Jul. 1992.
Tsuchimoto, et al. (1993) Autoregulation by cooperative binding of the PemI and PemK proteins to the promoter region of the pem operon. 237:81-88.
Union Nationale des Groupements de Distillateurs D'Alcool, "Kamoran", 2005.
U.S. Appl. No. 09/634,039, filed Aug. 8, 2000 by Bernard, et al.
Van Melderen, et al., "Bacterial Toxin-Antitoxin Systems: More Than Selfish Entities?", PLoS Genetics, vol. 5, No. 3, Mar. 2009, pp. 1-6.
Van Reeth, T., et al. (1998) "Positive Selection Vectors to Generate Fused Genes for the Expression of His-Tagged Proteins." BioTechniques. 25(5):898-904.
Vernet, T., et al. (1985) "A Direct-Selection Vector Derived from pColE3-CA38 and adapted for Foreign Gene Expression." Gene 34:87-93.
Wang et al., Genome Mining Demonstrates the Widespread Occurrence of Gene Clusters Encoding Bacteriocins in Cyanobacteria. PLoS ONE 6(7): e22384, 2011.
Wang, (1985), DNA Topoisomerases. Ann. Rev. Biochem. 54:665-697.
Wright et al., "Building-in biosafety for synthetic biology", Microbiology, vol. 159, pp. 1221-1235, 2013.
Yanisch-Perron, et al. (1985) Improved M13 phage closing vectors and host strains: Nucleotide sequence of the M13mp18 and DUC19 vectors. Gen, 33:103-119.
Yarmolinsky (1995) Programmed cell death in bacterial populations. Science, 267:836-837.
Yu et al. 2000 "An efficient recombination system for chromosome engineering in *Escherichia coli,*" PNAS USA 97:5978-5983.
Zuber, P et al., "Peptide Antibiotics", in Sonenshein ed, "Bacillus subtilis and Other Gram-Positive Bacteria", 1993 American Society for Microbiology, Washington D.C. pp. 897-916.
Kobayashi, M., et al., Promoter selectivity of *Escherichia coli* RNA polymerase: effect of base substitutions in the promoter—35 region on promoter strength. Nucleic Acids Res. 18:7367-7372, 1990.
Office Action with English Translation in Japanese Patent Application No. 2020-535048, dated May 17, 2023 in 19 pages.
International Search Report and Written Opinion Dated Mar. 11, 2019 in International Application No. PCT/EP2018/085941.
Duquesne et al., Microcins, Gene-Encoded Antibacterial Peptides From Enterobacteria, The Journal Of The Royal Society Of Chemistry, vol. 24, pp. 708-734, 2007.
Takala et al., A Food-Grade Cloning Vector For Lactic Acid Bacteria Based On The Nisin Immunity Gene nisl, Appl Microbiology Biotechnology, vol. 59, pp. 467-471, 2002.
Fang et al., Use of mchI Encoding Immunity to the antimicrobial peptide microcin H47 as a Plasmid Selection Marker in Attenuated Bacterial Live Vectors, Infection and Immunity, vol. 76, No. 10, pp. 4422-4430, 2008.
Brede et al., Identification Of The Propionicin F Bacteriocin Immunity Gene (Pcfi) And Development Of A Food0Grade Cloning System For Propionibacterium Freudenreichii, Applied And Enviromental Microbiology, vol. 73, No. 23, pp. 7542-7547, 2007.
Du, J. et al. Enhancing Bacteriophage Therapeutics Through In Situ Production And Release Of Heterologous Antimicrobial Effectors, Nature Communications, (2023) vol. 14, 4337, in 10 pages.

\* cited by examiner

SEQUENCE LISTING

```
Sequence total quantity: 698
SEQ ID NO: 1                moltype = AA   length = 40
FEATURE                     Location/Qualifiers
source                      1..40
                            mol_type = protein
                            organism = Enterococcus faecalis
SEQUENCE: 1
WLPPAGLLGR CGRWFRPWLL WLQSGAQYKW LGNLFGLGPK                            40

SEQ ID NO: 2                moltype = AA   length = 5
FEATURE                     Location/Qualifiers
REGION                      1..5
                            note = N-terminal motif of class terminal IIa
VARIANT                     3
                            note = Xaa = any amino acid
source                      1..5
                            mol_type = protein
                            organism = synthetic construct
SEQUENCE: 2
YGXGV                                                                  5

SEQ ID NO: 3                moltype = AA   length = 135
FEATURE                     Location/Qualifiers
REGION                      1..135
                            note = Hybrid bacteriocin Ent35-MccV
source                      1..135
                            mol_type = protein
                            organism = synthetic construct
SEQUENCE: 3
GKYYGNGVSC NKKGCSVDWG RAIGIIGNNS AANLATGGAA GWKSGGGASG RDIAMAIGTL      60
SGQFVAGGIG AAAGGVAGGA IYDYASTHKP NPAMSPSGLG GTIKQKPEGI PSEAWNYAAG     120
RLCNWSPNNL SDVCL                                                     135

SEQ ID NO: 4                moltype = AA   length = 46
FEATURE                     Location/Qualifiers
source                      1..46
                            mol_type = protein
                            organism = Lactobacillus acidophilus
SEQUENCE: 4
MISSHQKTLT DKELALISGG KTHYPTNAWK SLWKGFWESL RYTDGF                     46

SEQ ID NO: 5                moltype = DNA   length = 141
FEATURE                     Location/Qualifiers
source                      1..141
                            mol_type = genomic DNA
                            organism = Lactobacillus acidophilus
SEQUENCE: 5
atgatttcat ctcatcaaaa aacgttaact gataaagaat tagcattaat ttctgggggg      60
aaaacgcact acccgactaa tgcatggaaa agtctttgga aaggtttctg ggaaagcctt     120
cgttatactg acggttttta g                                              141

SEQ ID NO: 6                moltype = AA   length = 81
FEATURE                     Location/Qualifiers
source                      1..81
                            mol_type = protein
                            organism = Lactobacillus acidophilus
SEQUENCE: 6
MISMISSHQK TLTDKELALI SGGKTYYGTN GVHCTKKSLW GKVRLKNVIP GTLCRKQSLP      60
IKQDLKILLG WATGAFGKTF H                                               81

SEQ ID NO: 7                moltype = DNA   length = 246
FEATURE                     Location/Qualifiers
source                      1..246
                            mol_type = genomic DNA
                            organism = Lactobacillus acidophilus
SEQUENCE: 7
atgatttcaa tgatttcatc tcatcaaaaa acgttaactg ataaagaatt agcattaatt      60
tctgggggga aaacgtacta tggtactaat ggtgtgcatt gtactaaaaa gagtctttgg     120
ggtaaagtac gctaaaaaaa cgtgattcct ggaactcttt gtcgtaagca atcgttgccg     180
atcaaacagg atttaaaaat tttactgggc tgggctacag gtgcttttgg caagacattt     240
cattaa                                                               246

SEQ ID NO: 8                moltype = AA   length = 60
FEATURE                     Location/Qualifiers
source                      1..60
                            mol_type = protein
                            organism = Lactobacillus acidophilus
SEQUENCE: 8
```

```
MDKKTKILFE VLYIICIIGP QFILFVTAKN NMYQLVGSFV GIVWFSYIFW YIFFKQHKKM    60

SEQ ID NO: 9              moltype = DNA   length = 183
FEATURE                   Location/Qualifiers
source                    1..183
                          mol_type = genomic DNA
                          organism = Lactobacillus acidophilus
SEQUENCE: 9
atggataaga aaacaaaaat attatttgaa gtattataca tcatctgtat aataggccct    60
caatttatat tatttgtgac tgcaaaaaac aatatgtatc agttggtggg ttcgtttgtt   120
ggaatagtat ggttttcgta tattttttgg tatattttt tcaaacaaca taaaaaaatg   180
tag                                                                 183

SEQ ID NO: 10             moltype = AA    length = 65
FEATURE                   Location/Qualifiers
source                    1..65
                          mol_type = protein
                          organism = Lactobacillus gasseri
SEQUENCE: 10
MALKTLEKHE LRNVMGGNKW GNAVIGAATG ATRGVSWCRG FGPWGMTACA LGGAAIGGYL    60
GYKSN                                                               65

SEQ ID NO: 11             moltype = DNA   length = 198
FEATURE                   Location/Qualifiers
source                    1..198
                          mol_type = genomic DNA
                          organism = Lactobacillus gasseri
SEQUENCE: 11
atggctttaa aaacattaga aaacatgaa ttaagaaatg taatgggtgg aaacaagtgg    60
gggaatgctg taataggagc tgctacggga gctactcgcg gagtaagttg gtgcagagga   120
ttcggaccat ggggaatgac tgcctgtgcg ttaggaggtg ctgcaattgg aggatatctg   180
ggatataaga gtaattaa                                                 198

SEQ ID NO: 12             moltype = AA    length = 51
FEATURE                   Location/Qualifiers
source                    1..51
                          mol_type = protein
                          organism = Staphylococcus aureus
SEQUENCE: 12
MSWLNFLKYI AKYGKKAVSA AWKYKGKVLE WLNVGPTLEW VWQKLKKIAG L             51

SEQ ID NO: 13             moltype = DNA   length = 156
FEATURE                   Location/Qualifiers
source                    1..156
                          mol_type = genomic DNA
                          organism = Staphylococcus aureus
SEQUENCE: 13
atgagttggt taaattttt aaaatacatc gctaaatatg gcaaaaaagc ggtatctgct    60
gcttggaagt acaaaggtaa agtattagaa tggcttaatg ttggtcctac tcttgaatgg   120
gtatggcaaa aattaaagaa aattgctgga ttataa                             156

SEQ ID NO: 14             moltype = AA    length = 61
FEATURE                   Location/Qualifiers
source                    1..61
                          mol_type = protein
                          organism = Enterococcus avium
SEQUENCE: 14
MTRSKKLNLR EMKNVVGGTY YGNGVSCNKK GCSVDWGKAI SIIGNNSAAN LATGGAAGWK    60
S                                                                   61

SEQ ID NO: 15             moltype = DNA   length = 186
FEATURE                   Location/Qualifiers
source                    1..186
                          mol_type = genomic DNA
                          organism = Enterococcus avium
SEQUENCE: 15
atgacaagat caaaaaaatt aaatttacgc gaaatgaaga atgttgttgg tggtacctac    60
tatggaaatg gtgtatcttg taacaagaaa ggctgttcag ttgactgggg caaagccatc   120
agtattatag gaaataattc cgcagcaaac ttagcaactg tggtgctgc tggttggaag   180
tcataa                                                              186

SEQ ID NO: 16             moltype = AA    length = 67
FEATURE                   Location/Qualifiers
source                    1..67
                          mol_type = protein
                          organism = Enterococcus faecalis
SEQUENCE: 16
MKKKLVICGI IGIGFTALGT NVEAATYYGN GLYCNKQKCW VDWNKASREI GKIIVNGWVQ    60
HGPWAPR                                                             67
```

```
SEQ ID NO: 17              moltype = DNA  length = 204
FEATURE                    Location/Qualifiers
source                     1..204
                           mol_type = genomic DNA
                           organism = Enterococcus faecalis
SEQUENCE: 17
atgaaaaaga aattagttat ttgtggcatt attgggattg gttttacagc attaggaaca    60
aatgtagaag ctgctacgta ttacggaaat ggtttatatt gtaataagca aaaatgttgg   120
gtagactgga ataaagcttc aagggaaatt ggaaaaatta ttgttaatgg ttgggtacaa   180
catggccctt gggctcctag atag                                          204

SEQ ID NO: 18              moltype = AA  length = 51
FEATURE                    Location/Qualifiers
source                     1..51
                           mol_type = protein
                           organism = Lactococcus lactis
SEQUENCE: 18
MKEQNSFNLL QEVTESELDL ILGAKGGSGV IHTISHEVIY NSWNFVFTCC S              51

SEQ ID NO: 19              moltype = DNA  length = 156
FEATURE                    Location/Qualifiers
source                     1..156
                           mol_type = genomic DNA
                           organism = Lactococcus lactis
SEQUENCE: 19
atgaaagaac aaaactcttt taatcttctt caagaagtga cagaaagtga attggacctt    60
attttaggtg caaaaggcgg cagtggagtt attcatacaa tttctcatga agtaatatat   120
aatagctgga actttgtatt tacttgctgc tcttaa                             156

SEQ ID NO: 20              moltype = AA  length = 74
FEATURE                    Location/Qualifiers
source                     1..74
                           mol_type = protein
                           organism = Enterococcus faecium
SEQUENCE: 20
MKKKVLKHCV ILGILGTCLA GIGTGIKVDA ATYYGNGLYC NKEKCWVDWN QAKGEIGKII    60
VNGWVNHGPW APRR                                                      74

SEQ ID NO: 21              moltype = DNA  length = 225
FEATURE                    Location/Qualifiers
source                     1..225
                           mol_type = genomic DNA
                           organism = Enterococcus faecium
SEQUENCE: 21
atgaaaaaga aagtattaaa acattgtgtt attctaggaa tattaggaac ttgtctagct    60
ggcatcggta caggaataaa agttgatgca gctacttact atggaaattg tctttattgt   120
aacaaagaaa aatgttgggt agattggaat caagctaaag gagaaattgg aaaaattatt   180
gttaatggtt gggttaatca tggtccatgg gcacctagaa ggtag                   225

SEQ ID NO: 22              moltype = AA  length = 50
FEATURE                    Location/Qualifiers
source                     1..50
                           mol_type = protein
                           organism = Clostridium botulinum
SEQUENCE: 22
MQKPEIISAD LGLCAVNEFV ALAAIPGGAA TFAVCQMPNL DEIVSNAAYV                50

SEQ ID NO: 23              moltype = DNA  length = 153
FEATURE                    Location/Qualifiers
source                     1..153
                           mol_type = genomic DNA
                           organism = Clostridium botulinum
SEQUENCE: 23
atgcaaaaac cagaaattat tagtgctgat ttagggcttt gtgcagttaa tgaatttgta    60
gctcttgctg ccattcctgg tggtgctgct acatttgcag tatgccaaat gccaaacttg   120
gatgagattg ttagtaatgc agcatatgtt taa                                153

SEQ ID NO: 24              moltype = AA  length = 58
FEATURE                    Location/Qualifiers
source                     1..58
                           mol_type = protein
                           organism = Streptococcus equinus
SEQUENCE: 24
MMNATENQIF VETVSDQELE MLIGGADRGW IKTLTKDCPN VISSICAGTI ITACKNCA      58

SEQ ID NO: 25              moltype = DNA  length = 177
FEATURE                    Location/Qualifiers
source                     1..177
```

```
                            mol_type = genomic DNA
                            organism = Streptococcus equinus
SEQUENCE: 25
atgatgaatg ctactgaaaa ccaaattttt gttgagactg tgagtgacca agaattagaa    60
atgttaattg gtggtgcaga tcgtggatgg attaagactt taacaaaaga ttgtccaaat   120
gtaatttctt caatttgtgc aggtacaatt attacagctt gtaaaaattg tgcttaa      177

SEQ ID NO: 26               moltype = AA  length = 77
FEATURE                     Location/Qualifiers
source                      1..77
                            mol_type = protein
                            organism = Brochothrix campestris
SEQUENCE: 26
MHKVKKLNNQ ELQQIVGGYS SKDCLKDIGK GIGAGTVAGA AGGGLAAGLG AIPGAFVGAH    60
FGVIGGSAAC IGGLLGN                                                   77

SEQ ID NO: 27               moltype = DNA  length = 234
FEATURE                     Location/Qualifiers
source                      1..234
                            mol_type = genomic DNA
                            organism = Brochothrix campestris
SEQUENCE: 27
atgcacaagg taaaaaaatt aaacaatcaa gagttacaac agatcgtggg aggttacagt    60
tcaaaagatt gtctaaaaga tattggtaaa ggaattggtg ctggtacagt agctgggca    120
gccggcggtg gcctagctgc aggattaggt gctatcccag gagcattcgt tggagcacat   180
tttggagtaa tcggcggatc tgccgcatgc attggtggat tattaggtaa ctag         234

SEQ ID NO: 28               moltype = AA  length = 80
FEATURE                     Location/Qualifiers
source                      1..80
                            mol_type = protein
                            organism = Butyrivibrio fibrisolvens
SEQUENCE: 28
MSKKQIMSNC ISIALLIALI PNIYFIADKM GIQLAPAWYQ DIVNWVSAGG TLTTGFAIIV    60
GVTVPAWIAE AAAAFGIASA                                                80

SEQ ID NO: 29               moltype = DNA  length = 243
FEATURE                     Location/Qualifiers
source                      1..243
                            mol_type = genomic DNA
                            organism = Butyrivibrio fibrisolvens
SEQUENCE: 29
atgagtaaaa aacaaattat gagtaactgt atatcaattg cattattaat agcactaatt    60
cctaatatct atttattgc agataaaatg gaattcagt tagcacctgc ttggtatcaa    120
gatattgtga attgggtatc tgctggtgga cacttacta ctggttttgc gattattgta   180
ggagttacag taccggcatg gatagcagaa gcagctgcag cttttggtat agcttcagca   240
tga                                                                 243

SEQ ID NO: 30               moltype = AA  length = 48
FEATURE                     Location/Qualifiers
source                      1..48
                            mol_type = protein
                            organism = Butyrivibrio fibrisolvens
SEQUENCE: 30
MNKELNALTN PIDEKELEQI LGGGNGVIKT ISHECHMNTW QFIFTCCS                  48

SEQ ID NO: 31               moltype = DNA  length = 147
FEATURE                     Location/Qualifiers
source                      1..147
                            mol_type = genomic DNA
                            organism = Butyrivibrio fibrisolvens
SEQUENCE: 31
atgaacaaag aacttaatgc acttacaaat cctattgacg agaaggagct tgagcagatc    60
ctcggtggtg gcaatggtgt catcaagaca atcagccacg agtgccacat gaacacatgg   120
cagttcattt tcacatgttg ctcttaa                                       147

SEQ ID NO: 32               moltype = AA  length = 66
FEATURE                     Location/Qualifiers
source                      1..66
                            mol_type = protein
                            organism = Carnobacterium maltaromaticum
SEQUENCE: 32
MNSVKELNVK EMKQLHGGVN YGNGVSCSKT KCSVNWGQAF QERYTAGINS FVSGVASGAG    60
SIGRRP                                                               66

SEQ ID NO: 33               moltype = DNA  length = 201
FEATURE                     Location/Qualifiers
source                      1..201
                            mol_type = genomic DNA
```

```
                          organism = Carnobacterium maltaromaticum
SEQUENCE: 33
atgaatagcg taaaagaatt aaacgtgaaa gaaatgaaac aattcacgg tggagtaaat     60
tatggtaatg gtgtttcttg cagtaaaaca aaatgttcag ttaactgggg acaagccttt   120
caagaaagat acacagctgg aattaactca tttgtaagtg gagtcgcttc tggggcagga   180
tccattggta ggagaccgta a                                              201

SEQ ID NO: 34           moltype = AA  length = 61
FEATURE                 Location/Qualifiers
source                  1..61
                        mol_type = protein
                        organism = Carnobacterium maltaromaticum
SEQUENCE: 34
MKSVKELNKK EMQQINGGAI SYGNGVYCNK EKCWVNKAEN KQAITGIVIG GWASSLAGMG     60
H                                                                    61

SEQ ID NO: 35           moltype = DNA  length = 186
FEATURE                 Location/Qualifiers
source                  1..186
                        mol_type = genomic DNA
                        organism = Carnobacterium maltaromaticum
SEQUENCE: 35
atgaaaagcg ttaaagaact aaataaaaaa gaaatgcaac aaattaatgg tggagctatc     60
tcttatggca atggtgttta ttgtaacaaa gagaaatgtt gggtaaacaa ggcagaaaac   120
aaacaagcta ttactggaat agttatcggt ggatgggctt ctagtttagc aggaatggga   180
cattaa                                                               186

SEQ ID NO: 36           moltype = AA  length = 71
FEATURE                 Location/Qualifiers
source                  1..71
                        mol_type = protein
                        organism = Carnobacterium maltaromaticum
SEQUENCE: 36
MNNVKELSIK EMQQVTGGDQ MSDGVNYGKG SSLSKGGAKC GLGIVGGLAT IPSGPLGWLA     60
GAAGVINSCM K                                                         71

SEQ ID NO: 37           moltype = DNA  length = 216
FEATURE                 Location/Qualifiers
source                  1..216
                        mol_type = genomic DNA
                        organism = Carnobacterium maltaromaticum
SEQUENCE: 37
atgaataatg taaaagagtt aagtattaaa gaaatgcaac aagttactgg tggagaccaa     60
atgtcagatg gtgtaaatta tggaaaaggc tctagcttat caaaaggtgg tgccaaatgt   120
ggtttaggga tcgtcggcgg attagctact atcccttcag gtcctttagg ctggttagcc   180
ggagcagcag gtgtaattaa tagctgtatg aaataa                              216

SEQ ID NO: 38           moltype = AA  length = 64
FEATURE                 Location/Qualifiers
source                  1..64
                        mol_type = protein
                        organism = Carnobacterium maltaromaticum
SEQUENCE: 38
MLYELVAYGI AQGTAEKVVS LINAGLTVGS IISILGGVTV GLSGVFTAVK AAIAKQGIKK     60
AIQL                                                                 64

SEQ ID NO: 39           moltype = DNA  length = 195
FEATURE                 Location/Qualifiers
source                  1..195
                        mol_type = genomic DNA
                        organism = Carnobacterium maltaromaticum
SEQUENCE: 39
atgttatatg aattagttgc atatggtatc gcacaaggta cagctgaaaa ggttgtaagt     60
ctaattaacg caggtttaac agtagggtct attatttcaa ttttgggtgg ggtcacagtc   120
ggtttatcag gtgtcttcac agcagttaaa gcagcaattg ctaaacaagg aataaaaaaa   180
gcaattcaat tataa                                                     195

SEQ ID NO: 40           moltype = AA  length = 836
FEATURE                 Location/Qualifiers
source                  1..836
                        mol_type = protein
                        note = subsp. carotovorum
                        organism = Pectobacterium carotovorum
SEQUENCE: 40
MIKYRLYAPN DGDTMTVSGG GGWVSNDDRK GGNDRDNGKG GSAVDFSKNP EKQAIVNPYL     60
AIAIPMPVYP LYGKLGFTIN TTAIETELAN VRAAINTKLA TLSAVIGRSL PVVGRVFGVT   120
AAGMWPSSTA PSSLDSIYNQ AHQQALAQLA AQQGVLNKGY NVTAMPAGFV SSLPVSEIKS   180
LPTAPASLLA QSVINTELSQ RQLALTQPTT NAPVANIPVV KAEKTAMPGV YSAKIIAGEP   240
AFQIKVDNTK PALAQNPPKV KDDIQVSSFL SSPVADTHHA FIDFGSDHEP VYVSLSKIVT   300
```

```
AEEEKKQVEE AKRREQEWLL RHPITAAERK LTEIRQVISF AQQLKESSVA TISEKTKTVA    360
VYQEQVNTAA KNRDNFYNQN RGLLSAGITG GPGYPIYLAL WQTMNNFHQA YFRANNALEQ    420
ESHVLNLARS DLAKAEQLLA ENNRLQVETE RTLAEEKEIK RNRVNVSTFG TVQTQLSKLL    480
SDFYAVTSLS QSVPSGALAS FSYNPQGMIG SGKIVGKDVD VLFSIPVKDI PGYKSPINLD    540
DLAKKNGSLD LPIRLAFSDE NGERVLRAFK ADSLRIPSSV RGVAGSYDKN TGIFSAEIDG    600
VSSRLVLENP AFPPTGNVGN TGNTAPDYKA LLNTGVDVKP VDKITVTVTP VADPVDIDDY    660
IIWLPTASGS GVEPIYVVFN SNPYGGTEKG KYSKRYYNPD KAGGPILELD WKNVKIDHAG    720
VDNVKLHTGR FKASVENKVM IERLENILNG QITATDTDKR FYTHELRELN RYRNLGIKDG    780
EVPSSIQEES AVWNDTHTAT LEDYKINEKE QPLYTDAALQ AAYEQELKDA LGGKHG        836

SEQ ID NO: 41           moltype = DNA   length = 2511
FEATURE                 Location/Qualifiers
source                  1..2511
                        mol_type = genomic DNA
                        note = subsp. carotovorum
                        organism = Pectobacterium carotovorum
SEQUENCE: 41
atgattaaat accgtttata tgctccaaat gatggagaca ccatgacagt gagtggtggt     60
ggtggttggg tttcaaacga tgatcgcaaa ggtggtaatg acaggacaa tggcaaaggt    120
ggttctgccg ttgattttag taaaaatcca gaaaagcagg ctatcgttaa tccctatttg    180
gcaatcgcga taccgatgcc ggtctaccct ctttatggaa agctagggtt cacaataaat    240
acgacggcaa ttgagactga actcgcaaat gtcagagcag caattaacac taaacttgca    300
acactcagtg cagtgattgg cagatcactt ccggtcgttg ggcgggtatt tggtgttact    360
gccgccggaa tgtggccttc tagtaccgct cccagtagtc tcgattctat atacaatcaa    420
gcacatcagc aggctttagc ccagttagct gctcaacagg gagtattaaa taaagggtat    480
aacgttacag caatgcctgc aggtttcgtc agcagtttgc ctgttagtga aatcaaatca    540
ttgccaacag ctcccgccag tttactggca caaagtgtga ttaataccga actttcccag    600
cgtcaactgg ctcttactca gcccacgacg aatgcaccag tcgcgaatat tcccgtagtt    660
aaagcagaga aaacagcaat gccaggtgtg tattcagcga aaattattgc tggtgagcct    720
gcattccaaa tcaaggtcga taataccaaa cctgctttga cacagaatcc gccgaaagta    780
aaagatgata ttcaggtatc ttctttcctt tcctcgccag tagctgatac gcaccatgca    840
tttattgatt ttggcagcga tcatgaaccg gtatacgtgt ctctttcaaa gatcgtgaca    900
gccgaggagg agaaaaaaca ggttgaagag gccaagcgcc gtgagcagga gtggttgttg    960
cgtcatcgaa ttacagctgc ggagcagaaa ttaactgaaa tccgccaagt gatctctttt   1020
gctcaacagc taaagaaag ctctgtcgca accatttcag aaaaaactaa aactgttgcg   1080
gtttaccaag aacaggtgaa taccgctgca aaaaatcgcg acaattttta taatcaaaat   1140
agaggtctgt taagtgcggg tataactggg ggaccgggat atcctattta tcttgcttta   1200
tggcaaacga tgaataactt tcatcaggct tatttcagag caaataatgc attggaacaa   1260
gagagtcatg ttctgaacct ggctcgttct gatctggcta aggctgagca attgcttgct   1320
gagaataatc gacttcaggt tgaaacgag cgaacgcttg ccgaagaaaa agagataaaa   1380
cgcaacaggg ttaatgtatc aacatttggc acagtgcaaa ctcaacttag taaattgctg   1440
tcagattttt atgctgttac atcactttcc caaagtgttc cttcggggc attagcctct   1500
ttttcatata atccacaagg gatgattggc agcggtaaga ttgttgggaa ggatgtcgat   1560
gttttatttt ccatcccagt aaaagatatt ccgggatata atctcctat taacttggac   1620
gatttagcca agaaaatgg aagtctggat cttcccattc gtctggcatt ttctgatgag   1680
aatgagaaa gggttcttcg ggcattcaaa gcggatagtc tgcgaatccc ttcgagtgtc   1740
agaggtgtag cgggcagtta tgacaaaaat acgggtattt ttagtgcgaa aattgatggt   1800
gtttcatctc gccttgtact ggaaaaccca gcgtttcctc cgaccggaaa tgtcggtaat   1860
acgggtaata ctgcacctga ctataaagca ttactgaata ctggtgttga tgttaaacct   1920
gttgataaaa tcacagttac ggtaacacca gttgctgatc cagtggatat tgatgactat   1980
ataatctggt tgcaactgc gtctggttct ggcgtgaac tccatttatgt cgtgtttaac   2040
agtaatccgt atggtgggac ggaaaaagga aaatatagca aacgttatta taatccagat   2100
aaggcaggcg gtccgatctt ggagctggat tggaaaaacg ttaagattga ccatgcaggt   2160
gtggacaatg ttaaattaca cacagggcgt ttcaaagcgt cggttgaaaa caaagtgatg   2220
attgaacgtt tggaaaacat actgaatggt caaatcaccg ccacggatac tgacaagcga   2280
ttctatacgc atgaattaag agagttaaac cgctacagaa atttaggcat caaagacgtt   2340
gaagtgccta gtagcattca gaagaaagc gctgtttgga acgacacaca cacagcgacg   2400
cttgaagact caaaaattaa tgagaaagag caaccgttgt acactgatgc tgctttgcag   2460
gcagcctacg aacaggaact caaagacgca ttaggaggga acatggcta a             2511

SEQ ID NO: 42           moltype = AA   length = 74
FEATURE                 Location/Qualifiers
source                  1..74
                        mol_type = protein
                        organism = Bacillus cereus
SEQUENCE: 42
MENLQMLTEE ELMEIEGGGW WNSWGKCVAG TIGGAGTGGL GGAAAGSAVP VIGTGIGGAI     60
GGVSGGLTGA ATFC                                                       74

SEQ ID NO: 43           moltype = DNA   length = 225
FEATURE                 Location/Qualifiers
source                  1..225
                        mol_type = genomic DNA
                        organism = Bacillus cereus
SEQUENCE: 43
atggaaaact tacaaatgtt aactgaagaa gaattaatgg aaattgaagg tggaggctgg     60
tggaatagct ggggtaaatg tgttgctgga actatcggtg gagctggaac tggtggttta    120
ggtggagctg ctgcaggttc agctgttccg gttattggta ctggtattgg tggcgctatt    180
ggtggagtta gcggtggcct tacaggtgca gctacttttt gctaa                    225
```

```
SEQ ID NO: 44          moltype = AA   length = 78
FEATURE                Location/Qualifiers
source                 1..78
                       mol_type = protein
                       note = Streptoverticillium griseoverticillatum
                       organism = unidentified
SEQUENCE: 44
MTASILQQSV VDADFRAALL ENPAAFGASA AALPTPVEAQ DQASLDFWTK DIAATEAFAC    60
RQSCSFGPFT FVCDGNTK                                                 78

SEQ ID NO: 45          moltype = DNA   length = 237
FEATURE                Location/Qualifiers
source                 1..237
                       mol_type = genomic DNA
                       note = Streptoverticillium griseoverticillatum
                       organism = unidentified
SEQUENCE: 45
atgaccgctt ccattcttca gcagtccgtc gtggacgccg acttccgcgc ggcgctgctt    60
gagaaccccg ccgccttcgg cgcttccgcc gcggccctgc ccacgcccgt cgaggcccag   120
gaccaggcgt cccttgactt ctggaccaag gacatcgccg ccacggaagc cttcgcctgc   180
cgccagagct gcagcttcgg cccgttcacc ttcgtgtgca cggcaacac caagtaa       237

SEQ ID NO: 46          moltype = AA   length = 76
FEATURE                Location/Qualifiers
source                 1..76
                       mol_type = protein
                       organism = Geobacillus kaustophilus
SEQUENCE: 46
MSLLALVAGT LGVSQSIATT VVSIVLTGST LISIILGITA ILSGGVDAIL EIGWSAFVAT    60
VKKIVAERGK AAAIAW                                                   76

SEQ ID NO: 47          moltype = DNA   length = 231
FEATURE                Location/Qualifiers
source                 1..231
                       mol_type = genomic DNA
                       organism = Geobacillus kaustophilus
SEQUENCE: 47
atgagtttgc tggcgcttgt tgccgggacg ctcggcgtgt cacagtcaat cgcgacgacg    60
gttgtttcga ttgtgttgac cggctccact ctcatttcta ttattcttgg gatcaccgct   120
attttgtcag gtggagtcga cgccattttg gaaattgggt ggtcagcttt tgtcgcgacg   180
gtgaaaaaaa tagtggcgga acgaggaaaa gcggcagcga ttgcatggta a            231

SEQ ID NO: 48          moltype = AA   length = 309
FEATURE                Location/Qualifiers
source                 1..309
                       mol_type = protein
                       organism = Clostridium tyrobutyricum
SEQUENCE: 48
MRKVFLRSII STLVMCAFVS SSFSVNADES KPNDEKIINN IENVTTTKDI VKSNKNNIVY    60
LDEGVMSIPL SGRKPIAIKD DNNKEDLTVT LPIKNTGDIS KISSNGTILY KNNSSNSSNI   120
ALQPKNDGFK ALININDKLA NKEYEFTFNL PKNSKLISAA TYLGKEYDTK EVFVVDKNNI   180
ITSIISPAWA KDANGHNVST YYKIVSNNKL VQVVEFTENT AFPVVADPNW TKIGKCAGSI   240
AWAIGSGLFG GAKLIKIKKY IAELGGLQKA AKLLVGATTW EEKLHAGGYA LINLAAELTG   300
VAGIQANCF                                                          309

SEQ ID NO: 49          moltype = DNA   length = 930
FEATURE                Location/Qualifiers
source                 1..930
                       mol_type = genomic DNA
                       organism = Clostridium tyrobutyricum
SEQUENCE: 49
ttgagaaaag tattttttaag atcaataatt tcaacattag ttatgtgtgc atttgtttca    60
agcagctttt cagtaaatgc ggatgaaagc aaaccaaatg atgaaaaaat aattaataac   120
atagaaaacg ttactactac taaagatatt gtaaaaagta ataaaaataa tattgtatat   180
ttagatgaag gtgtaatgag tattccattg tctgggagaa aacccattgc tattaaagat   240
gataataata agaagatttt aactgttaca ttacctatta gaatactgga gatatatct   300
aaaattagta gtaatggtac tattctgtat aaaaataata gtagtaattc atctaatata   360
gctttacaac ctaaaaatga tgggtttaag gctttaataa atattaatga taagttagct   420
aataaagaat atgaatttac atttaattta cccaaaaaca gtaaattaat tagtgctgcc   480
acatatttgg gtaaagaata tgatacaaaa gaagtatttg tagtagacaa aaataatata   540
attacgagta ttattagtcc agcttgggct aaagatgcaa atggacataa tgtttctact   600
tattataaga gtatcgaa taataaatta gtacaagttg ttgaattcac agaaaatact   660
gcattccgtg tggctgtga tcctaattgg actaaaattg gtaaatgtgc tggtcaata   720
gcatgggcta taggttctgg cctttttggt ggagcaaagc taattaaaat aaaaaaatat   780
atagcagagc ttggaggact tcaaaaagca gctaaattat tagttggtgc aaccacttgg   840
gaagaaaaat tacacgcagg cggttatgca ttaattaact tagctgctga gctaacaggt   900
gtagcaggta tacaagcaaa ttgttttttaa                                   930
```

```
SEQ ID NO: 50              moltype = AA  length = 62
FEATURE                    Location/Qualifiers
source                     1..62
                           mol_type = protein
                           organism = Bacillus coagulans
SEQUENCE: 50
MKKIEKLTEK EMANIIGGKY YGNGVTCGKH SCSVDWGKAT TCIINNGAMA WATGGHQGTH    60
KC                                                                  62

SEQ ID NO: 51              moltype = DNA  length = 189
FEATURE                    Location/Qualifiers
source                     1..189
                           mol_type = genomic DNA
                           organism = Bacillus coagulans
SEQUENCE: 51
atgaaaaaaa ttgaaaaatt aactgaaaaa gaaatggcca atatcattgg tggtaaatac    60
tacggtaatg gggttacttg tggcaaacat tcctgctctg ttgactgggg taaggctacc   120
acctgcataa tcaataatgg agctatgcga tgggctactg gtggacatca aggtactcat   180
aaatgctag                                                           189

SEQ ID NO: 52              moltype = AA  length = 490
FEATURE                    Location/Qualifiers
source                     1..490
                           mol_type = protein
                           organism = Escherichia coli
SEQUENCE: 52
MDKVTDNSPD VESTESTEGS FPTVGVDTGD TITATLATGT ENVGGGGAF GGASESSAAI     60
HATAKWSTAQ LKKHQAEQAA RAAAAEAALA KAKSQRDALT QRLKDIVNDA LRANAARSPS   120
VTDLAHANNM AMQAEAERLR LAKAEQKARE EAEAAEKALR EAERQRDEIA RQQAETAHLL   180
AMAEAAEAEK NRQDSLDEEH RAVEVAEKKL AEAKAELAKA ESDVQSKQAI VSRVAGELEN   240
AQKSVDVKVT GFPGWRDVQK KLERQLQDKK NEYSSVTNAL NSAVSIRDAK KTEVQNAEIK   300
LKEAKDALEK SQVKDSVDTM VGFYQYITEQ YGEKYSRIAQ DLAEKAKGSK FNSVDEALAA   360
FEKYKNVLDK KFSKVDRDDI FNALESITYD EWAKHLEKIS RALKVTGYLS FGYDVWDGTL   420
KGLKTGDWKP LFVTLEKSAV DFGVAKIVAL MFSFIVGAPL GFWGIAIITG IVSSYIGDDE   480
LNKLNELLGI                                                          490

SEQ ID NO: 53              moltype = DNA  length = 1473
FEATURE                    Location/Qualifiers
source                     1..1473
                           mol_type = genomic DNA
                           organism = Escherichia coli
SEQUENCE: 53
atggataaag tcactgataa ttctccagat gtggagagca cagaatctac tgaggggtca    60
ttcccaactg ttggggttga tactggcgat acgattacag cgacgcttgc aactggaact   120
gaaaatgttg gtgaaggcgg tggagcattt ggtggggcca gtgaaagttc tgctgcgata   180
catgcaaccg ctaaatggtc taccgcgcag ttgaaaaaac atcaggctga acaggctgcc   240
cgtgctgctg cggctgaggc agcattggca aaagcgaaat ctcagcgtga tgccctgact   300
caacgtctca aggatattgt taatgacgct ttacgtgcta atgccgctcg tagtccatca   360
gtaactgacc ttgctcatgc caataatatg gcaatgcagg cagaggctga gcgtttcgc    420
cttgcgaagg cagagcaaaa agcccgtgaa gaagctgaag cagcagaaaa agcgctccgg   480
gaagcgaaac gccaacgtga tgagattgcc cgccaacagg ctgaaaccgc gcatttgtta   540
gcaatggcgg aggcagcaga ggctgagaaa aatcgacagg attctcttga tgaagagcat   600
cgggctgtgg aagtggcaga agaagctg gctgaggcta aagctgaact ggcgaaggcc     660
gaaagcgatg tacagagtaa gcaagcgatt gtttccagag ttgcagggga gcttgaaaac   720
gctcaaaaaa gtgttgatgt gaaggttacc ggatttcctg gatggcgtga tgttcagaaa   780
aaactggaga gacaattgca ggataagaag aatgaatatt cgtcagtgac gaatgctctt   840
aattctgctg ttagcattag agatgctaaa aaaacagaag ttcagaatgc tgagataaaa   900
ttaaaagaag ctaaggatgc tcttgagaag agtcaggtaa agactctgtt tgatactatg   960
gttggcttt atcaatatat aaccgaacaa tatgggaaa aatattccag aatagctcag   1020
gatttagctg aaaaggcgaa gggtagtaaa tttaatagtg ttgatgaagc acttgctgca  1080
tttgaaaagt ataaaaatgt actggataag aaattcagta aggttgatag ggatgatatt  1140
tttaatgctt tagagtctat tacttatgat gagtgggcca agcatctaga aaagatctct  1200
agggctctta aggttactgg atatttgtct ttcgggtatg atgtatggga tggtacccta  1260
aaggaattaa aaacaggaga ctggaagcct ttatttgtca ctctggagaa gagcgcggta  1320
gatttcggcg tggcaaaaat tgtggcatta atgtttagtt ttattgttgg tgcgcctctt  1380
ggcttctggg gaattgcaat tatcacaggt attgttcctt cttacatagg ggatgatgag  1440
ttgaacaagc ttaatgaatt actaggtatt taa                                1473

SEQ ID NO: 54              moltype = AA  length = 522
FEATURE                    Location/Qualifiers
source                     1..522
                           mol_type = protein
                           organism = Escherichia coli
SEQUENCE: 54
METAVAYYKD GVPYDDKGQV IITLLNGTPD GSGSGGGGGK GGSKSESSAA IHATAKWSTA    60
QLKKTQAEQA ARAKAAAEAQ AKAKANRDAL TQRLKDIVNE ALRHNASRTP SATELAHANN   120
AAMQAEDERL RLAKAEEKAR KEAEAAEKAF QEAEQRRKEI EREKAETERQ LKLAEAEEKR   180
LAALSEEAKA VEIAQKKLSA AQSEVVKMDG EIKTLNSRLS SSIHARDAEM KTLAGKRNEL   240
AQASAKYKEL DELVKKLSPR ANDPLQNRPF FEATRRRVGA GKIREEKQKQ VTASETRINR   300
```

```
INADITQIQK AISQVSNNRN AGIARVHEAE ENLKKAQNNL LNSQIKDAVD ATVSFYQTLT  360
EKYGEKYSKM AQELADKSKG KKIGNVNEAL AAFEKYKDVL NKKFSKADRD AIFNALASVK  420
YDDWAKHLDQ FAKYLKITGH VSFGYDVVSD ILKIKDTGDW KPLFLTLEKK AADAGVSYVV  480
ALLFSLLAGT TLGIWGIAIV TGILCSYIDK NKLNTINEVL GI                    522

SEQ ID NO: 55           moltype = DNA  length = 1569
FEATURE                 Location/Qualifiers
source                  1..1569
                        mol_type = genomic DNA
                        organism = Escherichia coli
SEQUENCE: 55
atggaaaccg cggtagcgta ctataaagat ggtgttcctt atgatgataa gggacaggta   60
attattactc ttttgaatgg tactcctgac gggagtggcc ctggcggcgg aggtggaaaa  120
ggaggcagta aaagtgaaag ttctgcagct attcatgcaa ctgctaaatg gtctactgct  180
caattaaaga aaacacaggc agagcaggct gcccgggcaa aagctgcagc ggaagcacag  240
gcgaaagcaa aggcaaacag ggatgcgctg actcagcgcc tgaaggatat cgtgaatgag  300
gctcttcgtc acaatgcctc acgtacgcct tcagcaacag agcttgctca tgctaataat  360
gcagctatgc aggcggaaga cgagcgtttg cgccttgcga aagcagaaga aaaagccgg   420
aaagaagcgg aagcagcaga aaaggctttt caggaagcag aacaacgacg taaagagatt  480
gaacgggaga aggctgaaac agaacgccag ttgaaactgg ctgaagctga gagaaacga   540
ctggctgcat tgagtgaaga agctaaagct gttgagatcg cccaaaaaaa actttctgct  600
gcacaatctg aagtggtgaa aatggatgga gagattaaca ctctcaattc tcgtttaagc  660
tccagtatcc atgccgtgaa tgcagaaatg aaaacgctcg tggaaaacg aaatgaactg  720
gctcaggcat ccgctaaata taagaactg gatgagctgg tcaaaaaact atcaccaaga  780
gccaatgatc cgcttcagaa ccgtcctttt tttgaagcaa ccagacgacg ggttggggcc  840
ggtaagatta gagaagaaaa acaaaaaacag gtaacagcat cagaaacgca tattaaccgg  900
ataaatgctg atataactca gatccagaag gctatttctc aggtcagtaa taatcgtaat  960
gccggtatcc ctcgtgttca tgaagctgaa gaaaaatttga aaaagcaca gaataatctc 1020
cttaattcac agattaagga tgctgttgat gcaacagtta gcttttatca aacgctgact 1080
gaaaaatatg gtgaaaaata ttcgaaaatg gcacaggaat ttgctgataa gtctaaaggt 1140
aagaaaatcg gcaatgtgaa tgaagctctc gctgcttttg aaaaatacaa ggatgttta  1200
aataagaaat tcagcaaagc cgatcgtgat gctatttta atgcgttggc atcggtgaag 1260
tatgatgact gggctaaaca tttagatcag tttgccaagt acttgaagat tacggggcat 1320
gtttcttttg gatatgatgt ggtatctgat atcctaaaaa ttaaggatac aggtgactgg 1380
aagccactat ttcttacatt agagaagaaa gctgcagatg caggggtgag ttatgttgtt 1440
gctttacttt ttagcttgct tgctggaact acattaggta tttgggtat tgctattgtt 1500
acaggaattc tatgctccta tattgataag aataaactta atactataaa tgaggtgtta 1560
gggatttaa                                                         1569

SEQ ID NO: 56           moltype = AA  length = 626
FEATURE                 Location/Qualifiers
source                  1..626
                        mol_type = protein
                        organism = Escherichia coli
SEQUENCE: 56
MSDPVRITNP GAESLGYDSD GHEIMAVDIY VNPPRVDVFH GTPPAWSSFG NKTIWGGNEW   60
VDDSPTRSDI EKRDKEITAY KNTLSAQQKE NENKRTEAGK RLSAAIAARE KDENTLKTLR  120
AGNADAADIT RQEFRLLQAE LREYGFRTEI AGYDALRLHT ESRMLFADAD SLRISPREAR  180
SLIEQAEKRQ KDAQNADKKA ADMLAEYERR KGILDTRLSE LEKNGGAALA VLDAQQARLL  240
GQQTRNDRAI SEARNKLSSV TESLNTARNA LTRAEQQLTQ QKNTPDGKTI VSPEKFPGRS  300
STNHSIVVSG DPRFAGTIKI TTSAVIDNRA NLNYLLSHSG LDYKRNILND RNPVVTEDVE  360
GDKKIYNAEV AEWDKLRQRL LDARNKITSA ESAVNSARNN LSARTNEQKH ANDALNALLK  420
EKENIRNQLS GINQKIAEEK RKQDELKATK DAINFTTEFL KSVSEKYGAK AEQLAREMAG  480
QAKGKKIRNV EEALKTYEKY RADINKKINA KDRAAIAAAL ESVKLSDISS NLNRFSRGLG  540
YAGKFTSLAD WITEFGKAVR TENWRPLFVK TETIIAGNAA TALVALVFSI LTGSALGIIG  600
YGLLMAVTGA LIDESLVEKA NKFWGI                                       626

SEQ ID NO: 57           moltype = DNA  length = 1881
FEATURE                 Location/Qualifiers
source                  1..1881
                        mol_type = genomic DNA
                        organism = Escherichia coli
SEQUENCE: 57
atgtctgacc ctgtacgtat tacaaatccc ggtgcagaat cgctgggggta tgattcagat   60
ggccatgaaa ttatgccgt tgatatttat gtaaaccctc cacgtgtcga tgtctttcat  120
ggtaccccgc ctgcatggag ttccttcggg aacaaaacca tctggggcgg aaacgagtgg  180
gttgatgatt ccccaacccg aagtgatatc gaaaaaggg acaaggaaat cacagcgtac  240
aaaaacacgc tcagcgcgca gcagaaagag aatgagaata gcgctactga agcggaaaa   300
cgcctctctg cggcgattgc tgcaagggaa aagatgaaa acacactgaa aacactccgc  360
gccggaaacg cagatgccgc tgatattaca cgacaggagt tcagactcct gcaggcagag  420
ctgagagaat acggattccg tactgaaatc gccggatatg acgccctccg gctgcataca  480
gagagccgga tgctgtttgc tgatgctgat tctcttcgta tatctccccg ggaggccagg  540
tcgttaatcg aacaggctga aaaacggcag aaggatgcgc agaacgcaga caagaaggcc  600
gctgatatga ttgctgaata cgagcgcaga aaggtattgg atacacgcg gttgtcagaa  660
ctgaaaaaa atggcggggc agcccttgcc gttcttgatg cacaacaggc ccgtctgctc  720
gggcagcaga cacggaatga cagggccatt tcagaggccc ggaataaact cagttcagtg  780
acggaatcgc ttaacacggc ccgtaatgca ttaaccagag ctgaacaaca gctgacgcaa  840
cagaaaaaca cgcctgacgg caaaacgata gtttccctg aaaaattccc ggggcgttca  900
tcaacaaatg attctattgt tgtgagcggt gatccgagat ttgccggtac gataaaaatc  960
```

```
acaaccagcg cagtcatcga taaccgtgca aacctgaatt atcttctgag ccattccggt   1020
ctggactata aacgcaatat tctgaatgac cggaatccgg tggtgacaga ggatgtggaa   1080
ggtgacaaga aaatttataa tgctgaagtt gctgaatggg ataagttacg gcaaagattg   1140
cttgatgcca gaaataaaat cacctctgct gaatctgcgg taaattcggc gagaaataac   1200
ctcagtgcca gaacaaatga gcaaaagcat gcaaatgacg ctcttaatgc cctgttgaag   1260
gaaaaagaga atatccgtaa ccagcttttcc ggcatcaatc agaagatagc ggaagagaaa   1320
agaaaacagg atgaactgaa ggcaacgaaa gacgcaatta atttcacaac agagttcctg   1380
aaatcagttt cagaaaaata tggtgcaaaa gctgagcagt tagccagaga gatggccggg   1440
caggctaaag ggaagaaaat acgtaatgtt gaagaggcat taaaaacgta tgaaaagtac   1500
cgggctgaca ttaacaaaaa aattaatgca aaagatcgtg cagcgattgc cgcagcccct   1560
gagtctgtga agctgtctga tatatcgtct aatctgaaca gattcagtcg gggactggga   1620
tatgcaggaa aatttacaag tcttgctgac tggatcactg agtttggtaa ggctgtccgg   1680
acagagaact ggcgtcctct ttttgttaaa acagaaacca tcatagcagg caatgccgca   1740
acggctcttg tggcactggt cttcagtatt cttaccggaa gcgctttagg cattatccgg   1800
tatggtttac tgatggctgt caccggtgcg ctgattgatg aatcgcttgt ggaaaaagcg   1860
aataagttct ggggtattta a                                             1881

SEQ ID NO: 58              moltype = AA  length = 626
FEATURE                    Location/Qualifiers
source                     1..626
                           mol_type = protein
                           organism = Escherichia coli
SEQUENCE: 58
MSDPVRITNP GAESLGYDSD GHEIMAVDIY VNPPRVDVFH GTPPAWSSFG NKTIWGGNEW    60
VDDSPTRSDI EKRDKEITAY KNTLSAQQKE NENKRTEAGK RLSAAIAARE KDENTLKTLR   120
AGNADAADIT RQEFRLLQAE LREYGFRTEI AGYDALRLHT ESRMLFADAD SLRISPREAR   180
SLIEQAEKRQ KDAQNADKKA ADMLAEYERR KGILDTRLSE LEKNGGAALA VLDAQQARLL   240
GQQTRNDRAI SEARNKLSSV TESLKTARNA LTRAEQQLTQ QKNTPDGKTI VSPEKFPGRS   300
STNHSIVVSG DPRFAGTIKI TTSAVIDNRA NLNYLLTHSG LDYKRNILND RNPVVTEDVE   360
GDKKIYNAEV AEWDKLRQRL LDARNKITSA ESAINSARNN VSARTNEQKH ANDALNALLK   420
EKENIRSQLA DINQKIAEEK RKRDEINMVK DAIKLTSDFY RTIYDEFGKQ ASELAKELAS   480
VSQGKQIKSV DDALNAFDKF RNNLNKKYNI QDRMAISKAL EAINQVHMAE NFKLFSKAFG   540
FTGKVIERYD VAVELQKAVK TDNWRPFFVK LESLAAGRAA SAVTAWAFSV MLGTPVGILG   600
FAIIMAAVSA LVNDKFIEQV NKLIGI                                        626

SEQ ID NO: 59              moltype = DNA  length = 1881
FEATURE                    Location/Qualifiers
source                     1..1881
                           mol_type = genomic DNA
                           organism = Escherichia coli
SEQUENCE: 59
atgtctgacc ctgtacgtat tacaaatccc ggtgcagaat cgctgggata tgattcagat    60
ggccatgaaa ttatggccgt tgatatttat gtaaaccctc cacgtgtcga tgtctttcat   120
ggtaccccgc ctgcatggag ttccttcggg aacaaaacca tctggggtgg aaacgagtgg   180
gtcgatgatt ccccaacccg aagtgatatc gaaaaaaggg acaaggaaat cacagcgtac   240
aaaaacacgc tcagcgcgca gcagaaagag aatgagaata gcgtactga agctggaaaa   300
cgcctttctg cggcaattgc tgcaaggaga aaagatgaaa acactgaa aacactccgt   360
gccggaaacg cagatgccgc tgatattaca cgacaggagt tcagactcct gcaggcagag   420
ctgagagaat acggattccg tactgaaatc gccggatatg atgccctccg gctgcataca   480
gagagccgga tgctgtttgc tgatgctgat tctcttcgta tatctccccg cgaggccagg   540
tcgttaatcg aacaggctga aaaacgcag aaggatgcgc agaacgcaga caagaaggcc   600
gctgatatgc ttgctgaata cgagcgcaga aaaggtattc tggacacgcg gttgtcagag   660
ctggaaaaaa atggcgggc agcccttgcc gttcttgatg cacaacaggc ccgtctgctc   720
gggcagcaga cacggaatga cagggccatt tcagaggccc ggaataaact cagttcggtg   780
acggaatcgc ttaagacggc ccgtaatgca ttaaccagag ctgaacaaca gctgacgcaa   840
cagaaaaaca cgcctgacgg caaaacgata gtttccctg aaaaattccc gggcgttca   900
tcaacaaatc atttctattgt tgtgagtggt gatccgaggt ttgccggtac gataaaaatc   960
acaaccagcg cggtcatcga taaccgtgca aacctgaatt atcttctgac ccattccggt  1020
ctggactata aacgcaatat tctgaatgac cggaatccgg tggtgacaga ggatgtggaa  1080
ggtgacaaga aaatttataa tgctgaagtt gctgaatggg ataagttacg gcaacgattg  1140
cttgatgcca gaaataaaat cacctctgct gaatctgcga taaattcggc gagaaataac  1200
gtcagtgcca gaacaaatga acaaaagcat gcaaatgacg ctcttaatgc cctgttgaag  1260
gaaaaagaga atatccgtag ccagcttgct gacatcaatc agaaaatagc tgaagagaaa  1320
agaaaagggg atgaaataaa tatgtaaag gatgccataa aactcacctc tgatttctac  1380
agaacgatat atgatgagtt cggtaaacaa gcatccgaac ttgctaagga gctggcttct  1440
gtatctcaag gaaacagat taagagtgtg gatgatgcac tgaacgcttt tgataaattc  1500
cgtaataatc tgaacaagaa atataacata caagatcgca tggccatttc taaagccctg  1560
gaagctatta atcaggtcca tatggcggag aattttaagc tgttcagtaa ggcatttggt  1620
tttaccggaa aagttattga acgttatgat gttgctgtgg agttacaaaa ggctgtaaaa  1680
acggacaact ggcgtccatt ttttgtaaaa cttgaatcac tggcagcagg aagagctgct  1740
tcagcagtta cagcatgggc gttttccgtc atgctggaa ccctgtagg tattctgggt  1800
tttgcaatta ttatggcggc tgtgagtgcg cttgttaatg ataagtttat tgagcaggtc  1860
aataaactta ttggtatctg a                                            1881

SEQ ID NO: 60              moltype = AA  length = 271
FEATURE                    Location/Qualifiers
source                     1..271
                           mol_type = protein
                           organism = Escherichia coli
```

-continued

```
SEQUENCE: 60
METLTVHAPS PSTNLPSYGN GAFSLSAPHV PGAGPLLVQV VYSFFQSPNM CLQALTQLED   60
YIKKHGASNP LTLQIISTNI GYFCNADRNL VLHPGISVYD AYHFAKPAPS QYDYRSMNMK  120
QMSGNVTTPI VALAHYLWGN GAERSVNIAN IGLKISPMKI NQIKDIIKSG VVGTFPVSTK  180
FTHATGDYNV ITGAYLGNIT LKTEGTLTIS ANGSWTYNGV VRSYDDKYDF NASTHRGIIG  240
ESLTRLGAMF SGKEYQILLP GEIHIKESGK R                                271

SEQ ID NO: 61           moltype = DNA   length = 816
FEATURE                 Location/Qualifiers
source                  1..816
                        mol_type = genomic DNA
                        organism = Escherichia coli
SEQUENCE: 61
atggaaacct taactgttca tgcaccatca ccatcaacta acttaccaag ttatggcaat   60
ggtgcatttt ctctttcagc accacatgtg cctggtgctg ccctcttttt agtccaggtt  120
gtttatagtt ttttccagag tccaaacatg tgtcttcagg ctttaactca acttgaggat  180
tacatcaaaa acatggggc cagcaaccct ctcacattgc agatcatatc gacaaatatt   240
ggttacttct gtaacgccga ccgaaatctg gttcttcacc ctggaataag cgtttatgac  300
gcttaccact tcgcaaaacc agcgccaagt caatatgact atcgctcaat gaatatgaaa  360
caaatgagcg gtaatgtcac taccaccaatt gtggcgcttg ctcactattt atggggtaat  420
ggcgctgaaa ggagcgttaa tatcgccaac attggtctta aaatttcccc tatgaaaatt  480
aatcagataa aagacattat aaaatctggt gtagtaggca cattccctgt ttctacaaag  540
ttcacacatg ccactggtga ttataatgtt attaccggtg catatcttgg taatatcaca  600
ctgaaaacag aaggtacttt aactatctct gccaatggct cctggactta caatggcgtt  660
gttcgttcat atgatgataa atacgatttt aacgccagca ctcaccgtgg cattatcgga  720
gagtcgctca aaggctcgg ggcgatgttt tctggtaaag agtaccagat actgcttcct   780
ggtgaaattc acattaaaga aagtggtaag cgataa                            816

SEQ ID NO: 62           moltype = AA    length = 387
FEATURE                 Location/Qualifiers
source                  1..387
                        mol_type = protein
                        organism = Escherichia coli
SEQUENCE: 62
MGSNGADNAH NNAFGGGKNP GIGNTSGAGS NGSASSNRGN SNGWSWSNKP HKNDGFHSDG   60
SYHITFHGDN NSKPKPGGNS GNRGNNGDGA SAKVGEITIT PDNSKPGRYI SSNPEYSLLA  120
KLIDAESIKG TEVYTFHTRK GQYVKVTVPD SNIDKMRVDY VNWKGPKYNN KLVKRFVSQF  180
LLFRKEEKEK NEKEALLKAS ELVSGMGDKL GEYLGVKYKN VAKEVANDIK NFHGRNIRSY  240
NEAMASLNKV LANPKMKVNK SDKDAIVNAW KQVNAKDMAN KIGNLGKAFK VADLAIKVEK  300
IREKSIEGYN TGNWGPLLLE VESWIIGGVV AGVAISLFGA VLSFLPISGL AVTALGVIGI  360
MTISYLSSFI DANRVSNINN IISSVIR                                     387

SEQ ID NO: 63           moltype = DNA   length = 51
FEATURE                 Location/Qualifiers
source                  1..51
                        mol_type = genomic DNA
                        organism = Escherichia coli
SEQUENCE: 63
gcaaatcgag tttcgaatat aaataacatt atatctagtg ttattcgatg a            51

SEQ ID NO: 64           moltype = AA    length = 103
FEATURE                 Location/Qualifiers
source                  1..103
                        mol_type = protein
                        organism = Escherichia coli
SEQUENCE: 64
MRTLTLNELD SVSGGASGRD IAMAIGTLSG QFVAGGIGAA AGGVAGGAIY DYASTHKPNP   60
AMSPSGLGGT IKQKPEGIPS EAWNYAAGRL CNWSPNNLSD VCL                    103

SEQ ID NO: 65           moltype = DNA   length = 312
FEATURE                 Location/Qualifiers
source                  1..312
                        mol_type = genomic DNA
                        organism = Escherichia coli
SEQUENCE: 65
atgagaactc tgactctaaa tgaattagat tctgtttctg gtggtgcttc agggcgtgat   60
attgcgatgg ctataggaac actatccgga caatttgttg caggaggaat tggagcagct  120
gctgggggtg tggctggagg tgcaatatat gactatgcat ccactcacaa acctaatcct  180
gcaatgtctc catccggttt aggaggaaca attaagcaaa aacccgaagg gatacctttca 240
gaagcatgga actatgctgc gggaagattg tgtaattgga gtccaaataa tcttagtgat  300
gtttgtttat aa                                                     312

SEQ ID NO: 66           moltype = AA    length = 58
FEATURE                 Location/Qualifiers
source                  1..58
                        mol_type = protein
                        organism = Enterococcus columbae
SEQUENCE: 66
MMNATENQIF VETVSDQELE MLIGGAGRGW IKTLTKDCPN VISSICAGTI ITACKNCA     58
```

```
SEQ ID NO: 67            moltype = DNA  length = 177
FEATURE                  Location/Qualifiers
source                   1..177
                         mol_type = genomic DNA
                         organism = Enterococcus columbae
SEQUENCE: 67
atgatgaatg ctactgaaaa ccaaattttt gttgagactg tgagtgacca agaattagaa  60
atgttaattg gtggtgcagg tcgtggatgg attaagactt taacaaaaga ttgtccaaat 120
gtgatttctt caatttgtgc aggtacaatt attacagctt gtaaaaattg tgcttaa    177

SEQ ID NO: 68            moltype = AA  length = 59
FEATURE                  Location/Qualifiers
source                   1..59
                         mol_type = protein
                         organism = Lactobacillus curvatus
SEQUENCE: 68
MNNVKELSMT ELQTITGGAR SYGNGVYCNN KKCWVNRGEA TQSIIGGMIS GWASGLAGM    59

SEQ ID NO: 69            moltype = DNA  length = 180
FEATURE                  Location/Qualifiers
source                   1..180
                         mol_type = genomic DNA
                         organism = Lactobacillus curvatus
SEQUENCE: 69
atgaataatg taaaagaatt aagtatgaca gaattacaaa caattaccgg cggtgctaga  60
tcatatggca acggtgttta ctgtaataat aaaaaatgtt gggtaaatcg gggtgaagca 120
acgcaaagta ttattggtgg tatgattagc ggctgggcta gtggtttagc tggaatgtaa 180

SEQ ID NO: 70            moltype = AA  length = 64
FEATURE                  Location/Qualifiers
source                   1..64
                         mol_type = protein
                         organism = Streptomyces sp.
SEQUENCE: 70
MRSEMTLTST NSAEALAAQD FANTVLSAAA PGFHADCETP AMATPATPTV AQFVIQGSTI   60
CLVC                                                               64

SEQ ID NO: 71            moltype = DNA  length = 195
FEATURE                  Location/Qualifiers
source                   1..195
                         mol_type = genomic DNA
                         organism = Streptomyces sp.
SEQUENCE: 71
gtgcgatctg agatgactct tacgagcacg aattccgctg aggctctggc ggcgcaggac  60
tttgcgaaca ccgttctcag cgcggcggcc ccgggcttcc acgcggactg cgagacgccg 120
gccatggcca cccggccac gccgaccgtc gcccagttcg tgatccaggg cagcacgatc 180
tgcctggtct gctga                                                  195

SEQ ID NO: 72            moltype = AA  length = 65
FEATURE                  Location/Qualifiers
source                   1..65
                         mol_type = protein
                         organism = Bacillus halodurans
SEQUENCE: 72
MVNSKDLRNP EFRKAQGLQF VDEVNEKELS SLAGSGDVHA QTTWPCATVG VSVALCPTTK   60
CTSQC                                                              65

SEQ ID NO: 73            moltype = DNA  length = 198
FEATURE                  Location/Qualifiers
source                   1..198
                         mol_type = genomic DNA
                         organism = Bacillus halodurans
SEQUENCE: 73
atggtaaatt caaagatttt gcgtaatcct gaattccgca aagcccaagg tctacaattc  60
gttgacgagg tgaacgagaa ggaactttcg tctctagctg gttcaggaga tgtgcatgca 120
caaacaactt ggccttgcgc tacagttggt gtctccgtag ccttgtgccc aactacaaag 180
tgtacaagcc agtgctaa                                               198

SEQ ID NO: 74            moltype = AA  length = 66
FEATURE                  Location/Qualifiers
source                   1..66
                         mol_type = protein
                         organism = Carnobacterium divergens
SEQUENCE: 74
MKNLKEGSYT AVNTDELKSI NGGTKYYGNG VYCNSKKCWV DWGQASGCIG QTVVGGWLGG   60
AIPGKC                                                             66

SEQ ID NO: 75            moltype = DNA  length = 201
```

```
FEATURE                 Location/Qualifiers
source                  1..201
                        mol_type = genomic DNA
                        organism = Carnobacterium divergens
SEQUENCE: 75
atgaaaaact taaaagaagg ttcatacact gctgttaata ctgatgaatt aaaaagtatc    60
aatggtggaa caaatatta tgggaatggc gtttattgca attctaaaaa atgttgggta   120
gattggggac aagcttcagg ttgtatcggt caaactgttg ttggcggatg gctaggcgga   180
gctataccag gtaaatgcta a                                             201

SEQ ID NO: 76           moltype = AA   length = 63
FEATURE                 Location/Qualifiers
source                  1..63
                        mol_type = protein
                        organism = Carnobacterium divergens
SEQUENCE: 76
MIKREKNRTI SSLGYEEISN HKLQEIQGGK GILGKLGVVQ AGVDFVSGVW AGIKQSAKDH    60
PNA                                                                 63

SEQ ID NO: 77           moltype = DNA   length = 192
FEATURE                 Location/Qualifiers
source                  1..192
                        mol_type = genomic DNA
                        organism = Carnobacterium divergens
SEQUENCE: 77
atgattaaaa gagaaaagaa cagaacaatt tcttcccttg gttatgaaga aatttctaat    60
cataaattgc aagaaataca aggtggaaaa ggaattcttg gtaaactagg agtagtacag   120
gcaggagtgg attttgtatc aggagtgtgg gctggaataa aacagtctgc caaagatcat   180
cctaatgcgt aa                                                       192

SEQ ID NO: 78           moltype = AA   length = 75
FEATURE                 Location/Qualifiers
source                  1..75
                        mol_type = protein
                        organism = Carnobacterium divergens
SEQUENCE: 78
MKKQILKGLV IVVCLSGATF FSTPQQASAA APKITQKQKN CVNGQLGGML AGALGGPGGV    60
VLGGIGGAIA GGCFN                                                    75

SEQ ID NO: 79           moltype = DNA   length = 228
FEATURE                 Location/Qualifiers
source                  1..228
                        mol_type = genomic DNA
                        organism = Carnobacterium divergens
SEQUENCE: 79
atgaaaaaac aaattttaaa agggttggtt atagttgttt gttatctgg ggcaacattt     60
ttctcaacac cacaacaagc ttctgctgct gcaccgaaaa ttactcaaaa acaaaaaaat   120
tgtgttaatg gacaattagg tggaatgctt gctggagctt tgggtggacc tggcggagtt   180
gtgttaggtg gtataggtgg tgcaatagca ggaggttgtt ttaattaa                228

SEQ ID NO: 80           moltype = AA   length = 72
FEATURE                 Location/Qualifiers
source                  1..72
                        mol_type = protein
                        organism = Enterococcus durans
SEQUENCE: 80
MQTIKELNTM ELQEIIGGEN DHRMPYELNR PNNLSKGGAK CAAGILGAGL GAVGGGPGGF    60
ISAGISAVLG CM                                                       72

SEQ ID NO: 81           moltype = DNA   length = 219
FEATURE                 Location/Qualifiers
source                  1..219
                        mol_type = genomic DNA
                        organism = Enterococcus durans
SEQUENCE: 81
atgcaaacga tcaaagaatt gaacacgatg gaattacaag aaataattgg aggtgaaaat    60
gaccatcgga tgccttacga attgaaccgt ccaaataatt tatccaaagg tggggctaag   120
tgtgctgctg gaatacttgg cgctggacta ggcgcagtag gcggtggacc tggcggatttt   180
attagtgccg gaatcagtgc tgttcttggt tgtatgtaa                           219

SEQ ID NO: 82           moltype = AA   length = 72
FEATURE                 Location/Qualifiers
source                  1..72
                        mol_type = protein
                        organism = Enterococcus durans
SEQUENCE: 82
MQTIKELNTM ELQKIIGGEN DHRMPYELNR PNNLSKGGAK CAAGILGAGL GAVGGGPGGF    60
ISAGISAVLG CM                                                       72
```

```
SEQ ID NO: 83              moltype = DNA   length = 219
FEATURE                    Location/Qualifiers
source                     1..219
                           mol_type = genomic DNA
                           organism = Enterococcus durans
SEQUENCE: 83
atgcaaacga tcaagaatt  gaacacgatg gaattacaaa aaataattgg aggtgaaaat    60
gaccatcgga tgccttacga attgaaccgt ccaataattt tatccaaagg tggagctaag   120
tgcgctgccg gaatacttgg tgctggatta ggcgcagtag gcggtggacc tggcggattt   180
attagtgccg gaatcagtgc tgttcttggt tgtatgtaa                          219

SEQ ID NO: 84              moltype = AA    length = 220
FEATURE                    Location/Qualifiers
source                     1..220
                           mol_type = protein
                           note = subsp. equisimilis
                           organism = Streptococcus dysgalactiae
SEQUENCE: 84
MKKLKRLVIS LVTSLLVISS TVPALVYANE TNNFAETQKE ITTNSEATLT NEDYTKLTSE    60
VKTIYTNLIQ YDQTKNKFYV DEDKTEQYYN YDDESIKGVY LMKDSLNDEL NNNNSSNYSE   120
IINQKISEID YVLQGNDINN LIPSNTRVKR SADFSWIQRC LEEAWGYAIS LVTLKGIINL   180
FKAGKFEAAA AKLASATAGR IAGMAALFAF VATCGATTVS                         220

SEQ ID NO: 85              moltype = DNA   length = 663
FEATURE                    Location/Qualifiers
source                     1..663
                           mol_type = genomic DNA
                           note = subsp. equisimilis
                           organism = Streptococcus dysgalactiae
SEQUENCE: 85
atgaaaaaat taaaacgtct tgttatctct cttgttactt cattactagt aatttcaagt    60
acagttccag cacttgttta cgctaatgaa acaaataact tgcagaaac tcaaaaagaa   120
attacaacaa attcagaagc aacattaacc aatgaagact cactaaatt aacttccgaa   180
gtaaaaacaa tttatacaaa tctgattcaa tacgaccaaa caaaaaacaa attttacgtc   240
gatgaagaca aaactgaaca atattataac tacgatgatg aaagtataaa agggggttat   300
ctcatgaaag atagtttgaa cgatgagtta aacaataata actcttcaaa ctattctgaa   360
ataattaatc aaaaaatctc tgaaattgac tatgtccttc aaggaaacga tataaataat   420
ttaattccta gcaataccag agtaaaaaga tcagcagatt tttcttggat tcaaagatgt   480
ctagaagaag catggggata tgctattagt ctagttactc taaaaggaat aatcaatcta   540
tttaaagcag gaaaatttga agctgctgct gctaaattag cttctgctac agcaggtaga   600
atcgctggaa tggctgcctt atttgctttc gtagcaactt gcggtgcgac aactgtatca   660
taa                                                                 663

SEQ ID NO: 86              moltype = AA    length = 57
FEATURE                    Location/Qualifiers
source                     1..57
                           mol_type = protein
                           organism = Enterococcus faecalis
SEQUENCE: 86
MKQYKVLNEK EMKKPIGGES VFSKIGNAVG PAAYWILKGL GNMSDVNQAD RINRKKH       57

SEQ ID NO: 87              moltype = DNA   length = 174
FEATURE                    Location/Qualifiers
source                     1..174
                           mol_type = genomic DNA
                           organism = Enterococcus faecalis
SEQUENCE: 87
atgaagcaat ataaagtatt gaatgaaaaa gaaatgaaaa aacctattgg gggagagtcg    60
gttttagta aaataggtaa tgctgtaggt ccagctgctt attggatttt aaaaggatta   120
ggtaaatatga gtgatgtaaa ccaagctgat agaattaata gaaagaaaca ttaa        174

SEQ ID NO: 88              moltype = AA    length = 44
FEATURE                    Location/Qualifiers
source                     1..44
                           mol_type = protein
                           organism = Enterococcus faecalis
SEQUENCE: 88
MGAIAKLVAK FGWPIVKKYY KQIMQFIGEG WAINKIIDWI KKHI                     44

SEQ ID NO: 89              moltype = DNA   length = 135
FEATURE                    Location/Qualifiers
source                     1..135
                           mol_type = genomic DNA
                           organism = Enterococcus faecalis
SEQUENCE: 89
atgggagcaa tcgcaaaatt agtagcaaag tttggatggc caattgttaa aaagtattac    60
aaacaaatta tgcaatttat tggagaagga tgggcaatta caaaaattat tgattggatc   120
aaaaaacata tttaa                                                    135
```

```
SEQ ID NO: 90            moltype = AA   length = 43
FEATURE                  Location/Qualifiers
source                   1..43
                         mol_type = protein
                         organism = Enterococcus faecalis
SEQUENCE: 90
MGAIAKLVAK FGWPFIKKFY KQIMQFIGQG WTIDQIEKWL KRH                        43

SEQ ID NO: 91            moltype = DNA   length = 132
FEATURE                  Location/Qualifiers
source                   1..132
                         mol_type = genomic DNA
                         organism = Enterococcus faecalis
SEQUENCE: 91
atgggagcaa tcgcaaaatt agtagcaaag tttggatggc catttattaa aaaattctac     60
aaacaaatta tgcagtttat cggacaagga tggacaatag atcaaattga aaaatggtta    120
aaaagacatt ga                                                        132

SEQ ID NO: 92            moltype = AA   length = 74
FEATURE                  Location/Qualifiers
source                   1..74
                         mol_type = protein
                         organism = Enterococcus faecalis
SEQUENCE: 92
MLNKKLLENG VVNAVTIDEL DAQFGGMSKR DCNLMKACCA GQAVTYAIHS LLNRLGGDSS     60
DPAGCNDIVR KYCK                                                       74

SEQ ID NO: 93            moltype = DNA   length = 225
FEATURE                  Location/Qualifiers
source                   1..225
                         mol_type = genomic DNA
                         organism = Enterococcus faecalis
SEQUENCE: 93
atgttaaata aaaaattatt agaaaatggt gtagtaaatg ctgtaacaat tgatgaactt     60
gatgctcaat ttggtggaat gagcaaacgt gattgtaact tgatgaaggc gtgttgtgct    120
ggacaagcag taacatatgc tattcatagt cttttaaatc gattaggtgg agactctagt    180
gatccagctg gttgtaatga tattgtaaga aaatattgta aataa                    225

SEQ ID NO: 94            moltype = AA   length = 65
FEATURE                  Location/Qualifiers
source                   1..65
                         mol_type = protein
                         organism = Enterococcus faecium
SEQUENCE: 94
MKHLKILSIK ETQLIYGGTT HSGKYYGNGV YCTKNKCTVD WAKATTCIAG MSIGGFLGGA     60
IPGKC                                                                 65

SEQ ID NO: 95            moltype = DNA   length = 195
FEATURE                  Location/Qualifiers
source                   1..195
                         mol_type = genomic DNA
                         organism = Enterococcus faecium
SEQUENCE: 95
atgaaacatt taaaaatttt gtctattaaa gagacacaac ttatctatgg gggtaccact     60
catagtggaa aatattatgg aaatggagtg tattgcacta aaaataaatg tacggtcgat    120
tgggccaagg caactacttg tattgcagga atgtctatag gtggttttt aggtggagca    180
attccaggga agtgc                                                     195

SEQ ID NO: 96            moltype = AA   length = 105
FEATURE                  Location/Qualifiers
source                   1..105
                         mol_type = protein
                         organism = Enterococcus faecalis
SEQUENCE: 96
MVKENKFSKI FILMALSFLG LALFSASLQF LPIAHMAKEF GIPAAVAGTV LNVVEAGGWV     60
TTIVSILTAV GSGGLSLLAA AGRESIKAYL KKEIKKKGKR AVIAW                    105

SEQ ID NO: 97            moltype = DNA   length = 318
FEATURE                  Location/Qualifiers
source                   1..318
                         mol_type = genomic DNA
                         organism = Enterococcus faecalis
SEQUENCE: 97
atggttaaag aaaataaatt ttctaagatt tttatttaa tggctttgag ttttttgggg      60
ttagccttgt ttagtgcaag tcttcagttt ttgcccattg cacatatggc taaagagttc    120
ggtataccag cagcagttgc aggaactgtg cttaatgtag ttgaagctgg tggatgggtc    180
actactattg tatcaattct tactgctgta ggtagcggag gtcttctttt actcgctgca    240
gcaggaagag agtcaattaa agcataccct aagaaagaaa ttaagaaaaa aggaaaaaga    300
gcagttattg cttggtaa                                                  318
```

```
SEQ ID NO: 98              moltype = AA  length = 71
FEATURE                    Location/Qualifiers
source                     1..71
                           mol_type = protein
                           organism = Enterococcus faecium
SEQUENCE: 98
MQNVKELSTK EMKQIIGGEN DHRMPNELNR PNNLSKGGAK CGAAIAGGLF GIPKGPLAWA    60
AGLANVYSKC N                                                        71

SEQ ID NO: 99              moltype = DNA  length = 216
FEATURE                    Location/Qualifiers
source                     1..216
                           mol_type = genomic DNA
                           organism = Enterococcus faecium
SEQUENCE: 99
atgcaaaatg taaagaatt aagtacgaaa gagatgaaac aaattatcgg tggagaaaat     60
gatcacagaa tgcctaatga gttaaataga cctaacaact tatctaaagg tggagcaaaa   120
tgtggtgctg caattgctgg gggattattt ggaatcccaa aaggaccact agcatgggct   180
gctgggttag caaatgtata ctctaaatgc aactaa                             216

SEQ ID NO: 100             moltype = AA  length = 58
FEATURE                    Location/Qualifiers
source                     1..58
                           mol_type = protein
                           organism = Enterococcus mundtii
SEQUENCE: 100
MKKLTSKEMA QVVGGKYYGN GVSCNKKGCS VDWGKAIGII GNNSAANLAT GGAAGWKS      58

SEQ ID NO: 101             moltype = DNA  length = 177
FEATURE                    Location/Qualifiers
source                     1..177
                           mol_type = genomic DNA
                           organism = Enterococcus mundtii
SEQUENCE: 101
ttgaagaaat taacatcaaa agaaatggca caagtagtag gtggaaaata ctacggtaat    60
ggagtctcat gtaataaaaa agggtgcagt gttgattggg gaaaagctat tggcattatt   120
ggaaataatt ctgctgcgaa tttagctact ggtggagcag ctggttggaa aagttaa      177

SEQ ID NO: 102             moltype = AA  length = 44
FEATURE                    Location/Qualifiers
source                     1..44
                           mol_type = protein
                           organism = Enterococcus faecalis
SEQUENCE: 102
MLAKIKAMIK KFPNPYTLAA KLTTYEINWY KQQYGRYPWE RPVA                     44

SEQ ID NO: 103             moltype = DNA  length = 135
FEATURE                    Location/Qualifiers
source                     1..135
                           mol_type = genomic DNA
                           organism = Enterococcus faecalis
SEQUENCE: 103
atgttagcaa aaattaaagc gatgattaag aagtttccga acccttatac tttagcagct    60
aagctaacga cttacgaaat taattggtat aaacaacaat acggtcgtta ccttgggag    120
cgccctgtag cataa                                                    135

SEQ ID NO: 104             moltype = AA  length = 71
FEATURE                    Location/Qualifiers
source                     1..71
                           mol_type = protein
                           organism = Enterococcus faecium
SEQUENCE: 104
MRKKLFSLAL IGIFGLVVTN FGTKVDAATR SYGNGVYCNN SKCWVNWGEA KENIAGIVIS    60
GWASGLAGMG H                                                        71

SEQ ID NO: 105             moltype = DNA  length = 216
FEATURE                    Location/Qualifiers
source                     1..216
                           mol_type = genomic DNA
                           organism = Enterococcus faecium
SEQUENCE: 105
atgagaaaaa aattatttag tttagctctt attggaatat ttgggttagt tgtgacaaat    60
tttggtacaa aagttgatgc agctacgcgt tcatatggta atggtgttta ttgtaataat   120
agtaaatgct gggttaactg gggagaagct aaagagaata ttgcaggaat cgttattagt   180
ggctgggctt ctggttttgc aggtatggga cattaa                             216

SEQ ID NO: 106             moltype = AA  length = 34
FEATURE                    Location/Qualifiers
```

```
source                  1..34
                        mol_type = protein
                        organism = Enterococcus faecium
SEQUENCE: 106
MNFLKNGIAK WMTGAELQAY KKKYGCLPWE KISC                               34

SEQ ID NO: 107          moltype = DNA   length = 105
FEATURE                 Location/Qualifiers
source                  1..105
                        mol_type = genomic DNA
                        organism = Enterococcus faecium
SEQUENCE: 107
atgaattttc ttaaaaatgg tatcgcaaaa tggatgaccg gtgctgaatt gcaagcgtat    60
aaaaagaaat atggatgctt gccatgggaa aaaatttctt gttaa                  105

SEQ ID NO: 108          moltype = AA   length = 76
FEATURE                 Location/Qualifiers
source                  1..76
                        mol_type = protein
                        organism = Enterococcus faecalis
SEQUENCE: 108
MKKKLVKGLV ICGMIGIGFT ALGTNVEAAT YYGNGVYCNK QKCWVDWSRA RSEIIDRGVK    60
AYVNGFTKVL GGIGGR                                                   76

SEQ ID NO: 109          moltype = DNA   length = 231
FEATURE                 Location/Qualifiers
source                  1..231
                        mol_type = genomic DNA
                        organism = Enterococcus faecalis
SEQUENCE: 109
atgaaaaaga aattagttaa aggcttagtt atttgtggca tgattgggat tggtttttaca   60
gcattaggaa caaatgtaga agccgccacg tattacggaa atggtgtcta ttgcaataag  120
caaaaatgtt gggtagattg gagtagagca cgttctgaaa ttatagacag aggcgtaaaa  180
gcatacgtca atggatttac gaaagtgtta ggtggtatag gtggaagata a            231

SEQ ID NO: 110          moltype = AA   length = 60
FEATURE                 Location/Qualifiers
source                  1..60
                        mol_type = protein
                        organism = Enterococcus faecalis
SEQUENCE: 110
MKKEELVGMA KEDFLNVICE NDNKLENSGA KCPWWNLSCH LGNDGKICTY SHECTAGCNA    60

SEQ ID NO: 111          moltype = DNA   length = 183
FEATURE                 Location/Qualifiers
source                  1..183
                        mol_type = genomic DNA
                        organism = Enterococcus faecalis
SEQUENCE: 111
atgaaaaaag aagaattagt aggaatggct aaggaagact ttttaaatgt tatttgtgaa    60
aatgacaaca aactagaaaa tagtggagca aaatgtcctt ggtggaatct ttcttgtcat  120
ttaggcaatg atggtaaaat ttgcacttat tcacatgaat gtaccgcagg ttgtaatgca  180
taa                                                                 183

SEQ ID NO: 112          moltype = AA   length = 61
FEATURE                 Location/Qualifiers
source                  1..61
                        mol_type = protein
                        organism = Enterococcus faecalis
SEQUENCE: 112
MTELNKRLQL KRDVSTENSL KKISNTDETH GGVTTSIPCT VMVSAAVCPT LVCSNKCGGR    60
G                                                                   61

SEQ ID NO: 113          moltype = DNA   length = 186
FEATURE                 Location/Qualifiers
source                  1..186
                        mol_type = genomic DNA
                        organism = Enterococcus faecalis
SEQUENCE: 113
atgactgaac ttaacaaaag attacaatta aaaagagatg tttcaacaga aaatagtttg    60
aaaaaaattt ctaatactga tgaaacacat gggggagtta ctacatcaat tccatgtaca  120
gtaatggtta gtgcggcagt atgtcctacc cttgtttgct cgaataaatg tggcggtaga  180
ggctag                                                              186

SEQ ID NO: 114          moltype = AA   length = 58
FEATURE                 Location/Qualifiers
source                  1..58
                        mol_type = protein
                        organism = Enterococcus faecium
```

```
SEQUENCE: 114
MQNVKEVSVK EMKQIIGGSN DSLWYGVGQF MGKQANCITN HPVKHMIIPG YCLSKILG      58

SEQ ID NO: 115          moltype = DNA   length = 177
FEATURE                 Location/Qualifiers
source                  1..177
                        mol_type = genomic DNA
                        organism = Enterococcus faecium
SEQUENCE: 115
atgcaaaatg taaaagaagt ttctgtaaaa gagatgaaac aaattatcgg tggttctaat      60
gatagtcttt ggtatggtgt aggacaattt atgggtaaac aagcaaactg tataacaaac     120
catcctgtta aacacatgat aattcctgga tattgtttat cgaaaatttt agggtaa         177

SEQ ID NO: 116          moltype = AA   length = 55
FEATURE                 Location/Qualifiers
source                  1..55
                        mol_type = protein
                        organism = Enterococcus faecium
SEQUENCE: 116
MKKYNELSKK ELLQIQGGIA PIIVAGLGYL VKDAWDHSDQ IISGFKKGWN GGRRK            55

SEQ ID NO: 117          moltype = DNA   length = 168
FEATURE                 Location/Qualifiers
source                  1..168
                        mol_type = genomic DNA
                        organism = Enterococcus faecium
SEQUENCE: 117
atgaaaaaat ataatgagtt atctaaaaaa gaacttctac agattcaagg aggaatagca      60
cctattatag ttgctggcct tggctattta gtaaagatg catgggatca ctcagatcaa      120
ataatctcag gatttaaaaa aggttggaat ggtggacgta gaaaataa                   168

SEQ ID NO: 118          moltype = AA   length = 343
FEATURE                 Location/Qualifiers
source                  1..343
                        mol_type = protein
                        organism = Enterococcus faecalis
SEQUENCE: 118
MKNILLSILG VLSIVVSLAF SSYSVNAASN EWSWPLGKPY AGRYEEGQQF GNTAFNRGGT       60
YFHDGFDFGS AIYGNGSVYA VHDGKILYAG WDPVGGGSLG AFIVLQAGNT NVIYQEFSRN      120
VGDIKVSTGQ TVKKGQLIGK FTSSHLHLGM TKKEWRSAHS SWNKDDGTWF NPIPILQGGS      180
TPTPPNPGPK NFTTNVRYGL RVLGGSWLPE VTNFNNTNDG FAGYPNRQHD MLYIKVDKGQ      240
MKYRVHTAQS GWLPWVSKGD KSDTVNGAAG MPGQAIDGVQ LNYITPKGEK LSQAYYRSQT      300
TKRSGWLKVS ADNGSIPGLD SYAGIFGEPL DRLQIGISQS NPF                       343

SEQ ID NO: 119          moltype = DNA   length = 1032
FEATURE                 Location/Qualifiers
source                  1..1032
                        mol_type = genomic DNA
                        organism = Enterococcus faecalis
SEQUENCE: 119
atgaaaaaata ttttactttc tattctaggg gtattatcta tcgttgtttc tttggcgttt      60
tcttcttatt ctgtcaacgc agcttctaat gagtggtcgt ggccactggg caaaccatat     120
gcgggaagat atgaagaagg acaacaattc gggaacactg catttaaccg aggaggtact     180
tatttccatg atgggtttga ctttggttct gctatttatg gaaatggcag tgtgtatgct     240
gtgcatgatg gtaaaatttt atatgctggt tgggatcctg taggtggagg ctcattaggt     300
gcatttattg tactacaagc gggaaacaca aatgtgattt atcaagaatt agccgaaat      360
gttggagata ttaaagttag cactggacaa actgttaaaa aaggacagct gataggaaag     420
tttacttcta gtcatttaca tttaggaatg acaaaaaaag aatggcgttc tgctcattca     480
tcttggaata aagatgatgg cacttggttt aacccaattc ctatacttca aggaggatct     540
acgcctacgc ctccaaatcc aggaccaaaa aatttcacaa caaatgttcg ttacggattg     600
cgggtcctcg gaggttcatg gttaccagaa gtaccaact ttaacaatac caatgatggt      660
ttcgcaggtt acccctaatcg tcaacatgat atgctttata aaggtaga taagggcaa       720
atgaaatatc gtgttcacac ggctcaaagt ggatggttgc cttgggtaag taagggat      780
aagagcgata cagtaaatgg agcgcaggt atgcctggac aagcaattga tggtgttcag      840
ctaaactata taactcctaa gggagaaaaa ttatcacagg cttactatcg ttcacaaact     900
acgaaacgat caggctggtt aaagtaagt gcagataatg gttctattcc tggactagac     960
agttatgcag gaatctttgg agaaccgttg atcgcttgc aaataggtat ttcacagtca    1020
aatccatttt aa                                                      1032

SEQ ID NO: 120          moltype = AA   length = 56
FEATURE                 Location/Qualifiers
source                  1..56
                        mol_type = protein
                        organism = Staphylococcus epidermidis
SEQUENCE: 120
MENKKDLFDL EIKKDNMENN NELEAQSLGP AIKATRQVCP KATRFVTVSC KKSDCQ         56

SEQ ID NO: 121          moltype = DNA   length = 171
FEATURE                 Location/Qualifiers
```

```
source                    1..171
                          mol_type = genomic DNA
                          organism = Staphylococcus epidermidis
SEQUENCE: 121
atggaaaaca aaaaagattt atttgattta gaaatcaaaa agataatat ggaaataat    60
aatgaattag aagctcaatc tcttggtcct gcaattaagg caactagaca ggtatgtcct  120
aaagcaacac gttttgttac agtttcttgt aaaaaagtg attgtcaata g            171

SEQ ID NO: 122            moltype = AA   length = 51
FEATURE                   Location/Qualifiers
source                    1..51
                          mol_type = protein
                          organism = Staphylococcus epidermidis
SEQUENCE: 122
MAAFMKLIQF LATKGQKYVS LAWKHKGTIL KWINAGQSFE WIYKQIKKLW A            51

SEQ ID NO: 123            moltype = DNA   length = 156
FEATURE                   Location/Qualifiers
source                    1..156
                          mol_type = genomic DNA
                          organism = Staphylococcus epidermidis
SEQUENCE: 123
atggcagcat ttatgaagtt aattcagttc ttagcaacta aaggtcaaaa gtatgtttca   60
cttgcatgga acataaagg tactatttta aaatggatta cgccggtca aagttttgaa   120
tggatttata aacaaatcaa aaaattatgg gcataa                            156

SEQ ID NO: 124            moltype = AA   length = 52
FEATURE                   Location/Qualifiers
source                    1..52
                          mol_type = protein
                          organism = Staphylococcus epidermidis
SEQUENCE: 124
MEAVKEKNDL FNLDVKVNAK ESNDSGAEPR IASKFICTPG CAKTGSFNSY CC           52

SEQ ID NO: 125            moltype = DNA   length = 159
FEATURE                   Location/Qualifiers
source                    1..159
                          mol_type = genomic DNA
                          organism = Staphylococcus epidermidis
SEQUENCE: 125
atggaagcag taaagaaaa aaatgatctt tttaatcttg atgttaaagt taatgcaaaa    60
gaatctaacg attcaggagc tgaaccaaga attgctagta aatttatatg tactcctgga  120
tgtgcaaaaa caggtagttt taacagttat tgttgttaa                         159

SEQ ID NO: 126            moltype = AA   length = 55
FEATURE                   Location/Qualifiers
source                    1..55
                          mol_type = protein
                          organism = Staphylococcus epidermidis
SEQUENCE: 126
MNNSLFDLNL NKGVETQKSD LSPQSASVLK TSIKVSKKYC KGVTLTCGCN ITGGK        55

SEQ ID NO: 127            moltype = DNA   length = 168
FEATURE                   Location/Qualifiers
source                    1..168
                          mol_type = genomic DNA
                          organism = Staphylococcus epidermidis
SEQUENCE: 127
atgaataact cattattcga tttaaaccta aacaaaggtg tagaaactca aaagagtgat   60
ttaagtccgc aatctgctag tgtcttgaag acttctatta agtatctaa aaaatattgt   120
aaaggtgtta ctttaacatg cggttgcaat attactggtg gtaaataa              168

SEQ ID NO: 128            moltype = AA   length = 52
FEATURE                   Location/Qualifiers
source                    1..52
                          mol_type = protein
                          organism = Staphylococcus gallinarum
SEQUENCE: 128
MEAVKEKNEL FDLDVKVNAK ESNDSGAEPR IASKFLCTPG CAKTGSFNSY CC           52

SEQ ID NO: 129            moltype = DNA   length = 159
FEATURE                   Location/Qualifiers
source                    1..159
                          mol_type = genomic DNA
                          organism = Staphylococcus gallinarum
SEQUENCE: 129
atggaagcag taaagagaa aaatgaactt tttgatcttg acgttaaagt aaatgcaaaa    60
gagtctaatg attcaggcgc agaaccacga attgctagta aatttttatg tactcctgga  120
tgtgccaaaa caggtagctt caatagctac tgttgttaa                         159
```

```
SEQ ID NO: 130          moltype = AA   length = 63
FEATURE                 Location/Qualifiers
source                  1..63
                        mol_type = protein
                        organism = Lactococcus garvieae
SEQUENCE: 130
MENNNYTVLS DEELQKIDGG IGGALGNALN GLGTWANMMN GGGFVNQWQV YANKGKINQY   60
RPY                                                                63

SEQ ID NO: 131          moltype = DNA   length = 192
FEATURE                 Location/Qualifiers
source                  1..192
                        mol_type = genomic DNA
                        organism = Lactococcus garvieae
SEQUENCE: 131
atggaaaaca acaattacac agtactttca gatgaagaac tacaaaaaat tgatggtgga   60
atcggcgggg ctcttggtaa tgctctcaac ggattaggta cctgggcaaa catgatgaac  120
ggtggaggat tgttaatca gtggcaagtt tatgctaata aggaaaaat aaatcaatac    180
cgtccgtatt aa                                                     192

SEQ ID NO: 132          moltype = AA   length = 63
FEATURE                 Location/Qualifiers
source                  1..63
                        mol_type = protein
                        organism = Lactococcus garvieae
SEQUENCE: 132
MFDLVATGMA AGVAKTIVNA VSAGMDIATA LSLFSGAFTA AGGIMALIKK YAQKKLWKQL   60
IAA                                                                63

SEQ ID NO: 133          moltype = DNA   length = 192
FEATURE                 Location/Qualifiers
source                  1..192
                        mol_type = genomic DNA
                        organism = Lactococcus garvieae
SEQUENCE: 133
atgtttgatt tagtcgcgac tggaatggct gcaggtgtag caaaaactat tgttaatgcc   60
gttagtgctg gtatggatat tgccactgct ttatcattgt tctcaggagc ttttactgca  120
gctggggaa ttatggcact cattaaaaaa tatgctcaaa agaaattatg gaaacagctt   180
attgctgcat aa                                                     192

SEQ ID NO: 134          moltype = AA   length = 91
FEATURE                 Location/Qualifiers
source                  1..91
                        mol_type = protein
                        organism = Lactobacillus gasseri
SEQUENCE: 134
MVTKYGRNLG LNKVELFAIW AVLVVALLLT TANIYWIADQ FGIHLATGTA RKLLDAMASG   60
ASLGTAFAAI LGVTLPAWAL AAAGALGATA A                                 91

SEQ ID NO: 135          moltype = DNA   length = 276
FEATURE                 Location/Qualifiers
source                  1..276
                        mol_type = genomic DNA
                        organism = Lactobacillus gasseri
SEQUENCE: 135
atggttacta agtacggacg taatttaggt ttgaacaagg tagagttgtt tgcaatttgg   60
gcggttttag tagttgctct tttattgacc acagcgaaca tttattggat tgctgatcaa  120
ttcgggattc atttagcgac tggaacagcc cgtaagttat tagatgcaat ggcttctggt  180
gcctcattgg gaactgcctt tgctgctatt ttgggcgtga cattacctgc atgggctttg  240
gcagctgcag gagcattggg agcgactgca gcctag                           276

SEQ ID NO: 136          moltype = AA   length = 75
FEATURE                 Location/Qualifiers
source                  1..75
                        mol_type = protein
                        organism = Lactobacillus gasseri
SEQUENCE: 136
MKNFNTLSFE TLANIVGGRN NWAANIGGVG GATVAGWALG NAVCGPACGF VGAHYVPIAW   60
AGVTAATGGF GKIRK                                                   75

SEQ ID NO: 137          moltype = DNA   length = 228
FEATURE                 Location/Qualifiers
source                  1..228
                        mol_type = genomic DNA
                        organism = Lactobacillus gasseri
SEQUENCE: 137
atgaaaaatt ttaatacatt atcatttgaa acattggcta acatagttgg tgggagaaat   60
aattgggctc taatataggt tggagtaggt ggagcgacag tcgctggatg ggctcttgga  120
```

```
aatgcagttt gcggtcctgc ttgtggcttt gttggagcac actatgttcc aatagcatgg    180
gctggcgtaa cggcagctac tggtggattc ggaaagataa gaaagtag                 228

SEQ ID NO: 138            moltype = AA  length = 64
FEATURE                   Location/Qualifiers
source                    1..64
                          mol_type = protein
                          organism = Lactobacillus plantarum
SEQUENCE: 138
MSKLVKTLTI SEISKAQNNG GKPAWCWYTL AMCGAGYDSG TCDYMYSHCF GIKHHSSGSS    60
SYHC                                                                 64

SEQ ID NO: 139            moltype = DNA  length = 195
FEATURE                   Location/Qualifiers
source                    1..195
                          mol_type = genomic DNA
                          organism = Lactobacillus plantarum
SEQUENCE: 139
atgagtaaat tggttaagac acttactata agtgaaattt ctaaggctca aaacaacggt    60
ggaaaacctg catggtgttg gtatacttta gcaatgtgtg gtgctggtta tgattcggga   120
acctgtgatt atatgtattc gcattgtttt ggtataaagc atcatagtag tggtagtagc   180
agttatcatt gttag                                                    195

SEQ ID NO: 140            moltype = AA  length = 359
FEATURE                   Location/Qualifiers
source                    1..359
                          mol_type = protein
                          organism = Haloferax mediterranei
SEQUENCE: 140
MSKDRDGRRT SRRGTLKKIG GFSLGALSFG AVGRTQAATG SSVTTADIAP PGPNGDPKSV    60
QIDDKYTGAE MYGEGDFRVG LGTDLTMYPP VYRESLGNGS GGWEFDFTVC GSTACRFVDS   120
NGDVKEDDKA KEMWWQEINF NDINQDLYSR NDSDWVGSTP ADTQPEFDYT EPALARDGVT   180
LALTALNPAM GSLALGATYF LSDMVNWIAS QHEDDSSLKR KWDYDGLSGP LYADSSTYLL   240
ARDEMTSNSY ESFTIDNIAV AFPEPPVRTK YYVTFTAPDD PSTQSISTLE EEGIYRVPAT   300
EVAAARPPGS RRSKSAADEM VYVADPKKFI EVEPVKNPSI PDRIYEEIEQ KKKQRSRKQ    359

SEQ ID NO: 141            moltype = DNA  length = 1080
FEATURE                   Location/Qualifiers
source                    1..1080
                          mol_type = genomic DNA
                          organism = Haloferax mediterranei
SEQUENCE: 141
atgtcgaaag acagagatgg gagaaggaca gtcggcgag gcacgttaaa gaaaatcggc     60
ggtttcagtc tcggagcgct tagttttcggg gcagtcggac gaactcaagc ggcgaccggc  120
tcatcggtta cgaccgctga tatcgcacct cccggaccga acggagaccc gaagagtgtt  180
cagatagatg ataaatacac cggagccgag atgtacggcg agggtgactt cagagtcggt  240
ctcggaactg acctgacgat gtatccgccc gtgtaccgtg agagtcttgg aaatggaagc  300
gggggttggg aattcgactt caccgttgt gggtccactg cctgtcgatt tgtggacagt   360
aacggtgacg tcaaagagga cgacaaggcg aaagaaatgt ggtggcagga aattaacttc  420
aacgacataa atcaggattt atacagtcgg aacgattccg actgggtcgg gtcgacccct  480
gccgcatcc aaccggagtt cgattacacc gactttgtc tcgctcggga ggagtgacgtg  540
ctcgctctca cggcactcaa ccccgcaatg gggagtcttg cactcggtgc cacgtacttc  600
ctcagcgaca tggtgaactg gattgcgagc cagcacgaag acgacagttc gctcaagaga  660
aaatgggatt acgacgggct aagtgggccg ttgtacgccg attcgtcgac gtacctactg  720
gcacgcgacg agatgacttc gaactcgtac gaatcattca cgatcgataa catcgccgtt  780
gccttcccag agtttccccgt ccggaccaag tactacgtca cattcactgc gccggatgac  840
ccgtcaacgc agtcgatatc tacgctcgaa gaggagggaa tctaccgagt gcccgctacg  900
gaagtggctg cggccagacc accggggtcc cgacgttcca aatcggcagc cgacgagatg  960
gtgtacgttg ccgatccgaa gaagttcata gaggtcgagc cggtgaagaa cccaagtatc 1020
ccggaccgaa tctacgagga gatagagcaa aaaaagaaac aacggagtag gaaacagtag 1080

SEQ ID NO: 142            moltype = AA  length = 311
FEATURE                   Location/Qualifiers
source                    1..311
                          mol_type = protein
                          note = Haloarchaeon S8a
                          organism = unidentified
SEQUENCE: 142
MSDKDSINRR NVLRKIGGIG VASAVGFSGL ASGESLSDDE KQDVIDTIYK SQRVEQIKKK    60
FGGVNIEPKK VQSVTTNQSG DLVTAKLSVS DGDLVYSSVK DTTVIVQFDR SASEIGESWP   120
KNTEAFIKST SSGVDLLRTA TDEEIKDVTE GVNTSEIESA DAVNIFIDPE SQTYYMEKYD   180
FNNKVLEMFE LATGGTSSGK ISPTREDQNH EYNVREHKVF NSEKQNIQLQ SDCNINSNTA   240
ADVILCFNQV GSCALCSPTL VGGPVPTVAC LLVVCFGTPN AVSAILEEVD NSCFNLIKDV   300
ISCWDEWTSF W                                                       311

SEQ ID NO: 143            moltype = DNA  length = 936
FEATURE                   Location/Qualifiers
source                    1..936
                          mol_type = genomic DNA
```

```
                        note = Haloarchaeon S8a
                        organism = unidentified
SEQUENCE: 143
atgtcggata aagacagcat taacagaaga aatgtattaa gaaaaattgg cggtatcggt    60
gtggcttcag ctgtcggatt ttctggtttg gcaagcgggg aaagtcttag cgatgatgag   120
aaacaagatg ttattgacac aatttacaaa tcacaaagag ttgaacagat aaagaaaaag   180
ttcggaggag tgaatattga gccgaaaaag gttcaatctg taacgaccaa tcagagcgga   240
gatcttgtta cggcgaagct gtcggttagt gatggggatt ggtatattc gagtgtcaaa   300
gatacaactg taatagttca gttcgataga tcggcttctg aaattggtga aagttggccc   360
aagaatactg aggcattcat caaatcgacg tcctctgggg tcgatcttct acgtacagca   420
actgatgaag aaataaagga cgttactgag ggagtcaaca catctgaaat tgaatctgcg   480
gatgctgtta acatatttat tgatcctgaa tcacagacat actatatgga gaaatatgac   540
tttaataata aggtacttga gatgtttgaa ttagcgacag gtgggacaag tagtggtaaa   600
atctccccca cacgtgaaga ccagaatcac gaatatatta ttagggaaca taaagtattt   660
aactcagaaa aacagaatat acaacttcag agtgactgta atataaacag taacaccgct   720
gctgatgtta ttcatgctt caaccaggtt ggttcttgtg cactctgctc cccgacttta   780
gtcggaggtc cagtccctac agttgcatgt ctcttagtcg tctgtttcgg cactccaaat   840
gctgtgtccg cgatacttga agaagtcgat aattcttgct ttaacttgat caaggatgta   900
atttcgtgtt gggatgaatg gactagcttc tggtga                            936

SEQ ID NO: 144          moltype = AA  length = 333
FEATURE                 Location/Qualifiers
source                  1..333
                        mol_type = protein
                        organism = Lactobacillus helveticus
SEQUENCE: 144
MKHLNETTNV RILSQFDMDT GYQAVVQKGN VGSKYVYGLQ LRKGATTILR GYRGSKINNP    60
ILELSGQAGG HTQTWEFAGD RKDINGEERA GQWFIGVKPS KIEGSKIIWA KQIARVDLRN   120
QMGPHYSNTD FPRLSYLNRA GSNPFAGNKM THAEAAVSPD YTKFLIATVE NNCIGHFTIY   180
NLDTINEKLD EKGNSEDVNL ETVKYEDSFI IDNLYGDDNN SIVNSIQGYD LDNDGNIYIS   240
SQKAPDFDGS YYAHHKQIVK IPYYARSKES EDQWRAVNLS EFGGLDIPGK HSEVESIQII   300
GENHCYLTVA YHSKNKAGEN KTTLNEIYEL SWN                                333

SEQ ID NO: 145          moltype = DNA  length = 1002
FEATURE                 Location/Qualifiers
source                  1..1002
                        mol_type = genomic DNA
                        organism = Lactobacillus helveticus
SEQUENCE: 145
atgaagcatt taaatgaaac aactaatgtt agaattttaa gtcaatttga tatggatact    60
ggctatcaag cagtagttca aaaaggcaat gtaggttcaa aatatgtata tggattacaa   120
cttcgcaaag gtgctactac tatccttcgt ggttaccgtg gaagtaaaat taataaccct   180
attcttgaat tatctggtca agcaggtggt cacacacaga ctggggaatt tgctggtgat   240
cgtaaagaca ttaatggtga agaaagagca ggtcaatggt ttataggtgt aaaaccatcg   300
aaaattggag gaagcaaaat tatttgggca aagcaaattg caagagttga tcttagaaat   360
caaatgggac tcattattc aaatactgac tttcctcgat tatcctactt gaatcgcgcc   420
ggttctaatc catttgctgg taataagatg acgcatgccg aagccgcagt atcacctgat   480
tatactaagt ttttaattgc tactgttgaa aataactgta ttggtcattt tactatatac   540
aatttagata caattaatga aaacttgat gaaaagggaa atagtgaaga tgttaatctc   600
gaaactgtta aatacgaaga tagttttatc attgataatt tatatggtga tgataataat   660
tctattgtaa attcaattca agggtatgat ttggataatg atggaaatat ttatatttcc   720
agtcaaaaag cgccagattt tgatggctct tattatgcac atcataagca gattgttaag   780
attccatatt atgctcggtc taaagaaagc gaagaccaat ggagagctgt aaatttaagc   840
gaattcggtg gcttggatat tccaggtaaa catagtgaag ttgaaagcat ccaaattatt   900
ggtgagaatc attgttactt aactgttgca tcattctca aaaataaagc gggtgaaaat   960
aaaactactt tgaatgagat ttatgaatta tcttggaatt ag                     1002

SEQ ID NO: 146          moltype = AA  length = 74
FEATURE                 Location/Qualifiers
source                  1..74
                        mol_type = protein
                        organism = Enterococcus hirae
SEQUENCE: 146
MKKKVLKHCV ILGILGTCLA GIGTGIKVDA ATYYGNGLYC NKEKCWVDWN QAKGEIGKII    60
VNGWVNHGPW APRR                                                      74

SEQ ID NO: 147          moltype = DNA  length = 225
FEATURE                 Location/Qualifiers
source                  1..225
                        mol_type = genomic DNA
                        organism = Enterococcus hirae
SEQUENCE: 147
atgaaaaaga aagtattaaa acattgtgtt attctaggaa tattaggaac ttgtctagct    60
ggcatcggta caggaataaa agttgatgca gctacttact atggaaatgg tctttattgt   120
aacaaagaaa aatgttgggt agattggaat caagctaaag gagaaattgg aaaaattatt   180
gttaatggtt gggttaatca tggtccatgg gcacctagaa ggtag                   225

SEQ ID NO: 148          moltype = AA  length = 75
FEATURE                 Location/Qualifiers
```

```
                          -continued source                    1..75
                          mol_type = protein
                          organism = Lactobacillus johnsonii
SEQUENCE: 148
MKQFNYLSHK DLAVVVGGRN NWQTNVGGAV GSAMIGATVG GTICGPACAV AGAHYLPILW    60
TAVTAATGGF GKIRK                                                    75

SEQ ID NO: 149            moltype = DNA   length = 228
FEATURE                   Location/Qualifiers
source                    1..228
                          mol_type = genomic DNA
                          organism = Lactobacillus johnsonii
SEQUENCE: 149
atgaaacaat ttaattattt atcacataaa gatttagcag tcgttgttgg tggaagaaat    60
aattggcaaa caaatgtggg aggagcagtg ggatcagcta tgattgggc tacagttggt   120
ggtacaattt gtggacctgc atgtgctgta gctggtgccc attatcttcc tatttatgg   180
acagcggtta cagctgcaac aggtggtttt ggcaagataa gaaagtag               228

SEQ ID NO: 150            moltype = AA   length = 62
FEATURE                   Location/Qualifiers
source                    1..62
                          mol_type = protein
                          organism = Lactobacillus johnsonii
SEQUENCE: 150
MKLNDKELSK IVGGNRWGDT VLSAASGAGT GIKACKSFGP WGMAICGVGG AAIGGYFGYT    60
HN                                                                  62

SEQ ID NO: 151            moltype = DNA   length = 189
FEATURE                   Location/Qualifiers
source                    1..189
                          mol_type = genomic DNA
                          organism = Lactobacillus johnsonii
SEQUENCE: 151
atgaaattaa atgacaaaga attatcaaag attgttggtg gaaatcgatg gggagatact    60
gttttatcag ctgctagtgg cgcaggaact ggtattaaag catgtaaaag ttttggccca   120
tgggaatgg caatttgtgg tgtaggaggt gcagcaatag gaggttattt tggctatact   180
cataattaa                                                          189

SEQ ID NO: 152            moltype = AA   length = 59
FEATURE                   Location/Qualifiers
source                    1..59
                          mol_type = protein
                          note = subsp. lactis
                          organism = Lactococcus lactis
SEQUENCE: 152
MNKNEIETQP VTWLEEVSDQ NFDEDVFGAC STNTFSLSDY WGNNGAWCTL THECMAWCK     59

SEQ ID NO: 153            moltype = DNA   length = 180
FEATURE                   Location/Qualifiers
source                    1..180
                          mol_type = genomic DNA
                          note = subsp. lactis
                          organism = Lactococcus lactis
SEQUENCE: 153
atgaacaaaa atgaaattga aacacaacca gttacatggt tggaagaagt atctgatcaa    60
aattttgatg aagatgtatt tggtgcgtgt agtactaaca cattctcgct cagtgattac   120
tggggaaata acggggcttg gtgtacactc actcatgaat gtatggcttg gtgtaaataa   180

SEQ ID NO: 154            moltype = AA   length = 65
FEATURE                   Location/Qualifiers
source                    1..65
                          mol_type = protein
                          note = subsp. lactis
                          organism = Lactococcus lactis
SEQUENCE: 154
MKEKNMKKND TIELQLGKYL EDDMIELAEG DESHGGTTPA TPAISILSAY ISTNTCPTTK    60
CTRAC                                                               65

SEQ ID NO: 155            moltype = DNA   length = 198
FEATURE                   Location/Qualifiers
source                    1..198
                          mol_type = genomic DNA
                          note = subsp. lactis
                          organism = Lactococcus lactis
SEQUENCE: 155
atgaagaaa aaatatgaa aagaatgac actattgaat tacaattggg aaatacctt       60
gaagatgata tgattgaatt agctgaaggg gatgagtctc atggaggaac aacaccagca   120
actcctgcaa tctctattct cagtgcatat attagtacca atacttgtcc aacaacaaaa   180
tgtacacgtg cttgttaa                                                198
```

```
SEQ ID NO: 156         moltype = AA  length = 51
FEATURE                Location/Qualifiers
source                 1..51
                       mol_type = protein
                       note = subsp. lactis
                       organism = Lactococcus lactis
SEQUENCE: 156
MKEQNSFNLL QEVTESELDL ILGAKGGSGV IHTISHECNM NSWQFVFTCC S         51

SEQ ID NO: 157         moltype = DNA  length = 156
FEATURE                Location/Qualifiers
source                 1..156
                       mol_type = genomic DNA
                       note = subsp. lactis
                       organism = Lactococcus lactis
SEQUENCE: 157
atgaaagaac aaaactcttt taatcttctt caagaagtga cagaaagtga attggacctt    60
attttaggtg caaaaggcgg cagtggagtt attcatacaa tttctcatga atgtaatatg   120
aatagctggc aatttgtatt tacttgctgc tcttaa                             156

SEQ ID NO: 158         moltype = AA  length = 53
FEATURE                Location/Qualifiers
source                 1..53
                       mol_type = protein
                       organism = Lactococcus lactis
SEQUENCE: 158
MAGFLKVVQL LAKYGSKAVQ WAWANKGKIL DWLNAGQAID WVVSKIKQIL GIK         53

SEQ ID NO: 159         moltype = DNA  length = 162
FEATURE                Location/Qualifiers
source                 1..162
                       mol_type = genomic DNA
                       organism = Lactococcus lactis
SEQUENCE: 159
atggcagggt ttttaaaagt agttcaatta ctagctaaat atggttctaa agctgtacaa    60
tgggcttggg caaacaaggg taagatttta gattggctta atgcaggtca ggctattgat   120
tgggtagttt cgaaaattaa gcaaatttta ggtattaagt aa                      162

SEQ ID NO: 160         moltype = AA  length = 53
FEATURE                Location/Qualifiers
source                 1..53
                       mol_type = protein
                       organism = Lactococcus lactis
SEQUENCE: 160
MAGFLKVVQI LAKYGSKAVQ WAWANKGKIL DWINAGQAID WVVEKIKQIL GIK         53

SEQ ID NO: 161         moltype = DNA  length = 162
FEATURE                Location/Qualifiers
source                 1..162
                       mol_type = genomic DNA
                       organism = Lactococcus lactis
SEQUENCE: 161
atggcagggt ttttaaaagt agtccaaatt ttggctaagt atggttctaa agccgtacaa    60
tgggcatggg caaataaagg aaaaatctta gattggatta atgcaggtca agctattgac   120
tgggtagttg aaaagattaa gcaaattttg ggtattaat aa                       162

SEQ ID NO: 162         moltype = AA  length = 65
FEATURE                Location/Qualifiers
source                 1..65
                       mol_type = protein
                       organism = Lactobacillus amylovorus
SEQUENCE: 162
MKQLNSEQLQ NIIGGNRWTN AYSAALGCAV PGVKYGKKLG GVWGAVIGGV GGAAVCGLAG    60
YVRKG                                                               65

SEQ ID NO: 163         moltype = DNA  length = 198
FEATURE                Location/Qualifiers
source                 1..198
                       mol_type = genomic DNA
                       organism = Lactobacillus amylovorus
SEQUENCE: 163
atgaaacaat tgaattcaga acaattacaa aatattatcg gtggaaatag atggactaat    60
gcatacagcg cagctttggg atgcgctgtc cctggagtta aatatggaaa aaaacttggt   120
ggcgtatggg gtgctgtaat tggtggcgta ggcggtgcag cagtctgtgg cttggcgggt   180
tatgttcgta aaggctaa                                                 198

SEQ ID NO: 164         moltype = AA  length = 68
FEATURE                Location/Qualifiers
```

```
source                  1..68
                        mol_type = protein
                        note = L45
                        organism = Lactobacillus sakei
SEQUENCE: 164
MKTEKKVLDE LSLHASAKMG ARDVESSMNA DSTPVLASVA VSMELLPTAS VLYSDVAGCF    60
KYSAKHHC                                                             68

SEQ ID NO: 165          moltype = DNA   length = 207
FEATURE                 Location/Qualifiers
source                  1..207
                        mol_type = genomic DNA
                        note = L45
                        organism = Lactobacillus sakei
SEQUENCE: 165
atgaaaacag aaaaaaaggt tttagatgaa ctgagcttac acgcttctgc aaaaatggga    60
gcacgtgatg ttgaatccag catgaatgca gactcaacac cagttttagc atcagtcgct   120
gtatccatgg aattattgcc aactgcgtct gttcttatt cggatgttgc aggttgcttc    180
aaatattctg caaaacatca ttgttag                                       207

SEQ ID NO: 166          moltype = AA   length = 91
FEATURE                 Location/Qualifiers
source                  1..91
                        mol_type = protein
                        note = subsp. lactis
                        organism = Lactococcus lactis
SEQUENCE: 166
MKTKSLVLAL SAVTLFSAGG IVAQAEGTWQ HGYGVSSAYS NYHHGSKTHS ATVVNNNTGR    60
QGKDTQRAGV WAKATVGRNL TEKASFYYNF W                                   91

SEQ ID NO: 167          moltype = DNA   length = 276
FEATURE                 Location/Qualifiers
source                  1..276
                        mol_type = genomic DNA
                        note = subsp. lactis
                        organism = Lactococcus lactis
SEQUENCE: 167
atgaaaacca agtctctcgt attggcatta tctgcggtta cgttattctc tgccggagga    60
attgtagctc aagctgaagg aacatggcaa catggatatg gtgttagttc ggcatattca   120
aattatcatc atggtagcaa aactcattca gccacagttg taaataataa tactggccga   180
caaggtaagg atacacaacg tgccggtgtt tgggcaaaag ctactgttgg acgtaactta   240
actgaaaaag cttcatttta ttataacttt tggtaa                             276

SEQ ID NO: 168          moltype = AA   length = 75
FEATURE                 Location/Qualifiers
source                  1..75
                        mol_type = protein
                        note = subsp. cremoris
                        organism = Lactococcus lactis
SEQUENCE: 168
MKNQLNFNIV SDEELSEANG GKLTFIQSTA AGDLYYNTNT HKYVYQQTQN AFGAAANTIV    60
NGWMGGAAGG FGLHH                                                     75

SEQ ID NO: 169          moltype = DNA   length = 228
FEATURE                 Location/Qualifiers
source                  1..228
                        mol_type = genomic DNA
                        note = subsp. cremoris
                        organism = Lactococcus lactis
SEQUENCE: 169
atgaaaaatc aattaaattt taatattgtt tcagatgaag aactttcaga agctaacgga    60
ggaaaattaa catttattca atcgacagcg gctggagatt tatattacaa tactaataca   120
cacaaatatg tttaccaaca aactcaaaac gcttttgggg ctgctgctaa taccattgtt   180
aatggatgga tgggtggcgc tgctggaggt ttcgggttgc accattga               228

SEQ ID NO: 170          moltype = AA   length = 68
FEATURE                 Location/Qualifiers
source                  1..68
                        mol_type = protein
                        note = subsp. cremoris
                        organism = Lactococcus lactis
SEQUENCE: 170
MKNQLNFNIV SDEELAEVNG GSLQYVMSAG PYTWYKDTRT GKTICKQTID TASYTFGVMA    60
EGWGKTFH                                                             68

SEQ ID NO: 171          moltype = DNA   length = 207
FEATURE                 Location/Qualifiers
source                  1..207
                        mol_type = genomic DNA
```

```
                            note = subsp. cremoris
                            organism = Lactococcus lactis
SEQUENCE: 171
atgaaaaatc aattaaattt taatattgtt tctgatgaag aacttgcaga agttaatgga     60
ggaagcttgc agtatgttat gagtgctgga ccatatactt ggtataaaga tactagaaca    120
ggaaaaacaa tatgtaaaca gacaattgac acagcaagtt atacatttgg tgtaatggca    180
gaaggatggg gaaaaacatt ccactaa                                        207

SEQ ID NO: 172          moltype = AA   length = 63
FEATURE                 Location/Qualifiers
source                  1..63
                        mol_type = protein
                        note = QU 12
                        organism = Lactococcus sp.
SEQUENCE: 172
MKLIDHLGAP RWAVDTILGA IAVGNLASWV LALVPGPGWA VKAGLATAAA IVKHQGKAAA     60
AAW                                                                   63

SEQ ID NO: 173          moltype = DNA   length = 192
FEATURE                 Location/Qualifiers
source                  1..192
                        mol_type = genomic DNA
                        note = QU 12
                        organism = Lactococcus sp.
SEQUENCE: 173
atgaaattaa ttgatcattt aggtgctcca agatgggccg ttgatactat tttaggtgca     60
atcgcagttg ggaacttagc aagttgggtt ctagcgcttg tccctggtcc agggtgggca    120
gtaaaagctg gtttagcaac tgctgctgcc atcgttaaac atcaaggtaa agctgccgct    180
gctgcttggt aa                                                        192

SEQ ID NO: 174          moltype = AA   length = 50
FEATURE                 Location/Qualifiers
source                  1..50
                        mol_type = protein
                        note = GI-9
                        organism = Brevibacillus sp.
SEQUENCE: 174
MACQCPDAIS GWTHTDYQCH GLENKMYRHV YAICMNGTQV YCRTEWGSSC                 50

SEQ ID NO: 175          moltype = DNA   length = 153
FEATURE                 Location/Qualifiers
source                  1..153
                        mol_type = genomic DNA
                        note = GI-9
                        organism = Brevibacillus sp.
SEQUENCE: 175
atggcttgcc aatgtccaga tgcgatctca ggttggacgc atacagatta ccagtgtcac     60
ggttttggaga ataaaatgta tagacatgtt tatgcaattt gcatgaacgg tactcaagta   120
tattgcagaa cagagtgggg tagcagctgc tag                                 153

SEQ ID NO: 176          moltype = AA   length = 57
FEATURE                 Location/Qualifiers
source                  1..57
                        mol_type = protein
                        organism = Leuconostoc pseudomesenteroides
SEQUENCE: 176
MNKEYNSISN FKKITNKDLQ NINGGFIGRA IGDFVYFGAK GLRESGKLLN YYYKHKH         57

SEQ ID NO: 177          moltype = DNA   length = 174
FEATURE                 Location/Qualifiers
source                  1..174
                        mol_type = genomic DNA
                        organism = Leuconostoc pseudomesenteroides
SEQUENCE: 177
atgaataaag aatataatag cattagcaat tttaaaaaaa ttactaataa agacttgcaa     60
aacataaatg gtggatttat tggtagggca ataggtgact tgtgtacttt ggagcgaag    120
ggactaagag aatctggtaa actacttaat tattactata agcataagca ttga           174

SEQ ID NO: 178          moltype = AA   length = 53
FEATURE                 Location/Qualifiers
source                  1..53
                        mol_type = protein
                        organism = Leuconostoc pseudomesenteroides
SEQUENCE: 178
MKNQLMSFEV ISEKELSTVQ GGKGLGKLIG IDWLLGQAKD AVKQYKKDYK RWH             53

SEQ ID NO: 179          moltype = DNA   length = 162
FEATURE                 Location/Qualifiers
source                  1..162
```

```
                                mol_type = genomic DNA
                                organism = Leuconostoc pseudomesenteroides
SEQUENCE: 179
atgaaaaatc agttaatgtc tttcgaagtg atatcagaaa aagaattgtc cacggtacaa   60
ggtggcaaag gcttaggtaa actcatagga attgattggc ttttgggtca agctaaggac  120
gctgttaaac agtacaagaa ggattacaaa cgttggcact aa                     162

SEQ ID NO: 180                  moltype = AA   length = 61
FEATURE                         Location/Qualifiers
source                          1..61
                                mol_type = protein
                                organism = Leuconostoc gelidum
SEQUENCE: 180
MMNMKPTESY EQLDNSALEQ VVGGKYYGNG VHCTKSGCSV NWGEAFSAGV HRLANGGNGF    60
W                                                                   61

SEQ ID NO: 181                  moltype = DNA   length = 186
FEATURE                         Location/Qualifiers
source                          1..186
                                mol_type = genomic DNA
                                organism = Leuconostoc gelidum
SEQUENCE: 181
atgatgaaca tgaaacctac ggaaagctat gagcaattgg ataatagtgc tctcgaacaa   60
gtcgtaggag gtaagtatta tggtaacgga gttcattgca caaaaagtgg ttgttctgta  120
aactggggag aagcctttc agctggagta catcgtttag caaatggtgg aaatggtttc  180
tggtaa                                                              186

SEQ ID NO: 182                  moltype = AA   length = 61
FEATURE                         Location/Qualifiers
source                          1..61
                                mol_type = protein
                                organism = Leuconostoc carnosum
SEQUENCE: 182
MNNMKSADNY QQLDNNALEQ VVGGKYYGNG VHCTKSGCSV NWGEAFSAGV HRLANGGNGF    60
W                                                                   61

SEQ ID NO: 183                  moltype = DNA   length = 186
FEATURE                         Location/Qualifiers
source                          1..186
                                mol_type = genomic DNA
                                organism = Leuconostoc carnosum
SEQUENCE: 183
atgaataaca tgaaatctgc ggataattat cagcaattgg ataataatgc tctcgaacaa   60
gtcgtaggag gtaagtatta tggtaacgga gttcattgca caaaaagtgg ttgttctgta  120
aactggggag aagcctttc agctggagta catcgtttag caaatggtgg aaatggtttc  180
tggtaa                                                              186

SEQ ID NO: 184                  moltype = AA   length = 63
FEATURE                         Location/Qualifiers
source                          1..63
                                mol_type = protein
                                organism = Leuconostoc mesenteroides
SEQUENCE: 184
MFLVNQLGIS KSLANTILGA IAVGNLASWL LALVPGPGWA TKAALATAET IVKHEGKAAA    60
IAW                                                                 63

SEQ ID NO: 185                  moltype = DNA   length = 192
FEATURE                         Location/Qualifiers
source                          1..192
                                mol_type = genomic DNA
                                organism = Leuconostoc mesenteroides
SEQUENCE: 185
atgttcttgg taaatcagtt agggatttca aaatcgttag ctaatactat tcttggtgca   60
attgctgttg gtaatttggc cagttggtta ttagcttggg ttcctggtcc gggttgggca  120
acaaaagcag cacttgcgac agctgaaaca attgtgaagc atgaaggaaa agcagctgct  180
attgcgtggt aa                                                       192

SEQ ID NO: 186                  moltype = AA   length = 74
FEATURE                         Location/Qualifiers
source                          1..74
                                mol_type = protein
                                organism = Bacillus licheniformis
SEQUENCE: 186
MSKKEMILSW KNPMYRTESS YHPAGNILKE LQEEEQHSIA GGTITLSTCA ILSKPLGNNG    60
YLCTVTKECM PSCN                                                     74

SEQ ID NO: 187                  moltype = DNA   length = 225
FEATURE                         Location/Qualifiers
source                          1..225
```

```
                        mol_type = genomic DNA
                        organism = Bacillus licheniformis
SEQUENCE: 187
atgtcaaaaa aggaaatgat tctttcatgg aaaaatccta tgtatcgcac tgaatcttct    60
tatcatccag cagggaacat ccttaaagaa ctccagaaag aggaacagca cagcatcgcc   120
ggaggcacaa tcacgctcag cacttgtgcc atcttgagca agccgttagg aaataacgga   180
tacctgtgta cagtgacaaa agaatgcatg ccaagctgta actaa                   225

SEQ ID NO: 188         moltype = AA  length = 266
FEATURE                Location/Qualifiers
source                 1..266
                       mol_type = protein
                       organism = Brevibacterium linens
SEQUENCE: 188
MNNLYRELAP IPGPAWAEIE EEARRTFKRN IAGRRIVDVA GPTGFETSAV TTGHIRDVQS    60
ETSGLQVKQR IVQEYIELRT PFVTRQAID DVARGSGDSD WQPVKDAATT IAMAEDRAIL    120
HGLDAAGIGG IVPGSSNAAV AIPDAVEDFA DAVAQALSVL RTVGVDGPYS LLLSSAEYTK   180
VSESTDHGYP IREHLSRQLG AGEIIWAPAL EGALLVSTRG GDYELHLGQD LSIGYYSHDS   240
ETVELYLQET FGFLALTDES SVPLSL                                        266

SEQ ID NO: 189         moltype = DNA  length = 801
FEATURE                Location/Qualifiers
source                 1..801
                       mol_type = genomic DNA
                       organism = Brevibacterium linens
SEQUENCE: 189
gtgaataacc tctatcgcga gcttgccccc atccccggcc cggcctgggc ggagatcgag    60
gaggaggctc gacggacatt caaacgcaat atcgccggcc gccggatcgt cgatgtcgca   120
gggcccacgg gcttcgagac ctccgcggtg accactggcc acatccgaga cgtccagtcg   180
gagacgagcg gactgcaggt taagcagcgc atcgtgcagg aatacatcga gctgcggacc   240
ccattcaccg tgactcggca ggccatcgat gacgtggccc gcgggtccgg tgactcggac   300
tggcagcccg tcaaggatgc ggccacgacg atcgcgatgg ctgaagatcg ggccattctc   360
cacgggctcg atgcggccgg gatcggcgga atcgttcccg gcagctcgaa tgccgcagtg   420
gccatcccg acgccgtcga ggacttcgcc gacgccgtcg cccaggcgct gagtgtgctg   480
cgcacggtcg gagtcgacgg gccctacagc ctgttgctct cctccgcgga gtacaccaag   540
gtctccgagt ccaccgacca cggctacccg atccgcgagc acctctcccg gcagctcggc   600
gccggagaga tcatctgggc gcccgcgctc aaggggcgc tgctcgtctc cacgcgcggg   660
ggtgactacg agctccacct cggccaggac ctgtcgatcg gttactacag ccacgacagc   720
gagaccgtcg aactctatct gcaggagacc ttcggattcc tcgcgctgac cgacgaatcc   780
agtgtgcctt tgagcctctg a                                             801

SEQ ID NO: 190         moltype = AA  length = 71
FEATURE                Location/Qualifiers
source                 1..71
                       mol_type = protein
                       organism = Listeria innocua
SEQUENCE: 190
MKKAALKFII VIAILGFSFS FFSIQSEAKS YGNGVQCNKK KCWVDWGSAI STIGNNSAAN    60
WATGGAAGWK S                                                         71

SEQ ID NO: 191         moltype = DNA  length = 216
FEATURE                Location/Qualifiers
source                 1..216
                       mol_type = genomic DNA
                       organism = Listeria innocua
SEQUENCE: 191
ttgaagaagg cagcgttaaa atttattatt gttattgcta ttctaggttt cagttttctt    60
ttctttagca tacaatctga agctaaatct tatggaaatg gagttcagtg taataagaaa   120
aaatgttggg tagattgggg tagtgctata agtactattg gaaataattc tgcagcgaat   180
tgggctacag gtggagcagc tggttggaaa agctga                             216

SEQ ID NO: 192         moltype = AA  length = 68
FEATURE                Location/Qualifiers
source                 1..68
                       mol_type = protein
                       organism = Bacillus sp.
SEQUENCE: 192
MSQEAIIRSW KDPFSRENST QNPAGNPFSE LKEAQMDKLV GAGDMEAACT FTLPGGGGVC    60
TLTSECIC                                                             68

SEQ ID NO: 193         moltype = DNA  length = 207
FEATURE                Location/Qualifiers
source                 1..207
                       mol_type = genomic DNA
                       organism = Bacillus sp.
SEQUENCE: 193
atgagtcaag aagctatcat tcgttcatgg aaagatcctt tttcccgtga aaattctaca    60
caaaatccag ctggtaaccc attcagtgag ctgaaagaag cacaaatgga taagttagta   120
ggtgcgggag acatggaagc agcatgtact tttacattgc ctggtggcgg cggtgtttgt   180
```

```
actctaactt ctgaatgtat ttgttaa                                         207

SEQ ID NO: 194          moltype = AA   length = 61
FEATURE                 Location/Qualifiers
source                  1..61
                        mol_type = protein
                        organism = Leuconostoc mesenteroides
SEQUENCE: 194
MTNMKSVEAY QQLDNQNLKK VVGGKYYGNG VHCTKSGCSV NWGEAASAGI HRLANGGNGF     60
W                                                                     61

SEQ ID NO: 195          moltype = DNA   length = 186
FEATURE                 Location/Qualifiers
source                  1..186
                        mol_type = genomic DNA
                        organism = Leuconostoc mesenteroides
SEQUENCE: 195
atgacgaata tgaagtctgt ggaagcatat cagcaattag ataaccagaa tctcaagaaa     60
gttgttggtg gaaagtatta tgggaatggt gttcactgta caaaaagtgg atgctctgtt    120
aactggggag aagctgcctc agctggcata catcgtttgg ccaatggtgg aaatggattt    180
tggtaa                                                               186

SEQ ID NO: 196          moltype = AA   length = 68
FEATURE                 Location/Qualifiers
source                  1..68
                        mol_type = protein
                        note = subsp. michiganensis
                        organism = Clavibacter michiganensis
SEQUENCE: 196
MNDILETETP VMVSPRWDML LDAGEDTSPS VQTQIDAEFR RVVSPYMSSS GWLCTLTIEC     60
GTIICACR                                                              68

SEQ ID NO: 197          moltype = DNA   length = 207
FEATURE                 Location/Qualifiers
source                  1..207
                        mol_type = genomic DNA
                        note = subsp. michiganensis
                        organism = Clavibacter michiganensis
SEQUENCE: 197
atgaacgaca tcctcgagac ggagaccccc gtcatggtca gccccggtg ggacatgctg      60
ctcgacgcgg gcgaggacac cagcccgtcc gtccagaccc agatcgacgc ggagttccgt    120
cgcgtcgtga gcccgtacat gtccagcagc ggctggctct gcacgctcac catcgaatgt    180
ggcaccatca tctgcgcgtg tcgctga                                        207

SEQ ID NO: 198          moltype = AA   length = 69
FEATURE                 Location/Qualifiers
source                  1..69
                        mol_type = protein
                        organism = Escherichia coli
SEQUENCE: 198
MELKASEFGV VLSVDALKLS RQSPLGVGIG GGGGGGGGGS CGGQGGGCGG CSNGCSGGNG     60
GSGGSGSHI                                                             69

SEQ ID NO: 199          moltype = DNA   length = 207
FEATURE                 Location/Qualifiers
source                  1..207
                        mol_type = genomic DNA
                        organism = Escherichia coli
SEQUENCE: 199
atggaattaa aagcgagtga atttggtgta gttttgtccg ttgatgctct taaattatca     60
cgccagtctc cattaggtgt tggcattggt ggtggtggcg gcggcggcgg cggcggtagc    120
tgcggtggtc aaggtggcgg ttgtggtggt tgcagcaacg gttgtagtgg tggaaacggt    180
ggcagcggcg gaagtggttc acatatc                                        207

SEQ ID NO: 200          moltype = AA   length = 7
FEATURE                 Location/Qualifiers
source                  1..7
                        mol_type = protein
                        organism = Escherichia coli
SEQUENCE: 200
MRTGNAN                                                                7

SEQ ID NO: 201          moltype = DNA   length = 24
FEATURE                 Location/Qualifiers
source                  1..24
                        mol_type = genomic DNA
                        organism = Escherichia coli
SEQUENCE: 201
atgcgtactg gtaatgcaaa ctaa                                            24
```

```
SEQ ID NO: 202          moltype = AA   length = 99
FEATURE                 Location/Qualifiers
source                  1..99
                        mol_type = protein
                        organism = Klebsiella pneumoniae
SEQUENCE: 202
MREISQKDLN LAFGAGETDP NTQLLNDLGN NMAWGAALGA PGGLGSAALG AAGGALQTVG    60
QGLIDHGPVN VPIPVLIGPS WNGSGSGYNS ATSSSGSGS                          99

SEQ ID NO: 203          moltype = DNA  length = 300
FEATURE                 Location/Qualifiers
source                  1..300
                        mol_type = genomic DNA
                        organism = Klebsiella pneumoniae
SEQUENCE: 203
atgagagaaa ttagtcaaaa ggacttaaat cttgcttttg gtgcaggaga gaccgatcca    60
aatactcaac ttctaaacga ccttggaaat aaatatggca gggggtgctgc tcttggcgct  120
cctggcggat taggatcagc agctttgggg gccgcgggag gtgcattaca aactgtaggg   180
caaggattaa ttgaccatgg tcctgtaaat gtccccatcc ctgtactcat cgggccaagc   240
tggaatggta gcggtagtgg ttataacagc gcaacatcca gttccggtag tggtagttaa   300

SEQ ID NO: 204          moltype = AA   length = 75
FEATURE                 Location/Qualifiers
source                  1..75
                        mol_type = protein
                        organism = Escherichia coli
SEQUENCE: 204
MREITESQLR YISGAGGAPA TSANAAGAAA IVGALAGIPG GPLGVVVGAV SAGLTTAIGS    60
TVGSGSASSS AGGGS                                                    75

SEQ ID NO: 205          moltype = DNA  length = 228
FEATURE                 Location/Qualifiers
source                  1..228
                        mol_type = genomic DNA
                        organism = Escherichia coli
SEQUENCE: 205
atgcgagaaa taacagaatc acagttaaga tatatttccg gggcgggagg tgcgccagcg    60
acttcagcta atgccgcagg tgctgcagct attgttggag ctctcgcggg aatacctggt   120
ggtccacttg gggttgtagt tggagccgta tctgccggtt tgacaacagc aattggctcg   180
accgtgggaa gtggtagtgc cagttcttct gctggtggcg gtagctaa                228

SEQ ID NO: 206          moltype = AA   length = 58
FEATURE                 Location/Qualifiers
source                  1..58
                        mol_type = protein
                        organism = Escherichia coli
SEQUENCE: 206
MIKHFHFNKL SSGKKNNVPS PAKGVIQIKK SASQLTKGGA GHVPEYFVGI GTPISFYG      58

SEQ ID NO: 207          moltype = DNA  length = 177
FEATURE                 Location/Qualifiers
source                  1..177
                        mol_type = genomic DNA
                        organism = Escherichia coli
SEQUENCE: 207
atgattaagc attttcattt taataaactg tcttctggta aaaaaaataa tgttccatct    60
cctgcaaagg gggttataca aataaaaaaa tcagcatcgc aactcacaaa aggtggtgca   120
ggacatgtgc ctgagtattt tgtggggatt ggtacaccta tctttcta tggctga        177

SEQ ID NO: 208          moltype = AA   length = 90
FEATURE                 Location/Qualifiers
source                  1..90
                        mol_type = protein
                        organism = Escherichia coli
SEQUENCE: 208
MYMRELDREE LNCVGGAGDP LADPNSQIVR QIMSNAAWGP PLVPERFRGM AVGAAGGVTQ    60
TVLQGAAAHM PVNVPIPKVP MGPSWNGSKG                                    90

SEQ ID NO: 209          moltype = DNA  length = 273
FEATURE                 Location/Qualifiers
source                  1..273
                        mol_type = genomic DNA
                        organism = Escherichia coli
SEQUENCE: 209
atgtatatga gagagttaga tagagaggaa ttaaattgcg ttggtggggc tggagatccg    60
cttgcagatc ctaattccca aattgtaaga cagataatgt ctaatgcggc atggggcccg   120
cctttggtgc cagagcggtt tagggggaatg gctgttggag ccgcaggtgg ggttacgcag  180
acagttcttc aaggagcagc agctcatatg ccggttaatg tccctatacc taagttccg    240
```

```
atgggaccct catggaacgg aagtaaagga taa                              273

SEQ ID NO: 210          moltype = AA  length = 50
FEATURE                 Location/Qualifiers
source                  1..50
                        mol_type = protein
                        organism = Enterococcus mundtii
SEQUENCE: 210
MSQVVGGKYY GNGVSCNKKG CSVDWGKAIG IIGNNSAANL ATGGAAGWKS            50

SEQ ID NO: 211          moltype = DNA  length = 153
FEATURE                 Location/Qualifiers
source                  1..153
                        mol_type = genomic DNA
                        organism = Enterococcus mundtii
SEQUENCE: 211
atgtcacagg tagtaggtgg aaaatactac ggtaatggag tctcatgtaa taaaaaggg  60
tgcagtgttg attggggaaa agcgattggc attattggaa ataattctgc tgcgaattta 120
gctactggtg gagcagctgg ttggaaaagt taa                             153

SEQ ID NO: 212          moltype = AA  length = 58
FEATURE                 Location/Qualifiers
source                  1..58
                        mol_type = protein
                        organism = Enterococcus mundtii
SEQUENCE: 212
MKKLTSKEMA QVVGGKYYGN GLSCNKKGCS VDWGKAIGII GNNSAANLAT GGAAGWKS   58

SEQ ID NO: 213          moltype = DNA  length = 177
FEATURE                 Location/Qualifiers
source                  1..177
                        mol_type = genomic DNA
                        organism = Enterococcus mundtii
SEQUENCE: 213
ttgaagaaat taacatcaaa agaaatggca caagtagtag gtgggaaata ctacggtaat 60
ggattatcat gtaataaaaa agggtgcagt gttgattggg gaaaagctat tggcattatt 120
ggaaataatt ctgctgcgaa tttagctact ggtggagcag ctggttggaa aagttaa    177

SEQ ID NO: 214          moltype = AA  length = 63
FEATURE                 Location/Qualifiers
source                  1..63
                        mol_type = protein
                        organism = Streptococcus mutans
SEQUENCE: 214
MSNTQLLEVL GTETFDVQED LFAFDTTDTT IVASNDDPDT RFKSWSLCTP GCARTGSFNS 60
YCC                                                              63

SEQ ID NO: 215          moltype = DNA  length = 192
FEATURE                 Location/Qualifiers
source                  1..192
                        mol_type = genomic DNA
                        organism = Streptococcus mutans
SEQUENCE: 215
atgtcaaaca cacaattatt agaagtcctt ggtactgaaa cttttgatgt tcaagaagat 60
ctcttttgctt ttgatacaac agatactact attgtggcaa gcaacgacga tccagatact 120
cgtttcaaaa gttggagcct ttgtacgcct ggttgtgcaa ggacaggtag tttcaatagt 180
tactgttgct ga                                                    192

SEQ ID NO: 216          moltype = AA  length = 53
FEATURE                 Location/Qualifiers
source                  1..53
                        mol_type = protein
                        organism = Streptococcus mutans
SEQUENCE: 216
MNKLNSNAVV SLNEVSDSEL DTILGGNRWW QGVVPTVSYE CRMNSWQHVF TCC        53

SEQ ID NO: 217          moltype = DNA  length = 162
FEATURE                 Location/Qualifiers
source                  1..162
                        mol_type = genomic DNA
                        organism = Streptococcus mutans
SEQUENCE: 217
atgaacaagt taaacagtaa cgcagtagtt tctttgaatg aagtttcaga ttctgaattg 60
gatactattt tgggtggtaa tcgttggtgg caaggtgttg tgccaacggt ctcatatgag 120
tgtcgcatga attcatggca acatgttttc acttgctgtt aa                   162

SEQ ID NO: 218          moltype = AA  length = 57
FEATURE                 Location/Qualifiers
source                  1..57
```

```
                        mol_type = protein
                        note = subsp. lactis
                        organism = Lactococcus lactis
SEQUENCE: 218
MSTKDFNLDL VSVSKKDSGA SPRITSISLC TPGCKTGALM GCNMKTATCH CSIHVSK        57

SEQ ID NO: 219          moltype = DNA   length = 174
FEATURE                 Location/Qualifiers
source                  1..174
                        mol_type = genomic DNA
                        note = subsp. lactis
                        organism = Lactococcus lactis
SEQUENCE: 219
atgagtacaa aagattttaa cttggatttg gtatctgttt cgaagaaaga ttcaggtgca     60
tcaccacgca ttacaagtat ttcgctatgt acacccggtt gtaaaacagg agctctgatg    120
ggttgtaaca tgaaaacagc aacttgtcat tgtagtattc acgtaagcaa ataa          174

SEQ ID NO: 220          moltype = AA    length = 57
FEATURE                 Location/Qualifiers
source                  1..57
                        mol_type = protein
                        organism = Lactococcus lactis
SEQUENCE: 220
MSTKDFNLDL VSVSKKDSGA SPRITSISLC TPGCKTGALM GCNMKTATCN CSVHVSK        57

SEQ ID NO: 221          moltype = DNA   length = 171
FEATURE                 Location/Qualifiers
source                  1..171
                        mol_type = genomic DNA
                        organism = Lactococcus lactis
SEQUENCE: 221
atgagtacaa aagattttaa cttggatttg gtatctgttt cgaagaaaga ttcaggtgca     60
tcaccacgca ttacaagtat ttcgctatgt acacccggtt gtaaaacagg agctctgatg    120
ggttgtaaca tgaaaacagc aacttgtaat tgtagcgttc acgtaagcaa a             171

SEQ ID NO: 222          moltype = AA    length = 57
FEATURE                 Location/Qualifiers
source                  1..57
                        mol_type = protein
                        organism = Lactococcus lactis
SEQUENCE: 222
MSTKDFNLDL VSVSKTDSGA STRITSISLC TPGCKTGVLM GCNLKTATCN CSVHVSK        57

SEQ ID NO: 223          moltype = DNA   length = 174
FEATURE                 Location/Qualifiers
source                  1..174
                        mol_type = genomic DNA
                        organism = Lactococcus lactis
SEQUENCE: 223
atgagtacaa aagattttaa cttagatttg gtatctgttt caaaaacaga ttctggcgct     60
tcaacacgta ttaccagcat ttcgctttgt acaccaggtt gtaaaacagg tgttctgatg    120
ggatgtaacc tgaaaacagc aacttgtaat tgtagcgttc acgtaagcaa ataa          174

SEQ ID NO: 224          moltype = AA    length = 55
FEATURE                 Location/Qualifiers
source                  1..55
                        mol_type = protein
                        organism = Streptococcus uberis
SEQUENCE: 224
MNNEDFNLDL IKISKENNSG ASPRITSKSL CTPGCKTGIL MTCPLKTATC GCHFG          55

SEQ ID NO: 225          moltype = DNA   length = 168
FEATURE                 Location/Qualifiers
source                  1..168
                        mol_type = genomic DNA
                        organism = Streptococcus uberis
SEQUENCE: 225
atgaacaatg aagattttaa tttggatctc atcaaaatct caaaggaaaa caactcagga     60
gcttcacctc gaataactag taaatcatta tgtactcctg gatgtaagac gggtattttg    120
atgacttgtc cactaaaaac tgcaacctgt ggttgtcatt ttggataa                 168

SEQ ID NO: 226          moltype = AA    length = 57
FEATURE                 Location/Qualifiers
source                  1..57
                        mol_type = protein
                        note = subsp. lactis
                        organism = Lactococcus lactis
SEQUENCE: 226
MSTKDFNLDL VSVSKKDSGA SPRITSISLC TPGCKTGALM GCNMKTATCN CSIHVSK        57
```

```
SEQ ID NO: 227         moltype = DNA   length = 174
FEATURE                Location/Qualifiers
source                 1..174
                       mol_type = genomic DNA
                       note = subsp. lactis
                       organism = Lactococcus lactis
SEQUENCE: 227
atgagtacaa aagattttaa cttggatttg gtatctgttt cgaagaaaga ttcaggtgca    60
tcaccacgca ttacaagtat ttcgctatgt acaccggtt gtaaaacagg agctctgatg   120
ggttgtaaca tgaaaacagc aacttgtaat tgtagtattc acgtaagcaa ataa         174

SEQ ID NO: 228         moltype = AA   length = 57
FEATURE                Location/Qualifiers
source                 1..57
                       mol_type = protein
                       organism = Staphylococcus warneri
SEQUENCE: 228
MENSKVMKDI EVANLLEEVQ EDELNEVLGA KKKSGVIPTV SHDCHMNSFQ FVFTCCS      57

SEQ ID NO: 229         moltype = DNA   length = 174
FEATURE                Location/Qualifiers
source                 1..174
                       mol_type = genomic DNA
                       organism = Staphylococcus warneri
SEQUENCE: 229
atggaaaatt ctaaagttat gaaggacatt gaagtagcaa atttattaga agaggttcaa    60
gaagatgaat tgaatgaagt cttaggagct aagaaaaagt caggagtaat cccaactgtg   120
tcacacgatt gccatatgaa ttcttttcaa tttgtattta cttgttgttc ataa          174

SEQ ID NO: 230         moltype = AA   length = 58
FEATURE                Location/Qualifiers
source                 1..58
                       mol_type = protein
                       organism = Paenibacillus polymyxa
SEQUENCE: 230
MAENLFDLDI QVNKSQGSVE PQVLSIVACS SGCGSGKTAA SCVETCGNRC FTNVGSLC      58

SEQ ID NO: 231         moltype = DNA   length = 177
FEATURE                Location/Qualifiers
source                 1..177
                       mol_type = genomic DNA
                       organism = Paenibacillus polymyxa
SEQUENCE: 231
atggctgaaa acttatttga tctggacatt caagtaaaca atctcaagg ttctgtagag    60
cctcaggttc tgagcattgt tgcatgttct agcggatgtg gtagcggtaa acagctgcc   120
agttgtgttg aaacttgtgg caaccggtgc tttactaacg ttggttcact ctgctaa      177

SEQ ID NO: 232         moltype = AA   length = 62
FEATURE                Location/Qualifiers
source                 1..62
                       mol_type = protein
                       organism = Pediococcus acidilactici
SEQUENCE: 232
MKKIEKLTEK EMANIIGGKY YGNGVTCGKH SCSVDWGKAT TCIINNGAMA WATGGHQGNH    60
KC                                                                  62

SEQ ID NO: 233         moltype = DNA   length = 189
FEATURE                Location/Qualifiers
source                 1..189
                       mol_type = genomic DNA
                       organism = Pediococcus acidilactici
SEQUENCE: 233
atgaaaaaaa ttgaaaaatt aactgaaaaa gaaatggcca atatcattgg tggtaaatac    60
tacggtaatg gggttacttg tggcaaacat tcctgtctg ttgactgggg taaggctacc   120
acttgcataa tcaataatgg agctatggca tgggctactg gtggacatca aggtaatcat   180
aaatgctag                                                           189

SEQ ID NO: 234         moltype = AA   length = 60
FEATURE                Location/Qualifiers
source                 1..60
                       mol_type = protein
                       organism = Pediococcus pentosaceus
SEQUENCE: 234
MTEIKVLNDK ELKNVVGGKY YGNGVHCGKK TCYVDWGQAT ASIGKIIVNG WTQHGPWAHR    60

SEQ ID NO: 235         moltype = DNA   length = 183
FEATURE                Location/Qualifiers
source                 1..183
```

```
                        mol_type = genomic DNA
                        organism = Pediococcus pentosaceus
SEQUENCE: 235
atgactgaaa ttaaagtact aaacgataag gaactaaaaa atgtcgtagg aggaaagtat    60
tacggtaacg gagtgcattg tggtaaaaag acttgctatg tggactgggg acaagctaca   120
gctagcattg gaaaaattat agtgaacgga tggacacaac acgggccttg ggcacataga   180
taa                                                                  183

SEQ ID NO: 236          moltype = AA   length = 60
FEATURE                 Location/Qualifiers
source                  1..60
                        mol_type = protein
                        organism = Staphylococcus epidermidis
SEQUENCE: 236
MKNNKNLFDL EIKKETSQNT DELEPQTAGP AIRASVKQCQ KTLKATRLFT VSCKGKNGCK    60

SEQ ID NO: 237          moltype = DNA   length = 183
FEATURE                 Location/Qualifiers
source                  1..183
                        mol_type = genomic DNA
                        organism = Staphylococcus epidermidis
SEQUENCE: 237
atgaaaaata acaaaaattt atttgattta gaaattaaaa aagaaacaag tcaaaacact    60
gatgaacttg aacctcaaac tgctggacca gcgattagac cttctgtgaa acaatgtcag   120
aaaactttga aagctacgcg tttatttaca gtgtcttgca aaggaaaaaa cggatgtaaa   180
tag                                                                  183

SEQ ID NO: 238          moltype = AA   length = 62
FEATURE                 Location/Qualifiers
source                  1..62
                        mol_type = protein
                        organism = Carnobacterium maltaromaticum
SEQUENCE: 238
MKTVKELSVK EMQLTTGGKY YGNGVSCNKN GCTVDWSKAI GIIGNNAAAN LTTGGAAGWN    60
KG                                                                   62

SEQ ID NO: 239          moltype = DNA   length = 189
FEATURE                 Location/Qualifiers
source                  1..189
                        mol_type = genomic DNA
                        organism = Carnobacterium maltaromaticum
SEQUENCE: 239
atgaaaactg ttaaagaact tagcgttaaa gaaatgcaac taactacagg aggtaagtat    60
tacggaaatg gcgtttcctg taataaaaat ggttgtactg tagattggag caaagctatt   120
gggattatag gaaacaatgc agcagcaaat ttgactacag gtggagccgc tggttggaac   180
aaaggataa                                                            189

SEQ ID NO: 240          moltype = AA   length = 69
FEATURE                 Location/Qualifiers
VARIANT                 40
                        note = Xaa = any amino acid
source                  1..69
                        mol_type = protein
                        organism = Lactobacillus plantarum
SEQUENCE: 240
MYKELTVDEL ALIDGGKKKK KKVACTWGNA ATAAASGAVX GILGGPTGAL AGAIWGVSQC    60
ASNNLHGMH                                                            69

SEQ ID NO: 241          moltype = DNA   length = 210
FEATURE                 Location/Qualifiers
misc_feature            119
                        note = n = a, c, t or g
source                  1..210
                        mol_type = genomic DNA
                        organism = Lactobacillus plantarum
SEQUENCE: 241
atgtataaag aattaacagt tgatgaatta gcattgattg atggaggaaa aaagaagaag    60
aaaaaagtag cttgtacttg gggaaatgca gcaacagccg ctgcttctgg tgcagttang   120
ggtattcttg gtgggcctac tggtgcactg gctggagcta tctggggcgt ttcacaatgc   180
gcgtctaaca acttacacgg catgcactaa                                     210

SEQ ID NO: 242          moltype = AA   length = 56
FEATURE                 Location/Qualifiers
source                  1..56
                        mol_type = protein
                        organism = Lactobacillus plantarum
SEQUENCE: 242
MMKKIEKLTE KEMANIIGGK YYGNGVTCGK HSCSVNWGQA FSCSVSHLAN FGHGKC         56
```

```
SEQ ID NO: 243              moltype = DNA   length = 171
FEATURE                     Location/Qualifiers
source                      1..171
                            mol_type = genomic DNA
                            organism = Lactobacillus plantarum
SEQUENCE: 243
atgatgaaaa aaattgaaaa attaactgaa aagaaatgg ccaatatcat tggtggtaaa      60
tactatggta atggggttac ttgtggtaaa cattcctgct ctgttaactg gggccaagca   120
ttttcttgta gtgtgtcaca tttagctaac ttcggtcatg aaagtgcta a             171

SEQ ID NO: 244              moltype = AA    length = 64
FEATURE                     Location/Qualifiers
source                      1..64
                            mol_type = protein
                            organism = Lactobacillus plantarum
SEQUENCE: 244
MSKLVKTLTV DEISKIQTNG GKPAWCWYTL AMCGAGYDSG TCDYMYSHCF GVKHSSGGGG      60
SYHC                                                                  64

SEQ ID NO: 245              moltype = DNA   length = 195
FEATURE                     Location/Qualifiers
source                      1..195
                            mol_type = genomic DNA
                            organism = Lactobacillus plantarum
SEQUENCE: 245
atgagtaaac tagttaaaac attaactgtc gatgaaatct ctaagattca aaccaatggt      60
ggaaaacctg catggtgttg gtacacattg gcaatgtgcg gtgctggtta tgattcaggc   120
acttgtgatt atatgtattc acactgcttt ggtgtaaaac actctagcgg tggtggcggt   180
agctaccatt gttag                                                   195

SEQ ID NO: 246              moltype = AA    length = 56
FEATURE                     Location/Qualifiers
source                      1..56
                            mol_type = protein
                            organism = Lactobacillus plantarum
SEQUENCE: 246
MLQFEKLQYS RLPQKKLAKI SGGFNRGGYN FGKSVRHVVD AIGSVAGIRG ILKSIR          56

SEQ ID NO: 247              moltype = DNA   length = 171
FEATURE                     Location/Qualifiers
source                      1..171
                            mol_type = genomic DNA
                            organism = Lactobacillus plantarum
SEQUENCE: 247
atgctacagt ttgagaaatt acaatattcc aggttgccgc aaaaaaagct tgccaaaata      60
tctggtggtt ttaatcgggg cggttataac tttggtaaaa gtgttcgaca tgttgttgat   120
gcaattggtt cagttgcagg cattcgtggt attttgaaaa gtattcgtta a             171

SEQ ID NO: 248              moltype = AA    length = 52
FEATURE                     Location/Qualifiers
source                      1..52
                            mol_type = protein
                            organism = Lactobacillus plantarum
SEQUENCE: 248
MKKFLVLRDR ELNAISGGVF HAYSARGVRN NYKSAVGPAD WVISAVRGFI HG              52

SEQ ID NO: 249              moltype = DNA   length = 159
FEATURE                     Location/Qualifiers
source                      1..159
                            mol_type = genomic DNA
                            organism = Lactobacillus plantarum
SEQUENCE: 249
atgaaaaaat ttctagtttt gcgtgaccgt gaattaaatg ctatttcagg tggcgttttc      60
catgcctata gcgcgcgtgg cgttcggaat aattataaaa gtgctgttgg gcctgccgat   120
tgggtcatta gcgctgtccg aggattcatc cacggatag                          159

SEQ ID NO: 250              moltype = AA    length = 55
FEATURE                     Location/Qualifiers
source                      1..55
                            mol_type = protein
                            organism = Lactobacillus plantarum
SEQUENCE: 250
MTVNKMIKDL DVVDAFAPIS NNKLNGVVGG GAWKNFWSSL RKGFYDGEAG RAIRR           55

SEQ ID NO: 251              moltype = DNA   length = 168
FEATURE                     Location/Qualifiers
source                      1..168
                            mol_type = genomic DNA
                            organism = Lactobacillus plantarum
```

```
SEQUENCE: 251
atgactgtga acaaaatgat taaggatttg gatgtagtag atgcatttgc acctatttct      60
aataataagt tgaacggggt tgttgggga ggcgcttgga aaaatttctg gtctagttta     120
agaaaaggat tttatgatgg cgaagctggc agagcaatcc gtcgttaa                 168

SEQ ID NO: 252         moltype = AA   length = 57
FEATURE                Location/Qualifiers
source                 1..57
                       mol_type = protein
                       organism = Lactobacillus plantarum
SEQUENCE: 252
MKIKLTVLNE FEELTADAEK NISGGRRSRK NGIGYAIGYA FGAVERAVLG GSRDYNK         57

SEQ ID NO: 253         moltype = DNA   length = 174
FEATURE                Location/Qualifiers
source                 1..174
                       mol_type = genomic DNA
                       organism = Lactobacillus plantarum
SEQUENCE: 253
atgaaaatta aattaactgt tttaaatgaa tttgaagaat taactgctga cgctgaaaag      60
aatatttctg gtggccgtcg gagtcgtaaa atggaattg gatacgctat tggttatgcg     120
tttggcgcgg ttgaacgggc cgtgcttggt ggttcaaggg attataataa gtga          174

SEQ ID NO: 254         moltype = AA   length = 47
FEATURE                Location/Qualifiers
source                 1..47
                       mol_type = protein
                       organism = Lactobacillus plantarum
SEQUENCE: 254
MDKFEKISTS NLEKISGGDL TTKLWSSWGY YLGKKARWNL KHPYVQF                    47

SEQ ID NO: 255         moltype = DNA   length = 141
FEATURE                Location/Qualifiers
source                 1..141
                       mol_type = genomic DNA
                       organism = Lactobacillus plantarum
SEQUENCE: 255
atggataaat ttgaaaaaat tagtacatct aacctagaaa agatctctgg cggtgattta      60
acaaccaagt tatggagctc ttggggatat tatcttggca agaaagcacg ttggaattta     120
aagcacccat atgttcaatt t                                              141

SEQ ID NO: 256         moltype = AA   length = 55
FEATURE                Location/Qualifiers
source                 1..55
                       mol_type = protein
                       organism = Lactobacillus plantarum
SEQUENCE: 256
MNNLNKFSTL GKSSLSQIEG GSVPTSVYTL GIKILWSAYK HRKTIEKSFN KGFYH           55

SEQ ID NO: 257         moltype = DNA   length = 168
FEATURE                Location/Qualifiers
source                 1..168
                       mol_type = genomic DNA
                       organism = Lactobacillus plantarum
SEQUENCE: 257
atgaataact tgaataaatt ttctactcta ggcaagagta gcttgtctca aattgagggc      60
ggatcagtcc caacttcagt atatacgctt ggaattaaaa ttctatggtc tgcgtataag     120
catcgcaaaa cgattgaaaa aagttttaat aaaggctttt atcattaa                 168

SEQ ID NO: 258         moltype = AA   length = 55
FEATURE                Location/Qualifiers
source                 1..55
                       mol_type = protein
                       organism = Lactobacillus plantarum
SEQUENCE: 258
MNNALSFEQQ FTDFSTLSDS ELESVEGGRN KLAYNMGHYA GKATIFGLAA WALLA           55

SEQ ID NO: 259         moltype = DNA   length = 168
FEATURE                Location/Qualifiers
source                 1..168
                       mol_type = genomic DNA
                       organism = Lactobacillus plantarum
SEQUENCE: 259
atgaataacg cattaagttt tgaacaacaa tttacagact tcagcacctt atcggactct      60
gaattagaat ccgttgaggg tggccgaaat aagcttgcat ataatatggg gcattacgct     120
ggtaaggcaa ccatttttgg acttgcagca tgggcactcc ttgcatga                 168

SEQ ID NO: 260         moltype = AA   length = 47
FEATURE                Location/Qualifiers
```

```
source                   1..47
                         mol_type = protein
                         organism = Lactobacillus plantarum
SEQUENCE: 260
MDKIIKFQGI SDDQLNAVIG GKKKKQSWYA AAGDAIVSFG EGFLNAW                    47

SEQ ID NO: 261           moltype = DNA   length = 144
FEATURE                  Location/Qualifiers
source                   1..144
                         mol_type = genomic DNA
                         organism = Lactobacillus plantarum
SEQUENCE: 261
atggataaga ttattaagtt tcaagggatt tctgatgatc aattaaatgc tgttatcggt      60
gggaaaaaga aaaacaatc ttggtacgca gcagctggtg atgcaatcgt tagttttggt     120
gaaggatttt taaatgcttg gtaa                                            144

SEQ ID NO: 262           moltype = AA    length = 59
FEATURE                  Location/Qualifiers
source                   1..59
                         mol_type = protein
                         organism = Lactobacillus plantarum
SEQUENCE: 262
MKISKIEAQA RKDFFKKIDT NSNLLNVNGA KCKWWNISCD LGNNGHVCTL SHECQVSCN       59

SEQ ID NO: 263           moltype = DNA   length = 180
FEATURE                  Location/Qualifiers
source                   1..180
                         mol_type = genomic DNA
                         organism = Lactobacillus plantarum
SEQUENCE: 263
atgaaaattt ctaagattga agctcaggct cgtaaagatt ttttaaaaa aatcgatact      60
aactcgaact tattaaatgt aaatggtgcc aaatgcaagt ggtggaatat ttcgtgtgat    120
ttaggaaata atggccatgt ttgtaccttg tcacatgaat gccaagtatc ttgtaactaa    180

SEQ ID NO: 264           moltype = AA    length = 67
FEATURE                  Location/Qualifiers
source                   1..67
                         mol_type = protein
                         organism = Lactobacillus plantarum
SEQUENCE: 264
MTKTSRRKNA IANYLEPVDE KSINESFGAG DPEARSGIPC TIGAAVAASI AVCPTTKCSK      60
RCGKRKK                                                                67

SEQ ID NO: 265           moltype = DNA   length = 204
FEATURE                  Location/Qualifiers
source                   1..204
                         mol_type = genomic DNA
                         organism = Lactobacillus plantarum
SEQUENCE: 265
atgactaaaa ctagtcgtcg taagaatgct attgctaatt atttagaacc agtcgacgaa     60
aaaagtatta atgaatcttt tggggctggg gatccggaag caagatccgg aattccatgt   120
acaatcggcg cagctgtcgc agcatcaatt gcagtttgtc caactactaa gtgtagtaaa   180
cgttgtggca agcgtaagaa ataa                                           204

SEQ ID NO: 266           moltype = AA    length = 48
FEATURE                  Location/Qualifiers
source                   1..48
                         mol_type = protein
                         organism = Lactobacillus plantarum
SEQUENCE: 266
MKIQIKGMKQ LSNKEMQKIV GGKSSAYSLQ MGATAIKQVK KLFKKWGW                   48

SEQ ID NO: 267           moltype = DNA   length = 147
FEATURE                  Location/Qualifiers
source                   1..147
                         mol_type = genomic DNA
                         organism = Lactobacillus plantarum
SEQUENCE: 267
atgaaaattc aaattaaagg tatgaagcaa cttagtaata aggaaatgca aaaaatagta     60
ggtggaaaga gtagtgcgta ttcttttgcag atggggggcaa ctgcaattaa acaggtaaag  120
aaactgttta aaaatggggg atggtaa                                        147

SEQ ID NO: 268           moltype = AA    length = 207
FEATURE                  Location/Qualifiers
source                   1..207
                         mol_type = protein
                         organism = Propionibacterium jensenii
SEQUENCE: 268
MNKTHKMATL VIAAILAAGM TAPTAYADSP GNTRITASEQ SVLTQILGHK PTQTEYNRYV     60
```

```
ETYGSVPTEA DINAYIEASE SEGSSSQTAA HDDSTSPGTS TEIYTQAAPA RFSMFFLSGT   120
WITRSGVVSL SLKPRKGGIG NEGDERTWKT VYDKFHNAGQ WTRYKNNGVD ASMKKQYMCH   180
FKYGMVKTPW NLEPHKKAAD VSPVKCN                                      207

SEQ ID NO: 269         moltype = DNA   length = 624
FEATURE                Location/Qualifiers
source                 1..624
                       mol_type = genomic DNA
                       organism = Propionibacterium jensenii
SEQUENCE: 269
atgaacaaaa cacacaaaat ggcgacgctg gtaattgccg cgatcttggc cgccggaatg    60
accgcaccaa ctgcctatgc agattctcct ggaaacacca gaattacagc cagcgagcaa   120
agcgtcctta cccagatact cggccacaaa cctacacaaa ctgaatataa ccgatacgtt   180
gagacttacg gaagcgtacc gaccgaagca gacatcaacg catatataga agcgtctgaa   240
tctgagggat catccagtca aacggctgct cacgatgact cgacatcacc ggcacgagt    300
accgaaatct acacgcaggc agcccctgcc aggttctcaa tgttttttcct gtccggaact   360
tggatcacta ggagtggtgt agtatcgctc tccttgaagc caaggaaggg tggtattggc   420
aacgaggggg acgagcgtac ctggaagact gtatacgaca aattccataa cgctgggcaa   480
tggacacgat acaagaacaa cggcgtagac gccagcatga aaaagcagta catgtgccac   540
ttcaagtacg ggatggtgaa gacgccatgg aatctggagc cccacaagaa ggctgcagac   600
gtcagtccag tcaagtgcaa ctag                                         624

SEQ ID NO: 270         moltype = AA  length = 96
FEATURE                Location/Qualifiers
source                 1..96
                       mol_type = protein
                       organism = Propionibacterium thoenii
SEQUENCE: 270
MKKTLLRSGT IALATAAAFG ASLAAAPSAM AVPGGCTYTR SNRDVIGTCK TGSGQFRIRL    60
DCNNAPDKTS VWAKPKVMVS VHCLVGQPRS ISFETK                             96

SEQ ID NO: 271         moltype = DNA   length = 291
FEATURE                Location/Qualifiers
source                 1..291
                       mol_type = genomic DNA
                       organism = Propionibacterium thoenii
SEQUENCE: 271
atgaagaaga ccctcctgcg aagtggaacg atcgcactgg cgaccgcggc tgcatttggc    60
gcatcattgg cagccgcccc atctgccatg gccgttcctg gtggttgcac gtacacagga   120
agcaatcgcg acgtcatcgg tacctgcaag actggaagcg gccagttccg aatccgactt   180
gactgcaaca acgctccaga caaaacttca gtctgggcca agcccaaggt aatggtgtcg   240
gttcactgtc ttgttggtca accgaggtcc atctcgttcg agaccaagtg a            291

SEQ ID NO: 272         moltype = AA  length = 255
FEATURE                Location/Qualifiers
source                 1..255
                       mol_type = protein
                       note = subsp. freudenreii
                       organism = Propionibacterium freudenreichii
SEQUENCE: 272
MNTKAVNLKS ENTTKLVSYL TENQLDEFIR RIRIDGALVE EVSQNAKQAL DNTGLNGWIN    60
TDCDEGLLSD FISKIASARW IPLAESIRPA VTDRDKYRVS CWFYQGMNIA IYANIGGVAN   120
IIGYTEAAVA TLLGAVVAVA PVVPGTPTPP KDKSSQYKEV PLAVRLSETY HEEGVRGLFD   180
ELNYSESRMI STLRRASTDG VLINSWNDGQ DTILLKKYNF QDLQLTVRSR IVGNQTIIEE   240
CKITDGRKTL SDETV                                                   255

SEQ ID NO: 273         moltype = DNA   length = 768
FEATURE                Location/Qualifiers
source                 1..768
                       mol_type = genomic DNA
                       note = subsp freudenreii
                       organism = Propionibacterium freudenreichii
SEQUENCE: 273
atgaatacca aagctgtaaa tctgaagtca gaaaacacga ctaagttggt gagctacctt    60
acggaaaatc aattggatga gtttattaga aggattcgca ttgatggcgc tcttgtggaa   120
gaggtcagtc aaaatgctaa gcaggcctta gataatactg gctcaatggg ctggataaat   180
actgattgcg atgaaggcct tctctctgat ttcatttcaa agatagcaag tgctagatgg   240
attccattag ctgagtcaat tcgacctgcg gtgactgaca gggataagta tcgagtaagt   300
tgctggttct accaggggat gaatatagca atttacgcaa atattggtag cgtggccaat   360
attatcggct atacggaggc cgcagtcgca acactccttg gtgcagttgt ggcggtagct   420
cctgtggtcc ctgtaactcc aaccccctcca aggacaaga gttcgcaata taggaggtt    480
ccccttgccg ttcgtctttc cgaaacatac cacgaagagg gagtacgagg tctattcgac   540
gagctgaact actccgagag ccgtatgatc tctactctaa ggcgagcatc aaccgatgga   600
gtcctaatta ttcttgaa cgatgggcag gatacaactg tgcttaagaa gtacaatttc   660
caagacttgc aactgactgt caggagccgc attgttggga atcaaacaat aattgaagaa   720
tgcaaaatca ctgatggtag aaaaaactct tcagacgaga ctgtgtag              768

SEQ ID NO: 274         moltype = AA  length = 618
FEATURE                Location/Qualifiers
```

```
source                          1..618
                                mol_type = protein
                                organism = Pseudomonas aeruginosa
SEQUENCE: 274
MARPIADLIH FNSTTVTASG DVYYGPGGGT GIGPIARPIE HGLDSSTENG WQEFESYADV    60
GVDPRRYVPL QVKEKRREIE LQFRDAEKKL EASVQAELDK ADAALGPAKN LAPLDVINRS   120
LTIVGNALQQ KNQKLLLNQK KITSLGAKNF LTRTAEEIGE QAVREGNING PEAYMRFLDR   180
EMEGLTAAYN VKLFTEAISS LQIRMNTLTA AKASIEAAAA NKAREQAAAE AKRKAEEQAR   240
QQAAIRAANT YAMPANGSVV ATAAGRGLIQ VAQGAASLAQ AISDAIAVLG RVLASAPSVM   300
AVGFASLTYS SRTAEQWQDQ TPDSVRYALG MDAAKLGLPP SVNLNAVAKA SGTVDLPMRL   360
TNEARGNTTT LSVVSTDGVS VPKAVPVRMA AYNATTGLYE VTVPSTTAEA PPLILTWTPA   420
SPPGNQNPSS TTPVVPKPVP VYEGATLTPV KATPETYPGV ITLPEDLIIG FPADSGIKPI   480
YVMFRDPRDV PGAATGKGQP VSGNWLGAAS QGEGAPIPSQ IADKLRGKTF KNWRDFREQF   540
WIAVANDPEL SKQFNPGSLA VMRDGGAPYV RESEQAGGRI KIEIHHKVRV ADGGGVYNMG   600
NLVAVTPKRH IEIHKGGK                                                618

SEQ ID NO: 275                  moltype = DNA    length = 1857
FEATURE                         Location/Qualifiers
source                          1..1857
                                mol_type = genomic DNA
                                organism = Pseudomonas aeruginosa
SEQUENCE: 275
atggcacgac ccattgctga ccttatccac ttcaactcta caactgtcac ggcaagcgga    60
gacgtttatt acggccctgg gggaggtacc ggcattggcc ccattgccag acctatagag   120
cacggcttgg attcgtccac tgaaaatggc tggcaagagt ttgaaagtta tgctgatgtg   180
ggcgttgacc ccagacgcta tgttcctctt caggttaaag aaaaacgcag ggagatcgaa   240
cttcagttcc gagatgccga gaaaaaactt gaggcgtcgg tacaagccga gctggataag   300
gctgatgccg ctcttggtcc ggcaaagaat cttgcaccat ggacgtcat caaccgcagt   360
ctgaccatcg ttgaaacgc cctccagcaa agaatcaaa aactactgct gaatcagaag   420
aagattacca gcctgggtgc aaagaatttc cttacccgta cggcggaaga gatcggtgaa   480
caagcggtgc gagaaggcaa tattaacggg cctgaagcct atatgcgctt cctcgacagg   540
gaaatggaag gtctcacggc agcttataac gtaaaactct tcaccgaagc gatcagtagt   600
ctccagatcc gcatgaatac gttgaccgcc gccaaagcaa gtattgaggc ggccgcagca   660
aacaaggcgc gtgaacaagc agcggctgag gccaaacgca aagccgaaga agcaagcccgc   720
cagcaagcgg cgataagagc tgccaatacc tatgccatgc cggccaatgg cagcgttgtc   780
gccaccgccg caggccgggg tctgatccag gtcgcacaag gcgccgcatc ccttgctcaa   840
gcgatctccg atgcgattgc cgtcctgggc cgggtcctgg cttcagcacc ctcggtgatg   900
gccgtgggct ttgccagtct gacctactcc tcccggactg ccgagcaatg gcaggaccaa   960
acgcccgata gcgttcgtta cgccctgggc atggatgccg ctaaattggg gcttcccca  1020
agcgtaaacc tgaacgcggt tgcaaaagcc agcggtaccg tcgatctgcc gatgcgcctg  1080
accaacgagg cacgagcgaa cacgacgacc ctttcggtgg tcagcaccga tggtgtgagc  1140
gttccgaaag ccgttccggt ccggatgcg gcctacaatg ccacgacagg cctgtacgag  1200
gttacggttc cctctacgac cgcagaagcg cctgcactga tcctgacctg gacgccggcg  1260
agtcctccag gaaaccagaa cccttcgagt accactccgg tcgtaccgaa gccggtgccg  1320
gtatatgagg gagcgaccct tacaccggtg aaggctaccc ggaaaccta tcctggggtg  1380
attacactac cggaagacct gatcatcggc ttccccgccg actcggggat caagccgatc  1440
tatgtgatgt tcagggatcc gcgggatgta cctggtgctg gggacagccg  1500
gtcagcggta attggctcgg cgccgcctct caaggtgagg gggctccaat tccaagccag  1560
attgcggata aactacgtgg taagacattc aaaaactggc gggactttcg ggaacaattc  1620
tggatagctg tggctaatga tcctgagtta agtaaacagt ttaatcctgg tagtttagct  1680
gtaatgagag atggagggc tccttatgtc agagagtcag aacaggctgg cgggagaata  1740
aagatcgaaa tccaccacaa ggttcgagta gcagatggga gcggcgttta caatatgggg  1800
aaccttgttg cagtaacgcc aaaacgtcat atagaaatcc acaagggagg gaagtga    1857

SEQ ID NO: 276                  moltype = AA    length = 689
FEATURE                         Location/Qualifiers
source                          1..689
                                mol_type = protein
                                organism = Pseudomonas aeruginosa
SEQUENCE: 276
MAVNDYEPGS MVITHVQGGG RDIIQYIPAR SSYGTPPFVP PGPSPYVGTG MQEYRKLRST    60
LDKSHSELKK NLKNETLKEV DELKSEAGLP GKAVSANDIR DEKSIVDALM DAKAKSLKAI   120
EDRPANLYTA SDFPQKSESM YQSQLLASRK FYGEFLDRHM SELAKAYSAD IYKAQIAILK   180
QTSQELENKA RSLEAEAQRA AAEVEADYKA RKANVEKKVQ SELDQAGNAL PQLTNPTPEQ   240
WLERATQLVT QAIANKKKLQ TANNALIAKA PNALEKQKAT YNADLLVDEI ASLQARLDKL   300
NAETARRKEI ARQAAIRAAN TYAMPANGSV VATAAGRGLI QVAQGAASLA QAISDAIAVL   360
GRVLASAPSV MAVGFASLTY SSRTAEQWQD QTPDSVRYAL GMDAAKLGLP PSVNLNAVAK   420
ASGTVDLPMR LTNEARGNTT TLSVVSTDGV SVPKAVPVRM AAYNATTGLY EVTVPSTTAE   480
APPLILTWTP ASPPGNQNPS STTPVVPKPV PVYEGATLTP VKATPETYPG VITLPEDLII   540
GFPADSGIKP IYVMFRDPRD VPGAATGKGQ PVSGNWLGAA SQGEGAPIPS QIADKLRGKT   600
FKNWRDFREQ FWIAVANDPE LSKQFNPGSL AVMRDGGAPY VRESEQAGGR IKIEIHHKVR   660
IADGGGVYNM GNLVAVTPKR HIEIHKGGK                                    689

SEQ ID NO: 277                  moltype = DNA    length = 2070
FEATURE                         Location/Qualifiers
source                          1..2070
                                mol_type = genomic DNA
                                organism = Pseudomonas aeruginosa
SEQUENCE: 277
```

```
atggctgtca atgattacga acctggttcg atggttatta cacatgtgca gggtggtggg   60
cgtgacataa tccagtatat tcctgctcga tcaagctacg gtactccacc atttgtccca  120
ccaggaccaa gtccgtatgt cggtactgga atgcaggagt acaggaagct aagaagtacg  180
cttgataagt cccattcaga actcaagaaa aacctgaaaa atgaaccct gaaggaggtt   240
gatgaactca agagtgaagc gggggttgcca ggtaaagcgg tcagtgccaa tgcatccgat  300
gatgaaaaga gtatcgttga tgcactcatg gatgccaaag caaaatcgct aaaggcatt   360
gaggatcgcc cggccaatct ttatacggct tcagactttc ctcagaagtc agagtcgatg  420
taccagagtc agttgctggc cagccgaaaa ttctatggag agttcctgga tcgccatatg  480
agtgagctgg ccaaagcgta cagcgccgat atctataagg cgcaaatcgc tatcttgaaa  540
caaacgtctc aagagctgga gaataaagcc cggtcattgg aagcagaagc ccagcgagcc  600
gctgctgagg tggaggcgga ctacaaggcc aggaaggcaa atgtcgagaa aaaagtgcag  660
tccgagcttg accaggctgg gaatgctttg cctcaactga ccaatccaac gccagagcag  720
tggcttgaac gcgctactca actggttacg caggcgatcg ccaataagaa gaaattgcag  780
actgcaaaca atgccttgat tgccaaggca cccaatgcac tggagaaaca aaaggcaacc  840
tacaacgccg atctcctagt ggatgaaatc gccagcctgc aagcacggct ggacaagctg  900
aacgccgaaa cggcaaggcg caaggaaatc gctcgtcaag cggcgatcag ggctgccaat  960
acttatgcca tgccagccaa tggcagcgtt gtcgccaccg ccgcaggccg gggtctgatc 1020
caggtcgcac aaggcgccgc atcccttgct caagcgatct ccgatgcgat tgccgtcctg 1080
ggccgggtcc tggcttcagc accctcggtg atggccgtgg gctttgccag tctgacctac 1140
tcctcccgga ctgccgagca atggcaggac caaacgcccg atagcgttcg ttacgccctg 1200
ggcatggatg ccgctaaatt ggggcttccc ccaagcgtaa acctgaacgc ggttcaaaa  1260
gccagcgta ccgtcgatct gccgatgcgc ctgaccaacg aggcacgagg caacacgacg 1320
acccttcgg tggtcagcac cgatggtgtg agcgttccga aagccgttcc ggtccggatg 1380
gcggcctaca tgccacgac aggcctgtac gaggttacgg ttccctctac gaccgcagaa 1440
gcgccgccac tgatcctgac ctggacgccg gcgagtcctc caggaaaacca gaaccctcg 1500
agtaccactc cggtcgtacc gaagccggtg ccggtatatg agggagcgac ccttacaccg 1560
gtgaaggcta ccccgaaaac ctatcctggg gtgattacac taccggaaga cctgatcatc 1620
ggcttcccgg ccgactcggg gatcaagccg atctatgtga tgttcaggga tccgcgggat 1680
gtacctggtc ctgcgactgg caaggacag cccgtcagcg gtaattggct cggcgccgcc 1740
tctcaaggtg aggggctcc aattccaagc cagattgcag ataaactacg tggtaagaca 1800
ttcaaaaact ggcgggactt tcgggaacaa ttctgatag ctgtggctaa tgatcctgag 1860
ttaagtaaac agtttaatcc tggtagttta gctgtaatga gagatggagg ggctccttat 1920
gtcagagagt cagaacaggc tggcgggaga ataaagatcg aaatccacca aaggttcga  1980
atagcagatg gaggcggcgt ttacaatatg gggaaccttg ttgcagtaac gccaaaacgt 2040
catatagaaa tccacaaggg agggaagtga                                 2070

SEQ ID NO: 278         moltype = AA  length = 47
FEATURE                Location/Qualifiers
source                 1..47
                       mol_type = protein
                       organism = Ruminococcus gnavus
SEQUENCE: 278
MRNDVLTLTN PMEEKELEQI LGGGNGVLKT ISHECNMNTW QFLFTCC                47

SEQ ID NO: 279         moltype = DNA  length = 144
FEATURE                Location/Qualifiers
source                 1..144
                       mol_type = genomic DNA
                       organism = Ruminococcus gnavus
SEQUENCE: 279
atgagaaatg acgtattaac attaacaaac ccaatggaag agaacgaact ggagcagatc   60
ttaggtggtg gcaatggtgt gttaaaaacg attagccacg aatgcaatat gaacacatgg  120
cagttcctgt ttacttgttg ctaa                                        144

SEQ ID NO: 280         moltype = AA  length = 55
FEATURE                Location/Qualifiers
source                 1..55
                       mol_type = protein
                       organism = Lactobacillus sakei
SEQUENCE: 280
MKNAKSLTIQ EMKSITGGKY YGNGVSCNSH GCSVNWGQAW TCGVNHLANG GHGVC        55

SEQ ID NO: 281         moltype = DNA  length = 168
FEATURE                Location/Qualifiers
source                 1..168
                       mol_type = genomic DNA
                       organism = Lactobacillus sakei
SEQUENCE: 281
atgaaaaacg caaaaagcct aacaattcaa gaaatgaaat ctattacagg tggtaaatac   60
tatggtaatg gcgttagctg taactctcac ggctgttcag taaattgggg gcaagcatgg  120
acttgtggag taaaccatct agctaatggc ggtcatggag tttgttaa               168

SEQ ID NO: 282         moltype = AA  length = 59
FEATURE                Location/Qualifiers
source                 1..59
                       mol_type = protein
                       organism = Lactobacillus sakei
SEQUENCE: 282
MNNVKELSMT ELQTITGGAR SYGNGVYCNN KKCWVNRGEA TQSIIGGMIS GWASGLAGM    59
```

```
SEQ ID NO: 283          moltype = DNA  length = 180
FEATURE                 Location/Qualifiers
source                  1..180
                        mol_type = genomic DNA
                        organism = Lactobacillus sakei
SEQUENCE: 283
atgaataatg taaaagaatt aagtatgaca gaattacaaa caattaccgg cggtgctaga   60
tcatatggca acggtgttta ctgtaataat aaaaaatgtt gggtaaatcg gggtgaagca  120
acgcaaagta ttattggtgg tatgattagc ggctgggcta gtggtttagc tggaatgtaa  180

SEQ ID NO: 284          moltype = AA  length = 61
FEATURE                 Location/Qualifiers
source                  1..61
                        mol_type = protein
                        organism = Lactobacillus sakei
SEQUENCE: 284
MEKFIELSLK EVTAITGGKY YGNGVHCGKH SCTVDWGTAI GNIGNNAAAN WATGGNAGWN   60
K                                                                  61

SEQ ID NO: 285          moltype = DNA  length = 186
FEATURE                 Location/Qualifiers
source                  1..186
                        mol_type = genomic DNA
                        organism = Lactobacillus sakei
SEQUENCE: 285
atggaaaagt ttattgaatt atctttaaaa gaagtaacag caattacagg tggaaaatat   60
tatggtaacg gtgtacactg tggaaaacat tcatgtaccg tagactgggg aacagctatt  120
ggaaatatcg gaaataatgc agctgcaaac tgggccacag gcggaaacgc tggctggaat  180
aaataa                                                             186

SEQ ID NO: 286          moltype = AA  length = 56
FEATURE                 Location/Qualifiers
source                  1..56
                        mol_type = protein
                        organism = Streptococcus salivarius
SEQUENCE: 286
MKSTNNQSIA EIAAVNSLQE VSMEELDQII GAGNGVVLTL THECNLATWT KKLKCC       56

SEQ ID NO: 287          moltype = DNA  length = 171
FEATURE                 Location/Qualifiers
source                  1..171
                        mol_type = genomic DNA
                        organism = Streptococcus salivarius
SEQUENCE: 287
atgaaatcaa caaataatca aagtatcgca gaaattgcag cagtaaactc actacaagaa   60
gtaagtatgg aggaactaga ccaaattatt ggtgccggaa acggagtggt tcttactctt  120
actcatgaat gtaacctagc aacttggaca aaaaaactaa aatgttgcta a            171

SEQ ID NO: 288          moltype = AA  length = 51
FEATURE                 Location/Qualifiers
source                  1..51
                        mol_type = protein
                        note = serotype M28
                        organism = Streptococcus pyogenes
SEQUENCE: 288
MSFMKNSKDI LTNAIEEVSE KELMEVAGGK KGSGWFATIT DDCPNSVFVC C            51

SEQ ID NO: 289          moltype = DNA  length = 156
FEATURE                 Location/Qualifiers
source                  1..156
                        mol_type = genomic DNA
                        note = serotype M28
                        organism = Streptococcus pyogenes
SEQUENCE: 289
atgagtttta tgaaaaattc aaaggatatt ttgactaatg ctatcgaaga agtttctgaa   60
aaagaactta tggaagtagc tggtggtaaa aaaggttccg gttggtttgc aactattact  120
gatgactgtc cgaactcagt attcgtttgt tgttaa                            156

SEQ ID NO: 290          moltype = AA  length = 48
FEATURE                 Location/Qualifiers
source                  1..48
                        mol_type = protein
                        organism = Streptococcus salivarius
SEQUENCE: 290
MKNSKDVLNN AIEEVSEKEL MEVAGGKKGP GWIATITDDC PNSIFVCC                48

SEQ ID NO: 291          moltype = DNA  length = 147
FEATURE                 Location/Qualifiers
```

```
source                  1..147
                        mol_type = genomic DNA
                        organism = Streptococcus salivarius
SEQUENCE: 291
atgaaaaact caaagatgt tttgaacaat gctatcgaag aggtttctga aaaagaactt    60
atggaagtag ctggtggtaa aaaaggtcca ggttggattg caactattac tgatgactgt   120
ccaaactcaa tattcgtttg ttgttaa                                      147

SEQ ID NO: 292          moltype = AA  length = 48
FEATURE                 Location/Qualifiers
source                  1..48
                        mol_type = protein
                        organism = Streptococcus salivarius
SEQUENCE: 292
MKNSKDILNN AIEEVSEKEL MEVAGGKRGS GWIATITDDC PNSVFVCC                48

SEQ ID NO: 293          moltype = DNA  length = 147
FEATURE                 Location/Qualifiers
source                  1..147
                        mol_type = genomic DNA
                        organism = Streptococcus salivarius
SEQUENCE: 293
atgaaaaact caaagatat tttgaacaat gctatcgaag aagtttctga aaaagaactt    60
atggaagtag ctggtggtaa aagaggttca ggttggattg caactattac tgatgactgt   120
ccaaactcag tattcgtttg ttgttaa                                      147

SEQ ID NO: 294          moltype = AA  length = 62
FEATURE                 Location/Qualifiers
source                  1..62
                        mol_type = protein
                        organism = Staphylococcus aureus
SEQUENCE: 294
MKSSFLEKDI EEQVTWFEEV SEQEFDDDIF GACSTNTFSL SDYWGNKGNW CTATHECMSW   60
CK                                                                 62

SEQ ID NO: 295          moltype = DNA  length = 189
FEATURE                 Location/Qualifiers
source                  1..189
                        mol_type = genomic DNA
                        organism = Staphylococcus aureus
SEQUENCE: 295
atgaaaagtt cttttttaga aaaagatata gaagaacaag tgacatggtt cgaggaagtt    60
tcagaacaag aatttgacga tgatattttt ggagcttgta gtacaaacac ttttttcttg   120
agtgactatt ggggtaataa aggaaattgg tgtactgcta ctcacgaatg tatgtcttgg   180
tgtaaataa                                                          189

SEQ ID NO: 296          moltype = AA  length = 67
FEATURE                 Location/Qualifiers
source                  1..67
                        mol_type = protein
                        organism = Staphylococcus aureus
SEQUENCE: 296
MKNELGKFLE ENELELGKFS ESDMLEITDD EVYAAGTPLA LLGGAATGVI GYISNQTCPT   60
TACTRAC                                                            67

SEQ ID NO: 297          moltype = DNA  length = 204
FEATURE                 Location/Qualifiers
source                  1..204
                        mol_type = genomic DNA
                        organism = Staphylococcus aureus
SEQUENCE: 297
atgaaaaatg aattaggtaa gttttagaa gaaaacgaat tagagttagg taaatttca     60
gaatcagaca tgctagaaat tactgatgat gaagtatatg cagctggaac acctttagcc   120
ttattgggtg gagctgccac cggggtgata ggttatattt ctaaccaaac atgtccaaca   180
actgcttgta cacgcgcttg ctag                                         204

SEQ ID NO: 298          moltype = AA  length = 46
FEATURE                 Location/Qualifiers
source                  1..46
                        mol_type = protein
                        organism = Streptococcus pyogenes
SEQUENCE: 298
MNNTIKDFDL DLKTNKKDTA TPYVGSRYLC TPGSCWKLVC FTTTVK                  46

SEQ ID NO: 299          moltype = DNA  length = 141
FEATURE                 Location/Qualifiers
source                  1..141
                        mol_type = genomic DNA
                        organism = Streptococcus pyogenes
```

-continued

```
SEQUENCE: 299
atgaataaca caattaaaga ctttgatctc gatttgaaaa caaataaaaa agacactgct    60
acaccttatg ttggtagccg ttacctatgt accctggtt cttgttggaa attagtttgc   120
tttacaacaa ctgttaaata a                                             141

SEQ ID NO: 300           moltype = AA    length = 51
FEATURE                  Location/Qualifiers
source                   1..51
                         mol_type = protein
                         organism = Streptococcus pyogenes
SEQUENCE: 300
MEKNNEVINS IQEVSLEELD QIIGAGKNGV FKTISHECHL NTWAFLATCC S             51

SEQ ID NO: 301           moltype = DNA    length = 156
FEATURE                  Location/Qualifiers
source                   1..156
                         mol_type = genomic DNA
                         organism = Streptococcus pyogenes
SEQUENCE: 301
atggaaaaaa ataatgaagt aatcaactct attcaagaag ttagtcttga agaactcgat    60
caaattatcg gtgctggaaa aaatggtgtg tttaaaacaa tttctcatga gtgtcatttg   120
aatacatggg cattccttgc tacttgttgt tcataa                             156

SEQ ID NO: 302           moltype = AA    length = 51
FEATURE                  Location/Qualifiers
source                   1..51
                         mol_type = protein
                         note = serotype M49
                         organism = Streptococcus pyogenes
SEQUENCE: 302
MTKEHEIINS IQEVSLEELD QIIGAGKNGV FKTISHECHL NTWAFLATCC S             51

SEQ ID NO: 303           moltype = DNA    length = 156
FEATURE                  Location/Qualifiers
source                   1..156
                         mol_type = genomic DNA
                         note = serotype M49
                         organism = Streptococcus pyogenes
SEQUENCE: 303
atggaaaaaa ataatgaagt aatcaactct attcaagaag ttagtcttga agaactcgat    60
caaattatcg gtgctggaaa aaatggtgtg tttaaaacaa tttctcatga gtgtcatttg   120
aatacatggg cattccttgc tacttgttgc tcataa                             156

SEQ ID NO: 304           moltype = AA    length = 56
FEATURE                  Location/Qualifiers
source                   1..56
                         mol_type = protein
                         organism = Bacillus subtilis
SEQUENCE: 304
MEKLFKEVKL EELENQKGSG LGKAQCAALW LQCASGGTIG CGGGAVACQN YRQFCR        56

SEQ ID NO: 305           moltype = DNA    length = 171
FEATURE                  Location/Qualifiers
source                   1..171
                         mol_type = genomic DNA
                         organism = Bacillus subtilis
SEQUENCE: 305
atggaaaagc tatttaaaga agttaaacta gaggaactcg aaaaccaaaa aggtagtgga    60
ttaggaaaag ctcagtgtgc tgcgttgtgg ctacaatgtg ctagtggcgg tacaattggt   120
tgtggtggcg gagctgttgc ttgtcaaaac tatcgtcaat tctgcagata a             171

SEQ ID NO: 306           moltype = AA    length = 56
FEATURE                  Location/Qualifiers
source                   1..56
                         mol_type = protein
                         organism = Bacillus subtilis
SEQUENCE: 306
MSKFDDFDLD VVKVSKQDSK ITPQWKSESL CTPGCVTGAL QTCFLQTLTC NCKISK        56

SEQ ID NO: 307           moltype = DNA    length = 171
FEATURE                  Location/Qualifiers
source                   1..171
                         mol_type = genomic DNA
                         organism = Bacillus subtilis
SEQUENCE: 307
atgtcaaagt tcgatgattt cgatttggat gttgtgaaag tctctaaaca agactcaaaa    60
atcactccgc aatggaaaag tgaatcactt tgtacaccag atgtgtaac tggtgcattg   120
caaacttgct ccttcaaaac actaacttgt aactgcaaaa tctctaaata a             171
```

| | | |
|---|---|---|
| SEQ ID NO: 308 | moltype = AA length = 50 | |
| FEATURE | Location/Qualifiers | |
| source | 1..50 | |
| | mol_type = protein | |
| | organism = Bacillus subtilis | |
| SEQUENCE: 308 | | |
| MKLPVQQVYS VYGGKDLPKG HSHSTMPFLS KLQFLTKIYL LDIHTQPFFI | | 50 |
| | | |
| SEQ ID NO: 309 | moltype = DNA length = 153 | |
| FEATURE | Location/Qualifiers | |
| source | 1..153 | |
| | mol_type = genomic DNA | |
| | organism = Bacillus subtilis | |
| SEQUENCE: 309 | | |
| ttgaaattgc cggtgcaaca ggtctattcg gtctatgggg gtaaggatct cccaaaaggg | | 60 |
| catagtcatt ctactatgcc cttttttaagt aaattacaat ttttaactaa aatctacctc | | 120 |
| ttggatatac atacacaacc gtttttcatt tga | | 153 |
| | | |
| SEQ ID NO: 310 | moltype = AA length = 43 | |
| FEATURE | Location/Qualifiers | |
| source | 1..43 | |
| | mol_type = protein | |
| | organism = Bacillus subtilis | |
| SEQUENCE: 310 | | |
| MKKAVIVENK GCATCSIGAA CLVDGPIPDF EIAGATGLFG LWG | | 43 |
| | | |
| SEQ ID NO: 311 | moltype = DNA length = 132 | |
| FEATURE | Location/Qualifiers | |
| source | 1..132 | |
| | mol_type = genomic DNA | |
| | organism = Bacillus subtilis | |
| SEQUENCE: 311 | | |
| atgaaaaaag ctgtcattgt agaaaacaaa ggttgtgcaa catgctcgat cggagccgct | | 60 |
| tgtctagtgg acggtcctat ccctgatttt gaaattgccg gtgcaacagg tctattcggt | | 120 |
| ctatgggggt aa | | 132 |
| | | |
| SEQ ID NO: 312 | moltype = AA length = 58 | |
| FEATURE | Location/Qualifiers | |
| source | 1..58 | |
| | mol_type = protein | |
| | organism = Streptococcus thermophilus | |
| SEQUENCE: 312 | | |
| MMNATENQIF VETVSDQELE MLIGGADRGW IKTLTKDCPN VISSICAGTI ITACKNCA | | 58 |
| | | |
| SEQ ID NO: 313 | moltype = DNA length = 177 | |
| FEATURE | Location/Qualifiers | |
| source | 1..177 | |
| | mol_type = genomic DNA | |
| | organism = Streptococcus thermophilus | |
| SEQUENCE: 313 | | |
| atgatgaatg ctactgaaaa ccaaattttt gttgagactg tgagtgacca agaattagaa | | 60 |
| atgttaattg gtggtgcaga tcgtggatgg attaagactt taacaaaaga ttgtccaaat | | 120 |
| gtaatttctt caatttgtgc aggtacaatt attacagcct gtaaaaattg tgcttaa | | 177 |
| | | |
| SEQ ID NO: 314 | moltype = AA length = 64 | |
| FEATURE | Location/Qualifiers | |
| source | 1..64 | |
| | mol_type = protein | |
| | organism = Streptococcus thermophilus | |
| SEQUENCE: 314 | | |
| MKQYNGFEVL HELDLANVTG GQINWGSVVG HCIGGAIIGG AFSGGAAAGV GCLVGSGKAI | | 60 |
| INGL | | 64 |
| | | |
| SEQ ID NO: 315 | moltype = DNA length = 195 | |
| FEATURE | Location/Qualifiers | |
| source | 1..195 | |
| | mol_type = genomic DNA | |
| | organism = Streptococcus thermophilus | |
| SEQUENCE: 315 | | |
| atgaagcagt ataatggttt tgaggttcta catgaacttg acttagcaaa tgtaactggc | | 60 |
| ggtcaaatta attggggatc agttgtagga cactgtatag gtggagctat tatcggaggt | | 120 |
| gcattttcag gaggtgcagc ggctggagta ggatgccttg ttgggagcgg aaaggcaatc | | 180 |
| ataaatggat tataa | | 195 |
| | | |
| SEQ ID NO: 316 | moltype = AA length = 85 | |
| FEATURE | Location/Qualifiers | |
| source | 1..85 | |
| | mol_type = protein | |
| | organism = Streptococcus thermophilus | |

```
SEQUENCE: 316
MNTITICKFD VLDAELLSTV EGGYSGKDCL KDMGGYALAG AGSGALWGAP AGGVGALPGA    60
FVGAHVGAIA GGFACMGGMI GNKFN                                        85

SEQ ID NO: 317              moltype = DNA   length = 258
FEATURE                     Location/Qualifiers
source                      1..258
                            mol_type = genomic DNA
                            organism = Streptococcus thermophilus
SEQUENCE: 317
atgaatacaa taactatttg taaatttgat gttttagatg ctgaacttct ttcgacagtt    60
gagggtggat actctggtaa ggattgttta aaagacatgg gaggatatgc attggcagga   120
gctggaagtg gagctctgtg gggagctcca gcaggaggtg ttggagcact tccaggtgca   180
tttgtcggag ctcatgttgg ggcaattgca ggaggctttg catgtatggg tggaatgatt   240
ggtaataagt ttaactaa                                                258

SEQ ID NO: 318              moltype = AA    length = 52
FEATURE                     Location/Qualifiers
source                      1..52
                            mol_type = protein
                            organism = Bacillus cereus
SEQUENCE: 318
MSEIKKALNT LEIEDFDAIE MVDVDAMPEN EALEIMGASC TTCVCTCSCC TT           52

SEQ ID NO: 319              moltype = DNA   length = 159
FEATURE                     Location/Qualifiers
source                      1..159
                            mol_type = genomic DNA
                            organism = Bacillus cereus
SEQUENCE: 319
atgagtgaaa ttaaaaaagc attaaatacg cttgaaattg aagatttga tgcaattgaa     60
atggttgatg ttgatgctat gccagaaaac gaagcgcttg aaattatggg agcgtcatgt   120
acgacatgcg tatgtacatg cagttgttgt acaacttga                         159

SEQ ID NO: 320              moltype = AA    length = 47
FEATURE                     Location/Qualifiers
source                      1..47
                            mol_type = protein
                            organism = Bacillus cereus
SEQUENCE: 320
MEVMNNALIT KVDEEIGGNA ACVIGCIGSC VISEGIGSLV GTAFTLG                 47

SEQ ID NO: 321              moltype = DNA   length = 144
FEATURE                     Location/Qualifiers
source                      1..144
                            mol_type = genomic DNA
                            organism = Bacillus cereus
SEQUENCE: 321
atggaagtta tgaacaatgc tttaattaca aaagtagatg aggagattgg aggaaacgct    60
gcttgtgtaa ttggttgtat tggcagttgc gtaattagtg aaggaattgg ttcacttgta   120
ggaacagcat ttactttagg ttaa                                         144

SEQ ID NO: 322              moltype = AA    length = 49
FEATURE                     Location/Qualifiers
source                      1..49
                            mol_type = protein
                            organism = Bacillus cereus
SEQUENCE: 322
MEVLNKQNVN IIPESEEVGG WVACVGACGT VCLASGGVGT EFAAASYFL               49

SEQ ID NO: 323              moltype = DNA   length = 150
FEATURE                     Location/Qualifiers
source                      1..150
                            mol_type = genomic DNA
                            organism = Bacillus cereus
SEQUENCE: 323
atggaagttt taaacaaaca aaatgtaaat attattccag aatctgaaga agtaggtgga    60
tgggtagcat gtgttggagc atgtggtaca gtatgtcttg ctagtggtgg tgttggaaca   120
gagtttgcag ctgcatctta tttcctataa                                   150

SEQ ID NO: 324              moltype = AA    length = 40
FEATURE                     Location/Qualifiers
source                      1..40
                            mol_type = protein
                            organism = Bacillus thuringiensis
SEQUENCE: 324
METPVVQPRD WTCWSCLVCA ACSVELLNLV TAATGASTAS                        40

SEQ ID NO: 325              moltype = DNA   length = 123
```

```
FEATURE                 Location/Qualifiers
source                  1..123
                        mol_type = genomic DNA
                        organism = Bacillus thuringiensis
SEQUENCE: 325
atggaaacac cagtagtaca accaagggat tggacttgtt ggagttgctt agtatgtgca    60
gcatgttctg tggaattatt aaatttagtt actgcggcaa caggggctag tactgcaagc   120
taa                                                                 123

SEQ ID NO: 326          moltype = AA  length = 42
FEATURE                 Location/Qualifiers
source                  1..42
                        mol_type = protein
                        note = bv. trifolii
                        organism = Rhizobium leguminosarum
SEQUENCE: 326
MDNKVAKNVE VKKGSIKATF KAAVLKSKTK VDIGGSRQGC VA                       42

SEQ ID NO: 327          moltype = DNA  length = 129
FEATURE                 Location/Qualifiers
source                  1..129
                        mol_type = genomic DNA
                        note = bv. trifolii
                        organism = Rhizobium leguminosarum
SEQUENCE: 327
atggataaca aggttgcgaa gaatgtcgaa gtgaagaagg gctccatcaa ggcgaccttc    60
aaggctgctg ttctgaagtc gaagacgaag gtcgacatcg gaggtagccg tcagggctgc   120
gtcgcttaa                                                           129

SEQ ID NO: 328          moltype = AA  length = 70
FEATURE                 Location/Qualifiers
source                  1..70
                        mol_type = protein
                        organism = Streptococcus uberis
SEQUENCE: 328
MNTIEKFENI KLFSLKKIIG GKTVNYGNGL YCNQKKCWVN WSETATTIVN SIMNGLTGG     60
NAGWHSGGRA                                                           70

SEQ ID NO: 329          moltype = DNA  length = 213
FEATURE                 Location/Qualifiers
source                  1..213
                        mol_type = genomic DNA
                        organism = Streptococcus uberis
SEQUENCE: 329
atgaatacaa ttgaaaaatt tgaaaatatt aaacttttt cactaaagaa aattatcggt     60
ggcaaaactg taaattatgg taatggcctt tattgtaacc aaaaaaaatg ctgggtaaac   120
tggtcagaaa ctgctacaac aatagtaaat aattccatca tgaacgggct cacaggtggt   180
aatgcgggtt ggcactcagg cgggagagca taa                                213

SEQ ID NO: 330          moltype = AA  length = 76
FEATURE                 Location/Qualifiers
source                  1..76
                        mol_type = protein
                        organism = Streptococcus uberis
SEQUENCE: 330
MDILLELAGY TGIASGTAKK VVDAIDKGAA AFVIISIIST VISAGALGAV SASADFIILT     60
VKNYISRNLK AQAVIW                                                    76

SEQ ID NO: 331          moltype = DNA  length = 231
FEATURE                 Location/Qualifiers
source                  1..231
                        mol_type = genomic DNA
                        organism = Streptococcus uberis
SEQUENCE: 331
atggacattt tattagaact cgcaggatat actgggatag cctcaggtac tgcaaaaaaa    60
gttgttgatg ccattgataa aggagctgca gcctttgtta ttatttcaat tatctcaaca   120
gtaattagtg cggagcatt gggagcagtt tcagcctcag ctgattttat tattttaact    180
gtaaaaaatt acattagtag aaatttaaaa gcacaagctg tcatttggta a            231

SEQ ID NO: 332          moltype = AA  length = 64
FEATURE                 Location/Qualifiers
source                  1..64
                        mol_type = protein
                        organism = Clostridium perfringens
SEQUENCE: 332
MDSELFKLMA TQGAFAILFS YLLFYVLKEN SKREDKYQNI IEELTELLPK IKEDVEDIKE     60
KLNK                                                                 64

SEQ ID NO: 333          moltype = DNA  length = 195
```

```
FEATURE                 Location/Qualifiers
source                  1..195
                        mol_type = genomic DNA
                        organism = Clostridium perfringens
SEQUENCE: 333
atggatagtg aattatttaa gttaatggca acacaaggag cctttgcaat attattttcg    60
tatttattgt tttatgtttt aaaagagaat agtaaaagag aagataagta tcaaaatata  120
atagaggagc ttacagaatt attgccaaaa ataaaagaag atgtagaaga tataaagaa   180
aaacttaata aatag                                                   195

SEQ ID NO: 334          moltype = AA   length = 47
FEATURE                 Location/Qualifiers
source                  1..47
                        mol_type = protein
                        note = Micrococcus varians
                        organism = Micrococcus sp.
SEQUENCE: 334
MTNAFQALDE VTDAELDAIL GGGSGVIPTI SHECHMNSFQ FVFTCCS                  47

SEQ ID NO: 335          moltype = DNA   length = 144
FEATURE                 Location/Qualifiers
source                  1..144
                        mol_type = genomic DNA
                        note = Micrococcus varians
                        organism = Micrococcus sp.
SEQUENCE: 335
atgacgaacg catttcaggc actggacgaa gtcacggacg ccgagctcga cgccatcctt    60
ggcgggggca gtggtgttat tcccacgatc agccacgagt gccacatgaa ctccttccag  120
ttcgtgttca cctgctgctc ctga                                         144

SEQ ID NO: 336          moltype = AA   length = 285
FEATURE                 Location/Qualifiers
source                  1..285
                        mol_type = protein
                        note = subsp. zooepidemicus
                        organism = Streptococcus equi
SEQUENCE: 336
MKRIFFAFLS LCLFIFGTQT VSAATYTRPL DTGNITTGFN GYPGHVGVDY AVPVGTPVRA    60
VANGTVKFAG NGANHPWMLW MAGNCVLIQH ADGMHTGYAH LSKISVSTDS TVKQGQIIGY  120
TGATGQVTGP HLHFEMLPAN PNWQNGFSGR IDPTGYIANA PVFNGTTPTE PTTPTTNLKI  180
YKVDDLQKIN GIWQVRNNIL VPTDFTWVDN GIAADDVIEV TSNGTRTSDQ VLQKGGYFVI  240
NPNNVKSVGT PMKGSGGLSW AQVNFTTGGN VWLNTTSKDN LLYGK                  285

SEQ ID NO: 337          moltype = DNA   length = 858
FEATURE                 Location/Qualifiers
source                  1..858
                        mol_type = genomic DNA
                        note = subsp. zooepidemicus
                        organism = Streptococcus equi
SEQUENCE: 337
atgaaacgta tattttttgc tttcttaagt ttatgcttat ttatattcgg aacacaaacg    60
gtatctgcag ctacttatac tcggccatta gatacgggaa atatcactac agggtttaac  120
ggataccctg gtcatgttgg agtcgattat gcagtacccg ttggaactcc ggttagagca  180
gttgcaaatg gtacagtcaa atttgcaggt aatggggcta atcacccatg gatgctttgg  240
atggctggaa actgtgttct aattcaacat gctgacggga tgcatactgg atatgcacac  300
ttatcaaaaa tttcagttag cacagatagt acagttaaac aaggacaaat cataggttat  360
actggtgcca ccggccaagt taccggtcca catttgcatt ttgaaatgtt gccagcaaat  420
cctaactggc aaaatggttt ttctggaaga atagatccaa ccggatacat cgctaatgcc  480
cctgtattta tggaacaac  acctacagaa cctactactc ctacaacaaa tttaaaaatc  540
tataaagttg atgatttaca aaaaattaat ggtatttggc aagtaagaaa taacatactt  600
gtaccaactg atttcacatg ggttgataat ggaattgcag cagatgatgt aattgaagta  660
actagcaatg gaacaagaac ctctgaccaa gttcttcaaa aggtggtta ttttgtcatc  720
aatcctaata atgttaaaag tgttggaact ccgatgaaag gtagtggtgg tctatcttgg  780
gctcaagtaa actttacaac aggtggaaat gtctggttaa atactactag caagacaac   840
ttactttacg gaaaataa                                                858

SEQ ID NO: 338          moltype = AA   length = 45
FEATURE                 Location/Qualifiers
source                  1..45
                        mol_type = protein
                        organism = Myxococcus fulvus
SEQUENCE: 338
ANCSCSTASD YCPILTFCTT GTACSYTPTG CGTGWVYCAC NGNFY                    45

SEQ ID NO: 339          moltype = DNA   length = 135
FEATURE                 Location/Qualifiers
misc_feature            1..135
                        note = Polynucleotide encoding the polypeptide of SEQ IDNO:
                        338
```

```
source                  1..135
                        mol_type = other DNA
                        organism = synthetic construct
SEQUENCE: 339
gcgaactgca gctgcagcac cgcgagcgat tattgcccga ttctgacctt ttgcaccacc   60
ggcaccgcgt gcagctatac cccgaccggc tgcggcaccg gctgggtgta ttgcgcgtgc  120
aacggcaact tttat                                                  135

SEQ ID NO: 340          moltype = AA  length = 19
FEATURE                 Location/Qualifiers
source                  1..19
                        mol_type = protein
                        organism = Streptomyces griseoluteus
SEQUENCE: 340
CANSCSYGPL TWSCDGNTK                                               19

SEQ ID NO: 341          moltype = DNA  length = 57
FEATURE                 Location/Qualifiers
misc_feature            1..57
                        note = Polynucleotide encoding the polypeptide of SEQ IDNO:
                         340
source                  1..57
                        mol_type = other DNA
                        organism = synthetic construct
SEQUENCE: 341
tgcgcgaaca gctgcagcta tggcccgctg acctggagct gcgatggcaa caccaaa     57

SEQ ID NO: 342          moltype = AA  length = 19
FEATURE                 Location/Qualifiers
source                  1..19
                        mol_type = protein
                        note = Streptoverticillium griseoverticillatum
                        organism = unidentified
SEQUENCE: 342
CKQSCSFGPF TFVCDGNTK                                               19

SEQ ID NO: 343          moltype = DNA  length = 57
FEATURE                 Location/Qualifiers
misc_feature            1..57
                        note = Polynucleotide encoding the polypeptide of SEQ IDNO:
                         342
source                  1..57
                        mol_type = other DNA
                        organism = synthetic construct
SEQUENCE: 343
tgcaaacaga gctgcagctt tggcccgttt acctttgtgt gcgatggcaa caccaaa     57

SEQ ID NO: 344          moltype = AA  length = 7
FEATURE                 Location/Qualifiers
source                  1..7
                        mol_type = protein
                        organism = Carnobacterium sp.
SEQUENCE: 344
GSEIQPR                                                             7

SEQ ID NO: 345          moltype = DNA  length = 21
FEATURE                 Location/Qualifiers
misc_feature            1..21
                        note = Polynucleotide encoding the polypeptide of SEQ IDNO:
                         344
source                  1..21
                        mol_type = other DNA
                        organism = synthetic construct
SEQUENCE: 345
ggcagcgaaa ttcagccgcg c                                            21

SEQ ID NO: 346          moltype = AA  length = 39
FEATURE                 Location/Qualifiers
source                  1..39
                        mol_type = protein
                        note = subsp. lactis
                        organism = Lactococcus lactis
SEQUENCE: 346
GTWDDIGQGI GRVAYWVGKA MGNMSDVNQA SRINRKKKH                          39

SEQ ID NO: 347          moltype = DNA  length = 117
FEATURE                 Location/Qualifiers
misc_feature            1..117
                        note = Polynucleotide encoding the polypeptide of SEQ IDNO:
```

```
                          346
source                    1..117
                          mol_type = other DNA
                          organism = synthetic construct
SEQUENCE: 347
ggcacctggg atgatattgg ccagggcatt ggccgcgtgg cgtattgggt gggcaaagcg    60
atgggcaaca tgagcgatgt gaaccaggcg agccgcatta accgcaaaaa aaaacat     117

SEQ ID NO: 348            moltype = AA   length = 35
FEATURE                   Location/Qualifiers
source                    1..35
                          mol_type = protein
                          note = subsp. lactis
                          organism = Lactococcus lactis
SEQUENCE: 348
KKWGWLAWVD PAYEFIKGFG KGAIKEGNKD KWKNI                               35

SEQ ID NO: 349            moltype = DNA   length = 105
FEATURE                   Location/Qualifiers
misc_feature              1..105
                          note = Polynucleotide encoding the polypeptide of SEQ IDNO:
                          348
source                    1..105
                          mol_type = other DNA
                          organism = synthetic construct
SEQUENCE: 349
aaaaaatggg gctggctggc gtgggtggat ccggcgtatg aatttattaa aggctttggc    60
aaaggcgcga ttaaagaagg caacaaagat aaatggaaaa acatt                  105

SEQ ID NO: 350            moltype = AA   length = 19
FEATURE                   Location/Qualifiers
source                    1..19
                          mol_type = protein
                          organism = Streptomyces sp.
SEQUENCE: 350
CVQSCSFGPL TWSCDGNTK                                                 19

SEQ ID NO: 351            moltype = DNA   length = 57
FEATURE                   Location/Qualifiers
misc_feature              1..57
                          note = Polynucleotide encoding the polypeptide of SEQ IDNO:
                          350
source                    1..57
                          mol_type = other DNA
                          organism = synthetic construct
SEQUENCE: 351
tgcgtgcaga gctgcagctt tggcccgctg acctggagct gcgatggcaa caccaaa       57

SEQ ID NO: 352            moltype = AA   length = 19
FEATURE                   Location/Qualifiers
source                    1..19
                          mol_type = protein
                          note = Actinoplanes liguriae
                          organism = Actinoplanes sp.
SEQUENCE: 352
SSGWVCTLTI ECGTVICAC                                                 19

SEQ ID NO: 353            moltype = DNA   length = 57
FEATURE                   Location/Qualifiers
misc_feature              1..57
                          note = Polynucleotide encoding the polypeptide of SEQ IDNO:
                          352
source                    1..57
                          mol_type = other DNA
                          organism = synthetic construct
SEQUENCE: 353
agcagcggct gggtgtgcac cctgaccatt gaatgcggca ccgtgatttg cgcgtgc       57

SEQ ID NO: 354            moltype = AA   length = 38
FEATURE                   Location/Qualifiers
VARIANT                   37
                          note = Xaa = any amino acid
source                    1..38
                          mol_type = protein
                          organism = Lactobacillus curvatus
VARIANT                   34
                          note = Xaa = any amino acid
SEQUENCE: 354
YTAKQCLQAI GSCGIAGTGA GAAGGPAGAF VGAXVVXI                             38
```

```
SEQ ID NO: 355          moltype = DNA  length = 114
FEATURE                 Location/Qualifiers
misc_feature            1..114
                        note = Polynucleotide encoding the polypeptide of SEQ IDNO:
                        354
misc_feature            100..102
                        note = nnn = any amino acid-coding triplet
misc_feature            109..111
                        note = nnn = any amino acid-coding triplet
source                  1..114
                        mol_type = other DNA
                        organism = synthetic construct
SEQUENCE: 355
tataccgcga aacagtgcct gcaggcgatt ggcagctgcg gcattgcggg caccggcgcg   60
ggcgcggcgg gcggcccggc gggcgcgttt gtgggcgcgn nngtggtgnn natt        114

SEQ ID NO: 356          moltype = AA  length = 42
FEATURE                 Location/Qualifiers
VARIANT                 32
                        note = Xaa = any amino acid
source                  1..42
                        mol_type = protein
                        organism = Lactobacillus sakei
SEQUENCE: 356
TKYYGNGVYC NSKKCWVDWG QAAGGIGQTV VXGWLGGAIP GK                     42

SEQ ID NO: 357          moltype = DNA  length = 126
FEATURE                 Location/Qualifiers
misc_feature            1..126
                        note = Polynucleotide encoding the polypeptide of SEQ IDNO:
                        356
misc_feature            94..96
                        note = nnn = any amino acid-coding triplet
source                  1..126
                        mol_type = other DNA
                        organism = synthetic construct
SEQUENCE: 357
accaaatatt atggcaacgg cgtgtattgc aacagcaaaa aatgctgggt ggattggggc   60
caggcggcgg gcggcattgg ccagaccgtg gtgnnnggct ggctgggcgg cgcgattccg  120
ggcaaa                                                             126

SEQ ID NO: 358          moltype = AA  length = 22
FEATURE                 Location/Qualifiers
source                  1..22
                        mol_type = protein
                        organism = Streptococcus mutans
SEQUENCE: 358
FKSWSFCTPG CAKTGSFNSY CC                                           22

SEQ ID NO: 359          moltype = DNA  length = 132
FEATURE                 Location/Qualifiers
misc_feature            1..132
                        note = Polynucleotide encoding the polypeptide of SEQ IDNO:
                        358
source                  1..132
                        mol_type = other DNA
                        organism = synthetic construct
SEQUENCE: 359
tttaaaagct ggagcttttg caccccgggc tgcgcgaaaa ccggcagctt taacagctat   60
tgctgcttta aaagctggag cttttgcacc ccgggctgcg cgaaaaccgg cagctttaac  120
agctattgct gc                                                     132

SEQ ID NO: 360          moltype = AA  length = 43
FEATURE                 Location/Qualifiers
source                  1..43
                        mol_type = protein
                        organism = Enterococcus mundtii
SEQUENCE: 360
KYYGNGVSCN KKGCSVDWGK AIGIIGNNSA ANLATGGAAG WSK                    43

SEQ ID NO: 361          moltype = DNA  length = 129
FEATURE                 Location/Qualifiers
misc_feature            1..129
                        note = Polynucleotide encoding the polypeptide of SEQ IDNO:
                        360
source                  1..129
                        mol_type = other DNA
                        organism = synthetic construct
```

```
SEQUENCE: 361
aaatattatg gcaacggcgt gagctgcaac aaaaaaggct gcagcgtgga ttggggcaaa    60
gcgattggca ttattggcaa caacagcgcg gcgaacctgg cgaccggcgg cgcggcgggc   120
tggagcaaa                                                           129

SEQ ID NO: 362         moltype = AA   length = 41
FEATURE                Location/Qualifiers
VARIANT                9
                       note = Xaa = any amino acid
source                 1..41
                       mol_type = protein
                       organism = Lactobacillus sakei
VARIANT                14
                       note = Xaa = any amino acid
VARIANT                33
                       note = Xaa = any amino acid
VARIANT                37
                       note = Xaa = any amino acid
SEQUENCE: 362
KYYGNGVHXG KHSXTVDWGT AIGNIGNNAA ANXATGXNAG G                        41

SEQ ID NO: 363         moltype = DNA   length = 123
FEATURE                Location/Qualifiers
misc_feature           1..123
                       note = Polynucleotide encoding the polypeptide of SEQ IDNO:
                        362
misc_feature           25..27
                       note = nnn = any amino acid-coding triplet
misc_feature           40..42
                       note = nnn = any amino acid-coding triplet
misc_feature           97..99
                       note = nnn = any amino acid-coding triplet
misc_feature           109..111
                       note = nnn = any amino acid-coding triplet
source                 1..123
                       mol_type = other DNA
                       organism = synthetic construct
SEQUENCE: 363
aaatattatg gcaacggcgt gcatnnnggc aaacatagcn nnaccgtgga ttggggcacc    60
gcgattggca acattggcaa caacgcggcg gcgaacnnng cgaccggcnn naacgcgggc   120
ggc                                                                 123

SEQ ID NO: 364         moltype = AA   length = 31
FEATURE                Location/Qualifiers
source                 1..31
                       mol_type = protein
                       organism = Lactobacillus paracasei
SEQUENCE: 364
GMSGYIQGIP DFLKGYLHGI SAANKHKKGR L                                   31

SEQ ID NO: 365         moltype = DNA   length = 93
FEATURE                Location/Qualifiers
misc_feature           1..93
                       note = Polynucleotide encoding the polypeptide of SEQ IDNO:
                        364
source                 1..93
                       mol_type = other DNA
                       organism = synthetic construct
SEQUENCE: 365
ggcatgagcg gctatattca gggcattccg gatttctga aaggctatct gcatggcatt    60
agcgcggcga acaaacataa aaaaggccgc ctg                                 93

SEQ ID NO: 366         moltype = AA   length = 31
FEATURE                Location/Qualifiers
source                 1..31
                       mol_type = protein
                       organism = Leuconostoc mesenteroides
SEQUENCE: 366
KGKGFWSWAS KATSWLTGPQ QPGSPLLKKH R                                   31

SEQ ID NO: 367         moltype = DNA   length = 93
FEATURE                Location/Qualifiers
misc_feature           1..93
                       note = Polynucleotide encoding the polypeptide of SEQ IDNO:
                        366
source                 1..93
                       mol_type = other DNA
                       organism = synthetic construct
SEQUENCE: 367
```

```
aaaggcaaag gcttttggag ctgggcgagc aaagcgacca gctggctgac cggcccgcag    60
cagccgggca gcccgctgct gaaaaaacat cgc                                 93
```

SEQ ID NO: 368         moltype = AA  length = 43
FEATURE                Location/Qualifiers
source                 1..43
                       mol_type = protein
                       organism = Leuconostoc mesenteroides
SEQUENCE: 368
KNYGNGVHCT KKGCSVDWGY AWTNIANNSV MNGLTGGNAG WHN                      43

SEQ ID NO: 369         moltype = DNA  length = 129
FEATURE                Location/Qualifiers
misc_feature           1..129
                       note = Polynucleotide encoding the polypeptide of SEQ IDNO:
                        368
source                 1..129
                       mol_type = other DNA
                       organism = synthetic construct
SEQUENCE: 369
```
aaaaactatg gcaacggcgt gcattgcacc aaaaaaggct gcagcgtgga ttggggctat    60
gcgtggacca acattgcgaa caacagcgtg atgaacggcc tgaccggcgg caacgcgggc   120
tggcataac                                                          129
```

SEQ ID NO: 370         moltype = AA  length = 47
FEATURE                Location/Qualifiers
source                 1..47
                       mol_type = protein
                       organism = Bacillus subtilis
SEQUENCE: 370
AIKLVQSPNG NFAASFVLDG TKWIFKSKYY DSSKGYWVGI YEVWDRK                  47

SEQ ID NO: 371         moltype = DNA  length = 141
FEATURE                Location/Qualifiers
misc_feature           1..141
                       note = Polynucleotide encoding the polypeptide of SEQ IDNO:
                        370
source                 1..141
                       mol_type = other DNA
                       organism = synthetic construct
SEQUENCE: 371
```
gcgattaaac tggtgcagag cccgaacggc aactttgcgg cgagctttgt gctggatggc    60
accaaatgga ttttttaaaag caatattat gatagcagca aaggctattg ggtgggcatt   120
tatgaagtgt gggatcgcaa a                                            141
```

SEQ ID NO: 372         moltype = AA  length = 12
FEATURE                Location/Qualifiers
VARIANT                7
                       note = Xaa = any amino acid
source                 1..12
                       mol_type = protein
                       organism = Bacillus licheniformis
SEQUENCE: 372
ISLEICXIFH DN                                                        12

SEQ ID NO: 373         moltype = DNA  length = 36
FEATURE                Location/Qualifiers
misc_feature           1..36
                       note = Polynucleotide encoding the polypeptide of SEQ IDNO:
                        372
misc_feature           19..21
                       note = nnn = any amino acid-coding triplet
source                 1..36
                       mol_type = other DNA
                       organism = synthetic construct
SEQUENCE: 373
```
attagcctgg aaatttgcnn nattttcat gataac                              36
```

SEQ ID NO: 374         moltype = AA  length = 37
FEATURE                Location/Qualifiers
source                 1..37
                       mol_type = protein
                       note = subsp. lactis
                       organism = Lactococcus lactis
SEQUENCE: 374
TSYGNGVHCN KSKCWIDVSE LETYKAGTVS NPKDILW                             37

SEQ ID NO: 375         moltype = DNA  length = 111
FEATURE                Location/Qualifiers

```
misc_feature        1..111
                    note = Polynucleotide encoding the polypeptide of SEQ IDNO:
                    374
source              1..111
                    mol_type = other DNA
                    organism = synthetic construct
SEQUENCE: 375
accagctatg gcaacggcgt gcattgcaac aaaagcaaat gctggattga tgtgagcgaa    60
ctggaaacct ataaagcggg caccgtgagc aacccgaaag atattctgtg g            111

SEQ ID NO: 376      moltype = AA   length = 9
FEATURE             Location/Qualifiers
source              1..9
                    mol_type = protein
                    organism = Serratia plymuthica
SEQUENCE: 376
DYHHGVRVL                                                            9

SEQ ID NO: 377      moltype = DNA   length = 27
FEATURE             Location/Qualifiers
misc_feature        1..27
                    note = Polynucleotide encoding the polypeptide of SEQ IDNO:
                    376
source              1..27
                    mol_type = other DNA
                    organism = synthetic construct
SEQUENCE: 377
gattatcatc atggcgtgcg cgtgctg                                        27

SEQ ID NO: 378      moltype = AA   length = 15
FEATURE             Location/Qualifiers
source              1..15
                    mol_type = protein
                    organism = Halobacterium sp.
SEQUENCE: 378
DIDITGCSAC KYAAG                                                     15

SEQ ID NO: 379      moltype = DNA   length = 45
FEATURE             Location/Qualifiers
misc_feature        1..45
                    note = Polynucleotide encoding the polypeptide of SEQ IDNO:
                    378
source              1..45
                    mol_type = other DNA
                    organism = synthetic construct
SEQUENCE: 379
gatattgata ttaccggctg cagcgcgtgc aaatatgcgg cgggc                    45

SEQ ID NO: 380      moltype = AA   length = 12
FEATURE             Location/Qualifiers
VARIANT             1
                    note = Xaa = any amino acid
source              1..12
                    mol_type = protein
                    organism = Bacillus subtilis
VARIANT             2
                    note = Xaa = any amino acid
VARIANT             6
                    note = Xaa = any amino acid
SEQUENCE: 380
XXKEIXHIFH DN                                                        12

SEQ ID NO: 381      moltype = DNA   length = 36
FEATURE             Location/Qualifiers
misc_feature        1..36
                    note = Polynucleotide encoding the polypeptide of SEQ IDNO:
                    380
misc_feature        1..3
                    note = nnn = any amino acid-coding triplet
misc_feature        4..6
                    note = nnn = any amino acid-coding triplet
misc_feature        16..18
                    note = nnn = any amino acid-coding triplet
source              1..36
                    mol_type = other DNA
                    organism = synthetic construct
SEQUENCE: 381
nnnnnnaaag aaattnnnca tatttttcat gataac                              36
```

```
SEQ ID NO: 382          moltype = AA  length = 12
FEATURE                 Location/Qualifiers
source                  1..12
                        mol_type = protein
                        organism = Lactobacillus curvatus
SEQUENCE: 382
TPVVNPPFLQ QT                                                         12

SEQ ID NO: 383          moltype = DNA  length = 36
FEATURE                 Location/Qualifiers
misc_feature            1..36
                        note = Polynucleotide encoding the polypeptide of SEQ IDNO:
                         382
source                  1..36
                        mol_type = other DNA
                        organism = synthetic construct
SEQUENCE: 383
accccggtgg tgaacccgcc gtttctgcag cagacc                               36

SEQ ID NO: 384          moltype = AA  length = 10
FEATURE                 Location/Qualifiers
VARIANT                 10
                        note = Xaa = any amino acid
source                  1..10
                        mol_type = protein
                        organism = Lactobacillus curvatus
SEQUENCE: 384
VAPFPEQFLX                                                            10

SEQ ID NO: 385          moltype = DNA  length = 30
FEATURE                 Location/Qualifiers
misc_feature            1..30
                        note = Polynucleotide encoding the polypeptide of SEQ IDNO:
                         384
misc_feature            28..30
                        note = nnn = any amino acid-coding triplet
source                  1..30
                        mol_type = other DNA
                        organism = synthetic construct
SEQUENCE: 385
gtggcgccgt ttccggaaca gtttctgnnn                                      30

SEQ ID NO: 386          moltype = AA  length = 9
FEATURE                 Location/Qualifiers
source                  1..9
                        mol_type = protein
                        organism = Lactobacillus curvatus
SEQUENCE: 386
NIPQLTPTP                                                             9

SEQ ID NO: 387          moltype = DNA  length = 27
FEATURE                 Location/Qualifiers
misc_feature            1..27
                        note = Polynucleotide encoding the polypeptide of SEQ IDNO:
                         386
source                  1..27
                        mol_type = other DNA
                        organism = synthetic construct
SEQUENCE: 387
aacattccgc agctgacccc gaccccg                                         27

SEQ ID NO: 388          moltype = AA  length = 18
FEATURE                 Location/Qualifiers
VARIANT                 4
                        note = Xaa = any amino acid
                        note = Xaa = any amino acid
source                  1..18
                        mol_type = protein
                        note = subsp. entomocidus
                        organism = Bacillus thuringiensis
VARIANT                 7
                        note = Xaa = any amino acid
VARIANT                 10
                        note = Xaa = any amino acid
SEQUENCE: 388
DWTXWSXLVX AACSVELL                                                   18

SEQ ID NO: 389          moltype = DNA  length = 54
FEATURE                 Location/Qualifiers
```

```
misc_feature              1..54
                          note = Polynucleotide encoding the polypeptide of SEQ IDNO:
                            388
misc_feature              10..12
                          note = nnn = any amino acid-coding triplet
misc_feature              19..21
                          note = nnn = any amino acid-coding triplet
misc_feature              28..30
                          note = nnn = any amino acid-coding triplet
source                    1..54
                          mol_type = other DNA
                          organism = synthetic construct
SEQUENCE: 389
gattggaccn nntggagcnn nctggtgnnn gcggcgtgca gcgtggaact gctg          54

SEQ ID NO: 390           moltype = AA  length = 30
FEATURE                  Location/Qualifiers
source                   1..30
                         mol_type = protein
                         organism = Lactobacillus curvatus
SEQUENCE: 390
AYPGNGVHCG KYSCTVDKQT AIGNIGNNAA                                     30

SEQ ID NO: 391           moltype = DNA  length = 90
FEATURE                  Location/Qualifiers
misc_feature             1..90
                         note = Polynucleotide encoding the polypeptide of SEQ IDNO:
                           390
source                   1..90
                         mol_type = other DNA
                         organism = synthetic construct
SEQUENCE: 391
gcgtatccgg gcaacggcgt gcattgcggc aaatatagct gcaccgtgga taaacagacc    60
gcgattggca acattggcaa caacgcggcg                                     90

SEQ ID NO: 392           moltype = AA  length = 43
FEATURE                  Location/Qualifiers
source                   1..43
                         mol_type = protein
                         organism = Carnobacterium divergens
SEQUENCE: 392
TKYYGNGVYC NSKKCWVDWG TAQGCIDVVI GQLGGGIPGK GKC                      43

SEQ ID NO: 393           moltype = DNA  length = 129
FEATURE                  Location/Qualifiers
misc_feature             1..129
                         note = Polynucleotide encoding the polypeptide of SEQ IDNO:
                           392
source                   1..129
                         mol_type = other DNA
                         organism = synthetic construct
SEQUENCE: 393
accaaatatt atggcaacgg cgtgtattgc aacagcaaaa aatgctgggt ggattggggc    60
accgcgcagg gctgcattga tgtggtgatt ggccagctgg gcggcggcat tccgggcaaa   120
ggcaaatgc                                                           129

SEQ ID NO: 394           moltype = AA  length = 62
FEATURE                  Location/Qualifiers
source                   1..62
                         mol_type = protein
                         organism = Enterococcus sp.
SEQUENCE: 394
NRWYCNSAAG GVGGAAVCGL AGYVGEAKEN IAGEVRKGWG MAGGFTHNKA CKSFPGSGWA    60
SG                                                                  62

SEQ ID NO: 395           moltype = DNA  length = 186
FEATURE                  Location/Qualifiers
misc_feature             1..186
                         note = Polynucleotide encoding the polypeptide of SEQ IDNO:
                           394
source                   1..186
                         mol_type = other DNA
                         organism = synthetic construct
SEQUENCE: 395
aaccgctggt attgcaacag cgcggcgggc ggcgtgggcg gcgcggcggt gtgcggcctg    60
gcgggctatg tgggcgaagc gaaagaaaac attgcgggcg aagtgcgcaa aggctggggc   120
atggcgggcg gctttaccca taacaaagcg tgcaaaagct ttccgggcag cggctgggcg   180
agcggc                                                              186
```

```
SEQ ID NO: 396            moltype = AA  length = 39
FEATURE                   Location/Qualifiers
source                    1..39
                          mol_type = protein
                          organism = Enterococcus faecium
SEQUENCE: 396
TTKNYGNGVC NSVNWCQCGN VWASCNLATG CAAWLCKLA                              39

SEQ ID NO: 397            moltype = DNA  length = 117
FEATURE                   Location/Qualifiers
misc_feature              1..117
                          note = Polynucleotide encoding the polypeptide of SEQ IDNO:
                           396
source                    1..117
                          mol_type = other DNA
                          organism = synthetic construct
SEQUENCE: 397
accaccaaaa actatggcaa cggcgtgtgc aacagcgtga actggtgcca gtgcggcaac       60
gtgtgggcga gctgcaacct ggcgaccggc tgcgcggcgt ggctgtgcaa actggcg         117

SEQ ID NO: 398            moltype = AA  length = 30
FEATURE                   Location/Qualifiers
source                    1..30
                          mol_type = protein
                          organism = Paenibacillus polymyxa
SEQUENCE: 398
ASIIKTTIKV SKAVCKTLTC ICTGSCSNCK                                        30

SEQ ID NO: 399            moltype = DNA  length = 90
FEATURE                   Location/Qualifiers
misc_feature              1..90
                          note = Polynucleotide encoding the polypeptide of SEQ IDNO:
                           398
source                    1..90
                          mol_type = other DNA
                          organism = synthetic construct
SEQUENCE: 399
gcgagcatta ttaaaaccac cattaaagtg agcaaagcgg tgtgcaaaac cctgacctgc       60
atttgcaccg gcagctgcag caactgcaaa                                        90

SEQ ID NO: 400            moltype = AA  length = 31
FEATURE                   Location/Qualifiers
source                    1..31
                          mol_type = protein
                          organism = Staphylococcus epidermidis
SEQUENCE: 400
SASIVKTTIK ASKKLCRGFT LTCGCHFTGK K                                      31

SEQ ID NO: 401            moltype = DNA  length = 93
FEATURE                   Location/Qualifiers
misc_feature              1..93
                          note = Polynucleotide encoding the polypeptide of SEQ IDNO:
                           400
source                    1..93
                          mol_type = other DNA
                          organism = synthetic construct
SEQUENCE: 401
agcgcgagca ttgtgaaaac caccattaaa gcgagcaaaa aactgtgccg cggctttacc       60
ctgacctgcg gctgccattt taccggcaaa aaa                                    93

SEQ ID NO: 402            moltype = AA  length = 43
FEATURE                   Location/Qualifiers
source                    1..43
                          mol_type = protein
                          organism = Enterococcus faecium
SEQUENCE: 402
KYYGNGVSCN KKGCSVDWGK AIGIIGNNAA ANLTTGGKAA WAC                         43

SEQ ID NO: 403            moltype = DNA  length = 129
FEATURE                   Location/Qualifiers
misc_feature              1..129
                          note = Polynucleotide encoding the polypeptide of SEQ IDNO:
                           402
source                    1..129
                          mol_type = other DNA
                          organism = synthetic construct
SEQUENCE: 403
aaatattatg gcaacggcgt gagctgcaac aaaaaaggct gcagcgtgga ttggggcaaa       60
gcgattggca ttattggcaa caacgcggcg gcgaacctga ccaccggcgg caaagcggcg      120
``` tgggcgtgc 129

SEQ ID NO: 404         moltype = AA   length = 39
FEATURE                Location/Qualifiers
source                 1..39
                       mol_type = protein
                       organism = Paenibacillus polymyxa
SEQUENCE: 404
ATYYGNGLYC NKQKHYTWVD WNKASREIGK ITVNGWVQH 39

SEQ ID NO: 405         moltype = DNA   length = 117
FEATURE                Location/Qualifiers
misc_feature           1..117
                       note = Polynucleotide encoding the polypeptide of SEQ IDNO:
                       404
source                 1..117
                       mol_type = other DNA
                       organism = synthetic construct
SEQUENCE: 405
gcgacctatt atggcaacgg cctgtattgc aacaaacaga acattatac ctgggtggat      60
tggaacaaag cgagccgcga aattggcaaa attaccgtga acggctgggt gcagcat       117

SEQ ID NO: 406         moltype = AA   length = 35
FEATURE                Location/Qualifiers
source                 1..35
                       mol_type = protein
                       organism = Bacillus circulans
SEQUENCE: 406
VNYGNGVSCS KTKCSVNWGI ITHQAFRVTS GVASG 35

SEQ ID NO: 407         moltype = DNA   length = 105
FEATURE                Location/Qualifiers
misc_feature           1..105
                       note = Polynucleotide encoding the polypeptide of SEQ IDNO:
                       406
source                 1..105
                       mol_type = other DNA
                       organism = synthetic construct
SEQUENCE: 407
gtgaactatg gcaacggcgt gagctgcagc aaaaccaaat gcagcgtgaa ctggggcatt    60
attaccatc aggcgtttcg cgtgaccagc ggcgtggcga gcggc                    105

SEQ ID NO: 408         moltype = AA   length = 30
FEATURE                Location/Qualifiers
source                 1..30
                       mol_type = protein
                       organism = Paenibacillus polymyxa
SEQUENCE: 408
FVYGNGVTSI LVQAQFLVNG QRRFFYTPDK 30

SEQ ID NO: 409         moltype = DNA   length = 90
FEATURE                Location/Qualifiers
misc_feature           1..90
                       note = Polynucleotide encoding the polypeptide of SEQ IDNO:
                       408
source                 1..90
                       mol_type = other DNA
                       organism = synthetic construct
SEQUENCE: 409
tttgtgtatg gcaacggcgt gaccagcatt ctggtgcagg cgcagtttct ggtgaacggc    60
cagcgccgct ttttttatac cccggataaa                                     90

SEQ ID NO: 410         moltype = AA   length = 13
FEATURE                Location/Qualifiers
source                 1..13
                       mol_type = protein
                       organism = Lactobacillus rhamnosus
SEQUENCE: 410
AVPAVRKTNE TLD 13

SEQ ID NO: 411         moltype = DNA   length = 39
FEATURE                Location/Qualifiers
misc_feature           1..39
                       note = Polynucleotide encoding the polypeptide of SEQ IDNO:
                       410
source                 1..39
                       mol_type = other DNA
                       organism = synthetic construct
SEQUENCE: 411

```
gcggtgccgg cggtgcgcaa aaccaacgaa accctggat                    39

SEQ ID NO: 412          moltype = AA   length = 69
FEATURE                 Location/Qualifiers
source                  1..69
                        mol_type = protein
                        organism = Bacillus licheniformis
SEQUENCE: 412
MKNSAAREAF KGANHPAGMV SEEELKALVG GNDVNPETTP ATTSSWTCIT AGVTVSASLC   60
PTTKCTSRC                                                           69

SEQ ID NO: 413          moltype = DNA   length = 207
FEATURE                 Location/Qualifiers
misc_feature            1..207
                        note = Polynucleotide encoding the polypeptide of SEQ IDNO:
                         412
source                  1..207
                        mol_type = other DNA
                        organism = synthetic construct
SEQUENCE: 413
atgaaaaaca gcgcggcgcg cgaagcgttt aaaggcgcga accatccggc gggcatggtg   60
agcgaagaag aactgaaagc gctggtgggc ggcaacgatg tgaacccgga aaccacccg   120
gcgaccacca gcagctggac ctgcattacc gcgggcgtga ccgtgagcgc gagcctgtgc  180
ccgaccacca aatgcaccag ccgctgc                                      207

SEQ ID NO: 414          moltype = AA   length = 36
FEATURE                 Location/Qualifiers
source                  1..36
                        mol_type = protein
                        organism = Lactobacillus plantarum
SEQUENCE: 414
KYYGNLSCS KKGCTVNWGQ AFSCGVNRVA TAGHGK                              36

SEQ ID NO: 415          moltype = DNA   length = 108
FEATURE                 Location/Qualifiers
misc_feature            1..108
                        note = Polynucleotide encoding the polypeptide of SEQ IDNO:
                         414
source                  1..108
                        mol_type = other DNA
                        organism = synthetic construct
SEQUENCE: 415
aaatattatg gcaacggcct gagctgcagc aaaaaaggct gcaccgtgaa ctggggccag   60
gcgtttagct gcggcgtgaa ccgcgtggcg accgcgggcc atggcaaa               108

SEQ ID NO: 416          moltype = AA   length = 24
FEATURE                 Location/Qualifiers
source                  1..24
                        mol_type = protein
                        organism = Lactobacillus acidophilus
SEQUENCE: 416
GNPKVAHCAS QIGRSTAWGA VSGA                                          24

SEQ ID NO: 417          moltype = DNA   length = 72
FEATURE                 Location/Qualifiers
misc_feature            1..72
                        note = Polynucleotide encoding the polypeptide of SEQ IDNO:
                         416
source                  1..72
                        mol_type = other DNA
                        organism = synthetic construct
SEQUENCE: 417
ggcaacccga aagtggcgca ttgcgcgagc cagattggcc gcagcaccgc gtggggcgcg   60
gtgagcggcg cg                                                       72

SEQ ID NO: 418          moltype = AA   length = 40
FEATURE                 Location/Qualifiers
source                  1..40
                        mol_type = protein
                        organism = Enterococcus faecalis
SEQUENCE: 418
WLPPAGLLGR CGRWFRPWLL WLQSGAQYKW LGNLFGLGPK                         40

SEQ ID NO: 419          moltype = DNA   length = 120
FEATURE                 Location/Qualifiers
misc_feature            1..120
                        note = Polynucleotide encoding the polypeptide of SEQ IDNO:
                         418
source                  1..120
```

```
                        mol_type = other DNA
                        organism = synthetic construct
SEQUENCE: 419
tggctgccgc cggcgggcct gctgggccgc tgcggccgct ggtttcgccc gtggctgctg    60
tggctgcaga gcgcgcgcca gtataaatgg ctgggcaacc tgtttggcct gggcccgaaa   120

SEQ ID NO: 420          moltype = AA   length = 40
FEATURE                 Location/Qualifiers
source                  1..40
                        mol_type = protein
                        organism = Anabaena variabilis
SEQUENCE: 420
NLDQWLTEQV HEFQDMYLEP QAISNQDITF KLSDLDFIHN                          40

SEQ ID NO: 421          moltype = DNA   length = 124
FEATURE                 Location/Qualifiers
source                  1..124
                        mol_type = genomic DNA
                        organism = Anabaena variabilis
SEQUENCE: 421
taatttagat cagtggttaa cagaacaagt tcatgagttt caagatatgt acttggaacc    60
acaagcaata tccaatcaag acattacctt caaactatct gacctagatt ttattcataa   120
ttga                                                                124

SEQ ID NO: 422          moltype = AA   length = 40
FEATURE                 Location/Qualifiers
source                  1..40
                        mol_type = protein
                        organism = Nostoc sp.
SEQUENCE: 422
NLDQWLTEQV HEFQDMYLEP QAISNQDITF KLSDLDFIHN                          40

SEQ ID NO: 423          moltype = DNA   length = 123
FEATURE                 Location/Qualifiers
source                  1..123
                        mol_type = genomic DNA
                        organism = Nostoc sp.
SEQUENCE: 423
aatttagatc aatggttaac agaacaagtt catgagtttc aagatatgta cttggaacca    60
caagcaatat ccaatcaaga cattaccttc aaactgtcag acctagattt tattcataat   120
tga                                                                 123

SEQ ID NO: 424          moltype = AA   length = 7
FEATURE                 Location/Qualifiers
source                  1..7
                        mol_type = protein
                        note = Nostoc azollae
                        organism = Nostoc sp.
SEQUENCE: 424
HREKKSA                                                              7

SEQ ID NO: 425          moltype = DNA   length = 24
FEATURE                 Location/Qualifiers
source                  1..24
                        mol_type = genomic DNA
                        note = Nostoc azollae
                        organism = Nostoc sp.
SEQUENCE: 425
cacagagaga aaaaatcagc atag                                           24

SEQ ID NO: 426          moltype = AA   length = 23
FEATURE                 Location/Qualifiers
source                  1..23
                        mol_type = protein
                        note = Acaryochloris marina
                        organism = unidentified
SEQUENCE: 426
TSNNWLAKNY LSMWNKKSSN PNL                                            23

SEQ ID NO: 427          moltype = DNA   length = 72
FEATURE                 Location/Qualifiers
source                  1..72
                        mol_type = genomic DNA
                        note = Acaryochloris marina
                        organism = unidentified
SEQUENCE: 427
acaagcaata actggctagc caaaactat ctttctatgt ggaataaaaa gagcagtaat     60
ccaaaccttt ag                                                        72
```

```
SEQ ID NO: 428           moltype = AA  length = 6
FEATURE                  Location/Qualifiers
source                   1..6
                         mol_type = protein
                         note = Cyanothece sp.
                         organism = unidentified
SEQUENCE: 428
FRYFWW                                                                    6

SEQ ID NO: 429           moltype = DNA  length = 21
FEATURE                  Location/Qualifiers
source                   1..21
                         mol_type = genomic DNA
                         note = Cyanothece sp.
                         organism = unidentified
SEQUENCE: 429
tttagatatt tttggtggta a                                                  21

SEQ ID NO: 430           moltype = AA  length = 6
FEATURE                  Location/Qualifiers
source                   1..6
                         mol_type = protein
                         note = Cyanothece sp.
                         organism = unidentified
SEQUENCE: 430
FRYFWW                                                                    6

SEQ ID NO: 431           moltype = DNA  length = 21
FEATURE                  Location/Qualifiers
source                   1..21
                         mol_type = genomic DNA
                         note = Cyanothece sp.
                         organism = unidentified
SEQUENCE: 431
tttagatatt tttggtggta a                                                  21

SEQ ID NO: 432           moltype = AA  length = 9
FEATURE                  Location/Qualifiers
source                   1..9
                         mol_type = protein
                         note = Cyanothece sp.
                         organism = unidentified
SEQUENCE: 432
CGEKWRIFS                                                                 9

SEQ ID NO: 433           moltype = DNA  length = 27
FEATURE                  Location/Qualifiers
source                   1..27
                         mol_type = genomic DNA
                         note = Cyanothece sp.
                         organism = unidentified
SEQUENCE: 433
tgtggagaaa aatggagaat ttttagc                                            27

SEQ ID NO: 434           moltype = AA  length = 8
FEATURE                  Location/Qualifiers
source                   1..8
                         mol_type = protein
                         note = Cyanothece sp.
                         organism = unidentified
SEQUENCE: 434
FRLQLWQF                                                                  8

SEQ ID NO: 435           moltype = DNA  length = 24
FEATURE                  Location/Qualifiers
source                   1..24
                         mol_type = genomic DNA
                         note = Cyanothece sp.
                         organism = unidentified
SEQUENCE: 435
tttcgcttac aactgtggca attt                                               24

SEQ ID NO: 436           moltype = AA  length = 16
FEATURE                  Location/Qualifiers
source                   1..16
                         mol_type = protein
                         note = Cyanothece sp.
                         organism = unidentified
SEQUENCE: 436
```

```
LGCNQSSIWS IFFWNH                                                      16

SEQ ID NO: 437          moltype = DNA   length = 51
FEATURE                 Location/Qualifiers
source                  1..51
                        mol_type = genomic DNA
                        note = Cyanothece sp.
                        organism = unidentified
SEQUENCE: 437
ctaggatgta accagagcag tatctggtca attttttttct ggaatcatta a              51

SEQ ID NO: 438          moltype = AA    length = 40
FEATURE                 Location/Qualifiers
source                  1..40
                        mol_type = protein
                        organism = Microcoleus chthonoplastes
SEQUENCE: 438
YNLQGLPAIE SEDCIPDSVA PSDDWFSGVS SLFNRLTGLG                             40

SEQ ID NO: 439          moltype = DNA   length = 123
FEATURE                 Location/Qualifiers
source                  1..123
                        mol_type = genomic DNA
                        organism = Microcoleus chthonoplastes
SEQUENCE: 439
tataacctac aggggttgcc agcaattgag tcagaagact gtatcccaga ttctgtagcg      60
ccttcggatg attggttttc aggcgtatcg tctctgttta accgcttgac tgggttgggt     120
tag                                                                   123

SEQ ID NO: 440          moltype = AA    length = 37
FEATURE                 Location/Qualifiers
source                  1..37
                        mol_type = protein
                        organism = Nostoc sp.
SEQUENCE: 440
WMAIRRILRC HPFHPGGYDP VPELGEHCCH HDSGNKG                                37

SEQ ID NO: 441          moltype = DNA   length = 114
FEATURE                 Location/Qualifiers
source                  1..114
                        mol_type = genomic DNA
                        organism = Nostoc sp.
SEQUENCE: 441
tggatggcga ttcgccgcat tttgcgttgt catccattcc acccaggggg ttatgatcct      60
gtaccagagt tgggtgagca ttgttgtcat catgatagcg ggaataaggg gtga           114

SEQ ID NO: 442          moltype = AA    length = 35
FEATURE                 Location/Qualifiers
source                  1..35
                        mol_type = protein
                        organism = Anabaena variabilis
SEQUENCE: 442
WMGIRRILRC HPFHPGGYDP VPEVGEHCCH HDSGK                                  35

SEQ ID NO: 443          moltype = DNA   length = 108
FEATURE                 Location/Qualifiers
source                  1..108
                        mol_type = genomic DNA
                        organism = Anabaena variabilis
SEQUENCE: 443
tggatgggga ttcgccgcat tttgcgttgt catccattcc acccaggcgg ttatgatcct      60
gtaccagagg tgggtgagca ttgttgtcat catgatagcg ggaagtag                  108

SEQ ID NO: 444          moltype = AA    length = 48
FEATURE                 Location/Qualifiers
source                  1..48
                        mol_type = protein
                        organism = Nodularia spumigena
SEQUENCE: 444
WMATRRILRC HPFHPGGYDP VPEVKHNCCD QHLSDSGKQT TEDHHKGS                    48

SEQ ID NO: 445          moltype = DNA   length = 147
FEATURE                 Location/Qualifiers
source                  1..147
                        mol_type = genomic DNA
                        organism = Nodularia spumigena
SEQUENCE: 445
tggatggcga ctcggcggat tttgcgttgt catcccttcc atcctggtgg atatgatcca      60
gttccagagg taaaacacaa ttgctgcgat cagcatctgt ccgattctgg gaaacagacc    120
```

```
acagaagacc atcacaaagg ctcgtag                                             147

SEQ ID NO: 446          moltype = AA  length = 34
FEATURE                 Location/Qualifiers
source                  1..34
                        mol_type = protein
                        note = Nostoc azollae
                        organism = Nostoc sp.
SEQUENCE: 446
WMATLRILRC HPFHPGGYDP VPGLAEKSCC DHHD                                      34

SEQ ID NO: 447          moltype = DNA  length = 105
FEATURE                 Location/Qualifiers
source                  1..105
                        mol_type = genomic DNA
                        note = Nostoc azollae
                        organism = Nostoc sp.
SEQUENCE: 447
tggatggcaa ctttgcggat tttacgctgt catcctttcc atcctggtgg ttatgatcct          60
gtaccaggac tagcggaaaa atcctgttgt gaccatcatg attga                         105

SEQ ID NO: 448          moltype = AA  length = 28
FEATURE                 Location/Qualifiers
source                  1..28
                        mol_type = protein
                        organism = Synechococcus sp.
SEQUENCE: 448
WLTAKRFCRC HPLHPGGYDP VPEKKSVL                                             28

SEQ ID NO: 449          moltype = DNA  length = 87
FEATURE                 Location/Qualifiers
source                  1..87
                        mol_type = genomic DNA
                        organism = Synechococcus sp.
SEQUENCE: 449
tggctaacag ccaagcgctt ttgtcgctgt catccgcttc atcctggcgg gtatgatccg          60
gtaccggaga agaaatcggt actctaa                                              87

SEQ ID NO: 450          moltype = AA  length = 23
FEATURE                 Location/Qualifiers
source                  1..23
                        mol_type = protein
                        organism = Prochlorococcus marinus
SEQUENCE: 450
WLTLRRLSRC HPFTPCGCDP VPD                                                  23

SEQ ID NO: 451          moltype = DNA  length = 72
FEATURE                 Location/Qualifiers
source                  1..72
                        mol_type = genomic DNA
                        organism = Prochlorococcus marinus
SEQUENCE: 451
tggctcaccc tgcggcgcct gtctcgttgc catcctttta cccctgtgg ttgcgacccg           60
gtgcctgatt aa                                                              72

SEQ ID NO: 452          moltype = AA  length = 69
FEATURE                 Location/Qualifiers
source                  1..69
                        mol_type = protein
                        organism = Escherichia coli
SEQUENCE: 452
MSYKKLYQLT AIFSLPLTIL LVSLSSLRIV GEGNSYVDVF LSFIIFLGFI ELIHGIRKIL          60
VWSGWKNGS                                                                  69

SEQ ID NO: 453          moltype = DNA  length = 210
FEATURE                 Location/Qualifiers
source                  1..210
                        mol_type = genomic DNA
                        organism = Escherichia coli
SEQUENCE: 453
atgagttata aaaaactgta ccaattgacg gctatattta gtttacctct tactatctta          60
ttggtttcac tttcatccct tcggattgtt ggcgaaggga attcttatgt tgacgttttt        120
ctaagcttta taatatttct tggttttatt gagctgattc atgggattcg aaagattttg        180
gtctggtcag gctggaaaaa cggaagttaa                                         210

SEQ ID NO: 454          moltype = AA  length = 85
FEATURE                 Location/Qualifiers
source                  1..85
                        mol_type = protein
```

```
                                    organism = Escherichia coli
SEQUENCE: 454
MGLKLDLTWF DKSTEDFKGE EYSKDFGDDG SVMESLGVPF KDNVNNGCFD VIAEWVPLLQ      60
PYFNHQIDIS DNEYFVSFDY RDGDW                                            85

SEQ ID NO: 455           moltype = DNA   length = 258
FEATURE                  Location/Qualifiers
source                   1..258
                         mol_type = genomic DNA
                         organism = Escherichia coli
SEQUENCE: 455
atgggactta aattggattt aacttggttt gataaaagta cagaagattt taagggtgag      60
gagtattcaa aagattttgg agatgacggt tcagttatgg aaagtctagg tgtgcctttt     120
aaggataatg ttaataacgg ttgctttgat gttatagctg aatgggtacc tttgctacaa     180
ccatactttt atcatcaaat tgatatttcc gataatgagt attttgtttc gtttgattat     240
cgtgatggtg attggtga                                                    258

SEQ ID NO: 456           moltype = AA   length = 113
FEATURE                  Location/Qualifiers
source                   1..113
                         mol_type = protein
                         organism = Escherichia coli
SEQUENCE: 456
MSLRYYIKNI LFGLYCTLIY IYLITKNSEG YYFLVSDKML YAIVISTILC PYSKYAIEYI      60
AFNFIKKDFF ERRKNLNNAP VAKLNLFMLY NLLCLVLAIP FGLLGLFISI KNN            113

SEQ ID NO: 457           moltype = DNA   length = 342
FEATURE                  Location/Qualifiers
source                   1..342
                         mol_type = genomic DNA
                         organism = Escherichia coli
SEQUENCE: 457
atgagcttaa gatactacat aaaaaatatt ttatttggcc tgtactgcac acttatatat      60
ataccttta taacaaaaaa cagcgaaggg tattatttcc ttgtgtcaga taagatgcta     120
tatgcaatag tgataagcac tattctatgt ccatattcaa aatatgctat tgaatacata     180
gcttttaact tcataaagaa agattttttt gaaagaagaa aaaacctaaa taacgccccc     240
gtagcaaaat taaacctatt tatgctatat aatctacttt gtttggtcct agcaatccca     300
tttggattgc taggacttt tatatcaata aagaataatt aa                         342

SEQ ID NO: 458           moltype = AA   length = 85
FEATURE                  Location/Qualifiers
source                   1..85
                         mol_type = protein
                         organism = Escherichia coli
SEQUENCE: 458
MGLKLHIHWF DKKTEEFKGG EYSKDFGDDG SVIESLGMPL KDNINNGWFD VEKPWVSILQ      60
PHFKNVIDIS KFDYFVSFVY RDGNW                                            85

SEQ ID NO: 459           moltype = DNA   length = 258
FEATURE                  Location/Qualifiers
source                   1..258
                         mol_type = genomic DNA
                         organism = Escherichia coli
SEQUENCE: 459
atggggctta aattacatat tcattggttt gataagaaaa ccgaagagtt taaaggcggt      60
gaatactcaa aagacttcgg tgatgatggt tctgtcattg aaagtctggg gatgcctta     120
aaggataata ttaataatgg ttggtttgat gttgaaaaac catgggttc gatattcag     180
ccacacttta aaaatgtaat cgatattagt aaatttgatt actttgtatc ctttgtttac     240
cgggatggta actggtaa                                                    258

SEQ ID NO: 460           moltype = AA   length = 86
FEATURE                  Location/Qualifiers
source                   1..86
                         mol_type = protein
                         organism = Escherichia coli
SEQUENCE: 460
MELKHSISDY TEAEFLEFVK KICRAEGATE EDDNKLVREF ERLTEHPDGS DLIYYPRDDR      60
EDSPEGIVKE IKEWRAANGK SGFKQG                                           86

SEQ ID NO: 461           moltype = DNA   length = 261
FEATURE                  Location/Qualifiers
source                   1..261
                         mol_type = genomic DNA
                         organism = Escherichia coli
SEQUENCE: 461
atggaactga acatagtat tagtgattat accgaggctg aatttctgga gtttgtaaaa       60
aaaatatgta gagctgaagg tgctactgaa gaggatgaca ataaattagt gagagagttt    120
gagcgattaa ctgagcaccc agatggttca gatctgattt attatcctcg cgatgacagg    180
gaagatagtc ctgaagggat tgtcaaggaa attaaagaat ggcgagctgc taacggtaag    240
```

```
tcaggattta aacagggctg a                                                  261

SEQ ID NO: 462          moltype = AA  length = 178
FEATURE                 Location/Qualifiers
source                  1..178
                        mol_type = protein
                        organism = Citrobacter freundii
SEQUENCE: 462
MMNEHSIDTD NRKANNALYL FIIIGLIPLL CIFVVYYKTP DALLLRKIAT STENLPSITS    60
SYNPLMTKVM DIYCKTAPFL ALILYILTFK IRKLINNTDR NTVLRSCLLS PLVYAAIVYL   120
FCFRNFELTT AGRPVRLMAT NDATLLLFYI GLYSIIFFTT YITLFTPVTA FKLLKKRQ     178

SEQ ID NO: 463          moltype = DNA  length = 537
FEATURE                 Location/Qualifiers
source                  1..537
                        mol_type = genomic DNA
                        organism = Citrobacter freundii
SEQUENCE: 463
atgatgaatg aacactcaat agatacggac aacagaaagg ccaataacgc attgtattta    60
tttataataa tcggattaat accattattg tgcattttg ttgtttacta caaaacgcca   120
gacgctttac ttttacgtaa aattgctaca agcactgaga atctcccgtc aataacatcc   180
tcctacaacc cattaatgac aaaggttatg gatatttatt gtaaaacgc gcctttcctt    240
gccttaatac tatacatcct aacctttaaa atcagaaaat taatcaacaa caccgacagg   300
aacactgtac ttagatcttg tttattaagt ccattggtct atgcagcaat tgtttatcta   360
ttctgcttcc gaaattttga gttaacaaca gccggaaggc ctgtcagatt aatggccacc   420
aatgacgcaa cactattgtt attttatatt ggtctgtact caataatttt ctttacaacc   480
tatatcacgc tattcacacc agtcactgca tttaaattat aaaaaaaag gcagtaa       537

SEQ ID NO: 464          moltype = AA  length = 111
FEATURE                 Location/Qualifiers
source                  1..111
                        mol_type = protein
                        organism = Escherichia coli
SEQUENCE: 464
MNRKYYFNNM WWGWVTGGYM LYMSWDYEFK YRLLFWCISL CGMVLYPVAK WYIEDTALKF    60
TRPDFWNSGF FADTPGKMGL LAVYTGTVFI LSLPLSMIYI LSVIIKRLSV R            111

SEQ ID NO: 465          moltype = DNA  length = 336
FEATURE                 Location/Qualifiers
source                  1..336
                        mol_type = genomic DNA
                        organism = Escherichia coli
SEQUENCE: 465
atgaacagaa aatattattt taataatatg tggtggggat gggtgacggg gggatatatg    60
ctgtatatgt catgggatta tgagtttaaa tacagattac tgttctggtg tatttctctc   120
tgcggaatgg ttttgtatcc ggttgcaaaa tggtatattg aagatacagc tctaaaattt   180
acccggcctg atttctggaa cagcggtttt tttgctgata ccectggaaa atggggttg    240
cttgcggttt atacgggtac tgttttcata ttatctcttc cgttaagtat gatatatatt   300
ctttctgtta ttataaaaag gctgtctgta agatag                             336

SEQ ID NO: 466          moltype = AA  length = 115
FEATURE                 Location/Qualifiers
source                  1..115
                        mol_type = protein
                        organism = Escherichia coli
SEQUENCE: 466
MKLDISVKYL LKSLIPILII LTVFYLGWKD NQENARMFYA FIGCIISAIT FPFSMRIIQK    60
MVIRFTGKEF WQKDFFTNPV GGSLTAIFEL FCFVISPVV AIYLIFILCK ALSGK         115

SEQ ID NO: 467          moltype = DNA  length = 348
FEATURE                 Location/Qualifiers
source                  1..348
                        mol_type = genomic DNA
                        organism = Escherichia coli
SEQUENCE: 467
atgaaactgg atatatctgt aaagtattta ctgaaaagcc tgataccaat cctcattatt    60
cttacagttt tttatctggg atggaaagat aaccaggaaa atgcaagaat gttttatgcg   120
ttcatcggat gcattatcag tgccattact tttccttttt caatggaggat aatacagaaa   180
atggtaataa ggtttacagg aaagaattc tggcaaaaag acttctttac aaatccagtt   240
ggcggaagct taactgcaat atttgaatta ttctgtttcg ttatatcagt tcctgtggtt   300
gccattact taattttat actctgcaaa gccctttcag gaaaatga                  348

SEQ ID NO: 468          moltype = AA  length = 131
FEATURE                 Location/Qualifiers
source                  1..131
                        mol_type = protein
                        organism = Escherichia coli
SEQUENCE: 468
MHNTLLEKII AYLSLPGFHS LNNPPLSEAF NLYVHTAPLA ATSLFIFTHK ELELKPKSSP    60
```

```
LRALKILTPF TILYISMIYC FLLTDTELTL SSKTFVLIVK KRSVFVFFLY NTIYWDIYIH   120
IFVLLVPYRN I                                                      131

SEQ ID NO: 469          moltype = DNA  length = 396
FEATURE                 Location/Qualifiers
source                  1..396
                        mol_type = genomic DNA
                        organism = Escherichia coli
SEQUENCE: 469
atgcacaata cactcctcga aaaaatcatc gcatacctat ccctaccagg atttcattca    60
ttaaacaacc cgcccctaag cgaagcattc aatctctatg ttcatacagc cccttttagct  120
gcaaccagct tattcatatt cacacacaaa gaattagagt taaaaccaaa gtcgtcacct  180
ctgcgggcac taaagatatt aactcctttc actattcttt atatatccat gatatactgt  240
ttcttgctaa ctgacacaga actaaccttg tcatcaataa catttgtatt aatagtcaaa  300
aaacgatctg tttttgtctt ttttctatat aacactatat attgggatat atatattcac  360
atatttgtac ttttggttcc ttataggaac atataa                            396

SEQ ID NO: 470          moltype = AA  length = 85
FEATURE                 Location/Qualifiers
source                  1..85
                        mol_type = protein
                        organism = Escherichia coli
SEQUENCE: 470
MELKNSISDY TETEFKKIIE DIINCEGDEK KQDDNLEHFI SVTEHPSGSD LIYYPEGNND    60
GSPEAVIKEI KEWRAANGKS GFKQG                                         85

SEQ ID NO: 471          moltype = DNA  length = 258
FEATURE                 Location/Qualifiers
source                  1..258
                        mol_type = genomic DNA
                        organism = Escherichia coli
SEQUENCE: 471
atggaactga aaacagcat tagtgattac actgaaactg aattcaaaaa aattattgaa     60
gacatcatca attgtgaagg tgatgaaaaa aacaggatg ataacctcga gcattttata   120
agtgttactg agcatcctag tggttctgat ctgatttatt acccagaagg taataatgat  180
ggtagccctg aagctgttat taaagagatt aaagaatggc gagctgctaa cggtaagtca  240
ggatttaaac agggctga                                                258

SEQ ID NO: 472          moltype = AA  length = 98
FEATURE                 Location/Qualifiers
source                  1..98
                        mol_type = protein
                        note = subsp. lactis
                        organism = Lactococcus lactis
SEQUENCE: 472
MKKKQIEFEN ELRSMLATAL EKDISQEERN ALNIAEKALD NSEYLPKIIL NLRKALTPLA    60
INRTLNHDLS ELYKFITSSK ASNKNLGGGL IMSWGRLF                           98

SEQ ID NO: 473          moltype = DNA  length = 297
FEATURE                 Location/Qualifiers
source                  1..297
                        mol_type = genomic DNA
                        note = subsp. lactis
                        organism = Lactococcus lactis
SEQUENCE: 473
atgaaaaaaa aacaaataga atttgaaaac gagctaagaa gtatgttggc taccgcccctt   60
gaaaaagaca ttagtcaaga ggaaagaaat gctctgaata ttgcagaaaa ggcgcttgac  120
aattctgaat atttaccaaa aattatttta aacctcagaa aagccctaac tccattagct  180
ataaatcgaa cacttaacca tgatttatct gaactgtata aattcattac aagttccaaa  240
gcatcaaaca aaaatttagg tggtggttta attatgtcgt ggggacgact attctaa     297

SEQ ID NO: 474          moltype = AA  length = 98
FEATURE                 Location/Qualifiers
source                  1..98
                        mol_type = protein
                        note = subsp. cremoris
                        organism = Lactococcus lactis
SEQUENCE: 474
MKKKQIEFEN ELRSMLATAL EKDISQEERN ALNIAEKALD NSEYLPKIIL NLRKALTPLA    60
INRTLNHDLS ELYKFITSSK ASNKNLGGGL IMSWGRLF                           98

SEQ ID NO: 475          moltype = DNA  length = 297
FEATURE                 Location/Qualifiers
source                  1..297
                        mol_type = genomic DNA
                        note = subsp. cremoris
                        organism = Lactococcus lactis
SEQUENCE: 475
atgaaaaaaa aacaaataga atttgaaaac gagctaagaa gtatgttggc taccgcccctt   60
```

```
gaaaaagaca ttagtcaaga ggaaagaaat gctctgaata ttgcagaaaa ggcgcttgac    120
aattctgaat atttaccaaa aattatttta aacctcagaa aagccctaac tccattagct    180
ataaatcgaa cacttaacca tgatttatct gaactgtata aattcattac aagttccaaa    240
gcatcaaaca aaaatttagg tggtggttta attatgtcgt ggggacgact attctaa      297

SEQ ID NO: 476          moltype = AA   length = 87
FEATURE                 Location/Qualifiers
source                  1..87
                        mol_type = protein
                        organism = Escherichia coli
SEQUENCE: 476
MNKMAMIDLA KLFLASKITA IEFSERICVE RRRLYGVKDL SPNILNCGEE LFMAAERFEP    60
DADRANYEID DNGLKVEVRS ILEKFKL                                       87

SEQ ID NO: 477          moltype = DNA   length = 249
FEATURE                 Location/Qualifiers
source                  1..249
                        mol_type = genomic DNA
                        organism = Escherichia coli
SEQUENCE: 477
atgatcgatt tggcgaaatt atttttagct tcgaaaatta cagtgattga gttttcagag    60
cgaatttgtg ttgaacggag aagattgtat ggtgttaagg atttgtctcc gaatatatta    120
aattgtgggg aagagttgtc tatggctgct gagcgatttg agcctgatgc agataggget    180
aattatgaaa ttgatgataa tggacttaag gtcgaggtcc gatctatctt ggaaaaactt    240
aaatcataa                                                            249

SEQ ID NO: 478          moltype = AA   length = 83
FEATURE                 Location/Qualifiers
source                  1..83
                        mol_type = protein
                        organism = Escherichia coli
SEQUENCE: 478
MKLSPKAAIE VCNEAAKKGL WILGIDGGHW LNPGFRIDSS ASWTYDMPEE YKSKIPENNR    60
LAIENIKDDI ENGYTAFIIT LKM                                           83

SEQ ID NO: 479          moltype = DNA   length = 243
FEATURE                 Location/Qualifiers
source                  1..243
                        mol_type = genomic DNA
                        organism = Escherichia coli
SEQUENCE: 479
atgaagttat caccaaaagc tgcaatagaa gtttgtaatg aagcagcgaa aaaaggctta    60
tggattttgg gcattgatgg tgggcattgg ctgaatccgg gattcaggat agtagttca    120
gcatcatgga catatgatat gccggagaat acaaatcaaa atccctgaa ataatagat    180
tggctattga aaatattaaa gatgatattg agaatggata cactgctttc attatcacgt    240
taa                                                                  243

SEQ ID NO: 480          moltype = AA   length = 85
FEATURE                 Location/Qualifiers
source                  1..85
                        mol_type = protein
                        organism = Escherichia coli
SEQUENCE: 480
MGLKLHINWF DKRTEEFKGG EYSKDFGDDG SVIERLGMPF KDNINNGWFD VIAEWVPLLQ    60
PYFNHQIDIS DNEYFVSFDY RDGDW                                         85

SEQ ID NO: 481          moltype = DNA   length = 258
FEATURE                 Location/Qualifiers
source                  1..258
                        mol_type = genomic DNA
                        organism = Escherichia coli
SEQUENCE: 481
atggggctta aattacatat taattggttt gataagacga ccgaggaatt taaaggtggt    60
gagtattcaa aagattttgg agatgatggc tcggtcattg aacgtcttgg aatgccttca    120
aaagataata tcaataatgg ttggtttgat gttatagctg aatgggtacc tttgctacaa    180
ccatacttta atcatcaaat tgatatttcc gataatgagt attttgtttc gtttgattat    240
cgtgatggtg attggtga                                                  258

SEQ ID NO: 482          moltype = AA   length = 85
FEATURE                 Location/Qualifiers
source                  1..85
                        mol_type = protein
                        organism = Escherichia coli
SEQUENCE: 482
MELKKSIGDY TETEFKKIIE NIINCEGDEK KQDDNLEHFI SVTEHPSGSD LIYYPEGNND    60
GSPEAVIKEI KEWRAANGKS GFKQG                                         85

SEQ ID NO: 483          moltype = DNA   length = 258
FEATURE                 Location/Qualifiers
```

```
source                  1..258
                        mol_type = genomic DNA
                        organism = Escherichia coli
SEQUENCE: 483
gtggagctaa agaaaagtat tggtgattac actgaaaccg aattcaaaaa aattattgaa    60
aacatcatca attgtgaagg tgatgaaaaa aaacaggatg ataacctcga gcatttttata  120
agtgttactg agcatcctag tggttctgat ctgatttatt acccagaagg taataatgat   180
ggtagccctg aagctgttat taaagagatt aaagaatggc gagctgctaa cggtaagtca   240
ggatttaaac agggctga                                                 258

SEQ ID NO: 484          moltype = AA  length = 86
FEATURE                 Location/Qualifiers
source                  1..86
                        mol_type = protein
                        organism = Escherichia coli
SEQUENCE: 484
MELKHSISDY TEAEFLQLVT TICNADTSSE EELVKLVTHF EEMTEHPSGS DLIYYPKEGD    60
DDSPSGIVNT VKQWRAANGK SGFKQG                                        86

SEQ ID NO: 485          moltype = DNA  length = 261
FEATURE                 Location/Qualifiers
source                  1..261
                        mol_type = genomic DNA
                        organism = Escherichia coli
SEQUENCE: 485
atggaactga agcatagcat tagtgattat acagaagctg aattttttaca acttgtaaca   60
acaatttgta atgcgaacac ttccagtgaa gaagaactgg ttaaattggt tacacacttt   120
gaggaaatga ctgagcaccc tagtggtagt gatttaatat attacccaaa agaaggtgat   180
gatgactcac cttcaggtat tgtaaacaca gtaaaacaat ggcgagccgc taacggtaag   240
tcaggattta aacagggcta a                                             261

SEQ ID NO: 486          moltype = AA  length = 141
FEATURE                 Location/Qualifiers
source                  1..141
                        mol_type = protein
                        organism = Escherichia coli
SEQUENCE: 486
MLTLYGYIRN VFLYRMNDRS CGDFMKVISM KFIFILTIIA LAAVFFWSED KGPACYQVSD    60
EQARTFVKND YLQRMKRWDN DVQLLGTEIP KITWEKIERS LTDVEDEKTL LVPFKAEGPD   120
GKRMYYGMYH CEEGYVEYAN D                                             141

SEQ ID NO: 487          moltype = DNA  length = 354
FEATURE                 Location/Qualifiers
source                  1..354
                        mol_type = genomic DNA
                        organism = Escherichia coli
SEQUENCE: 487
atgaaagtaa ttagcatgaa atttattttt attttaacga ttattgctct tgctgctgtt    60
ttttttctggt ctgaagataa aggtccggca tgctatcagg tcagcgatga acaggccaga  120
acgtttgtaa aaaatgatta cctgcaaaga atgaaacgct gggacaacga tgtacaactt   180
cttggtacag aaatcccgaa aattacatgg gaaaagattg agagaagttt aacagatgtc   240
gaagatgaaa aaacacttct tgtcccattt aaagctgaag gcccggacgg taagagaatg   300
tattatggca tgtaccttg tgaggaggga tatgttgaat atgcgaatga ctaa          354

SEQ ID NO: 488          moltype = AA  length = 175
FEATURE                 Location/Qualifiers
source                  1..175
                        mol_type = protein
                        organism = Escherichia coli
SEQUENCE: 488
MTSNKDKNKK ANEILYAFSI IGIIPLMAIL ILRINDPYSQ VLYYLYNKVA FLPSITSLHD    60
PVMTTLMSNY NKTAPVMGIL VFLCTYKTRE IIKPVTRKLV VQSCFWGPVF YAILIYITLF   120
YNLETTAGG FFKLLSHNVI TLFILYCSIY FTVLTMTYAI LLMPLLVIKY FKGRQ         175

SEQ ID NO: 489          moltype = DNA  length = 528
FEATURE                 Location/Qualifiers
source                  1..528
                        mol_type = genomic DNA
                        organism = Escherichia coli
SEQUENCE: 489
atgaccagca ataaagataa gaacaagaaa gcaaacgaaa tattatatgc attttccata    60
atcgggatta ttccattaat ggctatatta atacttcgaa taaatgatcc atattctcaa   120
gtgctgtact acttatataa taaggtgcca tttctcccctt ctattcacatc attgcatgat  180
cccgtcatga caacacttat gtcaaactac aacaagacag cgccagttat gggtattctc   240
gttttttcttt gcacatataa gacaagagaa atcataaagc cagtaacaag aaaacttgtt   300
gtgcaatcct gttctggggg gcccgttttt tatgccattc tgatttatat cacactgttc   360
tataatctgg aactaacaac agcaggtggt ttttttaaat tattatctca taatgtcatc   420
actctgttta ttttatattg ctccatttac tttactgttt taaccatgac atatgcgatt   480
ttactgatgc cattacttgt cattaaatat tttaaaggga ggcagtaa                528
```

```
SEQ ID NO: 490            moltype = AA   length = 78
FEATURE                   Location/Qualifiers
source                    1..78
                          mol_type = protein
                          organism = Escherichia coli
SEQUENCE: 490
MDRKRTKLEL LFAFIINATA IYIALAIYDC VFRGKDFLSM HTFCFSALMS AICYFVGDNY    60
YSISDKIKRR SYENSDSK                                                 78

SEQ ID NO: 491            moltype = DNA   length = 237
FEATURE                   Location/Qualifiers
source                    1..237
                          mol_type = genomic DNA
                          organism = Escherichia coli
SEQUENCE: 491
atggatagaa aaagaacaaa attagagttg ttatttgcat ttataataaa tgccaccgca    60
atatatattg cattagctat atatgattgt gtttttagag gaaaggactt tttatccatg   120
catacatttt gcttctctgc attaatgtct gcaatatgtt actttgttgg tgataattat   180
tattcaatat ccgataagat aaaaaggaga tcatatgaga actctgactc taaatga     237

SEQ ID NO: 492            moltype = AA   length = 113
FEATURE                   Location/Qualifiers
source                    1..113
                          mol_type = protein
                          organism = Shigella sonnei
SEQUENCE: 492
MSLRYYIKNI LFGLYCALIY IYLITKNNEG YYFLASDKML YAIVISTILC PYSKYAIEHI    60
FFKFIKKDFF RKRKNLNKCP RGKIKPYLCV YNLLCLVLAI PFGLLGLVYI NKE          113

SEQ ID NO: 493            moltype = DNA   length = 342
FEATURE                   Location/Qualifiers
source                    1..342
                          mol_type = genomic DNA
                          organism = Shigella sonnei
SEQUENCE: 493
atgagtttaa gatactacat aaaaaatatt ttgtttggcc tatactgcgc acttatatat    60
atataccttta taacaaaaaa caacgaaggg tattatttcc tagcgtcaga taagatgcta   120
tacgcaatag tgataagcac tattctatgc ccatatcaaa aatatgctat tgaacacata   180
ttttttaagt tcataaagaa agatttttttc agaaaaagaa aaaacctaaa taaatgcccc   240
cgtggcaaaa ttaaaccgta tttatgcgta tacaatctac tttgtttggt cctagcaatc   300
ccatttggat tgctaggact tgtttatatc aataaagaat aa                     342

SEQ ID NO: 494            moltype = AA   length = 113
FEATURE                   Location/Qualifiers
source                    1..113
                          mol_type = protein
                          organism = Escherichia coli
SEQUENCE: 494
MSLRYYIKNI LFGLYCTLIY IYLITKNSEE YYFLVTDKML YAIVISTILC PYSKYAIEHI    60
AFNFIKKHFF ERRKNLNNAP VAKLNLFMLY NLLCLVLAIP FGLLGLFISI KNN          113

SEQ ID NO: 495            moltype = DNA   length = 342
FEATURE                   Location/Qualifiers
source                    1..342
                          mol_type = genomic DNA
                          organism = Escherichia coli
SEQUENCE: 495
atgagcttaa gatactacat aaaaaatatt ttatttggcc tgtactgcac acttatatat    60
atataccttta taacaaaaaa cagcgaagag tattatttcc ttgtgacaga taagatgcta   120
tatgcaatag tgataagcac tattctatgt ccatattcaa aatatgctat tgaacacata   180
gcttttaact tcataaagaa acatttttttc gaaagaagaa aaaacctaaa taacgccccc   240
gtagcaaaat taaaccctatt tatgctatat aatctacttt gtttggtcct agcaatccca   300
tttggattgc taggactttt tatatcaata agaataatt aa                      342

SEQ ID NO: 496            moltype = AA   length = 113
FEATURE                   Location/Qualifiers
source                    1..113
                          mol_type = protein
                          organism = Leuconostoc gelidum
SEQUENCE: 496
MRKNNILLDD AKIYTNKLYL LLIDRKDDAG YGDICDVLFQ VSKKLDSTKN VEALINRLVN    60
YIRITASTNR IKFSKDEEAV IIELGVIGQK AGLNGQYMAD FSDKSQFYSI FER          113

SEQ ID NO: 497            moltype = DNA   length = 342
FEATURE                   Location/Qualifiers
source                    1..342
                          mol_type = genomic DNA
                          organism = Leuconostoc gelidum
```

```
SEQUENCE: 497
ttgagaaaaa ataacatttt attggacgat gctaaaatat acacgaacaa actctatttg    60
ctattaatcg atagaaaaga tgacgctggg tatggagata tttgtgatgt tttgtttcag   120
gtatccaaaa aattagatag cacaaaaaat gtagaagcat tgattaaccg attggtcaat   180
tatatacgaa ttaccgcttc aacaaacaga attaagtttt caaaagatga agaggctgta   240
attatagaac ttggtgtaat tggtcagaag gctggattaa acggccaata catggctgat   300
ttttctgaca aatctcagtt ttatagtatc tttgaaagat aa                      342

SEQ ID NO: 498           moltype = AA   length = 91
FEATURE                  Location/Qualifiers
source                   1..91
                         mol_type = protein
                         note = subsp. cremoris
                         organism = Lactococcus lactis
SEQUENCE: 498
MKKKVDTEKQ ITSWASDLAS KNETKVQEKL ILSSYIQDIE NHVYFPKAMI SLEKKLRDQN    60
NICALSKEVN QFYFKVVEVN QRKSWMVGLI V                                   91

SEQ ID NO: 499           moltype = DNA   length = 276
FEATURE                  Location/Qualifiers
source                   1..276
                         mol_type = genomic DNA
                         note = subsp. cremoris
                         organism = Lactococcus lactis
SEQUENCE: 499
atgaaaaaaa aagttgatac agaaaaacaa attacttctt gggcatctga cttagcttcc    60
aaaaatgaaa caaaggttca agaaaaatta atactgtctt cttatattca ggacatcgaa   120
aaccatgttt actttccaaa agcaatgatt tctttagaaa aaaaattacg agaccaaaat   180
aatatttgcg ctttatcaaa agaagtcaat cagttttatt ttaaagttgt tgaagtaaat   240
caaagaaaat cctggatggt aggtttgata gtttaa                             276

SEQ ID NO: 500           moltype = AA   length = 112
FEATURE                  Location/Qualifiers
source                   1..112
                         mol_type = protein
                         organism = Pediococcus acidilactici
SEQUENCE: 500
MNKTKSEHIK QQALDLFTRL QFLLQKHDTI EPYQYVLDIL ETGISKTKHN QQTPERQARV    60
VYNKIASQAL VDKLHFTAEE NKVLAAINEL AHSQKGWGEF NMLDTTNTWP SQ           112

SEQ ID NO: 501           moltype = DNA   length = 339
FEATURE                  Location/Qualifiers
source                   1..339
                         mol_type = genomic DNA
                         organism = Pediococcus acidilactici
SEQUENCE: 501
atgaataaga ctaagtcgga acatattaaa caacaagctt tggacttatt tactaggcta    60
cagtttttac tacagaagca cgatactatc gaaccttacc agtacgtttt agatattctg   120
gagactggta tcagtaaaac taaacataac cagcaaacgc ctgaacgaca agctcgtgta   180
gtctacaaca agattgccag ccaagcgtta gtagataagt tacattttac tgccgaagaa   240
aacaaagttc tagcagccat caatgaattg gcgcattctc aaaaagggtg gggcgagttt   300
aacatgctag atactaccaa tacgtggcct agccaatag                          339

SEQ ID NO: 502           moltype = AA   length = 88
FEATURE                  Location/Qualifiers
source                   1..88
                         mol_type = protein
                         organism = Carnobacterium maltaromaticum
SEQUENCE: 502
MIKDEKINKI YALVKSALDN TDVKNDKKLS LLLMRIQETS INGELFYDYK KELQPAISMY    60
SIQHNFRVPD DLVKLLALVQ TPKAWSGF                                       88

SEQ ID NO: 503           moltype = DNA   length = 267
FEATURE                  Location/Qualifiers
source                   1..267
                         mol_type = genomic DNA
                         organism = Carnobacterium maltaromaticum
SEQUENCE: 503
atgataaaag atgaaaaaat aaataaaatc tatgctttag ttaagagcgc acttgataat    60
acggatgtta agaatgataa aaacttttct ttacttctta tgagaataca agaaacatca   120
attaatggag aactattta cgattataaa aaagaattac agccagctat tagtatgtac    180
tctattcaac ataactttcg ggttcctgac gatctagtaa aactgttagc attagttcaa   240
acacctaaag cttggtcagg gttttaa                                       267

SEQ ID NO: 504           moltype = AA   length = 111
FEATURE                  Location/Qualifiers
source                   1..111
                         mol_type = protein
                         organism = Carnobacterium maltaromaticum
```

```
SEQUENCE: 504
MDIKSQTLYL NLSEAYKDPE VKANEFLSKL VVQCAGKLTA SNSENSYIEV ISLLSRGISS    60
YYLSHKRIIP SSMLTIYTQI QKDIKNGNID TEKLRKYEIA KGLMSVPYIY F            111

SEQ ID NO: 505           moltype = DNA   length = 336
FEATURE                  Location/Qualifiers
source                   1..336
                         mol_type = genomic DNA
                         organism = Carnobacterium maltaromaticum
SEQUENCE: 505
atggatataa agtctcaaac attatatttg aatctaagcg aggcatataa agaccctgaa    60
gtaaaagcta atgaattctt atcaaaatta gttgtacaat gtgctgggaa attaacagct   120
tcaaacagtg agaacagtta tattgaagta atatcattgc tatctagggg tatttctagt   180
tattatttat cccataaacg tataattcct tcaagtatgt taactatata tactcaaata   240
caaaaggata taaaaacgg gaatattgac accgaaaaat taaggaaata tgagatagca    300
aaaggattaa tgtccgttcc ttatatatat ttctaa                             336

SEQ ID NO: 506           moltype = AA    length = 245
FEATURE                  Location/Qualifiers
source                   1..245
                         mol_type = protein
                         note = subsp. lactis
                         organism = Lactococcus lactis
SEQUENCE: 506
MRRYLILIVA LIGITGLSGC YQTSHKKVRF DEGSYTNFIY DNKSYFVTDK EIPQENVNNS    60
KVKFYKLLIV DMKSEKLLSS SNKNSVTLVL NNIYEASKIS LCMGINDRYY KILPESDKGA   120
VKALRLQNFD VTSDISDDNF VIDKNDSRKI DYMGNIYSIS DTTVSDEELG EYQDVLAEVR   180
VFDSVSGKSI PRSEWGRIDK DGSNSKQSRT EWDYGEIHSI RGKSLTEAFA VEINDDFKLA   240
TKVGN                                                               245

SEQ ID NO: 507           moltype = DNA   length = 738
FEATURE                  Location/Qualifiers
source                   1..738
                         mol_type = genomic DNA
                         note = subsp. lactis
                         organism = Lactococcus lactis
SEQUENCE: 507
atgagaagat atttaatact tattgtggcc ttaatagggga taacaggttt atcagggtgt   60
tatcaaacaa gtcataaaaa ggtgaggttt gacgaaggaa gttatactaa tttttatttat  120
gataataaat cgtatttcgt aactgataag gagattcctc aggagaacgt taacaattcc   180
aaagtaaaat tttataagct gttgattgtt gacatgaaaa gtgagaaact tttatcaagt   240
agcaacaaaa atagtgtgac tttggtctta ataatatttt atgaggcttc tgacaagtcg   300
ctatgtatgg gtattaacga cagatactat aagtacttca cagaaagtca taaggggggcg   360
gtcaaagctt tgagattaca aaactttgat gtgacaagcg atatttctga tgataatttt   420
gttattgata aaaatgattc acgaaaaatt gactatatgg gaaatatta cagtatatcg    480
gacaccaccg tatctgatga agaattggga gaatatcagg atgttttagc tgaagtacgt   540
gtgtttgatt cagttagtgg caaaagtatc ccgagtgtcg aatgggggag aattgataag   600
gatggttcaa attccaaaca gagtaggacg gaatgggatt atggcgaaat ccattctatt   660
agaggaaaat ctcttactga agcatttgcc gttgagataa atgatgattt taagcttgca   720
acgaaggtag gaaactag                                                 738

SEQ ID NO: 508           moltype = AA    length = 261
FEATURE                  Location/Qualifiers
source                   1..261
                         mol_type = protein
                         note = bv. trifolii
                         organism = Rhizobium leguminosarum
SEQUENCE: 508
MNDEICLTGG GRTTVTRRGG VVYREGGPWS STVISLLRHL EASGFAEAPS VVGTGFDERG    60
RETLSFIEGE FVHPGPWSEE AFPQFGMMLR RLHDATASFK PPENSMWRDW FGRNLGEGQH   120
VIGHCDTGPW NIVCRSGLPV GLIDWEVAGP VRADIELAQA CWLNAQLYDD DIAERVGLGS   180
VTMRAHQVRL LLDGYGLSRK QRGGFVDKLI TFAVHDAAEQ AKEAAVTPES NDAEPLWAIA   240
WRTRSASWML HHRQTLEAAL A                                             261

SEQ ID NO: 509           moltype = DNA   length = 786
FEATURE                  Location/Qualifiers
source                   1..786
                         mol_type = genomic DNA
                         note = bv. trifolii
                         organism = Rhizobium leguminosarum
SEQUENCE: 509
atgaatgatg agatttgcct gacaggtggc ggacgaacga ctgtcacgcg gcgcggcgga    60
gtcgtgtatc gcgaaggcgg cccgtggtca tcaaccgtca tttcgctcct gcggcatctg   120
gaagcctctg gcttcgctga agctccttcc gttgtcggca ccgttttcga tgagcgcggc   180
cgggagacat tatcgtttat cgagggtgag tttgttcacc caggcccttg gtcggaggag   240
gcttttccgc aatttggaat gatgttgcgg cgactcacg atgccaccgc ctcgttcaaa    300
cctcccgaaa actcgatgtg gcgcgattgg ttcgggcgta acctcggtga gggtcaaaca   360
gtaataggac actgcgacac aggcccatgg aacattgttt gccggtcagg attgcctgtc   420
gggttgatag attgggaggt ggctgggcct gtcagggcgg atatcgaatt ggcccaggct   480
```

```
tgttggctga atgcccagct ctacgatgac gacattgcgg agagggtcgg attaggctct    540
gtgaccatga gagcgcatca agttcgcctg ctgcttgacg gctatggtct gtctcggaag    600
caacgcggcg gcttcgtcga caagctaatc acgttcgcag ttcacgatgc ggccgagcag    660
gcgaaagagg cggctgtcac gccagagtcg aacgatgcgg aaccgctatg ggcaattgcc    720
tggcgcacta gaagtgcctc ctggatgctc catcatcggc aaaacactgga agcagcgctg    780
gcatag                                                               786
```

```
SEQ ID NO: 510              moltype = AA   length = 436
FEATURE                     Location/Qualifiers
source                      1..436
                            mol_type = protein
                            organism = Bacillus subtilis
SEQUENCE: 510
MNNIIPIMSL LFKQLYSRQG KKDAIRIAAG LVILAVFEIG LIRQAGIDES VLRKTYIILA     60
LLLMNTYMVF LSVTSQWKES YMKLSCLLPI SSRSFWLAQS VVLFVDTCLR RTLFFFILPL    120
FLFGNGTLSG AQTLFWLGRF SFFTVYSIIF GVVLSNHFVK KKNLMFLLHA AIFACVCISA    180
ALMPAATIPL CAVHILWAVV IDFPVFLQAP PQQGKMHSFM RRSEFSFYKR EWNRFISSKA    240
MLLNYAVMAV FSGFFSFQMM NTGIFNQQVI YIVISALLLI CSPIALLYSI EKNDRMLLIT    300
LPIKRKTMFW AKYRFYSGLL AGGFLLVVMI VGFISGRSIS VLTFLQCIEL LLAGAYIRLT    360
ADEKRPSFSW QTEQQLWSGF SKYRSYLFCL PLFLAILAGT AVSLAVIPIA GLVIVYYLQK    420
QDGGFFDTSK RERLGS                                                   436
```

```
SEQ ID NO: 511              moltype = DNA   length = 1000
FEATURE                     Location/Qualifiers
source                      1..1000
                            mol_type = genomic DNA
                            organism = Bacillus subtilis
SEQUENCE: 511
atgaataaca taatccctat catgtctttg ctgttcaaac agctttacag ccggcaaggg     60
aaaaaggacg ccatccgcat tgccgcaggc ctttgtcattc tggccgtgtt tgaaatcggg    120
ctgatccgcc aggccggcat tgatgaatcg tgttgcgca aaacgtatat catactcgcg     180
cttcttttga tgaacacata tatggtgttt ctttccgtga catcacaatg gaaggaatct    240
tatatgaagc tgagctgcct gctgccgatt tcttcacgga gcttttggct cgcccagagt    300
gtcgtttttgt ttgtcgatac ctgtttgaga agaactttat tctttttat tttaccgctg    360
ttcttatttg gaaacggaac gctgtcaggg gcgcaaacat tgttttggct cggcaggttt    420
tcgttttttta ccgtttactc cattattttc ggagttgtgc taagcaacca cttcgtcaaa    480
aagaagaact tgatgtttct gctgcatgcg gcgatattcg cctgtgtatg tatcagcgcc    540
gctttgatgc cggccgccac gattccgctt tgcgcggttc atatcctgtg gcggtggtc    600
attgactttc ctgtctttct gcaggcgcct ccgcagcagg gcaagatgca ttcatttatg    660
cggccgatctg aatttccgtt ttacaaaaga gaatgaaacc gatttatctc ttctaaagcg    720
atgctgttaa attacgcggt aatggcggta ttcagcggct tctttttcgtt ccagatgatg    780
aacaccggca tcttcaatca gcaagtgatt tatatcgtga tttccgcgct tttgctcatc    840
tgctcgccga tcgccctttt gtattcgatt gaaaaaaatg accggatgct gctcatcacg    900
cttccgatca agcgaaaaac gatgttttgg gcgaaatatc gcttttattc aggcctattg    960
gcaggcggat ttctccttgt cgtgatgatt gtgggtttca                        1000
```

```
SEQ ID NO: 512              moltype = AA   length = 239
FEATURE                     Location/Qualifiers
source                      1..239
                            mol_type = protein
                            organism = Bacillus subtilis
SEQUENCE: 512
MSILDIHDVS VWYERDNVIL EQVDLHLEKG AVYGLLGVNG AGKTTLINTL TGVNRNFSGR     60
FTLCGIEAEA GMPQKTSDQL KTHRYFAADY PLLFTEITAK DYVSFVHSLY QKDFSEQQFA    120
SLAEAPHFSK YINRRISELS LGNRQKVVLM TGLLLRAPLF ILDEPLVGLD VESIEVFYQK    180
MREYCEAGGT ILFSSHLLDV VQRFCDYAAI LHNKQIQKVI PIGEETDLRR EFFEVIGHE    239
```

```
SEQ ID NO: 513              moltype = DNA   length = 716
FEATURE                     Location/Qualifiers
source                      1..716
                            mol_type = genomic DNA
                            organism = Bacillus subtilis
SEQUENCE: 513
gcattttgga tatacacgat gtatccgttt ggtatgaacg ggacaacgtc atcttagagc     60
acgtggactt acacttagaa aaaggcgccg tttacggatt gcttgggta acggtgccg     120
gcaaaacaac actgatcaat acgctgacag gagtgaaccg caattacagc gggggcttta    180
cgctgtgcgg cattgaagct gaggccggca tgccgcagaa aacatcagat caactgaaga    240
ttcaccgtta cttcgccgct gattatccgc tgctgtttac agaaattacg gcgaaggact    300
atgtgtcttt cgtccattcg ctttatcaaa aggattttc agagcgacag tttgccagtt    360
tggctgaggc ctttcatttt tcaaaatca tcaacaggag aatctcggag ctgtccttgg    420
ggaacaggca aaaggttgtg ttgatgacag gattattgct gcgggctccc ctgtttattt    480
tggatgagcc gctcgtcggt ttggatgtgg aatcaataga ggtctttat cagaaaatgc    540
gggagtactg tgaggaaggc ggaacctttt tgttttcttc ccatctgctc gatgtcgtgc    600
agagattttg tgattttgcg gccattctgc acaacaaaca gatccaaaag gtcattccga    660
ttggggagga gaccgatctg cggcgggaat ttttgaggt tatcggccat gaataa        716
```

```
SEQ ID NO: 514              moltype = AA   length = 53
FEATURE                     Location/Qualifiers
source                      1..53
```

```
                        mol_type = protein
                        organism = Bacillus subtilis
SEQUENCE: 514
MSPAQRRILL YILSFIFVIG AVVYFVKSDY LFTLIFIAIA ILFGMRARKA DSR        53

SEQ ID NO: 515          moltype = DNA  length = 162
FEATURE                 Location/Qualifiers
source                  1..162
                        mol_type = genomic DNA
                        organism = Bacillus subtilis
SEQUENCE: 515
ttgtcaccag cacaaagaag aattttactg tatatccttt catttatctt tgtcatcggc  60
gcagtcgtct attttgtcaa aagcgattat ctgtttacgc tgattttcat tgccattgcc 120
attctgttcg ggatgcgcgc gcggaaggct gactcgcgat ga                    162

SEQ ID NO: 516          moltype = AA  length = 87
FEATURE                 Location/Qualifiers
source                  1..87
                        mol_type = protein
                        organism = Escherichia coli
SEQUENCE: 516
MELKNSISDY TEAEFVQLLK EIEKENVAAT DDVLDVLLEH FVKITEHPDG TDLIYYPSDN  60
RDDSPEGIVK EIKEWRAANG KPGFKQG                                     87

SEQ ID NO: 517          moltype = DNA  length = 264
FEATURE                 Location/Qualifiers
source                  1..264
                        mol_type = genomic DNA
                        organism = Escherichia coli
SEQUENCE: 517
atggaactga aaatagtat tagtgattac acagaggctg agtttgttca acttcttaag   60
gaaattgaaa aagagaatgt tgctgcaact gatgatgtgt tagatgtgtt actcgaacac 120
tttgtaaaaa ttactgagca tccagatgga acggatctga tttattatcc tagtgataat 180
agagacgata gccccgaagg gattgtcaag gaaattaaag aatggcgagc tgctaacggt 240
aagccaggat ttaaacaggg ctga                                        264

SEQ ID NO: 518          moltype = AA  length = 87
FEATURE                 Location/Qualifiers
source                  1..87
                        mol_type = protein
                        organism = Pseudomonas aeruginosa
SEQUENCE: 518
MKSKISEYTE KEFLEFVEDI YTNNKKKFPT EESHIQAVLE FKKLTEHPSG SDLLYYPNEN  60
REDSPAGVVK EVKEWRASKG LPGFKAG                                     87

SEQ ID NO: 519          moltype = DNA  length = 264
FEATURE                 Location/Qualifiers
source                  1..264
                        mol_type = genomic DNA
                        organism = Pseudomonas aeruginosa
SEQUENCE: 519
atgaagtcca agatttccga atatacggaa aaagagtttc ttgagtttgt tgaagacata  60
tacacaaaca ataagaaaaa gttccctacc gaggagtctc atattcaagc cgtgcttgaa 120
tttaaaaaac taacggaaca cccaagcggc tcagaccttc tttactaccc caacgaaaat 180
agagaagata gcccagctgg agttgtaaag gaagttaaag aatggcgtgc ttccaagggg 240
cttcctggct taaggccgg ttag                                         264

SEQ ID NO: 520          moltype = AA  length = 87
FEATURE                 Location/Qualifiers
source                  1..87
                        mol_type = protein
                        organism = Pseudomonas aeruginosa
SEQUENCE: 520
MKSKISEYTE KEFLEFVKDI YTNNKKKFPT EESHIQAVLE FKKLTEHPSG SDLLYYPNEN  60
REDSPAGVVK EVKEWRASKG LPGFKAG                                     87

SEQ ID NO: 521          moltype = DNA  length = 264
FEATURE                 Location/Qualifiers
source                  1..264
                        mol_type = genomic DNA
                        organism = Pseudomonas aeruginosa
SEQUENCE: 521
atgaagtcca agatttccga atatacggaa aaagagtttc ttgagtttgt taaagacata  60
tacacaaaca ataagaaaaa gttccctacc gaggagtctc atattcaagc cgtgcttgaa 120
tttaaaaaac taacggaaca cccaagcggc tcagaccttc tttactaccc caacgaaaat 180
agagaagata gcccagctgg agttgtaaag gaagttaaag aatggcgtgc ttccaagggg 240
cttcctggct taaggccgg ttag                                         264

SEQ ID NO: 522          moltype = AA  length = 95
```

| FEATURE | Location/Qualifiers |
|---|---|
| source | 1..95<br>mol_type = protein<br>organism = Enterococcus hirae |

SEQUENCE: 522
```
MDFTKEEKLL NAISKVYNEA TIDDYPDLKE KLFLYSKEIS EGKSVGEVSM KLSSFLGRYI    60
LKHKFGLPKS LIELQEIVSK ESQVYRGWAS IGIWS                              95
```

| SEQ ID NO: 523 | moltype = DNA  length = 288 |
|---|---|
| FEATURE | Location/Qualifiers |
| source | 1..288<br>mol_type = genomic DNA<br>organism = Enterococcus hirae |

SEQUENCE: 523
```
atggatttta ctaagaaga aaaactttta aatgcaatta gtaaagtata caatgaagca    60
actatagatg actatcctga cttaaaagaa aagctctttc tttattctaa agaaatcagt   120
gagggaaaaa gtgttggtga agttagtatg aaattagta gttttcttgg aagatatatt   180
ttaaaacata aatttggatt acctaaatct ttaatagaat acaagaaat tgttagtaag   240
gaatctcaag tatatagagg atgggcttct attggtattt ggagttaa               288
```

| SEQ ID NO: 524 | moltype = AA  length = 113 |
|---|---|
| FEATURE | Location/Qualifiers |
| source | 1..113<br>mol_type = protein<br>organism = Leuconostoc mesenteroides |

SEQUENCE: 524
```
MKKKYRYLED SKNYTSTLYS LLVDNVDKPG YSDICDVLLQ VSKKLDNTQS VEALINRLVN    60
YIRITASTYK IIFSKKEEEL IIKLGVIGQK AGLNGQYMAD FSDKSQFYSV FDQ          113
```

| SEQ ID NO: 525 | moltype = DNA  length = 342 |
|---|---|
| FEATURE | Location/Qualifiers |
| source | 1..342<br>mol_type = genomic DNA<br>organism = Leuconostoc mesenteroides |

SEQUENCE: 525
```
ttgaaaaaaa agtatcggta tttagaagat agcaaaaatt acactagtac actctattct    60
ctgttagttg ataatgttga caaacctgga tactcagata tttgcgatgt tttgcttcaa   120
gtttctaaga agttggataa tactcaaagt gttgaagcgc taattaatcg attggttaat   180
tatattcgta ttactgcttc aacatacaaa attatttttt caaaaaaaga agaggaattg   240
attataaaac ttggtgttat tggacaaaaa gctggactta atggtcagta tatggctgat   300
ttttcagaca gtctcagtt ttacagcgtt ttcgatcagt aa                       342
```

| SEQ ID NO: 526 | moltype = AA  length = 93 |
|---|---|
| FEATURE | Location/Qualifiers |
| source | 1..93<br>mol_type = protein<br>organism = Escherichia coli |

SEQUENCE: 526
```
MSFLNFAFSP VFFSIMACYF IVWRNKRNEF VCNRLLSIII ISFLICFIYP WLNYKIEVKY    60
YIFEQFYLFC FLSSLVAVVI NLIVYFILYR RCI                                93
```

| SEQ ID NO: 527 | moltype = DNA  length = 282 |
|---|---|
| FEATURE | Location/Qualifiers |
| source | 1..282<br>mol_type = genomic DNA<br>organism = Escherichia coli |

SEQUENCE: 527
```
atgagttttc ttaattttgc attttctcct gtattcttct ccattatggc gtgttatttc    60
attgtatgga gaaataaacg aaacgaaattt gtctgcaata gattgctatc aattataata   120
atatcttttt tgatatgctt catatatcca tggctaaatt acaaaatcga agttaaatat   180
tatatatttg aacagtttta tctttttttgt tttttatcgt cactcgtggc tgttgtaata   240
aacctaattg tatactttat attatacagg agatgtatat ga                      282
```

| SEQ ID NO: 528 | moltype = AA  length = 96 |
|---|---|
| FEATURE | Location/Qualifiers |
| source | 1..96<br>mol_type = protein<br>organism = Escherichia coli |

SEQUENCE: 528
```
MHLKYYLHNL PESLIPWILI LIFNDNDNTP LLFIFISSIH VLLYPYSKLT ISRYIKENTK    60
LKKEPWYLCK LSALFYLLMA IPVGLPSFIY YTLKRN                             96
```

| SEQ ID NO: 529 | moltype = DNA  length = 291 |
|---|---|
| FEATURE | Location/Qualifiers |
| source | 1..291<br>mol_type = genomic DNA<br>organism = Escherichia coli |

SEQUENCE: 529
```
atgcatttaa aatactacct acataattta cctgaatcac ttataccatg gattcttatt    60
```

```
ttaatattta acgacaatga taacactcct ttgttattta tatttatatc atcaatacat    120
gtattgctat atccatactc taaattaacc atatctagat atatcaaaga aaatacaaag    180
ttaaaaaaag aaccctggta cttatgcaag ttatctgcat tgtttatttt attaatggca    240
atcccagtag gattgccaag tttcatatat tacactctaa agagaaatta a             291
```

```
SEQ ID NO: 530          moltype = AA   length = 344
FEATURE                 Location/Qualifiers
source                  1..344
                        mol_type = protein
                        organism = Escherichia coli
SEQUENCE: 530
MMIQSHPLLA APLAVGDTIG FFSSSAPATV TAKNRFFRGV EFLQRKGFKL VSGKLTGKTD     60
FYRSGTIKER AQEFNELVYN PDITCIMSTI GGDNSNSLLP FLDYDAIIAN PKIIIGYSDT    120
TALLAGIYAK TGLITFYGPA LIPSFGEHPP LVDITYESFI KILTRKQSGI YTYTLPEKWS    180
DESINWNENK ILRPKKLYKN NCAFYGSGKV EGRVIGGNLN TLTGIWGSEW MPEILNGDIL    240
FIEDSRKSIA TIERLFSMLK LNRVFDKVSA IILGKHELFD CAGSKRRPYE VLTEVLDGKQ    300
IPVLDGFDCS HTHPMLTLPL GVKLAIDFDN KNISITEQYL STEK                     344
```

```
SEQ ID NO: 531          moltype = DNA   length = 1000
FEATURE                 Location/Qualifiers
source                  1..1000
                        mol_type = genomic DNA
                        organism = Escherichia coli
SEQUENCE: 531
atgatgatac aatctcatcc actactggcc gctcccctgg cagtaggaga tacaattggt     60
ttcttttcat catctgctcc ggcaacagtt actgcaaaaa atcgtttttt tcggggagtt    120
gagtttcttc agagaaaggg atttaagctg gtatcaggga agcttaccgg taaaacagat    180
ttttatcgtt caggtactat taaagaaaga gctcaagaat ttaatgagtt agtctacaat    240
cctgatatta cctgtataat gtcaacgatc ggtggagata cagtaattc actactaccg     300
tttctggact atgatgctat cattgcaaac cccaaaatta tcataggtta ctcagataca    360
actgctttat tagcaggaat atatgcaaaa acagggttaa taacattcta tggaccagct    420
cttattcctt cgtttggtga acatccacct cttgtggata aacatatga atcatttatt    480
aaaatactaa caagaaaaca atcaggaata tatacctaca cattacctga aaagtggagt    540
gatgagagca taaactggaa tgaaaacaag atattaaggc ctaagaagct atataaaaag    600
aactgtgcct tttatggttc cggaaaagtt gaggggcgtg taattgggga aaatctaaat    660
actttgacag gtatatgggg gagtgaatgg atgcctgaaa ttcttaatgg agatatattg    720
tttattgagg acagtcggaa aagcattgca acaattgaac gattattctc tatgctaaag    780
cttaatcgcg tgtttgataa agttagtgca ataaactcg ggaacatga gctttttgat     840
tgtgcaggaa gtaaacgcag accatatgaa gtattaacag aggtattaga tgggaaacag    900
attcctgtac tggatggatt tgattgttca catacacatc caatgctaac tcttccactt    960
ggtgtaaaat tagctattga ctttgacaac aaaaatatat                         1000
```

```
SEQ ID NO: 532          moltype = AA   length = 90
FEATURE                 Location/Qualifiers
source                  1..90
                        mol_type = protein
                        organism = Lactobacillus sakei
SEQUENCE: 532
MKADYKKINS ILTYTSTALK NPKIIKDKDL VVLLTIIQEE AKQNRIFYDY KRKFRPAVTR     60
FTIDNNFEIP DCLVKLLSAV ETPKAWSGFS                                      90
```

```
SEQ ID NO: 533          moltype = DNA   length = 268
FEATURE                 Location/Qualifiers
source                  1..268
                        mol_type = genomic DNA
                        organism = Lactobacillus sakei
SEQUENCE: 533
ggcagattat aaaaaaataa attcaatact aacttacaca tctactgctt taaaaaaccc     60
taaaattata aaagataaag atttagtagt ccttctaact attattcaag aagaagccaa    120
acaaaataga atctttttatg attataaaag aaaatttcgt ccagcggtta ctcgctttac    180
aattgataat aattttgaga ttcctgattg tttggttaaa ctactgtcag ctgttgaaac    240
acctaaggcg tggtctggat ttagttag                                       268
```

```
SEQ ID NO: 534          moltype = AA   length = 83
FEATURE                 Location/Qualifiers
source                  1..83
                        mol_type = protein
                        organism = Escherichia coli
SEQUENCE: 534
MKLSPKAAIE VCNEAAKKGL WILGIDGGHW LNPGFRIDSS ASWTYDMPEE YKSKTPENNR     60
LAIENIKDDI ENGYTAFIIT LKM                                             83
```

```
SEQ ID NO: 535          moltype = DNA   length = 251
FEATURE                 Location/Qualifiers
source                  1..251
                        mol_type = genomic DNA
                        organism = Escherichia coli
SEQUENCE: 535
tgaagttatc accaaaagct gcaatagaag tttgtaatga agcagcgaaa aaaggcttat     60
```

```
ggattttggg cattgatggt gggcattggc tgaatcctgg attcaggata gatagttcag    120
catcatggac atatgatatg ccggaggaat acaaatcaaa aaccctgaa aataatagat     180
tggctattga aaatattaaa gatgatattg agaatggata cactgctttc attatcacgt    240
taaagatgta a                                                         251

SEQ ID NO: 536          moltype = AA   length = 436
FEATURE                 Location/Qualifiers
source                  1..436
                        mol_type = protein
                        organism = Bacillus subtilis
SEQUENCE: 536
MNNIFPIMSL LFKQLYSRQG KKDAIRIAAG LVILAVFEIG LIRQAGIDES VLGKTYIILA     60
LLLMNTYMVF LSVTSQWKES YMKLSCLLPI SSRSFWLAQS VVLFVDTCLR RTLFFFILPL    120
FLFGNGTLSG AQTLFWLGRF SFFTVYSILF GVMLSNHFVK KKNSMFLLHA AVFAFVCLSA    180
AFMPAVTIPL CAVHMLWAVI IDFPVFLQAP PHQSKMHFFM RRSEFSFYKR EWNRFISSKA    240
MLLNYVVMAA FSGFFSFQMM NTGIFNQQVI YIVISALLLI CSPIALLYSI EKNDRMLLIT    300
LPIKRRTMFW AKYRFYSGLL AGGFLLVAII VGFISGRPIS ALTFVQCMEL LLAGAFIRLT    360
ADEKRPSFGW QTEQQLWSGF SKYRSYLFCL PLFLATLAGT AVSLAVIPIA ALIIVYYLQK    420
QDGGFFDTSK RERIGS                                                    436

SEQ ID NO: 537          moltype = DNA   length = 1000
FEATURE                 Location/Qualifiers
source                  1..1000
                        mol_type = genomic DNA
                        organism = Bacillus subtilis
SEQUENCE: 537
ttggggagga gaccgatctg cggcgggaat ttttttgagt tatcggccat gaataacata     60
ttccccatca tgtcgttgct gttcaaacag ctgtacagcc ggcaagggaa aaaggacgct    120
atccgcattg ctgcagggct tgtgattctc gccgtgtttg aaatcgggct gatccgacaa    180
gccgcattg acgaatcggt gttgggaaaa acgtatatca tattggcgct tctcttaatg    240
aacacgtata tggtgtttct ttccgtgaca tcacaatgga aggaatctta tatgaagctg    300
agctgtctgc tgccgatttc atcacggagc ttttggctcg cccagagtgt cgttctgttt    360
gtcgatacct gtttgagaag aacgttattc tttttttattt taccgctgtt cttatttgga    420
aacggaacgc tgtcagggc gcaaacattg ttttggcttg gcagattttc gtttttttacc    480
gtttactcga ttctattcgg agttatgcta agcaaccatt tcgtcaaaaa gaagaactcg    540
atgtttctgc tgcatgcggc ggtattcgcc tttgtatgcc tcagtgccgc ttttatgccg    600
gccgtcacga tcccgctatg cgcggttcac atgctatggg cggtgatcat tgactttccg    660
gtctttctgc aggcgcctcc gcatcagagc aagatgcatt ttttatgcg gcgatctgaa    720
ttttcgtttt acaaaagaga atggaaccga tttatttcgt ctaaagcgat gctgttaaat    780
tacgtggtga tggcggcgtt cagcggattc ttttcgttcc agatgatgaa cactggcatc    840
ttcaatcagc aagtgattta tattgtgatt ccgctctat tgctgatttg ctcgccgatc    900
gcccttttgt actctattga aaaaaacgat cgcatgctgc tcatcacgct tccaattaaa    960
agaagaacga tgttttgggc gaaatatcgc ttttattcag                         1000

SEQ ID NO: 538          moltype = AA   length = 580
FEATURE                 Location/Qualifiers
source                  1..580
                        mol_type = protein
                        organism = Escherichia coli
SEQUENCE: 538
MERKQKNSLF NYIYSLMDVR GKFLFFSMLF ITSLSSSIIS ISPLILAKIT DLLSGSLSNF     60
SYEYLVLLAC LYMFCVISNK ASVFLFMILQ SSLRINMQKK MSLKYLRELY NENITNLSKN    120
NAGYTTQSLN QASNDIYILV RNVSQNILSP VIQLISTIVV VLSTKDWFSA GVFFLYILVF    180
VIFNTRLTGS LASLRKHSMD ITLNSYSLLS DTVDNMIAAK KNNALRLISE RYEDALTQEN    240
NAQKKYWLLS SKVLLLNSLL AVILFGSVFI YNILGVLNGV VSIGHFIMIT SYIILLSTPV    300
ENIGALLSEI RQSMSSLAGF IQRHAENKAT SPSIPFLNME RKLNLSIREL SFSYSDDKKI    360
LNSVSLDLFT GKMYSLTGPS GSGKSTLVKI ISGYYKNYFG DIYLNDISLR NISDEDLNDA    420
IYYLTQDDYI FMDTLRFNLR LANYDASENE IFKVLKLANL SVVNNEPVSL DTHLINRGNN    480
YSGGQKQRIS LARLFLRKPA IIIIDEATSA LDYINESEIL SSIRTHFPDA LIINISHRIN    540
LLECSDCVYV LNEGNIVASG HFRDLMVSNE YISGLASVTE                          580

SEQ ID NO: 539          moltype = DNA   length = 1000
FEATURE                 Location/Qualifiers
source                  1..1000
                        mol_type = genomic DNA
                        organism = Escherichia coli
SEQUENCE: 539
atggaaagaa aacagaaaaa ctcattattt aattatattt attcattaat ggatgtaaga     60
ggtaaatttt tattctttc catgttattc attacatcat tatcatcgat aatcatatct    120
atttcaccat tgattcttgc aaagattaca gatttactgt ctggctcatt gtcaaatttt    180
agttatgaat atctggtttt acttgcctgt ttatacatgt tttgcgttat atctaataaa    240
gcaagtgttt tttatttat gatactgcaa agtagtctac gtattaacat gcagaaaaaa    300
atgtcgctaa agtatttgag agaattgtat aacgaaaata taactaactt gagtaaaaat    360
aatgctgaat atacaacgca aagtcttaac caggcttcaa atgacattta tattcttgtg    420
agaaatgttt cccagaatat cctgtcacct gttatacaac ttatttccac tattgttgtt    480
gttttatcta cgaaggactg gttttctgcc ggtgtgtttt ttctctatat tctggtatttt    540
gtaatttta ataccagact gactggcagt ttagcgtctc tcagaaaaca cagcatggat    600
atcactctta actcttatag tctgttatct gatactgttg ataacatgat agcagctaaa    660
aagaataatg cattaagact tatttctgaa cgttatgaag atgctctcac tcaggaaaac    720
```

```
aatgctcaga aaaaatactg gttactcagt tctaaagttc ttttattgaa ctctttactt    780
gctgtaatat tatttggttc tgtattcata tataatattt taggtgtgct gaatggtgta    840
gttagtatcg gccacttcat tatgattaca tcatatatca ttcttctttc aacgccagtg    900
gaaaatatag gggcattgct aagtgagatc aggcagtcaa tgtctagcct ggcaggtttt    960
attcaacgtc atgccgagaa taaagccaca tctccttcaa                         1000

SEQ ID NO: 540           moltype = AA  length = 95
FEATURE                  Location/Qualifiers
source                   1..95
                         mol_type = protein
                         organism = Klebsiella pneumoniae
SEQUENCE: 540
MTLLSFGFSP VFFSVMAFCI ISRSKFYPQR TRNKVIVLIL LTFFICFLYP LTKVYLVGSY    60
GIFDKFYLFC FISTLIAIAI NVVILTINGA KNERN                               95

SEQ ID NO: 541           moltype = DNA  length = 288
FEATURE                  Location/Qualifiers
source                   1..288
                         mol_type = genomic DNA
                         organism = Klebsiella pneumoniae
SEQUENCE: 541
atgacattac tttcatttgg attttctcct gttttctttt cagtcatggc gttctgtatc    60
atttcacgta gtaaattcta tccgcagaga acgcgaaaca aagttattgt tctgatttta   120
ctaactttt ttatttgttt tttatatcca ttaacaaaag tgtatctggt gggaagttac   180
ggtatatttg acaaattcta cctctttgc tttatttcta cgttaattgc aatagcaatt   240
aacgtagtga tacttacaat aaatggagct aagaatgaga gaaattag                288

SEQ ID NO: 542           moltype = RNA  length = 13
FEATURE                  Location/Qualifiers
misc_feature             1..13
                         note = Kozak sequence
source                   1..13
                         mol_type = other RNA
                         organism = synthetic construct
SEQUENCE: 542
gccgccrcca tgg                                                       13

SEQ ID NO: 543           moltype =   length =
SEQUENCE: 543
000

SEQ ID NO: 544           moltype = DNA  length = 30
FEATURE                  Location/Qualifiers
misc_feature             1..30
                         note = Lead promoter
source                   1..30
                         mol_type = other DNA
                         organism = synthetic construct
SEQUENCE: 544
gaaaaccttg tcaatgaaga gcgatctatg                                     30

SEQ ID NO: 545           moltype = DNA  length = 30
FEATURE                  Location/Qualifiers
misc_feature             1..30
                         note = FecA promoter
source                   1..30
                         mol_type = other DNA
                         organism = synthetic construct
SEQUENCE: 545
ttctcgttcg actcatagct gaacacaaca                                     30

SEQ ID NO: 546           moltype = DNA  length = 16
FEATURE                  Location/Qualifiers
misc_feature             1..16
                         note = Cu-sensitive promoter
source                   1..16
                         mol_type = other DNA
                         organism = synthetic construct
SEQUENCE: 546
atgacaaaat tgtcat                                                    16

SEQ ID NO: 547           moltype = DNA  length = 30
FEATURE                  Location/Qualifiers
misc_feature             1..30
                         note = Fe promoter
source                   1..30
                         mol_type = other DNA
                         organism = synthetic construct
SEQUENCE: 547
```

```
accaatgctg ggaacggcca gggcaccταα                                    30

SEQ ID NO: 548         moltype = DNA   length = 30
FEATURE                Location/Qualifiers
misc_feature           1..30
                       note = Fe and UV promoters
source                 1..30
                       mol_type = other DNA
                       organism = synthetic construct
SEQUENCE: 548
ctgaaagcgc ataccgctat ggagggggtt                                    30

SEQ ID NO: 549         moltype = DNA   length = 30
FEATURE                Location/Qualifiers
misc_feature           1..30
                       note = PrFe (PI + PII rus operon)
source                 1..30
                       mol_type = other DNA
                       organism = synthetic construct
SEQUENCE: 549
tagatatgcc tgaaagcgca taccgctatg                                    30

SEQ ID NO: 550         moltype = DNA   length = 30
FEATURE                Location/Qualifiers
misc_feature           1..30
                       note = Lux cassette right promoter
source                 1..30
                       mol_type = other DNA
                       organism = synthetic construct
SEQUENCE: 550
tgttatagtc gaatacctct ggcggtgata                                    30

SEQ ID NO: 551         moltype = DNA   length = 30
FEATURE                Location/Qualifiers
misc_feature           1..30
                       note = P(Las) TetO
source                 1..30
                       mol_type = other DNA
                       organism = synthetic construct
SEQUENCE: 551
ttttggtaca ctccctatca gtgatagaga                                    30

SEQ ID NO: 552         moltype = DNA   length = 30
FEATURE                Location/Qualifiers
misc_feature           1..30
                       note = P(Las) CIO
source                 1..30
                       mol_type = other DNA
                       organism = synthetic construct
SEQUENCE: 552
cttttggta cactacctct ggcggtgata                                     30

SEQ ID NO: 553         moltype = DNA   length = 30
FEATURE                Location/Qualifiers
misc_feature           1..30
                       note = P(Rhl)
source                 1..30
                       mol_type = other DNA
                       organism = synthetic construct
SEQUENCE: 553
tacgcaagaa aatggtttgt tatagtcgaa                                    30

SEQ ID NO: 554         moltype = DNA   length = 30
FEATURE                Location/Qualifiers
misc_feature           1..30
                       note = Double Promoter (LuxR/HSL, positive / cI,negative)
source                 1..30
                       mol_type = other DNA
                       organism = synthetic construct
SEQUENCE: 554
cgtgcgtgtt gataacaccg tgcgtgttga                                    30

SEQ ID NO: 555         moltype = DNA   length = 30
FEATURE                Location/Qualifiers
misc_feature           1..30
                       note = P2 promoter in agr operon from S. aureus
source                 1..30
                       mol_type = other DNA
                       organism = synthetic construct
```

```
SEQUENCE: 555
agattgtact aaatcgtata atgacagtga                              30

SEQ ID NO: 556         moltype = DNA  length = 30
FEATURE                Location/Qualifiers
misc_feature           1..30
                       note = plux-cI hybrid promoter
source                 1..30
                       mol_type = other DNA
                       organism = synthetic construct
SEQUENCE: 556
gtgttgatgc ttttatcacc gccagtggta                              30

SEQ ID NO: 557         moltype = DNA  length = 30
FEATURE                Location/Qualifiers
misc_feature           1..30
                       note = plux-lac hybrid promoter
source                 1..30
                       mol_type = other DNA
                       organism = synthetic construct
SEQUENCE: 557
agtgtgtgga attgtgagcg gataacaatt                              30

SEQ ID NO: 558         moltype = DNA  length = 30
FEATURE                Location/Qualifiers
misc_feature           1..30
                       note = CinR, CinL and glucose controlled promotor
source                 1..30
                       mol_type = other DNA
                       organism = synthetic construct
SEQUENCE: 558
acatcttaaa agttttagta tcatattcgt                              30

SEQ ID NO: 559         moltype = DNA  length = 30
FEATURE                Location/Qualifiers
misc_feature           1..30
                       note = RhlR promoter repressible by CI
source                 1..30
                       mol_type = other DNA
                       organism = synthetic construct
SEQUENCE: 559
tacgcaagaa aatggtttgt tatagtcgaa                              30

SEQ ID NO: 560         moltype = DNA  length = 30
FEATURE                Location/Qualifiers
misc_feature           1..30
                       note = Reverse Lux Promoter
source                 1..30
                       mol_type = other DNA
                       organism = synthetic construct
SEQUENCE: 560
tcttgcgtaa acctgtacga tcctacaggt                              30

SEQ ID NO: 561         moltype = DNA  length = 30
FEATURE                Location/Qualifiers
misc_feature           1..30
                       note = rhlI promoter
source                 1..30
                       mol_type = other DNA
                       organism = synthetic construct
SEQUENCE: 561
atcctccttt agtcttcccc ctcatgtgtg                              30

SEQ ID NO: 562         moltype = DNA  length = 30
FEATURE                Location/Qualifiers
misc_feature           1..30
                       note = lasI promoter
source                 1..30
                       mol_type = other DNA
                       organism = synthetic construct
SEQUENCE: 562
taaaattatg aaatttgcat aaattcttca                              30

SEQ ID NO: 563         moltype = DNA  length = 30
FEATURE                Location/Qualifiers
misc_feature           1..30
                       note = LuxR+3OC6HSL independent R0065
source                 1..30
                       mol_type = other DNA
```

```
                         organism = synthetic construct
SEQUENCE: 563
gtgttgacta ttttacctct ggcggtgata                                         30

SEQ ID NO: 564           moltype = DNA  length = 30
FEATURE                  Location/Qualifiers
misc_feature             1..30
                         note = LasR/LasI Inducible & RHLR/RHLI repressiblePromoter
source                   1..30
                         mol_type = other DNA
                         organism = synthetic construct
SEQUENCE: 564
gaaatctggc agtttttggt acacgaaagc                                         30

SEQ ID NO: 565           moltype = DNA  length = 30
FEATURE                  Location/Qualifiers
misc_feature             1..30
                         note = pLux/cI Hybrid Promoter
source                   1..30
                         mol_type = other DNA
                         organism = synthetic construct
SEQUENCE: 565
acaccgtgcg tgttgatata gtcgaataaa                                         30

SEQ ID NO: 566           moltype = DNA  length = 30
FEATURE                  Location/Qualifiers
misc_feature             1..30
                         note = pLas promoter
source                   1..30
                         mol_type = other DNA
                         organism = synthetic construct
SEQUENCE: 566
aaaattatga aatttgtata aattcttcag                                         30

SEQ ID NO: 567           moltype = DNA  length = 30
FEATURE                  Location/Qualifiers
misc_feature             1..30
                         note = pLas/cI Hybrid Promoter
source                   1..30
                         mol_type = other DNA
                         organism = synthetic construct
SEQUENCE: 567
ggttcttttt ggtacctctg gcggtgataa                                         30

SEQ ID NO: 568           moltype = DNA  length = 30
FEATURE                  Location/Qualifiers
misc_feature             1..30
                         note = pLas/Lux Hybrid Promoter
source                   1..30
                         mol_type = other DNA
                         organism = synthetic construct
SEQUENCE: 568
tgtaggatcg tacaggtata aattcttcag                                         30

SEQ ID NO: 569           moltype = DNA  length = 30
FEATURE                  Location/Qualifiers
misc_feature             1..30
                         note = pLux
source                   1..30
                         mol_type = other DNA
                         organism = synthetic construct
SEQUENCE: 569
caagaaaatg gtttgttata gtcgaataaa                                         30

SEQ ID NO: 570           moltype = DNA  length = 30
FEATURE                  Location/Qualifiers
misc_feature             1..30
                         note = pLux/Las Hybrid Promoter
source                   1..30
                         mol_type = other DNA
                         organism = synthetic construct
SEQUENCE: 570
ctatctcatt tgctagtata gtcgaataaa                                         30

SEQ ID NO: 571           moltype = DNA  length = 30
FEATURE                  Location/Qualifiers
misc_feature             1..30
                         note = Hybrid promoter: HSL-LuxR activated, P22 C2repressed
source                   1..30
```

```
                            mol_type = other DNA
                            organism = synthetic construct
SEQUENCE: 571
tagtttataa tttaagtgtt ctttaatttc                                         30

SEQ ID NO: 572          moltype = DNA    length = 30
FEATURE                 Location/Qualifiers
misc_feature            1..30
                        note = PAI+LasR - LuxI (AI)
source                  1..30
                        mol_type = other DNA
                        organism = synthetic construct
SEQUENCE: 572
caccttcggg tgggcctttc tgcgtttata                                         30

SEQ ID NO: 573          moltype = DNA    length = 30
FEATURE                 Location/Qualifiers
misc_feature            1..30
                        note = PAI+LasR - LasI & AI+LuxR --[m]LasI
source                  1..30
                        mol_type = other DNA
                        organism = synthetic construct
SEQUENCE: 573
aataactctg atagtgctag tgtagatctc                                         30

SEQ ID NO: 574          moltype = DNA    length = 30
FEATURE                 Location/Qualifiers
misc_feature            1..30
                        note = PAI+LasR - LasI+GFP & AI+LuxR --[\m]LasI+GFP
source                  1..30
                        mol_type = other DNA
                        organism = synthetic construct
SEQUENCE: 574
caccttcggg tgggcctttc tgcgtttata                                         30

SEQ ID NO: 575          moltype = DNA    length = 30
FEATURE                 Location/Qualifiers
misc_feature            1..30
                        note = Complex QS - LuxI & LasI circuit
source                  1..30
                        mol_type = other DNA
                        organism = synthetic construct
SEQUENCE: 575
caccttcggg tgggcctttc tgcgtttata                                         30

SEQ ID NO: 576          moltype = DNA    length = 30
FEATURE                 Location/Qualifiers
misc_feature            1..30
                        note = position 3 mutated promoter lux pR-3 (luxR &
                           HSLregulated)
source                  1..30
                        mol_type = other DNA
                        organism = synthetic construct
SEQUENCE: 576
caagaaaatg gtttgttata gtcgaataaa                                         30

SEQ ID NO: 577          moltype = DNA    length = 30
FEATURE                 Location/Qualifiers
misc_feature            1..30
                        note = position 5 mutated promoter lux pR-5 (luxR &
                           HSLregulated)
source                  1..30
                        mol_type = other DNA
                        organism = synthetic construct
SEQUENCE: 577
caagaaaatg gtttgttata gtcgaataaa                                         30

SEQ ID NO: 578          moltype = DNA    length = 30
FEATURE                 Location/Qualifiers
misc_feature            1..30
                        note = position 3&5 mutated promoter lux pR-3/5 (luxR &HSL
                           regulated)
source                  1..30
                        mol_type = other DNA
                        organism = synthetic construct
SEQUENCE: 578
caagaaaatg gtttgttata gtcgaataaa                                         30

SEQ ID NO: 579          moltype = DNA    length = 30
```

```
FEATURE                 Location/Qualifiers
misc_feature            1..30
                        note = Promoter (HSL-mediated luxR repressor)
source                  1..30
                        mol_type = other DNA
                        organism = synthetic construct
SEQUENCE: 579
ttgacacctg taggatcgta caggtataat                                          30

SEQ ID NO: 580          moltype = DNA  length = 30
FEATURE                 Location/Qualifiers
misc_feature            1..30
                        note = Promoter (luxR & HSL regulated -- lux pR)
source                  1..30
                        mol_type = other DNA
                        organism = synthetic construct
SEQUENCE: 580
caagaaaatg gtttgttata gtcgaataaa                                          30

SEQ ID NO: 581          moltype = DNA  length = 30
FEATURE                 Location/Qualifiers
misc_feature            1..30
                        note = Promoter (luxR & HSL regulated -- lux pL)
source                  1..30
                        mol_type = other DNA
                        organism = synthetic construct
SEQUENCE: 581
cacgcaaaac ttgcgacaaa caataggtaa                                          30

SEQ ID NO: 582          moltype = DNA  length = 30
FEATURE                 Location/Qualifiers
misc_feature            1..30
                        note = Promoter (RhlR & C4-HSL regulated)
source                  1..30
                        mol_type = other DNA
                        organism = synthetic construct
SEQUENCE: 582
gttagctttc gaattggcta aaaagtgttc                                          30

SEQ ID NO: 583          moltype = DNA  length = 30
FEATURE                 Location/Qualifiers
misc_feature            1..30
                        note = Promoter (cinR and HSL regulated)
source                  1..30
                        mol_type = other DNA
                        organism = synthetic construct
SEQUENCE: 583
ccattctgct ttccacgaac ttgaaaacgc                                          30

SEQ ID NO: 584          moltype = DNA  length = 30
FEATURE                 Location/Qualifiers
misc_feature            1..30
                        note = Promoter (LasR & PAI regulated)
source                  1..30
                        mol_type = other DNA
                        organism = synthetic construct
SEQUENCE: 584
ggccgcgggt tcttttggt acacgaaagc                                           30

SEQ ID NO: 585          moltype = DNA  length = 30
FEATURE                 Location/Qualifiers
misc_feature            1..30
                        note = Promoter, Standard (luxR and HSL regulated -- luxpR)
source                  1..30
                        mol_type = other DNA
                        organism = synthetic construct
SEQUENCE: 585
aagaaaatgg tttgttgata ctcgaataaa                                          30

SEQ ID NO: 586          moltype = DNA  length = 30
FEATURE                 Location/Qualifiers
misc_feature            1..30
                        note = P(Bla)
source                  1..30
                        mol_type = other DNA
                        organism = synthetic construct
SEQUENCE: 586
gtttatacat aggcgagtac tctgttatgg                                          30
```

```
SEQ ID NO: 587           moltype = DNA  length = 30
FEATURE                  Location/Qualifiers
misc_feature             1..30
                         note = P(Cat)
source                   1..30
                         mol_type = other DNA
                         organism = synthetic construct
SEQUENCE: 587
agaggttcca actttcacca taatgaaaca                                      30

SEQ ID NO: 588           moltype = DNA  length = 30
FEATURE                  Location/Qualifiers
misc_feature             1..30
                         note = P(Kat)
source                   1..30
                         mol_type = other DNA
                         organism = synthetic construct
SEQUENCE: 588
taaacaacta acggacaatt ctacctaaca                                      30

SEQ ID NO: 589           moltype = DNA  length = 30
FEATURE                  Location/Qualifiers
misc_feature             1..30
                         note = Template for Building Primer Family Member
source                   1..30
                         mol_type = other DNA
                         organism = synthetic construct
SEQUENCE: 589
acatcaagcc aaattaaaca ggattaacac                                      30

SEQ ID NO: 590           moltype = DNA  length = 30
FEATURE                  Location/Qualifiers
misc_feature             1..30
                         note = Reverse lambda cI-regulated promoter
source                   1..30
                         mol_type = other DNA
                         organism = synthetic construct
SEQUENCE: 590
gaggtaaaat agtcaacacg cacggtgtta                                      30

SEQ ID NO: 591           moltype = DNA  length = 30
FEATURE                  Location/Qualifiers
misc_feature             1..30
                         note = Key Promoter absorbs 3
source                   1..30
                         mol_type = other DNA
                         organism = synthetic construct
SEQUENCE: 591
caggccggaa taactcccta taatgcgcca                                      30

SEQ ID NO: 592           moltype = DNA  length = 30
FEATURE                  Location/Qualifiers
misc_feature             1..30
                         note = constitutive promoter family member
source                   1..30
                         mol_type = other DNA
                         organism = synthetic construct
SEQUENCE: 592
ggctagctca gtcctaggta cagtgctagc                                      30

SEQ ID NO: 593           moltype = DNA  length = 30
FEATURE                  Location/Qualifiers
misc_feature             1..30
                         note = constitutive promoter family member
source                   1..30
                         mol_type = other DNA
                         organism = synthetic construct
SEQUENCE: 593
agctagctca gtcctaggta ttatgctagc                                      30

SEQ ID NO: 594           moltype = DNA  length = 30
FEATURE                  Location/Qualifiers
misc_feature             1..30
                         note = constitutive promoter family member
source                   1..30
                         mol_type = other DNA
                         organism = synthetic construct
SEQUENCE: 594
agctagctca gtcctaggta ctgtgctagc                                      30
```

```
SEQ ID NO: 595           moltype = DNA   length = 30
FEATURE                  Location/Qualifiers
misc_feature             1..30
                         note = constitutive promoter family member
source                   1..30
                         mol_type = other DNA
                         organism = synthetic construct
SEQUENCE: 595
agctagctca gtcctaggga ttatgctagc                                          30

SEQ ID NO: 596           moltype = DNA   length = 30
FEATURE                  Location/Qualifiers
misc_feature             1..30
                         note = constitutive promoter family member
source                   1..30
                         mol_type = other DNA
                         organism = synthetic construct
SEQUENCE: 596
agctagctca gtcctaggta ttgtgctagc                                          30

SEQ ID NO: 597           moltype = DNA   length = 30
FEATURE                  Location/Qualifiers
misc_feature             1..30
                         note = constitutive promoter family member
source                   1..30
                         mol_type = other DNA
                         organism = synthetic construct
SEQUENCE: 597
ggctagctca gtcctaggta ctatgctagc                                          30

SEQ ID NO: 598           moltype = DNA   length = 30
FEATURE                  Location/Qualifiers
misc_feature             1..30
                         note = constitutive promoter family member
source                   1..30
                         mol_type = other DNA
                         organism = synthetic construct
SEQUENCE: 598
ggctagctca gtcctaggta tagtgctagc                                          30

SEQ ID NO: 599           moltype = DNA   length = 30
FEATURE                  Location/Qualifiers
misc_feature             1..30
                         note = constitutive promoter family member
source                   1..30
                         mol_type = other DNA
                         organism = synthetic construct
SEQUENCE: 599
ggctagctca gccctaggta ttatgctagc                                          30

SEQ ID NO: 600           moltype = DNA   length = 30
FEATURE                  Location/Qualifiers
misc_feature             1..30
                         note = constitutive promoter family member
source                   1..30
                         mol_type = other DNA
                         organism = synthetic construct
SEQUENCE: 600
agctagctca gtcctaggta taatgctagc                                          30

SEQ ID NO: 601           moltype = DNA   length = 30
FEATURE                  Location/Qualifiers
misc_feature             1..30
                         note = constitutive promoter family member
source                   1..30
                         mol_type = other DNA
                         organism = synthetic construct
SEQUENCE: 601
agctagctca gtcctaggga ctgtgctagc                                          30

SEQ ID NO: 602           moltype = DNA   length = 30
FEATURE                  Location/Qualifiers
misc_feature             1..30
                         note = constitutive promoter family member
source                   1..30
                         mol_type = other DNA
                         organism = synthetic construct
SEQUENCE: 602
```

```
ggctagctca gtcctaggta caatgctagc                                              30

SEQ ID NO: 603          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 603
ggctagctca gtcctaggta tagtgctagc                                              30

SEQ ID NO: 604          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 604
agctagctca gtcctaggga ttatgctagc                                              30

SEQ ID NO: 605          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 605
ggctagctca gtcctaggga ttatgctagc                                              30

SEQ ID NO: 606          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 606
ggctagctca gtcctaggta caatgctagc                                              30

SEQ ID NO: 607          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 607
agctagctca gcccttggta caatgctagc                                              30

SEQ ID NO: 608          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 608
agctagctca gtcctaggga ctatgctagc                                              30

SEQ ID NO: 609          moltype = DNA  length = 30
FEATURE                 Location/Qualifiers
misc_feature            1..30
                        note = constitutive promoter family member
source                  1..30
                        mol_type = other DNA
                        organism = synthetic construct
SEQUENCE: 609
agctagctca gtcctaggga ttgtgctagc                                              30

SEQ ID NO: 610          moltype = DNA  length = 30
FEATURE                 Location/Qualifiers
misc_feature            1..30
                        note = constitutive promoter family member
source                  1..30
                        mol_type = other DNA
                        organism = synthetic construct
```

```
SEQUENCE: 610
ggctagctca gtcctaggta ttgtgctagc                                              30

SEQ ID NO: 611           moltype = DNA  length = 30
FEATURE                  Location/Qualifiers
misc_feature             1..30
                         note = constitutive promoter family member
source                   1..30
                         mol_type = other DNA
                         organism = synthetic construct
SEQUENCE: 611
agctagctca gtcctaggta taatgctagc                                              30

SEQ ID NO: 612           moltype = DNA  length = 30
FEATURE                  Location/Qualifiers
misc_feature             1..30
                         note = 1bp mutant from J23107
source                   1..30
                         mol_type = other DNA
                         organism = synthetic construct
SEQUENCE: 612
ggctagctca gtcctaggta ttatgctagc                                              30

SEQ ID NO: 613           moltype = DNA  length = 30
FEATURE                  Location/Qualifiers
misc_feature             1..30
                         note = 1bp mutant from J23114
source                   1..30
                         mol_type = other DNA
                         organism = synthetic construct
SEQUENCE: 613
ggctagctca gtcctaggta caatgctagc                                              30

SEQ ID NO: 614           moltype = DNA  length = 30
FEATURE                  Location/Qualifiers
misc_feature             1..30
                         note = pBAD reverse
source                   1..30
                         mol_type = other DNA
                         organism = synthetic construct
SEQUENCE: 614
aaagtgtgac gccgtgcaaa taatcaatgt                                              30

SEQ ID NO: 615           moltype = DNA  length = 30
FEATURE                  Location/Qualifiers
misc_feature             1..30
                         note = NikR promoter, a protein of the ribbon
                          helix-helixfamily of trancription factors that repress
                          expre
source                   1..30
                         mol_type = other DNA
                         organism = synthetic construct
SEQUENCE: 615
gacgaatact taaaatcgtc atacttattt                                              30

SEQ ID NO: 616           moltype = DNA  length = 30
FEATURE                  Location/Qualifiers
misc_feature             1..30
                         note = lacq_Promoter
source                   1..30
                         mol_type = other DNA
                         organism = synthetic construct
SEQUENCE: 616
aaacctttcg cggtatggca tgatagcgcc                                              30

SEQ ID NO: 617           moltype = DNA  length = 30
FEATURE                  Location/Qualifiers
misc_feature             1..30
                         note = lacIQ - promoter sequence
source                   1..30
                         mol_type = other DNA
                         organism = synthetic construct
SEQUENCE: 617
tgatagcgcc cggaagagag tcaattcagg                                              30

SEQ ID NO: 618           moltype = DNA  length = 30
FEATURE                  Location/Qualifiers
misc_feature             1..30
                         note = E. Coli CreABCD phosphate sensing operon promoter
```

```
                                -continued source                  1..30
                        mol_type = other DNA
                        organism = synthetic construct
SEQUENCE: 618
ttatttaccg tgacgaacta attgctcgtg                                        30

SEQ ID NO: 619          moltype = DNA  length = 30
FEATURE                 Location/Qualifiers
misc_feature            1..30
                        note = GlnRS promoter
source                  1..30
                        mol_type = other DNA
                        organism = synthetic construct
SEQUENCE: 619
catacgccgt tatacgttgt ttacgctttg                                        30

SEQ ID NO: 620          moltype = DNA  length = 30
FEATURE                 Location/Qualifiers
misc_feature            1..30
                        note = Constitutive weak promoter of lacZ
source                  1..30
                        mol_type = other DNA
                        organism = synthetic construct
SEQUENCE: 620
ttatgcttcc ggctcgtatg ttgtgtggac                                        30

SEQ ID NO: 621          moltype = DNA  length = 30
FEATURE                 Location/Qualifiers
misc_feature            1..30
                        note = Mutated LacZ promoter
source                  1..30
                        mol_type = other DNA
                        organism = synthetic construct
SEQUENCE: 621
ttatgcttcc ggctcgtatg gtgtgtggac                                        30

SEQ ID NO: 622          moltype = DNA  length = 30
FEATURE                 Location/Qualifiers
misc_feature            1..30
                        note = constitutive promoter with (TA)10 between -10 and-35
                         elements
source                  1..30
                        mol_type = other DNA
                        organism = synthetic construct
SEQUENCE: 622
atatatatat atatataatg gaagcgtttt                                        30

SEQ ID NO: 623          moltype = DNA  length = 30
FEATURE                 Location/Qualifiers
misc_feature            1..30
                        note = constitutive promoter with (TA)9 between -10 and-35
                         elements
source                  1..30
                        mol_type = other DNA
                        organism = synthetic construct
SEQUENCE: 623
atatatatat atatataatg gaagcgtttt                                        30

SEQ ID NO: 624          moltype = DNA  length = 30
FEATURE                 Location/Qualifiers
misc_feature            1..30
                        note = constitutive promoter with (C)10 between -10 and-35
                         elements
source                  1..30
                        mol_type = other DNA
                        organism = synthetic construct
SEQUENCE: 624
ccccgaaagc ttaagaatat aattgtaagc                                        30

SEQ ID NO: 625          moltype = DNA  length = 30
FEATURE                 Location/Qualifiers
misc_feature            1..30
                        note = constitutive promoter with (C)12 between -10 and-35
                         elements
source                  1..30
                        mol_type = other DNA
                        organism = synthetic construct
SEQUENCE: 625
ccccgaaagc ttaagaatat aattgtaagc                                        30
```

```
SEQ ID NO: 626          moltype = DNA   length = 30
FEATURE                 Location/Qualifiers
misc_feature            1..30
                        note = optimized (TA) repeat constitutive promoter with13
                         bp between -10 and -35 elements
source                  1..30
                        mol_type = other DNA
                        organism = synthetic construct
SEQUENCE: 626
tgacaatata tatatatata taatgctagc                                             30

SEQ ID NO: 627          moltype = DNA   length = 30
FEATURE                 Location/Qualifiers
misc_feature            1..30
                        note = optimized (TA) repeat constitutive promoter with15
                         bp between -10 and -35 elements
source                  1..30
                        mol_type = other DNA
                        organism = synthetic construct
SEQUENCE: 627
acaatatata tatatatata taatgctagc                                             30

SEQ ID NO: 628          moltype = DNA   length = 30
FEATURE                 Location/Qualifiers
misc_feature            1..30
                        note = optimized (TA) repeat constitutive promoter with17
                         bp between -10 and -35 elements
source                  1..30
                        mol_type = other DNA
                        organism = synthetic construct
SEQUENCE: 628
aatatatata tatatatata taatgctagc                                             30

SEQ ID NO: 629          moltype = DNA   length = 30
FEATURE                 Location/Qualifiers
misc_feature            1..30
                        note = optimized (TA) repeat constitutive promoter with19
                         bp between -10 and -35 elements
source                  1..30
                        mol_type = other DNA
                        organism = synthetic construct
SEQUENCE: 629
tatatatata tatatatata taatgctagc                                             30

SEQ ID NO: 630          moltype = DNA   length = 30
FEATURE                 Location/Qualifiers
misc_feature            1..30
                        note = optimized (TA) repeat constitutive promoter with21
                         bp between -10 and -35 elements
source                  1..30
                        mol_type = other DNA
                        organism = synthetic construct
SEQUENCE: 630
tatatatata tatatatata taatgctagc                                             30

SEQ ID NO: 631          moltype = DNA   length = 30
FEATURE                 Location/Qualifiers
misc_feature            1..30
                        note = optimized (A) repeat constitutive promoter with 17bp
                         between -10 and -35 elements
source                  1..30
                        mol_type = other DNA
                        organism = synthetic construct
SEQUENCE: 631
aaaaaaaaaa aaaaaaaata taatgctagc                                             30

SEQ ID NO: 632          moltype = DNA   length = 30
FEATURE                 Location/Qualifiers
misc_feature            1..30
                        note = optimized (A) repeat constitutive promoter with 18bp
                         between -10 and -35 elements
source                  1..30
                        mol_type = other DNA
                        organism = synthetic construct
SEQUENCE: 632
aaaaaaaaaa aaaaaaaata taatgctagc                                             30

SEQ ID NO: 633          moltype = DNA   length = 30
```

-continued

```
FEATURE                 Location/Qualifiers
misc_feature            1..30
                        note = J23101:GFP
source                  1..30
                        mol_type = other DNA
                        organism = synthetic construct
SEQUENCE: 633
caccttcggg tgggcctttc tgcgtttata                                              30

SEQ ID NO: 634          moltype = DNA   length = 30
FEATURE                 Location/Qualifiers
misc_feature            1..30
                        note = J23119:IFP
source                  1..30
                        mol_type = other DNA
                        organism = synthetic construct
SEQUENCE: 634
caccttcggg tgggcctttc tgcgtttata                                              30

SEQ ID NO: 635          moltype = DNA   length = 30
FEATURE                 Location/Qualifiers
misc_feature            1..30
                        note = J23119:HO1
source                  1..30
                        mol_type = other DNA
                        organism = synthetic construct
SEQUENCE: 635
caccttcggg tgggcctttc tgcgtttata                                              30

SEQ ID NO: 636          moltype = DNA   length = 30
FEATURE                 Location/Qualifiers
misc_feature            1..30
                        note = Infrared signal reporter (J23119:IFP:J23119:HO1)
source                  1..30
                        mol_type = other DNA
                        organism = synthetic construct
SEQUENCE: 636
caccttcggg tgggcctttc tgcgtttata                                              30

SEQ ID NO: 637          moltype = DNA   length = 30
FEATURE                 Location/Qualifiers
misc_feature            1..30
                        note = Double terminator + constitutive promoter
source                  1..30
                        mol_type = other DNA
                        organism = synthetic construct
SEQUENCE: 637
ggctagctca gtcctaggta cagtgctagc                                              30

SEQ ID NO: 638          moltype = DNA   length = 30
FEATURE                 Location/Qualifiers
misc_feature            1..30
                        note = Double terminator + Constitutive promoter + StrongRBS
source                  1..30
                        mol_type = other DNA
                        organism = synthetic construct
SEQUENCE: 638
tgctagctac tagagattaa agaggagaaa                                              30

SEQ ID NO: 639          moltype = DNA   length = 30
FEATURE                 Location/Qualifiers
misc_feature            1..30
                        note = IPTG inducible Lac promoter cassette
source                  1..30
                        mol_type = other DNA
                        organism = synthetic construct
SEQUENCE: 639
ttgtgagcgg ataacaagat actgagcaca                                              30

SEQ ID NO: 640          moltype = DNA   length = 30
FEATURE                 Location/Qualifiers
misc_feature            1..30
                        note = IPTG inducible Lac promoter cassette
source                  1..30
                        mol_type = other DNA
                        organism = synthetic construct
SEQUENCE: 640
ttgtgagcgg ataacaagat actgagcaca                                              30
```

```
SEQ ID NO: 641          moltype = DNA   length = 30
FEATURE                 Location/Qualifiers
misc_feature            1..30
                        note = IPTG inducible Lac promoter cassette
source                  1..30
                        mol_type = other DNA
                        organism = synthetic construct
SEQUENCE: 641
ttgtgagcgg ataacaagat actgagcaca                                          30

SEQ ID NO: 642          moltype = DNA   length = 30
FEATURE                 Location/Qualifiers
misc_feature            1..30
                        note = M13K07 gene I promoter
source                  1..30
                        mol_type = other DNA
                        organism = synthetic construct
SEQUENCE: 642
cctgttttta tgttattctc tctgtaaagg                                          30

SEQ ID NO: 643          moltype = DNA   length = 30
FEATURE                 Location/Qualifiers
misc_feature            1..30
                        note = M13K07 gene II promoter
source                  1..30
                        mol_type = other DNA
                        organism = synthetic construct
SEQUENCE: 643
aaatatttgc ttatacaatc ttcctgtttt                                          30

SEQ ID NO: 644          moltype = DNA   length = 30
FEATURE                 Location/Qualifiers
misc_feature            1..30
                        note = M13K07 gene III promoter
source                  1..30
                        mol_type = other DNA
                        organism = synthetic construct
SEQUENCE: 644
gctgataaac cgatacaatt aaaggctcct                                          30

SEQ ID NO: 645          moltype = DNA   length = 30
FEATURE                 Location/Qualifiers
misc_feature            1..30
                        note = M13K07 gene IV promoter
source                  1..30
                        mol_type = other DNA
                        organism = synthetic construct
SEQUENCE: 645
ctcttctcag cgtcttaatc taagctatcg                                          30

SEQ ID NO: 646          moltype = DNA   length = 30
FEATURE                 Location/Qualifiers
misc_feature            1..30
                        note = M13K07 gene V promoter
source                  1..30
                        mol_type = other DNA
                        organism = synthetic construct
SEQUENCE: 646
atgagccagt tcttaaaatc gcataaggta                                          30

SEQ ID NO: 647          moltype = DNA   length = 30
FEATURE                 Location/Qualifiers
misc_feature            1..30
                        note = M13K07 gene VI promoter
source                  1..30
                        mol_type = other DNA
                        organism = synthetic construct
SEQUENCE: 647
ctattgattg tgacaaaata aacttattcc                                          30

SEQ ID NO: 648          moltype = DNA   length = 30
FEATURE                 Location/Qualifiers
misc_feature            1..30
                        note = M13K07 gene VIII promoter
source                  1..30
                        mol_type = other DNA
                        organism = synthetic construct
SEQUENCE: 648
gtttcgcgct tggtataatc gctgggggtc                                          30
```

```
SEQ ID NO: 649           moltype = DNA  length = 30
FEATURE                  Location/Qualifiers
misc_feature             1..30
                         note = M13110
source                   1..30
                         mol_type = other DNA
                         organism = synthetic construct
SEQUENCE: 649
ctttgcttct gactataata gtcagggtaa                                              30

SEQ ID NO: 650           moltype = DNA  length = 30
FEATURE                  Location/Qualifiers
misc_feature             1..30
                         note = Modified promoter sequence of g3.
source                   1..30
                         mol_type = other DNA
                         organism = synthetic construct
SEQUENCE: 650
aaaccgatac aattaaaggc tcctgctagc                                              30

SEQ ID NO: 651           moltype = DNA  length = 30
FEATURE                  Location/Qualifiers
misc_feature             1..30
                         note = Constitutive Promoter I
source                   1..30
                         mol_type = other DNA
                         organism = synthetic construct
SEQUENCE: 651
caccacactg atagtgctag tgtagatcac                                              30

SEQ ID NO: 652           moltype = DNA  length = 30
FEATURE                  Location/Qualifiers
misc_feature             1..30
                         note = Constitutive Promoter II
source                   1..30
                         mol_type = other DNA
                         organism = synthetic construct
SEQUENCE: 652
gccggaataa ctccctataa tgcgccacca                                              30

SEQ ID NO: 653           moltype = DNA  length = 30
FEATURE                  Location/Qualifiers
misc_feature             1..30
                         note = --Specify Parts List--
source                   1..30
                         mol_type = other DNA
                         organism = synthetic construct
SEQUENCE: 653
ttgacaagct tttcctcagc tccgtaaact                                              30

SEQ ID NO: 654           moltype = DNA  length = 30
FEATURE                  Location/Qualifiers
misc_feature             1..30
                         note = Full-length stationary phase osmY promoter
source                   1..30
                         mol_type = other DNA
                         organism = synthetic construct
SEQUENCE: 654
ggtttcaaaa ttgtgatcta tatttaacaa                                              30

SEQ ID NO: 655           moltype = DNA  length = 30
FEATURE                  Location/Qualifiers
misc_feature             1..30
                         note = Minimal stationary phase osmY promoter
source                   1..30
                         mol_type = other DNA
                         organism = synthetic construct
SEQUENCE: 655
ggtttcaaaa ttgtgatcta tatttaacaa                                              30

SEQ ID NO: 656           moltype = DNA  length = 30
FEATURE                  Location/Qualifiers
misc_feature             1..30
                         note = htpG Heat Shock Promoter
source                   1..30
                         mol_type = other DNA
                         organism = synthetic construct
SEQUENCE: 656
```

```
tctattccaa taaagaaatc ttcctgcgtg                                              30

SEQ ID NO: 657          moltype = DNA  length = 30
FEATURE                 Location/Qualifiers
misc_feature            1..30
                        note = Promoter veg a constitutive promoter for B.subtilis
source                  1..30
                        mol_type = other DNA
                        organism = synthetic construct
SEQUENCE: 657
aaaaatgggc tcgtgttgta caataaatgt                                              30

SEQ ID NO: 658          moltype = DNA  length = 30
FEATURE                 Location/Qualifiers
misc_feature            1..30
                        note = Promoter 43 a constitutive promoter for B.subtilis
source                  1..30
                        mol_type = other DNA
                        organism = synthetic construct
SEQUENCE: 658
aaaaaaagcg cgcgattatg taaaatataa                                              30

SEQ ID NO: 659          moltype = DNA  length = 30
FEATURE                 Location/Qualifiers
misc_feature            1..30
                        note = Strong constitutive promoter for Bacillus subtilis
source                  1..30
                        mol_type = other DNA
                        organism = synthetic construct
SEQUENCE: 659
aattgcagta ggcatgacaa aatggactca                                              30

SEQ ID NO: 660          moltype = DNA  length = 30
FEATURE                 Location/Qualifiers
misc_feature            1..30
                        note = PliaG
source                  1..30
                        mol_type = other DNA
                        organism = synthetic construct
SEQUENCE: 660
caagcttttc ctttataata gaatgaatga                                              30

SEQ ID NO: 661          moltype = DNA  length = 30
FEATURE                 Location/Qualifiers
misc_feature            1..30
                        note = PlepA
source                  1..30
                        mol_type = other DNA
                        organism = synthetic construct
SEQUENCE: 661
tctaagctag tgtatttttgc gtttaatagt                                             30

SEQ ID NO: 662          moltype = DNA  length = 30
FEATURE                 Location/Qualifiers
misc_feature            1..30
                        note = Pveg
source                  1..30
                        mol_type = other DNA
                        organism = synthetic construct
SEQUENCE: 662
aatgggctcg tgttgtacaa taaatgtagt                                              30

SEQ ID NO: 663          moltype = DNA  length = 30
FEATURE                 Location/Qualifiers
misc_feature            1..30
                        note = Promoter ctc for B. subtilis
source                  1..30
                        mol_type = other DNA
                        organism = synthetic construct
SEQUENCE: 663
atccttatcg ttatgggtat tgtttgtaat                                              30

SEQ ID NO: 664          moltype = DNA  length = 30
FEATURE                 Location/Qualifiers
misc_feature            1..30
                        note = Promoter gsiB for B. subtilis
source                  1..30
                        mol_type = other DNA
                        organism = synthetic construct
```

```
SEQUENCE: 664
taaaagaatt gtgagcggga atacaacaac                                    30

SEQ ID NO: 665          moltype = DNA  length = 30
FEATURE                 Location/Qualifiers
misc_feature            1..30
                        note = Promoter 43 a constitutive promoter for B.subtilis
source                  1..30
                        mol_type = other DNA
                        organism = synthetic construct
SEQUENCE: 665
aaaaaaagcg cgcgattatg taaaatataa                                    30

SEQ ID NO: 666          moltype = DNA  length = 30
FEATURE                 Location/Qualifiers
misc_feature            1..30
                        note = Pspv2 from Salmonella
source                  1..30
                        mol_type = other DNA
                        organism = synthetic construct
SEQUENCE: 666
tacaaaataa ttcccctgca aacattatca                                    30

SEQ ID NO: 667          moltype = DNA  length = 30
FEATURE                 Location/Qualifiers
misc_feature            1..30
                        note = Pspv from Salmonella
source                  1..30
                        mol_type = other DNA
                        organism = synthetic construct
SEQUENCE: 667
tacaaaataa ttcccctgca aacattatcg                                    30

SEQ ID NO: 668          moltype = DNA  length = 30
FEATURE                 Location/Qualifiers
misc_feature            1..30
                        note = T7 promoter (strong promoter from T7bacteriophage)
source                  1..30
                        mol_type = other DNA
                        organism = synthetic construct
SEQUENCE: 668
agggaataca agctacttgt tcttttttgca                                   30

SEQ ID NO: 669          moltype = DNA  length = 23
FEATURE                 Location/Qualifiers
misc_feature            1..23
                        note = T7 Promoter
source                  1..23
                        mol_type = other DNA
                        organism = synthetic construct
SEQUENCE: 669
taatacgact cactataggg aga                                           23

SEQ ID NO: 670          moltype = DNA  length = 28
FEATURE                 Location/Qualifiers
misc_feature            1..28
                        note = T7 Promoter
source                  1..28
                        mol_type = other DNA
                        organism = synthetic construct
SEQUENCE: 670
gaatttaata cgactcacta tagggaga                                      28

SEQ ID NO: 671          moltype = DNA  length = 19
FEATURE                 Location/Qualifiers
misc_feature            1..19
                        note = T7 consensus -10 and rest
source                  1..19
                        mol_type = other DNA
                        organism = synthetic construct
SEQUENCE: 671
taatacgact cactatagg                                                19

SEQ ID NO: 672          moltype = DNA  length = 30
FEATURE                 Location/Qualifiers
misc_feature            1..30
                        note = overlapping T7 promoter
source                  1..30
                        mol_type = other DNA
```

```
                        organism = synthetic construct
SEQUENCE: 672
gagtcgtatt aatacgactc actataggg                                      30

SEQ ID NO: 673          moltype = DNA  length = 30
FEATURE                 Location/Qualifiers
misc_feature            1..30
                        note = more overlapping T7 promoter
source                  1..30
                        mol_type = other DNA
                        organism = synthetic construct
SEQUENCE: 673
agtgagtcgt actacgactc actataggg                                      30

SEQ ID NO: 674          moltype = DNA  length = 30
FEATURE                 Location/Qualifiers
misc_feature            1..30
                        note = weaken overlapping T7 promoter
source                  1..30
                        mol_type = other DNA
                        organism = synthetic construct
SEQUENCE: 674
gagtcgtatt aatacgactc tctataggg                                      30

SEQ ID NO: 675          moltype = DNA  length = 23
FEATURE                 Location/Qualifiers
misc_feature            1..23
                        note = T7 Consensus Promoter Sequence
source                  1..23
                        mol_type = other DNA
                        organism = synthetic construct
SEQUENCE: 675
taatacgact cactataggg aga                                            23

SEQ ID NO: 676          moltype = DNA  length = 23
FEATURE                 Location/Qualifiers
misc_feature            1..23
                        note = T7 RNAP promoter
source                  1..23
                        mol_type = other DNA
                        organism = synthetic construct
SEQUENCE: 676
ttatacgact cactataggg aga                                            23

SEQ ID NO: 677          moltype = DNA  length = 23
FEATURE                 Location/Qualifiers
misc_feature            1..23
                        note = T7 RNAP promoter
source                  1..23
                        mol_type = other DNA
                        organism = synthetic construct
SEQUENCE: 677
gaatacgact cactataggg aga                                            23

SEQ ID NO: 678          moltype = DNA  length = 23
FEATURE                 Location/Qualifiers
misc_feature            1..23
                        note = T7 RNAP promoter
source                  1..23
                        mol_type = other DNA
                        organism = synthetic construct
SEQUENCE: 678
taatacgtct cactataggg aga                                            23

SEQ ID NO: 679          moltype = DNA  length = 23
FEATURE                 Location/Qualifiers
misc_feature            1..23
                        note = T7 RNAP promoter
source                  1..23
                        mol_type = other DNA
                        organism = synthetic construct
SEQUENCE: 679
tcatacgact cactataggg aga                                            23

SEQ ID NO: 680          moltype = DNA  length = 30
FEATURE                 Location/Qualifiers
misc_feature            1..30
                        note = T7 strong promoter
source                  1..30
```

```
                        mol_type = other DNA
                        organism = synthetic construct
SEQUENCE: 680
taatacgact cactataggg agaccacaac                                     30

SEQ ID NO: 681          moltype = DNA   length = 30
FEATURE                 Location/Qualifiers
misc_feature            1..30
                        note = T7 weak binding and processivity
source                  1..30
                        mol_type = other DNA
                        organism = synthetic construct
SEQUENCE: 681
taattgaact cactaaaggg agaccacagc                                     30

SEQ ID NO: 682          moltype = DNA   length = 30
FEATURE                 Location/Qualifiers
misc_feature            1..30
                        note = T7 weak binding promoter
source                  1..30
                        mol_type = other DNA
                        organism = synthetic construct
SEQUENCE: 682
cgaagtaata cgactcacta ttagggaaga                                     30

SEQ ID NO: 683          moltype = DNA   length = 30
FEATURE                 Location/Qualifiers
misc_feature            1..30
                        note = pCyc (Medium) Promoter
source                  1..30
                        mol_type = other DNA
                        organism = synthetic construct
SEQUENCE: 683
acaaacacaa atacacacac taaattaata                                     30

SEQ ID NO: 684          moltype = DNA   length = 30
FEATURE                 Location/Qualifiers
misc_feature            1..30
                        note = pAdh (Strong) Promoter
source                  1..30
                        mol_type = other DNA
                        organism = synthetic construct
SEQUENCE: 684
ccaagcatac aatcaactat ctcatataca                                     30

SEQ ID NO: 685          moltype = DNA   length = 30
FEATURE                 Location/Qualifiers
misc_feature            1..30
                        note = pSte5 (Weak) Promoter
source                  1..30
                        mol_type = other DNA
                        organism = synthetic construct
SEQUENCE: 685
gatacaggat acagcggaaa caacttttaa                                     30

SEQ ID NO: 686          moltype = DNA   length = 30
FEATURE                 Location/Qualifiers
misc_feature            1..30
                        note = yeast ADH1 promoter
source                  1..30
                        mol_type = other DNA
                        organism = synthetic construct
SEQUENCE: 686
tttcaagcta taccaagcat acaatcaact                                     30

SEQ ID NO: 687          moltype = DNA   length = 30
FEATURE                 Location/Qualifiers
misc_feature            1..30
                        note = cyc100 minimal promoter
source                  1..30
                        mol_type = other DNA
                        organism = synthetic construct
SEQUENCE: 687
cctttgcagc ataaattact atacttctat                                     30

SEQ ID NO: 688          moltype = DNA   length = 30
FEATURE                 Location/Qualifiers
misc_feature            1..30
                        note = cyc70 minimal promoter
```

```
source                  1..30
                        mol_type = other DNA
                        organism = synthetic construct
SEQUENCE: 688
cctttgcagc ataaattact atacttctat                                   30

SEQ ID NO: 689          moltype = DNA   length = 30
FEATURE                 Location/Qualifiers
misc_feature            1..30
                        note = cyc43 minimal promoter
source                  1..30
                        mol_type = other DNA
                        organism = synthetic construct
SEQUENCE: 689
cctttgcagc ataaattact atacttctat                                   30

SEQ ID NO: 690          moltype = DNA   length = 30
FEATURE                 Location/Qualifiers
misc_feature            1..30
                        note = cyc28 minimal promoter
source                  1..30
                        mol_type = other DNA
                        organism = synthetic construct
SEQUENCE: 690
cctttgcagc ataaattact atacttctat                                   30

SEQ ID NO: 691          moltype = DNA   length = 30
FEATURE                 Location/Qualifiers
misc_feature            1..30
                        note = cyc16 minimal promoter
source                  1..30
                        mol_type = other DNA
                        organism = synthetic construct
SEQUENCE: 691
cctttgcagc ataaattact atacttctat                                   30

SEQ ID NO: 692          moltype = DNA   length = 30
FEATURE                 Location/Qualifiers
misc_feature            1..30
                        note = pPGK1
source                  1..30
                        mol_type = other DNA
                        organism = synthetic construct
SEQUENCE: 692
ttatctactt tttacaacaa atataaaaca                                   30

SEQ ID NO: 693          moltype = DNA   length = 30
FEATURE                 Location/Qualifiers
misc_feature            1..30
                        note = pCYC Yeast Promoter
source                  1..30
                        mol_type = other DNA
                        organism = synthetic construct
SEQUENCE: 693
acaaacacaa atacacacac taaattaata                                   30

SEQ ID NO: 694          moltype = DNA   length = 30
FEATURE                 Location/Qualifiers
misc_feature            1..30
                        note = Yeast GPD (TDH3) Promoter
source                  1..30
                        mol_type = other DNA
                        organism = synthetic construct
SEQUENCE: 694
gtttcgaata aacacacata aacaaacaaa                                   30

SEQ ID NO: 695          moltype = DNA   length = 30
FEATURE                 Location/Qualifiers
misc_feature            1..30
                        note = yeast mid-length ADH1 promoter
source                  1..30
                        mol_type = other DNA
                        organism = synthetic construct
SEQUENCE: 695
ccaagcatac aatcaactat ctcatataca                                   30

SEQ ID NO: 696          moltype = DNA   length = 30
FEATURE                 Location/Qualifiers
misc_feature            1..30
```

```
                        note = Yeast CLB1 promoter region, G2/M cell cyclespecific
source                  1..30
                        mol_type = other DNA
                        organism = synthetic construct
SEQUENCE: 696
accatcaaag gaagctttaa tcttctcata                                           30

SEQ ID NO: 697          moltype = DNA  length = 30
FEATURE                 Location/Qualifiers
misc_feature            1..30
                        note = CMV promoter
source                  1..30
                        mol_type = other DNA
                        organism = synthetic construct
SEQUENCE: 697
agaacccact gcttactggc ttatcgaaat                                           30

SEQ ID NO: 698          moltype = DNA  length = 30
FEATURE                 Location/Qualifiers
misc_feature            1..30
                        note = Ubc Promoter
source                  1..30
                        mol_type = other DNA
                        organism = synthetic construct
SEQUENCE: 698
ggccgttttt ggctttttg ttagacgaag                                            30
```

CONTROLLED GROWTH OF MICROORGANISMS

RELATED APPLICATIONS

This Application is a continuation of U.S. application Ser. No. 16/227,371, filed Dec. 20, 2018, which is a continuation of U.S. application Ser. No. 15/087,706, filed Mar. 31, 2016, issued Jan. 19, 2019 as U.S. Pat. No. 10,188,114, which is a divisional of U.S. application Ser. No. 14/459,810, filed Aug. 14, 2014, issued May 10, 2016 as U.S. Pat. No. 9,333,227, which claims the benefit of U.S. Provisional Application No. 61/867,510, filed on Aug. 19, 2013, each of which is hereby incorporated by reference in its entirety.

REFERENCE TO SEQUENCE LISTING

The present application is being filed along with a Sequence Listing in electronic format. The Sequence Listing is provided as a file entitled SYNG001C2_SEQLIST.xml, created and last saved on Aug. 24, 2022, which is 798,899 bytes in size, which is replaced by a file entitled SYNG001C2_SUBST_SEQLIST.xml, created on Dec. 19, 2022, which is 811,739 bytes in size. The information in the electronic format of the Sequence Listing is incorporated herein by reference in its entirety.

BACKGROUND

Humans have used microbial organisms to generate products since the beginning of human history, for example in processing foods such as cheese, beer, and wine. During the centuries, microbial organism-mediated processes have been studied and scaled-up, often by controlling fermentation conditions or identification of phenotypic characteristics of microbial organisms.

Presently, many products are produced using a process that involves microbial organisms. In laboratories, and in some pharmaceutical manufacturing processes, microbial organisms, including genetically engineered microbial organisms, can be cultured in sterile, controlled environments. On the other hand, feedstocks used for various industrial processes involving microorganisms are not sterile, and may contain a variety of strains and species of microorganisms. As such, genetically engineered microorganisms for laboratory and pharmaceutical processes are not necessarily suited for processes, such as industrial processes, which involve using feedstocks or which are exposed to other microorganisms in the environment which could potentially contaminate the culture and which may also involve, changing environmental conditions. Herein microorganisms which have been engineered to control their own growth and the growth of other microorganisms and/or to respond to changes in their environment are described. Such microorganisms are suitable for growth in non-sterile, less rigidly controlled feedstocks. Such microorganisms can be useful for robust, consistent production of a desired product across a range of different feedstocks and environments.

Field

Embodiments herein relate generally to the control of growth of microorganisms. More particularly, some embodiments herein relate to microorganisms engineered for regulated growth in response to other microorganisms and/or conditions of the culture environment, and methods of making and using such engineered microorganisms.

SUMMARY

One embodiment disclosed herein includes a first microbial cell comprising a nucleic acid encoding a secreted bacteriocin which controls the growth of a second microbial cell and a nucleic acid which confers resistance to the secreted bacteriocin is provided, in which the first microbial cell has been genetically engineered to allow the expression or activity of the nucleic acid which confers resistance to the bacteriocin to be regulated. According to some aspects of this embodiment, the expression or activity of the nucleic acid which confers resistance to the bacteriocin is reduced to a level which causes the first microbial cell to be neutralized by the bacteriocin if the first microbial cell is released from a desired growth environment. According to some aspects of this embodiment, the first microbial cell has been genetically engineered to make a desired product. According to some aspects of this embodiment, the secreted bacteriocin further has been selected to maintain at least one condition within a culture in which the first microbial cell is producing the desired product. According to some aspects of this embodiment, the culture comprises at least one invading microbial organism. According to some aspects of this embodiment, the at least one condition of the culture comprises controlling the growth of the second microbial cell, wherein the second microbial cell is a common contaminate of the culture. According to some aspects of this embodiment, the second microbial cell is a different strain, species or genus than the first microbial cell. According to some aspects of this embodiment, the microbial cell further comprises a nucleic acid encoding a second secreted bacteriocin which controls the growth of a third microbial cell and a nucleic acid which confers resistance to the secreted second bacteriocin, and also the first microbial cell has been genetically engineered to allow the expression or activity of the nucleic acid which confers resistance to the bacteriocin to be regulated. According to some aspects of this embodiment, the bacteriocin kills the second microbial cell. According to some aspects of this embodiment, the bacteriocin reduces the growth rate of the second microbial cell. According to some aspects of this embodiment, the bacteriocin arrests the growth of the second microbial cell. According to some aspects of this embodiment, the transcription of the nucleic acid conferring resistance to the bacteriocin is under the control of a regulatable promoter. According to some aspects of this embodiment, the activity of a polypeptide encoded by the nucleic acid conferring resistance to the bacteriocin is regulatable. According to some aspects of this embodiment, the nucleic acid encoding the bacteriocin is on a chromosome of the microbial cell. According to some aspects of this embodiment, the nucleic acid conferring resistance to the bacteriocin is on a plasmid. According to some aspects of this embodiment, the nucleic acid encoding the bacteriocin is on a chromosome of the microbial cell, and the nucleic acid conferring resistance to the bacteriocin is on a plasmid. According to some aspects of this embodiment, the nucleic acid encoding the bacteriocin and the nucleic acid conferring resistance to the bacteriocin are on one or more plasmids. According to some aspects of this embodiment, the first microbial cell is selected from the group consisting of bacteria, yeast, and algae, for example photosynthetic microalgae.

Another embodiment disclosed herein includes a method of controlling the growth of a second microbial cell in a culture medium, in which the method includes comprising culturing a first microbial cell as described herein in a culture medium comprising the second microbial cell under conditions in which the first microbial cell produces a bacteriocin at a level sufficient to control the growth of the second microbial cell. According to some aspects of this embodiment, the culture is maintained continually for at least 30 days, for example at least 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or 500 days. According to some aspects of this embodiment, the method further includes detecting at least one change in the culture medium, the change comprising a presence or increase in the levels or activity of a third microbial cell, and reengineering the first microbial cell in response to the change to produce a second bacteriocin at a level sufficient to control the growth of the third microbial cell.

Another embodiment disclosed herein includes a method of detecting a presence, absence, or amount of a molecule in a culture is provided. The method can comprise culturing a first genetically engineered microbial cell comprising a bacteriocin under the control of a genetically regulatable promoter, such that the regulatable promoter is regulated by the molecule so that either (a) the regulatable promoter drives transcription in the presence of the molecule, but not in the absence of the molecule; or (b) the regulatable promoter drives transcription in the absence of the molecule, but not in the presence of the molecule. The method can comprise isolating an amount of genomic nucleic acid of the first microbial cell from the culture. The method can comprise detecting from the amount of genomic nucleic acid, a presence, absence, or quantity of a nucleic acid sequence characteristic of the first microbial cell. According to some aspects of this embodiment, the method further includes comparing the quantity of the nucleic acid sequence characteristic of the first microbial cell to a quantity of a reference nucleic acid sequence.

Another embodiment disclosed herein includes a genetically engineered vector comprising a nucleic acid conferring resistance to a bacteriocin, in which the expression or activity of the nucleic acid is configured to change in response to the presence, level or absence of a component of a feedstock. According to some aspects of this embodiment, the vector further comprises a nucleic acid encoding the bacteriocin. According to some aspects of this embodiment, the vector further comprises a nucleic acid which encodes a desired product.

Another embodiment disclosed herein includes a kit, which can includes a plurality of strains of a genetically engineered microbial organism, in which each strain has been genetically engineered to allow the expression or activity of a nucleic acid which confers resistance to a different bacteriocin to be regulated.

Another embodiment disclosed herein includes a method of identifying at least one bacteriocin which modulates the growth of at least one microbial cell in an industrial culture medium, in which the method includes contacting the industrial culture medium with a medium or composition comprising the at least one bacteriocin; and determining whether the at least one bacteriocin has a desired effect on the growth of the at least one microbial cell. According to some aspects of this embodiment, the method includes contacting the industrial culture medium with at least one bacteriocin produced by a first microbial cell as described herein. According to some aspects of this embodiment, the at least one bacteriocin produced by the first microbial cell is in a supernatant obtained from a culture comprising the first microbial cell. According to some aspects of this embodiment, the method further includes constructing a genetically engineered microbial cell to produce at least one bacteriocin which has been determined to have a desired effect on the growth of the at least one microbial cell. According to some aspects of this embodiment, the at least one microbial cell is an organism which is a common invader of the industrial culture medium. According to some aspects of this embodiment, the at least one microbial cell is an organism which has newly invaded an existing industrial culture.

Another embodiment disclosed herein includes a system for neutralizing undesired microbial organisms in a culture medium. The system can comprise a first environment comprising a culture medium, and a second environment comprising a second microbial organism that secretes two or more different bacteriocins, in which the second microbial organism comprises immunity modulators for each of the two or more different bacteriocins, in which the second environment is in fluid communication with the first environment, in which the second environment is physically separated from the first environment so that the second microbial organism cannot move from the second environment to the first environment, and in which the secreted two or more different bacteriocins enter the culture medium of the first environment. According to some aspects of this embodiment, the system further comprises a first microbial organism in the the culture medium, in which the first microbial organism does not secrete the two or more different bacteriocins, and in which the first microbial organism is not neutralized by any of the two or more different bacteriocins. According to some aspects of this embodiment, the first microbial organism is non-GMO. According to some aspects of this embodiment, the first microbial organism ferments a component of the culture medium. According to some aspects of this embodiment, the first microbial organism decontaminates the culture medium. According to some aspects of this embodiment, the first microbial organism conducts photosynthesis, and the photosynthesis comprises a substrate comprised by the culture medium. According to some aspects of this embodiment, the second environment is separated from the first environment by at least one of a membrane, a mesh, a filter, or a valve that is permeable to the two or more different bacteriocins, but is not permeable to the second microbial organisms. According to some aspects of this embodiment, the second microbial organism secretes at least 3 bacteriocins, for example at least 3, 4, 5, 6, 7, 8, 9, 10, 11, 12, 13, 14, 15, 16, 17, 18, 19, or 20 bacteriocins. According to some aspects of this embodiment, the second environment comprises at least a third microbial organism that is different from the second microbial organism, and also secretes bacteriocins. According to some aspects of this embodiment, the third microbial organism secretes at least 2 bacteriocins, for example at least 2, 3, 4, 5, 6, 7, 8, 9, 10, 11, 12, 13, 14, 15, 16, 17, 18, 19, or 20 bacteriocins.Another embodiment disclosed herein includes a method of storing a feedstock. The method can comprise providing a feedstock, providing a first microbial organism, in which the first microbial organism secretes two or more different bacteriocins, contacting the feedstock with the bacteriocins, and storing the feedstock for a desired period of time. According to some aspects of this embodiment, contacting the feedstock with the bacteriocins comprises contacting the feedstock with the microbial organism. According to some aspects of this embodiment, contacting the feedstock with the bacteriocins comprises placing the microbial organism in fluid communication with the feedstock, while maintaining physical separation between the microbial organism and the feedstock, so that the bacteriocins contact the feedstock, but the microbial organism does not directly contact the feedstock. According to some aspects of this embodiment, the separation is maintained by at least one or more of a membrane, a mesh, a filter, or a valve that is permeable to the two or more different bacteriocins, but is not permeable to the first microbial organism.

According to some aspects of this embodiment, the method further comprises fermenting the feedstock with a second microbial organism prior to or concurrently with contacting the feedstock with the bacteriocins. According to some aspects of this embodiment, the fermentation comprises at least one of producing a desired component in the feedstock or removing an undesired component from the feedstock. According to some aspects of this embodiment, the desired period of time comprises at least one month, for example at least one, two, three, four, five, six, seven, eight, nine, ten, eleven, or twelve months. According to some aspects of this embodiment, the desired period of time comprises at least six months, for example six, seven, eight nine, ten, eleven, or twelve months. According to some aspects of this embodiment, the first microbial organism secretes at least 3 bacteriocins, for example at least 3, 4, 5, 6, 7, 8, 9, 10, 11, 12, 13, 14, 15, 16, 17, 18, 19, or 20 bacteriocins.

DETAILED DESCRIPTION

Figure 1:
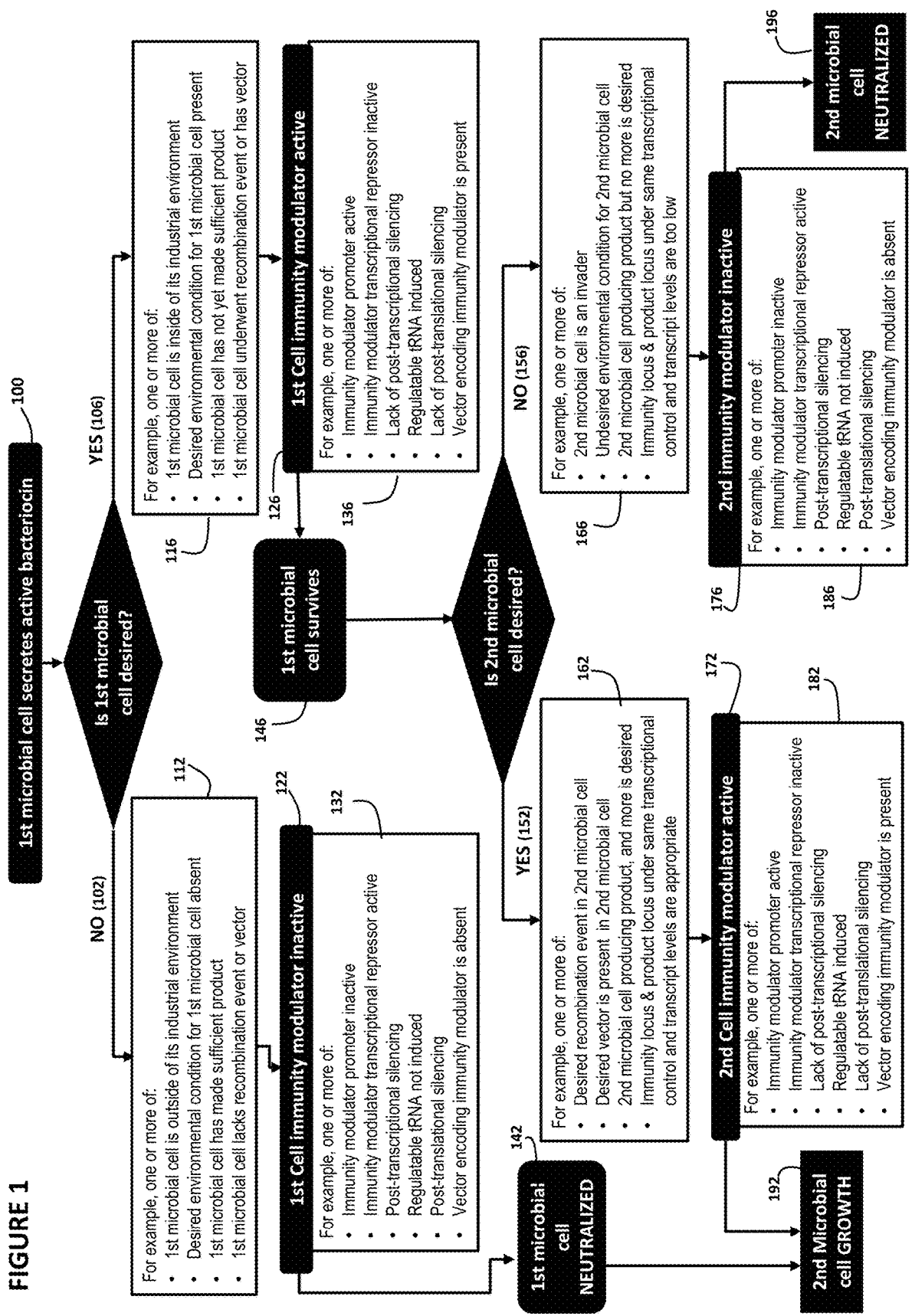
FIG. 1 is a flow diagram depicting options for configuring a microbial cell to control the growth of a second microbial cell according to some of the embodiments herein.

According to some of the embodiments herein, genetically engineered microbial organisms are provided. In some embodiments, the microbial organisms are engineered to control the growth of the microbial population in an environment such as those employing a feedstock. As used herein, "neutralizing" activity (and variations of the same root word) of bacteriocins can refer to either arrest of microbial reproduction, or cytotoxicity. Microbial organisms can be engineered to produce bacteriocins, which are secreted polypeptides that can neutralize microorganisms. However, microbial organisms that produce bacteriocin immunity modulators can resist certain bacteriocins. Thus, in some embodiments, a first microbial organism is engineered to secrete bacteriocins. In some embodiments, the particular bacteriocins are selected based on the type of microbial cell, the types of microbial cells being regulated, the composition of the culture medium, or geographic location (for example, to target particular contaminating microbial organisms associated with a particular type of culture medium and/or geographical location). Other microbial organisms that possess desired characteristics for a particular environment can produce bacteriocin immunity modulators (and thus survive in the presence of bacteriocins), while undesired other microbial organisms (for example contaminants, microbial organisms that have lost a desired characteristic or organisms which are involved in an industrial process but whose growth or production of a particular product is not desired under the prevailing conditions) fail to produce bacteriocin immunity modulators, and are thus neutralized by the bacteriocins.

Microbial Organisms

According to some aspects, genetically engineered microorganisms are provided. As used herein, genetically engineered "microbial organism," "microorganism," and variations of these root terms (such as pluralizations and the like), encompasses genetic modification of any naturally-occurring species or fully synthetic prokaryotic or eukaryotic unicellular organism, as well as Archae species. Thus, this expression can refer to cells of bacterial species, fungal species, and algae.

Exemplary microorganisms that can be used in accordance with embodiments herein include, but are not limited to, bacteria, yeast, and algae, for example photosynthetic microalgae. Furthermore, fully synthetic microorganism genomes can be synthesized and transplanted into single microbial cells, to produce synthetic microorganisms capable of continuous self-replication (see Gibson et al. (2010), "Creation of a Bacterial Cell Controlled by a Chemically Synthesized Genome," Science 329: 52-56, hereby incorporated by reference in its entirety). As such, in some embodiments, the microorganism is fully synthetic. A desired combination of genetic elements, including elements that regulate gene expression, and elements encoding gene products (for example bacteriocins, immunity modulators, poison, antidote, and industrially useful molecules) can be assembled on a desired chassis into a partially or fully synthetic microorganism. Description of genetically engineered microbial organisms for industrial applications can also be found in Wright, et al. (2013) "Building-in biosafety for synthetic biology" *Microbiology* 159: 1221-1235.

A variety of bacterial species and strains can be used in accordance with embodiments herein, and genetically modified variants, or synthetic bacteria based on a "chassis" of a known species can be provided. Exemplary bacteria with industrially applicable characteristics, which can be used in accordance with embodiments herein include, but are not limited to, *Bacillus* species (for example *Bacillus coagulans, Bacillus subtilis*, and *Bacillus licheniformis*), *Paenibacillus* species, *Streptomyces* species, *Micrococcus* species, *Corynebacterium* species, *Acetobacter* species, *Cyanobacteria* species, *Salmonella* species, *Rhodococcus* species, *Pseudomonas* species, *Lactobacillus* species, *Enterococcus* species, *Alcaligenes* species, *Klebsiella* species, *Paenibacillus* species, *Arthrobacter* species, *Corynebacterium* species, *Brevibacterium* species, *Thermus aquaticus, Pseudomonas stutzeri, Clostridium thermocellus*, and *Escherichia coli*.

A variety of yeast species and strains can be used in accordance with embodiments herein, and genetically modified variants, or synthetic yeast based on a "chassis" of a known species can be provided. Exemplary yeast with industrially applicable characteristics, which can be used in accordance with embodiments herein include, but are not limited to *Saccharomyces* species (for example, *Saccharomyces cerevisiae, Saccharomyces bayanus, Saccharomyces boulardii*), *Candida* species (for example, *Candida utilis, Candida krusei*), *Schizosaccharomyces* species (for example *Schizosaccharomyces pombe, Schizosaccharomyces japonicas*), *Pichia* or *Hansenula* species (for example, *Pichia pastoris* or *Hansenula polymorpha*) species, and *Brettanomyces* species (for example, *Brettanomyces claussenii*).

A variety of algae species and strains can be used in accordance with embodiments herein, and genetically modified variants, or synthetic algae based on a "chassis" of a known species can be created. In some embodiments, the algae comprises photosynthetic microalgae. Exemplary algae species that can be useful for biofuels, and can be used in accordance with embodiments herein, include *Botryococcus braunii, Chlorella* species, *Dunahella tertiolecta, Gracilaria* species, *Pleurochrysis carterae*, and *Sargassum* species. Additionally, many algaes can be useful for food products, fertilizer products, waste neutralization, environmental remediation, and carbohydrate manufacturing (for example, biofuels).

Bacteriocins

As used herein, "bacteriocin," and variations of this root term, refers to a polypeptide that is secreted by a host cell and can neutralize at least one cell other than the individual host cell in which the polypeptide is made, including cells clonally related to the host cell and other microbial cells. As used herein, "bacteriocin" also encompasses a cell-free or chemically synthesized version of such a polypeptide. A cell that expresses a particular "immunity modulator" (discussed in more detail herein) is immune to the neutralizing effects of a particular bacteriocin or group of bacteriocins. As such, bacteriocins can neutralize a cell producing the bacteriocin and/or other microbial cells, so long as these cells do not produce an appropriate immunity modulator. As such, a host cell can exert cytotoxic or growth-inhibiting effects on a plurality of other microbial organisms by secreting bacteriocins. In some embodiments, a bacteriocin is produced by the translational machinery (e.g. a ribosome, etc.) of a microbial cell. In some embodiments, a bacteriocin is chemically synthesized. Some bacteriocins can be derived from a polypeptide precursor. The polypeptide precursor can undergo cleavage (for example processing by a protease) to yield the polypeptide of the bacteriocin itself. As such, in some embodiments, a bacteriocin is produced from a precursor polypeptide. In some embodiments, a bacteriocin comprises a polypeptide that has undergone post-translational modifications, for example cleavage, or the addition of one or more functional groups.

"Antibiotic," and variations of this root term, refers to a metabolite, or an intermediate of a metabolic pathway which can kill or arrest the growth of at least one microbial cell. Some antibiotics can be produced by microbial cells, for example bacteria. Some antibiotics can be synthesized chemically. It is understood that bacteriocins are distinct from antibiotics, at least in that bacteriocins refer to gene products (which, in some embodiments, undergo additional post-translational processing) or synthetic analogs of the same, while antibiotics refer to intermediates or products of metabolic pathways or synthetic analogs of the same.

Neutralizing activity of bacteriocins can include arrest of microbial reproduction, or cytotoxicity. Some bacteriocins have cytotoxic activity (e.g. "bacteriocide" effects), and thus can kill microbial organisms, for example bacteria, yeast, algae, synthetic micoorganisms, and the like. Some bacteriocins can inhibit the reproduction of microbial organisms (e.g. "bacteriostatic" effects), for example bacteria, yeast, algae, synthetic micoorganisms, and the like, for example by arresting the cell cycle.

It is noted that non-bacteriocin approaches have been proposed to target various microbial organisms. For example, KAMORAN™ chemical has been proposed to target Lactic Acid Bacteria (LAB) family bacteria (see Union Nationale des Groupements de Distillateurs D'Alcool, (2005) "Kamoran"). It is noted that phage has also been proposed to target LAB family bacteria (see U.S. Pub. No. 2010/0330041). It is noted that pesticides have been proposed to target various contaminating microbial organsims (see McBride et al., "Contamination Management in Low Cost Open Algae Ponds for Biofuels Production" Industrial Biotechnology 10: 221-227 (2014)). However, bacteriocins can provide numerous advantages over chemicals, pesticides, or phages. For example, bacteriocins can avoid potentially toxic runoff or byproduct in a feedstock. For example, bacteriocins can have higher efficacy against particular undesired microbial organisms than phages, chemicals, or pesticides. For example, bacteriocins can be produced by microbial organisms that undergo logarithmic growth, and thus can readily be scaled-up or scaled down, whereas the scalability of phages or chemical/pesticide systems can be more limited. For example, bacteriocins can allow for precise control over which organsims are neutralized and which are not, for example to avoid neutralization of industrially useful microbial organisms in the culture medium. For example, phages can be difficult to produce at an industrial scale, and also can be difficult to control, in that phages can be infectious, can raise questions of gene control, and in that conservation of phages can be difficult. On the other hand, bacteriocins in accordance with some embodiments herein can comprise part of an industrial process and thus can be involved in gene containment and/or control a fermentation process via bacteriostatic activity. Additionally, the susceptibility of the microbial organisms involved in the industrial process can be tuned via immunity control. Additionally, bacteriocins typically have a low level of toxicity for industrial applications such as human or animal food, and it is contemplated that bacteriocins in accordance with some embodiments herein are suitable for use as a food preservative, such as an additive.

In some embodiments, a particular neutralizing activity (e.g. cytoxicity or arrest of microbial reproduction) is selected based on the type of microbial regulation that is desired. As such in some embodiments, microbial cells are engineered to express particular bacteriocins or combination of bacteriocins. For example, in some embodiments, microbial cells are engineered to express particular bacteriocins based on the cells being regulated. In some embodiments, for example if contaminating cells are to be killed at least one cytotoxic bacteriocin is provided. In some embodiments, a bacteriocin or combination of bacteriocins which is effective against contaminants which commonly occur in a particular culture, or a particular geographic location, or a particular type of culture grown in a particular geographic location are selected. In some embodiments, for example embodiments in which reversible regulation of microbial cell ratios is desired, a bacteriocin that inhibits microbial reproduction is provided. Without being limited by any particular theory, many bacteriocins can have neutralizing activity against microbial organisms that typically occupy the same ecological niche as the species that produces the bacteriocin. As such, in some embodiments, when a particular spectrum of bacteriocin activity is desired, a bacteriocin is selected from a host species that occupies the same (or similar) ecological niche as the microbial organism or organisms targeted by the bacteriocin.

In some embodiments, one or more bacteriocin activities are selected in advance of culture growth, and one or more microbial organisms are engineered to generate a desired culture environment. In some embodiments, bacteriocins may be selected based on their ability to neutralize one or more invading organisms which are likely to attempt to grow in a particular culture. In another embodiment, in an industrial environment in which strain A makes intermediate A, and strain B converts intermediate A into intermediate B, strains A and B can be engineered so that an abundance of intermediate A shifts the equilibrium to favor strain B by generating a bacteriocin activity profile such that growth of strain A is inhibited or prevented under these conditions, while a lack of intermediate A shifts the equilibrium to favor strain A by generating a bacteriocin activity profile such that growth of strain B is inhibited or prevented. In some embodiments, one or more bacteriocin activities are selected based on one or more conditions of an existing culture environment. For example, if particular invaders are identified in a culture environment, "neutralizer" microrganisms can be engineered to produce bacteriocins to neutralize the identified invaders. In some embodiments, genetically engineered cells that produce bacteriocins are added to an existing culture to re-equilibrate the culture, for example if a growth of a particular microbial cell type in the microbial cell culture is too high. In some embodiments, genetically engineered cells that produce bacteriocins are added to an existing culture to neutralize all or substantially all of the microbial cells in a culture, for example to eliminate an industrial culture in a culture environment so that a new industrial culture can be introduced to the culture environment.

For example, in some embodiments, an anti-fungal activity (such as anti-yeast activity) is desired. A number of bacteriocins with anti-fungal activity have been identified. For example, bacteriocins from *Bacillus* have been shown to have neutralizing activity against yeast strains (see Adetunji and Olaoye (2013) Malaysian Journal of Microbiology 9: 130-13, hereby incorporated by reference in its entirety), an *Enterococcus faecalis* peptide (WLPPAGLL-GRCGRWFRPWLLWLQ SGAQY KWLGNLFGLGPK, SEQ ID NO: 1) has been shown to have neutralizing activity against *Candida* species (see Shekh and Roy (2012) BMC Microbiology 12: 132, hereby incorporated by reference in its entirety), and bacteriocins from *Pseudomonas* have been shown to have neutralizing activity against fungi such as *Curvularia lunata, Fusarium* species, *Helminthosporium* species, and *Biopolaris* species (Shalani and Srivastava (2008) The Internet Journal of Microbiology. Volume 5 Number 2. DOI: 10.5580/27dd—accessible on the worldwide web at archive.ispub.comjournal/the-internet-journal-of-microbiology/volume-5-number-2/screening-for-antifungal-activity-of-pseudomonas-fluorescens-against-phytopathogenic-fungi.html#sthash.d0Ys03UO.1DKuT1US.dpuf, hereby incorporated by reference in its entirety). By way of example, botrycidin AJ1316 (see Zuber, P et al. (1993) Peptide Antibiotics. In *Bacillus subtilis* and Other Gram-Positive Bacteria: Biochemistry, Physiology, and Molecular Genetics ed Sonenshein et al., pp. 897-916, American Society for Microbiology, hereby incorporated by reference in its entirety) and alirin B1 (see Shenin et al. (1995) Antibiot Khimioter 50: 3-7, hereby incorporated by reference in its entirety) from *B. subtilis* have been shown to have antifungal activities. As such, in some embodiments, for example embodiments in which neutralization of a fungal microbial organism is desired, a bacteriocin comprises at least one of botrycidin AJ1316 or alirin B 1.

For example, in some embodiments, bacteriocin activity in a culture of cyanobacteria is desirable. In some embodiments, bacteriocins are provided to neutralize cyanobacteria. In some embodiments, bacteriocins are provided to neutralize invading microbial organisms typically found in a cyanobacteria culture environment. Clusters of conserved bacteriocin polypeptides have been identified in a wide variety of cyanobacteria species. For example, at least 145 putative bacteriocin gene clusters have been identified in at least 43 cyanobacteria species, as reported in Wang et al. (2011), Genome Mining Demonstrates the Widespread Occurrence of Gene Clusters Encoding Bacteriocins in Cyanobacteria. PLoS ONE 6(7): e22384, hereby incorporated by reference in its entirety. Exemplary cyanobacteria bacteriocins are shown in Table 1.2, as SEQ ID NO's 420, 422, 424, 426, 428, 30, 432, 434, 436, 438, 440, 442, 444, 446, 448, and 450.

In some embodiments, the host cell itself is a microbial cell. In some embodiments, bacteriocins neutralize cells of a different species or strain from the host cell. In some embodiments, bacteriocins neutralize cells of the same species or strain as the host cell if these cells lack an appropriate immunity modulator. As bacteriocins can mediate neutralization of both host and non-host microbial organisms, the skilled artisan will readily appreciate that a bacteriocin is distinct from poison-antidote systems (described in more detail herein), which involve an endogenous mechanism by which a host microorganism can neutralize only itself. In other words, bacteriocins can neutralize cells other than the cell in which they are produced (for example, bacteriocins can be selected and/or engineered to act as an ecological niche protector), while poison molecules kill only the individual cell in which they are produced (for example, to act as suicidal systems).

A number of bacteriocins have been identified and characterized. Without being limited by any particular theory, exemplary bacteriocins can be classified as "class I" bacteriocins, which typically undergo post-translational modification, and "class II" bacteriocins, which are typically unmodified. Additionally, exemplary bacteriocins in each class can be categorized into various subgroups, as summarized in Table 1.1, which is adapted from Cotter, P.D. et al. "Bacteriocins—a viable alternative to antibiotics" *Nature Reviews Microbiology* 11: 95-105, hereby incorporated by reference in its entirety.

Without being limited by any particular theory, bacteriocins can effect neutralization of a target microbial cell in a variety of ways. For example, a bacteriocin can permeablize a cell wall, thus depolarizing the cell wall and interfering with respiration.

TABLE 1

Classification of Exemplary Bacteriocins

| Group | Distinctive feature | Examples |
|---|---|---|
| Class I (typically modified) | | |
| MccC7-C51-type bacteriocins | Is covalently attached to a carboxy-terminal aspartic acid | MccC7-C51 |
| Lasso peptides | Have a lasso structure | MccJ25 |
| Linear azole- or azoline-containing peptides | Possess heterocycles but not other modifications | MccB17 |
| Lantibiotics | Possess lanthionine bridges | Nisin, planosporicin, mersacidin, actagardine, mutacin 1140 |
| Linaridins | Have a linear structure and contain dehydrated amino acids | Cypemycin |
| Proteusins | Contain multiple hydroxylations, epimerizations and methylations | Polytheonamide A |
| Sactibiotics | Contain sulphur-a-carbon linkages | Subtilosin A, thuricin CD |
| Group | Distinctive feature | Examples |
| Patellamide-like cyanobactins | Possess heterocycles and undergo macrocyclization | Patellamide A |
| Anacyclamide-like cyanobactins | Cyclic peptides consisting of proteinogenic amino acids with prenyl attachments | Anacyclamide A10 |
| Thiopeptides | Contain a central pyridine, dihydropyridine or piperidine ring as well as heterocycles | Thiostrepton, nocathiacin 1, GE2270 A, philipimycin |
| Bottromycins | Contain macrocyclic amidine, a decarboxylated carboxy-terminal thiazole and carbon-methylated amino acids | Bottromycin A2 |
| Glycocins | Contain S-linked glycopeptides | Sublancin 168 |
| Class II (typically unmodified or cyclic) | | |
| IIa peptides (pediocin PA-1-like bacteriocins) | Possess a conserved YGNGV motif (in which N represents any amino acid) | Pediocin PA-1, enterocin CRL35, carnobacteriocin BM1 |
| IIb peptides | Two unmodified peptides are required for activity | ABP118, lactacin F |
| IIc peptides | Cyclic peptides | Enterocin AS-48 |
| IId peptides | Unmodified, linear, non-pediocin-like, single-peptide bacteriocins | MccV, MccS, epidermicin NI01, lactococcin A |
| IIe peptides | Contain a serine-rich carboxy-terminal region with a non-ribosomal siderophore-type modification | MccE492, MccM |

A number of bacteriocins can be used in accordance with embodiments herein. Exemplary bacteriocins are shown in Table 1.2. In some embodiments, at least one bacteriocin comprising a polypeptide sequence of Table 1.2 is provided. As shown in Table 1.2, some bacteriocins function as pairs of molecules. As such, it will be understood that unless explicity stated otherwise, when a functional "bacteriocin" or "providing a bacteriocin," or the like is discussed herein, functional bacteriocin pairs are included along with bacteriocins that function individually. With reference to Table 1.2, "organisms of origin" listed in parentheses indicate alternative names and/or strain information for organisms known the produce the indicated bacteriocin.

Embodiments herein also include peptides and proteins with identity to bacteriocins described in Table 1.2. The term "identity" is meant to include nucleic acid or protein sequence homology or three-dimensional homology. Several techniques exist to determine nucleic acid or polypeptide sequence homology and/or three-dimensional homology to polypeptides. These methods are routinely employed to discover the extent of identity that one sequence, domain, or model has to a target sequence, domain, or model. A vast range of functional bacteriocins can incorporate features of bacteriocins disclosed herein, thus providing for a vast degree of identity to the bacteriocins in Table 1.2. In some embodiments, a bacteriocin has at least about 50% identity, for example, at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 1.2. Percent identity may be determined using the BLAST software (Altschul, S.F., et al. (1990) "Basic local alignment search tool." J. Mol. Biol. 215:403-410, accessible on the world wide web at blast.ncbi.nlm.nih.gov) with the default parameters.

In some embodiments, a polynucleotide encoding a bacteriocin as described herein is provided. In some embodiments, the polynucleotide is comprised within an expression vector. In some embodiments, the polynucleotide or expression vector is in a microbial cell. Exemplary polynucleotide sequences encoding the polypeptides of table 1.2 are indicated in table 1.2. SEQ ID NOs: 341 to 419 (odd SEQ ID numbers) represent exemplary polynucleotides based on the reverse translation of the respective polypeptide. The skilled artisan will readily understand that more than one polynucleotide can encode a particular polypeptide. For example, the genetic code is degenerate, and moreover, codon usage can vary based on the particular organism in which the gene product is being expressed. In some embodiments, a polynucleotide encoding a bacteriocin is selected based on the codon usage of the organism expressing the bacteriocin. In some embodiments, a polynucleotide encoding a bacteriocin is codon optimized based on the particular organism expressing the bacteriocin.

While the bacteriocins in Table 1.2 are naturally-occuring, the skilled artisan will appreciate that variants of the bacteriocins of Table 1.2, naturally-occuring bacteriocins other than the bacteriocins of Table 1.2 or variants thereof, or synthetic bacteriocins can be used according to some embodiments herein. In some embodiments, such variants have enhanced or decreased levels of cytotoxic or growth inhibition activity on the same or a different microorganism or species of microorganism relative to the wild type protein. Several motifs have been recognized as characteristic of bacteriocins. For example, the motif YGXGV (SEQ ID NO: 2), wherein X is any amino acid residue, is a N-terminal consensus sequence characteristic of class IIa bacteriocins. Accordingly, in some embodiments, a synthetic bacteriocin comprises an N-terminal sequence with at least about 50% identity to SEQ ID NO: 2, for example at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2. In some embodiments, a synthetic bacteriocin comprises a N-terminal sequence comprising SEQ ID NO: 2. Additionally, some class IIb bacteriocins comprise a GxxxG motif. Without being limited by any particular theory, it is believed that the GxxxG motif can mediate association between helical proteins in the cell membrane, for example to facilitate bacterioncin-mediated neutralization through cell membrane interactions. As such, in some embodiments, the bacteriocin comprises a motif that facilitates interactions with the cell membrane. In some embodiments, the bacteriocin comprises a GxxxG motif. Optionally, the bacteriocin comprising a GxxxG motif can comprise a helical structure. In addition to structures described herein, "bacteriocin" as used herein also encompasses structures that have substantially the same effect on microbial cells as any of the bacteriocins explicitly provided herein.

It has been shown that fusion polypeptides comprising two or more bacteriocins or portions thereof can have neutralizing activity against a broader range of microbial organisms than either individual bacteriocin. For example, it has been shown that a hybrid bacteriocin, Ent35-MccV (GKYYGNGVSCNKKGC SVDWGRAIGIIGNNSAAN-LATGGAAGWKSGGGASGRDIAM AIGTLSGQFVAG-GIGAAAGGVAGGAIYDYASTHKPNPAMSP SGLGG-TIKQKPEGIP SE AWNYAAGRLCNWSPNNLSDVCL, SEQ ID NO: 3), displays antimicrobial activity against pathogenic Gram-positive and Gram-negative bacteria (Acuña et al. (2012), FEBS Open Bio, 2: 12-19). It is noted that that Ent35-MccV fusion bacteriocin comprises, from N-terminus to C-terminus, an N-terminal glycine, Enterocin CRL35, a linker comprising three glycines, and a C-terminal Microcin V. It is contemplated herein that bacteriocins can comprise fusions of two or more polypeptides having bacteriocin activity. In some embodiments, a fusion polypeptide of two or more bacteriocins is provided. In some embodiments, the two or more bacteriocins comprise polypeptides from Table 1.2, or modifications thereof. In some embodiments, the fusion polypeptide comprising of two or more bacteriocins has a broader spectrum of activity than either individual bacteriocin, for example having neutralizing activity against more microbial organisms, neutralizing activity under a broader range of environmental conditions, and/or a higher efficiency of neutralization activity. In some embodiments, a fusion of two or more bacteriocins is provided, for example two, three, four, five, six, seven, eight, nine, or ten bacteriocins. In some embodiments, two or more bacteriocin polypeptides are fused to each other via a covalent bond, for example a peptide linkage. In some embodiments, a linker is positioned between the two bacteriocin polypeptides. In some embodiments, the linker comprises one or glycines, for example about 1, 2, 3, 4, 5, 6, 7, 8, 9, 10, 11, 12, 13, 14, 15, 16, 17, 18, 19, or 20 glycines. In some embodiments, the linker is cleaved within the cell to produce the individual bacteriocins included in the fusion protein. In some embodiments, a bacteriocin as provided herein is modified to provide a desired spectrum of activity relative to the unmodified bacteriocin. For example, the modified bacteriocin may have enhanced or decreased activity agains the same organisms as the unmodified bacteriocin. Alternatively, the modified bacteriocin may have enhanced activity against an organism against which the unmodified bacteriocin has less activity or no activity.

TABLE 1.2

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 4 | Acidocin 8912 | Unclassified | MISSHQKTL TDKELALISG GKTHYPTNA WKSLWKGF WESLRYTDG F | Lactobacillus acidophilus | 5 | ATGATTTCATC TCATCAAAAA ACGTTAACTG ATAAAGAATT AGCATTAATTT CTGGGGGGAA AACGCACTAC CCGACTAATG CATGGAAAAG TCTTTGGAAA GGTTTCTGGG AAAGCCTTCG TTATACTGAC GGTTTTTAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 6 | Acidocin A | class IIA/YG NGV | MISMISSHQ KTLTDKELA LISGGKTYY GTNGVHCTK KSLWGKVRL KNVIPGTLC RKQSLPIKQ DLKILLGWA TGAFGKTFH | *Lactobacillus acidophilus* | 7 | ATGATTTCAAT GATTTCATCTC ATCAAAAAAC GTTAACTGAT AAAGAATTAG CATTAATTTCT GGGGGGAAAA CGTACTATGG TACTAATGGT GTGCATTGTA CTAAAAAGAG TCTTTGGGGT AAAGTACGCT TAAAAAACGT GATTCCTGGA ACTCTTTGTCG TAAGCAATCG TTGCCGATCA AACAGGATTT AAAAATTTTA CTGGGCTGGG CTACAGGTGC TTTTGGCAAG ACATTTCATTA A |
| 8 | Acidocin B (AcdB) | Unclassified | MDKKTKILF EVLYIICIIGP QFILFVTAKN NMYQLVGSF VGIVWFSYIF WYIFFKQHK KM | *Lactobacillus acidophilus* | 9 | ATGGATAAGA AAACAAAAAT ATTATTTGAA GTATTATACAT CATCTGTATA ATAGGCCCTC AATTTATATTA TTTGTGACTGC AAAAAACAAT ATGTATCAGT TGGTGGGTTC GTTTGTTGGA ATAGTATGGT TTTCGTATATT TTTTGGTATAT TTTTTTCAAAC AACATAAAAA AATGTAG |
| 10 | Acidocin LF221B (Gassericin K7 B) | Unclassified | MALKTLEKH ELRNVMGG NKWGNAVI GAATGATRG VSWCRGFGP WGMTACAL GGAAIGGYL GYKSN | *Lactobacillus gasseri* | 11 | ATGGCTTTAA AAACATTAGA AAAACATGAA TTAAGAAATG TAATGGGTGG AAACAAGTGG GGGAATGCTG TAATAGGAGC TGCTACGGGA GCTACTCGCG GAGTAAGTTG GTGCAGAGGA TTCGGACCAT GGGGAATGAC TGCCTGTGCG TTAGGAGGTG CTGCAATTGG AGGATATCTG GGATATAAGA GTAATTAA |
| 12 | Aureocin A53 | Unclassified | MSWLNFLK YIAKYGKKA VSAAWKYK GKVLEWLN | *Staphylococcus aureus* | 13 | ATGAGTTGGT TAAATTTTTTA AAATACATCG CTAAATATGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | VGPTLEWV WQKLKKIAG L | | | CAAAAAGCG GTATCTGCTG CTTGGAAGTA CAAAGGTAAA GTATTAGAAT GGCTTAATGT TGGTCCTACTC TTGAATGGGT ATGGCAAAAA TTAAAGAAAA TTGCTGGATT ATAA |
| 14 | Avicin A | class IIA/YG NGV | MTRSKKLNL REMKNVVG GTYYGNGVS CNKKGCSVD WGKAISIIGN NSAANLATG GAAGWKS | Enterococcus avium (Streptococcus avium) | 15 | ATGACAAGAT CAAAAAAATT AAATTTACGC GAAATGAAGA ATGTTGTTGG TGGTACCTAC TATGGAAATG GTGTATCTTGT AACAAGAAAG GCTGTTCAGTT GACTGGGGCA AAGCCATCAG TATTATAGGA AATAATTCCG CAGCAAACTT AGCAACTGGT GGTGCTGCTG GTTGGAAGTC ATAA |
| 16 | Bacteriocin 31 | Unclassified | MKKKLVICG IIGIGFTALG TNVEAATYY GNGLYCNK QKCWVDWN KASREIGKII VNGWVQHG PWAPR | Enterococcus faecalis (Streptococcus faecalis) | 17 | ATGAAAAAGA AATTAGTTATT TGTGGCATTA TTGGGATTGG TTTTACAGCAT TAGGAACAAA TGTAGAAGCT GCTACGTATT ACGGAAATGG TTTATATTGTA ATAAGCAAAA ATGTTGGGTA GACTGGAATA AAGCTTCAAG GGAAATTGGA AAAATTATTG TTAATGGTTG GGTACAACAT GGCCCTTGGG CTCCTAGATA G |
| 18 | Bacteriocin J46 | Unclassified | MKEQNSFNL LQEVTESEL DLILGAKGG SGVIHTISHE VIYNSWNFV FTCCS | Lactococcus lactis | 19 | ATGAAAGAAC AAAACTCTTTT AATCTTCTTCA AGAAGTGACA GAAAGTGAAT TGGACCTTATT TTAGGTGCAA AAGGCGGCAG TGGAGTTATT CATACAATTTC TCATGAAGTA ATATATAATA GCTGGAACTT TGTATTTACTT GCTGCTCTTA A |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 20 | Bacteriocin T8 | class IIa | MKKKVLKHCVILGILGTCLAGIGTGIKVDAATYYGNGLYCNKEKCWVDWNQAKGEIGKIIVNGWVNHGPWAPRR | Enterococcus faecium (Streptococcus faecium) | 21 | ATGAAAAGAAAGTATTAAAACATTGTGTTATTCTAGGAATATTAGGAACTTGTCTAGCTGGCATCGGTACAGGAATAAAAGTTGATGCAGCTACTTACTATGGAAATGGTCTTTATTGTAACAAAGAAAATGTTGGGTAGATTGGAATCAAGCTAAAGGAGAAATTGGAAAAATTATTGTTAATGGTTGGGTTAATCATGGTCCATGGGCACCTAGAAGGTAG |
| 22 | Boticin B | Unclassified | MQKPEIISADLGLCAVNEFVALAAIPGGAATFAVCQMPNLDEIVSNAAYV | Clostridium botulinum | 23 | ATGCAAAAACCAGAAATTATTAGTGCTGATTTAGGGCTTTGTGCAGTTAATGAATTTGTAGCTCTTGCTGCCATTCCTGGTGGTGCTGCTACATTTGCAGTATGCCAAATGCCAAACTTGGATGAGATTGTTAGTAATGCAGCATATGTTTAA |
| 24 | Bovicin HJ50 | Lantibiotic | MMNATENQIFVETVSDQELEMLIGGADRGWIKTLTKDCPNVISSICAGTIITACKNCA | Streptococcus equinus (Streptococcus bovis) | 25 | ATGATGAATGCTACTGAAAACCAAATTTTTGTTGAGACTGTGAGTGACCAAGAATTAGAAATGTTAATTGGTGGTGCAGATCGTGGATGGATTAAGACTTTAACAAAAGATTGTCCAAATGTAATTTCTTCAATTTGTGCAGGTACAATTATTACAGCTTGTAAAAATTGTGCTTAA |
| 26 | Brochocin-c | Unclassified | MHKVKKLNNQELQQIVGGYSSKDCLKDIGKGIGAGTVAGAAGGGLAAGLGAIPGAFVGAHFGVIGGSAACIGGLLGN | Brochothrix campestris | 27 | ATGCACAAGGTAAAAAAATTAAACAATCAAGAGTTACAACAGATCGTGGGAGGTTACAGTTCAAAAGATTGTCTAAAAGATATTGGTAAAGGAATTGGTG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CTGGTACAGT AGCTGGGGCA GCCGGCGGTG GCCTAGCTGC AGGATTAGGT GCTATCCCAG GAGCATTCGT TGGAGCACAT TTTGGAGTAA TCGGCGGATC TGCCGCATGC ATTGGTGGAT TATTAGGTAA CTAG |
| 28 | Butyrivibriocin AR10 | Unclassified | MSKKQIMSN CISIALLIALI PNIYFIADKM GIQLAPAWY QDIVNWVSA GGTLTTGFAI IVGVTVPAW IAEAAAAFGI ASA | Butyrivibrio fibrisolvens | 29 | ATGAGTAAAA AACAAATTAT GAGTAACTGT ATATCAATTG CATTATTAATA GCACTAATTC CTAATATCTAT TTTATTGCAG ATAAAATGGG AATTCAGTTA GCACCTGCTT GGTATCAAGA TATTGTGAATT GGGTATCTGC TGGTGGAACA CTTACTACTG GTTTTGCGATT ATTGTAGGAG TTACAGTACC GGCATGGATA GCAGAAGCAG CTGCAGCTTTT GGTATAGCTT CAGCATGA |
| 30 | Butyrivibriocin OR79 | Lantibiotic | MNKELNALT NPIDEKELEQ ILGGGNGVI KTISHECHM NTWQFIFTC CS | Butyrivibrio fibrisolvens | 31 | ATGAACAAAG AACTTAATGC ACTTACAAAT CCTATTGACG AGAAGGAGCT TGAGCAGATC CTCGGTGGTG GCAATGGTGT CATCAAGACA ATCAGCCACG AGTGCCACAT GAACACATGG CAGTTCATTTT CACATGTTGC TCTTAA |
| 32 | Carnobacteriocin B2 (Carnocin CP52) | class IIA/YG NGV | MNSVKELN VKEMKQLH GGVNYGNG VSCSKTKCS VNWGQAFQ ERYTAGINSF VSGVASGAG SIGRRP | Carnobacterium maltaromaticum (Carnobacterium piscicola) | 33 | ATGAATAGCG TAAAAGAATT AAACGTGAAA GAAATGAAAC AATTACACGG TGGAGTAAAT TATGGTAATG GTGTTTCTTGC AGTAAAACAA AATGTTCAGT TAACTGGGGA CAAGCCTTTC AAGAAAGATA CACAGCTGGA ATTAACTCATT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGTAAGTGGA GTCGCTTCTG GGGCAGGATC CATTGGTAGG AGACCGTAA |
| 34 | Carnobacteriocin BM1 (Carnobacteriocin B1) | class IIA/YG NGV | MKSVKELNK KEMQQINGG AISYGNGVY CNKEKCWV NKAENKQAI TGIVIGGWA SSLAGMGH | Carnobacterium maltaromaticum (Carnobacterium piscicola) | 35 | ATGAAAAGCG TTAAAGAACT AAATAAAAAA GAAATGCAAC AAATTAATGG TGGAGCTATC TCTTATGGCA ATGGTGTTTAT TGTAACAAAG AGAAATGTTG GGTAAACAAG GCAGAAAACA AACAAGCTAT TACTGGAATA GTTATCGGTG GATGGGCTTC TAGTTTAGCA GGAATGGGAC ATTAA |
| 36 | Carnobacteriocin-A (Piscicolin-61) | class IIc, non subgrouped bacteriocins (problematic) | MNNVKELSI KEMQQVTG GDQMSDGV NYGKGSSLS KGGAKCGL GIVGGLATIP SGPLGWLAG AAGVINSCM K | Carnobacterium maltaromaticum (Carnobacterium piscicola) | 37 | ATGAATAATG TAAAAGAGTT AAGTATTAAA GAAATGCAAC AAGTTACTGG TGGAGACCAA ATGTCAGATG GTGTAAATTA TGGAAAAGGC TCTAGCTTATC AAAAGGTGGT GCCAAATGTG GTTTAGGGAT CGTCGGCGGA TTAGCTACTAT CCCTTCAGGT CCTTTAGGCT GGTTAGCCGG AGCAGCAGGT GTAATTAATA GCTGTATGAA ATAA |
| 38 | Carnocyclin-A | Unclassified | MLYELVAY GIAQGTAEK VVSLINAGL TVGSIISILG GVTVGLSGV FTAVKAAIA KQGIKKAIQ L | Carnobacterium maltaromaticum (Carnobacterium piscicola) | 39 | ATGTTATATG AATTAGTTGC ATATGGTATC GCACAAGGTA CAGCTGAAAA GGTTGTAAGT CTAATTAACG CAGGTTTAAC AGTAGGGTCT ATTATTTCAAT TTTGGGTGGG GTCACAGTCG GTTTATCAGG TGTCTTCACA GCAGTTAAAG CAGCAATTGC TAAACAAGGA ATAAAAAAAG CAATTCAATT ATAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 40 | Carocin D | Unclassified | MIKYRLYAP NDGDTMTV SGGGGWVS NDDRKGGN DRDNGKGG SAVDFSKNP EKQAIVNPY LAIAIPMPVY PLYGKLGFTI NTTAIETELA NVRAAINTK LATLSAVIGR SLPVVGRVF GVTAAGMW PSSTAPSSLD SIYNQAHQQ ALAQLAAQQ GVLNKGYN VTAMPAGFV SSLPVSEIKS LPTAPASLLA QSVINTELSQ RQLALTQPT TNAPVANIP VVKAEKTA MPGVYSAKI IAGEPAFQIK VDNTKPALA QNPPKVKDD IQVSSFLSSP VADTHHAFI DFGSDHEPV YVSLSKIVT AEEEKKQVE EAKRREQEW LLRHPITAAE RKLTEIRQVI SFAQQLKES SVATISEKTK TVAVYQEQ VNTAAKNR DNFYNQNR GLLSAGITG GPGYPIYLA LWQTMNNF HQAYFRANN ALEQESHVL NLARSDLAK AEQLLAENN RLQVETERT LAEEKEIKR NRVNVSTFG TVQTQLSKL LSDFYAVTS LSQSVPSGA LASFSYNPQ GMIGSGKIV GKDVDVLFS IPVKDIPGYK SPINLDDLAK KNGSLDLPIR LAFSDENGE RVLRAFKAD SLRIPSSVRG VAGSYDKNT GIFSAEIDGV SSRLVLENP AFPPTGNVG NTGNTAPDY KALLNTGVD | Pectobacterium carotovorum subsp. carotovorum (Erwinia carotovora subsp. carotovora) | 41 | ATGATTAAAT ACCGTTTATAT GCTCCAAATG ATGGAGACAC CATGACAGTG AGTGGTGGTG GTGGTTGGGT TTCAAACGAT GATCGCAAAG GTGGTAATGA CAGGGACAAT GGCAAAGGTG GTTCTGCCGTT GATTTTAGTA AAAATCCAGA AAAGCAGGCT ATCGTTAATCC CTATTTGGCA ATCGCGATAC CGATGCCGGT CTACCCTCTTT ATGGAAAGCT AGGGTTCACA ATAAATACGA CGGCAATTGA GACTGAACTC GCAAATGTCA GAGCAGCAAT TAACACTAAA CTTGCAACAC TCAGTGCAGT GATTGGCAGA TCACTTCCGGT CGTTGGGCGG GTATTTGGTG TTACTGCCGC CGGAATGTGG CCTTCTAGTAC CGCTCCCAGT AGTCTCGATT CTATATACAA TCAAGCACAT CAGCAGGCTT TAGCCCAGTT AGCTGCTCAA CAGGGAGTAT TAAATAAAGG GTATAACGTT ACAGCAATGC CTGCAGGTTT CGTCAGCAGT TTGCCTGTTAG TGAAATCAAA TCATTGCCAA CAGCTCCCGC CAGTTTACTG GCACAAAGTG TGATTAATAC CGAACTTTCCC AGCGTCAACT GGCTCTTACTC AGCCCACGAC GAATGCACCA GTCGCGAATA TTCCCGTAGTT AAAGCAGAGA AAACAGCAAT GCCAGGTGTG TATTCAGCGA AAATTATTGCT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | VKPVDKITV TVTPVADPV DIDDYIIWLP TASGSGVEPI YVVFNSNPY GGTEKGKYS KRYYNPDKA GGPILELDW KNVKIDHAG VDNVKLHT GRFKASVEN KVMIERLENI LNGQITATD TDKRFYTHE LRELNRYRN LGIKDGEVP SSIQEESAV WNDTHTAT LEDYKINEK EQPLYTDAA LQAAYEQEL KDALGGKH G | | | GGTGAGCCTG CATTCCAAAT CAAGGTCGAT AATACCAAAC CTGCTTTGGC ACAGAATCCG CCGAAAGTAA AAGATGATAT TCAGGTATCTT CTTTCCTTTCC TCGCCAGTAG CTGATACGCA CCATGCATTTA TTGATTTTGGC AGCGATCATG AACCGGTATA CGTGTCTCTTT CAAAGATCGT GACAGCCGAG GAGGAGAAAA AACAGGTTGA AGAGGCCAAG CGCCGTGAGC AGGAGTGGTT GTTGCGTCAT CCAATTACAG CTGCGGAGCG AAAATTAACT GAAATCCGCC AAGTGATCTC TTTTGCTCAAC AGCTAAAAGA AAGCTCTGTC GCAACCATTT CAGAAAAAAC TAAAACTGTT GCGGTTTACC AAGAACAGGT GAATACCGCT GCAAAAAATC GCGACAATTT TTATAATCAA AATAGAGGTC TGTTAAGTGC GGGTATAACT GGGGGACCGG GATATCCTATT TATCTTGCTTT ATGGCAAACG ATGAATAACT TTCATCAGGC TTATTTCAGA GCAAATAATG CATTGGAACA AGAGAGTCAT GTTCTGAACC TGGCTCGTTCT GATCTGGCTA AGGCTGAGCA ATTGCTTGCTG AGAATAATCG ACTTCAGGTT GAAACGGAGC GAACGCTTGC CGAAGAAAA GAGATAAAAC GCAACAGGGT TAATGTATCA ACATTTGGCA CAGTGCAAAC TCAACTTAGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AAATTGCTGT CAGATTTTTAT GCTGTTACAT CACTTTCCCAA AGTGTTCCTTC GGGGGCATTA GCCTCTTTTTC ATATAATCCA CAAGGGATGA TTGGCAGCGG TAAGATTGTT GGGAAGGATG TCGATGTTTTA TTTTCCATCCC AGTAAAAGAT ATTCCGGGAT ATAAATCTCCT ATTAACTTGG ACGATTTAGC CAAGAAAAAT GGAAGTCTGG ATCTTCCCATT CGTCTGGCAT TTTCTGATGA GAATGGAGAA AGGGTTCTTC GGGCATTCAA AGCGGATAGT CTGCGAATCC CTTCGAGTGT CAGAGGTGTA GCGGGCAGTT ATGACAAAAA TACGGGTATT TTTAGTGCAG AAATTGATGG TGTTTCATCTC GCCTTGTACT GGAAAACCCA GCGTTTCCTCC GACCGGAAAT GTCGGTAATA CGGGTAATAC TGCACCTGAC TATAAAGCAT TACTGAATAC TGGTGTTGAT GTTAAACCTG TTGATAAAAT CACAGTTACG GTAACACCAG TTGCTGATCC AGTGGATATT GATGACTATA TAATCTGGTT GCCAACTGCG TCTGGTTCTG GCGTGGAACC CATTTATGTCG TGTTTAACAG TAATCCGTAT GGTGGGACGG AAAAAGGAAA ATATAGCAAA CGTTATTATAA TCCAGATAAG GCAGGCGGTC CGATCTTGGA GCTGGATTGG AAAAACGTTA AGATTGACCA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGCAGGTGTG GACAATGTTA AATTACACAC AGGGCGTTTC AAAGCGTCGG TTGAAAACAA AGTGATGATT GAACGTTTGG AAAACATACT GAATGGTCAA ATCACGGCCA CGGATACTGA CAAGCGATTC TATACGCATG AATTAAGAGA GTTAAACCGC TACAGAAATT TAGGCATCAA AGACGGTGAA GTGCCTAGTA GCATTCAAGA AGAAAGCGCT GTTTGGAACG ACACACACAC AGCGACGCTT GAAGACTACA AAATTAATGA GAAAGAGCAA CCGTTGTACA CTGATGCTGC TTTGCAGGCA GCCTACGAAC AGGAACTCAA AGACGCATTA GGAGGGAAAC ATGGCTAA |
| 42 | Cerein 7B | Unclassified | MENLQMLT EEELMEIEG GGWWNSWG KCVAGTIGG AGTGGLGGA AAGSAVPVI GTGIGGAIG GVSGGLTGA ATFC | Bacillus cereus | 43 | ATGGAAAACT TACAAATGTT AACTGAAGAA GAATTAATGG AAATTGAAGG TGGAGGCTGG TGGAATAGCT GGGGTAAATG TGTTGCTGGA ACTATCGGTG GAGCTGGAAC TGGTGGTTTA GGTGGAGCTG CTGCAGGTTC AGCTGTTCCG GTTATTGGTA CTGGTATTGG TGGCGCTATT GGT TABLE 1.2-continued Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CGGCCCTGCC CACGCCCGTC GAGGCCCAGG ACCAGGCGTC CCTTGACTTCT GGACCAAGGA CATCGCCGCC ACGGAAGCCT TCGCCTGCCG CCAGAGCTGC AGCTTCGGCC CGTTCACCTTC GTGTGCGACG GCAACACCAA GTAA |
| 46 | Circularin A | Unclassified | MSLLALVAG TLGVSQSIAT TVVSIVLTGS TLISIILGIT AILSGGVDAIL EIGWSAFVA TVKKIVAER GKAAAIAW | Geobacillus kaustophilus (strain HTA426) | 47 | ATGAGTTTGC TGGCGCTTGT TGCCGGGACG CTCGGCGTGT CACAGTCAAT CGCGACGACG GTTGTTTCGAT TGTGTTGACC GGCTCCACTC TCATTTCTATT ATTCTTGGGA TCACCGCTATT TTGTCAGGTG GAGTCGACGC CATTTTGGAA ATTGGGTGGT CAGCTTTTGTC GCGACGGTGA AAAAAATAGT GGCGGAACGA GGAAAAGCGG CAGCGATTGC ATGGTAA |
| 48 | Closticin 574 | Unclassified | MRKVFLRSII STLVMCAFV SSSFSVNAD ESKPNDEKII NNIENVTTT KDIVKSNKN NIVYLDEGV MSIPLSGRKP IAIKDDNNK EDLTVTLPIK NTGDISKISS NGTILYKNN SSNSSNIALQ PKNDGFKAL ININDKLAN KEYEFTFNL PKNSKLISAA TYLGKEYDT KEVFVVDKN NIITSIISPAW AKDANGHN VSTYYKIVS NNKLVQVV EFTENTAFP VVADPNWT KIGKCAGSIA WAIGSGLFG GAKLIKIKKY IAELGGLQK AAKLLVGAT TWEEKLHAG | Clostridium tyrobutyricum | 49 | TTGAGAAAAG TATTTTTAAGA TCAATAATTTC AACATTAGTT ATGTGTGCAT TTGTTTCAAGC AGCTTTTCAGT AAATGCGGAT GAAAGCAAAC CAAATGATGA AAAAATAATT AATAACATAG AAAACGTTAC TACTACTAAA GATATTGTAA AAAGTAATAA AAATAATATT GTATATTTAG ATGAAGGTGT AATGAGTATT CCATTGTCTG GGAGAAAACC CATTGCTATTA AAGATGATAA TAATAAAGAA GATTTAACTG TTACATTACCT ATTAAGAATA CTGGAGATAT ATCTAAAATT AGTAGTAATG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | GYALINLAA ELTGVAGIQ ANCF | | | GTACTATTCTG TATAAAAATA ATAGTAGTAA TTCATCTAATA TAGCTTTACA ACCTAAAAAT GATGGATTTA AGGCTTTAAT AAATATTAAT GATAAGTTAG CTAATAAAGA ATATGAATTT ACATTTAATTT ACCCAAAAAC AGTAAATTAA TTAGTGCTGC CACATATTTG GGTAAAGAAT ATGATACAAA AGAAGTATTT GTAGTAGACA AAAAATAATAT AATTACGAGT ATTATTAGTCC AGCTTGGGCT AAAGATGCAA ATGGACATAA TGTTTCTACTT ATTATAAGAT AGTATCGAAT AATAAATTAG TACAAGTTGT TGAATTCACA GAAAATACTG CATTCCCGGT GGTAGCTGAT CCTAATTGGA CTAAAATTGG GAAATGCGCT GGGTCAATAG CATGGGCTAT AGGTTCTGGC CTTTTTGGTGG AGCAAAGCTA ATTAAAATAA AAAAATATAT AGCAGAGCTT GGAGGACTTC AAAAAGCAGC TAAATTATTA GTTGGTGCAA CCACTTGGGA AGAAAAATTA CACGCAGGCG GTTATGCATT AATTAACTTA GCTGCTGAGC TAACAGGTGT AGCAGGTATA CAAGCAAATT GTTTTTAA |
| 50 | Coagulin A | Unclassified | MKKIEKLTE KEMANIIGG KYYGNGVT CGKHSCSVD WGKATTCII NNGAMAWA TGGHQGTH KC | Bacillus coagulans | 51 | ATGAAAAAAA TTGAAAAATT AACTGAAAAA GAAATGGCCA ATATCATTGG TGGTAAATAC TACGGTAATG GGGTTACTTG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGGCAAACAT TCCTGCTCTGT TGACTGGGGT AAGGCTACCA CCTGCATAAT CAATAATGGA GCTATGGCAT GGGCTACTGG TGGACATCAA GGTACTCATA AATGCTAG |
| 52 | Colicin-10 | Unclassified | MDKVTDNSP DVESTESTE GSFPTVGVD TGDTITATL ATGTENVGG GGGAFGGAS ESSAAIHATA KWSTAQLKK HQAEQAAR AAAAEAALA KAKSQRDAL TQRLKDIVN DALRANAAR SPSVTDLAH ANNMAMQA EAERLRLAK AEQKAREEA EAAEKALRE AERQRDEIA RQQAETAHL LAMAEAAEA EKNRQDSLD EEHRAVEVA EKKLAEAKA ELAKAESDV QSKQAIVSR VAGELENAQ KSVDVKVTG FPGWRDVQ KKLERQLQD KKNEYSSVT NALNSAVSI RDAKKTEVQ NAEIKLKEA KDALEKSQV KDSVDTMV GFYQYITEQ YGEKYSRIA QDLAEKAKG SKFNSVDEA LAAFEKYKN VLDKKFSKV DRDDIFNAL ESITYDEWA KHLEKISRAL KVTGYLSFG YDVWDGTL KGLKTGDW KPLFVTLEKS AVDFGVAKI VALMFSFIV GAPLGFWGI AIITGIVSSYI GDDELNKLN ELLGI | Escherichia coli | 53 | ATGGATAAAG TCACTGATAA TTCTCCAGAT GTGGAGAGCA CAGAATCTAC TGAGGGGTCA TTCCCAACTGT TGGGGTTGAT ACTGGCGATA CGATTACAGC GACGCTTGCA ACTGGAACTG AAAATGTTGG TGGAGGCGGT GGAGCATTTG GTGGGGCCAG TGAAAGTTCT GCTGCGATAC ATGCAACCGC TAAATGGTCT ACCGCGCAGT TGAAAAAACA TCAGGCTGAA CAGGCTGCCC GTGCTGCTGC GGCTGAGGCA GCATTGGCAA AAGCGAAATC TCAGCGTGAT GCCCTGACTC AACGTCTCAA GGATATTGTT AATGACGCTT TACGTGCTAA TGCCGCTCGT AGTCCATCAG TAACTGACCTT GCTCATGCCA ATAATATGGC AATGCAGGCA GAGGCTGAGC GTTTGCGCCTT GCGAAGGCAG AGCAAAAAGC CCGTGAAGAA GCTGAAGCAG CAGAAAAAGC GCTCCGGGAA GCAGAACGCC AACGTGATGA GATTGCCCGC CAACAGGCTG AAACCGCGCA TTTGTTAGCA ATGGCGGAGG CAGCAGAGGC TGAGAAAAAT CGACAGGATT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CTCTTGATGA AGAGCATCGG GCTGTGGAAG TGGCAGAGAA GAAGCTGGCT GAGGCTAAAG CTGAACTGGC GAAGGCCGAA AGCGATGTAC AGAGTAAGCA AGCGATTGTT TCCAGAGTTG CAGGGGAGCT TGAAAACGCT CAAAAAGTG TTGATGTGAA GGTTACCGGA TTTCCTGGATG GCGTGATGTT CAGAAAAAAC TGGAGAGACA ATTGCAGGAT AAGAAGAATG AATATTCGTC AGTGACGAAT GCTCTTAATTC TGCTGTTAGC ATTAGAGATG CTAAAAAAAC AGAAGTTCAG AATGCTGAGA TAAAATTAAA AGAAGCTAAG GATGCTCTTG AGAAGAGTCA GGTAAAAGAC TCTGTTGATAC TATGGTTGGG TTTTATCAATA TATAACCGAA CAATATGGGG AAAAATATTC CAGAATAGCT CAGGATTTAG CTGAAAAGGC GAAGGGTAGT AAATTTAATA GTGTTGATGA AGCACTTGCT GCATTTGAAA AGTATAAAAA TGTACTGGAT AAGAAATTCA GTAAGGTTGA TAGGGATGAT ATTTTTAATGC TTTAGAGTCT ATTACTTATGA TGAGTGGGCC AAGCATCTAG AAAAGATCTC TAGGGCTCTT AAGGTTACTG GATATTTGTCT TTCGGGTATG ATGTATGGGA TGGTACCCTA AAGGGATTAA AAACAGGAGA CTGGAAGCCT TTATTTGTCAC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TCTGGAGAAG AGCGCGGTAG ATTTCGGCGT GGCAAAAATT GTGGCATTAA TGTTTAGTTTT ATTGTTGGTG CGCCTCTTGG CTTCTGGGGA ATTGCAATTAT CACAGGTATT GTTTCTTCTTA CATAGGGGAT GATGAGTTGA ACAAGCTTAA TGAATTACTA GGTATTTAA |
| 54 | Colicin-E1 | Unclassified | METAVAYY KDGVPYDD KGQVIITLLN GTPDGSGSG GGGGKGGS KSESSAAIHA TAKWSTAQL KKTQAEQAA RAKAAAEAQ AKAKANRD ALTQRLKDI VNEALRHNA SRTPSATELA HANNAAMQ AEDERLRLA KAEEKARKE AEAAEKAFQ EAEQRRKEI EREKAETER QLKLAEAEE KRLAALSEE AKAVEIAQK KLSAAQSEV VKMDGEIKT LNSRLSSSIH ARDAEMKTL AGKRNELAQ ASAKYKELD ELVKKLSPR ANDPLQNRP FFEATRRRV GAGKIREEK QKQVTASET RINRINADIT QIQKAISQVS NNRNAGIAR VHEAEENLK KAQNNLLNS QIKDAVDAT VSFYQTLTE KYGEKYSK MAQELADKS KGKKIGNVN EALAAFEKY KDVLNKKFS KADRDAIFN ALASVKYDD WAKHLDQF AKYLKITGH VSFGYDVVS DILKIKDTGD WKPLFLTLE KKAADAGVS | Escherichia coli | 55 | ATGGAAACCG CGGTAGCGTA CTATAAAGAT GGTGTTCCTTA TGATGATAAG GGACAGGTAA TTATTACTCTT TTGAATGGTA CTCCTGACGG GAGTGGCTCT GGCGGCGGAG GTGGAAAAGG AGGCAGTAAA AGTGAAAGTT CTGCAGCTAT TCATGCAACT GCTAAATGGT CTACTGCTCA ATTAAAGAAA ACACAGGCAG AGCAGGCTGC CCGGGCAAAA GCTGCAGCGG AAGCACAGGC GAAAGCAAAG GCAAACAGGG ATGCGCTGAC TCAGCGCCTG AAGGATATCG TGAATGAGGC TCTTCGTCACA ATGCCTCACG TACGCCTTCA GCAACAGAGC TTGCTCATGCT AATAATGCAG CTATGCAGGC GGAAGACGAG CGTTTGCGCCT TGCGAAAGCA GAAGAAAAAG CCCGTAAAGA AGCGGAAGCA GCAGAAAAGG CTTTTCAGGA AGCAGAACAA CGACGTAAAG AGATTGAACG GGAGAAGGCT GAAACAGAAC GCCAGTTGAA ACTGGCTGAA GCTGAAGAGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | YVVALLFSL LAGTTLGIW GIAIVTGILC SYIDKNKLN TINEVLGI | | | AACGACTGGC TGCATTGAGT GAAGAAGCTA AAGCTGTTGA GATCGCCCAA AAAAAACTTT CTGCTGCACA ATCTGAAGTG GTGAAAATGG ATGGAGAGAT TAAGACTCTC AATTCTCGTTT AAGCTCCAGT ATCCATGCCC GTGATGCAGA AATGAAAACG CTCGCTGGAA AACGAAATGA ACTGGCTCAG GCATCCGCTA AATATAAAGA ACTGGATGAG CTGGTCAAAA AACTATCACC AAGAGCCAAT GATCCGCTTC AGAACCGTCC TTTTTTTGAAG CAACCAGACG ACGGGTTGGG GCCGGTAAGA TTAGAGAAGA AAAACAAAAA CAGGTAACAG CATCAGAAAC ACGTATTAAC CGGATAAATG CTGATATAAC TCAGATCCAG AAGGCTATTT CTCAGGTCAG TAATAATCGT AATGCCGGTA TCGCTCGTGTT CATGAAGCTG AAGAAAATTT GAAAAAAGCA CAGAATAATC TCCTTAATTCA CAGATTAAGG ATGCTGTTGA TGCAACAGTT AGCTTTTATCA AACGCTGACT GAAAAATATG GTGAAAAATA TTCGAAAATG GCACAGGAAC TTGCTGATAA GTCTAAAGGT AAGAAAATCG GCAATGTGAA TGAAGCTCTC GCTGCTTTTGA AAAATACAAG GATGTTTTAA ATAAGAAATT CAGCAAAGCC GATCGTGATG CTATTTTTAAT GCGTTGGCAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CGGTGAAGTA TGATGACTGG GCTAAACATT TAGATCAGTT TGCCAAGTAC TTGAAGATTA CGGGGCATGT TTCTTTTGGAT ATGATGTGGT ATCTGATATCC TAAAAATTAA GGATACAGGT GACTGGAAGC CACTATTTCTT ACATTAGAGA AGAAAGCTGC AGATGCAGGG GTGAGTTATG TTGTTGCTTTA CTTTTTAGCTT GCTTGCTGGA ACTACATTAG GTATTTGGGG TATTGCTATTG TTACAGGAAT TCTATGCTCCT ATATTGATAA GAATAAACTT AATACTATAA ATGAGGTGTT AGGGATTTAA |
| 56 | Colicin-Ia | Unclassified | MSDPVRITN PGAESLGYD SDGHEIMAV DIYVNPPRV DVFHGTPPA WSSFGNKTI WGGNEWVD DSPTRSDIEK RDKEITAYK NTLSAQQKE NENKRTEAG KRLSAAIAA REKDENTLK TLRAGNADA ADITRQEFRL LQAELREYG FRTEIAGYD ALRLHTESR MLFADADSL RISPREARSL IEQAEKRQK DAQNADKK AADMLAEY ERRKGILDT RLSELEKNG GAALAVLDA QQARLLGQQ TRNDRAISE ARNKLSSVT ESLNTARNA LTRAEQQLT QQKNTPDGK TIVSPEKFPG RSSTNHSIVV SGDPRFAGTI KITTSAVIDN RANLNYLLS HSGLDYKRN ILNDRNPVV | Escherichia coli | 57 | ATGTCTGACC CTGTACGTATT ACAAATCCCG GTGCAGAATC GCTGGGGTAT GATTCAGATG GCCATGAAAT TATGGCCGTT GATATTTATGT AAACCCTCCA CGTGTCGATG TCTTTCATGGT ACCCCGCCTG CATGGAGTTC CTTCGGGAAC AAAACCATCT GGGGCGGAAA CGAGTGGGTT GATGATTCCC CAACCCGAAG TGATATCGAA AAAAGGGACA AGGAAATCAC AGCGTACAAA AACACGCTCA GCGCGCAGCA GAAAGAGAAT GAGAATAAGC GTACTGAAGC CGGAAAACGC CTCTCTGCGG CGATTGCTGC AAGGGAAAAA GATGAAAACA CACTGAAAAC ACTCCGTGCC GGAAACGCAG ATGCCGCTGA TATTACACGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | TEDVEGDKK | | | CAGGAGTTCA |
| | | | IYNAEVAEW | | | GACTCCTGCA |
| | | | DKLRQRLLD | | | GGCAGAGCTG |
| | | | ARNKITSAES | | | AGAGAATACG |
| | | | AVNSARNNL | | | GATTCCGTAC |
| | | | SARTNEQKH | | | TGAAATCGCC |
| | | | ANDALNALL | | | GGATATGACG |
| | | | KEKENIRNQ | | | CCCTCCGGCT |
| | | | LSGINQKIAE | | | GCATACAGAG |
| | | | EKRKQDELK | | | AGCCGGATGC |
| | | | ATKDAINFT | | | TGTTTGCTGAT |
| | | | TEFLKSVSE | | | GCTGATTCTCT |
| | | | KYGAKAEQL | | | TCGTATATCTC |
| | | | AREMAGQA | | | CCCGGGAGGC |
| | | | KGKKIRNVE | | | CAGGTCGTTA |
| | | | EALKTYEKY | | | ATCGAACAGG |
| | | | RADINKKIN | | | CTGAAAAACG |
| | | | AKDRAAIAA | | | GCAGAAGGAT |
| | | | ALESVKLSDI | | | GCGCAGAACG |
| | | | SSNLNRFSR | | | CAGACAAGAA |
| | | | GLGYAGKFT | | | GGCCGCTGAT |
| | | | SLADWITEF | | | ATGCTTGCTG |
| | | | GKAVRTEN | | | AATACGAGCG |
| | | | WRPLFVKTE | | | CAGAAAAGGT |
| | | | TIIAGNAATA | | | ATTCTGGACA |
| | | | LVALVFSILT | | | CCCGGTTGTC |
| | | | GSALGIIGYG | | | AGAGCTGGAA |
| | | | LLMAVTGAL | | | AAAAATGGCG |
| | | | IDESLVEKA | | | GGGCAGCCCT |
| | | | NKFWGI | | | TGCCGTTCTTG |
| | | | | | | ATGCACAACA |
| | | | | | | GGCCCGTCTG |
| | | | | | | CTCGGGCAGC |
| | | | | | | AGACACGGAA |
| | | | | | | TGACAGGGCC |
| | | | | | | ATTTCAGAGG |
| | | | | | | CCCGGAATAA |
| | | | | | | ACTCAGTTCA |
| | | | | | | GTGACGGAAT |
| | | | | | | CGCTTAACAC |
| | | | | | | GGCCCGTAAT |
| | | | | | | GCATTAACCA |
| | | | | | | GAGCTGAACA |
| | | | | | | ACAGCTGACG |
| | | | | | | CAACAGAAAA |
| | | | | | | ACACGCCTGA |
| | | | | | | CGGCAAAACG |
| | | | | | | ATAGTTTCCCC |
| | | | | | | TGAAAAATTC |
| | | | | | | CCGGGGCGTT |
| | | | | | | CATCAACAAA |
| | | | | | | TGATTCTATTG |
| | | | | | | TTGTGAGCGG |
| | | | | | | TGATCCGAGA |
| | | | | | | TTTGCCGGTA |
| | | | | | | CGATAAAAAT |
| | | | | | | CACAACCAGC |
| | | | | | | GCAGTCATCG |
| | | | | | | ATAACCGTGC |
| | | | | | | AAACCTGAAT |
| | | | | | | TATCTTCTGAG |
| | | | | | | CCATTCCGGT |
| | | | | | | CTGGACTATA |
| | | | | | | AACGCAATAT |
| | | | | | | TCTGAATGAC |
| | | | | | | CGGAATCCGG |
| | | | | | | TGGTGACAGA |
| | | | | | | GGATGTGGAA |
| | | | | | | GGTGACAAGA |
| | | | | | | AAATTTATAA |
| | | | | | | TGCTGAAGTT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCTGAATGGG ATAAGTTACG GCAAAGATTG CTTGATGCCA GAAATAAAAT CACCTCTGCT GAATCTGCGG TAAATTCGGC GAGAAATAAC CTCAGTGCCA GAACAAATGA GCAAAAGCAT GCAAATGACG CTCTTAATGCC CTGTTGAAGG AAAAAGAGAA TATCCGTAAC CAGCTTTCCG GCATCAATCA GAAGATAGCG GAAGAGAAAA GAAAACAGGA TGAACTGAAG GCAACGAAAG ACGCAATTAA TTTCACAACA GAGTTCCTGA AATCAGTTTC AGAAAAATAT GGTGCAAAAG CTGAGCAGTT AGCCAGAGAG ATGGCCGGGC AGGCTAAAGG GAAGAAAATA CGTAATGTTG AAGAGGCATT AAAAACGTAT GAAAAGTACC GGGCTGACAT TAACAAAAAA ATTAATGCAA AAGATCGTGC AGCGATTGCC GCAGCCCTTG AGTCTGTGAA GCTGTCTGAT ATATCGTCTA ATCTGAACAG ATTCAGTCGG GGACTGGGAT ATGCAGGAAA ATTTACAAGT CTTGCTGACT GGATCACTGA GTTTGGTAAG GCTGTCCGGA CAGAGAACTG GCGTCCTCTTT TTGTTAAAAC AGAAACCATC ATAGCAGGCA ATGCCGCAAC GGCTCTTGTG GCACTGGTCT TCAGTATTCTT ACCGGAAGCG CTTTAGGCATT ATCGGGTATG GTTTACTGAT GGCTGTCACC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGTGCGCTGA TTGATGAATC GCTTGTGGAA AAAGCGAATA AGTTCTGGGG TATTTAA |
| 58 | Colicin-Ib | Unclassified | MSDPVRITN PGAESLGYD SDGHEIMAV DIYVNPPRV DVFHGTPPA WSSFGNKTI WGGNEWVD DSPTRSDIEK RDKEITAYK NTLSAQQKE NENKRTEAG KRLSAAIAA REKDENTLK TLRAGNADA ADITRQEFRL LQAELREYG FRTEIAGYD ALRLHTESR MLFADADSL RISPREARSL IEQAEKRQK DAQNADKK AADMLAEY ERRKGILDT RLSELEKNG GAALAVLDA QQARLLGQQ TRNDRAISE ARNKLSSVT ESLKTARNA LTRAEQQLT QQKNTPDGK TIVSPEKFPG RSSTNHSIVV SGDPRFAGTI KITTSAVIDN RANLNYLLT HSGLDYKRN ILNDRNPVV TEDVEGDKK IYNAEVAEW DKLRQRLLD ARNKITSAES AINSARNNV SARTNEQKH ANDALNALL KEKENIRSQ LADINQKIAE EKRKRDEIN MVKDAIKLT SDFYRTIYDE FGKQASELA KELASVSQG KQIKSVDDA LNAFDKFRN NLNKKYNIQ DRMAISKAL EAINQVHMA ENFKLFSKAF GFTGKVIER YDVAVELQK AVKTDNWR PFFVKLESLA AGRAASAVT | Escherichia coli | 59 | ATGTCTGACC CTGTACGTATT ACAAATCCCG GTGCAGAATC GCTGGGATAT GATTCAGATG GCCATGAAAT TATGGCCGTT GATATTTATGT AAACCCTCCA CGTGTCGATG TCTTTCATGGT ACCCCGCCTG CATGGAGTTC CTTCGGGAAC AAAACCATCT GGGGTGGAAA CGAGTGGGTC GATGATTCCC CAACCCGAAG TGATATCGAA AAAAGGGACA AGGAAATCAC AGCGTACAAA AACACGCTCA GCGCGCAGCA GAAAGAGAAT GAGAATAAGC GTACTGAAGC TGGAAAACGC CTTTCTGCGGC AATTGCTGCA AGGGAAAAAG ATGAAAACAC ACTGAAAACA CTCCGTGCCG GAAACGCAGA TGCCGCTGAT ATTACACGAC AGGAGTTCAG ACTCCTGCAG GCAGAGCTGA GAGAATACGG ATTCCGTACT GAAATCGCCG GATATGATGC CCTCCGGCTG CATACAGAGA GCCGGATGCT GTTTGCTGAT GCTGATTCTCT TCGTATATCTC CCCGCGAGGC CAGGTCGTTA ATCGAACAGG CTGAAAAACG GCAGAAGGAT GCGCAGAACG CAGACAAGAA GGCCGCTGAT ATGCTTGCTG AATACGAGCG CAGAAAAGGT ATTCTGGACA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | AWAFSVML GTPVGILGF AIIMAAVSA LVNDKFIEQ VNKLIGI | | | CGCGGTTGTC AGAGCTGGAA AAAAATGGCG GGGCAGCCCT TGCCGTTCTTG ATGCACAACA GGCCCGTCTG CTCGGGCAGC AGACACGGAA TGACAGGGCC ATTTCAGAGG CCCGGAATAA ACTCAGTTCG GTGACGGAAT CGCTTAAGAC GGCCCGTAAT GCATTAACCA GAGCTGAACA ACAGCTGACG CAACAGAAAA ACACGCCTGA CGGCAAAACG ATAGTTTCCCC TGAAAAATTC CCGGGGCGTT CATCAACAAA TCATTCTATTG TTGTGAGTGG TGATCCGAGG TTTGCCGGTA CGATAAAAAT CACAACCAGC GCGGTCATCG ATAACCGTGC AAACCTGAAT TATCTTCTGAC CCATTCCGGT CTGGACTATA AACGCAATAT TCTGAATGAC CGGAATCCGG TGGTGACAGA GGATGTGGAA GGTGACAAGA AAATTTATAA TGCTGAAGTT GCTGAATGGG ATAAGTTACG GCAACGATTG CTTGATGCCA GAAATAAAAT CACCTCTGCT GAATCTGCGA TAAATTCGGC GAGAAATAAC GTCAGTGCCA GAACAAATGA ACAAAAGCAT GCAAATGACG CTCTTAATGCC CTGTTGAAGG AAAAAGAGAA TATCCGTAGC CAGCTTGCTG ACATCAATCA GAAAATAGCT GAAGAGAAAA GAAAAAGGGA TGAAATAAAT ATGGTAAAGG ATGCCATAAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ACTCACCTCTG ATTTCTACAG AACGATATAT GATGAGTTCG GTAAACAAGC ATCCGAACTT GCTAAGGAGC TGGCTTCTGTA TCTCAAGGGA AACAGATTAA GAGTGTGGAT GATGCACTGA ACGCTTTTGAT AAATTCCGTA ATAATCTGAA CAAGAAATAT AACATACAAG ATCGCATGGC CATTTCTAAA GCCCTGGAAG CTATTAATCA GGTCCATATG GCGGAGAATT TTAAGCTGTTC AGTAAGGCAT TTGGTTTTACC GGAAAAGTTA TTGAACGTTA TGATGTTGCT GTGGAGTTAC AAAAGGCTGT AAAAACGGAC AACTGGCGTC CATTTTTTGTA AAACTTGAAT CACTGGCAGC AGGAAGAGCT GCTTCAGCAG TTACAGCATG GGCGTTTTCC GTCATGCTGG GAACCCCTGT AGGTATTCTG GGTTTTGCAA TTATTATGGC GGCTGTGAGT GCGCTTGTTA ATGATAAGTT TATTGAGCAG GTCAATAAAC TTATTGGTATC TGA |
| 60 | Colicin-M | Unclassified | METLTVHAP SPSTNLPSYG NGAFSLSAP HVPGAGPLL VQVVYSFFQ SPNMCLQAL TQLEDYIKK HGASNPLTL QIISTNIGYF CNADRNLVL HPGISVYDA YHFAKPAPS QYDYRSMN MKQMSGNV TTPIVALAH YLWGNGAE RSVNIANIGL KISPMKINQI | Escherichia coli | 61 | ATGGAAACCT TAACTGTTCAT GCACCATCAC CATCAACTAA CTTACCAAGTT ATGGCAATGG TGCATTTTCTC TTTCAGCACC ACATGTGCCT GGTGCTGGCC CTCTTTTAGTC CAGGTTGTTT ATAGTTTTTTC CAGAGTCCAA ACATGTGTCTT CAGGCTTTAA CTCAACTTGA GGATTACATC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | KDIIKSGVV GTFPVSTKFT HATGDYNVI TGAYLGNIT LKTEGTLTIS ANGSWTYN GVVRSYDD KYDFNASTH RGIIGESLTR LGAMFSGKE YQILLPGEIH IKESGKR | | | AAAAAACATG GGGCCAGCAA CCCTCTCACAT TGCAGATCAT ATCGACAAAT ATTGGTTACTT CTGTAACGCC GACCGAAATC TGGTTCTTCAC CCTGGAATAA GCGTTTATGA CGCTTACCACT TCGCAAAACC AGCGCCAAGT CAATATGACT ATCGCTCAAT GAATATGAAA CAAATGAGCG GTAATGTCAC TACACCAATT GTGGCGCTTG CTCACTATTTA TGGGGTAATG GCGCTGAAAG GAGCGTTAAT ATCGCCAACA TTGGTCTTAA AATTTCCCCTA TGAAAATTAA TCAGATAAAA GACATTATAA AATCTGGTGT AGTAGGCACA TTCCCTGTTTC TACAAAGTTC ACACATGCCA CTGGTGATTA TAATGTTATTA CCGGTGCATA TCTTGGTAAT ATCACACTGA AAACAGAAGG TACTTTAACTA TCTCTGCCAAT GGCTCCTGGA CTTACAATGG CGTTGTTCGTT CATATGATGA TAAATACGAT TTTAACGCCA GCACTCACCG TGGCATTATC GGAGAGTCGC TCACAAGGCT CGGGGCGATG TTTTCTGGTAA AGAGTACCAG ATACTGCTTCC TGGTGAAATT CACATTAAAG AAAGTGGTAA GCGATAA |
| 62 | Colicin-N | Unclassified | MGSNGADN AHNNAFGG GKNPGIGNT SGAGSNGSA SSNRGNSNG WSWSNKPH KNDGFHSDG SYHITFHGD | Escherichia coli | 63 | GCAAATCGAG TTTCGAATATA AATAACATTA TATCTAGTGTT ATTCGATGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | NNSKPKPGG NSGNRGNN GDGASAKV GEITITPDNS KPGRYISSNP EYSLLAKLID AESIKGTEV YTFHTRKGQ YVKVTVPDS NIDKMRVDY VNWKGPKY NNKLVKRFV SQFLLFRKEE KEKNEKEAL LKASELVSG MGDKLGEY LGVKYKNV AKEVANDIK NFHGRNIRS YNEAMASLN KVLANPKM KVNKSDKD AIVNAWKQ VNAKDMAN KIGNLGKAF KVADLAIKV EKIREKSIEG YNTGNWGP LLLEVESWII GGVVAGVAI SLFGAVLSFL PISGLAVTAL GVIGIMTISY LSSFIDANRV SNINNIISSVI R | | | |
| 64 | Colicin-V (Microcin -v) | Unclassified | MRTLTLNEL DSVSGGASG RDIAMAIGT LSGQFVAGG IGAAAGGVA GGAIYDYAS THKPNPAMS PSGLGGTIK QKPEGIPSEA WNYAAGRL CNWSPNNLS DVCL | Escherichia coli | 65 | ATGAGAACTC TGACTCTAAA TGAATTAGAT TCTGTTTCTGG TGGTGCTTCA GGGCGTGATA TTGCGATGGC TATAGGAACA CTATCCGGAC AATTTGTTGC AGGAGGAATT GGAGCAGCTG CTGGGGGTGT GGCTGGAGGT GCAATATATG ACTATGCATC CACTCACAAA CCTAATCCTGC AATGTCTCCAT CCGGTTTAGG AGGAACAATT AAGCAAAAAC CCGAAGGGAT ACCTTCAGAA GCATGGAACT ATGCTGCGGG AAGATTGTGT AATTGGAGTC CAAATAATCT TAGTGATGTTT GTTTATAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 66 | Columbicin A | Lantibiotic | MMNATENQI FVETVSDQE LEMLIGGAG RGWIKTLTK DCPNVISSIC AGTIITACKN CA | Enterococcus columbae | 67 | ATGATGAATG CTACTGAAAA CCAAATTTTG TTGAGACTGT GAGTGACCAA GAATTAGAAA TGTTAATTGGT GGTGCAGGTC GTGGATGGAT TAAGACTTTA ACAAAAGATT GTCCAAATGT GATTTCTTCAA TTTGTGCAGG TACAATTATTA CAGCTTGTAA AAATTGTGCT TAA |
| 68 | Curvacin-A | class IIA/YG NGV | MNNVKELS MTELQTITG GARSYGNG VYCNNKKC WVNRGEAT QSIIGGMISG WASGLAGM | Lactobacillus curvatus | 69 | ATGAATAATG TAAAAGAATT AAGTATGACA GAATTACAAA CAATTACCGG CGGTGCTAGA TCATATGGCA ACGGTGTTTA CTGTAATAAT AAAAAATGTT GGGTAAATCG GGGTGAAGCA ACGCAAAGTA TTATTGGTGG TATGATTAGC GGCTGGGCTA GTGGTTTAGC TGGAATGTAA |
| 70 | Cypemycin | Unclassified tied | MRSEMTLTS TNSAEALAA QDFANTVLS AAAPGFHAD CETPAMATP ATPTVAQFV IQGSTICLVC | Streptomyces sp. | 71 | GTGCGATCTG AGATGACTCT TACGAGCACG AATTCCGCTG AGGCTCTGGC GGCGCAGGAC TTTGCGAACA CCGTTCTCAG CGCGGCGGCC CCGGGCTTCC ACGCGGACTG CGAGACGCCG GCCATGGCCA CCCCGGCCAC GCCGACCGTC GCCCAGTTCG TGATCCAGGG CAGCACGATC TGCCTGGTCT GCTGA |
| 72 | Cytolysin | Lantibiotic | MVNSKDLR NPEFRKAQG LQFVDEVNE KELSSLAGS GDVHAQTT WPCATVGVS VALCPTTKC TSQC | Bacillus halodurans (strain ATCC BAA-125/ DSM 18197/ FERM 7344 /JCM9153/ C-125) | 73 | ATGGTAAATT CAAAAGATTT GCGTAATCCT GAATTCCGCA AAGCCCAAGG TCTACAATTCG TTGACGAGGT GAACGAGAAG GAACTTCGT CTCTAGCTGG TTCAGGAGAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GTGCATGCAC AAACAACTTG GCCTTGCGCT ACAGTTGGTG TCTCCGTAGC CTTGTGCCCA ACTACAAAGT GTACAAGCCA GTGCTAA |
| 74 | Divercin V41 | class IIa/YGN GV | MKNLKEGSY TAVNTDELK SINGGTKYY GNGVYCNS KKCWVDWG QASGCIGQT VVGGWLGG AIPGKC | Carnobacterium divergens (Lactobacillus divergens) | 75 | ATGAAAAACT TAAAAGAAGG TTCATACACTG CTGTTAATACT GATGAATTAA AAAGTATCAA TGGTGGAACA AAATATTATG GGAATGGCGT TTATTGCAATT CTAAAAAATG TTGGGTAGAT TGGGGACAAG CTTCAGGTTGT ATCGGTCAAA CTGTTGTTGG CGGATGGCTA GGCGGAGCTA TACCAGGTAA ATGCTAA |
| 76 | Divergicin 750 | Unclassified | MIKREKNRT ISSLGYEEIS NHKLQEIQG GKGILGKLG VVQAGVDF VSGVWAGIK QSAKDHPNA | Carnobacterium divergens (Lactobacillus divergens) | 77 | ATGATTAAAA GAGAAAAGAA CAGAACAATT TCTTCCCTTGG TTATGAAGAA ATTTCTAATCA TAAATTGCAA GAAATACAAG GTGGAAAAGG AATTCTTGGT AAACTAGGAG TAGTACAGGC AGGAGTGGAT TTTGTATCAG GAGTGTGGGC TGGAATAAAA CAGTCTGCCA AAGATCATCC TAATGCGTAA |
| 78 | Divergicin A | Class IIc | MKKQILKGL VIVVCLSGA TFFSTPQQAS AAAPKITQK QKNCVNGQ LGGMLAGA LGGPGGVVL GGIGGAIAG GCFN | Carnobacterium divergens (Lactobacillus divergens) | 79 | ATGAAAAAAC AAATTTTAAA AGGGTTGGTT ATAGTTGTTTG TTTATCTGGG GCAACATTTT CTCAACACCA CAACAAGCTT CTGCTGCTGC ACCGAAAATT ACTCAAAAAC AAAAAAATTG TGTTAATGGA CAATTAGGTG GAATGCTTGC TGGAGCTTTG GGTGGACCTG GCGGAGTTGT GTTAGGTGGT ATAGGTGGTG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CAATAGCAGG AGGTTGTTTTA ATTAA |
| 80 | Durancin Q | Unclassified | MQTIKELNT MELQEIIGGE NDHRMPYEL NRPNNLSKG GAKCAAGIL GAGLGAVG GGPGGFISA GISAVLGCM | Enterococcus durans | 81 | ATGCAAACGA TCAAAGAATT GAACACGATG GAATTACAAG AAATAATTGG AGGTGAAAAT GACCATCGGA TGCCTTACGA ATTGAACCGT CCAAATAATT TATCCAAAGG TGGGGCTAAG TGTGCTGCTG GAATACTTGG CGCTGGACTA GGCGCAGTAG GCGGTGGACC TGGCGGATTT ATTAGTGCCG GAATCAGTGC TGTTCTTGGTT GTATGTAA |
| 82 | Durancin TW-49M | Unclassified | MQTIKELNT MELQKIIGG ENDHRMPYE LNRPNNLSK GGAKCAAGI LGAGLGAVG GGPGGFISA GISAVLGCM | Enterococcus durans | 83 | ATGCAAACGA TCAAAGAATT GAACACGATG GAATTACAAA AAATAATTGG AGGTGAAAAT GACCATCGGA TGCCTTACGA ATTGAACCGT CCAAATAATT TATCCAAAGG TGGAGCTAAG TGCGCTGCCG GAATACTTGG TGCTGGATTA GGCGCAGTAG GCGGTGGACC TGGCGGATTT ATTAGTGCCG GAATCAGTGC TGTTCTTGGTT GTATGTAA |
| 84 | Dysgalacticin | Unclassified | MKKLKRLVI SLVTSLLVIS STVPALVYA NETNNFAET QKEITTNSEA TLTNEDYTK LTSEVKTIYT NLIQYDQTK NKFYVDEDK TEQYYNYD DESIKGVYL MKDSLNDEL NNNNSSNYS EIINQKISEID YVLQGNDIN NLIPSNTRVK RSADFSWIQ RCLEEAWGY AISLVTLKGI INLFKAGKFE AAAAKLASA | Streptococcus dysgalactiae subsp. equisimilis (Streptococcus equisimilis) | 85 | ATGAAAAAAT TAAAACGTCT TGTTATCTCTC TTGTTACTTCA TTACTAGTAAT TTCAAGTACA GTTCCAGCAC TTGTTTACGCT AATGAAACAA ATAACTTTGC AGAAACTCAA AAAGAAATTA CAACAAATTC AGAAGCAACA TTAACCAATG AAGACTACAC TAAATTAACTT CCGAAGTAAA AACAATTTAT ACAAATCTGA TTCAATACGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | TAGRIAGMA ALFAFVATC GATTVS | | | CCAAACAAAA AACAAATTTT ACGTCGATGA AGACAAAACT GAACAATATT ATAACTACGA TGATGAAAGT ATAAAAGGGG TTTATCTCATG AAAGATAGTT TGAACGATGA GTTAAACAAT AATAACTCTTC AAACTATTCT GAAATAATTA ATCAAAAAAT CTCTGAAATT GACTATGTCC TTCAAGGAAA CGATATAAAT AATTTAATTCC TAGCAATACC AGAGTAAAAA GATCAGCAGA TTTTTCTTGGA TTCAAAGATG TCTAGAAGAA GCATGGGGAT ATGCTATTAG TCTAGTTACTC TAAAAGGAAT AATCAATCTA TTTAAAGCAG GAAAATTTGA AGCTGCTGCT GCTAAATTAG CTTCTGCTACA GCAGGTAGAA TCGCTGGAAT GGCTGCCTTA TTTGCTTTCGT AGCAACTTGC GGTGCGACAA CTGTATCATA A |
| 86 | Enterocin 1071A | Unclassified | MKQYKVLN EKEMKKPIG GESVFSKIGN AVGPAAYWI LKGLGNMSD VNQADRINR KKH | Enterococcus faecalis (Streptococcus faecalis) | 87 | ATGAAGCAAT ATAAAGTATT GAATGAAAAA GAAATGAAAA AACCTATTGG GGGAGAGTCG GTTTTTAGTAA AATAGGTAAT GCTGTAGGTC CAGCTGCTTA TTGGATTTTAA AAGGATTAGG TAATATGAGT GATGTAAACC AAGCTGATAG AATTAATAGA AAGAAACATT AA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 88 | Enterocin 7A (Enterocin L50A) | bacteriocins without sequence leader | MGAIAKLVA KFGWPIVKK YYKQIMQFI GEGWAINKII DWIKKHI | Enterococcus faecalis (Streptococcus faecalis) | 89 | ATGGGAGCAA TCGCAAAATT AGTAGCAAAG TTTGGATGGC CAATTGTTAA AAAGTATTAC AAACAAATTA TGCAATTTATT GGAGAAGGAT GGGCAATTAA CAAAATTATT GATTGGATCA AAAAACATAT TTAA |
| 90 | Enterocin 7B | Unclassified | MGAIAKLVA KFGWPFIKK FYKQIMQFIG QGWTIDQIE KWLKRH | Enterococcus faecalis (Streptococcus faecalis) | 91 | ATGGGAGCAA TCGCAAAATT AGTAGCAAAG TTTGGATGGC CATTTATTAAA AAATTCTACA AACAAATTAT GCAGTTTATC GGACAAGGAT GGACAATAGA TCAAATTGAA AAATGGTTAA AAAGACATTG A |
| 92 | Enterocin 96 | Class II | MLNKKLLEN GVVNAVTID ELDAQFGGM SKRDCNLMK ACCAGQAVT YAIHSLLNRL GGDSSDPAG CNDIVRKYC K | Enterococcus faecalis (strain ATCC 700802/ V583) | 93 | ATGTTAAATA AAAAATTATT AGAAAATGGT GTAGTAAATG CTGTAACAAT TGATGAACTT GATGCTCAAT TTGGTGGAAT GAGCAAACGT GATTGTAACT TGATGAAGGC GTGTTGTGCT GGACAAGCAG TAACATATGC TATTCATAGTC TTTTAAATCGA TTAGGTGGAG ACTCTAGTGA TCCAGCTGGT TGTAATGATA TTGTAAGAAA ATATTGTAAA TAA |
| 94 | Enterocin A | Class IIa, IIc (problematic) | MKHLKILSIK ETQLIYGGT THSGKYYGN GVYCTKNKC TVDWAKAT TCIAGMSIG GFLGGAIPG KC | Enterococcus faecium (Streptococcus faecium) | 95 | ATGAAACATT TAAAAATTTT GTCTATTAAA GAGACACAAC TTATCTATGG GGGTACCACT CATAGTGGAA AATATTATGG AAATGGAGTG TATTGCACTA AAAATAAATG TACGGTCGAT TGGGCCAAGG CAACTACTTGT ATTGCAGGAA TGTCTATAGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGGTTTTTTAG GTGGAGCAAT TCCAGGGAAG TGC |
| 96 | Enterocin AS-48 (BACTE RIOCIN AS-48) | Unclassified | MVKENKFSK IFILMALSFL GLALFSASL QFLPIAHMA KEFGIPAAV AGTVLNVVE AGGWVTTIV SILTAVGSG GLSLLAAAG RESIKAYLK KEIKKKGKR AVIAW | Enterococcus faecalis (Streptococcus faecalis) | 97 | ATGGTTAAAG AAAATAAATT TTCTAAGATTT TTATTTTAATG GCTTTGAGTTT TTTGGGGTTA GCCTTGTTTAG TGCAAGTCTT CAGTTTTTGCC CATTGCACAT ATGGCTAAAG AGTTCGGTAT ACCAGCAGCA GTTGCAGGAA CTGTGCTTAAT GTAGTTGAAG CTGGTGGATG GGTCACTACT ATTGTATCAAT TCTTACTGCTG TAGGTAGCGG AGGTCTTTCTT TACTCGCTGC AGCAGGAAGA GAGTCAATTA AAGCATACCT TAAGAAAGAA ATTAAGAAAA AAGGAAAAAG AGCAGTTATT GCTTGGTAA |
| 98 | Enterocin B | class IIc, non subgrouped bacteriocins (problematic) | MQNVKELST KEMKQIIGG ENDHRMPNE LNRPNNLSK GGAKCGAAI AGGLFGIPK GPLAWAAGL ANVYSKCN | Enterococcus faecium (Streptococcus faecium) | 99 | ATGCAAAATG TAAAAGAATT AAGTACGAAA GAGATGAAAC AAATTATCGG TGGAGAAAAT GATCACAGAA TGCCTAATGA GTTAAATAGA CCTAACAACT TATCTAAAGG TGGAGCAAAA TGTGGTGCTG CAATTGCTGG GGGATTATTT GGAATCCCAA AAGGACCACT AGCATGGGCT GCTGGGTTAG CAAATGTATA CTCTAAATGC AACTAA |
| 100 | Enterocin CRL35 (Mundticin KS) | Class IIa | MKKLTSKE MAQVVGGK YYGNGVSC NKKGCSVD WGKAIGIIGN NSAANLATG GAAGWKS | Enterococcus mundtii | 101 | TTGAAGAAAT TAACATCAAA AGAAATGGCA CAAGTAGTAG GTGGAAAATA CTACGGTAAT GGAGTCTCAT GTAATAAAAA AGGGTGCAGT GTTGATTGGG GAAAAGCTAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGGCATTATT GGAAATAATT CTGCTGCGAA TTTAGCTACTG GTGGAGCAGC TGGTTGGAAA AGTTAA |
| 102 | Enterocin EJ97 | Unclassified | MLAKIKAMI KKFPNPYTL AAKLTTYEI NWYKQQYG RYPWERPVA | Enterococcus faecalis (Streptococcus faecalis) | 103 | ATGTTAGCAA AAATTAAAGC GATGATTAAG AAGTTTCCGA ACCCTTATACT TTAGCAGCTA AGCTAACGAC TTACGAAATT AATTGGTATA AACAACAATA CGGTCGTTAT CCTTGGGAGC GCCCTGTAGC ATAA |
| 104 | Enterocin P | Class IIa, IIb and IIc (problematic) | MRKKLFSLA LIGIFGLVVT NFGTKVDAA TRSYGNGVY CNNSKCWV NWGEAKENI AGIVISGWA SGLAGMGH | Enterococcus faecium (Streptococcus faecium) | 105 | ATGAGAAAAA AATTATTTAGT TTAGCTCTTAT TGGAATATTT GGGTTAGTTG TGACAAATTTT GGTACAAAAG TTGATGCAGC TACGCGTTCA TATGGTAATG GTGTTTATTGT AATAATAGTA AATGCTGGGT TAACTGGGGA GAAGCTAAAG AGAATATTGC AGGAATCGTT ATTAGTGGCT GGGCTTCTGG TTTGGCAGGT ATGGGACATT AA |
| 106 | Enterocin Q | Class IIc | MNFLKNGIA KWMTGAEL QAYKKKYG CLPWEKISC | Enterococcus faecium (Streptococcus faecium) | 107 | ATGAATTTTCT TAAAAATGGT ATCGCAAAAT GGATGACCGG TGCTGAATTG CAAGCGTATA AAAAGAAATA TGGATGCTTG CCATGGGAAA AAATTTCTTGT TAA |
| 108 | Enterocin SE-K4 | Class IIa | MKKKLVKG LVICGMIGIG FTALGTNVE AATYYGNG VYCNKQKC WVDWSRAR SEIIDRGVKA YVNGFTKVL GGIGGR | Enterococcus faecalis (Streptococcus faecalis) | 109 | ATGAAAAAGA AATTAGTTAA AGGCTTAGTT ATTTGTGGCA TGATTGGGAT TGGTTTTACA GCATTAGGAA CAAATGTAGA AGCCGCCACG TATTACGGAA ATGGTGTCTA TTGCAATAAG CAAAAATGTT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGGTAGATTG GAGTAGAGCA CGTTCTGAAA TTATAGACAG AGGCGTAAAA GCATACGTCA ATGGATTTAC GAAAGTGTTA GGTGGTATAG GTGGAAGATA A |
| 110 | Enterocin W alfa | class IIb | MKKEELVG MAKEDFLNV ICENDNKLE NSGAKCPW WNLSCHLGN DGKICTYSH ECTAGCNA | Enterococcus faecalis (Streptococcus faecalis) | 111 | ATGAAAAAG AAGAATTAGT AGGAATGGCT AAGGAAGACT TTTTAAATGTT ATTTGTGAAA ATGACAACAA ACTAGAAAAT AGTGGAGCAA AATGTCCTTG GTGGAATCTT TCTTGTCATTT AGGCAATGAT GGTAAAATTT GCACTTATTCA CATGAATGTA CCGCAGGTTG TAATGCATAA |
| 112 | Enterocin W beta | class IIb | MTELNKRLQ LKRDVSTEN SLKKISNTDE THGGVTTSIP CTVMVSAA VCPTLVCSN KCGGRG | Enterococcus faecalis (Streptococcus faecalis) | 113 | ATGACTGAAC TTAACAAAAG ATTACAATTA AAAAGAGATG TTTCAACAGA AAATAGTTTG AAAAAAATTT CTAATACTGA TGAAACACAT GGGGGAGTTA CTACATCAATT CCATGTACAG TAATGGTTAG TGCGGCAGTA TGTCCTACCCT TGTTTGCTCGA ATAAATGTGG CGGTAGAGGC TAG |
| 114 | Enterocin Xalpha | class IIb | MQNVKEVS VKEMKQIIG GSNDSLWY GVGQFMGK QANCITNHP VKHMIIPGY CLSKILG | Enterococcus faecium (Streptococcus faecium) | 115 | ATGCAAAATG TAAAAGAAGT TTCTGTAAAA GAGATGAAAC AAATTATCGG TGGTTCTAAT GATAGTCTTT GGTATGGTGT AGGACAATTT ATGGGTAAAC AAGCAAACTG TATAACAAAC CATCCTGTTAA ACACATGATA ATTCCTGGAT ATTGTTTATCG AAAATTTTAG GGTAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 116 | Enterocin Xbeta | class IIb | MKKYNELSK KELLQIQGGI APIIVAGLGY LVKDAWDH SDQIISGFKK GWNGGRRK | *Enterococcus faecium* (*Streptococcus faecium*) | 117 | ATGAAAAAAT ATAATGAGTT ATCTAAAAAA GAACTTCTAC AGATTCAAGG AGGAATAGCA CCTATTATAGT TGCTGGCCTT GGCTATTTAG TAAAAGATGC ATGGGATCAC TCAGATCAAA TAATCTCAGG ATTTAAAAAA GGTTGGAATG GTGGACGTAG AAAATAA |
| 118 | Enterolysin A | class III | MKNILLSILG VLSIWSLAF SSYSVNAAS NEWSWPLG KPYAGRYEE GQQFGNTAF NRGGTYFHD GFDFGSAIY GNGSVYAV HDGKILYAG WDPVGGGS LGAFIVLQA GNTNVIYQE FSRNVGDIK VSTGQTVKK GQLIGKFTSS HLHLGMTK KEWRSAHSS WNKDDGTW FNPIPILQGG STPTPPNPGP KNFTTNVRY GLRVLGGSW LPEVTNFNN TNDGFAGYP NRQHDMLYI KVDKGQMK YRVHTAQSG WLPWVSKG DKSDTVNGA AGMPGQAID GVQLNYITP KGEKLSQAY YRSQTTKRS GWLKVSAD NGSIPGLDSY AGIFGEPLDR LQIGISQSNP F | *Enterococcus faecalis* (*Streptococcus faecalis*) | 119 | ATGAAAAATA TTTTACTTTCT ATTCTAGGGG TATTATCTATC GTTGTTTCTTT GGCGTTTTCTT CTTATTCTGTC AACGCAGCTT CTAATGAGTG GTCGTGGCCA CTGGGCAAAC CATATGCGGG AAGATATGAA GAAGGACAAC AATTCGGGAA CACTGCATTTA ACCGAGGAGG TACTTATTTCC ATGATGGGTT TGACTTTGGTT CTGCTATTTAT GGAAATGGCA GTGTGTATGC TGTGCATGAT GGTAAAATTT TATATGCTGG TTGGGATCCT GTAGGTGGAG GCTCATTAGG TGCATTTATTG TACTACAAGC GGGAAACACA AATGTGATTT ATCAAGAATT TAGCCGAAAT GTTGGAGATA TTAAAGTTAG CACTGGACAA ACTGTTAAAA AAGGACAGCT GATAGGAAAG TTTACTTCTAG TCATTTACATT TAGGAATGAC AAAAAAAGAA TGGCGTTCTG CTCATTCTTCT TGGAATAAAG ATGATGGCAC TTGGTTTAACC CAATTCCTATA CTTCAAGGAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GATCTACGCC TACGCCTCCA AATCCAGGAC CAAAAAATTT CACAACAAAT GTTCGTTACG GATTGCGGGT CCTCGGAGGT TCATGGTTAC CAGAAGTAAC CAACTTTAAC AATACCAATG ATGGTTTCGC AGGTTACCCT AATCGTCAAC ATGATATGCT TTATATAAAG GTAGATAAAG GGCAAATGAA ATATCGTGTTC ACACGGCTCA AAGTGGATGG TTGCCTTGGG TAAGTAAAGG GGATAAGAGC GATACAGTAA ATGGAGCGGC AGGTATGCCT GGACAAGCAA TTGATGGTGT TCAGCTAAAC TATATAACTCC TAAGGGAGAA AAATTATCAC AGGCTTACTA TCGTTCACAA ACTACGAAAC GATCAGGCTG GTTAAAAGTA AGTGCAGATA ATGGTTCTATT CCTGGACTAG ACAGTTATGC AGGAATCTTT GGAGAACCGT TGGATCGCTT GCAAATAGGT ATTTCACAGTC AAATCCATTTT AA |
| 120 | Epicidin 280 | Lantibiotic | MENKKDLFD LEIKKDNME NNNELEAQS LGPAIKATR QVCPKATRF VTVSCKKSD CQ | *Staphylococcus epidermidis* | 121 | ATGGAAAACA AAAAAGATTT ATTTGATTTAG AAATCAAAAA AGATAATATG GAAAATAATA ATGAATTAGA AGCTCAATCT CTTGGTCCTGC AATTAAGGCA ACTAGACAGG TATGTCCTAA AGCAACACGT TTTGTTACAGT TTCTTGTAAAA AAAGTGATTG TCAATAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 122 | Epidermicin NI01 | Unclassified | MAAFMKLIQ FLATKGQKY VSLAWKHK GTILKWINA GQSFEWIYK QIKKLWA | Staphylococcus epidermidis | 123 | ATGGCAGCAT TTATGAAGTT AATTCAGTTCT TAGCAACTAA AGGTCAAAAG TATGTTTCACT TGCATGGAAA CATAAAGGTA CTATTTTAAAA TGGATTAACG CCGGTCAAAG TTTTGAATGG ATTTATAAAC AAATCAAAAA ATTATGGGCA TAA |
| 124 | Epidermin | Lantibiotic | MEAVKEKN DLFNLDVKV NAKESNDSG AEPRIASKFI CTPGCAKTG SFNSYCC | Staphylococcus epidermidis | 125 | ATGGAAGCAG TAAAAGAAAA AAATGATCTTT TTAATCTTGAT GTTAAAGTTA ATGCAAAAGA ATCTAACGAT TCAGGAGCTG AACCAAGAAT TGCTAGTAAA TTTATATGTAC TCCTGGATGT GCAAAAACAG GTAGTTTTAA CAGTTATTGTT GTTAA |
| 126 | Epilancin K7 | Lantibiotic | MNNSLFDLN LNKGVETQK SDLSPQSAS VLKTSIKVSK KYCKGVTLT CGCNITGGK | Staphylococcus epidermidis Staphylococcus | 127 | ATGAATAACT CATTATTCGAT TTAAACCTAA ACAAAGGTGT AGAAACTCAA AAGAGTGATT TAAGTCCGCA ATCTGCTAGT GTCTTGAAGA CTTCTATTAAA GTATCTAAAA AATATTGTAA AGGTGTTACT TTAACATGCG GTTGCAATAT TACTGGTGGT AAATAA |
| 128 | Gallidermin | Lantibiotic | MEAVKEKN ELFDLDVKV NAKESNDSG AEPRIASKFL CTPGCAKTG SFNSYCC | Staphylococcus gallinarum | 129 | ATGGAAGCAG TAAAAGAGAA AAATGAACTT TTTGATCTTGA CGTTAAAGTA AATGCAAAAG AGTCTAATGA TTCAGGCGCA GAACCACGAA TTGCTAGTAA ATTTTTATGTA CTCCTGGATG TGCCAAAACA GGTAGCTTCA ATAGCTACTG TTGTTAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 130 | Garvicin A | IId | MENNNYTVLSDEELQKIDGGIGGALGNALNGLGTWANMMNGGGFVNQWQVYANKGKINQYRPY | Lactococcus garvieae | 131 | ATGGAAAACAACAATTACACAGTACTTTCAGATGAAGAACTACAAAAAATTGATGGTGGAATCGGCGGGGCTCTTGGTAATGCTCTCAACGGATTAGGTACCTGGGCAAACATGATGAACGGTGGAGGATTTGTTAATCAGTGGCAAGTTTATGCTAATAAAGGAAAAATAAATCAATACCGTCCGTATTAA |
| 132 | Garvicin ML | Unclassified | MFDLVATGMAAGVAKTIVNAVSAGMDIATALSLFSGAFTAAGGIMALIKKYAQKKLWKQLIAA | Lactococcus garvieae | 133 | ATGTTTGATTTAGTCGCGACTGGAATGGCTGCAGGTGTAGCAAAAACTATTGTTAATGCCGTTAGTGCTGGTATGGATATTGCCACTGCTTTATCATTGTTCTCAGGAGCTTTTACTGCAGCTGGGGGAATTATGGCACTCATTAAAAAATATGCTCAAAAGAAATTATGGAAACAGCTTATTGCTGCATAA |
| 134 | Gassericin A | Unclassified | MVTKYGRNLGLNKVELFAIWAVLVVALLLTTANIYWIADQFGIHLATGTARKLLDAMASGASLGTAFAAILGVTLPAWALAAAGALGATAA | Lactobacillus gasseri | 135 | ATGGTTACTAAGTACGGACGTAATTTAGGTTTGAACAAGGTAGAGTTGTTTGCAATTTGGGCGGTTTTAGTAGTTGCTCTTTTATTGACCACAGCGAACATTTATTGGATTGCTGATCAATTCGGGATTCATTTAGCGACTGGAACAGCCCGTAAGTTATTAGATGCAATGGCTTCTGGTGCCTCATTGGGAACTGCCTTTGCTGCTATTTTGGGCGTGACATTACCTGCATGGGCTTTGGCAGCTGCAGGAGCATTGGGAGCGACTGCAGCCTAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 136 | Gassericin T (gassericin K7 B) | Unclassified | MKNFNTLSF ETLANIVGG RNNWAANIG GVGGATVA GWALGNAV CGPACGFVG AHYVPIAWA GVTAATGGF GKIRK | Lactobacillus gasseri | 137 | ATGAAAAATT TTAATACATTA TCATTTGAAA CATTGGCTAA CATAGTTGGT GGGAGAAATA ATTGGGCTGC TAATATAGGT GGAGTAGGTG GAGCGACAGT CGCTGGATGG GCTCTTGGAA ATGCAGTTTG CGGTCCTGCTT GTGGCTTTGTT GGAGCACACT ATGTTCCAAT AGCATGGGCT GGCGTAACGG CAGCTACTGG TGGATTCGGA AAGATAAGAA AGTAG |
| 138 | Glycocin F | Unclassified | MSKLVKTLT ISEISKAQNN GGKPAWCW YTLAMCGA GYDSGTCDY MYSHCFGIK HHSSGSSSY HC | Lactobacillus plantarum | 139 | ATGAGTAAAT TGGTTAAGAC ACTTACTATA AGTGAAATTT CTAAGGCTCA AAACAACGGT GGAAAACCTG CATGGTGTTG GTATACTTTA GCAATGTGTG GTGCTGGTTA TGATTCGGGA ACCTGTGATT ATATGTATTC GCATTGTTTTG GTATAAAGCA TCATAGTAGT GGTAGTAGCA GTTATCATTGT TAG |
| 140 | Halocin H4 | Unclassified | MSKDRDGR RTSRRGTLK KIGGFSLGAL SFGAVGRTQ AATGSSVTT ADIAPPGPN GDPKSVQID DKYTGAEM YGEGDFRVG LGTDLTMYP PVYRESLGN GSGGWEFDF TVCGSTACR FVDSNGDVK EDDKAKEM WWQEINFND INQDLYSRN DSDWVGSTP ADTQPEFDY TEFALARDG VTLALTALN PAMGSLALG ATYFLSDMV NWIASQHED DSSLKRKWD | Haloferax mediterranei (strain ATCC 33500/DSM 1411/JCM 8866/ NBRC 14739 /NCIMB 2177/R-4) (Halobacterium mediterranei) | 141 | ATGTCGAAAG ACAGAGATGG GAGAAGGACA AGTCGGCGAG GCACGTTAAA GAAAATCGGC GGTTTCAGTCT CGGAGCGCTT AGTTTCGGGG CAGTCGGACG AACTCAAGCG GCGACCGGCT CATCGGTTAC GACCGCTGAT ATCGCACCTC CCGGACCGAA CGGAGACCCG AAGAGTGTTC AGATAGATGA TAAATACACC GGAGCCGAGA TGTACGGCGA GGGTGACTTC AGAGTCGGTC TCGGAACTGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | YDGLSGPLY ADSSTYLLA RDEMTSNSY ESFTIDNIAV AFPEFPVRTK YYVTFTAPD DPSTQSISTL EEEGIYRVP ATEVAAARP PGSRRSKSA ADEMVYVA DPKKFIEVEP VKNPSIPDRI YEEIEQKKK QRSRKQ | | | CCTGACGATG TATCCGCCCG TGTACCGTGA GAGTCTTGGA AATGGAAGCG GGGGTTGGGA ATTCGACTTCA CCGTTTGTGG GTCCACTGCC TGTCGATTTGT GGACAGTAAC GGTGACGTCA AAGAGGACGA CAAGGCGAAA GAAATGTGGT GGCAGGAAAT TAACTTCAAC GACATAAATC AGGATTTATA CAGTCGGAAC GATTCCGACT GGGTCGGGTC GACCCCTGCC GATACCCAAC CGGAGTTCGA TTACACCGAC TTTGCGCTCGC TCGGGACGGA GTGACGCTCG CTCTCACGGC ACTCAACCCC GCAATGGGGA GTCTTGCACTC GGTGCCACGT ACTTCCTCAGC GACATGGTGA ACTGGATTGC GAGCCAGCAC GAAGACGACA GTTCGCTCAA GAGAAAATGG GATTACGACG GGCTAAGTGG GCCGTTGTAC GCCGATTCGT CGACGTACCT ACTGGCACGC GACGAGATGA CTTCGAACTC GTACGAATCA TTCACGATCG ATAACATCGC CGTTGCCTTCC CAGAGTTCCC CGTCCGGACC AAGTACTACG TCACATTCACT GCGCCGGATG ACCCGTCAAC GCAGTCGATA TCTACGCTCG AAGAGGAGGG AATCTACCGA GTGCCCGCTA CGGAAGTGGC TGCGGCCAGA CCACCGGGGT CCCGACGTTC CAAATCGGCA GCCGACGAGA TGGTGTACGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGCCGATCCG AAGAAGTTCA TAGAGGTCGA GCCGGTGAAG AACCCAAGTA TCCCGGACCG AATCTACGAG GAGATAGAGC AAAAAAAGAA ACAACGGAGT AGGAAACAGT AG |
| 142 | Halocin-S8 | Unclassified | MSDKDSINR RNVLRKIGGI GVASAVGFS GLASGESLS DDEKQDVID TIYKSQRVE QIKKKFGGV NIEPKKVQS VTTNQSGDL VTAKLSVSD GDLVYSSVK DTTVIVQFD RSASEIGES WPKNTEAFI KSTSSGVDL LRTATDEEIK DVTEGVNTS EIESADAVNI FIDPESQTYY MEKYDFNN KVLEMFELA TGGTSSGKIS PTREDQNHE YNVREHKVF NSEKQNIQL QSDCNINSN TAADVILCF NQVGSCALC SPTLVGGPV PTVACLLVV CFGTPNAVS AILEEVDNS CFNLIKDVIS CWDEWTSF W | Haloarchaeon S8a | 143 | ATGTCGGATA AAGACAGCAT TAACAGAAGA AATGTATTAA GAAAAATTGG CGGTATCGGT GTGGCTTCAG CTGTCGGATTT TCTGGTTTGG CAAGCGGGGA AAGTCTTAGC GATGATGAGA AACAAGATGT TATTGACACA ATTTACAAAT CACAAAGAGT TGAACAGATA AAGAAAAAGT TCGGAGGAGT GAATATTGAG CCGAAAAAGG TTCAATCTGTA ACGACCAATC AGAGCGGAGA TCTTGTTACGG CGAAGCTGTC GGTTAGTGAT GGGGATTTGG TATATTCGAG TGTCAAAGAT ACAACTGTAA TAGTTCAGTTC GATAGATCGG CTTCTGAAATT GGTGAAAGTT GGCCCAAGAA TACTGAGGCA TTCATCAAATC GACGTCCTCT GGGGTCGATC TTCTACGTACA GCAACTGATG AAGAAATAAA GGACGTTACT GAGGGAGTCA ACACATCTGA AATTGAATCT GCGGATGCTG TTAACATATTT ATTGATCCTG AATCACAGAC ATACTATATG GAGAAATATG ACTTTAATAAT AAGGTACTTG AGATGTTTGA ATTAGCGACA GGTGGGACAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GTAGTGGTAA AATCTCCCCC ACACGTGAAG ACCAGAATCA CGAATATAAT GTTAGGGAAC ATAAAGTATT TAACTCAGAA AAACAGAATA TACAACTTCA GAGTGACTGT AATATAAACA GTAACACCGC TGCTGATGTT ATTCTATGCTT CAACCAGGTT GGTTCTTGTG CACTCTGCTCC CCGACTTTAG TCGGAGGTCC AGTCCCTACA GTTGCATGTCT CTTAGTCGTCT GTTTCGGCAC TCCAAATGCT GTGTCCGCGA TACTTGAAGA AGTCGATAAT TCTTGCTTTAA CTTGATCAAG GATGTAATTT CGTGTTGGGA TGAATGGACT AGCTTCTGGT GA |
| 144 | Helveticin -J | Unclassified | MKHLNETTN VRILSQFDM DTGYQAVV QKGNVGSK YVYGLQLRK GATTILRGY RGSKINNPIL ELSGQAGGH TQTWEFAGD RKDINGEER AGQWFIGVK PSKIEGSKII WAKQIARVD LRNQMGPH YSNTDFPRL SYLNRAGSN PFAGNKMTH AEAAVSPDY TKFLIATVEN NCIGHFTIYN LDTINEKLD EKGNSEDVN LETVKYEDS FIIDNLYGDD NNSIVNSIQG YDLDNDGNI YISSQKAPDF DGSYYAHH KQIVKIPYYA RSKESEDQW RAVNLSEFG GLDIPGKHS EVESIQIIGE NHCYLTVAY HSKNKAGEN | Lactobacillus helveticus (Lactobacillus suntoryeus) | 145 | ATGAAGCATT TAAATGAAAC AACTAATGTT AGAATTTTAA GTCAATTTGA TATGGATACT GGCTATCAAG CAGTAGTTCA AAAAGGCAAT GTAGGTTCAA AATATGTATA TGGATTACAA CTTCGCAAAG GTGCTACTAC TATCTTGCGTG GTTACCGTGG AAGTAAAATT AATAACCCTA TTCTTGAATTA TCTGGTCAAG CAGGTGGTCA CACACAGACA TGGGAATTTG CTGGTGATCG TAAAGACATT AATGGTGAAG AAAGAGCAGG TCAATGGTTT ATAGGTGTTA AACCATCGAA AATTGAAGGA AGCAAAATTA TTTGGGCAAA GCAAATTGCA AGAGTTGATC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | KTTLNEIYEL SWN | | | TTAGAAATCA AATGGGACCT CATTATTCAA ATACTGACTTT CCTCGATTATC CTACTTGAATC GCGCCGGTTC TAATCCATTTG CTGGTAATAA GATGACGCAT GCCGAAGCCG CAGTATCACC TGATTATACTA AGTTTTTAATT GCTACTGTTG AAAATAACTG TATTGGTCATT TTACTATATAC AATTTAGATA CAATTAATGA AAAACTTGAT GAAAAGGGAA ATAGTGAAGA TGTTAATCTCG AAACTGTTAA ATACGAAGAT AGTTTTATCAT TGATAATTTAT ATGGTGATGA TAATAATTCTA TTGTAAATTCA ATTCAAGGGT ATGATTTGGA TAATGATGGA AATATTTATAT TTCCAGTCAA AAAGCGCCAG ATTTTGATGG CTCTTATTATG CACATCATAA GCAGATTGTT AAGATTCCAT ATTATGCTCG GTCTAAAGAA AGCGAAGACC AATGGAGAGC TGTAAATTTA AGCGAATTCG GTGGCTTGGA TATTCCAGGT AAACATAGTG AAGTTGAAAG CATCCAAATT ATTGGTGAGA ATCATTGTTAC TTAACTGTTGC ATATCATTCTA AAAATAAAGC GGGTGAAAAT AAAACTACTT TGAATGAGAT TTATGAATTAT CTTGGAATTA G |
| 146 | Hiracin JM79 | Class II sec-dependent | MKKKVLKH CVILGILGTC LAGIGTGIKV DAATYYGN GLYCNKEKC WVDWNQAK | Enterococcus hirae | 147 | ATGAAAAAGA AAGTATTAAA ACATTGTGTT ATTCTAGGAA TATTAGGAAC TTGTCTAGCTG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | GEIGKIIVNG WVNHGPWA PRR | | | GCATCGGTAC AGGAATAAAA GTTGATGCAG CTACTTACTAT GGAAATGGTC TTTATTGTAAC AAAGAAAAAT GTTGGGTAGA TTGGAATCAA GCTAAAGGAG AAATTGGAAA AATTATTGTTA ATGGTTGGGT TAATCATGGT CCATGGGCAC CTAGAAGGTA G |
| 148 | Lactacin-F (lafA) | class IIB | MKQFNYLSH KDLAVVVG GRNNWQTN VGGAVGSA MIGATVGGT ICGPACAVA GAHYLPILW TAVTAATGG FGKIRK | Lactobacillus johnsonii (strain CNCM I-12250/Lal/NCC 533) | 149 | ATGAAACAAT TTAATTATTTA TCACATAAAG ATTTAGCAGT CGTTGTTGGT GGAAGAAATA ATTGGCAAAC AAATGTGGGA GGAGCAGTGG GATCAGCTAT GATTGGGGCT ACAGTTGGTG GTACAATTTG TGGACCTGCA TGTGCTGTAG CTGGTGCCCA TTATCTTCCTA TTTTATGGAC AGCGGTTACA GCTGCAACAG GTGGTTTTGG CAAGATAAGA AAGTAG |
| 150 | Lactacin-F (lafX) | class IIB | MKLNDKELS KIVGGNRWG DTVLSAASG AGTGIKACK SFGPWGMAI CGVGGAAIG GYFGYTHN | Lactobacillus johnsonii (strain CNCM I-12250/Lal/NCC 533) | 151 | ATGAAATTAA ATGACAAAGA ATTATCAAAG ATTGTTGGTG GAAATCGATG GGGAGATACT GTTTTATCAGC TGCTAGTGGC GCAGGAACTG GTATTAAAGC ATGTAAAAGT TTTGGCCCAT GGGGAATGGC AATTTGTGGT GTAGGAGGTG CAGCAATAGG AGGTTATTTTG GCTATACTCAT AATTAA |
| 152 | Lacticin 3147 A1 | Lantibiotic | MNKNEIETQ PVTWLEEVS DQNFDEDVF GACSTNTFS LSDYWGNN GAWCTLTHE CMAWCK | Lactococcus lactis subsp. lactis (Streptococcus lactis) | 153 | ATGAACAAAA ATGAAATTGA AACACAACCA GTTACATGGT TGGAAGAAGT ATCTGATCAA AATTTTGATG AAGATGTATT TGGTGCGTGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AGTACTAACA CATTCTCGCTC AGTGATTACT GGGGAAATAA CGGGGCTTGG TGTACACTCA CTCATGAATG TATGGCTTGG TGTAAATAA |
| 154 | Lacticin 3147 A2 | Lantibiotic | MKEKNMKK NDTIELQLG KYLEDDMIE LAEGDESHG GTTPATPAIS ILSAYISTNT CPTTKCTRA C | Lactococcus lactis subsp. lactis (Streptococcus lactis) | 155 | ATGAAAGAAA AAAATATGAA AAAGAATGAC ACTATTGAATT ACAATTGGGA AAATACCTTG AAGATGATAT GATTGAATTA GCTGAAGGGG ATGAGTCTCA TGGAGGAACA ACACCAGCAA CTCCTGCAATC TCTATTCTCAG TGCATATATTA GTACCAATAC TTGTCCAACA ACAAAATGTA CACGTGCTTG TTAA |
| 156 | Lacticin 481 (Lactococcin DR) | Lantibiotic | MKEQNSFNL LQEVTESEL DLILGAKGG SGVIHTISHE CNMNSWQF VFTCCS | Lactococcus lactis subsp. lactis (Streptococcus lactis) | 157 | ATGAAAGAAC AAAACTCTTTT AATCTTCTTCA AGAAGTGACA GAAAGTGAAT TGGACCTTATT TTAGGTGCAA AAGGCGGCAG TGGAGTTATT CATACAATTTC TCATGAATGT AATATGAATA GCTGGCAATT TGTATTTACTT GCTGCTCTTA A |
| 158 | Lacticin Q | Unclassified | MAGFLKVV QLLAKYGSK AVQWAWAN KGKILDWLN AGQAIDWV VSKIKQILGI K | Lactococcus lactis | 159 | ATGGCAGGGT TTTTAAAAGT AGTTCAATTA CTAGCTAAAT ATGGTTCTAA AGCTGTACAA TGGGCTTGGG CAAACAAGGG TAAGATTTTA GATTGGCTTA ATGCAGGTCA GGCTATTGAT TGGGTAGTTT CGAAAATTAA GCAAATTTTA GGTATTAAGT AA |
| 160 | Lacticin Z | Unclassified | MAGFLKVV QILAKYGSK AVQWAWAN KGKILDWIN AGQAIDWV | Lactococcus lactis | 161 | ATGGCAGGGT TTTTAAAAGT AGTCCAAATT TTGGCTAAGT ATGGTTCTAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | VEKIKQILGI K | | | AGCCGTACAA TGGGCATGGG CAAATAAAGG AAAAATCTTA GATTGGATTA ATGCAGGTCA AGCTATTGAC TGGGTAGTTG AAAAGATTAA GCAAATTTTG GGTATTAAAT AA |
| 162 | Lactobin-A (Amylovorin-L471) | class IIB | MKQLNSEQL QNIIGGNRW TNAYSAALG CAVPGVKYG KKLGGVWG AVIGGVGGA AVCGLAGY VRKG | Lactobacillus amylovorus | 163 | ATGAAACAAT TGAATTCAGA ACAATTACAA AATATTATCG GTGGAAATAG ATGGACTAAT GCATACAGCG CAGCTTTGGG ATGCGCTGTC CCTGGAGTTA AATATGGAAA AAAACTTGGT GGCGTATGGG GTGCTGTAAT TGGTGGCGTA GGCGGTGCAG CAGTCTGTGG CTTGGCGGGT TATGTTCGTA AAGGCTAA |
| 164 | Lactocin-S | Lantibiotic | MKTEKKVL DELSLHASA KMGARDVE SSMNADSTP VLASVAVSM ELLPTASVL YSDVAGCFK YSAKHHC | Lactobacillus sakei L45 | 165 | ATGAAAACAG AAAAAAAGGT TTTAGATGAA CTGAGCTTAC ACGCTTCTGC AAAAAATGGGA GCACGTGATG TTGAATCCAG CATGAATGCA GACTCAACAC CAGTTTTAGC ATCAGTCGCT GTATCCATGG AATTATTGCC AACTGCGTCT GTTCTTTATTC GGATGTTGCA GGTTGCTTCA AATATTCTGC AAAACATCAT TGTTAG |
| 166 | Lactococc in 972 | Unclassified | MKTKSLVLA LSAVTLFSA GGIVAQAEG TWQHGYGV SSAYSNYHH GSKTHSATV VNNNTGRQ GKDTQRAG VWAKATVG RNLTEKASF YYNFW | Lactococcus lactis subsp. lactis (Streptococcus lactis) | 167 | ATGAAAACCA AGTCTCTCGT ATTGGCATTA TCTGCGGTTA CGTTATTCTCT GCCGGAGGAA TTGTAGCTCA AGCTGAAGGA ACATGGCAAC ATGGATATGG TGTTAGTTCG GCATATTCAA ATTATCATCAT GGTAGCAAAA CTCATTCAGCC |

TABLE 1.2-continued

Exemplary Bacteriocins

| Poly-peptide SEQ ID NO: | Name | Class | Poly-peptide Sequence | Organism of origin | Poly-nucleo-tide SEQ ID NO: | Poly-nucleo-tide Sequence |
|---|---|---|---|---|---|---|
| | | | | | | ACAGTTGTAA ATAATAATAC TGGCCGACAA GGTAAGGATA CACAACGTGC CGGTGTTTGG GCAAAAGCTA CTGTTGGACG TAACTTAACT GAAAAAGCTT CATTTTATTAT AACTTTTGGT AA |
| 168 | Lactococcin-A | Unclassified | MKNQLNFNI VSDEELSEA NGGKLTFIQ STAAGDLYY NTNTHKYV YQQTQNAFG AAANTIVNG WMGGAAGG FGLHH | Lactococcus lactis subsp. cremoris (Streptococcus cremoris) | 169 | ATGAAAAATC AATTAAATTTT AATATTGTTTC AGATGAAGAA CTTTCAGAAG CTAACGGAGG AAAATTAACA TTTATTCAATC GACAGCGGCT GGAGATTTAT ATTACAATAC TAATACACAC AAATATGTTT ACCAACAAAC TCAAAACGCT TTTGGGGCTG CTGCTAATAC CATTGTTAAT GGATGGATGG GTGGCGCTGC TGGAGGTTTC GGGTTGCACC ATTGA |
| 170 | Lactococcin-B | Unclassified | MKNQLNFNI VSDEELAEV NGGSLQYV MSAGPYTW YKDTRTGKT ICKQTIDTAS YTFGVMAE GWGKTFH | Lactococcus lactis subsp. cremoris (Streptococcus cremoris) | 171 | ATGAAAAATC AATTAAATTTT AATATTGTTTC TGATGAAGAA CTTGCAGAAG TTAATGGAGG AAGCTTGCAG TATGTTATGA GTGCTGGACC ATATACTTGG TATAAAGATA CTAGAACAGG AAAAACAATA TGTAAACAGA CAATTGACAC AGCAAGTTAT ACATTTGGTG TAATGGCAGA AGGATGGGA AAAACATTCC ACTAA |
| 172 | Lactocyclicin Q | Unclassified | MKLIDHLGA PRWAVDTIL GAIAVGNLA SWVLALVPG PGWAVKAG LATAAAIVK HQGKAAAA AW | Lactococcus sp. QU 12 | 173 | ATGAAATTAA TTGATCATTTA GGTGCTCCAA GATGGGCCGT TGATACTATTT TAGGTGCAAT CGCAGTTGGG AACTTAGCAA GTTGGGTTCT AGCGCTTGTC CCTGGTCCAG |

TABLE 1.2-continued

Exemplary Bacteriocins

| Poly-peptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGTGGGCAGT AAAAGCTGGT TTAGCAACTG CTGCTGCCAT CGTTAAACAT CAAGGTAAAG CTGCCGCTGC TGCTTGGTAA |
| 174 | Laterosporulin | Unclassified | MACQCPDAI SGWTHTDY QCHGLENK MYRHVYAIC MNGTQVYC RTEWGSSC | Brevibacillus sp. GI-9 | 175 | ATGGCTTGCC AATGTCCAGA TGCGATCTCA GGTTGGACGC ATACAGATTA CCAGTGTCAC GGTTTGGAGA ATAAAATGTA TAGACATGTT TATGCAATTT GCATGAACGG TACTCAAGTA TATTGCAGAA CAGAGTGGGG TAGCAGCTGC TAG |
| 176 | Leucocin N | class IId | MNKEYNSIS NFKKITNKD LQNINGGFIG RAIGDFVYF GAKGLRESG KLLNYYYKH KH | Leuconostoc pseudo mesenteroides | 177 | ATGAATAAAG AATATAATAG CATTAGCAAT TTTAAAAAAA TTACTAATAA AGACTTGCAA AACATAAATG GTGGATTTATT GGTAGGGCAA TAGGTGACTT TGTGTACTTTG GAGCGAAGGG ACTAAGAGAA TCTGGTAAAC TACTTAATTAT TACTATAAGC ATAAGCATTG A |
| 178 | Leucocin Q | class IId | MKNQLMSFE VISEKELSTV QGGKGLGKL IGIDWLLGQ AKDAVKQY KKDYKRWH | Leuconostoc pseudo-mesenteroides | 179 | ATGAAAAATC AGTTAATGTC TTTCGAAGTG ATATCAGAAA AAGAATTGTC CACGGTACAA GGTGGCAAAG GCTTAGGTAA ACTCATAGGA ATTGATTGGC TTTTGGGTCA AGCTAAGGAC GCTGTTAAAC AGTACAAGAA GGATTACAAA CGTTGGCACT AA |
| 180 | Leucocin-A (Leucocin A-UAL 187) | class IIA/YG NGV | MMNMKPTE SYEQLDNSA LEQVVGGK YYGNGVHC TKSGCSVNW GEAFSAGVH RLANGGNF W | Leuconostoc gelidum | 181 | ATGATGAACA TGAAACCTAC GGAAAGCTAT GAGCAATTGG ATAATAGTGC TCTCGAACAA GTCGTAGGAG GTAAGTATTA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGGTAACGGA GTTCATTGCA CAAAAAGTGG TTGTTCTGTAA ACTGGGGAGA AGCCTTTTCA GCTGGAGTAC ATCGTTTAGC AAATGGTGGA AATGGTTTCT GGTAA |
| 182 | Leucocin-B (Leucocin B-Ta11a) | class IIA/YG NGV | MNNMKSAD NYQQLDNN ALEQVVGGK YYGNGVHC TKSGCSVNW GEAFSAGVH RLANGGNGF W | Leuconostoc carnosum | 183 | ATGAATAACA TGAAATCTGC GGATAATTAT CAGCAATTGG ATAATAATGC TCTCGAACAA GTCGTAGGAG GTAAGTATTA TGGTAACGGA GTTCATTGCA CAAAAAGTGG TTGTTCTGTAA ACTGGGGAGA AGCCTTTTCA GCTGGAGTAC ATCGTTTAGC AAATGGTGGA AATGGTTTCT GGTAA |
| 184 | Leucocyclicin Q | Unclassified tied | MFLVNQLGI SKSLANTILG AIAVGNLAS WLLALVPGP GWATKAAL ATAETIVKH EGKAAAIAW | Leuconostoc mesenteroides | 185 | ATGTTCTTGGT AAATCAGTTA GGGATTTCAA AATCGTTAGC TAATACTATTC TTGGTGCAAT TGCTGTTGGT AATTTGGCCA GTTGGTTATTA GCTTTGGTTCC TGGTCCGGGT TGGGCAACAA AAGCAGCACT TGCGACAGCT GAAACAATTG TGAAGCATGA AGGAAAAGCA GCTGCTATTG CGTGGTAA |
| 186 | Lichenicidin A1 | Lantibiotic (two-peptide) | MSKKEMILS WKNPMYRT ESSYHPAGNI LKELQEEEQ HSIAGGTITL STCAILSKPL GNNGYLCTV TKECMPSCN | Bacillus licheniformis (strain DSM 13/ATCC 14580) | 187 | ATGTCAAAAA AGGAAATGAT TCTTTCATGGA AAAATCCTAT GTATCGCACT GAATCTTCTTA TCATCCAGCA GGGAACATCC TTAAAGAACT CCAGGAAGAG GAACAGCACA GCATCGCCGG AGGCACAATC ACGCTCAGCA CTTGTGCCATC TTGAGCAAGC CGTTAGGAAA TAACGGATAC CTGTGTACAG |

TABLE 1.2-continued

Exemplary Bacteriocins

| Poly-peptide SEQ ID NO: | Name | Class | Poly-peptide Sequence | Organism of origin | Poly-nucleotide SEQ ID NO: | Poly-nucleotide Sequence |
|---|---|---|---|---|---|---|
| | | | | | | TGACAAAGA ATGCATGCCA AGCTGTAACT AA |
| 188 | Linocin M18 | Unclassified | MNNLYRELA PIPGPAWAEI EEEARRTFK RNIAGRRIV DVAGPTGFE TSAVTTGHI RDVQSETSG LQVKQRIVQ EYIELRTPFT VTRQAIDDV ARGSGDSD WQPVKDAA TTIAMAEDR AILHGLDAA GIGGIVPGSS NAAVAIPDA VEDFADAVA QALSVLRTV GVDGPYSLL LSSAEYTKV SESTDHGYPI REHLSRQLG AGEIIWAPAL EGALLVSTR GGDYELHLG QDLSIGYYS HDSETVELY LQETFGFLA LTDESSVPLS L | Brevibacterium linens | 189 | GTGAATAACC TCTATCGCGA GCTTGCCCCC ATCCCCGGCC CGGCCTGGGC GGAGATCGAG GAGGAGGCTC GACGGACATT CAAACGCAAT ATCGCCGGCC GCCGGATCGT CGATGTCGCA GGGCCCACGG GCTTCGAGAC CTCCGCGGTG ACCACTGGCC ACATCCGAGA CGTCCAGTCG GAGACGAGCG GACTGCAGGT TAAGCAGCGC ATCGTGCAGG AATACATCGA GCTGCGGACC CCATTCACCGT GACTCGGCAG GCCATCGATG ACGTGGCCCG CGGGTCCGGT GACTCGGACT GGCAGCCCGT CAAGGATGCG GCCACGACGA TCGCGATGGC TGAAGATCGG GCCATTCTCCA CGGGCTCGAT GCGGCCGGGA TCGGCGGAAT CGTTCCCGGC AGCTCGAATG CCGCAGTGGC CATCCCCGAC GCCGTCGAGG ACTTCGCGGA CGCCGTCGCC CAGGCGCTGA GTGTGCTGCG CACGGTGGGA GTCGACGGGC CCTACAGCCT GTTGCTCTCCT CCGCGGAGTA CACCAAGGTC TCCGAGTCCA CCGACCACGG CTACCCGATC CGCGAGCACC TCTCCCGGCA GCTCGGCGCC GGAGAGATCA TCTGGGCGCC CGCGCTCGAA GGGGCGCTGC TCGTCTCCAC GCGCGGGGGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GACTACGAGC TCCACCTCGG CCAGGACCTG TCGATCGGTT ACTACAGCCA CGACAGCGAG ACCGTCGAAC TCTATCTGCA GGAGACCTTC GGATTCCTCG CGCTGACCGA CGAATCCAGT GTGCCTTTGA GCCTCTGA |
| 190 | Listeriocin 743A | Class IIa | MKKAALKFII VIAILGFSFSF FSIQSEAKSY GNGVQCNK KKCWVDWG SAISTIGNNS AANWATGG AAGWKS | Listeria innocua | 191 | TTGAAGAAGG CAGCGTTAAA ATTTATTATTG TTATTGCTATT CTAGGTTTCA GTTTTTCTTTC TTTAGCATAC AATCTGAAGC TAAATCTTATG GAAATGGAGT TCAGTGTAAT AAGAAAAAAT GTTGGGTAGA TTGGGGTAGT GCTATAAGTA CTATTGGAAA TAATTCTGCA GCGAATTGGG CTACAGGTGG AGCAGCTGGT TGGAAAAGCT GA |
| 192 | Mersacidin | Lantibiotic, type B | MSQEAIIRS WKDPFSREN STQNPAGNP FSELKEAQM DKLVGAGD MEAACTFTL PGGGGVCTL TSECIC | Bacillus sp. (strain HIL-Y85/54728) | 193 | ATGAGTCAAG AAGCTATCAT TCGTTCATGG AAAGATCCTT TTTCCCGTGA AAATTCTACA CAAAATCCAG CTGGTAACCC ATTCAGTGAG CTGAAAGAAG CACAAATGGA TAAGTTAGTA GGTGCGGGAG ACATGGAAGC AGCATGTACT TTTACATTGCC TGGTGGCGGC GGTGTTTGTA CTCTAACTTCT GAATGTATTT GTTAA |
| 194 | Mesentericin Y105 | class IIA/YG NGV | MTNMKSVE AYQQLDNQ NLKKVVGG KYYGNGVH CTKSGCSVN WGEAASAGI HRLANGGN GFW | Leuconostoc mesenteroides | 195 | ATGACGAATA TGAAGTCTGT GGAAGCATAT CAGCAATTAG ATAACCAGAA TCTCAAGAAA GTTGTTGGTG GAAAGTATTA TGGGAATGGT GTTCACTGTA CAAAAAGTGG |

TABLE 1.2-continued

Exemplary Bacteriocins

| Poly-peptide SEQ ID NO: | Name | Class | Poly-peptide Sequence | Organism of origin | Poly-nucleo-tide SEQ ID NO: | Poly-nucleo-tide Sequence |
|---|---|---|---|---|---|---|
| | | | | | | ATGCTCTGTTA ACTGGGGAGA AGCTGCCTCA GCTGGCATAC ATCGTTTGGC CAATGGTGGA AATGGATTTT GGTAA |
| 196 | Michiganin-A | Lantibiotic | MNDILETET PVMVSPRW DMLLDAGE DTSPSVQTQI DAEFRRVVS PYMSSSGWL CTLTIECGTII CACR | Clavibacter michiganensis subsp. michiganensis | 197 | ATGAACGACA TCCTCGAGAC GGAGACCCCC GTCATGGTCA GCCCCCGGTG GGACATGCTG CTCGACGCGG GCGAGGACAC CAGCCCGTCC GTCCAGACCC AGATCGACGC GGAGTTCCGT CGCGTCGTGA GCCCGTACAT GTCCAGCAGC GGCTGGCTCT GCACGCTCAC CATCGAATGT GGCACCATCA TCTGCGCGTG TCGCTGA |
| 198 | Microcin B17 (MccB17) | Unclassified | MELKASEFG VVLSVDALK LSRQSPLGV GIGGGGGGG GGGSCGGQ GGGCGGCSN GCSGGNGGS GGSGSHI | Escherichia coli | 199 | ATGGAATTAA AAGCGAGTGA ATTTGGTGTA GTTTTGTCCGT TGATGCTCTTA AATTATCACG CCAGTCTCCAT TAGGTGTTGG CATTGGTGGT GGTGGCGGCG GCGGCGGCGG CGGTAGCTGC GGTGGTCAAG GTGGCGGTTG TGGTGGTTGC AGCAACGGTT GTAGTGGTGG AAACGGTGGC AGCGGCGGAA GTGGTTCACA TATC |
| 200 | Microcin C7 | Unclassified | MRTGNAN | Escherichia coli | 201 | ATGCGTACTG GTAATGCAAA CTAA |
| 202 | Microcin E492 | Unclassified | MREISQKDL NLAFGAGET DPNTQLLND LGNNMAWG AALGAPGGL GSAALGAAG GALQTVGQ GLIDHGPVN VPIPVLIGPS WNGSGSGY NSATSSSGS GS | Klebsiella pneumoniae | 203 | ATGAGAGAAA TTAGTCAAAA GGACTTAAAT CTTGCTTTTGG TGCAGGAGAG ACCGATCCAA ATACTCAACTT CTAAACGACC TTGGAAATAA TATGGCATGG GGTGCTGCTC TTGGCGCTCCT GGCGGATTAG GATCAGCAGC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TTTGGGGGCC GCGGGAGGTG CATTACAAAC TGTAGGGCAA GGATTAATTG ACCATGGTCC TGTAAATGTC CCCATCCCTGT ACTCATCGGG CCAAGCTGGA ATGGTAGCGG TAGTGGTTAT AACAGCGCAA CATCCAGTTCC GGTAGTGGTA GTTAA |
| 204 | Microcin H47 | Unclassified | MREITESQL RYISGAGGA PATSANAAG AAAIVGALA GIPGGPLGV VVGAVSAGL TTAIGSTVGS GSASSSAGG GS | Escherichia coli | 205 | ATGCGAGAAA TAACAGAATC ACAGTTAAGA TATATTTCCGG GGCGGGAGGT GCGCCAGCGA CTTCAGCTAAT GCCGCAGGTG CTGCAGCTAT TGTTGGAGCT CTCGCCGGAA TACCTGGTGG TCCACTTGGG GTTGTAGTTG GAGCCGTATC TGCCGGTTTG ACAACAGCAA TTGGCTCGAC CGTGGGAAGT GGTAGTGCCA GTTCTTCTGCT GGTGGCGGTA GCTAA |
| 206 | Microcin J25 | Unclassified | MIKHFHFNK LSSGKKNNV PSPAKGVIQI KKSASQLTK GGAGHVPEY FVGIGTPISF YG | Escherichia coli | 207 | ATGATTAAGC ATTTTCATTTT AATAAACTGT CTTCTGGTAA AAAAAATAAT GTTCCATCTCC TGCAAAGGGG GTTATACAAA TAAAAAAATC AGCATCGCAA CTCACAAAAG GTGGTGCAGG ACATGTGCCT GAGTATTTTGT GGGGATTGGT ACACCTATAT CTTTCTATGGC TGA |
| 208 | Microcin-24 | Unclassified | MYMRELDR EELNCVGGA GDPLADPNS QIVRQIMSN AAWGPPLVP ERFRGMAVG AAGGVTQT VLQGAAAH MPVNVPIPK VPMGPSWN GSKG | Escherichia coli | 209 | ATGTATATGA GAGAGTTAGA TAGAGAGGAA TTAAATTGCG TTGGTGGGGC TGGAGATCCG CTTGCAGATC CTAATTCCCA AATTGTAAGA CAGATAATGT CTAATGCGGC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ATGGGGCCCG CCTTTGGTGCC AGAGCGGTTT AGGGGAATGG CTGTTGGAGC CGCAGGTGGG GTTACGCAGA CAGTTCTTCAA GGAGCAGCAG CTCATATGCC GGTTAATGTC CCTATACCTA AAGTTCCGAT GGGACCCTCA TGGAACGGAA GTAAAGGATA A |
| 210 | Mundticin KS | Unclassified | MSQVVGGK YYGNGVSC NKKGCSVD WGKAIGIIGN NSAANLATG GAAGWKS | Enterococcus mundtii | 211 | ATGTCACAGG TAGTAGGTGG AAAATACTAC GGTAATGGAG TCTCATGTAAT AAAAAAGGGT GCAGTGTTGA TTGGGGAAAA GCGATTGGCA TTATTGGAAA TAATTCTGCTG CGAATTTAGC TACTGGTGGA GCAGCTGGTT GGAAAAGTTA A |
| 212 | Mundticin L | class IIA/YG NGV | MKKLTSKE MAQVVGGK YYGNGLSCN KKGCSVDW GKAIGIIGNN SAANLATGG AAGWKS | Enterococcus mundtii | 213 | TTGAAGAAAT TAACATCAAA AGAAATGGCA CAAGTAGTAG GTGGGAAATA CTACGGTAAT GGATTATCAT GTAATAAAAA AGGGTGCAGT GTTGATTGGG GAAAAGCTAT TGGCATTATT GGAAATAATT CTGCTGCGAA TTTAGCTACTG GTGGAGCAGC TGGTTGGAAA AGTTAA |
| 214 | Mutacin 1140 (Mutacin III) | Lantibiotic | MSNTQLLEV LGTETFDVQ EDLFAFDTT DTTIVASND DPDTRFKSW SLCTPGCAR TGSFNSYCC | Streptococcus mutans | 215 | ATGTCAAACA CACAATTATT AGAAGTCCTT GGTACTGAAA CTTTTGATGTT CAAGAAGATC TCTTTGCTTTT GATACAACAG ATACTACTATT GTGGCAAGCA ACGACGATCC AGATACTCGT TTCAAAAGTT GGAGCCTTTG TACGCCTGGT TGTGCAAGGA CAGGTAGTTT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CAATAGTTAC TGTTGCTGA |
| 216 | Mutacin-2 | Lantibiotic | MNKLNSNA VVSLNEVSD SELDTILGGN RWWQGVVP TVSYECRMN SWQHVFTCC | *Streptococcus mutans* | 217 | ATGAACAAGT TAAACAGTAA CGCAGTAGTT TCTTTGAATG AAGTTTCAGA TTCTGAATTG GATACTATTT GGGTGGTAAT CGTTGGTGGC AAGGTGTTGT GCCAACGGTC TCATATGAGT GTCGCATGAA TTCATGGCAA CATGTTTTCAC TTGCTGTTAA |
| 218 | Nisin A | Lantibiotic | MSTKDFNLD LVSVSKKDS GASPRITSISL CTPGCKTGA LMGCNMKT ATCHCSIHV SK | *Lactococcus lactis* subsp. *lactis* (*Streptococcus lactis*) | 219 | ATGAGTACAA AAGATTTTAA CTTGGATTTG GTATCTGTTTC GAAGAAAGAT TCAGGTGCAT CACCACGCAT TACAAGTATTT CGCTATGTAC ACCCGGTTGT AAAACAGGAG CTCTGATGGG TTGTAACATG AAAACAGCAA CTTGTCATTGT AGTATTCACG TAAGCAAATA A |
| 220 | Nisin F | Lantibiotic | MSTKDFNLD LVSVSKKDS GASPRITSISL CTPGCKTGA LMGCNMKT ATCNCSVHV SK | *Lactococcus lactis* | 221 | ATGAGTACAA AAGATTTCAA CTTGGATTTG GTATCTGTTTC GAAGAAAGAT TCAGGTGCAT CACCACGCAT TACAAGTATTT CGCTATGTAC ACCCGGTTGT AAAACAGGAG CTCTGATGGG TTGTAACATG AAAACAGCAA CTTGTAATTGT AGCGTTCACG TAAGCAAA |
| 222 | Nisin Q | Lantibiotic | MSTKDFNLD LVSVSKTDS GASTRITSIS LCTPGCKTG VLMGCNLKT ATCNCSVHV SK | *Lactococcus lactis* | 223 | ATGAGTACAA AAGATTTCAA CTTAGATTTG GTATCTGTTTC AAAAACAGAT TCTGGCGCTTC AACACGTATT ACCAGCATTT CGCTTTGTAC ACCAGGTTGT AAAACAGGTG TTCTGATGGG ATGTAACCTG AAAACAGCAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CTTGTAATTGT AGCGTTCACG TAAGCAAATA A |
| 224 | Nisin U | Lantibiotic | MNNEDFNL DLIKISKENN SGASPRITSK SLCTPGCKT GILMTCPLK TATCGCHFG | Streptococcus uberis | 225 | ATGAACAATG AAGATTTTAA TTTGGATCTCA TCAAAATCTC AAAGGAAAAC AACTCAGGAG CTTCACCTCGA ATAACTAGTA AATCATTATGT ACTCCTGGAT GTAAGACGGG TATTTTGATGA CTTGTCCACTA AAAACTGCAA CCTGTGGTTG TCATTTTGGAT AA |
| 226 | Nisin Z | Lantibiotic | MSTKDFNLD LVSVSKKDS GASPRITSISL CTPGCKTGA LMGCNMKT ATCNCSIHV SK | Lactococcus lactis subsp. lactis (Streptococcus lactis) | 227 | ATGAGTACAA AAGATTTTAA CTTGGATTTG GTATCTGTTTC GAAGAAAGAT TCAGGTGCAT CACCACGCAT TACAAGTATTT CGCTATGTAC ACCCGGTTGT AAAACAGGAG CTCTGATGGG TTGTAACATG AAAACAGCAA CTTGTAATTGT AGTATTCACG TAAGCAAATA A |
| 228 | Nukacin ISK-1 | Lantibiotic | MENSKVMK DIEVANLLE EVQEDELNE VLGAKKKSG VIPTVSHDC HMNSFQFVF TCCS | Staphylococcus warneri | 229 | ATGGAAAATT CTAAAGTTAT GAAGGACATT GAAGTAGCAA ATTTATTAGA AGAGGTTCAA GAAGATGAAT TGAATGAAGT CTTAGGAGCT AAGAAAAAGT CAGGAGTAAT CCCAACTGTG TCACACGATT GCCATATGAA TTCTTTCCAAT TTGTATTTACT TGTTGTTCATA A |
| 230 | Paenicidin A | Lantibiotic | MAENLFDLD IQVNKSQGS VEPQVLSIV ACSSGCGSG KTAASCVET CGNRCFTNV GSLC | Paenibacillus polymyxa (Bacillus polymyxa) | 231 | ATGGCTGAAA ACTTATTTGAT CTGGACATTC AAGTAAACAA ATCTCAAGGT TCTGTAGAGC CTCAGGTTCT GAGCATTGTT GCATGTTCTA GCGGATGTGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TAGCGGTAAA ACAGCTGCCA GTTGTGTTGA AACTTGTGGC AACCGGTGCT TTACTAACGTT GGTTCACTCT GCTAA |
| 232 | Pediocin PA-1 (Pediocin ACH) | class IIA/YG NGV | MKKIEKLTE KEMANIIGG KYYGNGVT CGKHSCSVD WGKATTCII NNGAMAWA TGGHQGNH KC | Pediococcus acidilactici | 233 | ATGAAAAAAA TTGAAAAATT AACTGAAAAA GAAATGGCCA ATATCATTGG TGGTAAATAC TACGGTAATG GGGTTACTTG TGGCAAACAT TCCTGCTCTGT TGACTGGGGT AAGGCTACCA CTTGCATAATC AATAATGGAG CTATGGCATG GGCTACTGGT GGACATCAAG GTAATCATAA ATGCTAG |
| 234 | Penocin A | class IIA/YG NGV | MTEIKVLND KELKNVVGG KYYGNGVH CGKKTCYVD WGQATASIG KIIVNGWTQ HGPWAHR | Pediococcus pentosaceus (strain ATCC 25745/183-iw) | 235 | ATGACTGAAA TTAAAGTACT AAACGATAAG GAACTAAAAA ATGTCGTAGG AGGAAAGTAT TACGGTAACG GAGTGCATTG TGGTAAAAAG ACTTGCTATGT GGACTGGGGA CAAGCTACAG CTAGCATTGG AAAAATTATA GTGAACGGAT GGACACAACA CGGGCCTTGG GCACATAGAT AA |
| 236 | Pep5 | Lantibiotic | MKNNKNLF DLEIKKETSQ NTDELEPQT AGPAIRASV KQCQKTLKA TRLFTVSCK GKNGCK | Staphylococcus epidermidis | 237 | ATGAAAAATA ACAAAAATTT ATTTGATTTAG AAATTAAAAA AGAAACAAGT CAAAACACTG ATGAACTTGA ACCTCAAACT GCTGGACCAG CGATTAGAGC TTCTGTGAAA CAATGTCAGA AAACTTTGAA AGCTACGCGT TTATTTACAGT GTCTTGCAAA GGAAAAAACG GATGTAAATA G |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 238 | Piscicolin 126 | class IIA/YG NGV | MKTVKELSV KEMQLTTGG KYYGNGVS CNKNGCTV DWSKAIGIIG NNAAANLTT GGAAGWNK G | Carnobacteriumum maltaromaticum (Carnobacterium piscicola) | 239 | ATGAAAACTG TTAAAGAACT TAGCGTTAAA GAAATGCAAC TAACTACAGG AGGTAAGTAT TACGGAAATG GCGTTTCCTGT AATAAAAATG GTTGTACTGT AGATTGGAGC AAAGCTATTG GGATTATAGG AAACAATGCA GCAGCAAATT TGACTACAGG TGGAGCCGCT GGTTGGAACA AAGGATAA |
| 240 | Plantaricin 1.25 β | Unclassified | MYKELTVDE LALIDGGKK KKKKVACT WGNAATAA ASGAVXGIL GGPTGALAG AIWGVSQCA SNNLHGMH | Lactobacillus plantarum | 241 | ATGTATAAAG AATTAACAGT TGATGAATTA GCATTGATTG ATGGAGGAAA AAAGAAGAAG AAAAAAGTAG CTTGTACTTGG GGAAATGCAG CAACAGCCGC TGCTTCTGGT GCAGTTANGG GTATTCTTGGT GGGCCTACTG GTGCACTGGC TGGAGCTATC TGGGGCGTTT CACAATGCGC GTCTAACAAC TTACACGGCA TGCACTAA |
| 242 | Plantaricin 423 | class IIa | MMKKIEKLT EKEMANIIG GKYYGNGV TCGKHSCSV NWGQAFSCS VSHLANFGH GKC | Lactobacillus plantarum | 243 | ATGATGAAAA AAATTGAAAA ATTAACTGAA AAAGAAATGG CCAATATCATT GGTGGTAAAT ACTATGGTAA TGGGGTTACT TGTGGTAAAC ATTCCTGCTCT GTTAACTGGG GCCAAGCATT TTCTTGTAGTG TGTCACATTTA GCTAACTTCG GTCATGGAAA GTGCTAA |
| 244 | Plantaricin ASM1 | Unclassified | MSKLVKTLT VDEISKIQTN GGKPAWCW YTLAMCGA GYDSGTCDY MYSHCFGVK HSSGGGGSY HC | Lactobacillus plantarum | 245 | ATGAGTAAAC TAGTTAAAAC ATTAACTGTC GATGAAATCT CTAAGATTCA AACCAATGGT GGAAAACCTG CATGGTGTTG GTACACATTG GCAATGTGCG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GTGCTGGTTA TGATTCAGGC ACTTGTGATT ATATGTATTCA CACTGCTTTG GTGTAAAACA CTCTAGCGGT GGTGGCGGTA GCTACCATTG TTAG |
| 246 | Plantaricin E | Unclassified | MLQFEKLQY SRLPQKKLA KISGGFNRG GYNFGKSVR HVVDAIGSV AGIRGILKSI R | Lactobacillus plantarum | 247 | ATGCTACAGT TTGAGAAATT ACAATATTCC AGGTTGCCGC AAAAAAAGCT TGCCAAAATA TCTGGTGGTT TAATCGGGGC GGTTATAACT TTGGTAAAAG TGTTCGACAT GTTGTTGATG CAATTGGTTC AGTTGCAGGC ATTCGTGGTA TTTTGAAAAG TATTCGTTAA |
| 248 | Plantaricin F | class IIb | MKKFLVLRD RELNAISGG VFHAYSARG VRNNYKSAV GPADWVISA VRGFIHG | Lactobacillus plantarum | 249 | ATGAAAAAAT TTCTAGTTTTG CGTGACCGTG AATTAAATGC TATTTCAGGT GGCGTTTTCC ATGCCTATAG CGCGCGTGGC GTTCGGAATA ATTATAAAAG TGCTGTTGGG CCTGCCGATT GGGTCATTAG CGCTGTCCGA GGATTCATCC ACGGATAG |
| 250 | Plantaricin J | class IIb | MTVNKMIK DLDVVDAFA PISNNKLNG VVGGGAWK NFWSSLRKG FYDGEAGRA IRR | Lactobacillus plantarum | 251 | ATGACTGTGA ACAAAATGAT TAAGGATTTG GATGTAGTAG ATGCATTTGC ACCTATTTCTA ATAATAAGTT GAACGGGGTT GTTGGGGGAG GCGCTTGGAA AAATTTCTGG TCTAGTTTAA GAAAAGGATT TTATGATGGC GAAGCTGGCA GAGCAATCCG TCGTTAA |
| 252 | Plantaricin K | Unclassified | MKIKLTVLN EFEELTADA EKNISGGRR SRKNGIGYAI GYAFGAVER AVLGGSRDY NK | Lactobacillus plantarum | 253 | ATGAAAATTA AATTAACTGTT TTAAATGAAT TTGAAGAATT AACTGCTGAC GCTGAAAAGA ATATTTCTGGT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGCCGTCGGA GTCGTAAAAA TGGAATTGGA TACGCTATTG GTTATGCGTTT GGCGCGGTTG AACGGGCCGT GCTTGGTGGT TCAAGGGATT ATAATAAGTG A |
| 254 | Plantaricin NC8 α | Unclassified | MDKFEKIST SNLEKISGG DLTTKLWSS WGYYLGKK ARWNLKHP YVQF | Lactobacillus plantarum | 255 | ATGGATAAAT TTGAAAAAAT TAGTACATCT AACCTAGAAA AGATCTCTGG CGGTGATTTA ACAACCAAGT TATGGAGCTC TTGGGGATAT TATCTTGGCA AGAAAGCACG TTGGAATTTA AAGCACCCAT ATGTTCAATTT |
| 256 | Plantaricin NC8 β | Unclassified | MNNLNKFST LGKSSLSQIE GGSVPTSVY TLGIKILWSA YKHRKTIEK SFNKGFYH | Lactobacillus plantarum | 257 | ATGAATAACT TGAATAAATT TTCTACTCTAG GCAAGAGTAG CTTGTCTCAAA TTGAGGGCGG ATCAGTCCCA ACTTCAGTAT ATACGCTTGG AATTAAAATT CTATGGTCTG CGTATAAGCA TCGCAAAACG ATTGAAAAAA GTTTTAATAA AGGCTTTTATC ATTAA |
| 258 | Plantaricin S α | Unclassified | MNNALSFEQ QFTDFSTLSD SELESVEGG RNKLAYNM GHYAGKATI FGLAAWALL A | Lactobacillus plantarum | 259 | ATGAATAACG CATTAAGTTTT GAACAACAAT TTACAGACTTC AGCACCTTAT CGGACTCTGA ATTAGAATCC GTTGAGGGTG GCCGAAATAA GCTTGCATAT AATATGGGGC ATTACGCTGG TAAGGCAACC ATTTTTGGACT TGCAGCATGG GCACTCCTTG CATGA |
| 260 | Plantaricin S β | Unclassified | MDKIIKFQGI SDDQLNAVI GGKKKKQS WYAAAGDAI VSFGEGFLN AW | Lactobacillus plantarum | 261 | ATGGATAAGA TTATTAAGTTT CAAGGGATTT CTGATGATCA ATTAAATGCT GTTATCGGTG GGAAAAAGAA AAAACAATCT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TGGTACGCAG CAGCTGGTGA TGCAATCGTT AGTTTTGGTG AAGGATTTTT AAATGCTTGG TAA |
| 262 | Plantaricin W α | Lantibiotic (two-peptide) | MKISKIEAQ ARKDFFKKI DTNSNLLNV NGAKCKWW NISCDLGNN GHVCTLSHE CQVSCN | Lactobacillus plantarum | 263 | ATGAAAATTT CTAAGATTGA AGCTCAGGCT CGTAAAGATT TTTTTAAAAA AATCGATACT AACTCGAACT TATTAAATGT AAATGGTGCC AAATGCAAGT GGTGGAATAT TTCGTGTGATT TAGGAAATAA TGGCCATGTTT GTACCTTGTC ACATGAATGC CAAGTATCTT GTAACTAA |
| 264 | Plantaricin W β | Lantibiotic (two-peptide) | MTKTSRRKN AIANYLEPV DEKSINESFG AGDPEARSG IPCTIGAAVA ASIAVCPTTK CSKRCGKRK K | Lactobacillus plantarum | 265 | ATGACTAAAA CTAGTCGTCG TAAGAATGCT ATTGCTAATTA TTTAGAACCA GTCGACGAAA AAAGTATTAA TGAATCTTTTG GGGCTGGGGA TCCGGAAGCA AGATCCGGAA TTCCATGTACA ATCGGCGCAG CTGTCGCAGC ATCAATTGCA GTTTGTCCAA CTACTAAGTG TAGTAAACGT TGTGGCAAGC GTAAGAAATA A |
| 266 | Plantaricin-A | Unclassified | MKIQIKGMK QLSNKEMQK IVGGKSSAY SLQMGATAI KQVKKLFKK WGW | Lactobacillus plantarum (strain ATCC BAA-793/ NCIMB 8826/ WCFS1) | 267 | ATGAAAATTC AAATTAAAGG TATGAAGCAA CTTAGTAATA AGGAAATGCA AAAAATAGTA GGTGGAAAGA GTAGTGCGTA TTCTTTGCAGA TGGGGGCAAC TGCAATTAAA CAGGTAAAGA AACTGTTTAA AAAATGGGGA TGGTAA |
| 268 | Propionicin SM1 | Unclassified | MNKTHKMA TLVIAAILAA GMTAPTAYA DSPGNTRITA SEQSVLTQIL GHKPTQTEY | Propioni bacterium jensenii | 269 | ATGAACAAAA CACACAAAAT GGCGACGCTG GTAATTGCCG CGATCTTGGC CGCCGGAATG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | NRYVETYGS VPTEADINA YIEASESEGS SSQTAAHDD STSPGTSTEI YTQAAPARF SMFFLSGTW ITRSGVVSLS LKPRKGGIG NEGDERTW KTVYDKFHN AGQWTRYK NNGVDASM KKQYMCHF KYGMVKTP WNLEPHKK AADVSPVKC N | | | ACCGCACCAA CTGCCTATGC AGATTCTCCT GGAAACACCA GAATTACAGC CAGCGAGCAA AGCGTCCTTA CCCAGATACT CGGCCACAAA CCTACACAAA CTGAATATAA CCGATACGTT GAGACTTACG GAAGCGTACC GACCGAAGCA GACATCAACG CATATATAGA AGCGTCTGAA TCTGAGGGAT CATCAAGTCA AACGGCTGCT CACGATGACT CGACATCACC CGGCACGAGT ACCGAAATCT ACACGCAGGC AGCCCCTGCC AGGTTCTCAA TGTTTTTCCTG TCCGGAACTT GGATCACTAG GAGTGGTGTA GTATCGCTCTC CTTGAAGCCA AGGAAGGGTG GTATTGGCAA CGAGGGGGAC GAGCGTACCT GGAAGACTGT ATACGACAAA TTCCATAACG CTGGGCAATG GACACGATAC AAGAACAACG GCGTAGACGC CAGCATGAAA AAGCAGTACA TGTGCCACTTC AAGTACGGGA TGGTGAAGAC GCCATGGAAT CTGGAGCCCC ACAAGAAGGC TGCAGACGTC AGTCCAGTCA AGTGCAACTA G |
| 270 | Propionicin T1 | Unclassified | MKKTLLRSG TIALATAAAF GASLAAAPS AMAVPGGC TYTRSNRDV IGTCKTGSSG QFRIRLDCN NAPDKTSVW AKPKVMVS VHCLVGQPR SISFETK | Propionibacterium thoenii | 271 | ATGAAGAAGA CCCTCCTGCG AAGTGGAACG ATCGCACTGG CGACCGCGGC TGCATTTGGC GCATCATTGG CAGCCGCCCC ATCTGCCATG GCCGTTCCTG GTGGTTGCAC GTACACAAGA AGCAATCGCG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ACGTCATCGG TACCTGCAAG ACTGGAAGCG GCCAGTTCCG AATCCGACTT GACTGCAACA ACGCTCCAGA CAAAACTTCA GTCTGGGCCA AGCCCAAGGT AATGGTGTCG GTTCACTGTCT TGTTGGTCAA CCGAGGTCCA TCTCGTTCGA GACCAAGTGA |
| 272 | Propionicin-F | Unclassified | MNTKAVNL KSENTTKLV SYLTENQLD EFIRRIRIDG ALVEEVSQN AKQALDNTG LNGWINTDC DEGLLSDFIS KIASARWIPL AESIRPAVTD RDKYRVSC WFYQGMNI AIYANIGGV ANIIGYTEAA VATLLGAVV AVAPVVPGT PTPPKDKSS QYKEVPLAV RLSETYHEE GVRGLFDEL NYSESRMIS TLRRASTDG VLINSWNDG QDTILLKKY NFQDLQLTV RSRIVGNQTI IEECKITDGR KTLSDETV | Propionibacterium freudenreichii subsp. freudenreichii | 273 | ATGAATACCA AAGCTGTAAA TCTGAAGTCA GAAAACACGA CTAAGTTGGT GAGCTACCTT ACGGAAAATC AATTGGATGA GTTTATTAGA AGGATTCGCA TTGATGGCGC TCTTGTGGAA GAGGTCAGTC AAAATGCTAA GCAGGCCTTA GATAATACTG GGCTCAATGG CTGGATAAAT ACTGATTGCG ATGAAGGCCT TCTCTCTGATT TCATTTCAAA GATAGCAAGT GCTAGATGGA TTCCATTAGCT GAGTCAATTC GACCTGCGGT GACTGACAGG GATAAGTATC GAGTAAGTTG CTGGTTCTACC AGGGGATGAA TATAGCAATTT ACGCAAATAT CGGTGGCGTG GCCAATATTA TCGGCTATAC GGAGGCCGCA GTCGCAACAC TCCTTGGTGC AGTTGTGGCG GTAGCTCCTG TGGTCCCTGG AACTCCAACC CCTCCAAAGG ACAAGAGTTC GCAATATAAG GAGGTTCCCC TTGCCGTTCGT CTTTCCGAAA CATACCACGA AGAGGGAGTA CGAGGTCTAT TCGACGAGCT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GAACTACTCC GAGAGCCGTA TGATCTCTACT CTAAGGCGAG CATCAACCGA TGGAGTCCTA ATTAATTCTTG GAACGATGGG CAGGATACAA TTCTGCTTAAG AAGTACAATT TCCAAGACTT GCAACTGACT GTCAGGAGCC GCATTGTTGG GAATCAAACA ATAATTGAAG AATGCAAAAT CACTGATGGT AGAAAAACTC TTTCAGACGA GACTGTGTAG |
| 274 | Pyocin S1 | Unclassified | MARPIADLIH FNSTTVTAS GDVYYGPG GGTGIGPIAR PIEHGLDSST ENGWQEFES YADVGVDP RRYVPLQVK EKRREIELQF RDAEKKLEA SVQAELDKA DAALGPAKN LAPLDVINRS LTIVGNALQ QKNQKLLLN QKKITSLGA KNFLTRTAE EIGEQAVRE GNINGPEAY MRFLDREME GLTAAYNVK LFTEAISSLQI RMNTLTAAK ASIEAAAAN KAREQAAAE AKRKAEEQA RQQAAIRAA NTYAMPAN GSVVATAAG RGLIQVAQG AASLAQAIS DAIAVLGRV LASAPSVMA VGFASLTYS SRTAEQWQ DQTPDSVRY ALGMDAAK LGLPPSVNL NAVAKASGT VDLPMRLTN EARGNTTTL SVVSTDGVS VPKAVPVRM AAYNATTGL YEVTVPSTT AEAPPLILTW TPASPPGNQ NPSSTTPVVP | Pseudomonas aeruginosa | 275 | ATGGCACGAC CCATTGCTGA CCTTATCCACT TCAACTCTAC AACTGTCACG GCAAGCGGAG ACGTTTATTAC GGCCCTGGGG GAGGTACCGG CATTGGCCCC ATTGCCAGAC CTATAGAGCA CGGCTTGGAT TCGTCCACTG AAAATGGCTG GCAAGAGTTT GAAAGTTATG CTGATGTGGG CGTTGACCCC AGACGCTATG TTCCTCTTCAG GTTAAAGAAA AACGCAGGGA GATCGAGCTT CAGTTCCGAG ATGCCGAGAA AAAACTTGAG GCGTCGGTAC AAGCCGAGCT GGATAAGGCT GATGCCGCTC TTGGTCCGGC AAAGAATCTT GCACCATTGG ACGTCATCAA CCGCAGTCTG ACCATCGTTG GAAACGCCCT CCAGCAAAAG AATCAAAAAC TACTGCTGAA TCAGAAGAAG ATTACCAGCC TGGGTGCAAA GAATTTCCTTA CCCGTACGGC GGAAGAGATC GGTGAACAAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | KPVPVYEGA | | | CGGTGCGAGA |
| | | | TLTPVKATP | | | AGGCAATATT |
| | | | ETYPGVITLP | | | AACGGGCCTG |
| | | | EDLIIGFPAD | | | AAGCCTATAT |
| | | | SGIKPIYVMF | | | GCGCTTCCTC |
| | | | RDPRDVPGA | | | GACAGGGAAA |
| | | | ATGKGQPVS | | | TGGAAGGTCT |
| | | | GNWLGAAS | | | CACGGCAGCT |
| | | | QGEGAPIPSQ | | | TATAACGTAA |
| | | | IADKLRGKT | | | AACTCTTCACC |
| | | | FKNWRDFRE | | | GAAGCGATCA |
| | | | QFWIAVAND | | | GTAGTCTCCA |
| | | | PELSKQFNP | | | GATCCGCATG |
| | | | GSLAVMRD | | | AATACGTTGA |
| | | | GGAPYVRES | | | CCGCCGCCAA |
| | | | EQAGGRIKIE | | | AGCAAGTATT |
| | | | IHHKVRVAD | | | GAGGCGGCCG |
| | | | GGGVYNMG | | | CAGCAAACAA |
| | | | NLVAVTPKR | | | GGCGCGTGAA |
| | | | HIEIHKGGK | | | CAAGCAGCGG |
| | | | | | | CTGAGGCCAA |
| | | | | | | ACGCAAAGCC |
| | | | | | | GAAGAGCAGG |
| | | | | | | CCCGCCAGCA |
| | | | | | | AGCGGCGATA |
| | | | | | | AGAGCTGCCA |
| | | | | | | ATACCTATGC |
| | | | | | | CATGCCGGCC |
| | | | | | | AATGGCAGCG |
| | | | | | | TTGTCGCCAC |
| | | | | | | CGCCGCAGGC |
| | | | | | | CGGGGTCTGA |
| | | | | | | TCCAGGTCGC |
| | | | | | | ACAAGGCGCC |
| | | | | | | GCATCCCTTG |
| | | | | | | CTCAAGCGAT |
| | | | | | | CTCCGATGCG |
| | | | | | | ATTGCCGTCCT |
| | | | | | | GGGCCGGGTC |
| | | | | | | CTGGCTTCAG |
| | | | | | | CACCCTCGGT |
| | | | | | | GATGGCCGTG |
| | | | | | | GGCTTTGCCA |
| | | | | | | GTCTGACCTA |
| | | | | | | CTCCTCCCGG |
| | | | | | | ACTGCCGAGC |
| | | | | | | AATGGCAGGA |
| | | | | | | CCAAACGCCC |
| | | | | | | GATAGCGTTC |
| | | | | | | GTTACGCCCT |
| | | | | | | GGGCATGGAT |
| | | | | | | GCCGCTAAAT |
| | | | | | | TGGGGCTTCC |
| | | | | | | CCCAAGCGTA |
| | | | | | | AACCTGAACG |
| | | | | | | CGGTTGCAAA |
| | | | | | | AGCCAGCGGT |
| | | | | | | ACCGTCGATC |
| | | | | | | TGCCGATGCG |
| | | | | | | CCTGACCAAC |
| | | | | | | GAGGCACGAG |
| | | | | | | GCAACACGAC |
| | | | | | | GACCCTTTCG |
| | | | | | | GTGGTCAGCA |
| | | | | | | CCGATGGTGT |
| | | | | | | GAGCGTTCCG |
| | | | | | | AAAGCCGTTC |
| | | | | | | CGGTCCGGAT |
| | | | | | | GGCGGCCTAC |
| | | | | | | AATGCCACGA |
| | | | | | | CAGGCCTGTA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | CGAGGTTACG GTTCCCTCTAC GACCGCAGAA GCGCCGCCAC TGATCCTGAC CTGGACGCCG GCGAGTCCTC CAGGAAACCA GAACCCTTCG AGTACCACTC CGGTCGTACC GAAGCCGGTG CCGGTATATG AGGGAGCGAC CCTTACACCG GTGAAGGCTA CCCCGGAAAC CTATCCTGGG GTGATTACAC TACCGGAAGA CCTGATCATC GGCTTCCCGG CCGACTCGGG GATCAAGCCG ATCTATGTGA TGTTCAGGGA TCCGCGGGAT GTACCTGGTG CTGCGACTGG CAAGGGACAG CCCGTCAGCG GTAATTGGCT CGGCGCCGCC TCTCAAGGTG AGGGGGCTCC AATTCCAAGC CAGATTGCGG ATAAACTACG TGGTAAGACA TTCAAAAACT GGCGGGACTT TCGGGAACAA TTCTGGATAG CTGTGGCTAA TGATCCTGAG TTAAGTAAAC AGTTTAATCCT GGTAGTTTAG CTGTAATGAG AGATGGAGGG GCTCCTTATGT CAGAGAGTCA GAACAGGCTG GCGGGAGAAT AAAGATCGAA ATCCACCACA AGGTTCGAGT AGCAGATGGA GGCGGCGTTT ACAATATGGG GAACCTTGTT GCAGTAACGC CAAAACGTCA TATAGAAATC CACAAGGGAG GGAAGTGA |
| 276 | Pyocin S2 | colicin/ pyosin nuclease family | MAVNDYEP GSMVITHVQ GGGRDIIQYI PARSSYGTPP | Pseudomonas aeruginosa (strain ATCC 15692/ | 277 | ATGGCTGTCA ATGATTACGA ACCTGGTTCG ATGGTTATTA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | FVPPGPSPYV | PA01/1C/ | | CACATGTGCA |
| | | | GTGMQEYR | PRS 101/ | | GGGTGGTGGG |
| | | | KLRSTLDKS | LMG 12228) | | CGTGACATAA |
| | | | HSELKKNLK | | | TCCAGTATATT |
| | | | NETLKEVDE | | | CCTGCTCGAT |
| | | | LKSEAGLPG | | | CAAGCTACGG |
| | | | KAVSANDIR | | | TACTCCACCAT |
| | | | DEKSIVDAL | | | TTGTCCCACCA |
| | | | MDAKAKSL | | | GGACCAAGTC |
| | | | KAIEDRPAN | | | CGTATGTCGG |
| | | | LYTASDFPQ | | | TACTGGAATG |
| | | | KSESMYQSQ | | | CAGGAGTACA |
| | | | LLASRKFYG | | | GGAAGCTAAG |
| | | | EFLDRHMSE | | | AAGTACGCTT |
| | | | LAKAYSADI | | | GATAAGTCCC |
| | | | YKAQIAILK | | | ATTCAGAACT |
| | | | QTSQELENK | | | CAAGAAAAAC |
| | | | ARSLEAEAQ | | | CTGAAAAATG |
| | | | RAAAEVEAD | | | AAACCCTGAA |
| | | | YKARKANV | | | GGAGGTTGAT |
| | | | EKKVQSELD | | | GAACTCAAGA |
| | | | QAGNALPQL | | | GTGAAGCGGG |
| | | | TNPTPEQWL | | | GTTGCCAGGT |
| | | | ERATQLVTQ | | | AAAGCGGTCA |
| | | | AIANKKKLQ | | | GTGCCAATGA |
| | | | TANNALIAK | | | CATCCGCGAT |
| | | | APNALEKQK | | | GAAAAGAGTA |
| | | | ATYNADLLV | | | TCGTTGATGC |
| | | | DEIASLQARL | | | ACTCATGGAT |
| | | | DKLNAETAR | | | GCCAAAGCAA |
| | | | RKEIARQAAI | | | AATCGCTAAA |
| | | | RAANTYAM | | | GGCCATTGAG |
| | | | PANGSVVAT | | | GATCGCCCGG |
| | | | AAGRGLIQV | | | CCAATCTTTAT |
| | | | AQGAASLAQ | | | ACGGCTTCAG |
| | | | AISDAIAVLG | | | ACTTTCCTCAG |
| | | | RVLASAPSV | | | AAGTCAGAGT |
| | | | MAVGFASLT | | | CGATGTACCA |
| | | | YSSRTAEQW | | | GAGTCAGTTG |
| | | | QDQTPDSVR | | | CTGGCCAGCC |
| | | | YALGMDAA | | | GAAAATTCTA |
| | | | KLGLPPSVN | | | TGGAGAGTTC |
| | | | LNAVAKASG | | | CTGGATCGCC |
| | | | TVDLPMRLT | | | ATATGAGTGA |
| | | | NEARGNTTT | | | GCTGGCCAAA |
| | | | LSVVSTDGV | | | GCGTACAGCG |
| | | | SVPKAVPVR | | | CCGATATCTAT |
| | | | MAAYNATT | | | AAGGCGCAAA |
| | | | GLYEVTVPS | | | TCGCTATCTTG |
| | | | TTAEAPPLIL | | | AAACAAACGT |
| | | | TWTPASPPG | | | CTCAAGAGCT |
| | | | NQNPSSTTP | | | GGAGAATAAA |
| | | | VVPKPVPVY | | | GCCCGGTCAT |
| | | | EGATLTPVK | | | TGGAAGCAGA |
| | | | ATPETYPGVI | | | AGCCCAGCGA |
| | | | TLPEDLIIGFP | | | GCCGCTGCTG |
| | | | ADSGIKPIYV | | | AGGTGGAGGC |
| | | | MFRDPRDVP | | | GGACTACAAG |
| | | | GAATGKGQP | | | GCCAGGAAGG |
| | | | VSGNWLGA | | | CAAATGTCGA |
| | | | ASQGEGAPIP | | | GAAAAAGTG |
| | | | SQIADKLRG | | | CAGTCCGAGC |
| | | | KTFKNWRDF | | | TTGACCAGGC |
| | | | REQFWIAVA | | | TGGGAATGCT |
| | | | NDPELSKQF | | | TTGCCTCAACT |
| | | | NPGSLAVMR | | | GACCAATCCA |
| | | | DGGAPYVRE | | | ACGCCAGAGC |
| | | | SEQAGGRIKI | | | AGTGGCTTGA |
| | | | EIHHKVRIA | | | ACGCGCTACT |
| | | | DGGGVYNM | | | CAACTGGTTA |
| | | | GNLVAVTPK | | | CGCAGGCGAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | RHIEIHKGG K | | | CGCCAATAAG AAGAAATTGC AGACTGCAAA CAATGCCTTG ATTGCCAAGG CACCCAATGC ACTGGAGAAA CAAAAGGCAA CCTACAACGC CGATCTCCTA GTGGATGAAA TCGCCAGCCT GCAAGCACGG CTGGACAAGC TGAACGCCGA AACGGCAAGG CGCAAGGAAA TCGCTCGTCA AGCGGCGATC AGGGCTGCCA ATACTTATGCC ATGCCAGCCA ATGGCAGCGT TGTCGCCACC GCCGCAGGCC GGGGTCTGAT CCAGGTCGCA CAAGGCGCCG CATCCCTTGCT CAAGCGATCT CCGATGCGAT TGCCGTCCTG GGCCGGGTCC TGGCTTCAGC ACCCTCGGTG ATGGCCGTGG GCTTTGCCAG TCTGACCTACT CCTCCCGGAC TGCCGAGCAA TGGCAGGACC AAACGCCCGA TAGCGTTCGTT ACGCCCTGGG CATGGATGCC GCTAAATTGG GGCTTCCCCC AAGCGTAAAC CTGAACGCGG TTGCAAAAGC CAGCGGTACC GTCGATCTGC CGATGCGCCT GACCAACGAG GCACGAGGCA ACACGACGAC CCTTTCGGTG GTCAGCACCG ATGGTGTGAG CGTTCCGAAA GCCGTTCCGG TCCGGATGGC GGCCTACAAT GCCACGACAG GCCTGTACGA GGTTACGGTT CCCTCTACGA CCGCAGAAGC GCCGCCACTG ATCCTGACCT GGACGCCGGC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GAGTCCTCCA GGAAACCAGA ACCCTTCGAG TACCACTCCG GTCGTACCGA AGCCGGTGCC GGTATATGAG GGAGCGACCC TTACACCGGT GAAGGCTACC CCGGAAACCT ATCCTGGGGT GATTACACTA CCGGAAGACC TGATCATCGG CTTCCCGGCC GACTCGGGGA TCAAGCCGAT CTATGTGATG TTCAGGGATC CGCGGGATGT ACCTGGTGCT GCGACTGGCA AGGGACAGCC CGTCAGCGGT AATTGGCTCG GCGCCGCCTC TCAAGGTGAG GGGGCTCCAA TTCCAAGCCA GATTGCGGAT AAACTACGTG GTAAGACATT CAAAAACTGG CGGGACTTTC GGGAACAATT CTGGATAGCT GTGGCTAATG ATCCTGAGTT AAGTAAACAG TTTAATCCTGG TAGTTTAGCT GTAATGAGAG ATGGAGGGGC TCCTTATGTCA GAGAGTCAGA ACAGGCTGGC GGGAGAATAA AGATCGAAAT CCACCACAAG GTTCGAATAG CAGATGGAGG CGGCGTTTAC AATATGGGGA ACCTTGTTGC AGTAACGCCA AAACGTCATA TAGAAATCCA CAAGGGAGGG AAGTGA |
| 278 | Ruminococcin-A | Lantibiotic | MRNDVLTLT NPMEEKELE QILGGGNGV LKTISHECN MNTWQFLFT CC | Ruminococcus gnavus | 279 | ATGAGAAATG ACGTATTAAC ATTAACAAAC CCAATGGAAG AGAACGAACT GGAGCAGATC TTAGGTGGTG GCAATGGTGT GTTAAAAACG ATTAGCCACG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AATGCAATAT GAACACATGG CAGTTCCTGTT TACTTGTTGCT AA |
| 280 | Sakacin G | Class IIa | MKNAKSLTI QEMKSITGG KYYGNGVS CNSHGCSVN WGQAWTCG VNHLANGG HGVC | Lactobacillus sakei | 281 | ATGAAAAACG CAAAAAGCCT AACAATTCAA GAAATGAAAT CTATTACAGG TGGTAAATAC TATGGTAATG GCGTTAGCTG TAACTCTCAC GGCTGTTCAG TAAATTGGGG GCAAGCATGG ACTTGTGGAG TAAACCATCT AGCTAATGGC GGTCATGGAG TTTGTTAA |
| 282 | Sakacin-A | class IIA/YG NGV | MNNVKELS MTELQTITG GARSYGNG VYCNNKKC WVNRGEAT QSIIGGMISG WASGLAGM | Lactobacillus sakei | 283 | ATGAATAATG TAAAGAATT AAGTATGACA GAATTACAAA CAATTACCGG CGGTGCTAGA TCATATGGCA ACGGTGTTTA CTGTAATAAT AAAAAATGTT GGGTAAATCG GGGTGAAGCA ACGCAAAGTA TTATTGGTGG TATGATTAGC GGCTGGGCTA GTGGTTTAGC TGGAATGTAA |
| 284 | Sakacin-P (Sakacin 674) | class IIA/YG NGV | MEKFIELSLK EVTAITGGK YYGNGVHC GKHSCTVD WGTAIGNIG NNAAANWA TGGNAGWN K | Lactobacillus sakei | 285 | ATGGAAAAGT TTATTGAATTA TCTTTAAAAG AAGTAACAGC AATTACAGGT GGAAAATATT ATGGTAACGG TGTACACTGT GGAAAACATT CATGTACCGT AGACTGGGGA ACAGCTATTG GAAATATCGG AAATAATGCA GCTGCAAACT GGGCCACAGG CGGAAACGCT GGCTGGAATA AATAA |
| 286 | Salivaricin 9 | lantibiotic | MKSTNNQSI AEIAAVNSL QEVSMEELD QIIGAGNGV VLTLTHECN LATWTKKLK CC | Streptococcus salivarius | 287 | ATGAAATCAA CAAATAATCA AAGTATCGCA GAAATTGCAG CAGTAAACTC ACTACAAGAA GTAAGTATGG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AGGAACTAGA CCAAATTATT GGTGCCGGAA ACGGAGTGGT TCTTACTCTTA CTCATGAATG TAACCTAGCA ACTTGGACAA AAAAACTAAA ATGTTGCTAA |
| 288 | Salivaricin A | Lantibiotic | MSFMKNSK DILTNAIEEV SEKELMEVA GGKKGSGW FATITDDCPN SVFVCC | Streptococcus pyogenes serotype M28 (strain MGAS6180) | 289 | ATGAGTTTTAT GAAAAATTCA AAGGATATTT TGACTAATGC TATCGAAGAA GTTTCTGAAA AAGAACTTAT GGAAGTAGCT GGTGGTAAAA AAGGTTCCGG TTGGTTTGCA ACTATTACTG ATGACTGTCC GAACTCAGTA TTCGTTTGTTG TTAA |
| 290 | Salivaricin A3 | Lantibiotic | MKNSKDVL NNAIEEVSE KELMEVAG GKKGPGWIA TITDDCPNSI FVCC | Streptococcus salivarius | 291 | ATGAAAAACT CAAAAGATGT TTTGAACAAT GCTATCGAAG AGGTTTCTGA AAAAGAACTT ATGGAAGTAG CTGGTGGTAA AAAAGGTCCA GGTTGGATTG CAACTATTACT GATGACTGTC CAAACTCAAT ATTCGTTTGTT GTTAA |
| 292 | Salivaricin -A sa | Lantibiotic | MKNSKDILN NAIEEVSEKE LMEVAGGK RGSGWIATIT DDCPNSVFV CC | Streptococcus salivarius | 293 | ATGAAAAACT CAAAAGATAT TTTGAACAAT GCTATCGAAG AAGTTTCTGA AAAAGAACTT ATGGAAGTAG CTGGTGGTAA AAGAGGTTCA GGTTGGATTG CAACTATTACT GATGACTGTC CAAACTCAGT ATTCGTTTGTT GTTAA |
| 294 | Staphylococcin C55 alpha | Lantibiotic (two-peptide) | MKSSFLEKDI EEQVTWFEE VSEQEFDDD IFGACSTNTF SLSDYWGNK GNWCTATH ECMSWCK | Staphylococcus aureus | 295 | ATGAAAAGTT CTTTTTTAGAA AAAGATATAG AAGAACAAGT GACATGGTTC GAGGAAGTTT CAGAACAAGA ATTTGACGAT GATATTTTTGG AGCTTGTAGT ACAAACACTT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | TTTCTTTGAGT GACTATTGGG GTAATAAAGG AAATTGGTGT ACTGCTACTC ACGAATGTAT GTCTTGGTGT AAATAA |
| 296 | Staphylococcin C55 beta | Lantibiotic (two-peptide) | MKNELGKFL EENELELGK FSESDMLEIT DDEVYAAG TPLALLGGA ATGVIGYISN QTCPTTACT RAC | Staphylococcus aureus | 297 | ATGAAAAATG AATTAGGTAA GTTTTTAGAA GAAAACGAAT TAGAGTTAGG TAAATTTTCAG AATCAGACAT GCTAGAAATT ACTGATGATG AAGTATATGC AGCTGGAACA CCTTTAGCCTT ATTGGGTGGA GCTGCCACCG GGGTGATAGG TTATATTTCTA ACCAAACATG TCCAACAACT GCTTGTACAC GCGCTTGCTA G |
| 298 | Streptin | lantibiotic | MNNTIKDFD LDLKTNKKD TATPYVGSR YLCTPGSCW KLVCFTTTV K | Streptococcus pyogenes | 299 | ATGAATAACA CAATTAAAGA CTTTGATCTCG ATTTGAAAAC AAATAAAAAA GACACTGCTA CACCTTATGTT GGTAGCCGTT ACCTATGTAC CCCTGGTTCTT GTTGGAAATT AGTTTGCTTTA CAACAACTGT TAAATAA |
| 300 | Streptococcin A-FF22 | Lantibiotic | MEKNNEVIN SIQEVSLEEL DQIIGAGKN GVFKTISHEC HLNTWAFLA TCCS | Streptococcus pyogenes | 301 | ATGGAAAAAA ATAATGAAGT AATCAACTCT ATTCAAGAAG TTAGTCTTGA AGAACTCGAT CAAATTATCG GTGCTGGAAA AAATGGTGTG TTTAAAACAA TTTCTCATGAG TGTCATTTGA ATACATGGGC ATTCCTTGCTA CTTGTTGTTCA TAA |
| 302 | Streptococcin A-M49 | Lantibiotic | MTKEHEIINS IQEVSLEELD QIIGAGKNG VFKTISHECH LNTWAFLAT CCS | Streptococcus pyogenes serotype M49 | 303 | ATGGAAAAAA ATAATGAAGT AATCAACTCT ATTCAAGAAG TTAGTCTTGA AGAACTCGAT CAAATTATCG GTGCTGGAAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AAATGGTGTG TTTAAAACAA TTTCTCATGAG TGTCATTTGA ATACATGGGC ATTCCTTGCTA CTTGTTGCTCA TAA |
| 304 | Sublancin 168 | Lantibiotic | MEKLFKEVK LEELENQKG SGLGKAQCA ALWLQCASG GTIGCGGGA VACQNYRQF CR | Bacillus subtilis (strain 168) | 305 | ATGGAAAAGC TATTTAAAGA AGTTAAACTA GAGGAACTCG AAAACCAAAA AGGTAGTGGA TTAGGAAAAG CTCAGTGTGC TGCGTTGTGG CTACAATGTG CTAGTGGCGG TACAATTGGT TGTGGTGGCG GAGCTGTTGC TTGTCAAAAC TATCGTCAATT CTGCAGATAA |
| 306 | Subtilin | Lantibiotic | MSKFDDFDL DVVKVSKQ DSKITPQWK SESLCTPGC VTGALQTCF LQTLTCNCK ISK | Bacillus subtilis | 307 | ATGTCAAAGT TCGATGATTTC GATTTGGATG TTGTGAAAGT CTCTAAACAA GACTCAAAAA TCACTCCGCA ATGGAAAAGT GAATCACTTT GTACACCAGG ATGTGTAACT GGTGCATTGC AAACTTGCTTC CTTCAAACAC TAACTTGTAA CTGCAAAATC TCTAAATAA |
| 308 | Subtilosin | Unclassified | MKLPVQQV YSVYGGKDL PKGHSHSTM PFLSKLQFLT KIYLLDIHTQ PFFI | Bacillus subtilis (strain 168) | 309 | TTGAAATTGC CGGTGCAACA GGTCTATTCG GTCTATGGGG GTAAGGATCT CCCAAAAGGG CATAGTCATTC TACTATGCCCT TTTTAAGTAA ATTACAATTTT TAACTAAAAT CTACCTCTTGG ATATACATAC ACAACCGTTTT TCATTTGA |
| 310 | Subtilosin -A | Unclassified | MKKAVIVEN KGCATCSIG AACLVDGPI PDFEIAGAT GLFGLWG | Bacillus subtilis (strain 168) | 311 | ATGAAAAAAG CTGTCATTGTA GAAAACAAAG GTTGTGCAAC ATGCTCGATC GGAGCCGCTT GTCTAGTGGA CGGTCCTATC CCTGATTTTGA AATTGCCGGT |

TABLE 1.2-continued

Exemplary Bacteriocins

| Poly- peptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCAACAGGTC TATTCGGTCTA TGGGGGTAA |
| 312 | Thermophilin 1277 | Lantibiotic | MMNATENQI FVETVSDQE LEMLIGGAD RGWIKTLTK DCPNVISSIC AGTIITACKN CA | Streptococcus thermophilus | 313 | ATGATGAATG CTACTGAAAA CCAAATTTTTG TTGAGACTGT GAGTGACCAA GAATTAGAAA TGTTAATTGGT GGTGCAGATC GTGGATGGAT TAAGACTTTA ACAAAAGATT GTCCAAATGT AATTTCTTCAA TTTGTGCAGG TACAATTATTA CAGCCTGTAA AAATTGTGCT TAA |
| 314 | Thermophilin 13 | Unclassified | MKQYNGFE VLHELDLAN VTGGQINWG SVVGHCIGG AIIGGAFSGG AAAGVGCL VGSGKAIIN GL | Streptococcus thermophilus | 315 | ATGAAGCAGT ATAATGGTTTT GAGGTTCTAC ATGAACTTGA CTTAGCAAAT GTAACTGGCG GTCAAATTAA TTGGGGATCA GTTGTAGGAC ACTGTATAGG TGGAGCTATT ATCGGAGGTG CATTTTCAGG AGGTGCAGCG GCTGGAGTAG GATGCCTTGTT GGGAGCGGAA AGGCAATCAT AAATGGATTA TAA |
| 316 | Thermophilin A | Unclassified | MNTITICKFD VLDAELLST VEGGYSGKD CLKDMGGY ALAGAGSGA LWGAPAGG VGALPGAFV GAHVGAIAG GFACMGGMI GNKFN | Streptococcus thermophilus | 317 | ATGAATACAA TAACTATTTGT AAATTTGATG TTTTAGATGCT GAACTTCTTTC GACAGTTGAG GGTGGATACT CTGGTAAGGA TTGTTTAAAA GACATGGGAG GATATGCATT GGCAGGAGCT GGAAGTGGAG CTCTGTGGGG AGCTCCAGCA GGAGGTGTTG GAGCACTTCC AGGTGCATTT GTCGGAGCTC ATGTTGGGGC AATTGCAGGA GGCTTTGCAT GTATGGGTGG AATGATTGGT AATAAGTTTA ACTAA |

TABLE 1.2-continued

Exemplary Bacteriocins

| Poly-peptide SEQ ID NO: | Name | Class | Polypeptide Sequence | Organism of origin | Polynucleotide SEQ ID NO: | Polynucleotide Sequence |
|---|---|---|---|---|---|---|
| 318 | Thiocillin (Micrococcin P1) (Micrococcin P2) (Thiocillin I) (Thiocillin II) (Thiocillin III) (Thiocillin IV) (Antibiotic YM-266183) (Antibiotic YM-266184) | Unclassified | MSEIKKALN TLEIEDFDAI EMVDVDAM PENEALEIM GASCTTCVC TCSCCTT | Bacillus cereus (strain ATCC 14579 /DSM31) | 319 | ATGAGTGAAA TTAAAAAAGC ATTAAATACG CTTGAAATTG AAGATTTTGA TGCAATTGAA ATGGTTGATG TTGATGCTAT GCCAGAAAAC GAAGCGCTTG AAATTATGGG AGCGTCATGT ACGACATGCG TATGTACATG CAGTTGTTGT ACAACTTGA |
| 320 | Thuricin CD alpha | two-peptide lantibiotic | MEVMNNALI TKVDEEIGG NAACVIGCI GSCVISEGIG SLVGTAFTL G | Bacillus cereus 95/8201 | 321 | ATGGAAGTTA TGAACAATGC TTTAATTACAA AAGTAGATGA GGAGATTGGA GGAAACGCTG CTTGTGTAATT GGTTGTATTG GCAGTTGCGT AATTAGTGAA GGAATTGGTT CACTTGTAGG AACAGCATTT ACTTTAGGTT AA |
| 322 | Thuricin CD beta | two-peptide lantibiotic | MEVLNKQN VNIIPESEEV GGWVACVG ACGTVCLAS GGVGTEFAA ASYFL | Bacillus cereus 95/8201 | 323 | ATGGAAGTTT TAAACAAACA AAATGTAAAT ATTATTCCAG AATCTGAAGA AGTAGGTGGA TGGGTAGCAT GTGTTGGAGC ATGTGGTACA GTATGTCTTGC TAGTGGTGGT GTTGGAACAG AGTTTGCAGC TGCATCTTATT TCCTATAA |
| 324 | Thuricin-17 | class IId | METPVVQPR DWTCWSCL VCAACSVEL LNLVTAATG ASTAS | Bacillus thuringiensis | 325 | ATGGAAACAC CAGTAGTACA ACCAAGGGAT TGGACTTGTT GGAGTTGCTT AGTATGTGCA GCATGTTCTGT GGAATTATTA AATTTAGTTAC TGCGGCAACA GGGGCTAGTA CTGCAAGCTA A |
| 326 | Trifolitoxin | Unclassified tied | MDNKVAKN VEVKKGSIK ATFKAAVLK SKTKVDIGG SRQGCVA | Rhizobium leguminosarum bv. trifolii | 327 | ATGGATAACA AGGTTGCGAA GAATGTCGAA GTGAAGAAGG GCTCCATCAA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GGCGACCTTC AAGGCTGCTG TTCTGAAGTC GAAGACGAAG GTCGACATCG GAGGTAGCCG TCAGGGCTGC GTCGCTTAA |
| 328 | Ubericin A | Class IIa | MNTIEKFENI KLFSLKKIIG GKTVNYGN GLYCNQKKC WVNWSETA TTIVNNSIM NGLTGGNA GWHSGGRA | *Streptococcus uberis* | 329 | ATGAATACAA TTGAAAAATT TGAAAATATT AAACTTTTTC ACTAAAGAAA ATTATCGGTG GCAAAACTGT AAATTATGGT AATGGCCTTT ATTGTAACCA AAAAAAATGC TGGGTAAACT GGTCAGAAAC TGCTACAACA ATAGTAAATA ATTCCATCATG AACGGGCTCA CAGGTGGTAA TGCGGGTTGG CACTCAGGCG GGAGAGCATA A |
| 330 | Uberolysin | Unclassified | MDILLELAG YTGIASGTA KKVVDAIDK GAAAFVIISII STVISAGAL GAVSASADF IILTVKNYIS RNLKAQAVI W | *Streptococcus uberis* | 331 | ATGGACATTT TATTAGAACT CGCAGGATAT ACTGGGATAG CCTCAGGTAC TGCAAAAAAA GTTGTTGATG CCATTGATAA AGGAGCTGCA GCCTTTGTTAT TATTTCAATTA TCTCAACAGT AATTAGTGCG GGAGCATTGG GAGCAGTTTC AGCCTCAGCT GATTTTATTAT TTTAACTGTAA AAAATTACAT TAGTAGAAAT TTAAAAGCAC AAGCTGTCAT TTGGTAA |
| 332 | UviB | Unclassified | MDSELFKLM ATQGAFAILF SYLLFYVLK ENSKREDKY QNIIEELTEL LPKIKEDVE DIKEKLNK | *Clostridium perfringens* | 333 | ATGGATAGTG

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AAAGAAGATG TAGAAGATAT AAAAGAAAAA CTTAATAAAT AG |
| 334 | Variacin | Lantibiotic, Type A | MTNAFQALD EVTDAELDA ILGGGSGVIP TISHECHMN SFQFVFTCCS | *Micrococcus varians* | 335 | ATGACGAACG CATTTCAGGC ACTGGACGAA GTCACGGACG CCGAGCTCGA CGCCATCCTT GGCGGGGGCA GTGGTGTTAT TCCCACGATC AGCCACGAGT GCCACATGAA CTCCTTCCAGT TCGTGTTCACC TGCTGCTCCTG A |
| 336 | Zoocin A | Unclassified | MKRIFFAFLS LCLFIFGTQT VSAATYTRP LDTGNITTGF NGYPGHVG VDYAVPVGT PVRAVANGT VKFAGNGA NHPWMLWM AGNCVLIQH ADGMHTGY AHLSKISVST DSTVKQGQII GYTGATGQ VTGPHLHFE MLPANPNW QNGFSGRID PTGYIANAP VFNGTTPTE pttpttnlki YKVDDLQKI NGIWQVRN NILVPTDFT WVDNGIAA DDVIEVTSN GTRTSDQVL QKGGYFVIN PNNVKSVGT PMKGSGGLS WAQVNFTT GGNVWLNT TSKDNLLYG K | *Streptococcus equi* subsp. *zooepidemicus* | 337 | ATGAAACGTA TATTTTTTGCT TTCTTAAGTTT ATGCTTATTTA TATTCGGAAC ACAAACGGTA TCTGCAGCTA CTTATACTCG GCCATTAGAT ACGGGAAATA TCACTACAGG GTTTAACGGA TACCCTGGTC ATGTTGGAGT CGATTATGCA GTACCCGTTG GAACTCCGGT TAGAGCAGTT GCAAATGGTA CAGTCAAATT TGCAGGTAAT GGGGCTAATC ACCCATGGAT GCTTTGGATG GCTGGAAACT GTGTTCTAATT CAACATGCTG ACGGGATGCA TACTGGATAT GCACACTTAT CAAAAATTTC AGTTAGCACA GATAGTACAG TTAAACAAGG ACAAATCATA GGTTATACTG GTGCCACCGG CCAAGTTACC GGTCCACATT TGCATTTTGA AATGTTGCCA GCAAATCCTA ACTGGCAAAA TGGTTTTTCTG GAAGAATAGA TCCAACCGGA TACATCGCTA ATGCCCCTGT ATTTAATGGA |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ACAACACCTA CAGAACCTAC TACTCCTACA ACAAATTTAA AAATCTATAA AGTTGATGAT TTACAAAAAA TTAATGGTATT TGGCAAGTAA GAAATAACAT ACTTGTACCA ACTGATTTCAC ATGGGTTGAT AATGGAATTG CAGCAGATGA TGTAATTGAA GTAACTAGCA ATGGAACAAG AACCTCTGAC CAAGTTCTTCA AAAAGGTGGT TATTTTGTCAT CAATCCTAAT AATGTTAAAA GTGTTGGAAC TCCGATGAAA GGTAGTGGTG GTCTATCTTGG GCTCAAGTAA ACTTTACAAC AGGTGGAAAT GTCTGGTTAA ATACTACTAG CAAAGACAAC TTACTTTACGG AAAATAA |
| 338 | Fulvocin-C | Unclassified | ANCSCSTAS DYCPILTFCT TGTACSYTP TGCGTGWV YCACNGNFY | Myxococcus fulvus | 339 | GCGAACTGCA GCTGCAGCAC CGCGAGCGAT TATTGCCCGA TTCTGACCTTT TGCACCACCG GCACCGCGTG CAGCTATACC CCGACCGGCT GCGGCACCGG CTGGGTGTAT TGCGCGTGCA ACGGCAACTT TTAT |
| 340 | Duramycin-C | Lantibiotic | CANSCSYGP LTWSCDGNT K | Streptomyces griseoluteus | 341 | TGCGCGAACA GCTGCAGCTA TGGCCCGCTG ACCTGGAGCT GCGATGGCAA CACCAAA |
| 342 | Duramycin (duramycin-B) (Leucopeptin) | Lantibiotic B | CKQSCSFGPF TFVCDGNTK | Streptoverticiilium griseo verticillatum | 343 | TGCAAACAGA GCTGCAGCTT TGGCCCGTTT ACCTTTGTGTG CGATGGCAAC ACCAAA |
| 344 | Carnocin UI49 | lantibiotic | GSEIQPR | Carnobacterium sp. (strain UI49) | 345 | GGCAGCGAAA TTCAGCCGCG C |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 346 | Lactococcin-G α | Unclassified | GTWDDIGQG IGRVAYWVG KAMGNMSD VNQASRINR KKKH | Lactococcus lactis subsp. lactis (Streptococcus lactis) | 347 | GGCACCTGGG ATGATATTGG CCAGGGCATT GGCCGCGTGG CGTATTGGGT GGGCAAAGCG ATGGGCAACA TGAGCGATGT GAACCAGGCG AGCCGCATTA ACCGCAAAAA AAAACAT |
| 348 | Lactococcin-G β | Unclassified | KKWGWLAW VDPAYEFIK GFGKGAIKE GNKDKWKN 1 | Lactococcus lactis subsp. lactis (Streptococcus lactis) | 349 | AAAAAATGGG GCTGGCTGGC GTGGGTGGAT CCGGCGTATG AATTTATTAA AGGCTTTGGC AAAGGCGCGA TTAAAGAAGG CAACAAAGAT AAATGGAAAA ACATT |
| 350 | Ancovenin | Lantibiotic | CVQSCSFGP LTWSCDGNT K | Streptomyces sp. (strain A647P-2) | 351 | TGCGTGCAGA GCTGCAGCTT TGGCCCGCTG ACCTGGAGCT GCGATGGCAA CACCAAA |
| 352 | Actagardine (Gardimycin) | Lantibiotic | SSGWVCTLT IECGTVICAC | Actinoplanes liguriae | 353 | AGCAGCGGCT GGGTGTGCAC CCTGACCATT GAATGCGGCA CCGTGATTTG CGCGTGC |
| 354 | Curvaticin FS47 | Unclassified | YTAKQCLQA IGSCGIAGTG AGAAGGPA GAFVGAXV VXI | Lactobacillus curvatus | 355 | TATACCGCGA AACAGTGCCT GCAGGCGATT GGCAGCTGCG GCATTGCGGG CACCGGCGCG GGCGCGGCGG GCGGCCCGGC GGGCGCGTTT GTGGGCGCGN NNGTGGTGNN NATT [IN WHICH NNN = ANY AMINO-ACID CODING TRIPLET] |
| 356 | Bavaricin-MN | class IIA/YG NGV | TKYYGNGV YCNSKKCW VDWGQAAG GIGQTVVXG WLGGAIPGK | Lactobacillus sakei | 357 | ACCAAATATT ATGGCAACGG CGTGTATTGC AACAGCAAAA AATGCTGGGT GGATTGGGGC CAGGCGGCGG GCGGCATTGG CCAGACCGTG GTGNNNGGCT GGCTGGGCGG CGCGATTCCG GGCAAA[IN WHICH NNN = |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | ANY AMINO-ACID CODING TRIPLET] |
| 358 | Mutacin B-Ny266 | Lantibiotic | FKSWSFCTP GCAKTGSFN SYCC | *Streptococcus mutans* | 359 | TTTAAAAGCT GGAGCTTTTG CACCCCGGGC TGCGCGAAAA CCGGCAGCTT TAACAGCTAT TGCTGCTTTAA AAGCTGGAGC TTTTGCACCCC GGGCTGCGCG AAAACCGGCA GCTTTAACAG CTATTGCTGC |
| 360 | Mundticin | class IIA/YG NGV | KYYGNGVS CNKKGCSVD WGKAIGIIGN NSAANLATG GAAGWSK | *Enterococcus mundtii* | 361 | AAATATTATG GCAACGGCGT GAGCTGCAAC AAAAAAGGCT GCAGCGTGGA TTGGGGCAAA GCGATTGGCA TTATTGGCAA CAACAGCGCG GCGAACCTGG CGACCGGCGG CGCGGCGGGC TGGAGCAAA |
| 362 | Bavaricin-A | class IIA/YG NGV | KYYGNGVH XGKHSXTVD WGTAIGNIG NNAAANXA TGXNAGG | *Lactobacillus sakei* | 363 | AAATATTATG GCAACGGCGT GCATNNNGGC AAACATAGCN NNACCGTGGA TTGGGGCACC GCGATTGGCA ACATTGGCAA CAACGCGGCG GCGAACNNNG CGACCGGCNN NAACGCGGGC GGC [IN WHICH NNN = ANY AMINO-ACID CODING TRIPLET] |
| 364 | Lactocin-705 | class IIb | GMSGYIQGI PDFLKGYLH GISAANKHK KGRL | *Lactobacillus paracasei* | 365 | GGCATGAGCG GCTATATTCA GGGCATTCCG GATTTTCTGA AAGGCTATCT GCATGGCATT AGCGCGGCGA ACAAACATAA AAAAGGCCGC CTG |
| 366 | Leucocin-B | Unclassified | KGKGFWSW ASKATSWLT GPQQPGSPL LKKHR | *Leuconostoc mesenteroides* | 367 | AAAGGCAAAG GCTTTTGGAG CTGGGCGAGC AAAGCGACCA GCTGGCTGAC CGGCCCGCAG CAGCCGGGCA GCCCGCTGCT GAAAAAACAT CGC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 368 | Leucocin C | class IIA/YG NGV | KNYGNGVH CTKKGCSVD WGYAWTNI ANNSVMNG LTGGNAGW HN | Leuconostoc mesenteroides | 369 | AAAAACTATG GCAACGGCGT GCATTGCACC AAAAAAGGCT GCAGCGTGGA TTGGGGCTAT GCGTGGACCA ACATTGCGAA CAACAGCGTG ATGAACGGCC TGACCGGCGG CAACGCGGGC TGGCATAAC |
| 370 | LCI | Unclassified | AIKLVQSPN GNFAASFVL DGTKWIFKS KYYDSSKGY WVGIYEVW DRK | Bacillus subtilis | 371 | GCGATTAAAC TGGTGCAGAG CCCGAACGGC AACTTTGCGG CGAGCTTTGT GCTGGATGGC ACCAAATGGA TTTTTAAAGC AAATATTATG ATAGCAGCAA AGGCTATTGG GTGGGCATTT ATGAAGTGTG GGATCGCAAA |
| 372 | Lichenin | Unclassified | ISLEICXIFHD N | Bacillus licheniformis | 373 | ATTAGCCTGG AAATTTGCNN NATTTTTCATG ATAAC [IN WHICH NNN = ANY AMINO-ACID CODING TRIPLET] |
| 374 | Lactococcin MMFII | class IIA/YG NGV | TSYGNGVHC NKSKCWIDV SELETYKAG TVSNPKDIL W | Lactococcus lactis subsp. lactis (Streptococcus lactis) | 375 | ACCAGCTATG GCAACGGCGT GCATTGCAAC AAAAGCAAAT GCTGGATTGA TGTGAGCGAA CTGGAAACCT ATAAAGCGGG CACCGTGAGC AACCCGAAAG ATATTCTGTG G |
| 376 | Serracin-P | Phage-Tail-Like | DYHHGVRV L | Serratia plymuthica | 377 | GATTATCATC ATGGCGTGCG CGTGCTG |
| 378 | Halocin-C8 | Unclassified | DIDITGCSAC KYAAG | Halobacterium sp. (strain AS7092) | 379 | GATATTGATA TTACCGGCTG CAGCGCGTGC AAATATGCGG CGGGC |
| 380 | Subpeptin JM4-B | Unclassified | XXKEIXHIFH DN | Bacillus subtilis | 381 | NNNNNNAAAG AAATTNNNCA TATTTTTCATG ATAAC [IN WHICH NNN = ANY AMINO-ACID CODING TRIPLET] |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 382 | Curvalicin-28a | Unclassified | TPVVNPPFLQQT | Lactobacillus curvatus | 383 | ACCCCGGTGGTGAACCCGCCGTTTCTGCAGCAGACC |
| 384 | Curvalicin-28b | Unclassified | VAPFPEQFLX | Lactobacillus curvatus | 385 | GTGGCGCCGTTTCCGGAACAGTTTCTGNNN [IN WHICH NNN = ANY AMINO-ACID CODING TRIPLET] |
| 386 | Curvalicin-28c | Unclassified | NIPQLTPTP | Lactobacillus curvatus | 387 | AACATTCCGCAGCTGACCCCGACCCCG |
| 388 | Thuricin-S | Unclassified | DWTXWSXLVXAACSVELL | Bacillus thuringiensis subsp. entomocidus | 389 | GATTGGACCNNNTGGAGCNNNCTGGTGNNNGCGGCGTGCAGCGTGGAACTGCTG [IN WHICH NNN = ANY AMINO-ACID CODING TRIPLET] |
| 390 | Curvaticin L442 | Unclassified | AYPGNGVHCGKYSCTVDKQTAIGNIGNNAA | Lactobacillus curvatus | 391 | GCGTATCCGGGCAACGGCGTGCATTGCGGCAAATATAGCTGCACCGTGGATAAACAGACCGCGATTGGCAACATTGGCAACAACGCGGCG |
| 392 | Divergicin M35 | class IIa/YGNGV | TKYYGNGVYCNSKKCWVDWGTAQGCIDVVIGQLGGGIPGKGKC | Carnobacterium divergens (Lactobacillus divergens) | 393 | ACCAAATATTATGGCAACGGCGTGTATTGCAACAGCAAAAAATGCTGGGTGGATTGGGGCACCGCGCAGGGCTGCATTGATGTGGTGATTGGCCAGCTGGGCGGCGGCATTCCGGGCAAAGGCAAATGC |
| 394 | Enterocin E-760 | class IIb | NRWYCNSAAGGVGGAAVCGLAGYVGEAKENIAGEVRKGWGMAGGFTHNKACKSFPGSGWASG | Enterococcus sp. | 395 | AACCGCTGGTATTGCAACAGCGCGGCGGGCGTGGGCGGCGCGGCGGTGTGCGGCCTGGCGGGCTATGTGGGCGAAGCGAAAGAAAACATTGCGGGCGAAGTGCGCAAAGGCTGGGGCATGGCGGGCGGCTTTACCCAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | AACAAAGCGT GCAAAAGCTT TCCGGGCAGC GGCTGGGCGA GCGGC |
| 396 | Bacteriocin E50-52 | Unclassified | TTKNYGNG VCNSVNWC QCGNVWAS CNLATGCAA WLCKLA | Enterococcus faecium (Streptococcus faecium) | 397 | ACCACCAAAA ACTATGGCAA CGGCGTGTGC AACAGCGTGA ACTGGTGCCA GTGCGGCAAC GTGTGGGCGA GCTGCAACCT GGCGACCGGC TGCGCGGCGT GGCTGTGCAA ACTGGCG |
| 398 | Paenibacillin | Unclassified | ASIIKTTIKVS KAVCKTLTC ICTGSCSNCK | Paenibacillus polymyxa (Bacillus polymyxa) | 399 | GCGAGCATTA TTAAAACCAC CATTAAAGTG AGCAAAGCGG TGTGCAAAAC CCTGACCTGC ATTTGCACCG GCAGCTGCAG CAACTGCAAA |
| 400 | Epilancin 15x | Unclassified | SASIVKTTIK ASKKLCRGF TLTCGCHFT GKK | Staphylococcus epidermidis | 401 | AGCGCGAGCA TTGTGAAAAC CACCATTAAA GCGAGCAAAA AACTGTGCCG CGGCTTTACC CTGACCTGCG GCTGCCATTTT ACCGGCAAAA AA |
| 402 | Enterocin -HF | class IIa | KYYGNGVS CNKKGCSVD WGKAIGIIGN NAAANLTTG GKAAWAC | Enterococcus faecium (Streptococcus faecium) | 403 | AAATATTATG GCAACGGCGT GAGCTGCAAC AAAAAAGGCT GCAGCGTGGA TTGGGGCAAA GCGATTGGCA TTATTGGCAA CAACGCGGCG GCGAACCTGA CCACCGGCGG CAAAGCGGCG TGGGCGTGC |
| 404 | Bacillocin 602 | Class IIa | ATYYGNGL YCNKQKHY TWVDWNKA SREIGKITVN GWVQH | Paenibacillus polymyxa (Bacillus polymyxa) | 405 | GCGACCTATT ATGGCAACGG CCTGTATTGC AACAAACAGA AACATTATAC CTGGGTGGAT TGGAACAAAG CGAGCCGCGA AATTGGCAAA ATTACCGTGA ACGGCTGGGT GCAGCAT |
| 406 | Bacillocin 1580 | Class IIa | VNYGNGVS CSKTKCSVN WGIITHQAF RVTSGVASG | Bacillus circulans | 407 | GTGAACTATG GCAACGGCGT GAGCTGCAGC AAAACCAAAT |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GCAGCGTGAA CTGGGGCATT ATTACCCATC AGGCGTTTCG CGTGACCAGC GGCGTGGCGA GCGGC |
| 408 | Bacillocin B37 | Unclassified | FVYGNGVTS ILVQAQFLV NGQRRFFYT PDK | Paenibacillus polymyxa (Bacillus polymyxa) | 409 | TTTGTGTATG GCAACGGCGT GACCAGCATT CTGGTGCAGG CGCAGTTTCT GGTGAACGGC CAGCGCCGCT TTTTTTATACC CCGGATAAA |
| 410 | Rhamnosin A | Unclassified | AVPAVRKTN ETLD | Lactobacillus rhamnosus | 411 | GCGGTGCCGG CGGTGCGCAA AACCAACGAA ACCCTGGAT |
| 412 | Lichenicidin A2 | Lantibiotic (two-peptide) | MKNSAARE AFKGANHPA GMVSEEELK ALVGGNDV NPETTPATTS SWTCITAGV TVSASLCPTT KCTSRC | Bacillus licheniformis (strain DSM 13/ATCC 14580) | 413 | ATGAAAAACA GCGCGGCGCG CGAAGCGTTT AAAGGCGCGA ACCATCCGGC GGGCATGGTG AGCGAAGAAG AACTGAAAGC GCTGGTGGGC GGCAACGATG TGAACCCGGA AACCACCCCG GCGACCACCA GCAGCTGGAC CTGCATTACC GCGGGCGTGA CCGTGAGCGC GAGCCTGTGC CCGACCACCA AATGCACCAG CCGCTGC |
| 414 | Plantaricin C19 | Class IIa | KYYGNGLSC SKKGCTVN WGQAFSCG VNRVATAG HGK | Lactobacillus plantarum | 415 | AAATATTATG GCAACGGCCT GAGCTGCAGC AAAAAAGGCT GCACCGTGAA CTGGGGCCAG GCGTTTAGCT GCGGCGTGAA CCGCGTGGCG ACCGCGGGCC ATGGCAAA |
| 416 | Acidocin J1132 β | class IIb | GNPKVAHCA SQIGRSTAW GAVSGA | Lactobacillus acidophilus | 417 | GGCAACCCGA AAGTGGCGCA TTGCGCGAGC CAGATTGGCC GCAGCACCGC GTGGGCGCG GTGAGCGGCG CG |
| 418 | factor with anti-Candida activity | Unclassified | WLPPAGLLG RCGRWFRP WLLWLQSG AQYKWLGN LFGLGPK | Enterococcus faecalis | 419 | TGGCTGCCGC CGGCGGGCCT GCTGGGCCGC TGCGGCCGCT GGTTTCGCCC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| | | | | | | GTGGCTGCTG TGGCTGCAGA GCGGCGCGCA GTATAAATGG CTGGGCAACC TGTTTGGCCT GGGCCCGAAA |
| 420 | Ava_1098 (putative heterocyst differentiation protein) | Unclassified | NLDQWLTE QVHEFQDM YLEPQAISN QDITFKLSDL DFIHN | Anabaena variabilis ATCC 29413 | 421 | TAATTTAGATC AGTGGTTAAC AGAACAAGTT CATGAGTTTC AAGATATGTA CTTGGAACCA CAAGCAATAT CCAATCAAGA CATTACCTTCA AACTATCTGA CCTAGATTTTA TTCATAATTGA |
| 422 | alr2818 (putative heterocyst differentiation protein) | Unclassified | NLDQWLTE QVHEFQDM YLEPQAISN QDITFKLSDL DFIHN | Nostoc sp 7120 | 423 | AATTTAGATC AATGGTTAAC AGAACAAGTT CATGAGTTTC AAGATATGTA CTTGGAACCA CAAGCAATAT CCAATCAAGA CATTACCTTCA AACTGTCAGA CCTAGATTTTA TTCATAATTGA |
| 424 | Aazo_072 4 (putative heterocyst differentiation protein) | Unclassified | HREKKSA | Nostoc azollae 0708 | 425 | CACAGAGAGA AAAAATCAGC ATAG |
| 426 | AM1_401 0 (putative heterocyst differentiation protein) | Unclassified | TSNNWLAK NYLSMWNK KSSNPNL | Acaryochloris marina MBIC11017 | 427 | ACAAGCAATA ACTGGCTAGC CAAAAACTAT CTTTCTATGTG GAATAAAAAG AGCAGTAATC CAAACCTTTA G |
| 428 | PCC8801 _3266 (putative heterocyst differentiation protein) | Unclassified | FRYFWW | Cyanothece PCC 8801 | 429 | TTTAGATATTT TTGGTGGTAA |
| 430 | Cyan8802 _2855 (putative heterocyst differentiation protein) | Unclassified | FRYFWW | Cyanothece PCC 8802 | 431 | TTTAGATATTT TTGGTGGTAA |
| 432 | PCC7424 3517 | Unclassified | CGEKWRIFS | Cyanothece PCC 7424 | 433 | TGTGGAGAAA AATGGAGAAT TTTTAGC |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 434 | cce_2677 (putative HetP protein) | Unclassified | FRLQLWQF | *Cyanothece* ATCC 51142 | 435 | TTTCGCTTACA ACTGTGGCAA TTT |
| 436 | CY0110_ 11572 (putative heterocyst differentiation protein) | Unclassified | LGCNQSSIW SIFFWNH | *Cyanothece* CCY0110 | 437 | CTAGGATGTA ACCAGAGCAG TATCTGGTCA ATTTTTTTCTG GAATCATTAA |
| 438 | MC7420_ 4637 | Unclassified | YNLQGLPAI ESEDCIPDSV APSDDWFSG VSSLFNRLT GLG | *Microcoleus chthonoplastes* PCC 7420 | 439 | TATAACCTAC AGGGGTTGCC AGCAATTGAG TCAGAAGACT GTATCCCAGA TTCTGTAGCG CCTTCGGATG ATTGGTTTTCA GGCGTATCGT CTCTGTTTAAC CGCTTGACTG GGTTGGGTTA G |
| 440 | asr1611 (putative DUF37 family protein) | Unclassified | WMAIRRILR CHPFHPGGY DPVPELGEH CCHHDSGNK G | *Nostoc* sp 7120 | 441 | TGGATGGCGA TTCGCCGCATT TTGCGTTGTCA TCCATTCCACC CAGGGGGTTA TGATCCTGTA CCAGAGTTGG GTGAGCATTG TTGTCATCATG ATAGCGGGAA TAAGGGGTGA |
| 442 | Ava_4222 (putative DUF37 family protein) | Unclassified | WMGIRRILR CHPFHPGGY DPVPEVGEH CCHHDSGK | *Anabaena variabilis* ATCC 29413 | 443 | TGGATGGGGA TTCGCCGCATT TTGCGTTGTCA TCCATTCCACC CAGGCGGTTA TGATCCTGTA CCAGAGGTGG GTGAGCATTG TTGTCATCATG ATAGCGGGAA GTAG |
| 444 | N9414_0 7129 (putative DUF37 family protein) | Unclassified | WMATRRILR CHPFHPGGY DPVPEVKHN CCDQHLSDS GKQTTEDHH KGS | *Nodularia spumigena* CCY9414 | 445 | TGGATGGCGA CTCGGCGGAT TTTGCGTTGTC ATCCCTTCCAT CCTGGTGGAT ATGATCCAGT TCCAGAGGTA AAACACAATT GCTGCGATCA GCATCTGTCC GATTCTGGGA AACAGACCAC AGAAGACCAT CACAAAGGCT CGTAG |

TABLE 1.2-continued

Exemplary Bacteriocins

| Polypeptide SEQ ID NO: | Name | Class | Polypeptide Sequence | Organism of origin | Polynucleotide SEQ ID NO: | Polynucleotide Sequence |
|---|---|---|---|---|---|---|
| 446 | Aazo_008 3 (putative DUF37 family protein) | Unclassified | WMATLRILC HPFHPGGYD PVPGLAEKS CCDHHD | Nostoc azollae 0708 | 447 | TGGATGGCAA CTTTGCGGATT TTACGCTGTC ATCCTTTCCAT CCTGGTGGTT ATGATCCTGT ACCAGGACTA GCGGAAAAAT CCTGTTGTGA CCATCATGATT GA |
| 448 | S7335_34 09 (putative DUF37 family protein) | Unclassified | WLTAKRFCR CHPLHPGGY DPVPEKKSV L | Synechococcus PCC 7335 | 449 | TGGCTAACAG CCAAGCGCTT TTGTCGCTGTC ATCCGCTTCAT CCTGGCGGGT ATGATCCGGT ACCGGAGAAG AAATCGGTAC TCTAA |
| 450 | P9303_21 151 (putative DUF37 family protein) | Unclassified | WLTLRRLSR CHPFTPCGC DPVPD | Prochlorococcus marinus MIT 9303 | 451 | TGGCTCACCC TGCGGCGCCT GTCTCGTTGCC ATCCTTTTACC CCCTGTGGTT GCGACCCGGT GCCTGATTAA |

As used herein "bacteriocin polynucleotide" refers to a polynucleotide encoding a bacteriocin. In some embodiments, the host cell comprises at least one bacteriocin.

Bacteriocin Immunity Modulators

Exemplary bacteriocin immunity modulators are shown in Table 2. While the immunity modulators in Table 2 are naturally-occuring, the skilled artisan will appreciate that variants of the immunity modulators of Table 2, naturally-occuring immunity modulators other than the immunity modulators of Table 2, or synthetic immunity modulators can be used according to some embodiments herein.

In some embodiments, a particular immunity modulator or particular combination of immunity modulators confers immunity to a particular bacteriocin, particular class or category of bacteriocins, or particular combination of bacteriocins. Exemplary bacteriocins to which immunity modulators can confer immunity are identified in Table 2. While Table 2 identifies an "organism of origin" for exemplary immunity modulators, these immunity modulators can readily be expressed in other naturally-occurring, genetically modified, or synthetic microorganisms to provide a desired bacteriocin immunity activity in accordance with some embodiments herein. As such, as used herein "immunity modulator" refers not only to structures expressly provided herein, but also to structure that have substantially the same effect as the "immunity modulator" structures described herein, including fully synthetic immunity modulators, and immunity modulators that provide immunity to bacteriocins that are functionally equivalent to the bacteriocins disclosed herein.

Exemplary polynucleotide sequences encoding the polypeptides of Table 2 are indicated in Table 2. The skilled artisan will readily understand that the genetic code is degenerate, and moreover, codon usage can vary based on the particular organism in which the gene product is being expressed, and as such, a particular polypeptide can be encoded by more than one polynucleotide. In some embodiments, a polynucleotide encoding a bacteriocin immunity modulator is selected based on the codon usage of the organism expressing the bacteriocin immunity modulator. In some embodiments, a polynucleotide encoding a bacteriocin immunity modulator is codon optimized based on the particular organism expressing the bacteriocin immunity modulator. A vast range of functional immunity modulators can incorporate features of immunity modulators disclosed herein, thus providing for a vast degree of identity to the immunity modulators in Table 2. In some embodiments, an immunity modulator has at least about 50% identity, for example, at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 2.

TABLE 2

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 452 | Microcin H47 immunity modulator MehI | MSYKKLY QLTAIFSLP LTILLVSLS SLRIVGEG NSYVDVFL SFIIFLGFIE LIHGIRKIL VWSGWKN GS | Escherichia coli | 453 | ATGAGTTATAAAAAAC TGTACCAATTGACGGCT ATATTTAGTTTACCTCT TACTATCTTATTGGTTT CACTTTCATCCCTTCGG ATTGTTGGCGAAGGGA ATTCTTATGTTGACGTT TTTCTAAGCTTTATAAT ATTTCTTGGTTTTATTG AGCTGATTCATGGGATT CGAAAGATTTTGGTCTG GTCAGGCTGGAAAAAC GGAAGTTAA |
| 454 | Colicin-E3 immunity modulator (Colicin-E3 chain B) (ImmE3) (Microcin-E3 immunity modulator) | MGLKLDLT WFDKSTED FKGEEYSK DFGDDGSV MESLGVPF KDNVNNG CFDVIAEW VPLLQPYF NHQIDISD NEYFVSFD YRDGDW | Escherichia coli | 455 | ATGGGACTTAAATTGG ATTTAACTTGGTTTGAT AAAAGTACAGAAGATT TTAAGGGTGAGGAGTA TTCAAAAGATTTTGGAG ATGACGGTTCAGTTATG GAAAGTCTAGGTGTGC CTTTTAAGGATAATGTT AATAACGGTTGCTTTGA TGTTATAGCTGAATGG GTACCTTTGCTACAACC ATACTTTAATCATCAAA TTGATATTTCGATAAT GAGTATTTTGTTTCGTT TGATTATCGTGATGGTG ATTGGTGA |
| 456 | Colicin-E1 immunity modulator (ImmE1) (Microcin-E1 immunity modulator) | MSLRYYIK NILFGLYC TLIYIYLIT KNSEGYYF LVSDKML YAIVISTIL CPYSKYAI EYIAFNFIK KDFFERRK NLNNAPVA KLNLFMLY NLLCLVLA IPFGLLGLF ISIKNN | Escherichia coli | 457 | ATGAGCTTAAGATACTA CATAAAAAATATTTTAT TTGGCCTGTACTGCACA CTTATATATATATACCT TATAACAAAAACAGC GAAGGGTATTATTTCCT TGTGTCAGATAAGATG CTATATGCAATAGTGAT AAGCACTATTCTATGTC CATATTCAAAATATGCT ATTGAATACATAGCTTT TAACTTCATAAAGAAA GATTTTTTCGAAAGAAG AAAAAAACCTAAATAAC GCCCCCGTAGCAAAATT AAACCTATTTATGCTAT ATAATCTACTTTGTTTG GTCCTAGCAATCCCATT TGGATTGCTAGGACTTT TTATATCAATAAGAAT AATTAA |
| 458 | Cloacin immunity modulator | MGLKLHIH WFDKKTEE FKGGEYSK DFGDDGSV IESLGMPL KDNINNG WFDVEKP WVSILQPH FKNVIDISK FDYFVSFV YRDGNW | Escherichia coli | 459 | ATGGGGCTTAAATTAC ATATTCATTGGTTTGAT AAGAAAACCGAAGAGT TTAAAGGCGGTGAATA CTCAAAAGACTTCGGT GATGATGGTTCTGTCAT TGAAAGTCTGGGGATG CCTTTTAAAGGATAATAT TAATAATGGTTGGTTTG ATGTTGAAAAACCATG GGTTTCGATATTACAGC CACACTTTAAAAATGTA ATCGATATTAGTAAATT TGATTACTTTGTATCCT TTGTTTACCGGGATGGT AACTGGTAA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 460 | Colicin-E2 immunity modulator (ImmE2) (Microcin-E2 immunity modulator) | MELKHSIS DYTEAEFL EFVKKICR AEGATEED DNKLVREF ERLTEHPD GSDLIYYP RDDREDSP EGIVKEIKE WRAANGK SGFKQG | Escherichia coli | 461 | ATGGAACTGAAACATA GTATTAGTGATTATACC GAGGCTGAATTTCTGG AGTTTGTAAAAAAAAT ATGTAGAGCTGAAGGT GCTACTGAAGAGGATG ACAATAAATTAGTGAG AGAGTTTGAGCGATTA ACTGAGCACCCAGATG GTTCAGATCTGATTTAT TATCCTCGCGATGACAG GGAAGATAGTCCTGAA GGGATTGTCAAGGAAA TTAAAGAATGGCGAGC TGCTAACGGTAAGTCA GGATTTAAACAGGGCT GA |
| 462 | Colicin-A immunity modulator (Microcin-A immunity modulator) | MMNEHSID TDNRKAN NALYLFIII GLIPLLCIF VVYYKTPD ALLLRKIA TSTENLPSI TSSYNPLM TKVMDIYC KTAPFLALI LYILTFKIR KLINNTDR NTVLRSCL LSPLVYAA IVYLFCFR NFELTTAG RPVRLMAT NDATLLLF YIGLYSIIFF TTYITLFTP VTAFKLLK KRQ | Citrobacter freundii | 463 | ATGATGAATGAACACT CAATAGATACGGACAA CAGAAAGGCCAATAAC GCATTGTATTTATTTAT AATAATCGGATTAATAC CATTATTGTGCATTTTT GTTGTTTACTACAAAAC GCCAGACGCTTTACTTT TACGTAAAATTGCTACA AGCACTGAGAATCTCCC GTCAATAACATCCTCCT ACAACCCATTAATGACA AAGGTTATGGATATTTA TTGTAAAACAGCGCCTT TCCTTGCCTTAATACTA TACATCCTAACCTTTAA AATCAGAAAATTAATC AACAACACCGACAGGA ACACTGTACTTAGATCT TGTTTATTAAGTCCATT GGTCTATGCAGCAATTG TTTATCTATTCTGCTTC CGAAATTTTGAGTTAAC AACAGCCGGAAGGCCT GTCAGATTAATGGCCA CCAATGACGCAACACT ATTGTTATTTTATATTG GTCTGTACTCAATAATT TTCTTTACAACCTATAT CACGCTATTCACACCAG TCACTGCATTTAAATTA TTAAAAAAAAGGCAGT AA |
| 464 | Colicin-Ia immunity modulator | MNRKYYF NNMWWG WVTGGYM LYMSWDY EFKYRLLF WCISLCGM VLYPVAK WYIEDTAL KFTRPDFW NSGFFADT PGKMGLLA VYTGTVFI LSLPLSMIY ILSVIIKRLS VR | Escherichia coli | 465 | ATGAACAGAAAATATT ATTTTAATAATATGTGG TGGGGATGGGTGACGG GGGGATATATGCTGTA TATGTCATGGGATTATG AGTTTAAATACAGATTA CTGTTCTGGTGTATTTC TCTCTGCGGAATGGTTT TGTATCCGGTTGCAAAA TGGTATATTGAAGTAC AGCTCTAAAATTTACCC GGCCTGATTTCTGGAAC AGCGGTTTTTTTGCTGA TACACCTGGAAAAATG GGGTTGCTTGCGGTTTA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | TACGGGTACTGTTTTCA TATTATCTCTTCCGTTA AGTATGATATATATTCT TTCTGTTATTATAAAAA GGCTGTCTGTAAGATA G |
| 466 | Colicin-Ib immunity modulator | MKLDISVK YLLKSLIPI LIILTVFYL GWKDNQE NARMFYAF IGCIISAITF PFSMRIIQK MVIRFTGK EFWQKDFF TNPVGGSL TAIFELFCF VISVPVVAI YLIFILCKA LSGK | Escherichia coli | 467 | ATGAAACTGGATATATC TGTAAAGTATTTACTGA AAAGCCTGATACCAAT CCTCATTATTCTTACAG TTTTTTATCTGGGATGG AAAGATAACCAGGAAA ATGCAAGAATGTTTTAT GCGTTCATCGGATGCAT TATCAGTGCCATTACTT TTCCTTTTTCAATGAGG ATAATACAGAAAATGG TAATAAGGTTTACAGG GAAAGAATTCTGGCAA AAAGACTTCTTTACAAA TCCAGTTGGCGGAAGC TTAACTGCAATATTTGA ATTATTCTGTTTCGTTA TATCAGTTCCTGTGGTT GCCATTTACTTAATTTT TATACTCTGCAAAGCCC TTTCAGGAAAATGA |
| 468 | Colicin-N immunity modulator (Microcin-N immunity modulator) | MHNTLLEK IIAYLSLPG FHSLNNPP LSEAFNLY VHTAPLAA TSLFIFTHK ELELKPKS SPLRALKIL TPFTILYIS MIYCFLLT DTELTLSS KTFVLIVK KRSVFVFF LYNTIYWD IYIHIFVLL VPYRNI | Escherichia coli | 469 | ATGCACAATACACTCCT CGAAAAAATCATCGCA TACCTATCCCTACCAGG ATTTCATTCATTAAACA ACCCGCCCCTAAGCGA AGCATTAATCTCTATG TTCATACAGCCCCTTTA GCTGCAACCAGCTTATT CATATTCACACACAAAG AATTAGAGTTAAAACC AAAGTCGTCACCTCTGC GGGCACTAAAGATATT AACTCCTTTCACTATTC TTTATATATCCATGATA TACTGTTTCTTGCTAAC TGACACAGAACTAACC TTGTCATCAAAAACATT TGTATTAATAGTCAAAA AACGATCGTTTTTGTC TTTTTTCTATATAACAC TATATATTGGGATATAT ATATTCACATATTTGTA CTTTTGGTTCCTTATAG GAACATATAA |
| 470 | Colicin-E8 immunity modulator (ImmE8) (Microcin-E8 immunity modulator) | MELKNSIS DYTETEFK KIIEDIINCE GDEKKQD DNLEHFIS VTEHPSGS DLIYYPEG NNDGSPEA VIKEIKEW RAANGKSG FKQG | Escherichia coli | 471 | ATGGAACTGAAAACA GCATTAGTGATTACACT GAAACTGAATTCAAAA AAATTATTGAAGACATC ATCAATTGTGAAGGTG ATGAAAAAAACAGGA TGATAACCTCGAGCATT TTATAAGTGTTACTGAG CATCCTAGTGGTTCTGA TCTGATTTATTACCCAG AAGGTAATAATGATGG TAGCCCTGAAGCTGTTA TTAAAGAGATTAAAGA ATGGCGAGCTGCTAAC GGTAAGTCAGGATTTA AACAGGGCTGA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 472 | Lactococcin-A immunity modulator | MKKKQIEF ENELRSML ATALEKDI SQEERNAL NIAEKALD NSEYLPKII LNLRKALT PLAINRTL NHDLSELY KFITSSKAS NKNLGGG LIMSWGRL F | Lactococcus lactis subsp. lactis (Streptococcus lactis) | 473 | ATGAAAAAAAAACAAA TAGAATTTGAAAACGA GCTAAGAAGTATGTTG GCTACCGCCCTTGAAAA AGACATTAGTCAAGAG GAAAGAAATGCTCTGA ATATTGCAGAAAAGGC GCTTGACAATTCTGAAT ATTTACCAAAAATTATT TTAAACCTCAGAAAAG CCCTAACTCCATTAGCT ATAAATCGAACACTTAA CCATGATTTATCTGAAC TGTATAAATTCATTACA AGTTCCAAAGCATCAA ACAAAAATTTAGGTGG TGGTTTAATTATGTCGT GGGGACGACTATTCTA A |
| 474 | Lactococcin-A immunity modulator | MKKKQIEF ENELRSML ATALEKDI SQEERNAL NIAEKALD NSEYLPKII LNLRKALT PLAINRTL NHDLSELY KFITSSKAS NKNLGGG LIMSWGRL F | Lactococcus lactis subsp. cremoris (Streptococcus cremoris) | 475 | ATGAAAAAAAAACAAA TAGAATTTGAAAACGA GCTAAGAAGTATGTTG GCTACCGCCCTTGAAAA AGACATTAGTCAAGAG GAAAGAAATGCTCTGA ATATTGCAGAAAAGGC GCTTGACAATTCTGAAT ATTTACCAAAAATTATT TTAAACCTCAGAAAAG CCCTAACTCCATTAGCT ATAAATCGAACACTTAA CCATGATTTATCTGAAC TGTATAAATTCATTACA AGTTCCAAAGCATCAA ACAAAAATTTAGGTGG TGGTTTAATTATGTCGT GGGGACGACTATTCTA A |
| 476 | Colicin-D immunity modulator (Microcin-D immunity modulator) | MNKMAMI DLAKLFLA SKITAIEFS ERICVERR RLYGVKDL SPNILNCG EELFMAAE RFEPDADR ANYEIDDN GLKVEVRS ILEKFKL | Escherichia coli | 477 | ATGATCGATTTGGCGA AATTATTTTTAGCTTCG AAAATTACAGTGATTG AGTTTTCAGAGCGAATT TGTGTTGAACGGAGAA GATTGTATGGTGTTAAG GATTTGTCTCCGAATAT ATTAAATTGTGGGGAA GAGTTGTCTATGGCTGC TGAGCGATTTGAGCCT GATGCAGATAGGGCTA ATTATGAAATTGATGAT AATGGACTTAAGGTCG AGGTCCGATCTATCTTG GAAAAACTTAAATCAT AA |
| 478 | Colicin-E5 immunity modulator (ImmE5) (Microcin-E5 immunity modulator) | MKLSPKAA IEVCNEAA KKGLWILG IDGGHWLN PGFRIDSSA SWTYDMP EEYKSKIPE NNRLAIENI KDDIENGY TAFIITLKM | Escherichia coli | 479 | ATGAAGTTATCACCAA AAGCTGCAATAGAAGT TGTAATGAAGCAGCG AAAAAAGGCTTATGGA TTTTGGGCATTGATGGT GGGCATTGGCTGAATC CTGGATTCAGGATAGA TAGTTCAGCATCATGGA CATATGATATGCCGGA GAATACAAATCAAAAA TCCCTGAAAATAATAG ATTGGCTATTGAAAATA TTAAAGATGATATTGA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | GAATGGATACACTGCTT TCATTATCACGTTAA |
| 480 | Colicin-E6 immunity modulator (ImmE6) (Microcin-E6 immunity modulator) | MGLKLHIN WFDKRTEE FKGGEYSK DFGDDGSV IERLGMPF KDNINNG WFDVIAEW VPLLQPYF NHQIDISD NEYFVSFD YRDGDW | Escherichia coli | 481 | ATGGGGCTTAAATTAC ATATTAATTGGTTTGAT AAGACGACCGAGGAAT TTAAAGGTGGTGAGTA TTCAAAAGATTTTGGAG ATGATGGCTCGGTCATT GAACGTCTTGGAATGC CTTTAAAAGATAATATC AATAATGGTTGGTTTGA TGTTATAGCTGAATGG GTACCTTTGCTACAACC ATACTTTAATCATCAAA TTGATATTTCCGATAAT GAGTATTTTGTTTCGTT TGATTATCGTGATGGTG ATTGGTGA |
| 482 | Colicin-E8 immunity modulator in ColE6 (E8Imm[E6]) | MELKKSIG DYTETEFK KIIENIINCE GDEKKQD DNLEHFIS VTEHPSGS DLIYYPEG NNDGSPEA VIKEIKEW RAANGKSG FKQG | Escherichia coli | 483 | GTGGAGCTAAAGAAAA GTATTGGTGATTACACT GAAACCGAATTCAAAA AAATTATTGAAAACATC ATCAATTGTGAAGGTG ATGAAAAAAAACAGGA TGATAACCTCGAGCATT TTATAAGTGTTACTGAG CATCCTAGTGGTTCTGA TCTGATTTATTACCCAG AAGGTAATAATGATGG TAGCCCTGAAGCTGTTA TTAAAGAGATTAAAGA ATGGCGAGCTGCTAAC GGTAAGTCAGGATTTA AACAGGGCTGA |
| 484 | Colicin-E9 immunity modulator (ImmE9) (Microcin-E9 immunity modulator) | MELKHSIS DYTEAEFL QLVTTICN ADTSSEEE LVKLVTHF EEMTEHPS GSDLIYYP KEGDDDSP SGIVNTVK QWRAANG KSGFKQG | Escherichia coli | 485 | ATGGAACTGAAGCATA GCATTAGTGATTATACA GAAGCTGAATTTTTACA ACTTGTAACAACAATTT GTAATGCGAACACTTCC AGTGAAGAAGAACTGG TTAAATTGGTTACACAC TTTGAGGAAATGACTG AGCACCCTAGTGGTAG TGATTTAATATATTACC CAAAAGAAGGTGATGA TGACTCACCTTCAGGTA TTGTAAACACAGTAAA ACAATGGCGAGCCGCT AACGGTAAGTCAGGAT TTAAACAGGGCTAA |
| 486 | Colicin-M immunity modulator (Microcin-M immunity modulator) | MLTLYGYI RNVFLYR MNDRSCG DFMKVISM KFIFILTIIA LAAVFFWS EDKGPACY QVSDEQAR TFVKNDYL QRMKRWD NDVQLLGT EIPKITWEK IERSLTDVE DEKTLLVP FKAEGPDG KRMYYGM YHCEEGY VEYAND | Escherichia coli | 487 | ATGAAAGTAATTAGCA TGAAATTTATTTTTATT TTAACGATTATTGCTCT TGCTGCTGTTTTTTTCT GGTCTGAAGATAAAGG TCCGGCATGCTATCAGG TCAGCGATGAACAGGC CAGAACGTTTGTAAAA AATGATTACCTGCAAA GAATGAAACGCTGGGA CAACGATGTACAACTTC TTGGTACAGAAATCCC GAAAATTACATGGGAA AAGATTGAGAGAAGTT TAACAGATGTTGAAGA TGAAAAAACACTTCTTG TCCCATTTAAAGCTGAA GGCCCGGACGGTAAGA TABLE 2-continued Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | GAATGTATTATGGCATG TACCATTGTGAGGAGG GATATGTTGAATATGCG AATGACTAA |
| 488 | Colicin-B immunity modulator (Microcin-B immunity modulator) | MTSNKDK NKKANEIL YAFSIIGIIP LMAILILRI NDPYSQVL YYLYNKV AFLPSITSL HDPVMTTL MSNYNKT APVMGILV FLCTYKTR E1IKPVTRK LVVQSCFW GPVFYAILI YITLFYNLE LTTAGGFF KLLSHNVI TLFILYCSI YFTVLTMT YAILLMPL LVIKYFKG RQ | Escherichia coli | 489 | ATGACCAGCAATAAAG ATAAGAACAAGAAAGC AAACGAAATATTATAT GCATTTTCCATAATCGG GATTATTCCATTAATGG CTATATTAATACTTCGA ATAAATGATCCATATTC TCAAGTGCTGTACTACT TATATAATAAGGTGGC ATTTCTCCCTTCTATTA CATCATTGCATGATCCC GTCATGACAACACTTAT GTCAAACTACAACAAG ACAGCGCCAGTTATGG GTATTCTCGTTTTTCTT TGCACATATAAGACAA GAGAAATCATAAAGCC AGTAACAAGAAAACTT GTTGTGCAATCCTGTTT CTGGGGGCCCGTTTTTT ATGCCATTCTGATTTAT ATCACACTGTTCTATAA TCTGGAACTAACAACA GCAGGTGGTTTTTTTAA ATTATTATCTCATAATG TCATCACTCTGTTTATT TTATATTGCTCCATTTA CTTTACTGTTTTAACCA TGACATATGCGATTTTA CTGATGCCATTACTTGT CATTAAATATTTTAAAG GGAGGCAGTAA |
| 490 | Colicin-V immunity modulator (Microcin-V immunity modulator) | MDRKRTK LELLFAFII NATAIYIAL AIYDCVFR GKDFLSMH TFCFSALM SAICYFVG DNYYSISD KIKRRSYE NSDSK | Escherichia coli | 491 | ATGGATAGAAAAGAA CAAAATTAGAGTTGTTA TTTGCATTTATAATAAA TGCCACCGCAATATATA TTGCATTAGCTATATAT GATTGTGTTTTTAGAGG AAAGGACTTTTTATCCA TGCATACATTTTGCTTC TCTGCATTAATGTCTGC AATATGTTACTTTGTTG GTGATAATTATTATTCA ATATCCGATAAGATAA AAAGGAGATCATATGA GAACTCTGACTCTAAAT GA |
| 492 | Colicin-E1* immunity modulator (ImmE1) (Microcin-E1* immunity modulator) | MSLRYYIK NILFGLYC ALIYIYLIT KNNEGYYF LASDKMLY AIVISTILCP YSKYAIEHI FFKFIKKDF FRKRKNLN KCPRGKIK PYLCVYNL LCLVLAIPF GLLGLVYI NKE | Shigella sonnei | 493 | ATGAGTTTAAGATACTA CATAAAAAATATTTTGT TTGGCCTATACTGCGCA CTTATATATATATACCT TATAACAAAAAACAAC GAAGGGTATTATTTCCT AGCGTCAGATAAGATG CTATACGCAATAGTGAT AAGCACTATTCTATGCC CATATTCAAAATATGCT ATTGAACACATATTTTT TAAGTTCATAAAGAAA GATTTTTTCAGAAAAAG AAAAAACCTAAATAAA TGCCCCCGTGGCAAAA TTAAACCGTATTTATGC GTATACAATCTACTTTG TTTGGTCCTAGCAATCC |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | CATTTGGATTGCTAGGA CTTGTTTATATCAATAA AGAATAA |
| 494 | Colicin-E1 immunity modulator (ImmE1) (Microcin-E1 immunity modulator) | MSLRYYIK NILFGLYC TLIYIYLIT KNSEEYYF LVTDKML YAIVISTIL CPYSKYAI EHIAFNFIK KHFFERRK NLNNAPVA KLNLFMLY NLLCLVLA IPFGLLGLF ISIKNN | Escherichia coli | 495 | ATGAGCTTAAGATACTA CATAAAAAATATTTTAT TTGGCCTGTACTGCACA CTTATATATATATACCT TATAACAAAAAACAGC GAAGAGTATTATTTCCT TGTGACAGATAAGATG CTATATGCAATAGTGAT AAGCACTATTCTATGTC CATATTCAAAATATGCT ATTGAACACATAGCTTT TAACTTCATAAAGAAAC ATTTTTTCGAAAGAAGA AAAAACCTAAATAACG CCCCCGTAGCAAATTA AACCTATTTATGCTATA TAATCTACTTTGTTTGG TCCTAGCAATCCCATTT GGATTGCTAGGACTTTT TATATCAATAAAGAATA ATTAA |
| 496 | Probable leucocin-A immunity modulator | MRKNNILL DDAKIYTN KLYLLLID RKDDAGY GDICDVLF QVSKKLDS TKNVEALI NRLVNYIRI TASTNRIKF SKDEEAVII ELGVIGQK AGLNGQY MADFSDKS QFYSIFER | Leuconostoc gelidum | 497 | TTGAGAAAAAATAACA TTTTATTGGACGATGCT AAAATATACACGAACA AACTCTATTTGCTATTA ATCGATAGAAAAGATG ACGCTGGGTATGGAGA TATTTGTGATGTTTTGT TTCAGGTATCCAAAAA ATTAGATAGCACAAAA AATGTAGAAGCATTGA TTAACCGATTGGTCAAT TATATACGAATTACCGC TTCAACAAACAGAATTA AGTTTTCAAAAGATGA AGAGGCTGTAATTATA GAACTTGGTGTAATTG GTCAGAAGGCTGGATT AAACGGCCAATACATG GCTGATTTTTCTGACAA ATCTCAGTTTTATAGTA TCTTTGAAAGATAA |
| 498 | Lactococcin-B immunity modulator | MKKKVDT EKQITSWA SDLASKNE TKVQEKLI LSSYIQDIE NHVYFPKA MISLEKKL RDQNNICA LSKEVNQF YFKVVEVN QRKSWMV GLIV | Lactococcus lactis subsp. cremoris (Streptococcus cremoris) | 499 | ATGAAAAAAAAGTTG ATACAGAAAAACAAAT TACTTCTTGGGCATCTG ACTTAGCTTCCAAAAAT GAAACAAAGGTTCAAG AAAAATTAATACTGTCT TCTTATATTCAGGACAT CGAAAACCATGTTTACT TTCCAAAAGCAATGATT TCTTTAGAAAAAAATT ACGAGACCAAAATAAT ATTTGCGCTTTATCAAA AGAAGTCAATCAGTTTT ATTTTAAAGTTGTTGAA GTAAATCAAAGAAAAT CCTGGATGGTAGGTTTG ATAGTTTAA |
| 500 | Pediocin PA-1 immunity modulator (Pediocin ACH | MNKTKSE HIKQQALD LFTRLQFLL QKHDTIEP YQYVLDIL ETGISKTK | Pediococcus acidilactici | 501 | ATGAATAAGACTAAGT CGGAACATATTAAACA ACAAGCTTTGGACTTAT TTACTAGGCTACAGTTT TTACTACAGAAGCACG ATACTATCGAACCTTAC |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | immunity modulator) | HNQQTPER QARVVYN KIASQALV DKLHFTAE ENKVLAAI NELAHSQK GWGEFNM LDTTNTWP SQ | | | CAGTACGTTTTAGATAT TCTGGAGACTGGTATCA GTAAAACTAAACATAA CCAGCAAACGCCTGAA CGACAAGCTCGTGTAG TCTACAACAAGATTGCC AGCCAAGCGTTAGTAG ATAAGTTACATTTTACT GCCGAAGAAAACAAAG TTCTAGCAGCCATCAAT GAATTGGCGCATTCTCA AAAAGGGTGGGGCGAG TTTAACATGCTAGATAC TACCAATACGTGGCCTA GCCAATAG |
| 502 | Putative carnobacteriocin-BM1 immunity modulator | MIKDEKIN KIYALVKS ALDNTDV KNDKKLSL LLMRIQET SINGELFY DYKKELQP AISMYSIQ HNFRVPDD LVKLLALV QTPKAWS GF | Carnobacterium maltaromaticum (Carnobacterium piscicola) | 503 | ATGATAAAGATGAAA AAATAAATAAAATCTAT GCTTTAGTTAAGAGCGC ACTTGATAATACGGAT GTTAAGAATGATAAAA AACTTTCTTTACTTCTT ATGAGAATACAAGAAA CATCAATTAATGGAGA ACTATTTTACGATTATA AAAAAGAATTACAGCC AGCTATTAGTATGTACT CTATTCAACATAACTTT CGGGTTCCTGACGATCT AGTAAAACTGTTAGCAT TAGTTCAAACACCTAAA GCTTGGTCAGGGTTTTA A |
| 504 | Putative carnobacteriocin-B2 immunity modulator (Carnocin-CP52 immunity modulator) | MDIKSQTL YLNLSEAY KDPEVKAN EFLSKLVV QCAGKLTA SNSENSYIE VISLLSRGI SSYYLSHK RIIPSSMLTI YTQIQKDI KNGNIDTE KLRKYEIA KGLMSVPY IYF | Carnobacterium maltaromaticum (Carnobacterium piscicola) | 505 | ATGGATATAAAGTCTCA AACATTATATTTGAATC TAAGCGAGGCATATAA AGACCCTGAAGTAAAA GCTAATGAATTCTTATC AAAATTAGTTGTACAAT GTGCTGGGAAATTAAC AGCTTCAAACAGTGAG AACAGTTATATTGAAGT AATATCATTGCTATCTA GGGGTATTTCTAGTTAT TATTTATCCCATAAACG TATAATTCCTTCAAGTA TGTTAACTATATATACT CAAATACAAAAGGATA TAAAAAACGGGAATAT TGACACCGAAAAATTA AGGAAATATGAGATAG CAAAAGGATTAATGTC CGTTCCTTATATATATT TCTAA |
| 506 | Nisin immunity modulator | MRRYLILI VALIGITGL SGCYQTSH KKVRFDEG SYTNFIYD NKSYFVTD KEIPQENV NNSKVKFY KLLIVDMK SEKLLSSSN KNSVTLVL NNIYEASD KSLCMGIN DRYYKILP ESDKGAVK ALRLQNFD | Lactococcus lactis subsp. lactis (Streptococcus lactis) | 507 | ATGAGAAGATATTTAAT ACTTATTGTGGCCTTAA TAGGGATAACAGGTTT ATCAGGGTGTTATCAA ACAAGTCATAAAAAGG TGAGGTTTGACGAAGG AAGTTATACTAATTTTA TTTATGATAATAAATCG TATTTCGTAACTGATAA GGAGATTCCTCAGGAG AACGTTAACAATTCCAA AGTAAAATTTTATAAGC TGTTGATTGTTGACATG AAAAGTGAGAAACTTT TATCAAGTAGCAACAA AAATAGTGTGACTTTGG |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | VTSDISDD NFVIDKND SRKIDYMG NIYSISDTT VSDEELGE YQDVLAE VRVFDSVS GKSIPRSE WGRIDKD GSNSKQSR TEWDYGEI HSIRGKSLT EAFAVEIN DDFKLATK VGN | | | TCTTAAATAATATTTAT GAGGCTTCTGACAAGT CGCTATGTATGGGTATT AACGACAGATACTATA AGATACTTCCAGAAAG TGATAAGGGGCGGTC AAAGCTTTGAGATTACA AAACTTTGATGTGACAA GCGATATTTCTGATGAT AATTTTGTTATTGATAA AAATGATTCACGAAAA ATTGACTATATGGGAA ATATTTACAGTATATCG GACACCACCGTATCTGA TGAAGAATTGGGAGAA TATCAGGATGTTTTAGC TGAAGTACGTGTGTTTG ATTCAGTTAGTGGCAA AAGTATCCCGAGGTCT GAATGGGGAGAATTG ATAAGGATGGTTCAAA TTCCAAACAGAGTAGG ACGGAATGGGATTATG GCGAAATCCATTCTATT AGAGGAAAATCTCTTA CTGAAGCATTTGCCGTT GAGATAAATGATGATT TTAAGCTTGCAACGAA GGTAGGAAACTAG |
| 508 | Trifolitoxin immunity modulator | MNDEICLT GGGRTTVT RRGGVVY REGGPWSS TVISLLRHL EASGFAEA PSVVGTGF DERGRETL SFIEGEFVH PGPWSEEA FPQFGMML RRLHDATA SFKPPENS TABLE 2-continued Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | ACGATGCGGAACCGCT ATGGGCAATTGCCTGG CGCACTAGAAGTGCCT CCTGGATGCTCCATCAT CGGCAAACACTGGAAG CAGCGCTGGCATAG |
| 510 | Antilisterial bacteriocin subtilosin biosynthesis protein AlbD | MNNIIPIMS LLFKQLYS RQGKKDAI RIAAGLVIL AVFEIGLIR QAGIDESV LRKTYIILA LLLMNTY MVFLSVTS QWKESYM KLSCLLPIS SRSFWLAQ SVVLFVDT CLRRTLFFF ILPLFLFGN GTLSGAQT LFWLGRFS FFTVYSIIF GVVLSNHF VKKKNLM FLLHAAIFA CVCISAAL MPAATIPL CAVHILWA VVIDFPVFL QAPPQQGK MHSFMRRS EFSFYKRE WNRFISSK AMLLNYA VMAVFSGF FSFQMMNT GIFNQQVI YIVISALLL ICSPIALLY SIEKNDRM LLITLPIKR KTMFWAK YRFYSGLL AGGFLLVV MIVGFISGR SISVLTFLQ CIELLLAG AYIRLTAD EKRPSFSW QTEQQLWS GFSKYRSY LFCLPLFLA ILAGTAVS LAVIPIAGL VIVYYLQK QDGGFFDT SKRERLGS | Bacillus subtilis (strain 168) | 511 | ATGAATAACATAATCCC TATCATGTCTTTGCTGT TCAAACAGCTTTACAGC CGGCAAGGGAAAAAGG ACGCCATCCGCATTGCC GCAGGCCTTGTCATTCT GGCCGTGTTTGAAATC GGGCTGATCCGCCAGG CCGGCATTGATGAATC GGTGTTGCGCAAAACG TATATCATACTCGCGCT TCTTTTGATGAACACAT ATATGGTGTTTCTTTCC GTGACATCACAATGGA AGGAATCTTATATGAA GCTGAGCTGCCTGCTGC CGATTTCTTCACGGAGC TTTTGGCTCGCCCAGAG TGTCGTTTTGTTTGTCG ATACCTGTTTGAGAAG AACTTTATTCTTTTTTA TTTTACCGCTGTTCTTA TTTGGAAACGGAACGC TGTCAGGGGCGCAAAC ATTGTTTTGGCTCGGCA GGTTTTCGTTTTTTACC GTTTACTCCATTATTTT CGGAGTTGTGCTAAGC AACCACTTCGTCAAAAA GAAGAACTTGATGTTTC TGCTGCATGCGGCGAT ATTCGCCTGTGTATGTA TCAGCGCCGCTTTGATG CCGGCCGCCACGATTCC GCTTTGCGCGGTTCATA TCCTGTGGGCGGTGGT CATTGACTTTCCTGTCT TTCTGCAGGCGCCTCCG CAGCAGGGCAAGATGC ATTCATTTATGCGGCGA TCTGAATTTTCGTTTTA CAAAAGAGAATGGAAC CGATTTATCTCTTCTAA AGCGATGCTGTTAAATT ACGCGGTAATGGCGGT ATTCAGCGGCTTCTTTT CGTTCCAGATGATGAA CACCGGCATCTTCAATC AGCAAGTGATTTATATC GTGATTTCCGCGCTTTT GCTCATCTGCTCGCCGA TCGCCCTTTTGTATTCG ATTGAAAAAAATGACC GGATGCTGCTCATCACG CTTCCGATCAAGCGAA AAACGATGTTTTGGGC GAAATATCGCTTTTATT CAGGCCTATTGGCAGG CGGATTTCTCCTTGTCG TGATGATTGTGGGTTTC A |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 512 | Putative ABC transporter ATP-binding protein AlbC (Antilisterial bacteriocin subtilosin biosynthesis protein AlbC) | MSILDIHD VSVWYER DNVILEQV DLHLEKGA VYGLLGV NGAGKTTL INTLTGVN RNFSGRFT LCGIEAEA GMPQKTSD QLKTHRYF AADYPLLF TEITAKDY VSFVHSLY QKDFSEQQ FASLAEAF HFSKYINR RISELSLGN RQKVVLM TGLLLRAP LFILDEPLV GLDVESIE VFYQKMR EYCEAGGT ILFSSHLLD VVQRFCDY AAILHNKQ IQKVIPIGE ETDLRREF FEVIGHE | Bacillus subtilis (strain 168) | 513 | GCATTTTGGATATACAC GATGTATCCGTTTGGTA TGAACGGGACAACGTC ATCTTAGAGCACGTGG ACTTACACTTAGAAAAA GGCGCCGTTTACGGATT GCTTGGGGTAAACGGT GCCGGCAAAACAACAC TGATCAATACGCTGACA GGAGTGAACCGCAATT ACAGCGGGGGCTTTAC GCTGTGCGGCATTGAA GCTGAGGCCGGCATGC CGCAGAAAACATCAGA TCAACTGAAGATTCACC GTTACTTCGCCGCTGAT TATCCGCTGCTGTTTAC AGAAATTACGGCGAAG GACTATGTGTCTTTCGT CCATTCGCTTTATCAAA AGGATTTTTCAGAGCG ACAGTTTGCCAGTTTGG CTGAGGCCTTTCATTTT TCAAAATACATCAACA GGAGAATCTCGGAGCT GTCCTTGGGGAACAGG CAAAAGGTTGTGTTGAT GACAGGATTATTGCTGC GGGCTCCCCTGTTTATT TTGGATGAGCCGCTCGT CGGTTTGGATGTGGAA TCAATAGAGGTCTTTTA TCAGAAAATGCGGGAG TACTGTGAGGAAGGCG GAACCATTTTGTTTTCT TCCCATCTGCTCGATGT CGTGCAGAGATTTTGTG ATTTTGCGGCCATTCTG CACAACAAACAGATCC AAAAGGTCATTCCGATT GGGGAGGAGACCGATC TGCGGCGGGAATTTTTT GAGGTTATCGGCCATG AATAA |
| 514 | Antilisterial bacteriocin subtilosin biosynthesis protein AlbB | MSPAQRRI LLYILSFIF VIGAVVYF VKSDYLFT LIFIAIAILF GMRARKA DSR | Bacillus subtilis (strain 168) | 515 | TTGTCACCAGCACAAA GAAGAATTTTACTGTAT ATCCTTTCATTTATCTT TGTCATCGGCGCAGTC GTCTATTTTGTCAAAAG CGATTATCTGTTTACGC TGATTTTCATTGCCATT GCCATTCTGTTCGGGAT GCGCGCGCGGAAGGCT GACTCGCGATGA |
| 516 | Colicin-E7 immunity modulator (ImmE7) (Microcin-E7 immunity modulator) | MELKNSIS DYTEAEFV QLLKEIEK ENVAATD DVLDVLLE HFVKITEH PDGTDLIY YPSDNRDD SPEGIVKEI KEWRAAN GKPGFKQG | Escherichia coli | 517 | ATGGAACTGAAAAATA GTATTAGTGATTACACA GAGGCTGAGTTTGTTCA ACTTCTTAAGGAAATTG AAAAAGAGAATGTTGC TGCAACTGATGATGTGT TAGATGTGTTACTCGAA CACTTTGTAAAAATTAC TGAGCATCCAGATGGA ACGGATCTGATTTATTA TCCTAGTGATAATAGA GACGATAGCCCCGAAG GGATTGTCAAGGAAAT TAAAGAATGGCGAGCT GCTAACGGTAAGCCAG |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | GATTTAAACAGGGCTGA |
| 518 | Pyocin-S1 immunity modulator | MKSKISEYTEKEFLEFVEDIYTNNKKKFPTEESHIQAVLEFKKLTEHPSGSDLLYYPNENREDSPAGVVKEVKEWRASKGLPGFKAG | Pseudomonas aeruginosa | 519 | ATGAAGTCCAAGATTTCCGAATATACGGAAAAAGAGTTTCTTGAGTTTGTTGAAGACATATACACAAACAATAAGAAAAAGTTCCCTACCGAGGAGTCTCATATTCAAGCCGTGCTTGAATTTAAAAAACTAACGGAACACCCAAGCGGCTCAGACCTTCTTTACTACCCCAACGAAAATAGAGAAGATAGCCCAGCTGGAGTTGTAAAGGAAGTTAAAGAATGGCGTGCTTCCAAGGGGCTTCCTGGCTTTAAGGCCGGTTAG |
| 520 | Pyocin-S2 immunity modulator | MKSKISEYTEKEFLEFVKDIYTNNKKKFPTEESHIQAVLEFKKLTEHPSGSDLLYYPNENREDSPAGVVKEVKEWRASKGLPGFKAG | Pseudomonas aeruginosa (strain ATCC 15692/ PAO1 / 1C /PRS 101 / LMG 12228) | 521 | ATGAAGTCCAAGATTTCCGAATATACGGAAAAAGAGTTTCTTGAGTTTGTTAAAGACATATACACAAACAATAAGAAAAAGTTCCCTACCGAGGAGTCTCATATTCAAGCCGTGCTTGAATTTAAAAAACTAACGGAACACCCAAGCGGCTCAGACCTTCTTTACTACCCCAACGAAAATAGAGAAGATAGCCCAGCTGGAGTTGTAAAGGAAGTTAAAGAATGGCGTGCTTCCAAGGGGCTTCCTGGCTTTAAGGCCGGTTAG |
| 522 | Hiracin-JM79 immunity factor | MDFTKEEKLLNAISKVYNEATIDDYPDLKEKLFLYSKEISEGKSVGEVSMKLSSFLGRYILKHKFGLPKSLIELQEIVSKESQVYRGWASIGIWS | Enterococcus hirae | 523 | ATGGATTTTACTAAAGAAGAAAAACTTTTAAATGCAATTAGTAAAGTATACAATGAAGCAACTATAGATGACTATCCTGACTTAAAAGAAAAGCTCTTTCTTTATTCTAAAGAAATCAGTGAGGGAAAAAGTGTTGGTGAAGTTAGTATGAAATTAAGTAGTTTTCTTGGAAGATATATTTTAAAACATAAATTTGGATTACCTAAATCTTTAATAGAATTACAAGAAATTGTTAGTAAGGAATCTCAAGTATATAGAGGATGGGCTTCTATTGGTATTTGGAGTTAA |
| 524 | Probable mesentericin-Y105 immunity modulator | MKKKYRYLEDSKNYTSTLYSLLVDNVDKPGYSDICDVLLQVSKKLDNTQSVEALINRLVNYIRITASTYKIIFSKKEEELIIKLGVIGQKAGLNGQYMADFSDKSQFYSVFDQ | Leuconostoc mesenteroides | 525 | TTGAAAAAAAGTATCGGTATTTAGAAGATAGCAAAAATTACACTAGTACACTCTATTCTCTGTTAGTTGATAATGTTGACAAACCTGGATACTCAGATATTTGCGATGTTTTGCTTCAAGTTTCTAAGAAGTTGGATAATACTCAAAGTGTTGAAGCGCTAATTAATCGATTGGTAATTATATTCGTATTACTGCTTCAACATACAAAATTATTTTTTCAAAAAAAGAAGA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | | | | GGAATTGATTATAAAA CTTGGTGTTATTGGACA AAAAGCTGGACTTAAT GGTCAGTATATGGCTG ATTTTTCAGACAAGTCT CAGTTTTACAGCGTTTT CGATCAGTAA |
| 526 | Microcin-24 immunity modulator | MSFLNFAF SPVFFSIMA CYFIVWRN KRNEFVCN RLLSIIISFL ICFIYPWLN YKIEVKYY IFEQFYLFC FLSSLVAV VINLIVYFI LYRRCI | Escherichia coli | 527 | ATGAGTTTTCTTAATTT TGCATTTTCTCCTGTAT TCTTCTCCATTATGGCG TGTTATTTCATTGTATG GAGAAATAAACGAAAC GAATTTGTCTGCAATAG ATTGCTATCAATTATAA TAATATCTTTTTTGATA TGCTTCATATATCCATG GCTAAATTACAAAATC GAAGTTAAATATTATAT ATTTGAACAGTTTTATC TTTTTTGTTTTTTATCGT CACTCGTGGCTGTTGTA ATAAACCTAATTGTATA CTTTATATTATACAGGA GATGTATATGA |
| 528 | Colicin-K immunity modulator | MHLKYYL HNLPESLIP WILILIFND NDNTPLLFI FISSIHVLL YPYSKLTIS RYIKENTK LKKEPWYL CKLSALFY LLMAIPVG LPSFIYYTL KRN | Escherichia coli | 529 | ATGCATTTAAAATACTA CCTACATAATTTACCTG AATCACTTATACCATGG ATTCTTATTTTAATATT TAACGACAATGATAAC ACTCCTTTGTTATTTAT ATTTATATCATCAATAC ATGTATTGCTATATCCA TACTCTAAATTAACCAT ATCTAGATATATCAAAG AAAATACAAAGTTAAA AAAAGAACCCTGGTAC TTATGCAAGTTATCTGC ATTGTTTTATTTATTAA TGGCAATCCCAGTAGG ATTGCCAAGTTTCATAT ATTACACTCTAAAGAG AAATTAA |
| 530 | Microcin C7 self-immunity modulator MccF | MMIQSHPL LAAPLAVG DTIGFFSSS APATVTAK NRFFRGVE FLQRKGFK LVSGKLTG KTDFYRSG TIKERAQE FNELVYNP DITCIMSTI GGDNSNSL LPFLDYDA IIANPKIIIG YSDTTALL AGIYAKTG LITFYGPAL IPSFGEHPP LVDITYESF IKILTRKQS GIYTYTLP EKWSDESI NWNENKIL RPKKLYKN NCAFYGSG KVEGRVIG GNLNTLTG | Escherichia coli | 531 | ATGATGATACAATCTCA TCCACTACTGGCCGCTC CCCTGGCAGTAGGAGA TACAATTGGTTTCTTTT CATCATCTGCTCCGGCA ACAGTTACTGCAAAAA ATCGTTTTTTCGGGGA GTTGAGTTTCTTCAGAG AAAGGGATTTAAGCTG GTATCAGGGAAGCTTA CCGGTAAAACAGATTTT TATCGTTCAGGTACTAT TAAAGAAAGAGCTCAA GAATTTAATGAGTTAGT CTACAATCCTGATATTA CCTGTATAATGTCAACG ATCGGTGGAGATAACA GTAATTCACTACTACCG TTTCTGGACTATGATGC TATCATTGCAAACCCCA AAATTATCATAGGTTAC TCAGATACAACTGCTTT ATTAGCAGGAATATAT GCAAAAACAGGGTTAA TAACATTCTATGGACCA GCTCTTATTCCTTCGTT TGGTGAACATCCACCTC |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | IWGSEWM PEILNGDIL FIEDSRKSI ATIERLFS MLKLNRVF DKVSAIILG KHELFDCA GSKRRPYE VLTEVLDG KQIPVLDG FDCSHTHP MLTLPLGV KLAIDFDN KNISITEQY LSTEK | | | TTGTGGATATAACATAT GAATCATTTATTAAAT ACTAACAAGAAAACAA TCAGGAATATATACCTA CACATTACCTGAAAAGT GGAGTGATGAGAGCAT AAACTGGAATGAAAAC AAGATATTAAGGCCTA AGAAGCTATATAAAA CAACTGTGCCTTTTATG GTTCCGGAAAAGTTGA GGGGCGTGTAATTGGA GGAAATCTAAATACTTT GACAGGTATATGGGGG AGTGAATGGATGCCTG AAATTCTTAATGGAGAT ATATTGTTTATTGAGGA CAGTCGGAAAAGCATT GCAACAATTGAACGAT TATTCTCTATGCTAAAG CTTAATCGCGTGTTTGA TAAAGTTAGTGCAATA ATACTCGGGAAACATG AGCTTTTTGATTGTGCA GGAAGTAAACGCAGAC CATATGAAGTATTAACA GAGGTATTAGATGGGA AACAGATTCCTGTACTG GATGGATTTGATTGTTC ACATACACATCCAATGC TAACTCTTCCACTTGGT GTAAAATTAGCTATTGA CTTTGACAACAAAATA TAT |
| 532 | Sakacin-A immunity factor | MKADYKKI NSILTYTST ALKNPKIIK DKDLVVLL TIIQEEAKQ NRIFYDYK RKFRPAVT RFTIDNNFE IPDCLVKL LSAVETPK AWSGFS | Lactobacillus sakei | 533 | GGCAGATTATAAAAA ATAAATTCAATACTAAC TTACACATCTACTGCTT TAAAAAACCCTAAAATT ATAAAAGATAAAGATT TAGTAGTCCTTCTAACT ATTATTCAAGAAGAAG CCAAACAAAATAGAAT CTTTTATGATTATAAAA GAAAATTTCGTCCAGC GGTTACTCGCTTTACAA TTGATAATAATTTTGAG ATTCCTGATTGTTTGGT TAAACTACTGTCAGCTG TTGAAACACCTAAGGC GTGGTCTGGATTTAGTT AG |
| 534 | Colicin-E5 immunity modulator in ColE9 (E5Imm[E 9]) | MKLSPKAA IEVCNEAA KKGLWILG IDGGHWLN PGFRIDSSA SWTYDMP EEYKSKTP ENNRLAIE NIKDDIEN GYTAFIITL KM | Escherichia coli | 535 | TGAAGTTATCACCAAA AGCTGCAATAGAAGTT TGTAATGAAGCAGCGA AAAAAGGCTTATGGAT TTTGGGCATTGATGGTG GCATTGGCTGAATCCT GGATTCAGGATAGATA GTTCAGCATCATGGAC ATATGATATGCCGGAG GAATACAAATCAAAA CCCCTGAAAATAATAG ATTGGCTATTGAAAATA TTAAAGATGATATTGA GAATGGATACACTGCTT TCATTATCACGTTAAAG ATGTAA |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| 536 | Antilisterial bacteriocin subtilosin biosynthesis protein AlbD | MNNIFPIM SLLFKQLY SRQGKKDA IRIAAGLVI LAVFEIGLI RQAGIDES VLGKTYIIL ALLLMNTY MVFLSVTS QWKESYM KLSCLLPIS SRSFWLAQ SVVLFVDT CLRRTLFFF ILPLFLFGN GTLSGAQT LFWLGRFS FFTVYSILF GVMLSNHF VKKKNSM FLLHAAVF AFVCLSAA FMPAVTIP LCAVHML WAVIIDFP VFLQAPPH QSKMHFF MRRSEFSF YKREWNR FISSKAMLL NYVVMAA FSGFFSFQ MMNTGIFN QQVIYIVIS ALLLICSPI ALLYSIEK NDRMLLIT LPIKRRTM FWAKYRF YSGLLAGG FLLVAIIVG FISGRPISA LTFVQCME LLLAGAFIR LTADEKRP SFGWQTEQ QLWSGFSK YRSYLFCL PLFLATLA GTAVSLAV IPIAALIIVY YLQKQDG GFFDTSKR ERIGS | Bacillus subtilis | 537 | TTGGGGAGGAGACCGA TCTGCGGCGGGAATTTT TTGAGGTTATCGGCCAT GAATAACATATTCCCCA TCATGTCGTTGCTGTTC AAACAGCTGTACAGCC GGCAAGGGAAAAGGA CGCTATCCGCATTGCTG CAGGGCTTGTGATTCTC GCCGTGTTTGAAATCG GGCTGATCCGACAAGC CGGCATTGACGAATCG GTGTTGGGAAAAACGT ATATCATATTGGCGCTT CTCTTAATGAACACGTA TATGGTGTTTCTTTCCG TGACATCACAATGGAA GGAATCTTATATGAAG CTGAGCTGTCTGCTGCC GATTTCATCACGGAGCT TTTGGCTCGCCCAGAGT GTCGTTCTGTTTGTCGA TACCTGTTTGAGAAGA ACGTTATTCTTTTTTAT TTTACCGCTGTTCTTAT TTGGAAACGGAACGCT GTCAGGGGCGCAAACA TTGTTTTGGCTTGGCAG ATTTTCGTTTTTTACCG TTTACTCGATTCTATTC GGAGTTATGCTAAGCA ACCATTTCGTCAAAAAG AAGAACTCGATGTTTCT GCTGCATGCGGCGGTA TTCGCCTTTGTATGCCT CAGTGCCGCTTTTATGC CGGCCGTCACGATCCC GCTATGCGCGGTTCACA TGCTATGGGCGGTGAT CATTGACTTTCCGGTCT TTCTGCAGGCGCCTCCG CATCAGAGCAAGATGC ATTTTTTTATGCGGCGA TCTGAATTTTCGTTTTA CAAAAGAGAATGGAAC CGATTTATTTCTTCTAA AGCGATGCTGTTAAATT ACGTGGTGATGGCGGC GTTCAGCGGATTCTTTT CGTTCCAGATGATGAA CACTGGCATCTTCAATC AGCAAGTGATTTATATT GTGATTTCCGCTCTATT GCTGATTTGCTCGCCGA TCGCCCTTTTGTACTCT ATTGAAAAAAACGATC GCATGCTGCTCATCACG CTTCCAATTAAAAGAA GAACGATGTTTTGGGC GAAATATCGCTTTTATT CAG |
| 538 | Microcin-J25 export ATP-binding/permease protein McjD (Microcin-J25 | MERKQKN SLFNYIYSL MDVRGKF LFFSMLFIT SLSSIIISISP LILAKITDL LSGSLSNFS YEYLVLLA CLYMFCVI | Escherichia coli | 539 | ATGGAAAGAAAACAGA AAAACTCATTATTTAAT TATATTTATTCATTAAT GGATGTAAGAGGTAAA TTTTTATTCTTTTCCAT GTATTCATTACATCAT TATCATCGATAATCATA TCTATTTCACCATTGAT TCTTGCAAAGATTACAG |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | immunity modulator) (Microcin-J25 secretion ATP-binding protein McjD) | SNKASVFL FMILQSSLR INMQKKM SLKYLREL YNENITNL SKNNAGYT TQSLNQAS NDIYILVR NVSQNILS PVIQLISTI VVVLSTKD WFSAGVFF LYILVFVIF NTRLTGSL ASLRKHSM DITLNSYSL LSDTVDN MIAAKKNN ALRLISERY EDALTQEN NAQKKYW LLSSKVLL LNSLLAVIL FGSVFIYNI LGVLNGV VSIGHFIMI TSYIILLST PVENIGAL LSEIRQSM SSLAGFIQR HAENKATS PSIPFLNME RKLNLSIRE LSFSYSDD KKILNSVS LDLFTGKM YSLTGPSG SGKSTLVK IISGYYKN YFGDIYLN DISLRNISD EDLNDAIY YLTQDDYI FMDTLRFN LRLANYDA SENEIFKVL KLANLSVV NNEPVSLD THLINRGN NYSGGQK QRISLARLF LRKPAIIIID EATSALDY INESEILSSI RTHFPDALI INISHRINL LECSDCVY VLNEGNIV ASGHFRDL MVSNEYIS GLASVTE | | | ATTTACTGTCTGGCTCA TTGTCAAATTTTAGTTA TGAATATCGGTTTTAC TTGCCTGTTTATACATG TTTTGCGTTATATCTAA TAAAGCAAGTGTTTTTT TATTTATGATACTGCAA AGTAGTCTACGTATTAA CATGCAGAAAAAAATG TCGCTAAAGTATTTGAG AGAATTGTATAACGAA AATATAACTAACTTGAG TAAAAATAATGCTGGA TATACAACGCAAAGTCT TAACCAGGCTTCAAATG ACATTTATATTCTTGTG AGAAATGTTTCCCAGA ATATCCTGTCACCTGTT ATACAACTTATTCCAC TATTGTTGTTGTTTTAT CTACGAAGGACTGGTTT TCTGCCGGTGTGTTTTT TCTCTATATTCTGGTAT TTGTAATTTTAATACC AGACTGACTGGCAGTTT AGCGTCTCTCAGAAAA CACAGCATGGATATCA CTCTTAACTCTTATAGT CTGTTATCTGATACTGT TGATAACATGATAGCA GCTAAAAAGAATAATG CATTAAGACTTATTTCT GAACGTTATGAAGATG CTCTCACTCAGGAAAAC AATGCTCAGAAAAAAT ACTGGTTACTCAGTTCT AAAGTTCTTTTATTGAA CTCTTTACTTGCTGTAA TATTATTTGGTTCTGTA TTCATATATAATATTTT AGGTGTGCTGAATGGT GTAGTTAGTATCGGCCA CTTCATTATGATTACAT CATATATCATTCTTCTT TCAACGCCAGTGGAAA ATATAGGGGCATTGCT AAGTGAGATCAGGCAG TCAATGTCTAGCCTGGC AGGTTTTATTCAACGTC ATGCCGAGAATAAAGC CACATCTCCTTCAA |
| 540 | Microcin E492 immunity modulator | MTLLSFGF SPVFFSVM AFCIISRSK FYPQRTRN KVIVLILLT FFICFLYPL TKVYLVGS YGIFDKFY LFCFISTLI AIAINVVIL | Klebsiella pneumoniae | 541 | ATGACATTACTTTCATT TGGATTTTCTCCTGTTT TCTGTATCATTTCACG TTCTGTATCATTTCACG TAGTAAATTCTATCCGC AGAGAACGCGAAACAA AGTATTGTTCTGATTT TACTAACTTTTTTTATT TGTTTTTTATATCCATT AACAAAAGTGTATCTG |

TABLE 2-continued

Exemplary bacteriocin immunity modulators

| Polypeptide SEQ ID NO: | Name | Polypeptide Sequence | Organism of origin | Polynucleotide SEQ ID NO: | Polynucleotide Sequence |
|---|---|---|---|---|---|
| | | TINGAKNERN | | | GTGGGAAGTTACGGTATATTTGACAAATTCTACCTCTTTTGCTTTATTTCTACGTTAATTGCAATAGCAATTAACGTAGTGATACTTACAATAAATGGAGCTAAGAATGAGAGAAATTAG |

Poison-Antidote Systems

It can be desirable to contain a particular microbial cell within a desired environment, for example by killing or arresting the growth of the microbial cell if it is no longer in the desired environment. Poison-antidote systems, which are distinct from bacteriocins, can be useful for accomplishing such containment, or for other selective growth of microbial cells. Exemplary poison antidote systems are described in U.S. Pat. Nos. 5,910,438, 6,180,407, 7,176,029, and 7,183,097, each of which is hereby incorporated by reference in its entirety. In some embodiments, a poison-antidote system comprises a cytotoxic (poison) polypeptide, and a corresponding antitoxin (antidote) polypeptide in a single cell. As used herein, a "poison polynucleotide" refers to a polynucleotide encoding a poison polypeptide, and an "antidote polynucleotide" refers to a polynucleotide encoding an antidote polypeptide.

In some embodiments, the poison polypeptide is expressed constitutively, while the antidote polypeptide is only expressed under desired conditions. In some embodiments, the poison polypeptide is only expressed under undesired conditions, while the antidote polypeptide is only expressed under desired conditions. For example, in some embodiments, a poison/antidote system is configured so that the microbial cell survives under desired environmental conditions, but dies under undesired environmental conditions. For example, in some embodiments, a poison antidote system is configured so that the microbial cell is killed if it escapes from the environment in which it is being used in an industrial process. In other embodiments, a poison antidote system is configured so that the microbial cell survives when a vector (e.g. a plasmid) encoding an antidote polypeptide is present, but dies when the vector is absent. In some embodiments, the poison polypeptide is encoded by a poison polynucleotide in the host genome, while the antidote polypeptide is encoded by an antidote polynucleotide on a vector (such as a plasmid or extrachromosomal array or episome or minichromosome), and as such is only expressed when the vector is present in the host cell. In some embodiments, the poison polypeptide is encoded by a poison polynucleotide on a first vector, while the antidote polypeptide is encoded by an antidote polynucleotide on a second vector, and as such is only expressed when the second vector is present. In some embodiments, the presence of the antidote polynucleotide (and thus the presence of the antidote polypeptide) depends on the presence or absence of a recombination event, for example the integration of a polynucleotide sequence encoding the antidote polynucleotide into the host genome. It should be appreciated that in some embodiments in which expression of the antidote polypeptide depends on the presence or absence of a vector or recombination event, the poison and antidote polypeptide can each be expressed constitutively. Optionally, in some embodiments in which expression of the antidote polypeptide depends on the presence or absence of a vector or a recombination event, expression of the poison polypeptide and/or antidote polypeptide is conditional, for example so that the poison is only expressed in conditions in which the microbial cell is not desired, and/or the antidote polypeptide is only expressed in conditions in which the microbial cell is desired.

Exemplary microbial toxin polypeptide/antitoxin polypeptide pairs (also referred to as "poison/antidote" pairs) that can used in poison antidote systems in conjunction with some embodiments herein include, but are not limited to RelE/RelB, CcdB/CcdA, Kis/Kid, SoK/HoK, PasB (or PasC)/PasA, PemK/PemI, Doc/Phd, MazE/MazF and ParE/ParD. Without being limited by any particular theory, many poison polypeptides, for example RelE, are highly conserved across Gram-positive and Gram-negative bacteria and Archae, and as such, can have cytotoxic activity in a broad range of naturally occurring, genetically modified, and fully synthetic microbial cells. Further, without being limited by any particular theory, it is contemplated that an antidote polypeptide can generally inhibit the activity of its poison polypeptide partner in a variety of host environments, and as such, poison/antidote pairs such as those described herein can readily be used in a broad range of naturally occurring, genetically modified, and fully synthetic microbial cells.

It is noted that a poison-antidote system is distinct from a bacteriocin system at least in that a poison-antidote system provides an endogenous system by which a microbial cell can kill or arrest itself, while a bacteriocin system provides an exogenous system by which a microbial cell can kill or arrest other cells. It is further noted, however, that, while a poison-antidote system cannot be used to kill or arrest cells other than the individual cell in which the poison is produced, in some embodiments, a poison-antidote system may be used along with a bacteriocin system as described herein. For example, in some embodiments a bacteriocin system as described herein may be used to kill or arrest the growth of cells other than the bacteriocin producing cell in a culture while the poison-antidote system may be used to kill or arrest the growth of the bacteriocin producing cell should it escape from its desired environment. A poison-antidote system may also be used to select for bacteriocin producing cells which have been genetically engineered to express a molecule useful in an industrial process (an "industrially useful molecule"). For example, in some embodiments, expression of an antidote can be tied to expression of an industrially useful molecule or bacteriocin by placing polynucleotides encoding the bacteriocin and the industrially useful molecule, or polynucleotides encoding the bacteriocin and antidote under the control of a single promoter. Accordingly, in some embodiments, a microbial cell encoding a bacteriocin or bacteriocin immunity modulator further comprises a poison antidote system. In some embodiments, the bacteriocin system is useful for regulating growth of the microbial cell or other microbial cells within a particular environment, while the poison-antidote system is useful for containing the microbial cell within a particular environment.

Promoters

Promoters are well known in the art. A promoter can be used to drive the transcription of one or more genes. In some embodiments, a promoter drives expression of polynucleotide encoding a desired gene product as described herein. In some embodiments, a promoter drives expression of a bacteriocin polynucleotide as described herein. In some embodiments, a promoter drives expression of an immunity modulator polynucleotide as described herein. In some embodiments, a promoter drives expression of a bacteriocin nucleotide and an immunity modulator polynucleotide. In some embodiments, a promoter drives expression of polynucleotide encoding at least one of a bacteriocin, immunity modulator, industrially useful molecule, poison molecule, or antidote molecule. Some promoters can drive transcription at all times ("constitutive promoters"). Some promoters can drive transcription under only select circumstances ("conditional promoters"), for example depending on the presence or absence of an environmental condition, chemical compound, gene product, stage of the cell cycle, or the like.

The skilled artisan will appreciate that depending on the desired expression activity, an appropriate promoter can be selected, and placed in cis with a sequence to be expressed. Exemplary promoters with exemplary activities are provided in Table 3.1-3.11 herein. The skilled artisan will appreciate that some promoters are compatible with particular transcriptional machinery (e.g. RNA polymerases, general transcription factors, and the like). As such, while compatible "species" are identified for some promoters described herein, it is contemplated that according to some embodiments herein, these promoters can readily function in microorganisms other than the identified species, for example in species with compatible endogenous transcriptional machinery, genetically modified species comprising compatible transcriptional machinery, or fully synthetic microbial organisms comprising compatible transcriptional machinery.

The promoters of Tables 3.1-3.11 herein are publicly available from the Biobricks foundation. Per the Biobricks foundation, use of these promoters in accordance with BioBrick™ Public Agreement (BPA) is encouraged.

It should be appreciated that any of the "coding" polynucleotides described herein (for example a bacteriocin polynucleotide, immunity polynucleotide, poison polynucleotide, antidote polynucleotide, or product polynucleotide) is generally amenable to being expressed under the control of a desired promoter. In some embodiments, a single "coding" polynucleotide is under the control of a single promoter. In some embodiments, two or more "coding" polynucleotides are under the control of a single promoter, for example two, three, four, five, six, seven, eight, nine, or ten polynucleotides. As such, in some embodiments, a "cocktail" of different bacteriocins can be produced by a single microbial organism. In some embodiments, a bacteriocin polynucleotide is under the control of a promoter. In some embodiments, an immunity modulator is under the control of a promoter. In some embodiments, a polynucleotide encoding a desired gene product is under the control of a promoter. In some embodiments, the bacteriocin polynucleotide and the polynucleotide encoding a desired gene product are under the control of the same promoter. In some embodiments, a bacteriocin polynucleotide and the polynucleotide encoding a desired gene product are under the control of different promoters. In some embodiments, the immunity modulator polynucleotide and the polynucleotide encoding a desired gene product are under the control of the same promoter. In some embodiments, the bacteriocin polynucleotide and the immunity modulator polynucelotide are under the control of different promoters.

Generally, translation initiation for a particular transcript is regulated by particular sequences at or 5' of the 5' end of the coding sequence of a transcript. For example, a coding sequence can begin with a start codon configured to pair with an initiator tRNA. While naturally-occurring translation systems typically use Met (AUG) as a start codon, it will be readily appreciated that an initiator tRNA can be engineered to bind to any desired triplet or triplets, and accordingly, triplets other than AUG can also function as start codons in certain embodiments. Additionally, sequences near the start codon can facilitate ribosomal assembly, for example a Kozak sequence ((gcc)gccRccAUGG, SEQ ID NO: 542, in which R represents "A" or "G") or Internal Ribosome Entry Site (IRES) in typical eukaryotic translational systems, or a Shine-Delgarno sequence (GGAGGU, SEQ ID NO: 543) in typical prokaryotic translation systems. As such in some embodiments, a transcript comprising a "coding" polynucleotide sequence, for example a bacteriocin polynucleotide or immunity modulator polynucleotide, or polynucleotide encoding a desired industrial product, comprises an appropriate start codon and translational initiation sequence. In some embodiments, for example if two or more "coding" polynucleotide sequences are positioned in cis on a transcript, each polynucleotide sequence comprises an appropriate start codon and translational initiation sequence(s). In some embodiments, for example if two or more "coding" polynucleotide sequences are positioned in cis on a transcript, the two sequences are under control of a single translation initiation sequence, and either provide a single polypeptide that can function with both encoded polypeptides in cis, or provide a means for separating two polypeptides encoded in cis, for example a 2A sequence or the like. In some embodiments, a translational intiator tRNA is regulatable, so as to regulate initiation of translation of a bacteriocin, immunity modulator, poison molecule, antidote molecule, or industrially useful molecule.

TABLE 3.1

Exemplary Metal-Sensitive Promoters

| SEQ ID NO: | Name | Description | Sequence |
|---|---|---|---|
| 544 | BBa_I721001 | Lead Promoter | gaaaaccttgtcaat gaagagcgatctatg |
| 545 | BBa_I731004 | FecA promoter | ttctcgttcgactca tagctgaacacaaca |

TABLE 3.1-continued

Exemplary Metal-Sensitive Promoters

| SEQ ID NO: | Name | Description | Sequence |
|---|---|---|---|
| 546 | BBa_I760005 | Cu-sensitive promoter | atgacaaaattgtcat |
| 547 | BBa_I765000 | Fe promoter | accaatgctgggaacggccagggcacctaa |
| 548 | BBa_I765007 | Fe and UV promoters | ctgaaagcgcataccgctatggagggggtt |
| 549 | BBa_J3902 | PrFe (PI + PII rus operon) | tagatatgcctgaaagcgcataccgctatg |

TABLE 3.2

Exemplary Cell Signaling-Responsive Promoters

| SEQ ID NO: | Name | Description | Sequence |
|---|---|---|---|
| 550 | BBa_I1051 | Lux cassette right promoter | tgttatagtcgaatacctctggcggtgata |
| 551 | BBa_I14015 | P(Las) TetO | ttttggtacactccctatcagtgatagaga |
| 552 | BBa_I14016 | P(Las) CIO | cttttggtacactacctctggcggtgata |
| 553 | BBa_I14017 | P(Rhl) | tacgcaagaaaatggtttgttatagtcgaa |
| 554 | BBa_I739105 | Double Promoter (LuxR/HSL, positive/cI, negative) | cgtgcgtgttgataacaccgtgcgtgttga |
| 555 | BBa_I746104 | P2 promoter in agr operon from S. aureus | agattgtactaaatcgtataatgacagtga |
| 556 | BBa_I751501 | plux-cI hybrid promoter | gtgttgatgctttatcaccgccagtggta |
| 557 | BBa_I751502 | plux-lac hybrid promoter | agtgtgtggaattgtgagcggataacaatt |
| 558 | BBa_I761011 | CinR, CinL and glucose controlled promotor | acatcttaaaagttttagtatcatattcgt |
| 559 | BBa_I06403 | RhIR promoter repressible by CI | tacgcaagaaaatggtttgttatagtcgaa |
| 560 | BBa_I102001 | Reverse Lux Promoter | tcttgcgtaaacctgtacgatcctacaggt |
| 561 | BBa_I64000 | rhlI promoter | atcctcctttagtcttcccccctcatgtgtg |
| 562 | BBa_I64010 | lasI promoter | taaaattatgaaatttgcataaaattcttca |
| 563 | BBa_I64067 | LuxR + 3OC6HSL independent R0065 | gtgttgactatttacctctggcggtgata |
| 564 | BBa_I64712 | LasR/LasI Inducible & RHLR/RHLI repressible Promoter | gaaatctggcagttttggtacacgaaagc |
| 565 | BBa_K091107 | pLux/cI Hybrid Promoter | acaccgtgcgtgttgatatagtcgaataaa |
| 566 | BBa_K091117 | pLas promoter | aaaattatgaaatttgtataaattcttcag |
| 567 | BBa_K091143 | pLas/cI Hybrid Promoter | ggttcttttggtacctctggcggtgataa |
| 568 | BBa_K091146 | pLas/Lux Hybrid Promoter | tgtaggatcgtacaggtataaattcttcag |
| 569 | BBa_K091156 | pLux | caagaaaatggtttgttatagtcgaataaa |
| 570 | BBa_K091157 | pLux/Las Hybrid Promoter | ctatctcatttgctagtatagtcgaataaa |
| 571 | BBa_K145150 | Hybrid promoter: HSL-LuxR activated, P22 C2 repressed | tagtttataatttaagtgttctttaatttc |
| 572 | BBa_K266000 | PAI + LasR -> LuxI (AI) | caccttcgggtgggcctttctgcgtttata |
| 573 | BBa_K266005 | PAI + LasR -> LasI & AI + LuxR --\|LasI | aataactctgatagtgctagtgtagatctc |

TABLE 3.2-continued

Exemplary Cell Signaling-Responsive Promoters

| SEQ ID NO: | Name | Description | Sequence |
|---|---|---|---|
| 574 | BBa_K266006 | PAI + LasR -> LasI + GFP & AI + LuxR --\| LasI + GFP | caccttcgggtgggcctttctgcgtttata |
| 575 | BBa_K266007 | Complex QS -> LuxI & LasI circuit | caccttcgggtgggcctttctgcgtttata |
| 576 | BBa_K658006 | position 3 mutated promoter lux pR-3 (luxR & HSL regulated) | caagaaaatggtttgttatagtcgaataaa |
| 577 | BBa_K658007 | position 5 mutated promoter lux pR-5 (luxR & HSL regulated) | caagaaaatggtttgttatagtcgaataaa |
| 578 | BBa_K658008 | position 3&5 mutated promoter lux pR-3/5 (luxR & HSL regulated) | caagaaaatggtttgttatagtcgaataaa |
| 579 | BBa_R0061 | Promoter (HSL-mediated luxR repressor) | ttgacacctgtaggatcgtacaggtataat |
| 580 | BBa_R0062 | Promoter (luxR & HSL regulated-lux pR) | caagaaaatggtttgttatagtcgaataaa |
| 581 | BBa_R0063 | Promoter (luxR & HSL regulated-lux pL) | cacgcaaaacttgcgacaaacaataggtaa |
| 582 | BBa_R0071 | Promoter (RhlR & C4-HSL regulated) | gttagctttcgaattggctaaaaagtgttc |
| 583 | BBa_R0078 | Promoter (cinR and HSL regulated) | ccattctgctttccacgaacttgaaaacgc |
| 584 | BBa_R0079 | Promoter (LasR & PAI regulated) | ggccgcgggttcttttttggtacacgaaagc |
| 585 | BBa_R1062 | Promoter, Standard (luxR and HSL regulated -- lux pR) | aagaaaatggtttgttgatactcgaataaa |

TABLE 3.3

Exemplary Constitutive E. coli $\sigma^{70}$ Promoters

| SEQ ID NO: | Name | Description | Sequence |
|---|---|---|---|
| 586 | BBa_I14018 | P(Bla) | gtttatacataggcgagtactctgttatgg |
| 587 | BBa_I14033 | P(Cat) | agaggttccaactttcaccataatgaaaca |
| 588 | BBa_I14034 | P(Kat) | taaacaactaacggacaattctacctaaca |
| 589 | BBa_I732021 | Template for Building Primer Family Member | acatcaagccaaattaaacaggattaacac |
| 590 | BBa_I742126 | Reverse lambda cI-regulated promoter | gaggtaaaatagtcaacacgcacggtgtta |
| 591 | BBa_J01006 | Key Promoter absorbs 3 | caggccggaataactccctataatgcgcca |
| 592 | BBa_I23100 | constitutive promoter family member | ggctagctcagtcctaggtacagtgctagc |
| 593 | BBa_I23101 | constitutive promoter family member | agctagctcagtcctaggtattatgctagc |
| 594 | BBa_I23102 | constitutive promoter family member | agctagctcagtcctaggtactgtgctagc |

TABLE 3.3-continued

Exemplary Constitutive E. coli σ[70] Promoters

| SEQ ID NO: | Name | Description | Sequence |
|---|---|---|---|
| 595 | BBa_I23103 | constitutive promoter family member | agctagctcagtcctagggattatgctagc |
| 596 | BBa_I23104 | constitutive promoter family member | agctagctcagtcctaggtattgtgctagc |
| 597 | BBa_I23105 | constitutive promoter family member | ggctagctcagtcctaggtactatgctagc |
| 598 | BBa_I23106 | constitutive promoter family member | ggctagctcagtcctaggtatagtgctagc |
| 599 | BBa_I23107 | constitutive promoter family member | ggctagctcagccctaggtattatgctagc |
| 600 | BBa_I23108 | constitutive promoter family member | agctagctcagtcctaggtataatgctagc |
| 601 | BBa_I23109 | constitutive promoter family member | agctagctcagtcctagggactgtgctagc |
| 602 | BBa_I23110 | constitutive promoter family member | ggctagctcagtcctaggtacaatgctagc |
| 603 | BBa_I23111 | constitutive promoter family member | ggctagctcagtcctaggtatagtgctagc |
| 604 | BBa_I23112 | constitutive promoter family member | agctagctcagtcctagggattatgctagc |
| 605 | BBa_I23113 | constitutive promoter family member | ggctagctcagtcctagggattatgctagc |
| 606 | BBa_I23114 | constitutive promoter family member | ggctagctcagtcctaggtacaatgctagc |
| 607 | BBa_I23115 | constitutive promoter family member | agctagctcagcccttggtacaatgctagc |
| 608 | BBa_I23116 | constitutive promoter family member | agctagctcagtcctagggactatgctagc |
| 609 | BBa_I23117 | constitutive promoter family member | agctagctcagtcctagggattgtgctagc |
| 610 | BBa_I23118 | constitutive promoter family member | ggctagctcagtcctaggtattgtgctagc |
| 611 | BBa_I23119 | constitutive promoter family member | agctagctcagtcctaggtataatgctagc |
| 612 | BBa_J23150 | 1 bp mutant from J23107 | ggctagctcagtcctaggtattatgctagc |
| 613 | BBa_J23151 | 1 bp mutant from J23114 | ggctagctcagtcctaggtacaatgctagc |
| 614 | BBa_J44002 | pBAD reverse | aaagtgtgacgccgtgcaaataatcaatgt |
| 615 | BBa_I48104 | NikR promoter, a protein of the ribbon helix-helix family of trancription factors that repress expre | gacgaatacttaaaatcgtcatacttattt |
| 616 | BBa_J54200 | lacq_Promoter | aaacctttcgcggtatggcatgatagcgcc |
| 617 | BBa_J56015 | lacIQ-promoter sequence | tgatagcgcccggaagagagtcaattcagg |
| 618 | BBa_I64951 | E. Coli CreABCD phosphate sensing operon promoter | ttatttaccgtgacgaactaattgctcgtg |
| 619 | BBa_K088007 | GlnRS promoter | catacgccgttatacgttgtttacgctttg |
| 620 | BBaKI 19000 | Constitutive weak promoter of lacZ | ttatgcttccggctcgtatgttgtgtggac |

TABLE 3.3-continued

Exemplary Constitutive *E. coli* σ⁷⁰ Promoters

| SEQ ID NO: | Name | Description | Sequence |
|---|---|---|---|
| 621 | BBa_K119001 | Mutated LacZ promoter | ttatgcttccggctcgtatggtgtgtggac |
| 622 | BBa_K137029 | constitutive promoter with (TA)10 between -10 and -35 elements | atatatatatatataatggaagcgtttt |
| 623 | BBa_K137030 | constitutive promoter with (TA)9 between -10 and -35 elements | atatatatatatataatggaagcgtttt |
| 624 | BBa_K137031 | constitutive promoter with (C)10 between -10 and -35 elements | ccccgaaagcttaagaatataattgtaagc |
| 625 | BBa_K137032 | constitutive promoter with (C)12 between -10 and -35 elements | ccccgaaagcttaagaatataattgtaagc |
| 626 | BBa_K137085 | optimized (TA) repeat constitutive promoter with 13 bp between -10 and -35 elements | tgacaatatatatatatataatgctagc |
| 627 | BBa_K137086 | optimized (TA) repeat constitutive promoter with 15 bp between -10 and -35 elements | acaatatatatatatatatataatgctagc |
| 628 | BBa_K137087 | optimized (TA) repeat constitutive promoter with 17 bp between -10 and -35 elements | aatatatatatatatatataatgctagc |
| 629 | BBa_K137088 | optimized (TA) repeat constitutive promoter with 19 bp between -10 and -35 elements | tatatatatatatatatataatgctagc |
| 630 | BBa_K137089 | optimized (TA) repeat constitutive promoter with 21 bp between -10 and -35 elements | tatatatatatatatatataatgctagc |
| 631 | BBa_K137090 | optimized (A) repeat constitutive promoter with 17 bp between -10 and -35 elements | aaaaaaaaaaaaaaaaatataatgctagc |
| 632 | BBa_K137091 | optimized (A) repeat constitutive promoter with 18 bp between -10 and -35 elements | aaaaaaaaaaaaaaaaatataatgctagc |
| 633 | BBa_K256002 | J23101:GFP | caccttcgggtgggcctttctgcgtttata |
| 634 | BBa_K256018 | J23119:IFP | caccttcgggtgggcctttctgcgtttata |
| 635 | BBa_K256020 | J23119:HO1 | caccttcgggtgggcctttctgcgtttata |
| 636 | BBa_K256033 | Infrared signal reporter (J23119:IFP:J23119:HO1) | caccttcgggtgggcctttctgcgtttata |
| 637 | BBa_K292000 | Double terminator + constitutive promoter | ggctagctcagtcctaggtacagtgctagc |
| 638 | BBa_K292001 | Double terminator + Constitutive promoter + Strong RBS | tgctagctactagagattaaagaggagaaa |

TABLE 3.3-continued

Exemplary Constitutive E. coli σ⁷⁰ Promoters

| SEQ ID NO: | Name | Description | Sequence |
|---|---|---|---|
| 639 | BBa_K418000 | IPTG inducible Lac promoter cassette | ttgtgagcggataacaagatactgagcaca |
| 640 | BBa_K418002 | IPTG inducible Lac promoter cassette | ttgtgagcggataacaagatactgagcaca |
| 641 | BBa_K418003 | IPTG inducible Lac promoter cassette | ttgtgagcggataacaagatactgagcaca |
| 642 | BBa_M13101 | M13K07 gene I promoter | cctgttttatgttattctctctgtaaagg |
| 643 | BBa_M13102 | M13K07 gene II promoter | aaatatttgcttatacaatcttcctgtttt |
| 644 | BBa_M13103 | M13K07 gene III promoter | gctgataaaccgatacaattaaaggctcct |
| 645 | BBa_M13104 | M13K07 gene IV promoter | ctcttctcagcgtcttaatctaagctatcg |
| 646 | BBa_M13105 | M13K07 gene V promoter | atgagccagttcttaaaatcgcataaggta |
| 647 | BBa_M13106 | M13K07 gene VI promoter | ctattgattgtgacaaaataaacttattcc |
| 648 | BBa_M13108 | M13K07 gene VIII promoter | gtttcgcgcttggtataatcgctggggggtc |
| 649 | BBa_M13110 | M13110 | ctttgcttctgactataatagtcagggtaa |
| 650 | BBa_M31519 | Modified promoter sequence of g3. | aaaccgatacaattaaaggctcctgctagc |
| 651 | BBa_R1074 | Constitutive Promoter I | caccacactgatagtgctagtgtagatcac |
| 652 | BBa_R1075 | Constitutive Promoter II | gccggaataactccctataatgcgccacca |
| 653 | BBa_S03331 | --Specify Parts List-- | ttgacaagcttttcctcagctccgtaaact |

TABLE 3.4

Exemplary Constitutive E. coli σˢ Promoters

| SEQ ID NO: | Name | Description | Sequence |
|---|---|---|---|
| 654 | BBa_J45992 | Full-length stationary phase osmY promoter | ggtttcaaaattgtgatctatatttaacaa |
| 655 | BBa_I45993 | Minimal stationary phase osmY promoter | ggtttcaaaattgtgatctatatttaacaa |

TABLE 3.5

Exemplary Constitutive E. coli σ³² Promoters

| SEQ ID NO: | Name | Description | Sequence |
|---|---|---|---|
| 656 | BBa_J45504 | htpG Heat Shock Promoter | tctattccaataaagaaatcttcctgcgtg |

TABLE 3.6

Exemplary Constitutive B. subtilis σ⁴ Promoters

| SEQ ID NO: | Name | Description | Sequence |
|---|---|---|---|
| 657 | BBa_K143012 | Promoter veg a constitutive promoter for B. subtilis | aaaaatgggctcgtgttgtacaataaatgt |
| 658 | BBa_K143013 | Promoter 43 a constitutive promoter for B. subtilis | aaaaaaagcgcgcgattatgtaaaatataa |
| 659 | BBa_K780003 | Strong constitutive promoter for Bacillus subtilis | aattgcagtaggcatgacaaaatggactca |
| 660 | BBa_K823000 | PliaG | caagcttttcctttataatagaatgaatga |
| 661 | BBa_K823002 | PlepA | tctaagctagtgtattttgcgtttaatagt |
| 662 | BBa_K823003 | Pveg | aatgggctcgtgttgtacaataaatgtagt |

TABLE 3.7

Exemplary Constitutive *B. subtilis* σ<sup>B</sup> Promoters

| SEQ ID NO: | Name | Description | Sequence |
|---|---|---|---|
| 663 | BBa_K143010 | Promoter etc for *B. subtilis* | atccttatcgttatg ggtattgtttgtaat |
| 664 | BBa_K143011 | Promoter gsiB for *B. subtilis* | taaagaattgtgag cgggaatacaacaac |
| 665 | BBa_K143013 | Promoter 43 a constitutive promoter for *B. subtilis* | aaaaaaagcgcgcga ttatgtaaaatataa |

TABLE 3.8

Exemplary Constitutive Promoters from miscellaneous prokaryotes

| SEQ ID NO: | Name | Description | Sequence |
|---|---|---|---|
| 666 | a_K112706 | Pspv2 from *Salmonella* | tacaaaataattccc ctgcaaacattatca |
| 667 | BBa_K112707 | Pspv from *Salmonella* | tacaaaataattccc ctgcaaacattatcg |

TABLE 3.9

Exemplary Constitutive Promoters from bacteriophage T7

| SEQ ID NO: | Name | Description | Sequence |
|---|---|---|---|
| 668 | BBa_I712074 | T7 promoter (strong promoter from T7 bacteriophage) | agggaatacaagcta cttgttcttttgca |
| 669 | BBa_I719005 | T7 Promoter | taatacgactcacta tagggaga |
| 670 | BBa_J34814 | T7 Promoter | gaatttaatacgact cactataggaga |
| 671 | BBa_J64997 | T7 consensus -10 and rest | taatacgactcacta tagg |
| 672 | BBa_K113010 | overlapping T7 promoter | gagtcgtattaatac gactcactataggg |
| 673 | BBa_K113011 | more overlapping T7 promoter | agtgagtcgtactac gactcactataggg |
| 674 | BBa_K113012 | weaken overlapping T7 promoter | gagtcgtattaatac gactctctataggg |
| 675 | BBa_R0085 | T7 Consensus Promoter Sequence | taatacgactcacta tagggaga |

TABLE 3.9-continued

Exemplary Constitutive Promoters from bacteriophage T7

| SEQ ID NO: | Name | Description | Sequence |
|---|---|---|---|
| 676 | BBa_R0180 | T7 RNAP promoter | ttatacgactcacta tagggaga |
| 677 | BBa_R0181 | T7 RNAP promoter | gaatacgactcacta tagggaga |
| 678 | BBa_R0182 | T7 RNAP promoter | taatacgtctcacta tagggaga |
| 679 | BBa_R0183 | T7 RNAP promoter | tcatacgactcacta tagggaga |
| 680 | BBa_Z0251 | T7 strong promoter | taatacgactcacta tagggagaccacaac |
| 681 | BBa_Z0252 | T7 weak binding and processivity | taattgaactcacta aagggagaccacagc |
| 682 | BBa_Z0253 | T7 weak binding promoter | cgaagtaatacgact cactatagggaaga |

TABLE 3.10

Exemplary Constitutive Promoters from yeast

| SEQ ID NO: | Name | Description | Sequence |
|---|---|---|---|
| 683 | BBa_1766555 | pCyc (Medium) Promoter | acaaacacaaatca cacactaaattaata |
| 684 | BBa_1766556 | pAdh (Strong) Promoter | ccaagcatacaatca actatctcatataca |
| 685 | BBa_1766557 | pSte5 (Weak) Promoter | gatacaggatacagc ggaaacaacttttaa |
| 686 | BBa_J63005 | yeast ADH1 promoter | tttcaagctataccα agcatacaatcaact |
| 687 | BBa_K105027 | cyc100 minimal promoter | cctttgcagcataaa ttactatacttctat |
| 688 | BBa_K105028 | cyc70 minimal promoter | cctttgcagcataaa ttactatacttctat |
| 689 | BBa_K105029 | cyc43 minimal promoter | cctttgcagcataaa ttactatacttctat |
| 690 | BBa_K105030 | cyc28 minimal promoter | cctttgcagcataaa ttactatacttctat |
| 691 | BBa_K105031 | eye 16 minimal promoter | cctttgcagcataaa ttactatacttctat |

TABLE 3.10-continued

Exemplary Constitutive Promoters from yeast

| SEQ ID NO: | Name | Description | Sequence |
|---|---|---|---|
| 692 | BBa_K122000 | pPGK1 | ttatctactttttac aacaaatataaaaca |
| 693 | BBa_K124000 | pCYC Yeast Promoter | acaaacacaaataca cacactaaattaata |
| 694 | BBa_K124002 | Yeast GPD (TDH3) Promoter | gtttcgaataaacac acataaacaaacaaa |
| 695 | BBa_K319005 | yeast mid-length ADH1 promoter | ccaagcatacaatca actatctcatataca |
| 696 | BBa_M31201 | Yeast CLBI promoter region, G2/M cell cycle specific | accatcaaaggaagc tttaatcttctcata |

TABLE 3.11

Exemplary Constitutive Promoters from miscellaneous eukaryotes

| SEQ ID NO: | Name | Description | Sequence |
|---|---|---|---|
| 697 | BBa_I712004 | CMV promoter | agaacccactgctta ctggcttatcgaaat |
| 698 | BBa_K076017 | Ube Promoter | ggccgtttttggctt ttttgttagacgaag |

The above-referenced promoters are provided by way of non-limiting example only. The skilled artisan will readily recognize that many variants of the above-referenced promoters, and many other promoters (including promoters isolated from naturally existing organisms, variations thereof, and fully synthetic promoters) can readily be used in accordance with some embodiments herein.

Regulation of Gene Activity

Gene activity can be regulated to either increase or decrease activity of the gene product. In some embodiments, the gene product for which activity is regulated comprises a bacteriocin, immunity modulator, industrially useful molecule, poison molecule, or antidote molecule. In some embodiments, two or more of such gene products are regulated under a single gene regulation system. In some embodiments, gene activity is regulated at the level of gene expression. In some embodiments, gene activity is regulated at the transcriptional level, for example by activating or repressing a promoter. In some embodiments, gene activity is regulated at the post-transcriptional level, for example through regulation of RNA stability. In some embodiments, gene activity is regulated at the translational level, for example through regulation of initiation of translation. In some embodiments, gene activity is regulated at the post-translational level, for example through regulation of polypeptide stability, post-translational modifications to the polypeptide, or binding of an inhibitor to the polypeptide.

In some embodiments, gene activity is increased. In some embodiments, activity of at least one of a bacteriocin, immunity modulator, industrially useful molecule, poison molecule, or antidote molecule is increased. Conceptually, gene activity can be increased by directly activating gene activity, or by decreasing the activity of an inhibitor of gene activity. In some embodiments, gene activity is activated by at least one of: inducing promoter activity, inhibiting a transcriptional repressor, increasing RNA stability, inhibiting a post-transcriptional inhibitor (for example, inhibiting a ribozyme or antisense oligonucleotide), inducing translation (for example, via a regulatable tRNA), making a desired post-translational modification, or inhibiting a post-translational inhibitor (for example a protease directed to a polypeptide encoded by the gene). In some embodiments, a compound present in a desired environment induces a promoter. For example, the presence of iron in culture medium can induce transcription by an iron-sensitive promoter as described herein. In some embodiments, a compound present in a desired culture medium inhibits a transcriptional repressor. For example, the presence of tetracycline in an environment can inhibit the tet repressor, and thus allow activity from the tetO promoter. In some embodiments, a compound found only outside of a desired culture medium induces transcription.

In some embodiments, gene activity is decreased. Conceptually, gene activity can be decreased by directly inhibiting gene activity, or by decreasing the activity of an activator of gene activity. In some embodiments, gene activity is reduced, but some level of activity remains. In some embodiments, gene activity is fully inhibited. In some embodiments, gene activity is decreased by at least one of inhibiting promoter activity, activating a transcriptional repressor, decreasing RNA stability, activating a post-transcriptional inhibitor (for example, expressing a ribozyme or antisense oligonucleotide), inhibiting translation (for example, via a regulatable tRNA), failing to make a required post-translational modification, inactivating a polypeptide (for example by binding an inhibitor or via a polypeptide-specific protease), or failing to properly localize a polypeptide (e.g. failing to secrete a bacteriocin). In some embodiments, gene activity is decreased by removing a gene from a desired location, for example by excising a gene using a FLP-FRT or cre-lox cassette, or through loss or degradation of a plasmid. In some embodiments, a gene product (e.g. a polypeptide) or a product produced by a gene product (e.g. the product of an enzymatic reaction) inhibits further gene activity (e.g. a negative feedback loop).

Genetic Modification of Microbial Organisms

Techniques of genetically modifying microorganisms are well known in the art. In some embodiments, a microorganism is genetically modified to comprise nucleic acid sequence regulating the expression of, and encoding, at least one of bacteriocins, immunity modulators, industrially useful molecules, poison molecules, or antidote molecules. Polynucleotides can be delivered to microorganisms, and can be stably integrated into the chromosomes of these microorganisms, or can exist free of the genome, for example in a plasmid, extrachromosomal array, episome, minichromosome, or the like.

Exemplary vectors for genetic modification of microbial cells include, but are not limited to, plasmids, viruses (including bacteriophage), and transposable elements. Additionally, it will be appreciated that entire microbial genomes comprising desired sequences can be synthesized and assembled in a cell (see, e.g. Gibson et al. (2010), Science 329: 52-56). As such, in some embodiments, a microbial genome (or portion thereof) is synthesized with desired features such as bacteriocin polynucleotide(s), and introduced into a microbial cell.

It can be useful to flexibly genetically modify a microbial cell, for example to engineer or reengineer a microbial cell to have a desired type and/or spectrum of bacteriocin or immunity modulator activity. In some embodiments, a cassette for inserting one or more desired bacteriocin and/or immunity modulator polynucleotides into a polynucleotide sequence is provided. Exemplary cassettes include, but are not limited to, a Cre/lox cassette or FLP/FRT cassette. In some embodiments, the cassette is positioned on a plasmid, so that a plasmid with the desired bacteriocin and/or immunity modulator combination can readily be introduced to the microbial cell. In some embodiments, the cassette is positioned in the genome of the microbial cell, so that a cassette with the desired bacteriocin and/or immunity modulator combination can be introduced to the desired location.

In some embodiments, plasmid conjugation can be used to introduce a desired plasmid from a "donor" microbial cell to a recipient microbial cell. Goñi-Moreno, et al. (2013) Multicellular Computing Using Conjugation for Wiring. PLoS ONE 8(6): e65986, hereby incorporated by reference in its entirety. In some embodiments, plasmid conjugation can genetically modify a recipient microbial cell by introducing a conjugation plasmid from a donor microbial cell to a recipient microbial cell. Without being limited by any particular theory, conjugation plasmids that comprise the same or functionally same set of replication genes typically cannot coexist in the same microbial cell. As such, in some embodiments, plasmid conjugation "reprograms" a recipient microbial cell by introducing a new conjugation plasmid to supplant another conjugation plasmid that was present in the recipient cell. In some embodiments, plasmid conjugation is used to engineer (or reengineer) a microbial cell with a particular combination of one or more bacteriocins and/or immunity modulators. According to some embodiments, a variety of conjugation plasmids comprising different combinations of bacteriocins and/or immunity modulators is provided. The plasmids can comprise additional genetic elements as described herein, for example promoters, translational initiation sites, and the like. In some embodiments the variety of conjugation plasmids is provided in a collection of donor cells, so that a donor cell comprising the desired plasmid can be selected for plasmid conjugation. In some embodiments, a particular combination of bacteriocins and/or immunity modulators is selected, and an appropriate donor cell is conjugated with a microbial cell of interest to introduce a conjugation plasmid comprising that combination into a recipient cell. In some embodiments, the recipient cell is a "newly engineered" cell, for example to be introduced into or for initiating a culture. In some embodiments, the recipient cell is a "reengineered cell," for example to introduce a new bacteriocin (and optionally immunity modulator) activity to an existing culture that has encountered a new type of invader cell, and/or to remove a bacteriocin activity that is no longer desired in the culture.

Culture Media

Microbial culture environments can comprise a wide variety of culture media, for example feedstocks. The selection of a particular culture medium can depend upon the desired application. Conditions of a culture medium include not only chemical composition, but also temperature, amounts of light, pH, $CO_2$ levels, and the like.

In some embodiments, a genetically engineered microorganism as described herein is added to a culture medium that comprises other microorganisms and at least one feedstock. In some embodiments, the culture medium comprises a compound that induces the activity or expression of a bacteriocin and/or immunity modulator. In some embodiments, the culture medium comprises a compound that represses the activity or expression of a bacteriocin and/or immunity modulator. In some embodiments, a compound that induces the activity of the bacteriocin is present outside of the feedstock, but not in the feedstock. In some embodiments, a compound that represses the activity of the immunity modulator is present outside the feedstock, but not in the feedstock.

The term "feedstock" is used herein in a broad sense to encompass material that can be consumed, fermented, purified, modified, or otherwise processed by microbial organisms, for example in the context of industrial processes. As such, "feedstock" is not limited to food or food products. As used herein a "feedstock" is a category of culture medium. Accordingly, as used herein "culture medium" includes, but it is not limited to feedstock. As such, whenever a "culture medium" is referred to herein, feedstocks are also expressly contemplated.

Genetically Engineered Microbial Cells

In some embodiments, genetically modified microbial cells are provided. Genetically modified microbial cells can be configured for a wide variety of purposes. In some embodiments, microbial cells comprise genetic modifications to regulate the expression of at least one of bacteriocins, immunity modulators, industrially useful molecules, poison molecules, or antidote molecules. In some embodiments, microbial cells comprise genetic modifications to regulate the expression of bacteriocins. In some embodiments, microbial cells comprise genetic modifications to regulate the expression of immunity modulators.

In some embodiments, the genetically modified microbial cells are modified to produce a product. In some embodiments, the product is a gene product, for example a polypeptide or RNA. As such, polynucleotide "coding" sequence as referred to herein can refer to sequence encoding either a polypeptide or an RNA. In some embodiments, microbial cells can be configured to produce one or more gene products that contribute to synthesis of a desired product, for example a carbohydrate, biofuel, lipid, small molecule, or metal. In some embodiments, the product is synthesized via the activity of one or more gene products of the microbial cell. Optionally, synthesis of the product can also involve the activity of one or more gene products of one or more other microbial cells. In some embodiments, microbial cells can be configured to decontaminate or decompose one or more substances in a culture media, for example a feedstock. The decontamination can be mediated wholly, or partially by one or more gene products of the microbial cells. In some embodiments, microbial cells can be configured to scavenge for a material, for example a metal such as iron or a rare earth metal.

Controlling the Growth of Microbial Cells

In some embodiments, genetically modified microbial cells are modified to regulate the growth of other microbial cells. In some embodiments, the microbial cells regulate the growth of other microbial cells of the same species or strain, for example their own clones. In some embodiments, the microbial cells regulated the growth of microbial cells of a different species or strain, for example invaders. In some embodiments, a microbial cell secretes a bacteriocin to regulate other microbial cells. The regulation of each of the other microbial cells can depend on its expression (or lack thereof) of an immunity modulator having protective effects against the particular the secreted bacteriocin.

As used herein "desired cell" and the like refer to a microbial cell with at least one characteristic for which survival, growth, and/or proliferation of the microbial cell is desired, or at least an absence of negative control of the cell's growth is desired. In some embodiments, a desired cell is in an appropriate environment, for example its industrially-applicable feedstock. In some embodiments, a desired cell is a cell that is positively selected for, for example a cell that has undergone a particular recombination even, or is expressing high levels of a useful gene product. In some embodiments, a desired cell is a cell configured to neutralize contaminating cells, for example pathogenic cells. In some embodiments a desired cell is positively selected for by its expression of an immunity modulator corresponding to at least one bacteriocin that can be present in the environment. Without being bound by any particular theory, it is contemplated that a microbial cell capable of neutralizing other microbial cells which lack a similar neutralizing function will have a competitive advantage. As such, in some embodiments, a desired cell is selected for through its ability to neutralize other cells. In some embodiments a desired cell is positively selected for by expressing both a bacteriocin and a corresponding immunity modulator.

As used herein "undesired cell" and the like refer to a microbial cell with at least one characteristic making survival, growth, or proliferation undesirable. In some embodiments, the undesired cell is an invading microbial cell, for example a contaminating cell that has entered a culture environment. In some embodiments, an undesired cell has escaped from an appropriate culture medium, for example its industrially-applicable feedstock. In some embodiments, an undesired cell has lost a particular plasmid, or has failed to undergo a particular recombination event. In some embodiments, an undesired cell has failed to produce, or produces low levels of desired gene product. In some embodiments, an undesired cell is selected against. In some embodiments, an undesired cell is selected against through by reducing the cell's expression or activity of an immunity modulator that protects against a bacteriocin in the environment. In some embodiments, an undesired cell is selected against through by reducing the cell's expression or activity of an immunity modulator that protects against a bacteriocin secreted by the cell and clones thereof. In some embodiments, an undesired cell is selected against by reducing the cell's expression of a bacteriocin, thereby putting the cell at a competitive disadvantage against other microbial cells.

FIG. 1 is a flow diagram depicting options for configuring a microbial cell to control the growth of a second microbial cell according to some embodiments herein. In some embodiments, a first microbial cell is provided. In some embodiments, the first microbial cell secretes an active bacteriocin 100. In some embodiments, the first microbial cell is not desired 102. For example, in some embodiments, one or more of the first microbial cell being outside its industrial environment, a desired environmental conditional for the first microbial cell being absent, the first microbial cell having made sufficient product, or the first microbial cell lacking a recombination event or vector can make the first microbial cell undesirable in a particular environment at a particular time 112. As such, when the first microbial cell is not desired, its immunity modulator (corresponding to the bacteriocin) can be inactive 122. For example, one or more of an immunity modulator promoter can be inactive, an immunity modulator transcriptional repressor can be active, post-transcriptional silencing (e.g. by a ribozyme or antisense) can occur, a regulatable tRNA can not be induced, post-transcriptional silencing can occur (e.g. by a site-specific protease, or a silencing post-translational modification), or a vector encoding an immunity modulator can be absent 132. In some embodiments, when the first cell does not have an active immunity modulator, the first cell is neutralized by the bacteriocin 142 produced by other cells in the culture. In some embodiments, a second microbial cell proceeds with growth 192 as a result of the first cell being neutralized.

In some embodiments, the first microbial cell is desired 106. For example, one or more of the first microbial cell being inside of its industrial environment, a desired environmental condition for the first microbial cell being present, the first microbial cell having not yet made sufficent product yet, or the first microbial cell having undergone a recombination event or comprising a particular vector can make the microbial cell desirable in a particular environment at a particular time 116. As such, when the first microbial cell is desired, it can produce an active immunity modulator 126. For example, in some embodiments, the first microbial cell can be configured to have one or more of a constitutive promoter for the immunity modulator polynucleotide, an activated (but not necessarily constitutive) promoter for the immunity modulator polynucleotide, an inactive repressor of immunity modulator transcription, a regulatable tRNA that is induced to facilitate production of the immunity modulator, an absence of post-translational and post-transcriptional silencing of the immunity modulator, or a vector encoding the immunity modulator can be present 136. As such, the first microbial cell can survive 146 in the presence of bacteriocin secreted by the first microbial cell. As a result of the bacteriocin secreted by the first microbial cell, a second microbial cell can grow 192 or be neutralized 196, depending on whether the second microbial cell has 172 or does not have 176 immunity modulator activity.

In some embodiments, the second microbial cell is desired 152. For example, one or more of a desired recombination event having occurred in the second microbial cell, a desired vector present in the second microbial cell, the second microbial cell producing a product of which more is desired (e.g. a positive feedback loop), or the immunity locus and the desired product being under the same transcriptional control when appropriate levels of desired product are being transcribed can a make the second microbial cell desirable 162. When the second microbial cell is desired, it can provide immunity modulator activity to protect against the particular bacteriocin (or bacterocins) produced by the first microbial cell 172. For example, in some embodiments, the second microbial cell can be configured such that an immunity modulator promoter is active (for example, a constitutive promoter), an immunity modulator transcriptional repressor is inactive, there is a lack of post-transcriptional silencing, a regulatable tRNA being induced to facilitate the expression of the immunity modulator, a lack of post-translational silencing (e.g. by a site-specific protease) of the immunity modulator, or a vector encoding an immunity modulator can be present 182. As such, in some embodiments, when immunity modulator activity is provided, the second microbial cell can survive 192.

In some embodiments, a second microbial cell is not desired 156. For example, one or more of the second microbial cell being an invader (e.g. a contaminating cell), an undesired environmental condition for the second microbial cell (e.g. the presence of an undesired compound or condition, or the absence of a desired compound or condition), the second microbial cell having produced product, but no more product being desired (e.g. a negative feedback loop), or an immunity modulator locus and desired product locus being under the same transcriptional control and transcript levels being undesirably low (e.g. indicating an inability to produce a desired product) can make the second microbial cell undesirable 166. As such, in some embodiments, there can be no immunity modulator activity or an insufficient amount of an immunity modulator to protect against the action of the bacteriocin in the second microbial cell 176. For example, one or more of an immunity modulator promoter can be inactive, an immunity modulator transcriptional repressor can be active, post-transcriptional silencing of the immunity modulator (e.g. by a ribozyme or antisense oligonucleotide) can occur, a regulatable tRNA can not be induced (so that expression of the immunity modulator is not facilitated), post-transcriptional silencing of the immunity modulator can occur (e.g. by a site-specific protease, or a silencing post-translational modification), or a vector encoding an immunity modulator can be absent 186. In some embodiments, the first microbial cell provides secreted bacteriocin activity 100. As such, in some embodiments, the second microbial cell can be killed by the bacteriocin 196.

One skilled in the art will appreciate that, for this and other functions, structures, and processes, disclosed herein, the functions, structures and steps may be implemented or performed in differing order or sequence. Furthermore, the outlined functions and structures are only provided as examples, and some of these functions and structures may be optional, combined into fewer functions and structures, or expanded into additional functions and structures without detracting from the essence of the disclosed embodiments.

For a large variety of genetically modified microbial cells, it can be useful to control the growth of other microbial cells in the culture. In some embodiments, a microbial cell controls the growth of other microbial cells in the culture. Exemplary functions and configurations by which a first microbial cell can control the growth of one or more other microbial cells according to some embodiments herein are described in Table 4.

TABLE 4

Exemplary uses of bacteriocin systems in genetically modified microbial cells according to some embodiments herein

| Exemplary Function | Exemplary configurations (according to some embodiments) |
|---|---|
| Biological containment: | Immunity modulator activity only in the desired culture medium, but not outside and bacteriocin activity at least outside of the desired culture medium; escape of the bacteriocin producing cell outside the desired culture environment results in cytotoxicity or growth inhibition of the bacteriocin producing cell |
| Genetic guard | Bacteriocin constitutively produced; genetic guard microbial organism does not produce gene products for modulating industrial process of interest; immunity modulator constitutively produced (e.g under control of constitutive promoter) and/or genetic guard microbial organism is insensitive to the bacteriocin (e.g. a *S. cerevisiae* genetic guard producing bacteriocins that target *E. coli*) |
| Selection of recombinants: | Desired recombination event causes an immunity modulator to be restored in a bacteriocin-expressing host. Alternatively the immunity modulator can be restored only after the desired recombination event. |
| Vector stability: | Immunity modulator (or at least one gene essential for immunity is encoded on a plasmid, and a corresponding bacteriocin locus is encoded on chromosome); clones that lose the desired plasmid lack immunity and are neutralized by the bacteriocin |
| Minimization of genetic drift | Immunity modulator activity dependent on production of industrial product (e.g. immunity modulator expression controlled by an operon, in which a repressor is active in the absence of industrial product, and inactive in the presence of industrial product); if a mutation causes the microbial organism's production of industrial product to fall below a desired level or cease, the microbial organism ceases to produce immunity modulator, and is neutralized by the bacteriocin. |
| Selection for microbes presenting a high yield of expression expression (and/or expressing clones) | Immunity modulator is co-expressed with the gene of interest; microbial organisms producing high levels of gene product of interest can be selected by increasing bacteriocin concentration; microbial organisms producing low levels of gene product of interest (e.g. having a low "industrial fitness") are neutralized |
| Destruction during fermentation of contaminating microbes. | Desired microbial cells constitutively express at least one type of bacteriocin; secreted bacteriocins neutralize invading microbial cells |
| | Desired microbial cells express at least one type of bacteriocin when in the desired environment (e.g. bacteriocin is under the control of an inducible promoter that is activated by an intermediate of the fermentation |

TABLE 4-continued

Exemplary uses of bacteriocin systems in genetically modified microbial cells according to some embodiments herein

| Exemplary Function | Exemplary configurations (according to some embodiments) |
|---|---|
| | process); secreted bacteriocins neutralize contaminating cells |
| Control of the ratio of a microbial flora. | Immunity modulator activity is repressed by accumulated product made by a microbial cell; bacteriocins secreted by the microbial cell (or other cells) neutralize the microbial cell |

Figure 2B:
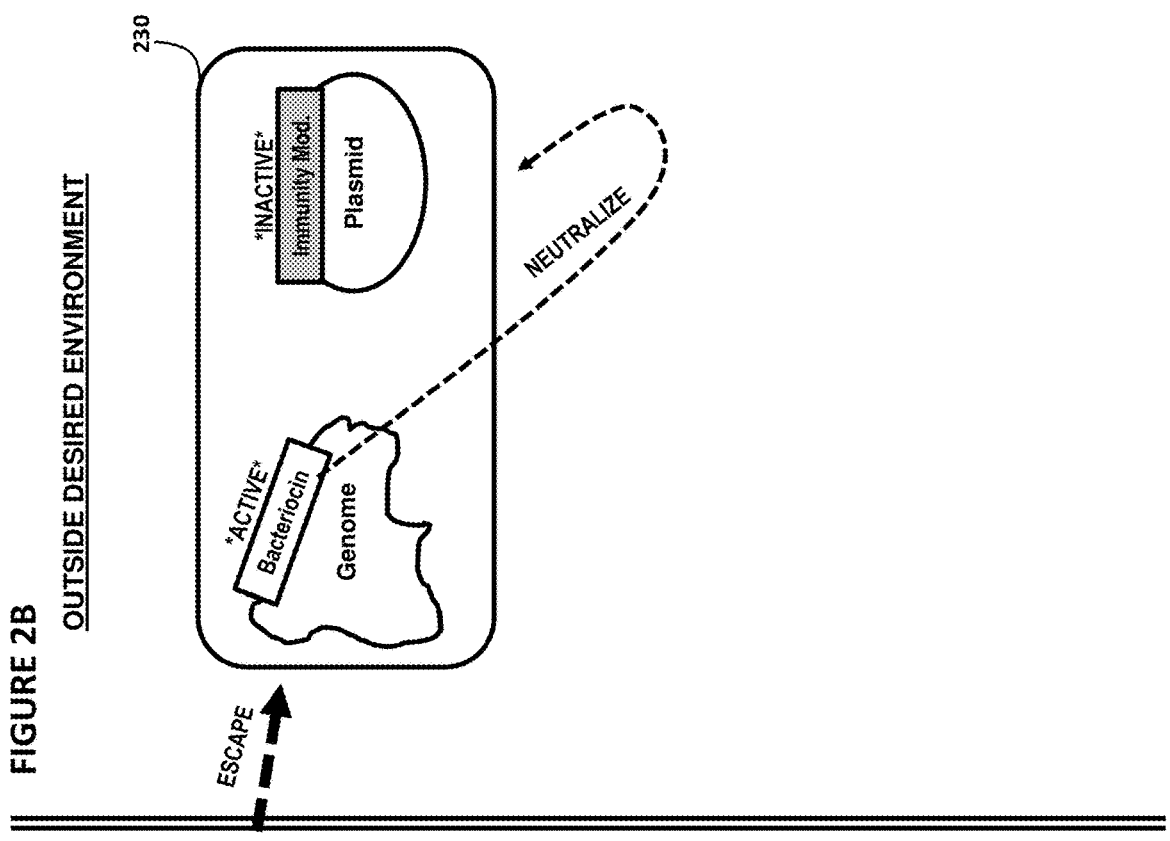
FIG. 2B is a schematic diagram illustrating control of the growth of a first microbial cell when the first microbial cell is no longer in a desired growth environment according to some of the embodiments herein.
Figure 2A:
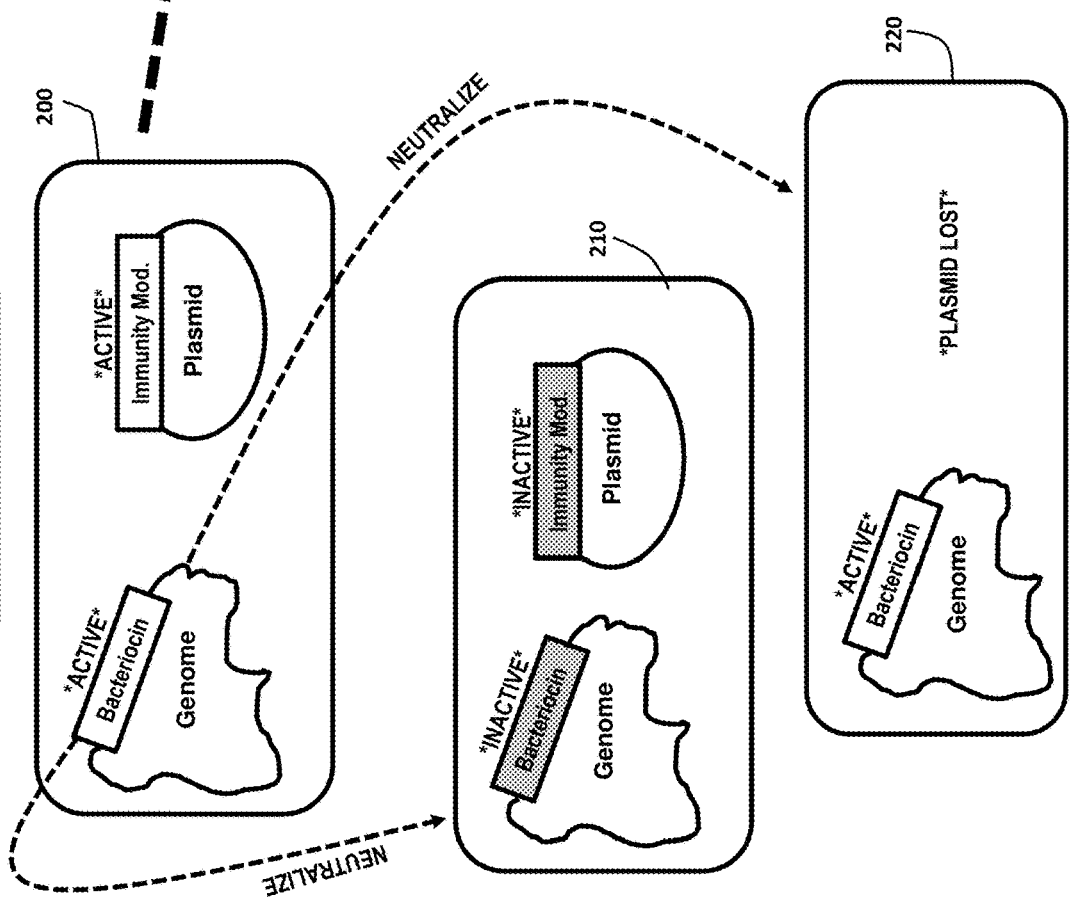
FIG. 2A is a schematic diagram illustrating a first microbial cell controlling the growth of other microbial cells according to some of the embodiments herein.

FIG. 2 is a schematic diagram depicting a genetically engineered microbial cell controlling the growth of at least one other microbial cell according to some embodiments herein. A first microbial cell 200 can comprise a bacteriocin polynucleotide and a corresponding immunity modulator polynucleotide. The bacteriocin polynucleotide can optionally be integrated into the cell's genome, while the immunity modulator polynucleotide can optionally be integrated into a plasmid present in the cell. In some embodiments an undesired clone of the cell 210 (a "non-expressing clone") can lack immunity modulator activity, and optionally can lack bacteriocin activity. The bacteriocin activity of the first microbial cell 200 can neutralize the non-expressing clone 210. In some embodiments, an undesired clone of the cell 220 can lose a plasmid comprising the immunity modulator polynucleotide. The bacteriocin activity of the first microbial cell 200 can neutralize the undesired clone 220. In some embodiments, the microbial cell 230 can escape from the desired environment, causing the clone to lack immunity modulator activity. Bacteriocin activity from the escaped cell 230 and/or clones of the escaped cell can neutralize the escaped cell 230. In some embodiments, the escaped cell 230 further comprises a poison-antidote system to facilitate killing of the escaped cell upon its escape.

Figure 3:
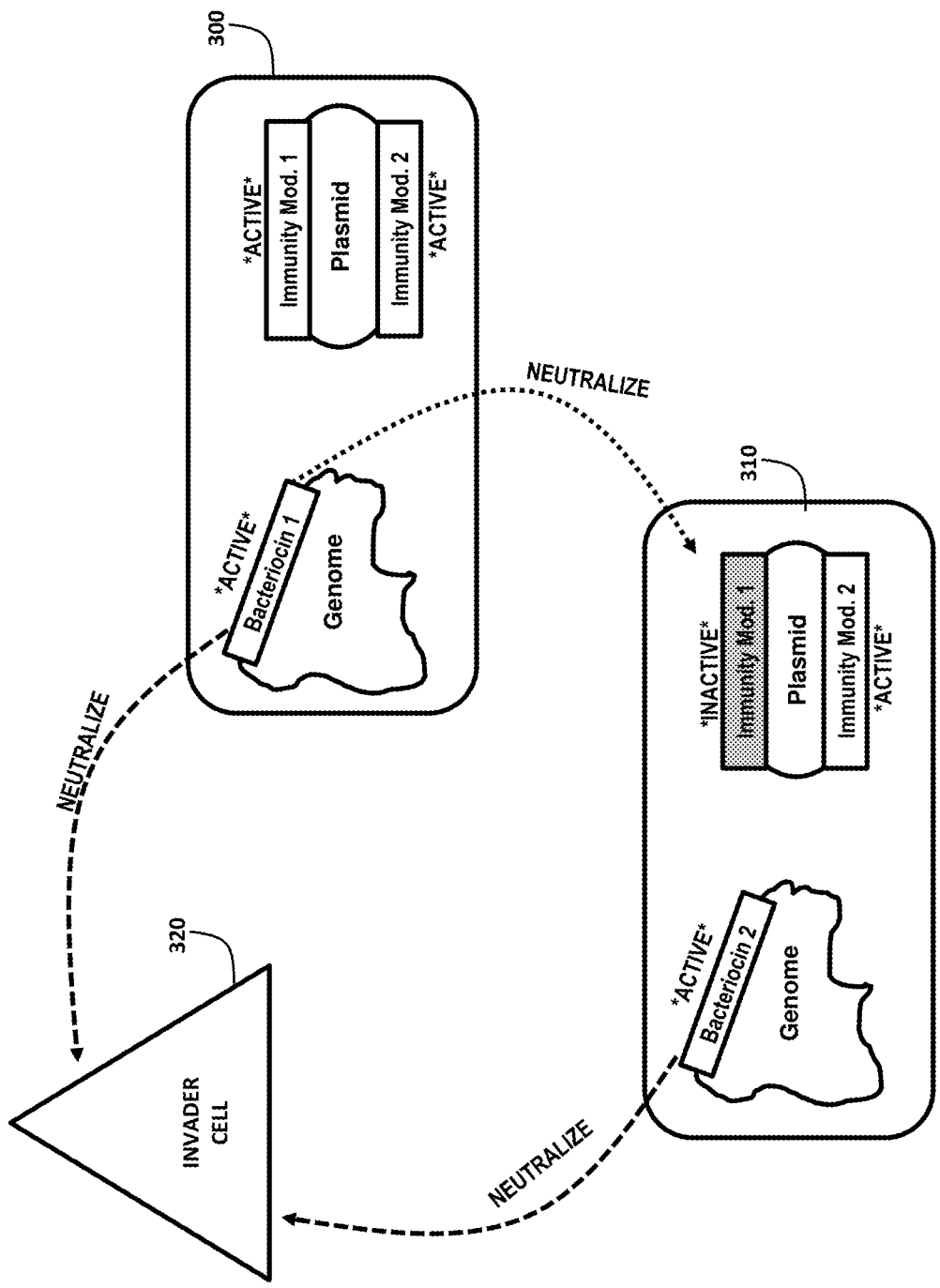
FIG. 3 is a schematic diagram illustrating a first microbial cell controlling growth of a second microbial cell and neutralizing an invading cell in a desired environment according to some of the embodiments herein.

FIG. 3 is a schematic diagram of a first genetically engineered microbial cell 300 controlling the growth of a second genetically engineered microbial cell 310 and an invader cell 320 in a desired environment according to some embodiments herein. The first genetically engineered microbial cell 300 can comprise a first bacteriocin polynucleotide. The second genetically engineered microbial cell 310 can comprise a second bacteriocin polynucleotide. Each of the first and second genetically engineered microbial cells (300 and 310) can comprise a first immunity modulator polynucleotide encoding resistance to the first bacteriocin, and a second immunity modulator polynucleotide encoding resistance to the second bacteriocin. If the second genetically engineered microbial cell 310 becomes undesired, it can lose first immunity modulator activity via any of the mechanisms discussed herein, and thus be controlled by the first bacteriocin activity from the first genetically engineered microbial cell 300. If an invader cell 320 enters the desired environment, the first bacteriocin from the first genetically engineered microbial cell 300 and the second bacteriocin from the second genetically engineered microbial cell 310 can neutralize the invader cell.

Figure 4:
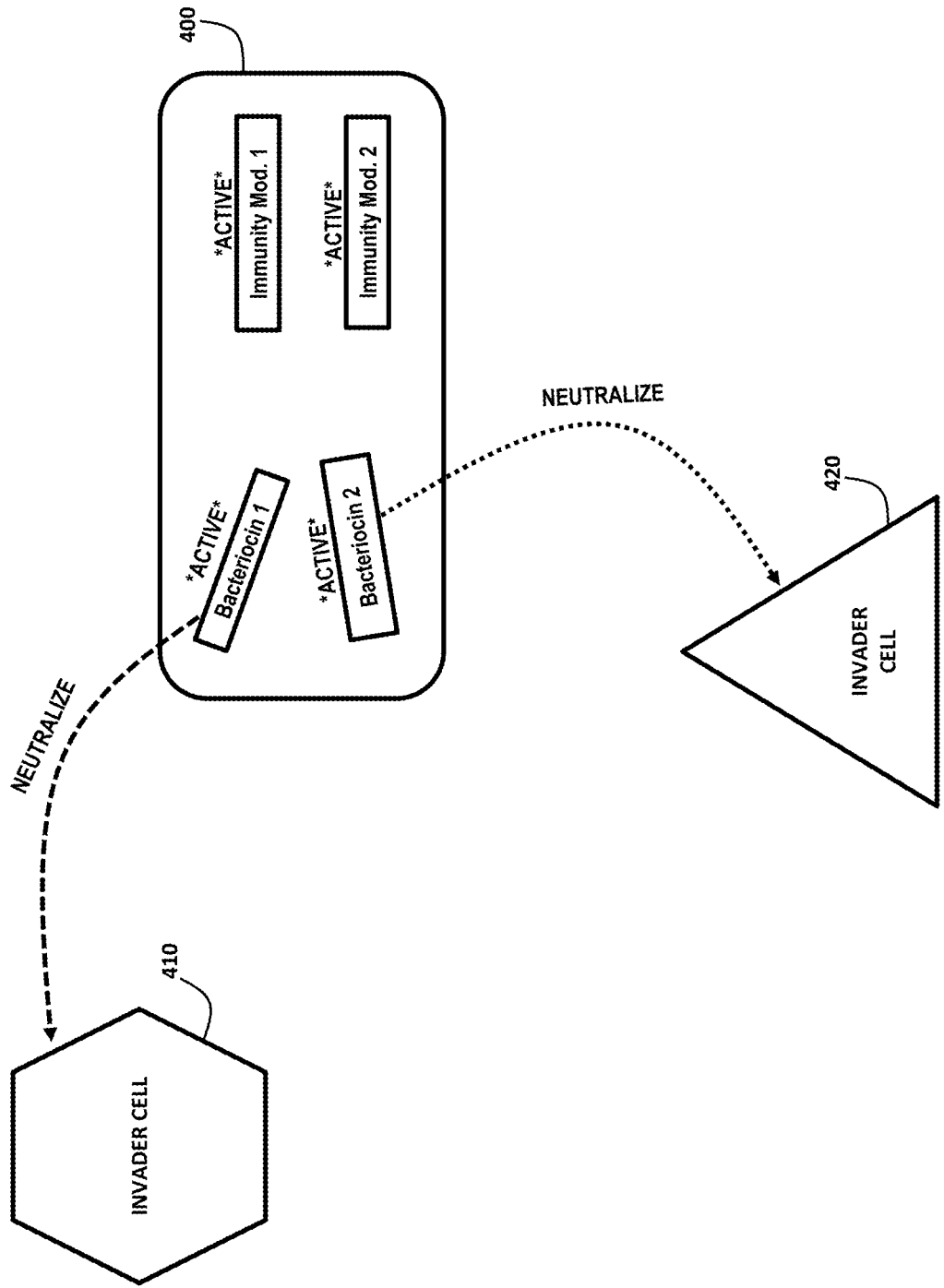
FIG. 4 is a schematic diagram illustrating a first microbial cell neutralizing a first invading cell with a first bacteriocin and second invading cells with a second bacteriocin in a desired environment according to some of the embodiments herein.

FIG. 4 is a schematic diagram of a first genetically engineered microbial cell 400 controlling the growth of a first invader cell 410 and a second invader cell 420 in a desired environment according to some embodiments herein. The first genetically engineered cell 400 can comprise at least a first bacteriocin polynucleotide encoding a first bacteriocin, and at least a second bacteriocin polynucleotide encoding a second bacteriocin. The first genetically engineered cell 400 can produce the first bacteriocin to neutralize a first invader cell 410. The first genetically engineered cell 410 can produce the second bacteriocin to neutralize a second invader cell 420. In some embodiments, the first invader cell is of a different strain or species from the second invader cell. In some embodiments, the first invader cell responds to a different spectrum of bacteriocin activity than the second invader cell. In some embodiments, the first invader cell typically occupies a different ecological niche than the second invader cell.

Figure 5:
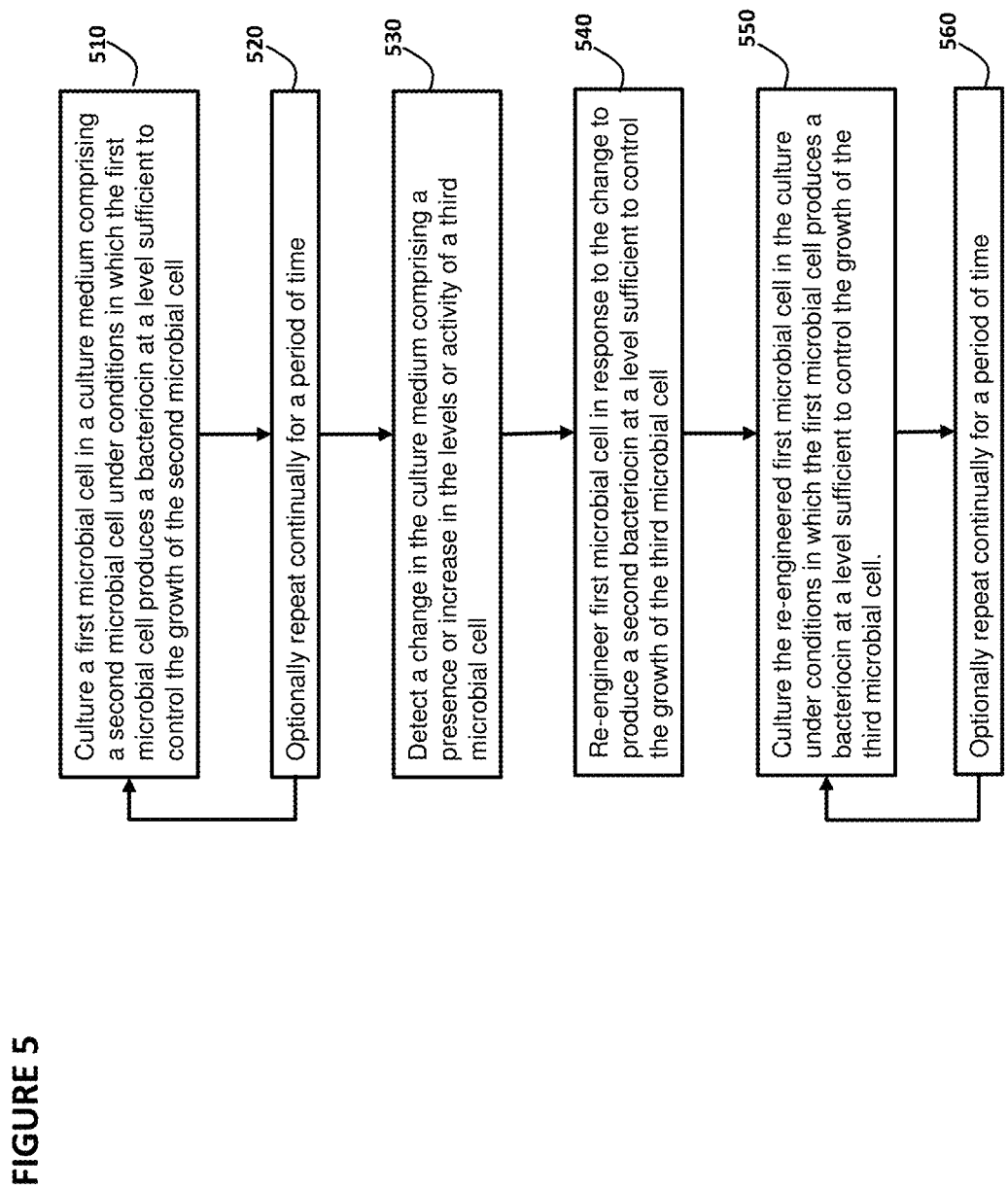
FIG. 5 is a flow diagram illustrating methods of controlling the growth of at least a second microbial cell in culture according to some embodiments herein.

FIG. 5 is a flow diagram illustrating methods of controlling the growth of at least a second microbial cell in culture according to some embodiments herein. The method can comprise culturing a first microbial cell in a culture medium comprising a second microbial cell under conditions in which the first microbial cell produces a bacteriocin at a level sufficient to control the growth of the second microbial cell 510. The culturing of the first microbial cell can optionally be continually maintained for a period of time 520. In some embodiments, the culturing of the first microbial cell is maintained continually for at least 3 days, for example at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, or 500 days, including ranges between any two of the listed values. A change in the culture medium comprising a presence or increase in the levels or activity of a third microbial cell can be detected 530. The first microbial cell can be re-engineered in response to the change to produce a second bacteriocin at a level sufficient to control the growth of the third microbial cell 540. The re-engineered first microbial cell can be cultured in the culture under conditions in which the first microbial cell produces a bacteriocin at a level sufficient to control the growth of the third microbial cell 550. The culture of the re-engineered microbial cell can be repeated continually for a period of time 560. In some embodiments, the culturing of the re-engineered microbial cell is maintained continually for at least 3 days, for example at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, or 500 days, including ranges between any two of the listed values.

In some embodiments, a first microbial cell can control the growth of a second microbial cell. In some embodiments, a first microbial cell can control the growth of a second microbial cell of the same strain as the first microbial cell. Each cell of the strain can comprise a bacteriocin polynucleotide and an immunity modulator polynucleotide, such that the immunity modulator, if expressed, protects against the bacteriocin. As such, if a clone of the strain loses expression of the immunity modulator, it will be neutralized by bacteriocin activity from the same strain. In some embodiments, the immunity modulator polynucleotide is in cis to the bacteriocin polynucleotide. As such, even if the bacteriocin polynucleotide and immunity modulator polynucleotide are both eliminated (e.g. if a plasmid is lost or a FLP-FRT cassette is excised), bacteriocin activity from other cells can still neutralize the cell. In some embodiments, the immunity modulator polynucleotide is in trans to the bacteriocin polynucleotide. The immunity modulator activity can be lost when the microbial cell is undesired (for example, if a plasmid is lost, or if a particular environmental condition induces a loss of immunity modulator activity). Accordingly, bacteriocin activity from both the microbial cell and also other cells of the strain can induce the neutralizing of the microbial cell.

In some embodiments, a ratio of two or more microbial species or strains is controlled. An exemplary control of ratios is illustrated in FIG. 3 (see cells 300 and 310). In some embodiments, a first microbial strain or species loses an immunity modulator activity via any of the mechanisms discussed herein when it is less desired than a bacteriocin-producing second strain or species, increasing the ratio of second strain or species to the first strain or species. In some embodiments in which the ratio of a first and second strain or species is controlled, a bacteriostatic bacteriocin or bacteriocins are selected (as opposed to bacteriocitic bacteriocins) so that the control of growth can be readily reversible, and/or to minimize the risk of eliminating either of the strains or species. In some embodiments, a first microbial strain or species produces a first bacteriocin under the control of a promoter that is activated in the presence of a compound or substance of interest, for example an intermediate or a product such as an industrially useful molecule. As such, levels of the bacteriocin increase as the levels of the compound of interest increase. In some embodiments, a second microbial strain or species produces (or catalyzes the production of) the compound or substance of interest, but does not have immunity modulator activity for the bacteriocin. As levels of the compound or substance of interest increase, levels of the bacteriocin increase, thus neutralizing the second strain (which lacks an appropriate immunity modulator or which has an insufficient amount of an appropriate immunity modulator to protect against the action of the bacteriocin). As such, relative levels of the first strain compared to the second strain increase. In some embodiments, a first microbial strain produces a first product and first bacteriocin activity, and a second microbial strain produces a second product and second bacteriocin activity. In some embodiments, the first product and the second product are intermediates in the same biosynthetic pathway. The first microbial strain can provide a first and second immunity modulator activity, in which the second immunity modulator activity can protect against the second bacteriocin and is negatively regulated by accumulation of the first product (e.g. expression of the second immunity modulator is repressed by the presence of the first product), and the first immunity modulator activity can protect against the first bacteriocin. The second microbial strain can also provide a first and second immunity modulator activity, except that the first immunity modulator activity is negatively regulated by accumulation of the second product (e.g. expression of the first immunity modulator is repressed by the presence of the second product). As such, when a relatively high amount of the first product has accumulated, the second immunity modulator in the first microbial strain is inactivated, and the microbial cells of the first strain are neutralized by the second bacteriocin, thus increasing the ratio of the second strain to the first strain, and increasing the relative amount of second product to first product. When a relatively high amount of the second product has accumulated, the first immunity modulator in the second microbial strain is inactivated, and the microbial cells of the second strain are neutralized by the first bacteriocin, the increasing the ratio of the first strain to the second strain and increasing the relative amount of first product to second product. As such, the ratio of the first stain to the second strain can be adjusted, depending on relative levels of product. In some embodiments, an equilibrium of ratios of the first strain to the second strain is maintained. In some embodiments, an equilibrium of ratios of the first product to the second product is maintained. In some embodiments, the first microbial strain's second immunity modulator responds to a first environmental condition or compound, and the ratio between the first and second microbial strain is otherwise controlled as above. In some embodiments, the second microbial strain's first immunity modulator responds to a second environmental condition or compound, and the ratio between the first and second microbial strain is otherwise controlled as above.

In some embodiments, it is desired that a microbial cell be contained within a particular environment, for example so that the first microbial cell can only survive in a particular culture medium such as industrial feedstock. In some embodiments, a microbial cell comprises a bacteriocin polynucleotide and an immunity modulator polynucleotide, such that the immunity modulator corresponds to the bacteriocin. In some embodiments, when the microbial cell is in a desired environment, the microbial cell produces an active bacteriocin and corresponding immunity modulator, but when the microbial cell escapes the desired environment, the microbial cell produces the active bacteriocin but no active immunity modulator. As a result, the microbial cell can grow in the desired environment, but is neutralized by its own bacteriocin when it escapes. For example, in some embodiments, the bacteriocin encoded by the bacteriocin polynucleotide is constitutively expressed, while the immunity modulator is expressed only when the microbial cell is in a desired environment. For example, in some embodiments, the bacteriocin encoded by the bacteriocin polynucleotide is constitutively expressed, while the immunity modulator is expressed only when the microbial cell is in an environment. For example, in some embodiments, a transcriptional activator of the immunity modulator is only present in the desired environment. For example, in some embodiments, the bacteriocin encoded by the bacteriocin polynucleotide and the immunity modulator is constitutively expressed, but if the microbial cell escapes, the immunity modulator is deleted (for example via the FLP-FRT system). Without being limited to any particular theory, if a genetic system for neutralizing an escaped microbial cell is not used within the culture itself, there may be little or no selective pressure to maintain the system within the culture, so that mutations can accumulate which reduce or eliminate the functioning of that genetic system. As such, if the microbial cell escapes from the culture, there is a possibility that the genetic system will no longer function. In contrast, it is appreciated herein that if a bacteriocin/immunity modulator system is useful both within a culture (for example, to control the growth of other genetically engineered cells in the culture, and/or to neutralize invading microbial cells), and also outside of a culture (for example, to neutralize a microbial cell that has escaped from culture), the use within the culture can provide selective pressure for the bacteriocin system to continue to function. Such selective pressure in accordance with some embodiments herein can minimize genetic drift. Such selective pressure in accordance with some embodiments herein can help to ensure that if the microbial cell escapes from the desired culture environment, the bacteriocin/immunity modulator system will be functioning to appropriately neutralize the escaped cell. As such, in some embodiments a single genetically engineered circuit, for example a bacteriocin/immunity modulator system is useful both to neutralize other microbial cells within a desired culture environment, and further to neutralize a microbial cell and/or its clones upon escape from a desired culture environment. It is contemplated in accordance with some embodiments herein, any or all of the configuration of bacteriocins disclosed herein can be tuned so that upon escape from the desired culture environment, the escaping microbial organism will be neutralized by its own bacteriocins (and/or bacteriocins of its direct or indirect progeny, and/or bacteriocins of another escaped cell and/or its direct or indirect progeny).

In some embodiments, a microbial cell can control growth in two or more ways. In some embodiments, a microbial cell can perform two or more of the functions described in Table 4. In some embodiments, the microbial cell uses the same bacteriocin/immunity modulator pair for two or more different functions. In some embodiments, the microbial cell uses a first bacteriocin/immunity modulator pair for a first function, and a second bacteriocin/immunity modulator pair for a second function. For example, in some embodiments, a microbial cell can express a bacteriocin which limits the growth of "non-expressing" clones that have lost immunity modulator activity in a desired environment, and can also provide containment within the desired environment by failing to express its own immunity modulator (while still expressing bacteriocin) if the microbial cell is outside of a desired environment. A schematic illustration of such two forms of growth regulation is illustrated in FIG. 2. For example, in some embodiments, a first microbial cell can express a bacteriocin which limits the growth of a second microbial cell, and can also neutralize the invading cell. A schematic illustration of such two forms of growth regulation is illustrated in FIG. 3. In some embodiments, two or more forms of growth control are provided using the same bacteriocin-immunity modulator pair. In some embodiments, each form of growth control is provided using a different bacteriocin immunity modulator pair. For example, a first immunity locus can be present on a plasmid that also includes a polynucleotide encoding a desired product. A clone that loses the plasmid will be neutralized by a corresponding first bacteriocin. A second immunity modulator polynucleotide (corresponding to a second immunity modulator) can be integrated into the genome of the microbial cell and can be silenced when the microbial cell escapes from its desired environment (for example, the second immunity modulator polypeptide can be in a FLP-FRT cassette that is excised upon escape). As such, upon escape, the microbial cell can be neutralized by the second bacteriocin.

It is noted that some embodiments described herein are compatible with poison-antidote systems. As such, in some embodiments a microbial cell, in addition to a bacteriocin and immunity modulator further comprises a poison-antidote system configured to kill or arrest the cell when it is not in a desired environment.

It can be useful to control the growth of two or more different types of microbial cells. For example, an environment can comprise, or can potentially comprise, two or more different types of undesired microbial organisms. As different microbial organisms can have different susceptibility to bacteriocins (for example, by possessing different profiles of immunity modulators), a combination of two or more bacteriocins (e.g. a "cocktail" of bacteriocins) can be useful for controlling the growth of two or more microbial organisms. In some embodiments, a single microbial cell produces two or more different bacteriocins for example, at least 2, 3, 4, 5, 6, 7, 8, 9, 10, 11, 12, 13, 14, 15, 16, 17, 18, 19, 20, 25, 30, 35, 40, 45, or 50 different bacteriocins, including ranges between any two of the listed values. In some embodiments, a mixture of two or more different bacteriocin-producing microbial cells are provided, for example, 2, 3, 4, 5, 6, 7, 8, 9, 10, 11, 12, 13, 14, 15, 16, 17, 18, 19, 20, 25, 30, 35, 40, 45, or 50 different bacteriocin-producing microbial cells, including ranges between any two of the listed values. Optionally, one or more of the bacteriocin-producing microbial cells can produce two or more different bacteriocins.

It can be useful for a single microbial cell to regulate the growth of two or more different types of microbial cells. For example, it can be possible for a first type of invading cell to possess immunity to a first type of bacteriocin but not a second type of bacteriocin. As such, in some embodiments, a microbial cell comprises two or more bacteriocin polynucleotides, each of which encodes a different bacteriocin (see, e.g. FIG. 4). In some embodiments, the microbial cell comprises polynucleotides encoding at least three different bacteriocins, for example at least three, four five, six, seven, eight, nine, ten, eleven, twelve, thirteen, fourteen, fifteen, sixteen, seventeen, eighteen, nineteen, twenty, or more different bacteriocins, including ranges between any two of the listed values. In some embodiments, two or more bacteriocin polynucleotides are under control of a single promoter. In some embodiments, each bacteriocin polynucleotide under the control of a single promoter comprises its own translational initiation site. In some embodiments, each bacteriocin polynucleotide is under the control of a different promoter. In some embodiments, two different bacteriocins are under the control of two different but structurally or functionally identical promoters.

It can be useful for a microbial cell to control the growth of other microbial cells in its industrial environment, so as to help ensure the consistent production of an industrial product, regardless of the geographical location of the culture environment. Without being limited by any particular theory, certain industrial products manufactured via microbial culture may have certain characteristics that result from local microbial flora associated with a certain region (for example, Camembert cheese can have particular characteristics that result from local microbial flora in Camembert, France, or sourdough bread can have particular characteristics that result from local microbial flora in San Francisco, CA). As such, it can be desirable to control the microbial flora in a particular feedstock, so that a consistent industrial product can be produced in a variety of geographical locations. In some embodiments, a microbial cell is engineered to produce bacteriocins to neutralize invading microbial cells found in a variety of geographical locations, which can ensure more consistent industrial product characteristics for product produced in a variety of locations. For example, a microbial cell designed to be used in a particular industrial process and to be grown in a first geographic location may be engineered to express one or more bacteriocins effective against one or more invading organisms commonly encountered in the first geographic location. A microbial cell designed to be used in the same industrial process and to be grown in a second geographic location may be engineered to express one or more bacteriocins effective against one or more invading organisms commonly encountered in the second geographic location. Alternatively, a microbial cell designed to be used in a particular industrial process and to be grown in two different geographical locations may be engineered to express on or more bacteriocins effective against one or more invading organisms commonly encountered in each of the two geographical locations.

Frequently in industrial biotechnology, the goal is to work in continuous process, and it is contemplated that the longer the process continues, the higher the probability of contamination. Accordingly, the capacity to fight against contaminants can be useful for a continuous industrial process. Synthetic microorganisms designed in laboratories are frequently used in industrial processes. As such, it can be useful for these lab-engineered "champions" to fight against undesired invading microbial strains (for example wild-type strains from the environment and/or cross-contaminants from another industrial process) and also control their potential genetic drift and escape in the environment. In accordance with some embodiments herein, invading microbial strains can be fought, genetic drift can be minimized, and escape can be minimized by inducing suicidal bacteriocins based genetic circuits.

It can be useful for a microbial culture to remain stable for a continuous period of time, for example to ensure consistent industrial product characteristics over a continuous period of time. In some embodiments, a culture is stably maintained, at least in part, by bacteriocin-mediated neutralization of invading microbial cells. In some embodiments, a culture is stably maintained, at least in part, by bacteriocin-mediated control of ratios of two or more types of genetically engineered microbial cell in the culture. In some embodiments, a culture is stably maintained, at least in part, by reengineering a microbial cell already present in the culture. In some embodiments, the microbial cell is reengineered to add at least one additional bacteriocin activity (for example by adding a new bacteriocin, or expanding the expression of a bacteriocin already present) to neutralize a new type of invading microbial organism. In some embodiments, the microbial cell is reengineered to remove at least one bacteriocin activity that is no longer needed. Exemplary methods of maintaining a stable culture according to some embodiments herein are illustrated in FIG. 5. In some embodiments, a stable culture is maintained for at least about 3 days, for example about 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, or 500 days, including ranges between any two of the listed values.

Method for Detection of Ratios of Microbial Organisms

According to some embodiments herein, the ratios of two or more microbial strains or species can be controlled, depending on relative quantities of product, and/or compounds in the environment. Accordingly, in some embodiments, the ratios of the two or more microbial strains or species can be indicative of relative quantities of the product and/or compounds in the environment. In some embodiments, relative quantities of microbes of a first strain or species and second strain or species as described herein are detected, thereby indicating relative ratios or quantities of a first product or compound to a second product or compound. Relative quantities of each microbial strain or species can be detected in a variety of ways. In some embodiments, each strain or species comprises a unique oligonucleotide or polypeptide "bar code" sequence to facilitate specific detection. In some embodiments, each strain or species comprises a different bacteriocin (and thus a different bacteriocin polynucleotide), which can serve as a bar code. In some embodiments, at least one of quantitative PCR, oligonucleotide array analysis, flow cytometry, immunocytochemistry, in situ hybridization, ELISA, immunoblotting, oligonucleotide spot blotting, or the like is performed to determine relative quantities of the two different microbial strains or species.

Method for Determining Modulation of Growth of Microbial Organisms in Industrial Medium In some embodiments, growth of microbial organisms in industrial medium is modulated. Before adding a particular genetically engineered microbial cell or combination of genetically engineered cells to an existing industrial culture of microbial cells, it can be useful to determine the effects, if any, of the bacteriocins on the growth of the microbial cells in the existing industrial culture. In some embodiments, the effect of a particular bacteriocin or combination of bacteriocins produced by genetically engineered cells on microbial organisms is assessed. A medium or other composition comprising one or more bacteriocins produced by genetically engineered microbial cells as described herein can be provided. In some embodiments, the medium comprises a supernatant comprising one or more bacteriocins. In some embodiments, the composition comprises one or more enriched or purified bacteriocins. In some embodiments, the supernatant or composition is thermally stable, for example to facilitate elimination of any microbes therein through high-temperature incubation, while retaining the function of any bacteriocins therein. In some embodiments, the medium or composition comprises a lyophilized material comprising bacteriocins. In some embodiments, the medium or composition comprises a substrate bound to bacteriocins, for example a gel, a matrix, or beads. The medium or compositions comprising bacteriocins can be added to the existing culture. In some embodiments, the medium or composition is added to a culture in an industrial culture environment. In some embodiments, the medium or composition is contacted with a sample of a culture from an industrial culture environment. The growth or absence of growth of microbial organisms in the industrial culture can be assessed for example to determine whether the one or more bacteriocins are effective against a new invading organism which has appeared in the culture or to determine the effects of the one or more bacteriocins on the existing organisms in the culture.

Before a genetically engineered microbial cell is produced, it can be useful to simulate the effects of one or more bacteriocins on a particular culture environment. In some embodiments, a particular bacteriocin or combination of bacteriocins with desired activity in a known culture environment is identified, and a microbial cell is constructed to produce the desired bacteriocin combination of bacteriocins. In some embodiments, a candidate bacteriocin or combination of bacteriocins is contacted with a portion of an industrial culture of interest, and effects of the bacteriocin or bacteriocins on microbial organisms in the culture are identified. In some embodiments, a variety of bacteriocins is provided. In some embodiments, the variety of bacteriocins is provided in a kit. In some embodiments, the bacteriocins were produced by microbial cells. In some embodiments, the bacteriocins are in supernatant from one or more microbial cells as described herein. In some embodiments, the bacteriocins were chemically synthesized. One or more candidate bacteriocins or mixtures of bacteriocins can be prepared, and can be contacted with a portion of the industrial culture environment. In some embodiments, one or more bacteriocins are added to the supernatant of a bacteriocin-producing genetically engineered cell that is already present in culture, for example to ascertain the effects of engineering the cell to produce at least one additional bacteriocin. In some embodiments, a sample from the industrial culture environment is contacted with each candidate bacteriocin or mixture of bacteriocins. In some embodiments, each candidate bacteriocin or mixture of bacteriocins is added to the culture environment. In some embodiments, effects of each candidate bacteriocin or mixture of bacteriocins are observed, for example as effects on the growth of at least one desired microbial cell in the culture, and/or the growth of at least one undesired microbial cell in the culture.

Upon identification of a desired combination of bacteriocins, a microbial cell can be constructed to produce the desired combination of bacteriocins. In some embodiments, an existing microbial cell, for example a microbial cell that is producing a desired product or intermediate in industrial culture is reengineered to produce the desired combination of bacteriocins. In some embodiments, the microbial cell is reengineered via plasmid conjugation. In some embodiments, a new cell is engineered to produce the desired combination of bacteriocins and added to the industrial culture.

Genetic Guard Microbial Organisms and Systems

It can be useful for a bacteriocin-producing microbial organism to protect other microbial organisms from undesired microbial organisms. Accordingly, in some embodiments, a "genetic guard microbial organism" is provided (which, as a shorthand, may also be referred to herein as a "genetic guard"). As used herein, a "genetic guard" refers to a microbial organism or collection of microbial organisms that produces one or more bacteriocins so as to protect a "protected" microbial organism that is immune to neutralizing effects of the bacteriocins, but does not itself produce the bacteriocins. The "protected" microbial organism can perform a desired industrial process (for example, fermentation), while, as used herein, the "genetic guard" itself does not perform the desired industrial process. The genetic guard microbial organsism can express and secrete one or more bacteriocins. Optionally, the genetic guard microbial organism can constititvely express and secrete one or more of the bacteriocins. The genetic guard microbial organism can be non-susceptible to the bacteriocins produced by the genetic guard, for example by producing immunity modulator(s) to the bacteriocin(s) secreted by the genetic guard, and/or by being a type of microbial organism that is not susceptible to the to the bacteriocin(s) produced by the genetic guard (e.g. if the genetic guard comprises a yeast and secretes bacteriocins that specifically neutralize particular bacteria such as lactic acid bacteria). In some embodiments, the protected microbial organism produces immunity modulator(s) to the bacteriocin(s) produced by the genetic guard. In some embodiments, the protected microbial organism is not susceptible to the bacteriocins produced by the genetic guard (e.g. if the protected microbial organism comprises a yeast, and the genetic guard microbial organism produces bacteriocins that specifically neutralize particular bacteria). In some embodiments, the protected microbial organism is not genetically modified ("non-GMO"). In some embodiments, the protected microbial organism is non-GMO, but is from a strain selected to have desired properties, for example via selective pressure, and/or classical mutagenesis. It is contemplated that even if the protected microbial organism has desirable industrial properties, the protected microbial organism may be insufficient at fighting-off one or more undesired microbial organisms, for example invading local flora. Accordingly, in some embodiments herein, a genetic guard protects a protected microbial organism from undesired microbial organisms. By way of example, non-GMO microbial organisms can be useful in a number of processes, for example food production, or purification such as water purification. In some embodiments, non-GMO "protected" microbial organisms are selected based on their ability to destroy one or more contaminants (for example, known water contaminants), and a genetic guard is provided to protect the protected microbial organisms from known or potential invading undesired microbial organisms. In some embodiments, systems comprising a genetic guard as described herein are provided.

It can be useful to maintain a culture medium that does not contain genetically modified organisms, for example to perform particular industrial processes, and/or to comply with certain production standards or specifications. It is contemplated that in accordance with some embodiments herein, genetic guards can be separated from the "protected" microbial organism by a membrane that is permeable to bacteriocins, but not to the genetic guard microbial organisms. As such, bacteriocins produced by the genetic guard can enter a culture medium occupied by the protected microbial organisms, thus protecting the protected organisms from one or more undesired microbial organisms while the genetic guard remains separated from the microbial organism.

It is contemplated herein that a particular culture medium can be invaded by and/or subject to a variety of undesired microbial organisms, which may susceptible to different bacteriocins or combinations of bacteriocins. Accordingly, in some embodiments, the genetic guard microbial organism produces two or more different bacteriocins, for example, 2, 3, 4, 5, 6, 7, 8, 9, 10, 11, 12, 13, 14, 15, 16, 17, 18, 19, 20, 2, 30, 35, 40, 45, 50, 55, 60, 65, 70, 75, 80, 85, 90, 95, or 100 different bacteriocins, including ranges between any two of the listed values, for example 2 to 100, 2 to 50, 2 to 20, 2 to 10, 5 to 100, 5 to 50, 5 to 20, 5 to 10, 10 to 100, 10 to 50, 10 to 20, 20 to 100, 20 to 50, or 50 to 100 different bacteriocins. By way of example, in some embodiments, the genetic guard comprises a single *E. coli* strains, which produces 20 different bacteriocins. In some embodiments, the genetic guard produces a cocktail of bacteriocins. In some embodiments, the genetic guard comprises a mixture of two or more different bacteriocin-producing microbial organisms, for example, 2, 3, 4, 5, 6, 7, 8, 9, 10, 11, 12, 13, 14, 15, 16, 17, 18, 19, 20, 2, 30, 35, 40, 45, or 50 different bacteriocin-producing microbial organisms, so as to provide a desired combination of bacteriocins. By way of example, in some embodiments, the genetic guard comprises a combination of 4 different *E. coli* strains, each of which produces 5 different bacteriocins (for a total of 20 different bacteriocins). In some embodiments, the genetic guard produces a cocktail of bacteriocins that target a particular category of microbial organism, for example lactic acid bacteria.

It can be useful for the genetic guard to be separated from a particular environment or culture medium, for example to maintain an industrial culture environment or feedstock free of genetically modified organisms (GMOs). In some embodiments, the genetic guard is physically separated from the protected microbial organism. Optionally, the protected microbial organism is non-GMO. In some embodiments, the genetic guard is temporally separated from the protected microbial organism. Optionally, the protected microbial organism is non-GMO. For example, temporal separation in accordance with some embodiments can comprise adding the genetic guard to a culture medium to neutralize invading organisms, and subsequently adding the protected microbial organism to the culture medium. Optionally, the genetic guard can be neutralized prior to adding the protected microbial organism, for example via bacteriocins or a poison-antidote system as described herein. Optionally, the genetic guard can be neutralized by their own bacteriocins, for example by repressing expression of the corresponding immunity modulator or immunity modulators in the genetic guard. For example, temporal separation in accordance with some embodiments can comprise culturing the protected microbial organism in a culture medium, and subsequently adding the genetic guard to the culture medium.

In some embodiments, the genetic guard is positioned in a first environment, and the protected microbial organism or organisms are positioned in a second environment. The first environment can be separated from a second environment by a membrane permeable to bacteriocins produced by the genetic guard but not the genetic guard itself. In some embodiments, the membrane is not permeable to the protected microbial organism. In some embodiments, the first environment is in fluid communication with the second environment. Without being limited by any theory it is contemplated that as bacteriocins typically comprise diffusible stable peptide molecules, the bacteriocins can readily move in aqueous solution from the first environment to the second environment. In some embodiments, the first environment comprises a first chamber, tank, or pond and the second environment comprises a second chamber, tank, or pond. In some embodiments, the second environment comprises an open-air environment. Optionally, an industrial process, for example fermentation, is taking place in the second environment. In some embodiments, the first environment comprises a capsule positioned inside of the second environment. A variety of membranes are suitable for arrangements and systems in accordance with embodiments herein, so long as the membranes are permeable to bacteriocins, but not to genetic guards. In some embodiments, the membrane comprises at least one of a mesh, strainer, filter, selective valve, unidirectional valve, or porous membrane. In some embodiments, the membrane comprises one or more pores having a diameter smaller than the diameter of the genetic guard. In some embodiments, the bacteriocins diffuse through the membrane. In some embodiments, fluidic motion from the first environment to the second environment drives the movement of the bacteriocins. In some embodiments, the genetic guard is selected based on known or likely undesired microbial organisms in the culture medium. In some embodiments, the genetic guard is changed after a period of time. For example, in response to changes in the invading undesired microbial organisms, the genetic guard can be adjusted so that additional bacteriocins are added, and/or some bacteriocins are removed.

In some embodiments, an existing microbially-mediated industrial process is performed in a new location, which is characterized by one or more potential undesired microbial organisms. As the microbial organisms of the existing industrial process may not produce bacteriocins against some or all of the undesired microbial organisms of the new location, a genetic guard producing bacteriocins targeting the undesired microbial organisms can be added to the culture medium in the new location. As such, the bacteriocins of the genetic guard can neutralize one or more undesired microbial organisms, if present in the culture medium.

In some embodiments, the genetic guard produces a cocktail of bacteriocins. The cocktail of bacteriocins can be collected while the genetic guard is not, and the cocktail of bacteriocins can be contacted with a culture medium of interest. As such, separation can be maintained between the culture medium and the genetic guard. The skilled artisan will appreciate that a number of methods are suitable for separating the bacteriocins from the genetic guard, so long as the methods do not substantially damage, denature, or destroy the bacteriocins. In some embodiments, the cocktail of bacteriocins is collected by filtering out the genetic guard. In some embodiments, the cocktail of bacteriocins is collected by centrifuging to separate the genetic guard from the bacteriocins. In some embodiments, the cocktail of bacteriocins is collected by neutralizing the genetic guard. In some embodiments, the cocktail is stored prior to contact with the culture medium.

Figure 6:
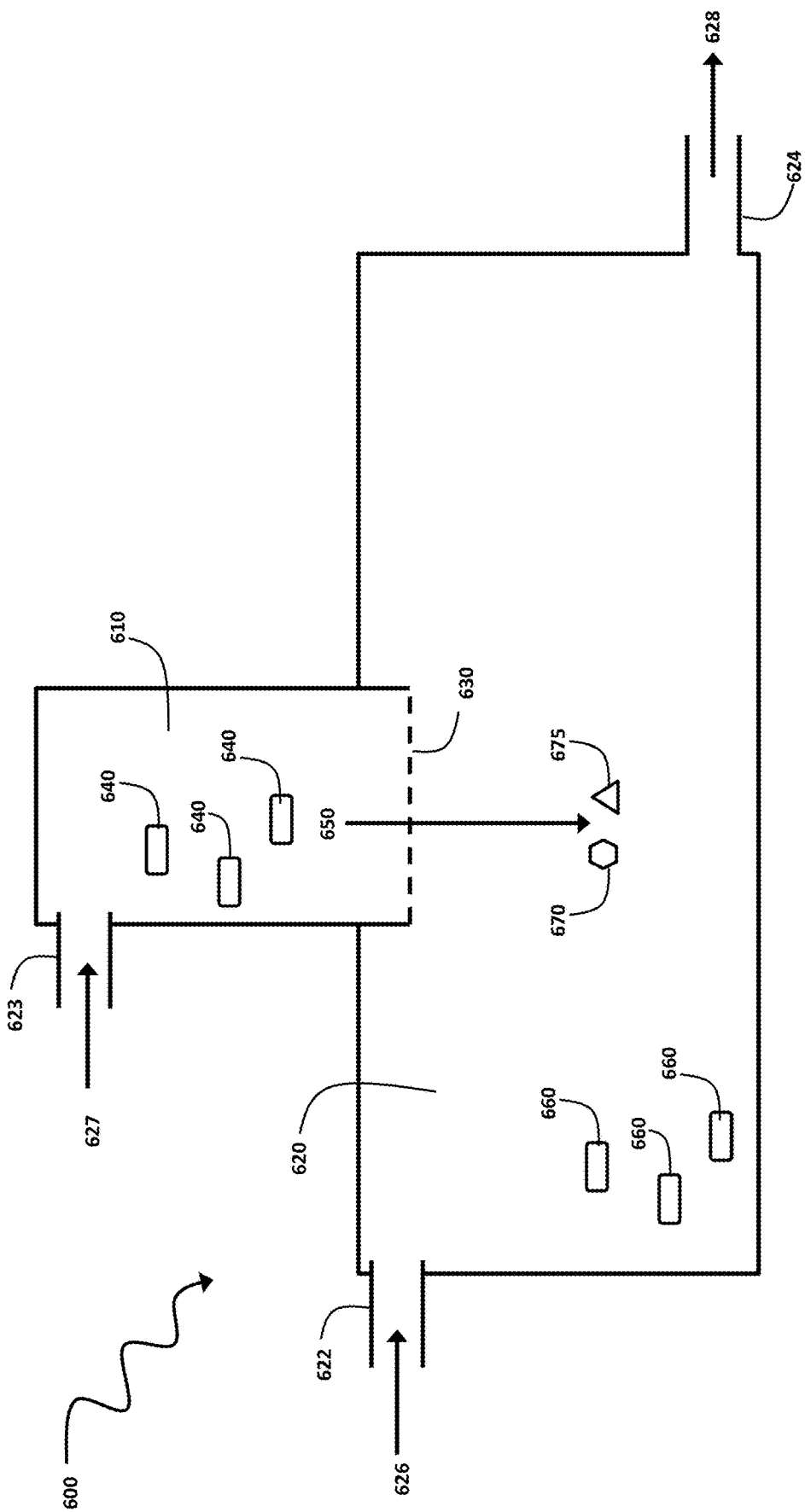
FIG. 6 is a schematic diagram illustrating a system comprising a genetic guard in accordance with some embodiments herein.

FIG. 6 is a schematic diagram illustrating a system 600 comprising a genetic guard in accordance with some embodiments herein. The system 600 can comprise a first environment 610 and a second environment 620. Optionally, the second environment 620 can comprise an inlet 622 and/or an outlet 624. A fluid or culture medium to be treated, for example polluted water or feedstock can enter 626 via the inlet 622, and exit 628 via the outlet. The first environment 610 can be separated from the second environment 620 by a membrane 630 that is permeable to bacteriocins, but is not permeable to genetic guard microbial organisms 640. The first environment 610 can comprise genetic guard microbial organisms 640, which produce bacteriocins that can move 650 between the first environment 610 and the second environment 620. The second environment 620 can comprise protected microbial organisms 660, which are not susceptible to the neutralizing effects of the bacteriocins produced by the genetic guard 640. Optionally, the protected microbial organisms 660 can be non-GMO. However, if undesired microbial organisms 670, 675 are present, the undesired microbial organisms 670, 675 can be neutralized by the bacteriocins. In some embodiments, the system 600 comprises a treatment system for polluted water. In some embodiments, the system comprises a second inlet 623 so that fluid to be treated enters 627 the first environment 610 before entering the second environment 620. Optionally, the system can comprise the second inlet 623 but not the first inlet 622. Optionally, the system can comprise the second inlet 623 and the first inlet 622. As such, the genetic guard microbial organisms 640 can secrete bacteriocins to neutralize invading undesired organisms 670, 675, while maintaining physical separation between the genetic guard microbial organisms 640 and protected microbial organisms 660.

Figure 7:
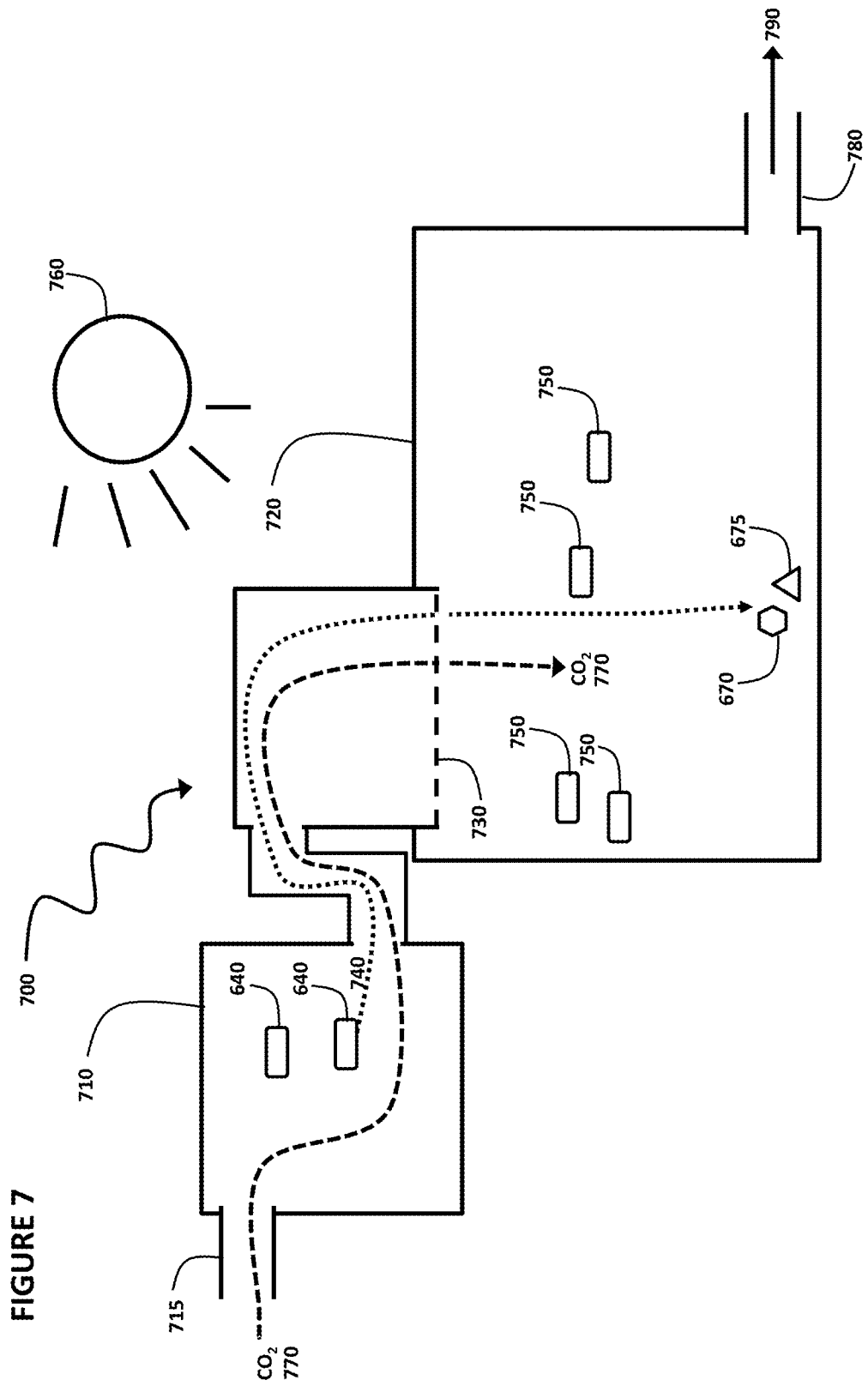
FIG. 7 is a schematic diagram illustrating a genetic guard system that can be useful for photosynthetic production in accordance with some embodiments herein.

FIG. 7 is a schematic diagram illustrating a genetic guard system 700 that can be useful for photosynthetic production in accordance with some embodiments herein. The system 700 can comprise a first environment 710. Optionally, the first environment 710 can comprise an inlet 715. The first environment 710 and optional inlet 715 can be in fluid and gas communication with a second environment 720. The first environment 710 can be separated from the second environment 720 by a membrane 730 that is permeable to bacteriocins and gas, but is not permeable to genetic guard microbial organisms 640. The first environment 710 can comprise genetic guard microbial organisms 640, which produce bacteriocins 740 that can move between the first environment 710 and the second environment 720. The second environment can comprise photosynthetic microbial organisms 750, for example photosynthetic microalgae. Optionally, the photosynthetic microbial organisms 750 are non-GMO. A source of light 760 can be in optical communication with the second environment 720. It is contemplated that the source of light 760 can comprise sunlight and/or artificial light. $CO_2$ 770 can enter the second environment 720, and can be used in combination with light from the light source 760 for photosynthetic production by the photosynthetic microbial organisms 750. Optionally the $CO_2$ 770 can enter the inlet 715 of the first environment 710, and enter the second environment 720 through the membrane 730. Bacteriocins 740 produced by the genetic guard microbial organisms 740 can enter the second environment 720 through the membrane 730, and can neutralize undesired microbial organisms 780, 785 in the second environment. Optionally, the second environment can comprise an outlet 780, and biomass 790 produced by the photosynthetic microbial organism 760 can exit the second environment 720 via the outlet 790. As such, the genetic guard microbial organisms 640 can secrete bacteriocins to neutralize invading undesired organisms 670, 675, while maintaining physical separation between the genetic guard microbial organisms 640 and photosynthetic microbial organisms 750 and biomass 790.

Preservation and/or Storage of Feedstock

It can be useful to store a feedstock without performing an industrial process in the feedstock, for example to build up a reserve in case additional output is needed later on, to decrease output for the time being, and/or to transport the feedstock to a different location. For example, a feedstock for feeding animals can be harvested in the summer, and stored until winter, when it is used to feed animals. For example, a feedstock may undergo an initial round of fermentation to produce a desired component in the feedstock, or to destroy or remove a desired component in the feedstock, and/or to stabilize the feedstock for storage, and the feedstock may then be preserved until it is to be consumed.

It is contemplated herein that undesired microbial organisms can contaminate a feedstock during storage, and/or consume or destroy one or more components of the feedstock. For example, microbial organisms can be selected or engineered to produce glucose from cellulose in a feedstock. However, in a feedstock comprising glucose, undesired microbial organisms can catabolize the glucose. Accordingly, in some embodiments, a genetic guard is added to a feedstock so as to protect the feedstock from one or more undesired microbial organisms during storage. In some embodiments, the feedstock undergoes an initial round of processing (e.g. fermentation) to produce, remove, or destroy at least one component (for example to stabilize the feedstock for storage and/or to provide a desired component in the feedstock such as glucose from cellulose), and the genetic guard then protects the feedstock from subsequent undesired microbial organisms. In some embodiments, the genetic guard is physically separated from the feedstock by a bacteriocin-permeable membrane during fermentation and/or during storage. It is contemplated that bacteriocin-mediated neutralization of undesired microbial organisms in a feedstock in accordance with some embodiments herein can permit a feedstock to be stored stably for long periods of time. In some embodiments, the feedstock is stably stored for at least one month, for example, at least one month, 2, 3, 4, 5, 6, 7, 8, 9, 10, 11, 12, 13, 14, 15, 16, 17, 18, 19, 20, 21, 22, 23, or 24 months.

In some embodiments, the genetic guard is contacted with the feedstock. In some embodiments, the genetic guard is already present in the feedstock, and proliferation of the genetic guard is induced prior to or during storage so that the genetic guard produces bacteriocins to neutralize undesired microbial organisms in the feedstock.

Methods of Preparing and using Bacteriocin-Producing Microbial Organisms:

In accordance with some embodiments herein, bacteriocin-producing microbial organisms can be prepared for use in an industrial process which is subject to, or at risk of contamination or interference by undesired microbial organisms. In some embodiments, a circuit for desired production of bacteriocins is designed, nucleic acid sequences are engineered, and the circuit is assembled and introduced to a host microbial organism.

Figure 8:
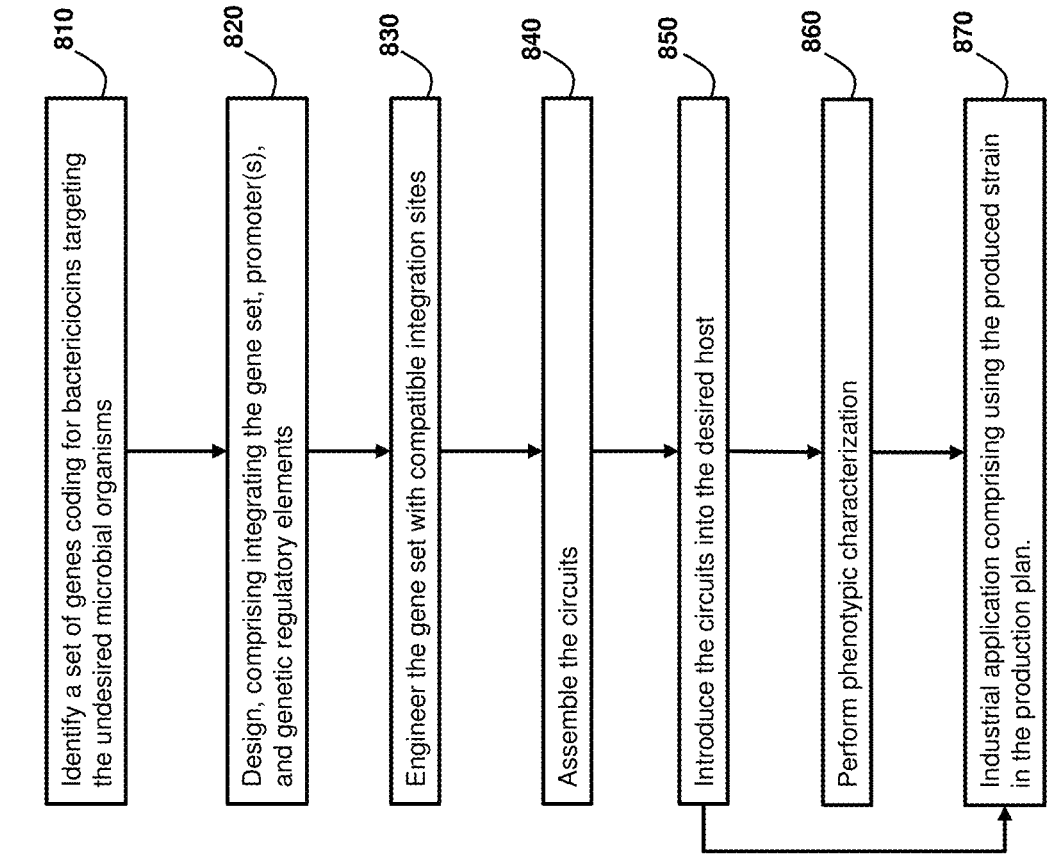
FIG. 8 is a flow diagram illustrating methods of producing and using bacteriocins in accordance with some embodiments herein.

FIG. 8 is a flow diagram illustrating methods of preparing and using bacteriocin. The method can comprise identifying a set of genes coding for bacteriocins targeting the undesired microbial organisms 810. An approach for identifying genes in accordance with some embodiments herein comprises identifying bacteriocin genes using an electronic database, for example bactibase, accessible on the world wide web at bactibase.pfba-lab-tun.org/main.php. The method can comprise designing a construct for expressing a bacteriocin, comprising integrating the gene set, promoter(s), and genetic regulatory elements 820. As such, a construct can be designed. Approaches for designing an appropriate construct in accordance with some embodiments herein can comprise using parts databases, for example electronic databases such as the Biobricks foundation parts database. It is contemplated herein that in accordance with some embodiments, the skilled artisan can selected desired components (including, but not limited to bacteriocin nucleotides, promoters, and genetic regulatory elements) based on their identified functions, and engineer a construct with a desired functionality based upon the identified functionality of these components. By way of example, functionalities of different possible components can be found in one or more databases, such as the Biobricks catalog. A catalog of Biobricks components is accessible on the world wide web at parts.igem.org. The method can comprise engineering the gene set with compatible integration sites 830, which can allow the genes to be assembled in a desired manner and/or appropriately introduced to a desired host. A variety of suitable integration sites can be used, for example restriction sites, substrates for an enzymatic recombination reaction, or sequences for homologous recombination. In some embodiments, the gene set is synthesized. In some embodiments, a nucleic acid comprising the gene set is synthesized. In some embodiments, the gene set is provided in one or more vectors such as plasmids. The method can comprise assembling the circuits 840. The circuits can include one or more bacteriocin nucleic acids, and a suitable promoter(s) and regulatory element(s). A variety of configurations of circuits can be suitable. In some embodiments, a single promoter drives expression of multiple bacteriocins and optional gene products of interest. In some embodiments, different bacteriocin nucleic acids are under the control of different promoters. In some embodiments, a circuit is comprised in a single construct such as a plasmid. In some embodiments, a circuit is comprised in two or more constructs such as plasmids. In some embodiments, a nucleic acid comprising the complete circuit is synthesized. In some embodiments, the circuit is assembled using conventional molecular cloning techniques, or a combination of nucleic acid synthesis and molecular cloning. Molecular cloning techniques are well known to the skilled artisan. Many suitable molecular cloning techniques are described in Green and Sambrook "Molecular Cloning: A Laboratory Manual" (2012) Cold Spring Harbor Laboratory Press; 4th edition, which is hereby incorporated by reference in its entirety. The method can comprise introducing the circuits into the desired host 850. Suitable hosts include, but are not limited to, naturally occurring, genetically engineered, and fully synthetic microbial organisms, including, but not limited to the exemplary microbial organisms described herein. Optionally, the method includes performing phenotypic characterization 860, for example strain behavior. For example, it can be useful to select for desired transformants or recombinants, confirm that a strain is producing the desired bacteriocins, and/or confirm that a regulatory circuit is responsive to an appropriate stimulus such as industrial precursor or product. The method can comprise industrial application comprising using the produced strain in the production plan 870. For example, a bacteriocin-producing strain can be introduced to an existing culture medium, or can be used as a starter culture for a new culture medium.

Kits

Kits are provided according to some embodiments herein. In some embodiments, the kits contain at least one of bacteriocins, bacteriocin polynucleotides, immunity modulators, immunity modulator polynucleotides, other genetic elements (such as promoters, expression vectors, conjugation plasmids, and the like), genetically engineered microbial cells, and/or culture medium as described herein. In some embodiments, the kits further contain packaging, and/or instructions for use of the contents therein. In some embodiments, the kits comprise a variety of bacteriocins, for example for use in ascertaining the effects of a candidate bacteriocin or combination thereof on a culture environment. In some embodiments, the kits comprise a variety of bacteriocin polynucleotides and immunity modulator polynucleotides, for example for constructing a microbial cell with desired characteristics. In some embodiments, the kits comprise a variety of donor microbial cells that comprise donor plasmids encoding a variety of combinations of at least one bacteriocin and/or at least one immunity modulator.

EXAMPLE 1

Protection of Cyanobacteria and Neutralization Upon Escape

A cyanobacterium comprising a biosynthetic pathway for a lipid is provided. The cyanobacterium has been genetically engineered to comprise a bacteriocin polynucleotide under the control of a first promoter that is constitutively active. The cyanobacterium comprises an immunity modulator polynucleotide for an immunity modulator that protects against the bacteriocin, and that is under the control of a second promoter that is only active in the presence of a precursor found in an industrially useful feedstock. The cyanobacterium is placed in the feedstock. While it is producing lipids in the feedstock, the cyanobacterium also secretes active bacteriocin, thus neutralizing invading microorganisms. Upon escape from the feedstock, the cyanobacterium no longer possesses immunity modulator activity, but still produces bacteriocin, and thus is neutralized by the bacteriocin.

EXAMPLE 2

Protection of *Bacillus*, Maintenance of a Plasmid, and Neutralization Upon Escape A genetically engineered *Bacillus* cell is provided, comprising a bacteriocin polynucleotide integrated into its chromosomal genome, and a plasmid comprising an immunity modulator polynucleotide for an immunity modulator that protects against the bacteriocin as well as a polynucleotide encoding a polypeptide to be manufactured. The bacteriocin is under the control of a constitutive promoter. The immunity modulator polynucleotide is under the control of a promoter that is only active in the presence of a precursor found in the industrially useful feedstock. As such, when the *Bacillus* is in the feedstock, it produces the bacteriocin to kill invading microbial cells. Moreover, when *Bacillus* clones lose the plasmid, they become undesirable (as they no longer can produce the polypeptide to be manufactured), and as a result of also losing the immunity modulator, are killed by the bacteriocin. Upon escape from the feedstock, the *Bacillus* cell no longer possesses immunity modulator activity, but still produces bacteriocin, and thus is neutralized by the bacteriocin produced by the other genetically engineered *Bacillus* cells in its environment.

EXAMPLE 3

Regulation of Levels of Two Partner Strains of *S. cerevisiae*

A first *S. cerevisiae* strain is provided. The first strain comprises a bacteriocin polynucleotide under the control of a first promoter that is induced by the presence of a metabolite. As such, the bacteriocin is expressed more strongly as levels of the metabolite increase. The encoded bacteriocin arrests the *S. cerevisiae* cell cycle, but is bacteriostatic, not bacteriolytic. The first strain also comprises an immunity modulator polynucleotide for conferring immunity to the first bacteriocin under control of a promoter that is activated by a compound present only in the industrial feedstock. A second, partner strain of *S. cerevisiae* comprises a polynucleotide encoding an enzyme that produces the metabolite, but does not comprise a corresponding immunity modulator activity. As levels of the metabolite increase through activity of the second strain, the first strain produces more and more bacteriocin, thus arresting the cell cycle of the second strain, and reducing the relative amount of cells of the second strain available. Meanwhile, the first strain continues to proliferate. Accordingly, the relative ratio of the first strain to the second strain is increased, and buildup of the metabolite is reduced.

EXAMPLE 4

Regulation of *A. ferrooxidans* by *E. coli*

An *Acidithiobacillus ferrooxidans* strain is engineered to produce stored energy from the oxidation of Fe(II) to Fe(III) in a feedstock comprising an iron source that diffuses Fe(II) into the feedstock. An *E. coli* strain is engineered to control the growth of the first strain of *A. ferrooxidans*. The *A. ferroxidans* strain comprises a nucleic acid encoding Colicin-Ia (SEQ ID NO: 56) under the control of a rus operon promoter (SEQ ID NO: 549), and a nucleic acid encoding a Colicin-Ia immunity modulator (SEQ ID NO: 464) under the control of a constitutive promoter (*B. subtilis* ctc promoter, SEQ ID NO: 663). However, the ferroxidans strain does not produce any Colicin-E1 immunity modulator. The *E. coli* strain comprises a nucleic acid encoding Colicin-E1 (SEQ ID NO: 54) and Colicin-E1 immunity modulator (SEQ ID NO: 465) under the control of a constitutive promoter (SEQ ID NO: 651) integrated into its genome. However, the *E. coli* strain does not produce Colicin-Ia immunity modulator (SEQ ID NO: 464). As the *A. ferroxidans* oxidizes Fe(II) to Fe(III), levels of Fe(II) decrease. As such, activity of the rus promoter decreases, and the *A. ferroxidans* produces lower levels of Colicin-Ia (SEQ ID NO: 54). Accordingly, any neutralization of the *E. coli* strain is minimized. The second strain of *E. coli* proliferates, producing higher levels of Colicin-E1 (SEQ ID NO: 54). The Colicin-E1 neutralizes the *A. ferroxidans*, so that less *A. ferroxidans* is present to oxidize Fe(II) into Fe(III). Accordingly levels of Fe(II) increase again. As Fe(II) accumulates, the *A. ferroxidans* produce higher levels of Colicin-Ia (SEQ ID NO: 56), neutralizing organisms the second strain of *E. coli*. Accordingly, there in minimal *E. coli* producing Colicin-E1, and neutralization of *A. ferroxidans* is minimal as well. The *A. ferroxidans* proliferates, oxidizing the Fe(II) into Fe(III) and storing energy.

EXAMPLE 5

Genetic Guard for Ethanol Synthesis by Non-GMO Microbial Organism

A genetic guard in accordance with some embodiments herein is used to protect a non-GMO microbial organism that produces ethanol from glucose in a feedstock. The genetic guard comprises an *E. coli* strain comprising and expressing 20 different bacteriocin nucleic acids under the control of a single constitutive promoter, and as such, produces 20 different bacteriocins in approximately stoichiometric ratios. It is also contemplated that in accordance with some embodiments herein, another suitable option is to provide a genetic guard comprising five different *E. coli* strains, each of which comprise and express five different bacteriocins. The genetic guard is disposed in the first environment 610 of a system as illustrated in FIG. 6. The bacteriocins diffuse through a porous membrane to enter the second environment. The porous membrane is made of porous polytetrafluoroethylene that is permeable to bacteriocins and liquid, but is not permeable to the genetic guard. Non-GMO fermenting *S. cerevisiae* are cultured in the second environment. The non-GMO fermenting *S. cerevisiae* produce ethanol from glucose in the feedstock. The bacteriocins from the genetic guard neutralize invading microbial organisms, preventing contamination of the feedstock and consumption of the ethanol by invading microbial organisms. The porous membrane maintains physical separation between the genetically-engineered genetic guard and non-GMO fermenting yeast. As such, the fermenting yeast is protected from undesired microbial organisms, while a portion of the feedstock is keep free of GMO's.

EXAMPLE 6

Protection of Non-GMO Photosynthetic Microalgae by Genetic Guard

A genetic guard in accordance with some embodiments herein is used to protect a non-GMO photosynthetic microalgae that produces biomass. The biomass can be suitable for a variety of downstream applications, for example extracting compounds of interest, energy, or animal feed. The genetic guard comprises a mixture of 50 different *B. subtilis* strains, each of which produces a different bacteriocin. The genetic guard is disposed in an aqueous first environment 710 of a system as illustrated in FIG. 7. The system further comprises an aqueous second environment 720, which contains non-GMO photosynthetic microalgae, which yield biomass. The first environment is separated from the second environment by a 0.5 µm fiberglass filter, so as to allow gas, liquid, and bacteriocins to pass between the first environment and second environment, while blocking bacteriocins from passing between the first environment and second environment. $CO_2$ enters the system through an inlet in the first environment, and diffuses through the first environment and second environment. Sunlight enters the second environment, and drives the photosynthetic microalgae to produce biomass. As a result, a high-glucose biomass is produced in the second environment. The 50 different bacteriocins also diffuse from the first environment to the second environment. The bacteriocins neutralize invading undesired microbial organisms, thus preventing contamination the biomass and preventing undesired microbial organisms from interfering with biomass production and/or catabolizing the biomass. Biomass is harvested from the second environment via an outlet. As such, physical separation is maintained between genetically engineered genetic guard and non-GMO photosynthetic microalgae, while neutralizing invading microorganisms in the second environment.

EXAMPLE 7

Protection of *Saccharomyces cerevisiae* against Lactic Acid Bacteria family (LAB)

A *Saccharomyces cerevisiae* is engineered to produce multiple bacteriocins active on Lactic Acid Bacteria (LAB). Leucococin C (SEQ ID NO: 368) and Diversin V41 (SEQ ID NO: 74) are shown to be active on LAB bacteria according to the bactibase database, which is accessible on the world wide web at bactibase.pfba-lab-tun.org/main.php. It is appreciated that as *S. cerevisiae* are not sensitive to Leucococin or Diversin V41, there is no need to integrate corresponding immunity loci into the *S. cerevisiae*. As such, Leucococin C (SEQ ID NO: 368) and Diversin V41 (SEQ ID NO: 74) are selected, and polynucleotides are encoding Leucococin C (SEQ ID NO: 369) and Diversin V41 (SEQ ID NO: 75) are provided. The polynucleotides encode Leucococin C (SEQ ID NO: 368) and Diversin V41 (SEQ ID NO: 74), each fused to signal peptide from yeast mating factor alpha to facilitate secretion by the *S. cerevisiae*. The polynucleotides are integrated into the genome of a single *S. cerevisiae* strain under the control of a strong constitutive promoter, PPGK1 (3-Phosphoglyceratekinase) (SEQ ID NO: 692). The transformation is performed using standard homologous recombination. It is contemplated herein that other suitable strong constitutive promoters include, but are not limited to PTEF1 (translation elongation factor) and PGAP (glycerinaldehyde-3-phosphate dehydrogenase) (a list of constitutive yeast promoters is accessible on the world wide web at parts.igem.org/Promoters/Catalog/Yeast/Constitutive). The bacteriocin activity expressed by the transformed *S. cerevisiae* is measured by inhibitory assays on LAB cultures invading the production plan. As the makeup of undesired microbial organisms invading the feedstock changes over time, *S. cerevisiae* strains producing additional, fewer, and/or different bacteriocins can be produced and introduced into the industrial feedstock.

What is claimed is:

1. A method of controlling the growth of a microbial cell, the method comprising:
   culturing a genetically engineered microbial cell under conditions in which the genetically engineered microbial cell produces a secreted bacteriocin at a level sufficient to control the growth of the genetically engineered microbial cell and/or a second microbial cell,
   wherein said genetically engineered microbial cell comprises:
      a first nucleic acid comprising a first nucleic acid sequence encoding the secreted bacteriocin that is capable of inhibiting or preventing reproduction of said genetically engineered microbial cell and/or second microbial cell in the absence of an immunity modulator that confers resistance to said secreted bacteriocin; and
      a second nucleic acid comprising a second nucleic acid sequence that encodes the immunity modulator that confers resistance to said secreted bacteriocin, wherein the second nucleic acid sequence is on a chromosome, and
   wherein said genetically engineered microbial cell has been genetically engineered to conditionally decrease or eliminate at least one of transcription, post-transcriptional expression or post-transcriptional activity of said immunity modulator concurrent with expression of the secreted bacteriocin, thereby causing the secreted bacteriocin to inhibit or prevent reproduction of the genetically engineered microbial cell.

2. The method of claim 1, comprising culturing continuously for at least 30 days.

3. The method of claim 1, further comprising:
   detecting a presence or increase in the levels or activity of a third microbial cell during the culturing; and
   reengineering the first microbial cell in response to the detected presence or increase in the levels or activity of the third microbial cell to produce a second bacteriocin at a level sufficient to control the growth of the third microbial cell.

4. A system for neutralizing undesired microbial organisms, the system comprising:
   a first environment comprising a first microbial organism that secretes two or more different bacteriocins, wherein the first microbial organism comprises immunity modulators for each of the two or more different bacteriocins; and
   a second environment that is physically separated from the first environment so that the first microbial organism cannot move from the first environment to the second environment,
   wherein the second environment is in fluid communication with the first environment, and
   wherein the secreted two or more different bacteriocins enter the second environment.

5. The system of claim 4, further comprising a second microbial organism in the second environment,
   wherein the second microbial organism does not secrete the two or more different bacteriocins, and
   wherein the second microbial organism is not neutralized by any of the two or more different bacteriocins.

6. The system of claim 4, wherein the second environment is separated from the first environment by at least one of a membrane, a mesh, a filter, or a valve that is permeable to the two or more different bacteriocins, but is not permeable to the first microbial organism.

7. The method of claim 1, comprising culturing the genetically engineered microbial cell in a culture medium comprising the second microbial cell.

8. The method of claim 1, wherein the first nucleic acid comprises a first promoter that drives expression from the first nucleic acid sequence, wherein the first promoter is regulatable.

9. The method of claim 1, wherein the genetically engineered microbial cell has been genetically engineered to decrease or eliminate at least one of transcription, post-transcriptional expression, or post-transcriptional activity of said immunity modulator via at least one of:
   (a) a second promoter operably linked to the second nucleic acid that encodes the immunity modulator, the second promoter genetically engineered to be inactive concurrent with transcription of the first nucleic acid by the first promoter;
(b) a second promoter operably linked to the second nucleic acid that encodes the immunity modulator; and a nucleic acid encoding a transcriptional repressor configured to repress the second promoter while the first promoter is active;
(c) a ribozyme or antisense oligonucleotide complementary to the second nucleic acid that encodes the immunity modulator, the ribozyme or antisense oligonucleotide genetically engineered to be expressed while the first promoter is active;
(d) a regulatable tRNA specific for a transcript of the second nucleic acid that encodes the immunity modulator, and genetically engineered to be inhibited while the first promoter is active;
(e) a site-specific protease specific for a site on the immunity modulator;
(f) a FLP-FRT or cre-lox cassette comprising the second nucleic acid that encodes the immunity modulator; or
(g) a plasmid comprising the second nucleic acid that encodes the immunity modulator.

10. The method of claim 1, wherein the genetically engineered microbial cell comprises a third nucleic acid encoding a second secreted bacteriocin capable of inhibiting or preventing reproduction of the second microbial cell.

11. The method of claim 10, wherein the second microbial cell is of a different species than the genetically engineered microbial cell.

12. The method of claim 10, wherein the third nucleic acid is under the control of the first promoter.

13. The method of claim 10, further comprising a third promoter, wherein the third nucleic acid is under the control of the third promoter.

14. The method of claim 10, further comprising a fourth nucleic acid which encodes a second immunity modulator that protects the genetically engineered microbial cell against the second secreted bacteriocin.

15. The method of claim 1, wherein the engineered microbial cell is selected from the group consisting of: *Bacillus* spp., *Paenibacillus* spp., *Streptomyces* spp., *Micrococcus* spp., *Corynebacterium* spp., *Acetobacter* spp., *Cyanobacteria* spp., *Salmonella* spp., *Rhodococcus* spp., *Pseudomonas* spp., *Lactobacillus* spp., *Enterococcus* spp., *Alcaligenes* spp., *Klebsiella* spp., *Paenibacillus* spp., *Arthrobacter* spp., *Corynebacterium* spp., *Brevibacterium* spp., *Thermus aquaticus, Pseudomonas stutzeri, Clostridium thermocellus*, and *Escherichia coli*.

16. The method of claim 1, further comprising culturing the second microbial cell, wherein the secreted bacteriocin is capable of conditionally inhibiting or preventing reproduction of the second microbial cell.

17. The method of claim 16, wherein the second microbial cell is of the same species or strain as the genetically engineered microbial cell.

18. The method of claim 1, comprising contacting the second microbial cell with the secreted bacteriocin, whereby the secreted bacteriocin inhibits or prevents reproduction of the second microbial cell.

19. The system of claim 4, wherein the second environment comprise a culture medium.

20. The system of claim 4, wherein the first microbial organism has been genetically engineered to conditionally decrease or eliminate at least one of transcription, post-transcriptional expression or post-transcriptional activity of two or more immunity modulators that confer resistance to the two or more different secreted bacteriocins in the first microbial organism, said decrease or elimination concurrent with expression of said two or more different secreted bacteriocins, thereby causing the two or more different secreted bacteriocins to inhibit or prevent reproduction of the first microbial organism.

21. A method of controlling the growth of microbial cells, the method comprising culturing genetically engineered microbial cells under conditions in which the genetically engineered microbial cells produce a bacteriocin, wherein said genetically engineered microbial cells comprise:
a first nucleic acid encoding the bacteriocin, wherein the bacteriocin is capable of preventing survival or reproduction of said genetically engineered microbial cells; and
a plasmid comprising a second nucleic acid encoding an immunity modulator that confers resistance to said bacteriocin, wherein transcription of the second nucleic acid is under control of a constitutive promoter, and wherein the plasmid does not comprise the first nucleic acid, and
wherein said genetically engineered microbial cells have been genetically engineered to conditionally decrease or eliminate expression of the immunity modulator concurrent with expression of the bacteriocin, whereby survival or reproduction of the genetically engineered microbial cells is prevented by expression of the bacteriocin and the decreased or eliminated expression of the immunity modulator.

22. The method of claim 21, further comprising generating the genetically modified microbial cells using a viral vector to introduce the first nucleic acid into microbial cells comprising the plasmid.

23. The method of claim 22, wherein the viral vector is a bacteriophage.

24. The method of claim 23, wherein the genetically engineered microbial cells are selected from an *Enterococcus* species, a *Klebsiella* species, and *Escherichia coli*.

25. The method of claim 24, wherein the genetically engineered microbial cells are *Escherichia coli*, and the bacteriocin is selected from: Colicin-E6, Colicin-E8, and Colicin-M.

26. The method of claim 21, wherein said conditionally decreasing or eliminating expression of the immunity modulator concurrent with expression of the bacteriocin comprises conditionally decreasing or eliminating transcription of the second nucleic acid encoding the immunity modulator concurrent with expression of the bacteriocin.

27. A system for controlling growth of microbial cells, comprising a culture medium comprising:
a first population of genetically engineered microbial cells comprising:
a first nucleic acid encoding a bacteriocin that is capable of preventing survival or reproduction of genetically engineered microbial cells of i) the first population; and ii) a second population of genetically engineered microbial cells; and
a first plasmid comprising a second nucleic acid encoding a first immunity modulator that confers resistance to the bacteriocin, wherein transcription of the second nucleic acid is under control of a first constitutive promoter, and wherein the first plasmid does not comprise the first nucleic acid,
wherein the genetically engineered microbial cells of the first population have been genetically engineered to conditionally decrease or eliminate expression of the first immunity modulator concurrent with expression of the bacteriocin, whereby survival or reproduction of the genetically engineered microbial cells of the first population is prevented by expression of the bacteriocin and the decreased or eliminated expression of the first immunity modulator;

the second population of genetically engineered microbial cells comprising a third nucleic acid encoding a second immunity modulator that confers resistance to the bacteriocin, wherein transcription of the third nucleic acid is under control of a second constitutive promoter, wherein genetically engineered microbial cells of the second population are clonally related to, or are of the same species or strain as, the genetically engineered microbial cells of the first population; and bacteriophages comprising a fourth nucleic acid encoding the bacteriocin, the bacteriophage configured to introduce the fourth nucleic acid into the genetically engineered microbial cells of the second population.

28. The system of claim 27, wherein said genetically engineered microbial cells of the first population have been genetically engineered to conditionally decrease or eliminate transcription of the second nucleic acid encoding the first immunity modulator concurrent with expression of the bacteriocin.

29. The system of claim 27, wherein the second and third nucleic acids have the same sequence, and wherein the first and second immunity modulators are the same.

30. The system of claim 27, wherein the first and fourth nucleic acids have the same sequence.

31. The system of claim 27, wherein the first and second constitutive promoters are the same.

* * * * *